US007390830B1

(12) United States Patent
Shiota et al.

(10) Patent No.: US 7,390,830 B1
(45) **Date of Patent: *Jun. 24, 2008**

(54) REMEDIES OR PROPHYLACTICS FOR DISEASES IN ASSOCIATION WITH CHEMOKINES

(75) Inventors: Tatsuki Shiota, Tokyo (JP); Fuminori Miyagi, Tokyo (JP); Takashi Kamimura, Tokyo (JP); Tomohiro Ohta, Tokyo (JP); Yasuhiro Takano, Tokyo (JP); Hideki Horiuchi, Tokyo (JP)

(73) Assignee: Teijin Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/959,635

(22) PCT Filed: May 18, 2000

(86) PCT No.: PCT/JP00/03203

§ 371 (c)(1), (2), (4) Date: Nov. 1, 2001

(87) PCT Pub. No.: WO00/69432

PCT Pub. Date: Nov. 23, 2000

(30) Foreign Application Priority Data

May 18, 1999 (JP) ................................ 11-175856
Sep. 6, 1999 (JP) ................................ 11-251464

(51) Int. Cl.
*A61K 31/40* (2006.01)

(52) U.S. Cl. ....................................................... 514/426

(58) Field of Classification Search ................. 514/212, 514/422, 426, 183, 291; 548/527, 525, 517, 548/557, 217
See application file for complete search history.

(56) References Cited

U.S. PATENT DOCUMENTS

| | | | | |
|---|---|---|---|---|
| 4,443,461 | A | 4/1984 | Ward | |
| 6,166,015 | A | 12/2000 | Rogers et al. | |
| 6,362,177 | B1 * | 3/2002 | Shiota et al. | 514/217.03 |
| 6,410,566 | B1 * | 6/2002 | Shiota et al. | 514/329 |
| 6,451,842 | B1 * | 9/2002 | Shiota et al. | 514/422 |

FOREIGN PATENT DOCUMENTS

| | | | |
|---|---|---|---|
| AU | 13825/00 | | 6/2000 |
| AU | 47967/00 | | 12/2000 |
| CN | 1279668 | | 1/2001 |
| EP | 217286 | | 4/1987 |
| EP | 217286 | A1 | 4/1987 |
| EP | 903349 | | 3/1999 |
| EP | 1 201 239 | A1 | 5/2002 |
| FI | 841 081 | A | 9/1984 |
| GB | 2106108 | A | 4/1983 |
| WO | WO 97/24325 | | 7/1997 |
| WO | WO 97/40051 | A1 | 10/1997 |
| WO | WO 97/44329 | | 11/1997 |
| WO | WO 98/02151 | | 1/1998 |
| WO | WO 98/04554 | | 2/1998 |
| WO | WO 98/06703 | | 2/1998 |
| WO | WO 98/25604 | | 6/1998 |
| WO | WO 98/25605 | | 6/1998 |
| WO | WO 98/25617 | | 6/1998 |
| WO | WO 98/27815 | | 7/1998 |
| WO | WO 98/30218 | | 7/1998 |
| WO | WO 98/31364 | | 7/1998 |
| WO | WO 98/38167 | | 9/1998 |
| WO | 98/50534 | | 11/1998 |
| WO | WO 98/50534 | | 11/1998 |
| WO | WO 98/50534 | A1 | 11/1998 |
| WO | WO 99/01127 | | 1/1999 |
| WO | 99/25686 | | 5/1999 |
| WO | WO 99/25686 | A1 | 5/1999 |
| WO | WO 00/9377 | | 2/2000 |
| WO | 00/31032 | | 6/2000 |
| WO | WO 00/31032 | A1 | 6/2000 |
| WO | WO 00/31033 | | 6/2000 |
| WO | WO 00/35449 | | 6/2000 |
| WO | WO 00/35451 | | 6/2000 |
| WO | WO 00/69815 | A | 11/2000 |
| WO | WO 69815 | A | 11/2000 |

OTHER PUBLICATIONS

Webster's II, New Riverside University Dictionary, 1988, pp. 944 and 933.*

Merck Manual of Diagnosis and Therapy, 17th Edition, 1999, pp. 416-423, 1473-1476, and 1864-1869.*

Khalid, M. et al., "N,N'—disubstituted L-isoglutamines as novel cancer chemotherapeutic agents", Drugs Exp. Clin. Res., vol. 13, Suppl.1, pp. 57-60 (1987).

Krishna Vaddi, "Chemokine Facts Book, Acad. Press," 1997 San Diego, CA.

Franklin H. Epstein, M.D., Luster, D. Andrew, "Chemokines—Chemotactic Cytokines that Mediate Inflammation", The New England Journal of Medicine (Feb. 12, 1998), vol. 338 pp. 436-445.

Marco Baggiolini "Chemokines and leukocyte traffic" NATURE vol. 392 pp. 565-568 Apr. 9, 1998.

(Continued)

*Primary Examiner*—Raymond J Henley, III
(74) *Attorney, Agent, or Firm*—Sughrue Mion, PLLC

(57) ABSTRACT

This invention provides remedies or prophylactics for diseases in association with chemokines such as MIP-1 α and/or MCP-1. Namely, remedies or prophylactics for diseases in association with the chemokines such as rheumatoid arthritis or nephritis contain, as the active ingredient, cyclic amine derivatives represented by the following formula (I), pharmaceutically acceptable acid addition salts thereof or pharmaceutically acceptable $C_1$-$C_6$ alkyl addition salts thereof.

4 Claims, 8 Drawing Sheets

OTHER PUBLICATIONS

Joseph Hesselgesser "Identification and Characterization of Small Molecule Functional Antagonists of the CCR1 Chemokine Receptor" The Journal of Biological Chemistry vol. 273, No. 25, Jun. 19, 1998 pp. 15687-15692.
European Communication Nov. 29, 2002.
Khalid, M. Burzynski S.R. et al., "N,N'—disubstituted L-isoglutamines as novel cancer chemotherapeutic agents", Drugs Exp. Clin. Res., vol. 13, Suppl. 1, pp. 57-60 (1987).
Bright, Colin, et al. Identification of a Non- Peptidic Rantes Antagonist, vol. 1, No. 1, Bioorganic & Medicinal Chemistry Letters, 1998 pp. 771-774.
Howard, O.M.Z., et al. Inhibition of in Vitro and in Vivo HIV Replication by a Distamycin Analogue that Interferes with Chemokin Receptor Function : A Candidate for Chemotherapeutic and Microbicidal Application, J. Med. Chem. 1998, 41, No. 13, pp. 2184-2193.
Ward, G. Stephen, et al., "Chemokines: understanding their role in T-lymphocyte biology", Biochem. J. (1998) 333, 457-470.
European Communication Sep. 17, 2003.
Rapport, Carol A., et al., "Molecular Cloning and Functional Characterization of a Novel Human CC Chemokine Receptor (CCR5) for Rantes, MIP-1β, and MIP-1α," The Journal of Biological Chemistry, The American Society for Biochemistry and Molecular Biology, Inc., 1996, pp. 17161-17166, vol. 271, No. 29, Issue of July $19^{th}$, USA.
Murai, Masako, et al., "Active participation of $CCR5^+CD8^+$ T lymphocytes in the pathogenesis of liver injury in graft-versus-host disease," The Journal of Clinical Investigations, Jul. 1999, pp. 49-57, vol. 104, No. 1.
Balashov, Konstantin E., "$CCR5^+$ and $CXCR3^+$ T cells are Increased in multiple sclerosis and their ligands MIP-1α and IP-10 are expressed in demyelinating brain lesions," Proc. Natl. Acad. Sci., Jun. 1999, pp. 6873-6878, vol. 90, USA.
Bradley, Linda, et al., The Journal of Immunology, vol. 162(5), pp. 2511-2520, Mar. 4, 1999.
N. Zimmerman, et al. "Polymorphisms in the human CC chemokine receptor-3 gene" *Biochimica et Biophysica Acta. Gene Structure and Expression*, Elsevier, Amsterdam, NL, vol. 1442, No. 2-3, Nov. 8, 1998, pp. 170-176, XP004275252.
H. Choe, et al. "The Beta-Chemokine Receptors CCR3 and CCR5 Facilitate Infection by Primary HIV-1 Isolates" *Cell, Cell Press*, Cambridge MA, US, vol. 85, No. 7, Jun. 28, 1996, pp. 1135-1148, XP002061250.
Chen, et al. "CCR3 and CCR5 are co-receptors for HIV-infection of microglia" *Nature, Macmillan Journals Ltd.*, London, GB, vol. 385, No. 6617, Feb. 13, 1997, pp. 645-649, XP002107165.
Canella, Barbara; Hoban, Carolyn J.; Gao, Yan-ling; Garcia-Arenas, Renee; Lawson, Deborah; Marchionni, Mark; Gwynne, David; Raine, Cedric S., "The neuregulin, glial growth factor 2, diminishes autoimmune demyelination and enhances remyelination in a chronic relapsing model for multiple sclerosis"; Proceedings of the National Academy of Sciences, Aug. 1998, pp. 10100-10105, vol. 95, USA.
Tran, Elise H.; Hoekstra, Karin; van Rooijen, Nico; Dijkstra, Christine D.; Owens, Trevor, "Immune Invasion of the Central Nervous System Parenchyma and Experimental Allergic Encephalomyelitis, But Not Leukocyte Extravasation from Blood, Are Prevented in Macrophage-Depleted Mice," The Journal of Immunology, 1998, pp. 3767-3775, vol. 161, U.S.A.
Butterfield, Russell J.; Sudweeks, Jayce D.; Blankenhorn, Elizabeth P.; Korngold, Robert; Marini, Joseph C.; Todd, John A.; Roper, Randall J.; Teuscher, Cory, "New Genetic Loci That Control Susceptability and Symptoms of Experimental Allergic Encephalomyelitis in Inbred Mice," The Journal of Immunology, 1998, pp. 1860-1867, vol. 161, U.S.A.
Karpus, William J.; Ransohoff, Richard M., "Cutting Edge Commentary: Chemokine Regulation of Experimental Autoimmune Encephalomyelitis: Temporal and Spatial Expression Patterns Govern Disease Pathogenesis," The Journal of Immunology, 1998, pp. 2667-2671, vol. 161, U.S.A.
Rajan, Alice J.; Klien, Jonathan D.S.; Brosnan, Celia F., "The Effect of γδ T Cell Depletion on Cytokine Gene Expression in Experimental Allergic Encephalomyelitis," The Journal of Immunology, 1998, pp. 5955-5962, vol. 160, U.S.A.

* cited by examiner

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: Primer, having restriction enzyme recognition
      sites applied on the basis of the known human MCP-1 gene sequence
      (see T. Yoshimura, et al. (1989))
<300> PUBLICATION INFORMATION:
<301> AUTHORS: T. Yoshimura, et al.
<303> JOURNAL: FEBS Letters
<304> VOLUME: 244
<306> PAGES: 487-493
<307> DATE: 1989
```

-continued

```
<400> SEQUENCE: 1

cactctagac tccagcatga                                                20


<210> SEQ ID NO 2
<211> LENGTH: 21
<212> TYPE: DNA
<213> ORGANISM: Artificial
<220> FEATURE:
<223> OTHER INFORMATION: Primer, having restriction enzyme recognition
      sites applied on the basis of the known human MCP-1 gene sequence
      (see T. Yoshimura, et al. (1989))
<300> PUBLICATION INFORMATION:
<301> AUTHORS: T. Yoshimura, et al.
<303> JOURNAL: FEBS Letter
<304> VOLUME: 244
<306> PAGES: 487-493
<307> DATE: 1989

<400> SEQUENCE: 2

tagctgcaga ttcttgggtt g                                              21
```

REMEDIES OR PROPHYLACTICS FOR DISEASES IN ASSOCIATION WITH CHEMOKINES

BACKGROUND OF THE INVENTION

1. Technical Field

The present invention relates to cyclic amine derivatives and more particularly it relates to chemokine receptor antagonists capable of expecting effects as remedies and/or prophylactics for diseases such as atherosclerosis, rheumatoid arthritis, psoriasis, asthma, ulcerative colitis, nephritis (nephropathy), multiple sclerosis, pulmonary fibrosis, cardiomyopathy, hepatitis, pancreatitis, sarcoidosis, Crohn's disease, endometriosis, congestive heart failure, viral meningitis, cerebral infarction, neuropathy, Kawasaki disease, sepsis, allergic rhinitis and allergic dermatitis wherein infiltration of blood leukocyte components such as monocytes or lymphocytes into tissues plays a principal role in progression and maintenance of diseases.

2. Background Art

Chemokines are a generic name of a group of inflammatory/immunomodulatory polypeptides having a molecular weight of 6 to 15 KD and produced in inflammatory sites by various kinds of cells, for example, macrophages, monocytes, eosinophils, neutrophils, fibroblasts, vascular endothelial cells, smooth muscle cells and mast cells. The chemokines are classified into two major subgroups of CXC chemokines (or α-chemokines) and CC chemokines (or β-chemokines) by the common location of four preserved cysteine residues and a difference in chromosomal locations of genes encoding the chemokines. The first two cysteines of the CXC chemokines are separated by one amino acid; however, the same cysteines of the CC chemokine are adjacent. For example, IL-8 (an abbreviation for interleukin-8) is the CXC chemokines. On the other hand, MIP-1 α/β (an abbreviation for macrophage inflammatory protein-1 α/β), MCP-1 (an abbreviation for monocyte chemoattractant protein-1) and RANTES (an abbreviation for regulated upon activation, normal T-cell expressed and secreted) are cited as the CC chemokines.

Furthermore, there also exist chemokines which do not fall into either of chemokine subgroups. Lymphotactin having only two cysteines and classified as C chemokines and fractalkine classified as CX3C chemokines because the first two cysteines are separated by three amino acids and having a chemokinelike domain in the mucin structure are cited as such a chemokine. The chemokines promote cell migration and have expression enhancing actions on cellular adhesion molecules such as integrins and further cellular adhesion enhancing actions. Therefore, the chemokines are thought to be protein factors closely involved in the adhesion and infiltration of leukocytes or the like into the pathogenic sites such as inflammatory tissues. See, for example, The Chemokine Facts Book, by Vaddi, K. et al., Academic Press, 1997; Chemoattractant Ligand and Their Receptors, edited by Horuk, R., CRC Press, 1996; Ward, G. W. et al., Biochem. J., 1998, 333, 457; Luster, A. D., New Engl. J. Med., 1998, 338, 436; Bagglioni, M., Nature, 1998, 392, 565; Rolins. B. J., Blood, 1997, 90, 909; Alam, R., J. Allergy Clin. Immunol., 1997, 99, 273; Hancock, W. W., Am. J. Pathol., 1996, 148, 681; Taub, D. D., Cytokine & Growth Factor Rev., 1996, 7, 335; Strieter, R. M. et al., J. Immunol., 1996, 156, 3583; Furie, M. B. et al., Am. J. Pathol., 1995, 146, 1287; Schall, T. J. et al., Current Opinion in Immunology, 1994, 6, 865; and Edginton, S. M., Biotechnology, 1993, 11, 676 as references.

For example, MIP-1 α causes a transient increase in intracellular calcium ion concentration levels and induces cell migration of T lymphocytes or B lymphocytes (see, for example, Tabu, D. D. et al., Science, 1993, 260, 355 and Shall, T. J. et al., J. Exp. Med., 1993, 177, 1821), cell migration of eosinophils (see, for example, Rot, A. et al., J. Exp. Med., 1992, 176, 1489), cell migration of NK cells (see, for example, Magazachi, A. A. et al., J. Immunol., 1994, 153, 4969), expression of integrins (see, for example, Vaddi, K. et al., J. Immunol., 1994, 153, 4721) and differentiation of osteoclasts (see, for example, Kukita, T. et al., Lab. Invest., 1997, 76, 399). MIP-1 α also increases the IgE and IgG4 production in B cells (see, for example, Kimata, H. et al., J. Exp. Med., 1996, 183, 2397) and inhibits the proliferation of hematopoietic stem cells (see, for example, Mayani, H. et al., Exp. Hematol., 1995, 23, 422; Keller, J. R. et al., Blood, 1994, 84, 2175; Eaves, C. J. et al., Proc. Natl. Acad. Sci. USA, 1993, 90, 12015; Bodine, D. M. et al., Blood, 1991, 78, 914; and Broxmeyer, H. E. et al., Blood, 1990, 76, 1110).

As to the association of MIP-1 α with in vivo actions or pathogenesis of diseases, it has been reported that the MIP-1 α is a pyrogen in rabbits (see, for example, Davatelis, G. et al., Science, 1989, 243, 1066) and the injection of the MIP-1 α into the footpads of mice results in inflammatory reactions such as infiltration of neutrophils or mononuclear cells (see, for example, Alam, R. et al., J. Immunol., 1994, 152, 1298).

It has been also reported that a neutralizing antibody to MIP-1 α has inhibitory effects or remedial effects in animal models of granuloma (see, for example, Lukacs, N. W. et al., J. Exp. Med., 1993, 177, 1551), asthma (see, for example, Lukacs, N. W. et al., Eur. J. Immunol., 1995, 25, 245 and Lukacs, N. W. et al., J. Immunol., 1997, 158, 4398), multiple sclerosis (see, for example, Karpus, W. J. et al., J. Immunol., 1995, 155, 5003 and Karpus, W. J. et al., J. Leukoc. Biol., 1997, 62, 681), idiopathic pulmonary fibrosis (see, for example, Smith, R. E. et al., J. Immunol., 1994, 153, 4704 and Smith, R. E., Biol. Signals, 1996, 5, 223), acute lung injury (see, for example, Shanley, T. P. et al., J. Immunol., 1995, 154, 4793 and Standiford, T. J. et al., J. Immunol., 1995, 155, 1515) and rheumatoid arthritis (see, for example, Kasama, T. et al., J. Clin. Invest., 1995, 95, 2868) and the like. Furthermore, it has been reported that coxsackie virus infection-induced myocarditis or herpes stromal keratitis is inhibited in MIP-1α gene deficient mice (see, for example, Cook, D. N. et al., Science, 1995, 269, 1583 and Tumpey, T. M. et al., J. Virology, 1998, 72, 3705).

In addition, significant expression of MIP-1 α was recognized in patients such as chronic pulmonary inflammatory diseases (see, for example, Standiford, T. J. et al., J. Immunol., 1993, 151, 2852), hypersensitivity pneumonitis (see, for example, Denis, M., Am. J. Respir. Crit. Care Med., 1995, 151, 164), rheumatoid arthritis (see, for example, Koch, A. E. et al., J. Clin. Invest., 1994, 93, 921), infectious meningitis (see, for example, Lahrtz, F. et al., J. Neuroimmunol., 1998, 85, 33) and chronic inflammation of muscle (see, for example, Adams, E. M. et al., Proc. Assoc. Am. Physicians, 1997, 109, 275). The studies indicate that MIP-1 α is deeply involved in the local accumulation of various subtypes of leukocytes in association with initiation, progression and maintenance of inflammatory diseases.

MCP-1 [also known as MCAF (an abbreviation for macrophage chemotactic and activating factor) or JE] is a CC chemokine produced by monocytes/macrophages, smooth muscle cells, fibroblasts and vascular endothelial cells and has a cell migration activity and cell adhesion enhancing actions on monocytes (see, for example, Valente, A. J. et al., Biochemistry, 1988, 27, 4162; Matsushima, K. et al., J. Exp. Med., 1989, 169, 1485; Yoshimura, T. et al., J. Immunol., 1989, 142, 1956; Rollins, B. J. et al., Proc. Natl. Acad. Sci.

USA, 1988, 85, 3738; Rollins, B. J. et al., Blood, 1991, 78, 1112; Jiang, Y. et al., J. Immunol., 1992, 148, 2423; and Vaddi, K. et al., J. Immunol., 1994, 153, 4721), memory T lymphocytes (see, for example, Carr., M. W. et al., Proc. Natl. Acad. Sci. USA, 1994, 91, 3652), T lymphocytes (see, for example, Loetscher, P. et al., FASEB J., 1994, 8, 1055) and natural killer cells (NK cells) (see, for example, Loetscher, P. et al., J. Immunol., 1996, 156, 322 and Allavena, P. et al., Eur. J. Immunol., 1994, 24, 3233) or the like and MCP-1 further has actions as a histamine releasing factor from basophils (see, for example, Alam R. et al., J. Clin. Invest., 1992, 89, 723; Bischoff, S. C. et al., J. Exp. Med., 1992, 175, 1271; and Kuna, P. et al., J. Exp. Med., 1992, 175, 489).

Moreover, remarkable expression of MCP-1 has been reported in diseases in which the accumulation of monocytes/macrophages and/or T cells is thought to be deeply involved in initiation, progression and maintenance of lesions such as atherosclerosis (see, for example, Hayes, I. M. et al., Arterioscler. Thromb, Vasc. Biol., 1998, 18, 397; Takeya, M. et al., Hum. Pathol., 1993, 24, 534; Yla-Herttuala, S. et al., Proc. Natl. Acad. Sci. USA, 1991, 88, 5252; and Nelken, N. A., J. Clin. Invest., 1991, 88, 1121), rheumatoid arthritis (see, for example, Koch, A. E. et al., J. Clin. Invest., 1992, 90, 772; Akahoshi, T. et al., Arthritis Rheum., 1993. 36, 762; and Robinson, E. et al., Clin. Exp. Immunol., 101, 398), nephritis (see, for example, Noris, M. et al., Lab. Invest., 1995, 73, 804; Wada, T. et al., Kidney Int., 1996, 49, 761; and Gesualdo, L. et al., Kidney Int., 1997, 51, 155), nephropathy (see, for example, Saitoh, A. et al., J. Clin. Lab. Anal., 1998, 12, 1; Yokoyama, H. et al., J. Leukoc. Biol., 1998, 63, 493), pulmonary fibrosis and pulmonary sarcoidosis (see, for example, Sugiyama, Y. et al., Internal Medicine, 1997, 36, 856), asthma (see, for example, Karina, M. et al., J. Invest. Allergol. Clin. Immunol., 1997, 7, 254; Stephene, T. H., Am. J. Respir. Crit. Care Med., 1997, 156, 1377; and Sousa, A. R. et al., Am. J. Respir. Cell Mol. Biol., 1994, 10, 142), multiple sclerosis (see, for example, McManus, C. et al., J. Neuroimmunol., 1998, 86, 20), psoriasis (see, for example, Gillitzer, R. et al., J. Invest. Dermatol., 1993. 101, 127), inflammatory bowel disease (see, for example, Grimm, M. C. et al., J. Leukoc. Biol., 1996, 59, 804 and Reinecker, H. C. et al., Gastroenterology, 1995, 106, 40), cardiomyopathy (see, for example, Seino, Y. et al., Cytokine, 1995, 7, 301), endometriosis (see, for example, Jolicoeur, C. et al., Am. J. Pathol., 1998, 152, 125), intraperitoneal adhesion (see, for example, Zeyneloglu, H. B. et al., Human Reproduction, 1998, 13, 1194), congestive heart failure (see, for example, Aurust, P. et al., Circulation, 1998, 97, 1136), chronic liver disease (see, for example, Marra, F. et al., Am. J. Pathol., 1998, 152, 423), viral meningitis (see, for example, Lahrtz, F. et al., Eur. J. Immunol., 1997, 27, 2484), Kawasaki disease (see, for example, Wong, M. et al., J. Rheumatol., 1997, 24, 1179) and sepsis (see, for example, Salkowski, C. A. et al., Infect. Immun., 1998, 66, 3569).

The inhibitory effects or remedial effects of an anti-MCP-1 antibody have been reported in animal models such as rheumatoid arthritis (see, for example, Schimmer, R. C. et al., J. Immunol., 1998, 160, 1466; Schrier, D. J., J. Leukoc. Biol., 1998, 63, 359; and Ogata H. et al., J. Pathol., 1997, 182, 106), multiple sclerosis (see, for example, Karpus, W. J., J. Leukoc. Biol., 1997, 62., 681), nephritis (see, for example, Lloyd, C. M. et al., J. Exp. Med., 1997, 185, 1371 and Wada T. et al., FASEB J., 1996, 10, 1418), asthma (see, for example, Gonzalo, J.-A. et al., J. Exp. Med., 1998, 188, 157 and Lukacs, N. W., J. Immunol., 1997, 158, 4398), atherosclerosis (see, for example, Guzman, L. A. et al., Circulation, 1993, 88 (suppl.), I-371), delayed type hypersensitivity (see, for example, Rand, M. L. et al., Am. J. Pathol., 1996, 148, 855), pulmonary hypertension (see, for example, Kimura, H. et al., Lab. Invest., 1998, 78, 571) and intraperitoneal adhesion (see, for example, Zeyneloglu, H. B. et al., Am. J. Obstet. Gynecol., 1998, 179, 438).

Further, it has been reported that MCP-1 (9-76) which is a peptide antagonist of MCP-1 inhibits arthritis in the mouse model (see, for example, Gong, J.-H., J. Exp. Med., 1997, 186, 131) and that MCP-1 is essential to monocyte mobilization in vivo in studies on MCP-1 gene deficient mice (see, for example, Lu, B. et al., J. Exp. Med., 1998, 187, 601 and Gu, L. et 41., Moll. Cell, 1998, 2, 275).

These data indicate that chemokines such as MIP-1 α and MCP-1 accumulate monocytes, lymphocytes or the like in disease sites and activate the cells and thus strongly suggest that the chemokines are deeply associated with initiation, progression and maintenance of diseases wherein monocytes, lymphocytes and the like are assumed to be deeply associated with the progression of lesion, for example, atherosclerosis, rheumatoid arthritis, psoriasis, asthma, ulcerative colitis, nephritis (nephropathy), multiple sclerosis, pulmonary fibrosis, myocarditis, hepatitis, pancreatitis, sarcoidosis, Crohn's disease, endometriosis, congestive heart failure, viral meningitis, cerebral infarction, neuropathy, Kawasaki disease and sepsis (see, for example, Rovin, B. H. et al., Am. J. Kidney. Dis., 1998, 31, 1065; Lloyd, C. et al., Curr. Opin. Nephrol. Hypertens., 1998, 7, 281; Conti, P. et al., Allergy and Asthma Proc., 1998, 19, 121; Ransohoff, R. M. et al., Trends Neuroscience., 1998, 21, 154; and MacDermott, R. P. et al., Inflammatory Bowel Diseases, 1998, 4, 54). A drug which inhibits actions of chemokines on target cells, therefore, can be expected to be useful as remedies and/or prophylactics for the diseases.

On the other hand, the cloning of genes encoding specific receptors for chemokines has been promoted, and it has become apparent that the receptors are G protein-coupled seven-transmembrane receptors present on various leukocytes. At least 5 CXC chemokine receptors (CXCR1 to CXCR5) and eight CC chemokine receptors (CCR1 to CCR8) have hitherto'been specified. For example, IL-8 is a ligand of CXCR1 and CXCR2. MIP-1 α is a ligand of CCR1 and CCR5, and MCP-1 is a ligand of CCR2A and CCR2B (see, for example, Holmes, W. E. et al., Science, 1991, 253, 1278-1280; Murphy, P. M. et al., Science, 253, 1280-1283; Neote, K. et al., Cell, 1993, 72, 415-425; Charo, I. F. et al., Proc. Natl. Acad. Sci., USA, 1994, 91, 2752-2756; Yamagami, S. et al., Biochem. Biophys. Res. Commun., 1994, 202, 1156-1162; Combadier, C. et al., The Journal of Biological Chemistry, 1995, 270, 16491-16494; Power, C. A. et al., J. Biol. Chem., 1995, 270, 19495-19500; Samson, M. et al., Biohemistry, 1996, 35, 3362-3367; and Murphy, P. M. et al., Annual Review of Immunology, 1994, 12, 592-633).

Further, it has been reported that the pulmonary inflammation and granuloma are suppressed in CCR1 gene deficient mice (see, for example, Gao, J.-L. et al., J. Exp. Med., 1997, 185, 1959 and Gerard, C. et al., J. Clin. Invest., 1997, 100, 2022) and that accumulation of macrophages and formation of atherosclerotic lesions are decreased in CCR2 gene deficient mice (see, for example, Boring, L. et al., Nature, 1998, 394, 894; Kuziel, W. A. et al., Proc. Natl. Acad. Sci. USA, 1997, 94, 12053; Kurihara, T. et al., J. Exp. Med., 1997, 186, 1757; and Boring, L. et al., J. Clin. Invest., 1997, 100, 2552). Therefore, compounds capable of inhibiting binding of chemokines such as MIP-1 α and/or MCP-1 to the receptors, i.e. chemokine receptor antagonists can be expected to be useful as a drug which inhibits the actions of the chemokines such as MIP-1 α and/or MCP-1 on target cells; however, the drug having the actions is not known.

Cyclic amine derivatives such as various kinds of piperidines or piperazines have recently been reported to have chemokine receptor antagonistic activity (see, for example, WO9724325; Hesselgesser, J. et al., J. Biol. Chem., 1998, 273, 15687; Howard, O. M. Z. et al., J. Med. Chem., 1998, 41, 2184; WO9744329; WO9802151; WO9804554; WO9825605; WO9825617; WO9825604; WO9831364; WO9856771; WO9909984; WO9904794; WO9917773; WO9937617; WO9937619; WO9737651; WO9938514; WO200014086; WO200014089; EP903349; JP9-249566; JP9-25572; and JP11-711350). The compounds, however, are different from the compounds used in the present invention.

BRIEF SUMMARY OF THE INVENTION

It is an object of the present invention to provide therapies for diseases wherein the binding of chemokines such as MIP-1 α and/or MCP-1 to receptors on target cells is one of the pathogenesis by using a small-molecular compound having an inhibitory activity against the binding of the chemokines such as MIP-1 α and/or MCP-1 to the receptors on the target cells.

As a result of intensive studies, the present inventors have found that cyclic amine derivatives having an arylalkyl group, pharmaceutically acceptable $C_1$-$C_6$ alkyl-addition salts thereof or pharmaceutically acceptable acid-addition salts thereof have an inhibitory activity against the binding of chemokines such as MIP-1 α and/or MCP-1 to the target cells and that the compounds can be useful as remedies or prophylactics for diseases considered to be associated with the chemokines such as MIP-1 α and/or MCP-1. The present invention has been accomplished on the basis of the findings.

That is, the present invention is remedies or prophylactics for diseases in association with chemokines or chemokine receptors comprising compounds represented by the following formula (I), pharmaceutically acceptable acid addition salts thereof or pharmaceutically acceptable $C_1$-$C_6$ alkyl addition salts thereof as an active ingredient, (I)

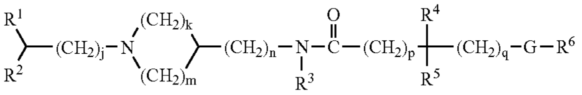

wherein $R^1$ is a phenyl group, a $C_3$-$C_8$ cycloalkyl group or an aromatic heterocyclic group having 1- to 3 oxygen atoms, sulfur atoms and/or nitrogen atoms as heteroatoms; the phenyl group or the aromatic heterocyclic group in the $R^1$ may be condensed with a benzene ring or an aromatic heterocyclic group having 1 to 3 oxygen atoms, sulfur atoms and/or nitrogen atoms as heteroatoms to form a condensed ring; the phenyl group, the $C_3$-$C_8$ cycloalkyl group, the aromatic heterocyclic group or the condensed ring in the above $R^1$ may be substituted with an optional number of halogen atoms, hydroxy groups, cyano groups, nitro groups, carboxy groups, carbamoyl groups, $C_1$-$C_6$ alkyl groups, $C_3$-$C_8$ cycloalkyl groups, $C_2$-$C_6$ alkenyl groups, $C_1$-$C_6$ alkoxy groups, $C_1$-$C_6$ alkylthio groups, $C_3$-$C_5$ alkylene groups, $C_2$-$C_4$ alkylenoxy groups, $C_1$-$C_3$ alkylenedioxy groups, phenyl groups, phenoxy groups, phenylthio groups, benzyl groups, benzyloxy groups, benzoylamino groups, $C_2$-$C_7$ alkanoyl groups, $C_2$-$C_7$ alkoxycarbonyl groups, $C_2$-$C_7$ alkanoyloxy groups, $C_2$-$C_7$ alkanoylamino groups, $C_2$-$C_7$ N-alkylcarbamoyl groups, $C_4$-$C_8$ N-cycloalkylcarbamoyl groups, $C_1$-$C_6$ alkylsulfonyl groups, $C_3$-$C_8$ (alkoxycarbonyl)methyl groups, N-phenylcarbamoyl groups, piperidinocarbonyl groups, morpholinocarbonyl groups, 1-pyrrolidinylcarbonyl groups, bivalent groups represented by the formula; —NH(C═O)O—, bivalent groups represented by the formula: —NH(C═S)O—, amino groups, mono($C_1$-$C_6$ alkyl)amino groups or di($C_1$-$C_6$ alkyl) amino groups; the substitutent groups of the phenyl group, the $C_3$-$C_8$ cycloalkyl group, the aromatic heterocyclic group or the condensed ring may further be substituted with an optional number of halogen atoms, hydroxy groups, amino groups, trifluoromethyl groups, $C_1$-$C_6$ alkyl groups or $C_1$-$C_6$ alkoxy groups, $R^2$ is a hydrogen atom, a $C_1$-$C_6$ alkyl group, a $C_2$-$C_7$ alkoxycarbonyl group, hydroxy group or a phenyl group; the $C_1$-$C_6$ alkyl group or the phenyl group in the $R^2$ may be substituted with an optional number of halogen atoms, hydroxy groups, $C_1$-$C_6$ alkyl groups or $C_1$-$C_6$ alkoxy groups, with the proviso that $R^2$ is not hydroxy group when j is 0;

j is an integer of 0 to 2;

k is an integer of 0 to 2;

m is an integer of 2 to 4;

n is 0 or 1;

$R^3$ is a hydrogen atom or a $C_1$-$C_6$ alkyl group which may be substituted with (one or two phenyl groups which may respectively be substituted with an optional number of the same or different halogen atoms, hydroxy groups, $C_1$-$C_6$ alkyl groups or $C_1$-$C_6$ alkoxy groups);

$R^4$ and $R^5$ are the same or different and are each a hydrogen atom, a hydroxy group, a phenyl group or a $C_1$-$C_6$ alkyl group; the $C_1$-$C_6$ alkyl group in the $R^4$ and $R^5$ may be substituted with an optional number of halogen atoms, hydroxy groups, cyano groups, nitro groups, carboxy groups, carbamoyl groups, mercapto groups, guanidino groups, $C_3$-$C_8$ cycloalkyl groups, $C_1$-$C_6$ alkoxy groups, $C_1$-$C_6$ alkylthio groups, (phenyl groups which may be substituted with an optional number of halogen atoms, hydroxy groups, $C_1$-$C_6$ alkyl groups, $C_1$-$C_6$ alkoxy groups or benzyloxy groups), phenoxy groups, benzyloxy groups, benzyloxycarbonyl groups, $C_2$-$C_7$ alkanoyl groups, $C_2$-$C_7$ alkoxycarbonyl groups, $C_2$-$C_7$ alkanoyloxy groups, $C_2$-$C_7$ alkanoylamino groups, $C_2$-$C_7$ N-alkylcarbamoyl groups, $C_1$-$C_6$ alkylsulfonyl groups, amino groups, mono($C_1$-$C_6$ alkyl)amino groups, di($C_1$-$C_6$ alkyl)amino groups or (aromatic heterocyclic groups having 1 to 3 oxygen atoms, sulfur atoms and/or nitrogen atoms as heteroatoms or condensed rings formed by condensation of the aromatic heterocyclic groups having the 1 to 3 oxygen atoms, sulfur atoms and/or nitrogen atoms as the heteroatoms with benzene rings) or both $R^4$ and $R^5$ together may form a 3- to a 6-membered cyclic hydrocarbon;

p is 0 or 1;

q is 0 or 1;

G is a group represented by —CO—, —$SO_2$—, —CO—O—, —$NR^7$—CO—, CO—$NR^7$—, —NH—CO—NH—, —NH—CS—NH—, —$NR^7$—$SO_2$—, —$SO_2$—$NR^7$—, —NH—CO—O— or —O—CO—NH—, wherein $R^7$ is a hydrogen atom or a $C_1$-$C_6$ alkyl group or $R^7$, together with $R^5$, may form a $C_2$-$C_5$ alkylene group;

$R^6$ is a phenyl group, a $C_3$-$C_8$ cycloalkyl group, a $C_3$-$C_6$ cycloalkenyl group, a benzyl group or an aromatic heterocyclic group having 1 to 3 oxygen atoms, sulfur atoms and/or nitrogen atoms as heteroatoms; the phenyl group, the benzyl group or the aromatic heterocyclic group in the $R^6$ may be condensed with a benzene ring or an aromatic heterocyclic group having 1 to 3 oxygen atoms, sulfur atoms and/or nitrogen atoms as heteroatoms to form a condensed ring; the phenyl group, the $C_3$-$C_8$ cycloalkyl group, the $C_3$-$C_6$ cycloalkenyl group, the benzyl group, the aromatic heterocyclic group or the condensed ring in the above $R^6$ may further be substituted with an optional number of halogen atoms, hydroxy groups, mercapto groups, cyano groups, nitro groups, thiocyanato groups, carboxy groups, carbamoyl groups, trifluoromethyl groups, $C_1$-$C_6$ alkyl groups, $C_3$-$C_8$ cycloalkyl groups, $C_2$-$C_6$ alkenyl groups, $C_1$-$C_6$ alkoxyl groups, $C_3$-$C_8$ cycloalkyloxy groups, $C_1$-$C_6$ alkylthio groups, $C_1$-$C_3$ alkylenedioxy groups, phenyl groups, phenoxy groups, phenylamino groups, benzyl groups, benzoyl groups, phenylsulfinyl groups, phenylsulfonyl groups, 3-phenylureido groups, $C_2$-$C_7$ alkanoyl groups, $C_2$-$C_7$ alkoxycarbonyl groups, $C_2$-$C_7$ alkanoyloxy groups, $C_2$-$C_7$ alkanoylamino groups, $C_2$-$C_7$ N-alkylcarbamoyl groups, $C_1$-$C_6$ alkylsulfonyl groups, phenylcarbamoyl groups, N,N-di($C_1$-$C_6$ alkyl) sulfamoyl groups, amino groups, mono($C_1$-$C_6$ alkyl)amino groups, di($C_1$-$C_6$ alkyl)amino groups, benzylamino groups, $C_2$-$C_7$ (alkoxycarbonyl)amino groups, $C_1$-$C_6$ (alkylsulfonyl) amino groups or bis($C_1$-$C_6$ alkylsulfonyl)amino groups; the substituent groups of the phenyl group, the $C_3$-$C_8$ cycloalkyl group, the $C_3$-$C_8$ cycloalkenyl group, the benzyl group, the aromatic heterocyclic group or the condensed ring may further be substituted with an optional number of halogen atoms, cyano groups, hydroxy groups, amino groups, trifluoromethyl groups, $C_1$-$C_6$ alkyl groups, $C_1$-$C_6$ alkoxyl groups, $C_1$-$C_6$ alkylthio groups, mono($C_1$-$C_6$ alkyl)amino groups or di($C_1$-$C_6$ alkyl)amino groups.

The compounds represented by the above formula (I) have an inhibitory activity against the binding of chemokines such as MIP-1 α and/or MCP-1 to target cells and an inhibitory activity against physiological actions of the chemokines such as MIP-1 α and/or MCP-1 on the target cells.

DETAILED DESCRIPTION OF THE INVENTION

Figure 1:
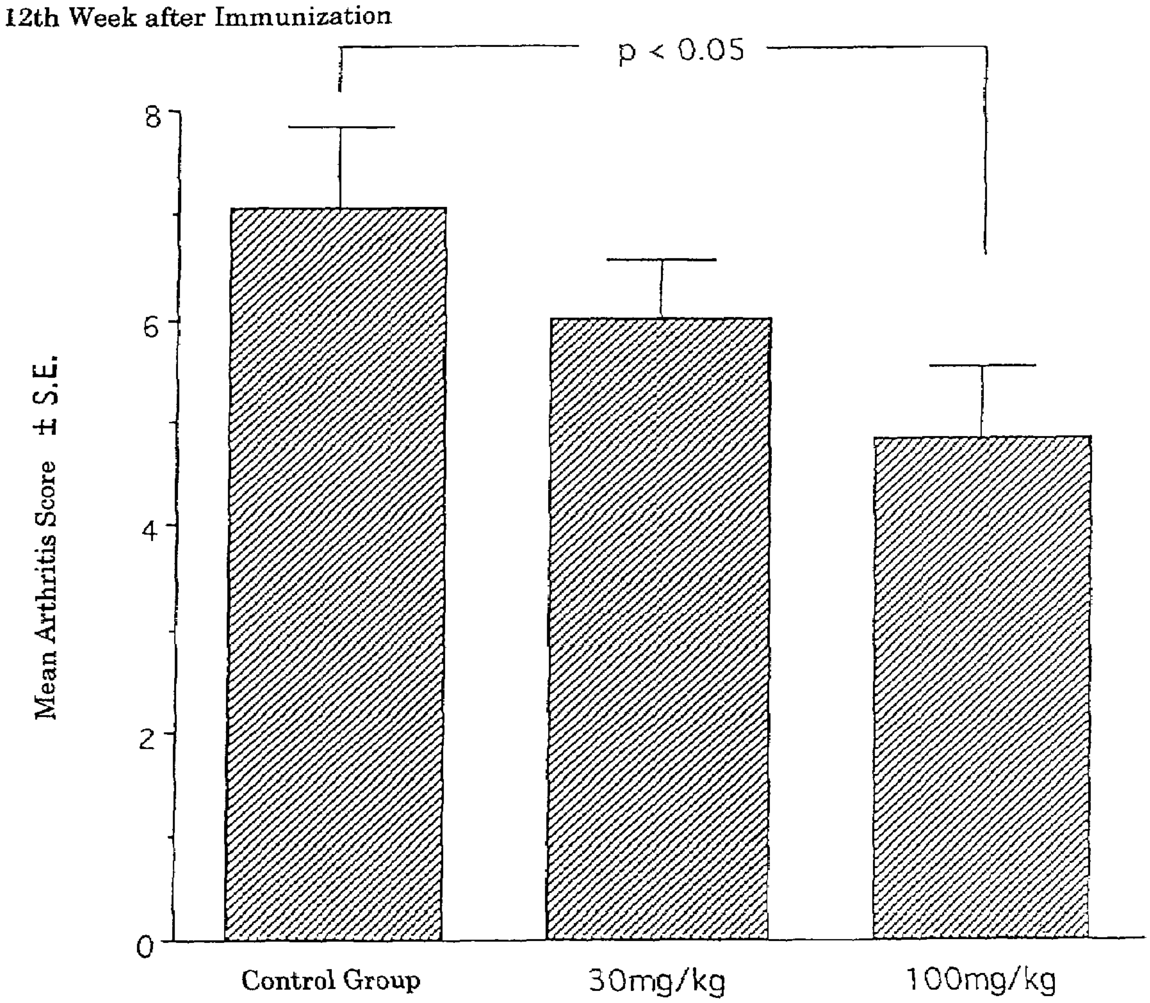
FIG. 1 is a drawing illustrating effects of Compd. No. 1583 on arthritis when the compound is orally administered for 12 weeks.

In the above formula (I), $R^1$ is a phenyl group, a $C_3$-$C_8$ cycloalkyl group or an aromatic heterocyclic group having 1 to 3 oxygen atoms, sulfur atoms and/or nitrogen atoms as heteroatoms; the phenyl group or the aromatic heterocyclic group in the above $R^1$ may be condensed with a benzene ring or an aromatic heterocyclic group having 1 to 3 oxygen atoms, sulfur atoms and/or nitrogen atoms as heteroatoms to form a condensed ring; the phenyl group, the $C_3$-$C_8$ cycloalkyl group, the aromatic heterocyclic group or the condensed ring in the above $R^1$ may further be substituted with an optional number of halogen atoms, hydroxy groups, cyano groups, nitro groups, carboxy groups, carbamoyl groups, $C_1$-$C_6$ alkyl groups, $C_3$-$C_8$ cycloalkyl groups, $C_2$-$C_6$alkenyl groups, $C_1$-$C_6$ alkoxy groups, $C_1$-$C_6$ alkylthio groups, $C_3$-$C_5$ alkylene groups, $C_2$-$C_4$ alkylenoxy groups, $C_1$-$C_3$ alkylenedioxy groups, phenyl groups, phenoxy groups, phenylthio groups, benzyl groups, benzyloxy groups, benzoylamino groups, $C_2$-$C_7$ alkanoyl groups, $C_2$-$C_7$ alkoxycarbonyl groups, $C_2$-$C_7$ alkanoyloxy groups, $C_2$-$C_7$ alkanoylamino groups, $C_2$-$C_7$ N-alkylcarbamoyl groups, $C_4$-$C_8$ N-cycloalkylcarbamoyl groups, $C_1$-$C_6$ alkylsulfonyl groups, $C_3$-$C_8$ (alkoxycarbonyl)methyl groups, N-phenylcarbamoyl groups, piperidinocarbonyl groups, morpholinocarbonyl groups, 1-pyrrolidinyl carbonyl groups, bivalent groups represented by the formula —NH(C═O)O—, bivalent groups represented by the formula —NH(C═S)O—, amino groups, mono($C_1$-$C_6$ alkyl)amino groups or di($C_1$-$C_6$ alkyl)amino groups.

The "$C_3$-$C_8$-cycloalkyl group" in $R^1$ means a cyclic alkyl group, and includes for example cyclopropyl group, cyclobutyl group, cyclopentyl group, cyclohexyl group, cycloheptyl group, cyclooctyl group and the like. The "$C_3$-$C_8$ cycloalkyl group" is preferably cyclopropyl group, cyclopentyl group, cyclohexyl group or the like.

The "aromatic heterocyclic group having 1 to 3 oxygen atoms, sulfur atoms and/or nitrogen atoms as heteroatoms" in $R^1$ means an aromatic heterocyclic group, and includes for example thienyl group, furyl group, pyrrolyl group, imidazolyl group, pyrazolyl group, oxazolyl group, isoxazolyl group, thiazolyl group, isothiazolyl group, pyridyl group, pyrimidinyl group, triazinyl group, triazolyl group, oxadiazolyl (furazanyl) group, thiadiazolyl group and the like. The "aromatic heterocyclic group having 1 to 3 oxygen atoms, sulfur atoms and/or nitrogen atoms as heteroatoms" is preferably thienyl group, furyl group, pyrrolyl group, isoxazolyl group, pyridyl group or the like.

The "condensed ring" in $R^1$ means a bicyclic aromatic heterocyclic group formed by condensing the phenyl group or the aromatic heterocyclic group with a benzene ring or the aromatic heterocyclic group having 1 to 3 oxygen atoms, sulfur atoms and/or nitrogen atoms as heteroatoms in an optional position, and includes for example naphthyl group, indolyl group, benzofuranyl group, benzothienyl group, quinolyl group, benzimidazolyl group, benzoxazolyl group, benzotriazolyl group, benzoxadiazolyl (benzofurazanyl) group, benzothiadiazolyl group and the like.

Among them, it is especially preferable for $R^1$ to be a phenyl group, an isoxazolyl group or an indolyl group.

The "halogen atoms" as the substituents of the phenyl group, the $C_3$-$C_8$ cycloalkyl group, the aromatic heterocyclic group or the condensed ring mean a fluorine atom, a chlorine atom, a bromine atom, an iodine atom and the like, and fluorine atom, chlorine atom or bromine atom is specifically preferable.

The "$C_1$-$C_6$ alkyl groups" as the substituents of $R^1$ mean $C_1$-$C_6$ straight or branched alkyl groups, and include for example, methyl group, ethyl group, n-propyl group, n-butyl group, n-pentyl group, n-hexyl group, n-heptyl group, n-octyl group, isopropyl group, isobutyl group, sec-butyl group, tert-butyl group, isopentyl group, neopentyl group, tert-pentyl group, isohexyl group, 2-methylpentyl group, 1-ethylbutyl group and the like. The "$C_1$-$C_6$ alkyl groups" are specifically preferably methyl group, ethyl group, propyl group, isopropyl group or the like.

The "$C_3$-$C_8$ cycloalkyl groups" as the substituents of $R^1$ are the same as defined in the "$C_3$-$C_8$ cycloalkyl group" in the above $R^1$, and specifically preferably include for example the same groups.

The "$C_2$-$C_6$ alkenyl groups" as the substituents of $R^1$ mean $C_2$-$C_6$ straight or branched alkenyl groups, and include for example vinyl group, allyl group, 1-propenyl group, 2-butenyl group, 3-butenyl group, 2-methyl-1-propenyl group, 4-pentenyl group, 5-hexenyl group, 4-methyl-3-pentenyl group and the like. The "$C_2$-$C_6$ alkenyl groups" are specifically preferably vinyl group and 2-methyl-1-propenyl group or the like.

The "$C_1$-$C_6$ alkoxy groups" as the substituents of $R^1$ mean groups composed of the above $C_1$-$C_6$ alkyl groups and oxy group, and methoxy group, ethoxy group or the like is specifically preferable.

The "$C_1$-$C_6$ alkylthio groups" as the substituents of $R^1$ mean groups composed of the above $C_1$-$C_6$ alkyl groups and thio group, and methylthio group, ethylthio group or the like is specifically preferable.

The "$C_3$-$C_5$ alkylene groups" as the substituents of $R^1$ mean $C_3$-$C_5$ bivalent alkylene groups, and include for example, trimethylene group, tetramethylene group, pentamethylene group, 1-methyltrimethylene group and the like. The "$C_3$-$C_5$ alkylene groups" are specifically preferably trimethylene group, tetramethylene group or the like.

The "$C_2$-$C_4$ alkylenoxy groups" as the substituents of $R^1$ mean groups composed of $C_2$-$C_4$ bivalent alkylene groups and oxy group and include, for example, ethylenoxy group ($—CH_2CH_2O—$), trimethylenoxy group ($—CH_2CH_2CH_2O—$), tetramethylenoxy group ($—CH_2CH_2CH_2CH_2O—$), 1,1-dimethylethylenoxy group ($—CH_2C(CH_3)_2O—$) and the like. The "$C_2$-$C_4$ alkylenoxy groups" are specifically preferably ethyleneoxy group, trimethylenoxy group or the like.

The "$C_1$-$C_3$ alkylenedioxy groups" as the substituents of $R^1$ mean groups composed of $C_1$-$C_3$ bivalent alkylene groups and two oxy groups and include, for example, methylenedioxy group ($—OCH_2O—$), ethylenedioxy group $OCH_2CH_2O—$), trimethylenedioxy ($—OCH_2CH_2CH_2O—$) group and propylenedioxy ($—OCH_2CH(CH_3)O—$) group and the like. The "$C_1$-$C_3$ alkylenedioxy groups" are specifically preferably methylenedioxy group, ethylenedioxy group or the like.

The "$C_2$-$C_7$ alkanoyl groups" as the substituents of $R^1$ mean $C_2$-$C_7$ straight or branched alkanoyl groups, and include for example, acetyl group, propanoyl group, butanoyl group, pentanoyl group, hexanoyl group, heptanoyl group, isobutyryl group, 3- methylbutanoyl group, 2- methylbutanoyl group, pivaloyl group, 4-methylpentanoyl group, 3,3-dimethylbutanoyl group, 5-methylhexanoyl group and the like, and acetyl group or the like is specifically preferable.

The "$C_2$-$C_7$ alkoxycarbonyl groups" as the substituents of $R^1$ mean groups composed of the above $C_1$-$C_6$ alkoxy groups and carbonyl group, and methoxycarbonyl group, ethoxycarbonyl group or the like is specifically preferable.

The "$C_2$-$C_7$ alkanoyloxy groups" as the substituents of $R^1$ mean groups composed of the above $C_2$-$C_7$ alkanoyl groups and oxy group, and acetyloxy group or the like is specifically preferable.

The "$C_2$-$C_7$ alkanoylamino groups" as the substituents of $R^1$ mean groups composed of the above $C_2$-$C_7$ alkanoyl groups and amino group, and acetylamino group or the like is specifically preferable.

The "$C_2$-$C_7$ alkylcarbamoyl groups" as the substituents of $R^1$ mean groups composed of the above $C_1$-$C_6$ alkyl groups and carbamoyl group, and N-methylcarbamoyl group, N-ethylcarbamoyl group or the like is specifically preferable.

The "$C_4$-$C_9$ N-cycloalkylcarbamoyl groups" as the substituents of $R^1$ mean the above $C_3$-$C_8$ cycloalkyl groups and carbamoyl group, and N-cyclopentylcarbamoyl group, N-cyclohexylcarbamoyl group or the like is preferable.

The "$C_1$-$C_6$ alkylsulfonyl groups" as the substituents of $R^1$ mean groups composed of the above $C_1$-$C_6$ alkyl groups and sulfonyl group, and methylsulfonyl group or the like is specifically preferable.

The "$C_3$-$C_8$ (alkoxycarbonyl)methyl groups" as the substituents of $R^1$ mean groups composed of the above $C_2$-$C_7$ alkoxycarbonyl groups and methyl group, and (methoxycarbonyl)methyl group, (ethoxycarbonyl)methyl group or the like is specifically preferable.

The "mono($C_1$-$C_6$ alkyl)amino groups" as the substituents of $R^1$ mean amino groups substituted with the above $C_1$-$C_6$ alkyl groups, and methylamino group, ethylamino group or the like is specifically preferable.

The "di($C_1$-$C_6$ alkyl)amino groups" as the substituents of $R^1$ mean amino groups substituted with the same or different two $C_1$-$C_6$ alkyl groups described above, and dimethylamino group, diethylamino group, N-ethyl-N-methylamino group or the like is specifically preferable.

Among those described above, examples of the substituents of the phenyl group, the $C_3$-$C_8$ cycloalkyl group, the aromatic heterocyclic group or the condensed ring in $R^1$ are specifically preferably halogen atoms, hydroxy groups, $C_1$-$C_6$ alkyl groups, $C_2$-$C_6$ alkenyl groups, $C_1$-$C_6$ alkoxy groups, $C_1$-$C_6$ alkylthio groups, $C_2$-$C_4$ alkylenoxy groups, methylenedioxy groups, N-phenylcarbamoyl groups, amino groups, mono($C_1$-$C_6$ alkyl)amino groups and di($C_1$-$C_6$ alkyl)amino groups.

Moreover, the substituents of the phenyl group, the $C_3$-$C_8$ cycloalkyl group, the aromatic heterocyclic group or the condensed ring in $R^1$ may further be substituted with an optional number of halogen atoms, hydroxy groups, amino groups, trifluoromethyl groups, $C_1$-$C_6$ alkyl groups or $C_1$-$C_6$ alkoxy groups. The halogen atoms, $C_1$-$C_6$ alkyl groups and $C_1$-$C_6$ alkoxy groups are the same as defined for the substituents of the phenyl group, the $C_3$-$C_8$ cycloalkyl group, the aromatic heterocyclic group or the condensed ring in $R^1$, and the same groups are specifically preferable.

In the above formula (I), $R^2$ is a hydrogen atom, a $C_1$-$C_6$ alkyl group, a $C_2$-$C_7$ alkoxycarbonyl group, a hydroxy group or a phenyl group; and the $C_1$-$C_6$ alkyl group or phenyl group in $R^2$ may be substituted with an optional number of halogen atoms, hydroxy groups, $C_1$-$C_6$ alkyl groups or $C_1$-$C_6$ alkoxy groups, with the proviso that $R^2$ is not a hydroxy group when j is 0.

The $C_1$-$C_6$ alkyl group and $C_2$-$C_7$ alkoxycarbonyl group in $R^2$ are each the same as defined for the substituents of the phenyl group, the $C_3$-$C_8$ cycloalkyl group, the aromatic heterocyclic group or the condensed ring in $R^1$, and the same examples are specifically preferable.

The halogen atoms, $C_1$-$C_6$ alkyl groups and $C_1$-$C_6$ alkoxy groups as the substituents of the $C_1$-$C_6$ alkyl group or the phenyl group in $R^2$ are the same as defined for the substituents of the phenyl group, the $C_3$-$C_8$ cycloalkyl group, the aromatic heterocyclic group or the condensed ring in the above $R^1$, and the same examples are specifically preferable.

Among them, it is especially preferable for $R^2$ to be a hydrogen atom.

In the above formula (I), j is an integer of 0 to 2, and it is especially preferable for j to be 0.

In the above formula (I), k is an integer of 0 to 2; m is an integer of 2 to 4. Among them, it is especially preferable for the compounds to be 2-substituted pyrrolidines wherein k is 0 and m is 3; 3-substituted pyrrolidines when k is 1 and m is 2; 3-substituted piperidines wherein k is 1 and m is 3; 4-substituted piperidines wherein k is 2 and m is 2; or 3-substituted hexahydroazepines wherein k is 1 and m is 4.

In the above formula (I), n is 0 or 1.

In particular, 3-amidopyrrolidines wherein k is 1; m is 2 and n is 0 and 4-(amidomethyl)piperidines wherein k is 2; m is 2 and n is 1 are especially preferable.

In the above formula (I), $R^3$ is a hydrogen atom or a $C_1$-$C_6$ alkyl group which may be substituted with (one or two phenyl groups which may respectively be substituted with an optional number of the same or different halogen atoms, hydroxy groups, $C_1$-$C_6$ alkyl groups or $C_1$-$C_6$ alkoxy groups).

The $C_1$-$C_6$ alkyl group in $R^3$ is the same as defined for the substituent group of the phenyl group, the $C_3$-$C_8$ cycloalkyl group, the aromatic heterocyclic group or the condensed ring in the above $R^1$, and methyl group, ethyl group or propyl group is specifically preferable.

The halogen atoms, $C_1$-$C_6$ alkyl groups and $C_1$-$C_6$ alkoxy groups as the substituents of the phenyl groups as the substituents of the $C_1$-$C_6$ alkyl group in $R^3$ are each the same as defined for substituents of the phenyl group, the $C_3$-$C_8$ cycloalkyl group, the aromatic heterocyclic group or the condensed ring in the above $R^1$, and the same examples are specifically preferable.

Among them, it is especially preferable for $R^3$ to be a hydrogen atom.

In the above formula (I), $R^4$ and $R^5$ are each the same or different and are each a hydrogen atom, a hydroxy group, a phenyl group or a $C_1$-$C_6$ alkyl group; and the $C_1$-$C_6$ alkyl group in $R^4$ and $R^5$ may be substituted with an optional number of halogen atoms, hydroxy groups, cyano groups, nitro groups, carboxy groups, carbamoyl groups, mercapto groups, guanidino groups, $C_3$-$C_8$ cycloalkyl groups, $C_1$-$C_6$ alkoxy groups, $C_1$-$C_6$ alkylthio groups, (phenyl groups which may be subst ituted with an optional number of halogen atoms, hydroxy groups, $C_1$-$C_6$ alkyl groups, $C_1$-$C_6$ alkoxy groups or benzyloxy groups), phenoxy groups, benzyloxy groups, benzyloxycarbonyl groups, $C_2$-$C_7$ alkanoyl groups, $C_2$-$C_7$ alkoxycarbonyl groups, $C_2$-$C_7$ alkanoyloxy groups, $C_2$-$C_7$ alkanoylamino groups, $C_2$-$C_7$ N-alkylcarbamoyl groups, $C_1$-$C_6$ alkylsulfonyl groups, amino groups, mono($C_1$-$C_6$ alkyl)amino groups, di($C_1$-$C_6$ alkyl)amino groups or (aromatic heterocyclic groups having 1 to 3 oxygen atoms, sulfur atoms and/or nitrogen atoms as heteroatoms or condensed rings formed by condensation thereof with benzene rings) or both $R^4$ and $R^5$ together may form a 3- to a 6-membered cyclic hydrocarbon.

The $C_1$-$C_6$ alkyl group in $R^4$ and $R^5$ is the same as defined for the substituents of the phenyl group, the $C_3$-$C_8$ cycloalkyl group, the aromatic heterocyclic group or the condensed ring in the above $R^1$, and the same examples are specifically preferable.

The halogen atoms, $C_1$-$C_6$ alkoxy groups, $C_1$-$C_6$ alkylthio groups, $C_2$-$C_7$ alkanoyl groups, $C_2$-$C_7$ alkoxycarbonyl groups, $C_2$-$C_7$ alkanoyloxy groups, $C_2$-$C_7$ alkanoylamino groups, $C_2$-$C_7$ N-alkylcarbamoyl groups, $C_1$-$C_6$ alkylsulfonyl groups, mono($C_1$-$C_6$ alkyl)amino groups and di($C_1$-$C_6$ alkyl)amino groups as the substituents of the $C_1$-$C_6$ alkyl group in $R^4$ and $R^5$ are the same as defined for the substituents of the phenyl group, the $C_3$-$C_8$ cycloalkyl group, the aromatic heterocyclic group or the condensed ring in the above $R^1$, and the same examples are specifically preferable.

The $C_3$-$C_8$ cycloalkyl groups and the aromatic heterocyclic groups having 1 to 3 oxygen atoms, sulfur atoms and/or nitrogen atoms as heteroatoms as the substituents of the $C_1$-$C_6$ alkyl group in $R^4$ and $R^5$ are the same as defined for the above $R^1$, and the same examples are preferable.

The halogen atoms, $C_1$-$C_6$ alkyl groups and $C_1$-$C_6$ alkoxy groups as the substituents of the phenyl groups as the substituents of the $C_1$-$C_6$ alkyl group in $R^4$ and $R^5$ are the same as defined for the substituents of the phenyl group, the $C_3$-$C_8$ cycloalkyl group, the aromatic heterocyclic group or the condensed ring in the above $R^1$, and the same examples are specifically preferable.

The "3- to 6-membered cyclic hydrocarbon" composed of $R^4$, $R^5$ and the adjacent carbon atoms are specifically preferably cyclopropane, cyclobutane, cyclopentane, cyclohexane or the like.

Among them, the hydrogen atom and $C_1$-$C_6$ alkyl group are especially preferable for $R^4$ and $R^5$.

In the above formula (I), p is 0 or 1; and q is 0 or 1. Both p and q are especially preferably 0.

In the above formula (I), G is a group represented by —CO—, —$SO_2$—, —CO—O—, —$NR^7$—CO—, —CO—$NR^7$—, —NH—CO—NH—, —NH—CS—NH—, —$NR^7$—$SO_2$—, —$SO_2$—$NR^7$—, —NH—CO—O— or —O—CO—NH—, wherein $R^7$ is a hydrogen atom or a $C_1$-$C_6$ alkyl group or $R^7$, together with $R^5$, may form a $C_2$-$C_5$ alkylene group, wherein, —CO— is a carbonyl group, —$SO_2$— is a sulfonyl group and —CS— is a thiocarbonyl group. G is especially preferably the group represented by —$NR^7$—CO— or —NH—CO—NH—.

The $C_1$-$C_6$ alkyl group in $R^7$ is the same as defined for the substituents of the phenyl group, the $C_3$-$C_8$ cycloalkyl group, the aromatic heterocyclic group or the condensed ring in the above $R^1$, and the same examples are specifically preferable.

The "$C_2$-$C_5$ alkylene group" composed of $R^5$ and $R^7$ means a $C_2$-$C_5$ straight or branched alkylene group, for example, methylene group, ethylene group, propylene group, trimethylene group, tetramethylene group, 1-methyltrimethylene group, pentamethylene group and the like, and ethylene group, trimethylene group, tetramethylene group or the like is specifically preferable.

Among them, it is especially preferable for $R^7$ to be a hydrogen atom.

In the above formula (I), $R^6$ is a phenyl group, a $C_3$-$C_8$ cycloalkyl group, a $C_3$-$C_6$ cycloalkenyl group, a benzyl group or an aromatic heterocyclic group having 1 to 3 oxygen atoms, sulfur atoms and/or nitrogen atoms as heteroatoms; and the phenyl group, the benzyl group or the aromatic heterocyclic group in the above $R^6$ may be condensed with a benzene ring or the aromatic heterocyclic group having 1 to 3 oxygen atoms, sulfur atoms and/or nitrogen atoms as heteroatoms to form a condensed ring; and the phenyl group, the $C_3$-$C_8$ cycloalkyl group, the $C_3$-$C_6$ cycloalkenyl group, the benzyl group, the aromatic heterocyclic group or the condensed ring in the above $R^6$ may be substituted with an optional number of halogen atoms, hydroxy groups, mercapto groups, cyano groups, nitro groups, thiocyanato groups, carboxy groups, carbamoyl groups, trifluoromethyl groups, $C_1$-$C_6$ alkyl groups, $C_3$-$C_8$ cycloalkyl groups, $C_2$-$C_6$ alkenyl groups, $C_1$-$C_6$ alkoxyl groups, $C_3$-$C_8$ cycloalkyloxy groups, $C_1$-$C_6$ alkylthio groups, $C_1$-$C_3$ alkylenedioxy groups, phenyl groups, phenoxy groups, phenylamino groups, benzyl groups, benzoyl groups, phenylsulfinyl groups, phenylsulfonyl groups, 3-phenylureido groups, $C_2$-$C_7$ alkanoyl groups, $C_2$-$C_7$ alkoxycarbonyl groups, $C_2$-$C_7$ alkanoyloxy groups, $C_2$-$C_7$ alkanoylamino groups, $C_2$-$C_7$ N-alkylcarbamoyl groups, $C_1$-$C_6$ alkylsulfonyl groups, phenylcarbamoyl groups, N,N-di($C_1$-$C_6$ alkyl)sulfamoyl groups, amino groups, mono($C_1$-$C_6$ alkyl)amino groups, di($C_1$-$C_6$ alkyl) amino groups, benzylamino groups, $C_2$-$C_7$ (alkoxycarbonyl) amino groups, $C_1$-$C_6$ (alkylsulfonyl)amino groups or bis($C_1$-$C_6$ alkylsulfonyl)amino groups.

The $C_3$-$C_8$ cycloalkyl groups, aromatic heterocyclic groups having oxygen atoms, sulfur atoms and/or nitrogen atoms as heteroatoms, or condensed rings in $R^6$ are the same as defined for the above $R^1$, and the same examples are specifically preferable.

The "$C_3$-$C_8$ cycloalkenyl groups" in $R^6$ mean cycloalkenyl groups, for example, cyclobutenyl group, cyclopentenyl group, cyclohexenyl group, cycloheptenyl group and cyclooctenyl group, and 1- cyclopentenyl group, 1-cyclohexenyl group or the like is specifically preferable.

Among them, it is especially preferable for $R^6$ to be a phenyl group, a furyl group and a theinyl group.

The halogen atoms, $C_1$-$C_6$ alkyl groups, $C_1$-$C_6$ alkenyl groups, $C_1$-$C_6$ alkoxy groups, $C_1$-$C_6$ alkylthio groups, $C_1$-$C_3$ alkylenedioxy groups, $C_2$-$C_7$- alkanoyl groups, $C_2$-$C_7$ alkoxycarbonyl groups, $C_2$-$C_7$ alkanoyloxy groups, $C_2$-$C_7$ alkanoylamino groups, $C_2$-$C_7$ N-alkylcarbamoyl groups, $C_1$-$C_6$ alkylsulfonyl groups, mono($C_1$-$C_6$ alkyl)amino groups and di($C_1$-$C_6$ alkyl)amino groups as the substituents of the phenyl group, the $C_3$-$C_8$ cycloalkyl group, the $C_3$-$C_8$ cycloalkenyl group, the benzyl group, the aromatic heterocyclic group or the condensed ring in $R^6$ are the same as defined for the substituents of the phenyl group, the $C_3$-$C_8$ cycloalkyl group, the aromatic heterocyclic group or the condensed ring in the above $R^1$, and the same examples are specifically preferable.

The $C_3$-$C_8$ cycloalkyl groups as the substituents of $R^6$ are the same as defined for the $C_3$-$C_8$ cycloalkyl groups in the above $R^1$, and the same examples are specifically preferable.

The "$C_3$-$C_8$ cycloalkyloxy groups" as the substituents of $R^6$ mean groups composed of the above $C_3$-$C_8$ cycloalkyl groups and oxy groups, and cyclopropyloxy group, cyclopentyloxy group, cyclohexyloxy group or the like is specifically preferable.

The "N,N-di($C_1$-$C_6$ alkyl)sulfamoyl groups" as the substituents of $R^6$ mean sulfamoyl groups substituted with the same or different two $C_1$-$C_6$ alkyl groups described above, and N,N-dimethylsulfamoyl group, N,N-diethylsulfamoyl group, N-ethyl- N-methylsulfamoyl group or the like is specifically preferable.

The "$C_2$-$C_7$ (alkoxycarbonyl)amino groups" as the substituents of $R^6$ mean groups composed of the above $C_2$-$C_7$ alkoxycarbonyl groups and amino groups, and (methoxycarbonyl)amino group, (ethoxycarbonyl)amino group or the like is specifically preferable.

The "$C_1$-$C_6$ (alkylsulfonyl)amino groups" as the substituents of $R^6$ mean groups composed of the above $C_1$-$C_6$ alkylsulfonyl groups and amino groups, and (methylsulfonyl) amino group or the like is specifically preferable.

The "bis($C_1$-$C_6$ alkylsulfonyl)amino groups" as the substituents of $R^6$ mean amino groups substituted with the same or different two $C_1$-$C_6$ alkylsulfonyl groups described above, and bis(methylsulfonyl)amino group or the like is specifically preferable.

Among them, halogen atoms, mercapto groups, nitro groups, thiocyanate groups, trifluoromethyl groups, $C_1$-$C_6$ alkyl groups, $C_1$-$C_6$ alkoxy groups, phenyl groups, phenylsulfonyl groups, $C_2$-$C_7$ alkanoylamino groups, amino groups and the like are especially preferable for the substituents of the phenyl groups, the $C_3$-$C_8$ cycloalkyl group, the $C_3$-$C_8$ cycloalkenyl group, the benzyl group, the aromatic heterocyclic group or the condensed group in $R^6$.

The substituents of the phenyl group, the $C_3$-$C_8$ cycloalkyl group, the $C_3$-$C_8$ cycloalkenyl group, the benzyl group, the aromatic heterocyclic group or the condensed ring in such $R^6$ may further be substituted with an optional number of halogen atoms, cyano groups, hydroxy groups, amino groups, trifluormethyl groups, $C_1$-$C_6$ alkyl groups, $C_1$-$C_6$ alkoxy groups, $C_1$-$C_6$ alkylthio groups, mono($C_1$-$C_6$ alkyl)amino groups or di($C_1$-$C_6$ alkyl)amino groups.

The halogen atoms, $C_1$-$C_6$ alkyl groups, $C_1$-$C_6$ alkoxy groups, $C_1$-$C_6$ alkylthio groups, mono($C_1$-$C_6$ alkyl)amino groups and di($C_1$-$C_6$ alkyl)amino groups as the substituents of the phenyl group, the $C_3$-$C_8$ cycloalkyl group, the $C_3$-$C_8$ cycloalkenyl group, the benzyl group, the aromatic heterocyclic group or the condensed ring are the same as defined for the substituents of the phenyl group, the $C_3$-$C_8$ cycloalkyl group, the aromatic heterocyclic aromatic group or the condensed ring in the above $R^1$, and the same examples are specifically preferable.

The remedially effective amount of the compounds represented by the above formula (I), pharmaceutically acceptable acid addition salts thereof or pharmaceutically acceptable $C_1$-$C_6$ alkyl-addition salts thereof together with a pharmaceutically acceptable carrier and/or a diluent can be prepared as a pharmaceutical composition and thus can be converted into medicines of the present invention capable of inhibiting the binding of chemokines to receptors on target cells, medicines having inhibitory actions on the binding of chemokines onto target cells or further remedies or prophylactics for diseases considered to be associated with chemokines or chemokine receptors. Namely, the cyclic amine derivatives represented by the above formula (I), pharmaceutically acceptable acid addition salts thereof or pharmaceutically acceptable $C_1$-$C_6$ alkyl addition salts thereof can be administered orally or parenterally such as intravenously, subcutaneously, intramuscularly, percutaneously or intrarectally.

For example, a tablet, a pill, a granule, a powder, a solution, a suspension or a capsule can be cited as the dosage form of the oral administration.

The tablet can be formed by using an vehicle, for example, lactose, starch or crystalline cellulose; a binder, for example, carboxymethylcellulose, methylcellulose or polyvinylpyrrolidone; or a disintegrator, for example, sodium alginate, sodium bicarbonate or sodium lauryl sulfate or the like according to a conventional method.

The pill, powder and granule can similarly be formed with using the above vehicle or the like according to a conventional method. The solution and suspension are produced with using glycerin esters, for example, tricaprylin or triacetin or alcohols, for example, ethanol according to a conventional method. The capsule is produced with filling a granule, powder or solution in a capsule such as gelatin.

A parenteral injection such as the form of an aqueous or a nonaqueous solution formulation is cited as the dosage form of subcutaneous, intramuscular or intravenous administration. For example, a isotonic sodium chloride solution is used as the aqueous solution. For example, propylene glycol, polyethylene glycol, olive oil or ethyl oleate is used for the nonaqueous solution. An antiseptic, a stabilizer or the like, if necessary, is added thereto. The parenteral injection is sterilized by suitably carrying out treatment such as filtration through a bacterial filter or combination of a disinfectant.

For example, an ointment or a cream is cited as the dosage form of percutaneous administration. The ointment is prepared by using oils and fats such as castor oil or olive oil or vaseline, and the cream is formed by using a fatty oil or an emulsifying agent such as diethylene glycol or sorbitan mono-fatty acid ester according to a conventional method.

A usual suppository such as a gelatin soft capsule is used for intrarectal administration.

The dose of the cyclic amine derivatives, pharmaceutically acceptable acid addition salts thereof or pharmaceutically acceptable $C_1$-$C_6$ alkyl addition salts thereof used in the present invention varies with the types of diseases, routs of administration, age and sex of patients and severity of diseases and the like, but is usually 1 to 500 mg/day for an adult.

Examples of the cyclic amine derivatives represented by the above formula (I) preferably include compounds having respective substituents shown in the following Tables 1.1 to 1.206

In Tables 1.1 to 1.206, "Table" means "Table", and "Compd. No." means "compound number". "Chirality" means the "absolute configuration", i.e. the absolute configuration of asymmetric carbon on the ring of the cyclic amine. "R" means that the asymmetric carbon atom on the ring of the cyclic amine has the absolute configuration of R, and "S" means that the asymmetric carbon atom has the absolute configuration of S. "-" means that the compound is a racemate or the compound has no asymmetric carbon atom on the cyclic amines.

TABLE 1.1

| Compd. No. | 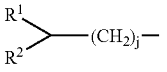 | k | m | n | chirality | $R^3$ | 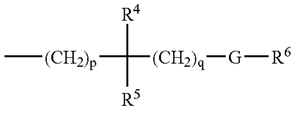 |
|---|---|---|---|---|---|---|---|
| 1 | 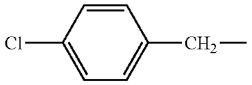 | 1 | 2 | 0 | — | H | 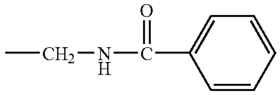 |
| 2 | 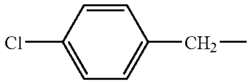 | 1 | 2 | 0 | — | H | 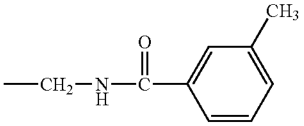 |
| 3 | 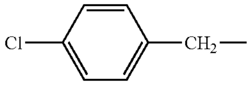 | 1 | 2 | 0 | — | H | 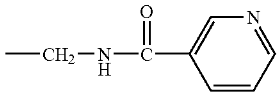 |
| 4 | 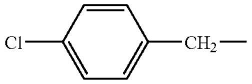 | 1 | 2 | 0 | — | H | 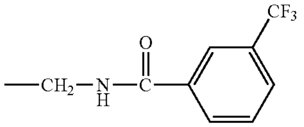 |
| 5 | 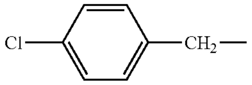 | 1 | 2 | 0 | S | H | 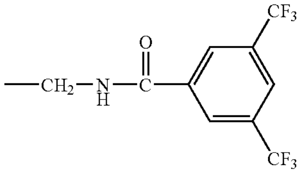 |
| 6 | 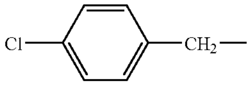 | 1 | 2 | 0 | S | H | 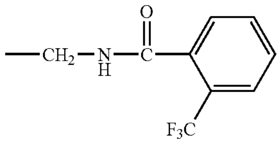 |
| 7 | 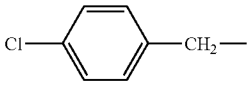 | 1 | 2 | 0 | S | H | 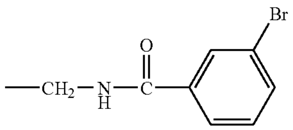 |
| 8 | 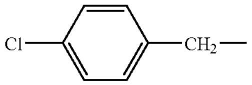 | 1 | 2 | 0 | S | H | 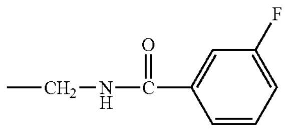 |

TABLE 1.1-continued
| Compd. No. | 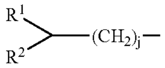 | k | m | n | chirality | $R^3$ | 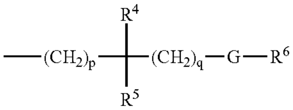 |
|---|---|---|---|---|---|---|---|
| 9 | 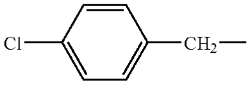 | 1 | 2 | 0 | S | H | 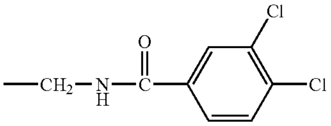 |
| 10 | 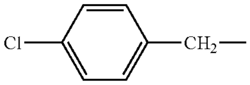 | 1 | 2 | 0 | S | H | 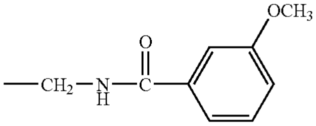 |
| 11 | 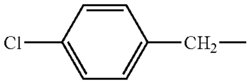 | 1 | 2 | 0 | S | H | 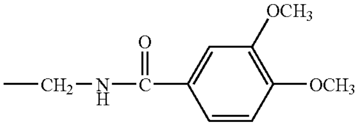 |
TABLE 1.2
| Compd. No. | 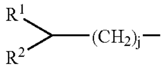 | k | m | n | chirality | $R^3$ | 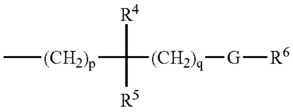 |
|---|---|---|---|---|---|---|---|
| 12 | 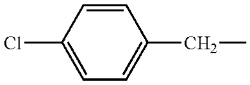 | 1 | 2 | 0 | S | H | 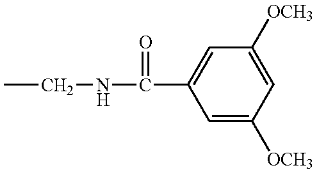 |
| 13 | 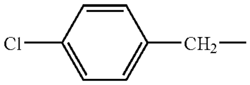 | 1 | 2 | 0 | S | H | 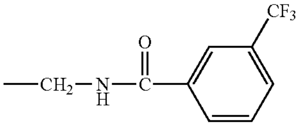 |
| 14 | 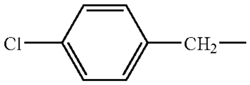 | 1 | 2 | 0 | S | H | 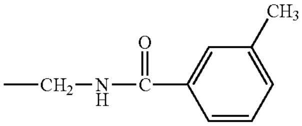 |
| 15 | 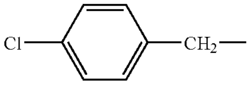 | 1 | 2 | 0 | S | H | 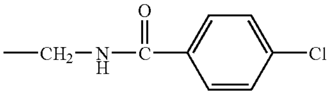 |
| 16 | 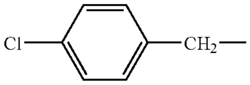 | 1 | 2 | 0 | S | H | 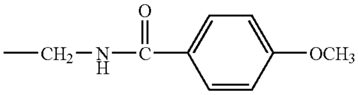 |
| 17 | 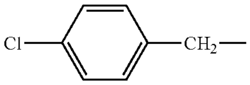 | 1 | 2 | 0 | S | H | 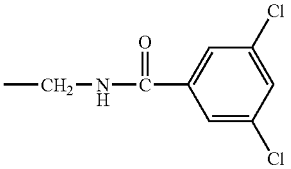 |

TABLE 1.2-continued
| Compd. No. | 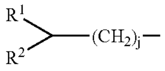 | k | m | n | chirality | $R^3$ | 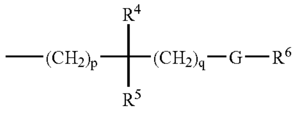 |
|---|---|---|---|---|---|---|---|
| 18 | 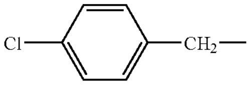 | 1 | 2 | 0 | S | H | 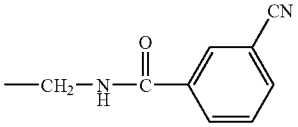 |
| 19 | 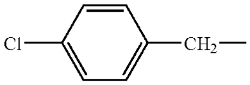 | 1 | 2 | 0 | S | H | 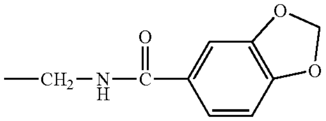 |
| 20 | 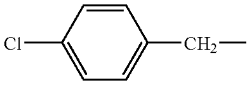 | 1 | 2 | 0 | S | H | 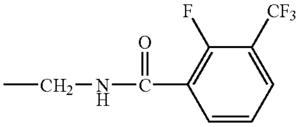 |
| 21 | 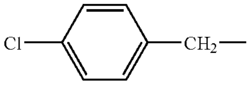 | 1 | 2 | 0 | S | H | 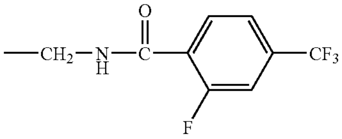 |
| 22 | 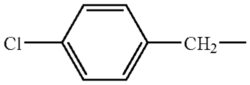 | 1 | 2 | 0 | S | H | 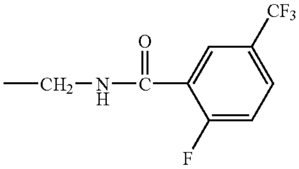 |
TABLE 1.3
| Compd. No. | 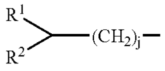 | k | m | n | chirality | $R^3$ | 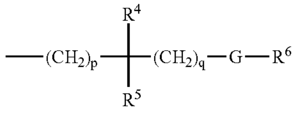 |
|---|---|---|---|---|---|---|---|
| 23 | 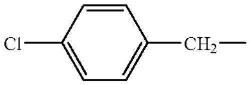 | 1 | 2 | 0 | S | H | 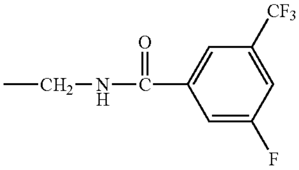 |
| 24 | 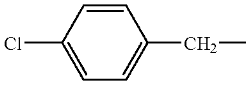 | 1 | 2 | 0 | S | H | 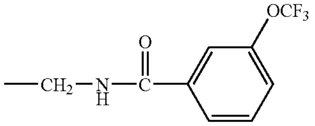 |
| 25 | 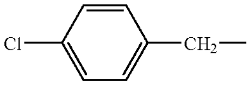 | 1 | 2 | 0 | S | H | 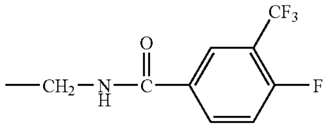 |

TABLE 1.3-continued
| Compd. No. | 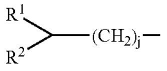 | k | m | n | chirality | $R^3$ | 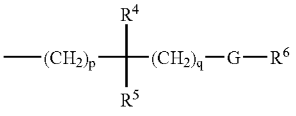 |
|---|---|---|---|---|---|---|---|
| 26 | 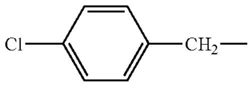 | 1 | 2 | 0 | S | H | 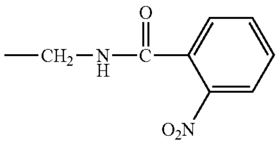 |
| 27 | 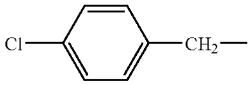 | 1 | 2 | 0 | S | H | 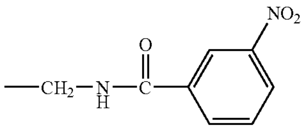 |
| 28 | 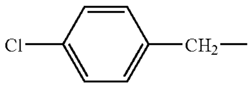 | 1 | 2 | 0 | S | H | 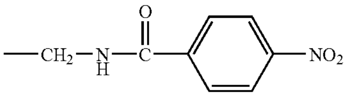 |
| 29 | 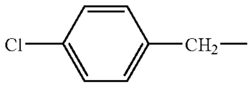 | 1 | 2 | 0 | R | H | 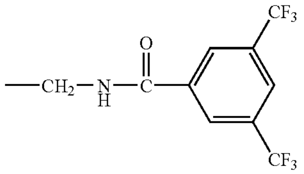 |
| 30 | 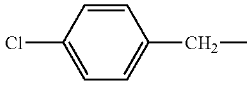 | 1 | 2 | 0 | R | H | 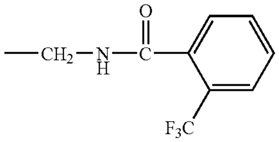 |
| 31 | 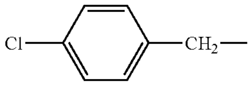 | 1 | 2 | 0 | R | H | 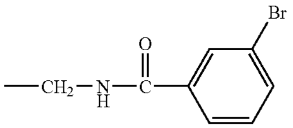 |
| 32 | 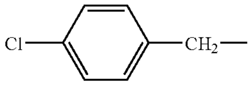 | 1 | 2 | 0 | R | H | 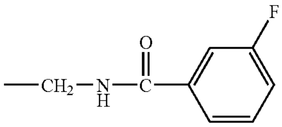 |
| 33 | 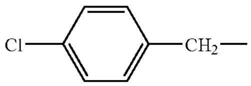 | 1 | 2 | 0 | R | H | 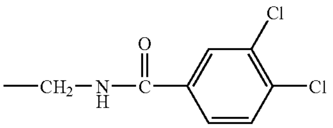 |

TABLE 1.4
| Compd. No. | 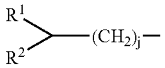 | k | m | n | chirality | $R^3$ | 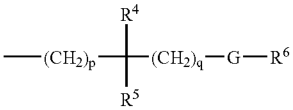 |
|---|---|---|---|---|---|---|---|
| 34 | 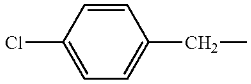 | 1 | 2 | 0 | R | H | 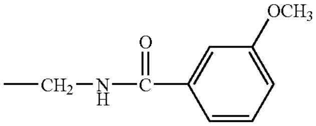 |
| 35 | 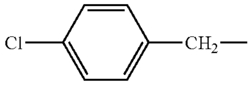 | 1 | 2 | 0 | R | H | 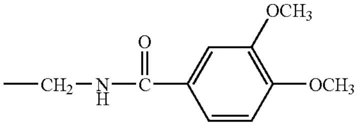 |
| 36 | 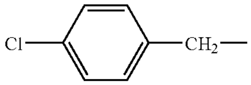 | 1 | 2 | 0 | R | H | 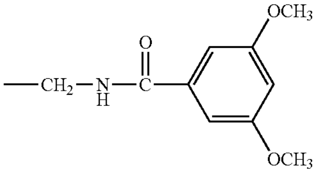 |
| 37 | 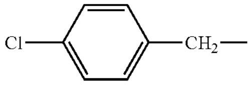 | 1 | 2 | 0 | R | H | 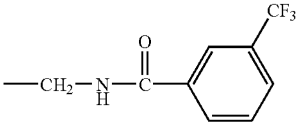 |
| 38 | 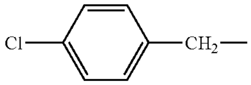 | 1 | 2 | 0 | R | H | 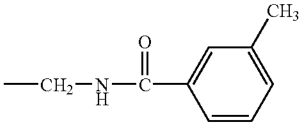 |
| 39 | 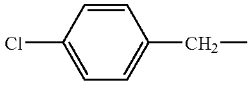 | 1 | 2 | 0 | R | H | 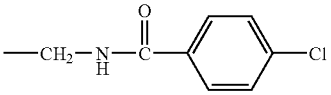 |
| 40 | 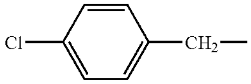 | 1 | 2 | 0 | R | H | 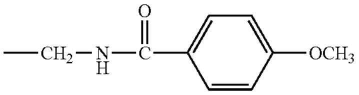 |
| 41 | 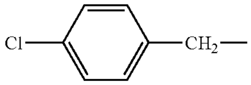 | 1 | 2 | 0 | R | H | 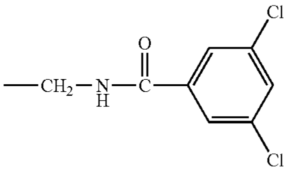 |
| 42 | 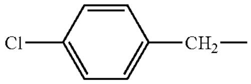 | 1 | 2 | 0 | R | H | 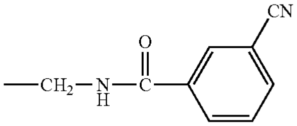 |
| 43 | 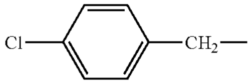 | 1 | 2 | 0 | R | H | 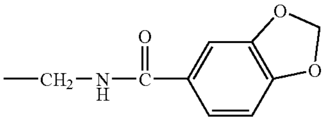 |

TABLE 1.4-continued
| Compd. No. | 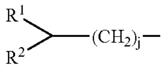 | k | m | n | chirality | $R^3$ | 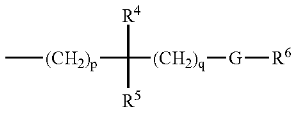 |
|---|---|---|---|---|---|---|---|
| 44 | 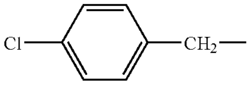 | 1 | 2 | 0 | R | H | 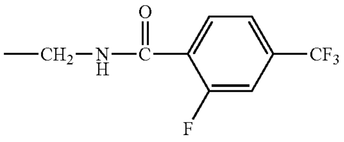 |
TABLE 1.5
| Compd. No. | 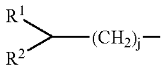 | k | m | n | chirality | $R^3$ | 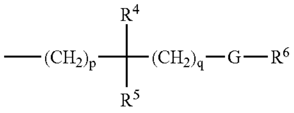 |
|---|---|---|---|---|---|---|---|
| 45 | 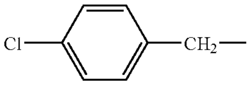 | 1 | 2 | 0 | R | H | 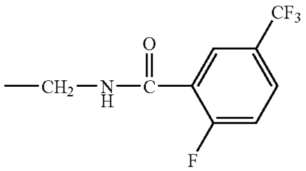 |
| 46 | 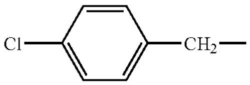 | 1 | 2 | 0 | R | H | 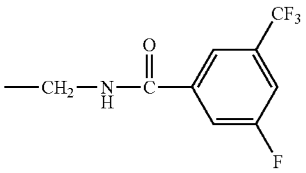 |
| 47 | 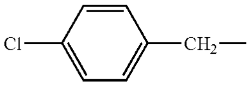 | 1 | 2 | 0 | R | H | 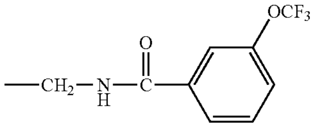 |
| 48 | 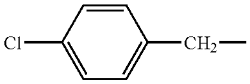 | 1 | 2 | 0 | R | H | 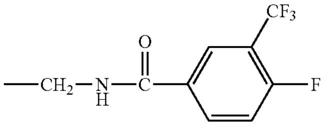 |
| 49 | 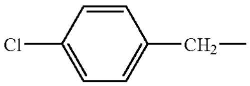 | 1 | 2 | 0 | R | H | 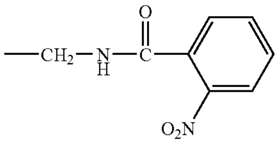 |
| 50 | 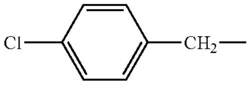 | 1 | 2 | 0 | R | H | 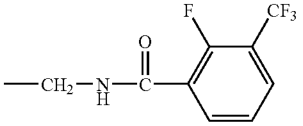 |
| 51 | 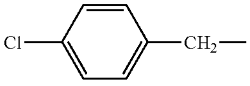 | 1 | 2 | 0 | R | H | 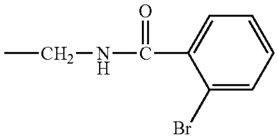 |

TABLE 1.5-continued
| Compd. No. | 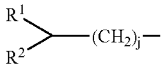 | k | m | n | chirality | $R^3$ | 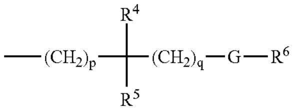 |
|---|---|---|---|---|---|---|---|
| 52 | 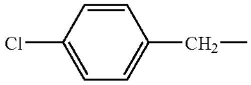 | 1 | 2 | 0 | R | H | 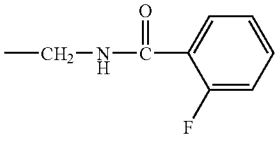 |
| 53 | 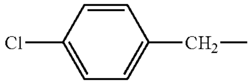 | 1 | 2 | 0 | R | H | 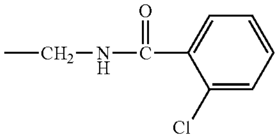 |
| 54 | 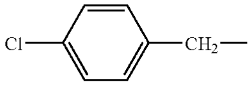 | 1 | 2 | 0 | R | H | 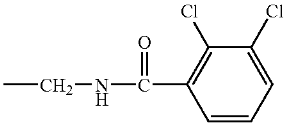 |
| 55 | 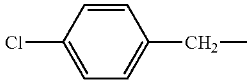 | 1 | 2 | 0 | R | H | 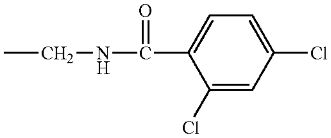 |
TABLE 1.6
| Compd. No. | 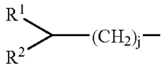 | k | m | n | chirality | $R^3$ | 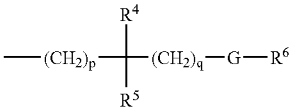 |
|---|---|---|---|---|---|---|---|
| 56 | 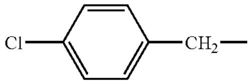 | 1 | 2 | 0 | R | H | 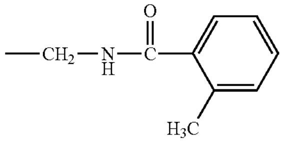 |
| 57 | 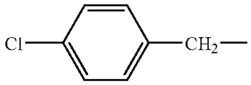 | 1 | 2 | 0 | R | H | 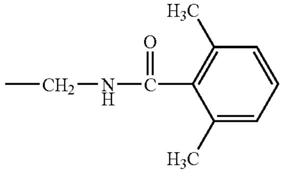 |
| 58 | 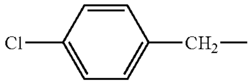 | 1 | 2 | 0 | R | H | 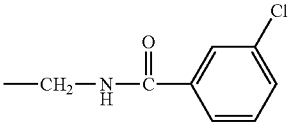 |
| 59 | 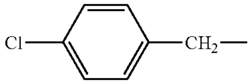 | 1 | 2 | 0 | R | H | 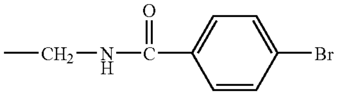 |
| 60 | 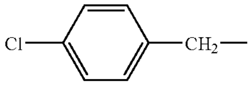 | 1 | 2 | 0 | R | H | 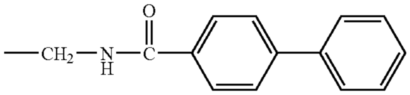 |

TABLE 1.6-continued
| Compd. No. | 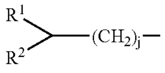 | k | m | n | chirality | $R^3$ | 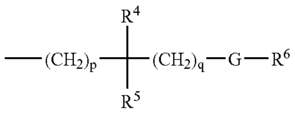 |
| --- | --- | --- | --- | --- | --- | --- | --- |
| 61 | 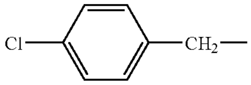 | 1 | 2 | 0 | R | H | 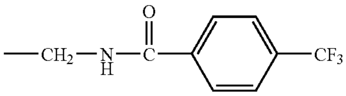 |
| 62 | 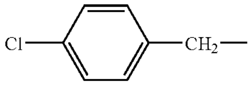 | 1 | 2 | 0 | R | H | 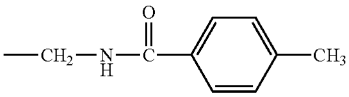 |
| 63 | 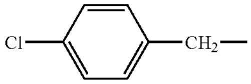 | 1 | 2 | 0 | R | H | 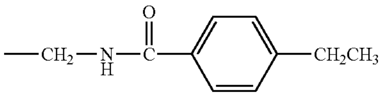 |
| 64 | 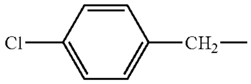 | 1 | 2 | 0 | R | H | 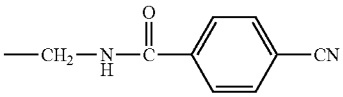 |
| 65 | 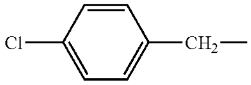 | 1 | 2 | 0 | R | H | 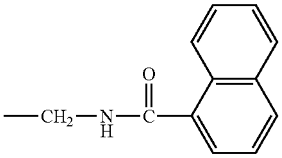 |
| 66 | 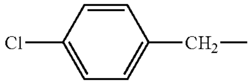 | 1 | 2 | 0 | R | H | 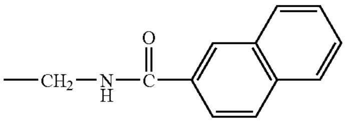 |
TABLE 1.7
| Compd. No. | 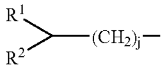 | k | m | n | chirality | $R^3$ | 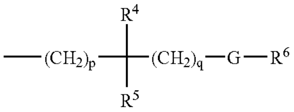 |
| --- | --- | --- | --- | --- | --- | --- | --- |
| 67 | 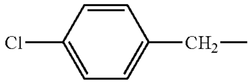 | 1 | 2 | 0 | R | H | 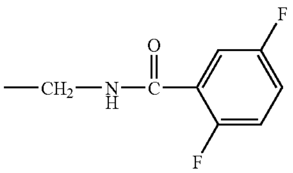 |
| 68 | 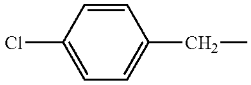 | 1 | 2 | 0 | R | H | 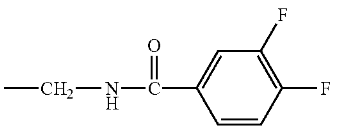 |
| 69 | 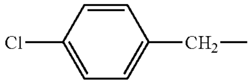 | 1 | 2 | 0 | R | H | 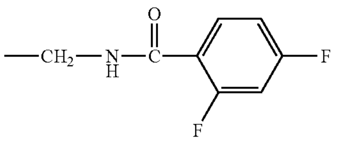 |

TABLE 1.7-continued
| Compd. No. | 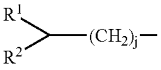 | k | m | n | chirality | $R^3$ | 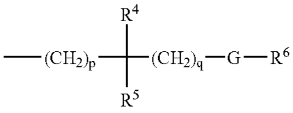 |
|---|---|---|---|---|---|---|---|
| 70 | 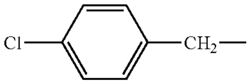 | 1 | 2 | 0 | R | H | 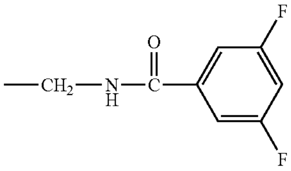 |
| 71 | 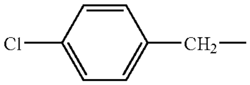 | 1 | 2 | 0 | R | H | 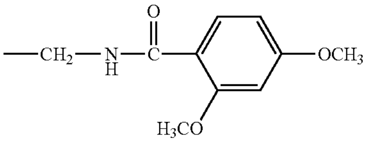 |
| 72 | 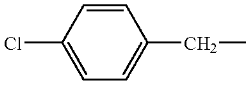 | 1 | 2 | 0 | R | H | 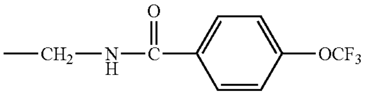 |
| 73 | 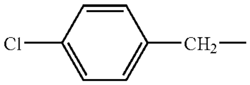 | 1 | 2 | 0 | R | H | 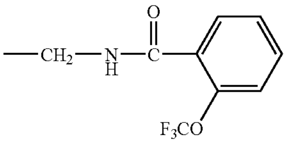 |
| 74 | 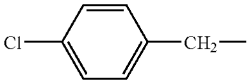 | 1 | 2 | 0 | R | H | 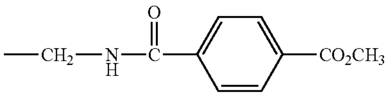 |
| 75 | 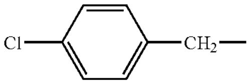 | 1 | 2 | 0 | R | H | 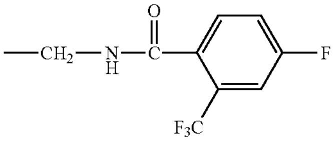 |
| 76 | 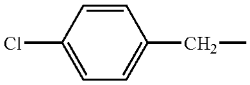 | 1 | 2 | 0 | R | H | 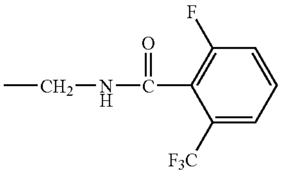 |
| 77 | 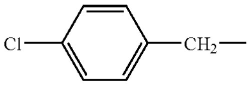 | 1 | 2 | 0 | R | H | 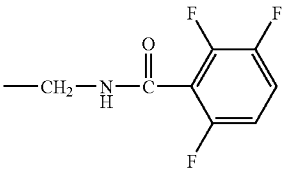 |

TABLE 1.8
| Compd. No. | 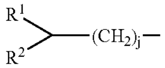 | k | m | n | chirality | $R^3$ | 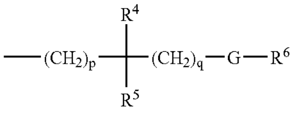 |
|---|---|---|---|---|---|---|---|
| 78 | 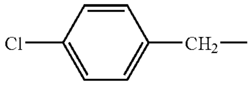 | 1 | 2 | 0 | R | H | 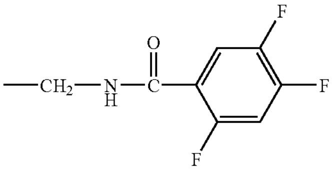 |
| 79 | 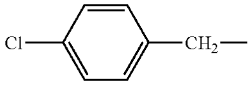 | 1 | 2 | 0 | R | H | 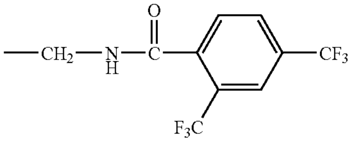 |
| 80 | 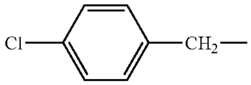 | 1 | 2 | 0 | R | H | 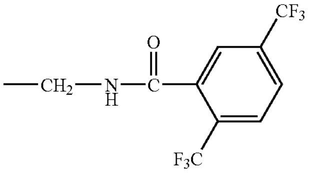 |
| 81 | 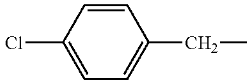 | 1 | 2 | 0 | R | H | 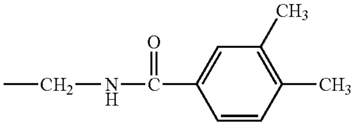 |
| 82 | 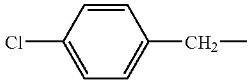 | 1 | 2 | 0 | — | $—CH_3$ | 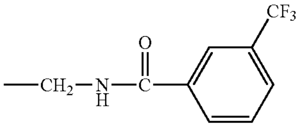 |
| 83 | 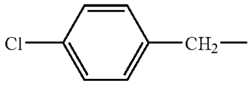 | 1 | 2 | 0 | R | H | 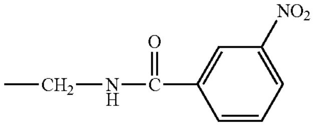 |
| 84 | 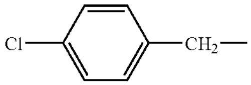 | 1 | 2 | 0 | R | H | 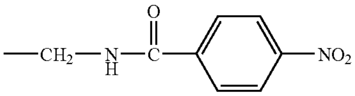 |
| 85 | 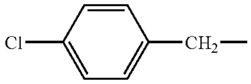 | 1 | 2 | 0 | — | H | 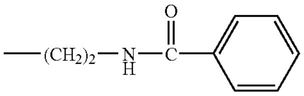 |
| 86 | 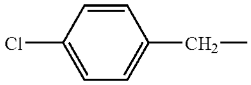 | 1 | 2 | 0 | — | H | 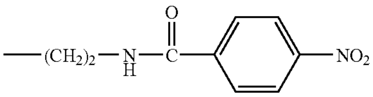 |
| 87 | 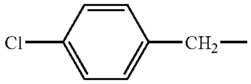 | 1 | 2 | 0 | S | H | 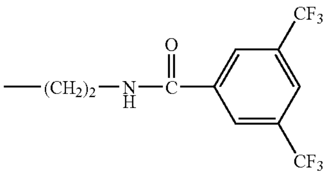 |

TABLE 1.8-continued
| Compd. No. | 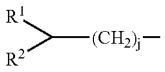 | k | m | n | chirality | $R^3$ | 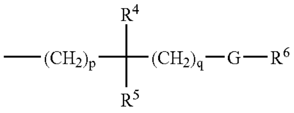 |
|---|---|---|---|---|---|---|---|
| 88 | 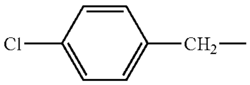 | 1 | 2 | 0 | S | H | 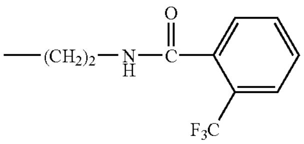 |
TABLE 1.9
| Compd. No. | 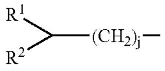 | k | m | n | chirality | $R^3$ | 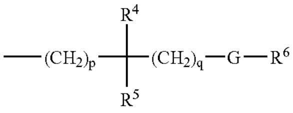 |
|---|---|---|---|---|---|---|---|
| 89 | 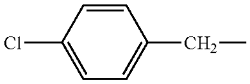 | 1 | 2 | 0 | S | H | 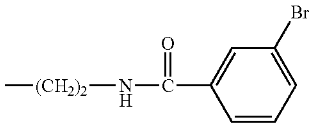 |
| 90 | 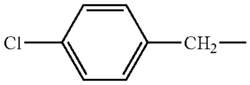 | 1 | 2 | 0 | S | H | 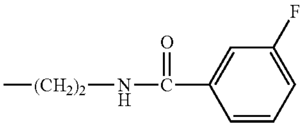 |
| 91 | 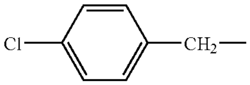 | 1 | 2 | 0 | S | H | 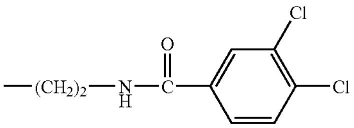 |
| 92 | 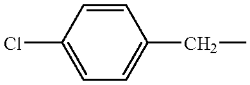 | 1 | 2 | 0 | S | H | 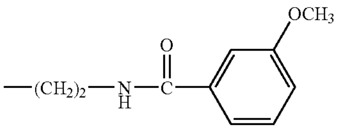 |
| 93 | 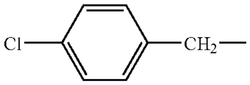 | 1 | 2 | 0 | S | H | 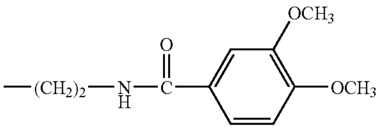 |
| 94 | 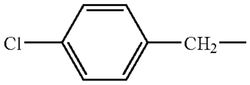 | 1 | 2 | 0 | S | H | 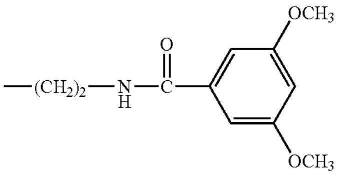 |
| 95 | 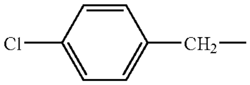 | 1 | 2 | 0 | S | H | 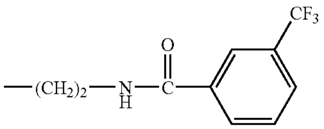 |

TABLE 1.9-continued
| Compd. No. | 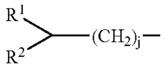 | k | m | n | chirality | $R^3$ | 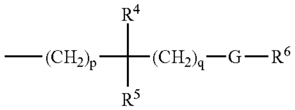 |
|---|---|---|---|---|---|---|---|
| 96 | 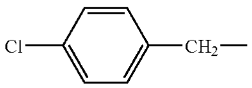 | 1 | 2 | 0 | S | H | 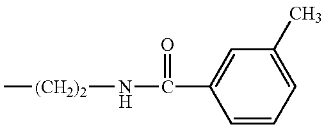 |
| 97 | 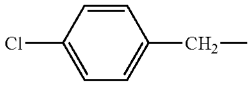 | 1 | 2 | 0 | S | H | 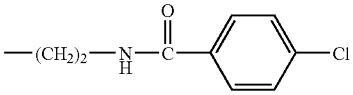 |
| 98 | 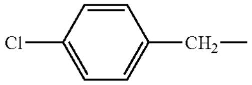 | 1 | 2 | 0 | S | H | 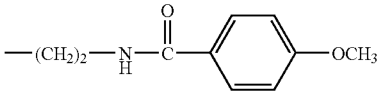 |
| 99 | 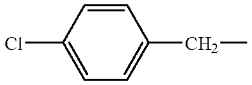 | 1 | 2 | 0 | S | H | 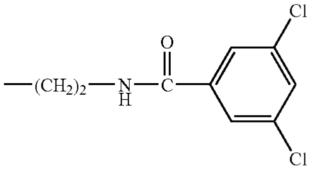 |
TABLE 1.10
| Compd. No. | 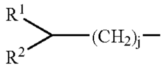 | k | m | n | chirality | $R^3$ | 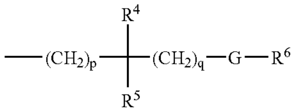 |
|---|---|---|---|---|---|---|---|
| 100 | 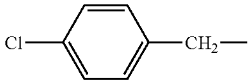 | 1 | 2 | 0 | S | H | 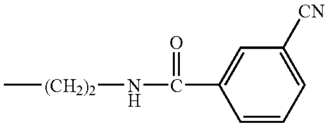 |
| 101 | 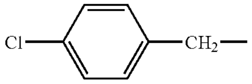 | 1 | 2 | 0 | S | H | 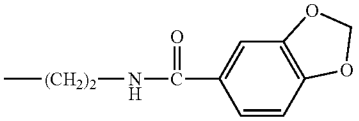 |
| 102 | 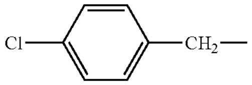 | 1 | 2 | 0 | S | H | 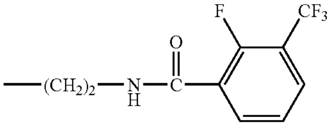 |
| 103 | 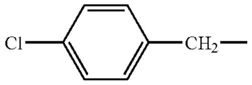 | 1 | 2 | 0 | S | H | 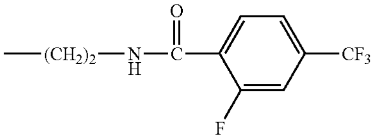 |
| 104 | 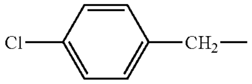 | 1 | 2 | 0 | S | H | 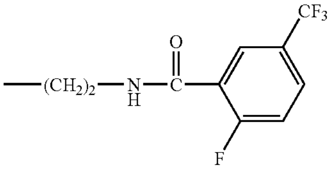 |

TABLE 1.10-continued
| Compd. No. | 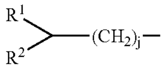 | k | m | n | chirality | $R^3$ | 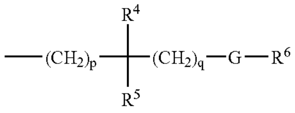 |
|---|---|---|---|---|---|---|---|
| 105 | 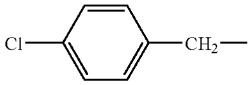 | 1 | 2 | 0 | S | H | 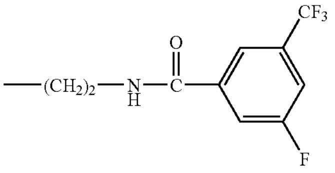 |
| 106 | 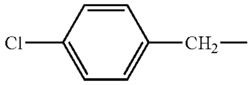 | 1 | 2 | 0 | S | H | 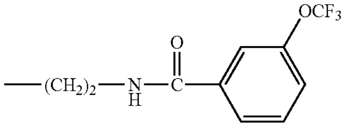 |
| 107 | 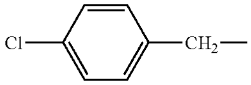 | 1 | 2 | 0 | S | H | 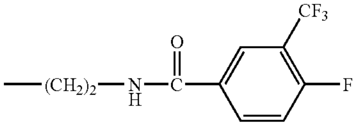 |
| 108 | 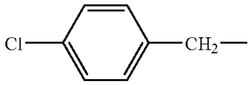 | 1 | 2 | 0 | S | H | 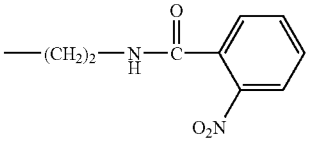 |
| 109 | 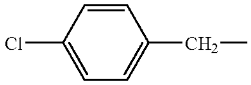 | 1 | 2 | 0 | S | H | 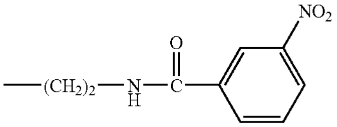 |
| 110 | 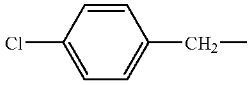 | 1 | 2 | 0 | S | H | 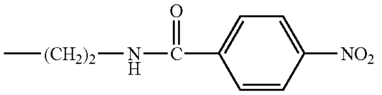 |
TABLE 1.11
| Compd. No. | 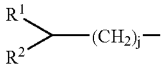 | k | m | n | chirality | $R^3$ | 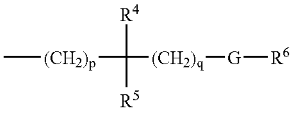 |
|---|---|---|---|---|---|---|---|
| 111 | 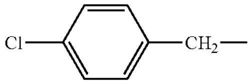 | 1 | 2 | 0 | R | H | 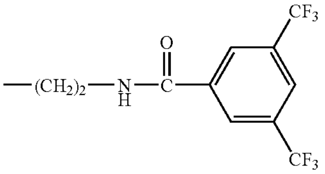 |
| 112 | 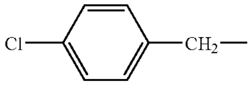 | 1 | 2 | 0 | R | H | 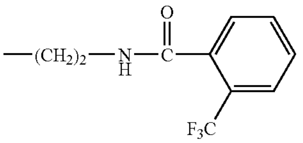 |

TABLE 1.11-continued
| Compd. No. | 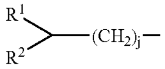 | k | m | n | chirality | $R^3$ | 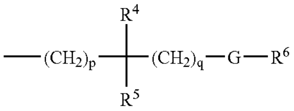 |
|---|---|---|---|---|---|---|---|
| 113 | 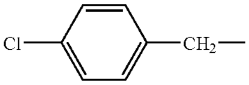 | 1 | 2 | 0 | R | H | 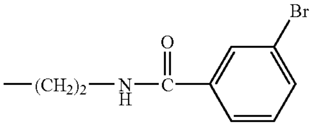 |
| 114 | 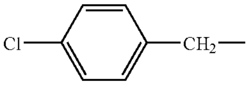 | 1 | 2 | 0 | R | H | 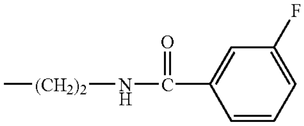 |
| 115 | 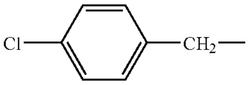 | 1 | 2 | 0 | R | H | 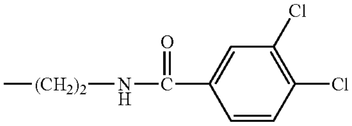 |
| 116 | 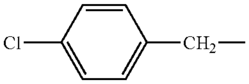 | 1 | 2 | 0 | R | H | 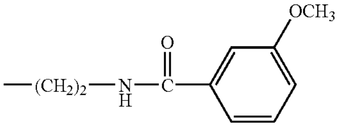 |
| 117 | 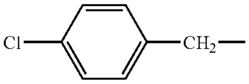 | 1 | 2 | 0 | R | H | 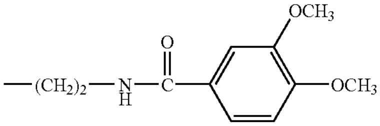 |
| 118 | 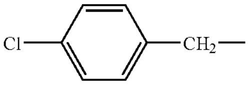 | 1 | 2 | 0 | R | H | 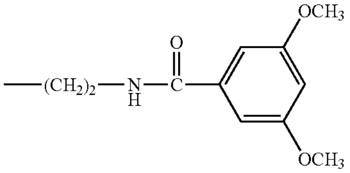 |
| 119 | 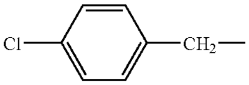 | 1 | 2 | 0 | R | H | 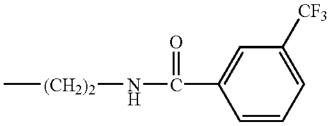 |
| 120 | 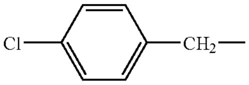 | 1 | 2 | 0 | R | H | 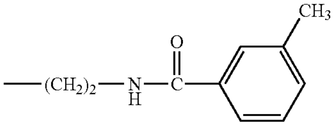 |
| 121 | 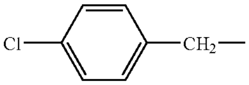 | 1 | 2 | 0 | R | H | 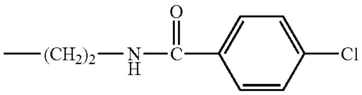 |

TABLE 1.12
| Compd. No. | 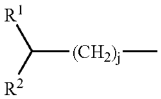 | k | m | n | chirality | $R^3$ | 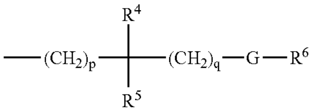 |
|---|---|---|---|---|---|---|---|
| 122 | 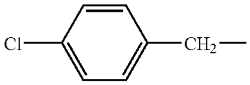 | 1 | 2 | 0 | R | H | 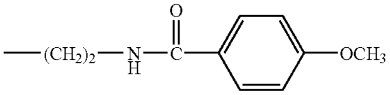 |
| 123 | 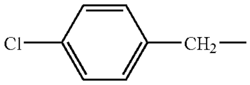 | 1 | 2 | 0 | R | H | 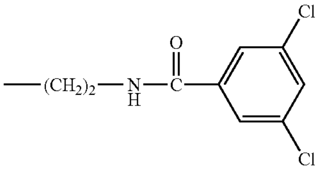 |
| 124 | 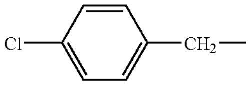 | 1 | 2 | 0 | R | H | 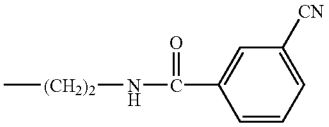 |
| 125 | 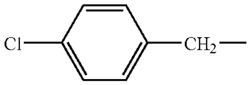 | 1 | 2 | 0 | R | H | 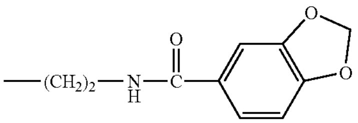 |
| 126 | 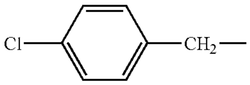 | 1 | 2 | 0 | R | H | 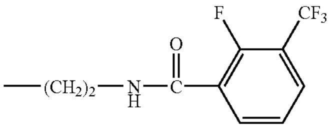 |
| 127 | 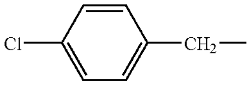 | 1 | 2 | 0 | R | H | 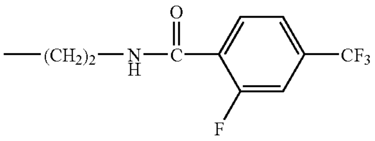 |
| 128 | 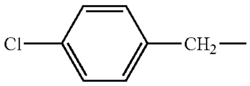 | 1 | 2 | 0 | R | H | 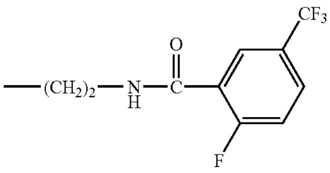 |
| 129 | 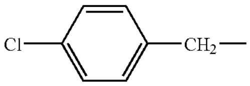 | 1 | 2 | 0 | R | H | 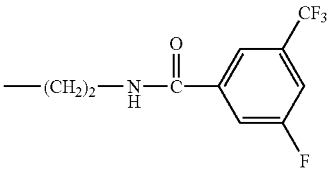 |
| 130 | 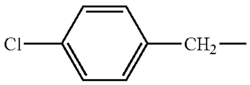 | 1 | 2 | 0 | R | H | 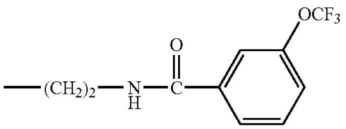 |
| 131 | 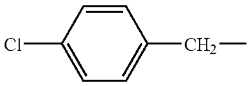 | 1 | 2 | 0 | R | H | 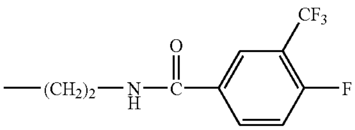 |

TABLE 1.12-continued
| Compd. No. | 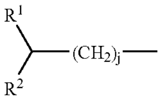 | k | m | n | chirality | $R^3$ | 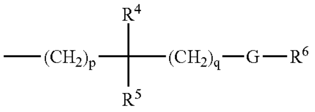 |
|---|---|---|---|---|---|---|---|
| 132 | 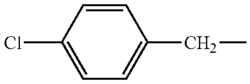 | 1 | 2 | 0 | R | H | 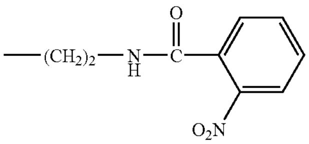 |
TABLE 1.13
| Compd. No. | 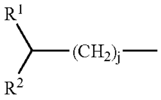 | k | m | n | chirality | $R^3$ | 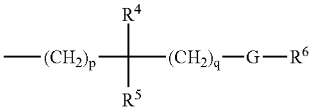 |
|---|---|---|---|---|---|---|---|
| 133 | 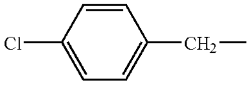 | 1 | 2 | 0 | R | H | 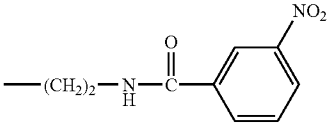 |
| 134 | 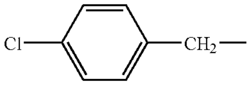 | 1 | 2 | 0 | R | H | 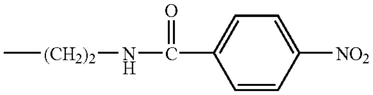 |
| 135 | 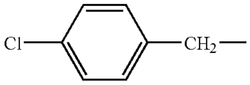 | 1 | 2 | 0 | R | H | 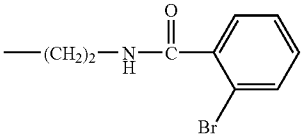 |
| 136 | 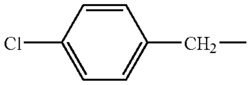 | 1 | 2 | 0 | R | H | 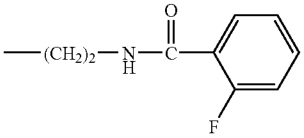 |
| 137 | 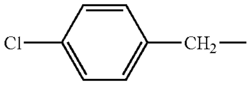 | 1 | 2 | 0 | R | H | 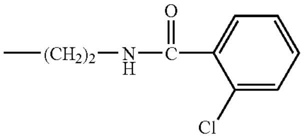 |
| 138 | 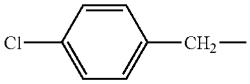 | 1 | 2 | 0 | R | H | 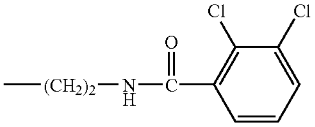 |
| 139 | 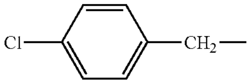 | 1 | 2 | 0 | R | H | 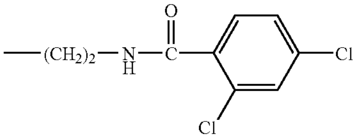 |

TABLE 1.13-continued
| Compd. No. | 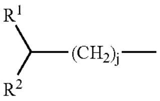 | k | m | n | chirality | $R^3$ | 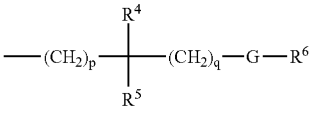 |
|---|---|---|---|---|---|---|---|
| 140 | 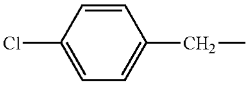 | 1 | 2 | 0 | R | H | 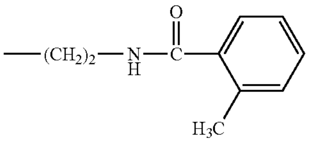 |
| 141 | 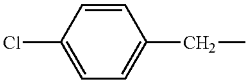 | 1 | 2 | 0 | R | H | 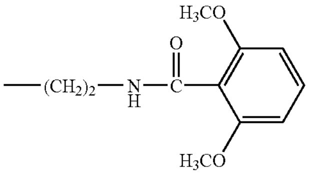 |
| 142 | 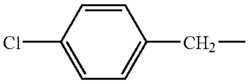 | 1 | 2 | 0 | R | H | 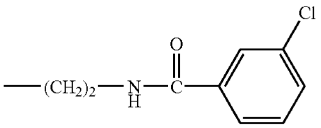 |
| 143 | 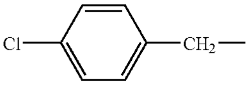 | 1 | 2 | 0 | R | H | 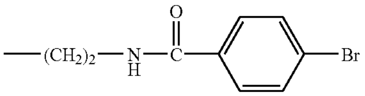 |
TABLE 1.14
| Compd. No. | 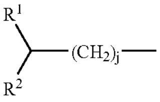 | k | m | n | chirality | $R^3$ | 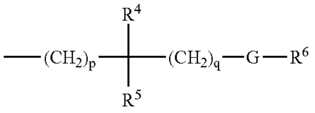 |
|---|---|---|---|---|---|---|---|
| 144 | 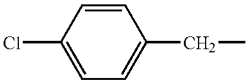 | 1 | 2 | 0 | R | H | 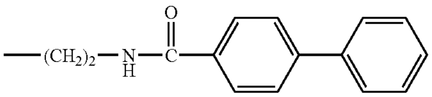 |
| 145 | 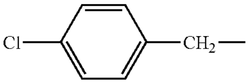 | 1 | 2 | 0 | R | H | 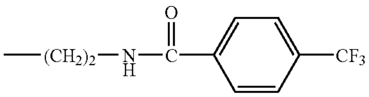 |
| 146 | 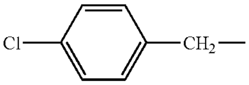 | 1 | 2 | 0 | R | H | 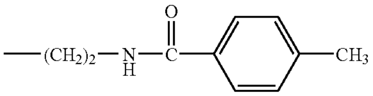 |
| 147 | 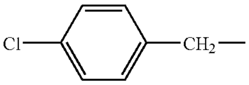 | 1 | 2 | 0 | R | H | 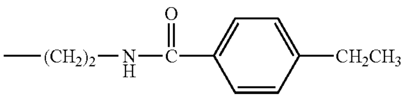 |
| 148 | 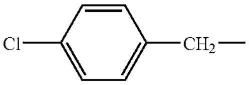 | 1 | 2 | 0 | R | H | 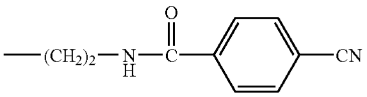 |

TABLE 1.14-continued
| Compd. No. | 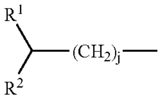 | k | m | n | chirality | $R^3$ | 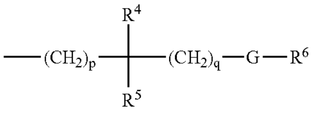 |
|---|---|---|---|---|---|---|---|
| 149 | 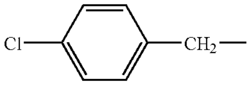 | 1 | 2 | 0 | R | H | 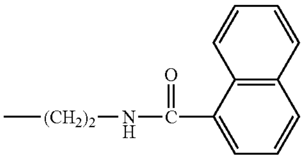 |
| 150 | 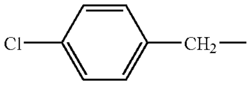 | 1 | 2 | 0 | R | H | 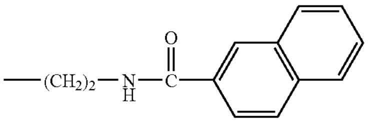 |
| 151 | 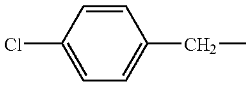 | 1 | 2 | 0 | R | H | 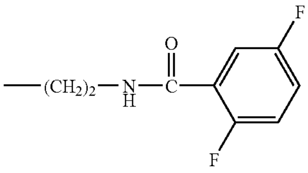 |
| 152 | 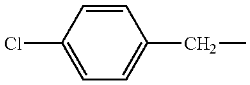 | 1 | 2 | 0 | R | H | 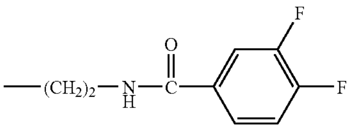 |
| 153 | 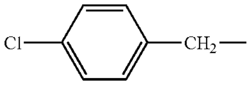 | 1 | 2 | 0 | R | H | 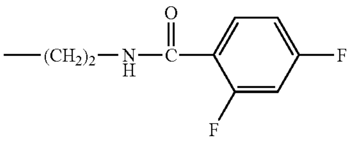 |
| 154 | 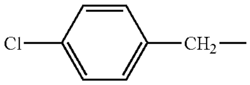 | 1 | 2 | 0 | R | H | 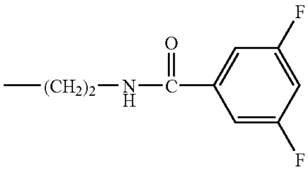 |
TABLE 1.15
| Compd. No. | 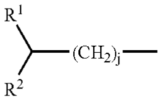 | k | m | n | chirality | $R^3$ | 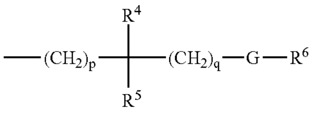 |
|---|---|---|---|---|---|---|---|
| 155 | 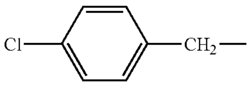 | 1 | 2 | 0 | R | H | 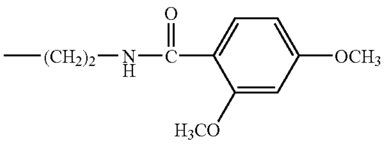 |
| 156 | 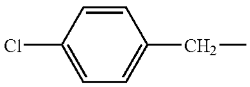 | 1 | 2 | 0 | R | H | 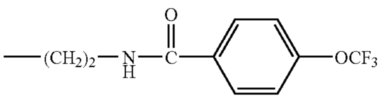 |

TABLE 1.15-continued
| Compd. No. | 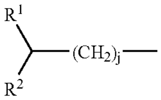 | k | m | n | chirality | $R^3$ | 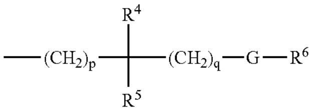 |
|---|---|---|---|---|---|---|---|
| 157 | 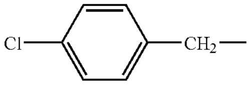 | 1 | 2 | 0 | R | H | 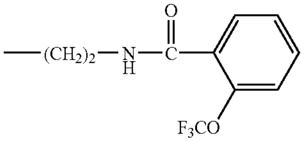 |
| 158 | 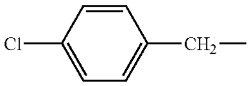 | 1 | 2 | 0 | R | H | 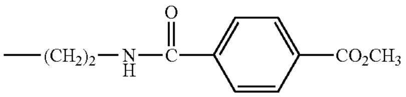 |
| 159 | 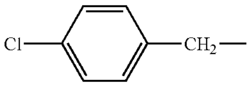 | 1 | 2 | 0 | R | H | 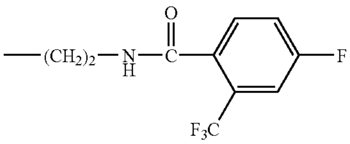 |
| 160 | 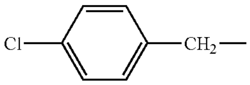 | 1 | 2 | 0 | R | H | 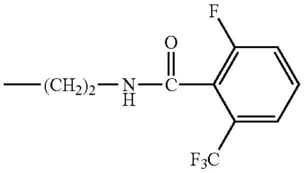 |
| 161 | 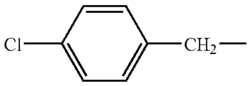 | 1 | 2 | 0 | R | H | 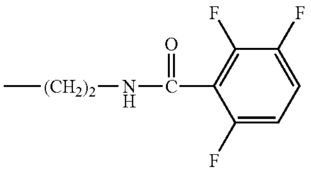 |
| 162 | 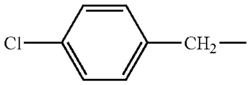 | 1 | 2 | 0 | R | H | 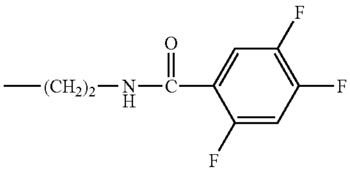 |
| 163 | 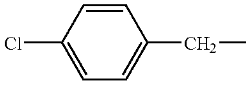 | 1 | 2 | 0 | R | H | 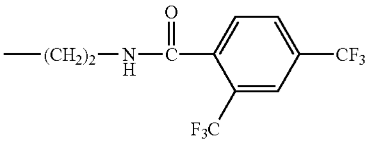 |
| 164 | 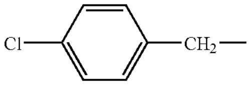 | 1 | 2 | 0 | R | H | 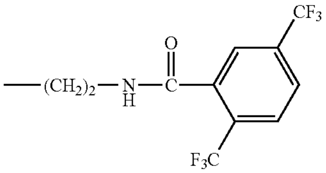 |
| 165 | 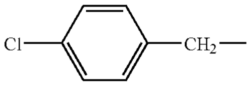 | 1 | 2 | 0 | R | H | 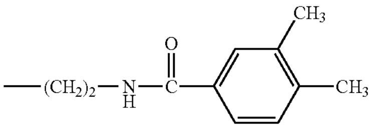 |

TABLE 1.16
| Compd. No. | 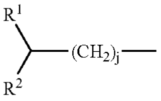 | k | m | n | chirality | $R^3$ | 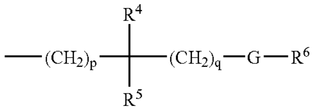 |
|---|---|---|---|---|---|---|---|
| 166 | 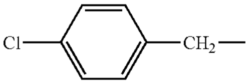 | 1 | 2 | 0 | R | H | 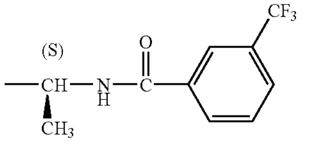 |
| 167 | 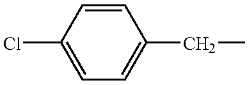 | 1 | 2 | 0 | R | H | 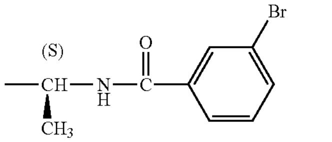 |
| 168 | 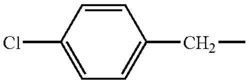 | 1 | 2 | 0 | R | H | 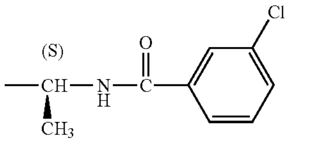 |
| 169 | 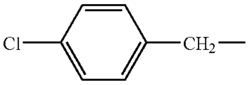 | 1 | 2 | 0 | R | H | 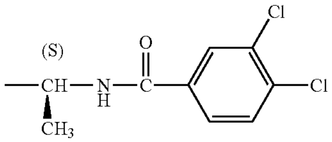 |
| 170 | 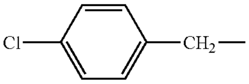 | 1 | 2 | 0 | R | H | 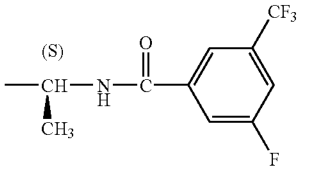 |
| 171 | 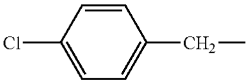 | 1 | 2 | 0 | R | H | 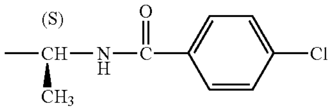 |
| 172 | 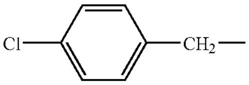 | 1 | 2 | 0 | R | H | 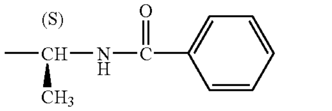 |
| 173 | 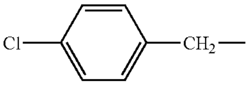 | 1 | 2 | 0 | R | H | 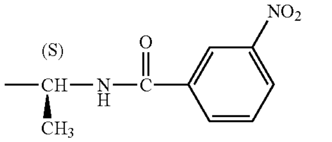 |
| 174 | 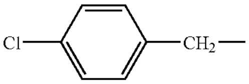 | 1 | 2 | 0 | R | H | 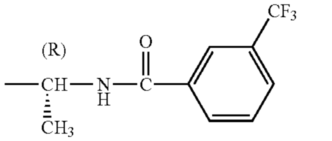 |

TABLE 1.16-continued
| Compd. No. | 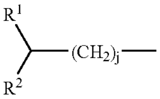 | k | m | n | chirality | $R^3$ | 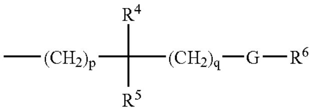 |
|---|---|---|---|---|---|---|---|
| 175 | 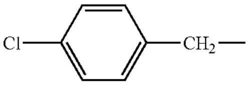 | 1 | 2 | 0 | R | H | 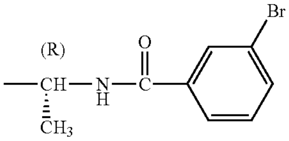 |
| 176 | 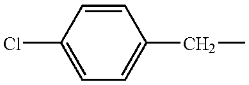 | 1 | 2 | 0 | R | H | 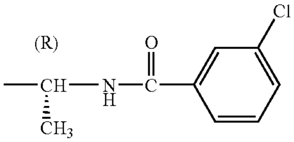 |
TABLE 1.17
| Compd. No. | 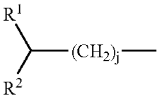 | k | m | n | chirality | $R^3$ | 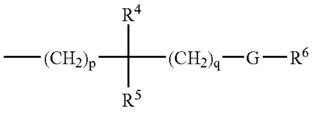 |
|---|---|---|---|---|---|---|---|
| 177 | 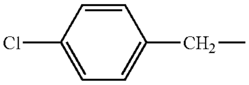 | 1 | 2 | 0 | R | H | 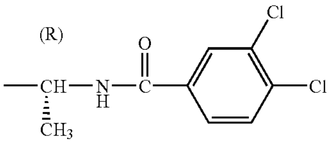 |
| 178 | 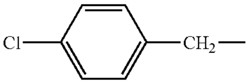 | 1 | 2 | 0 | R | H | 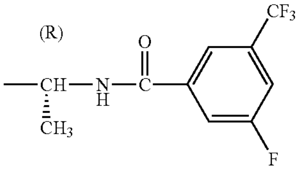 |
| 179 | 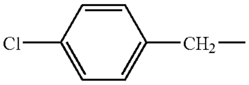 | 1 | 2 | 0 | R | H | 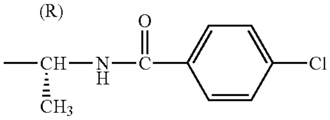 |
| 180 | 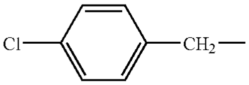 | 1 | 2 | 0 | R | H | 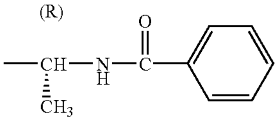 |
| 181 | 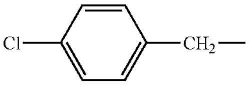 | 1 | 2 | 0 | R | H | 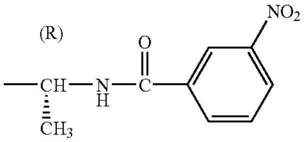 |
| 182 | 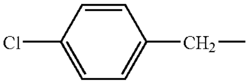 | 1 | 2 | 0 | R | H | 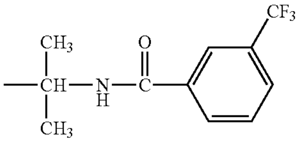 |

TABLE 1.17-continued
| Compd. No. | 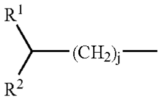 | k | m | n | chirality | $R^3$ | 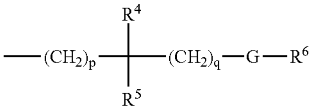 |
|---|---|---|---|---|---|---|---|
| 183 | 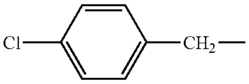 | 1 | 2 | 0 | R | H | 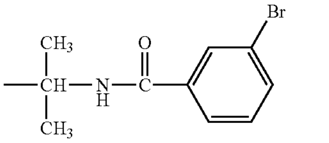 |
| 184 | 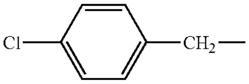 | 1 | 2 | 0 | R | H | 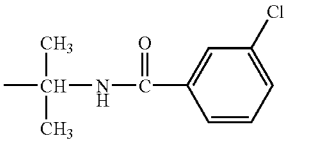 |
| 185 | 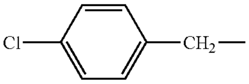 | 1 | 2 | 0 | R | H | 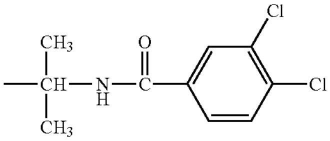 |
| 186 | 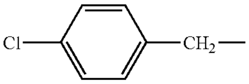 | 1 | 2 | 0 | R | H | 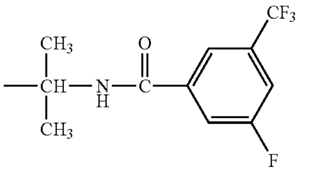 |
| 187 | 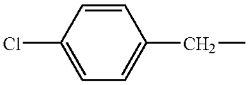 | 1 | 2 | 0 | R | H | 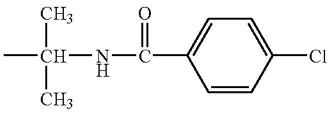 |
TABLE 1.18
| Compd. No. | 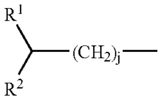 | k | m | n | chirality | $R^3$ | 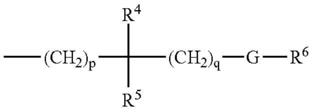 |
|---|---|---|---|---|---|---|---|
| 188 | 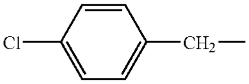 | 1 | 2 | 0 | R | H | 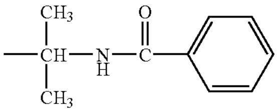 |
| 189 | 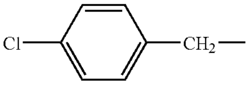 | 1 | 2 | 0 | R | H | 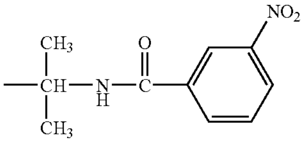 |
| 190 | 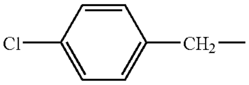 | 1 | 2 | 0 | R | H | 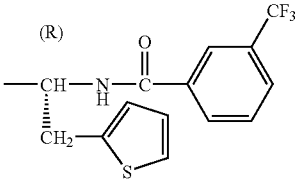 |

TABLE 1.18-continued
| Compd. No. | 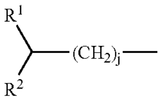 | k | m | n | chirality | $R^3$ | 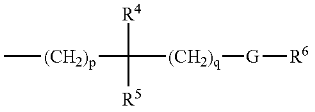 |
|---|---|---|---|---|---|---|---|
| 191 | 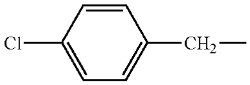 | 1 | 2 | 0 | R | H | 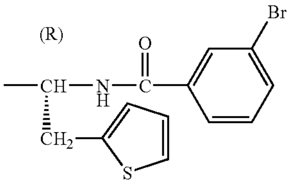 |
| 192 | 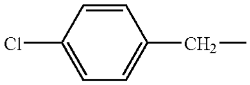 | 1 | 2 | 0 | R | H | 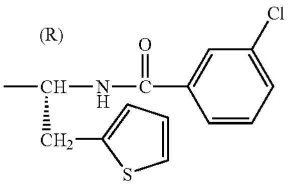 |
| 193 | 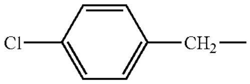 | 1 | 2 | 0 | R | H | 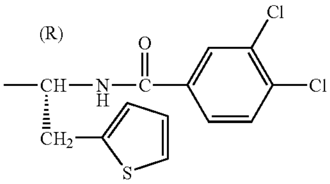 |
| 194 | 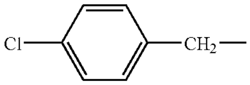 | 1 | 2 | 0 | R | H | 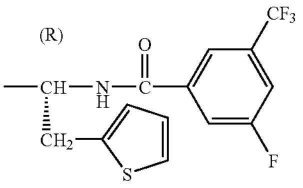 |
| 195 | 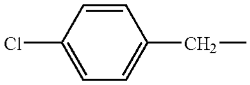 | 1 | 2 | 0 | R | H | 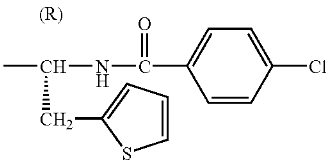 |
| 196 | 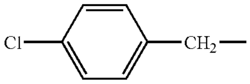 | 1 | 2 | 0 | R | H | 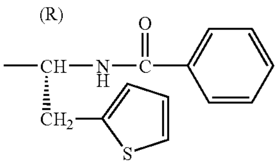 |
| 197 | 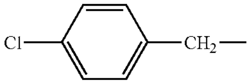 | 1 | 2 | 0 | R | H | 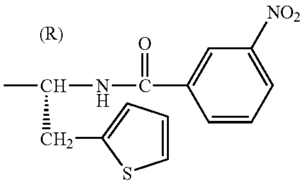 |

TABLE 1.18-continued
| Compd. No. | 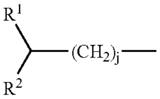 | k | m | n | chirality | $R^3$ | 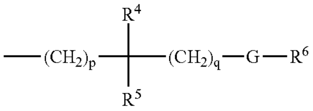 |
|---|---|---|---|---|---|---|---|
| 198 | 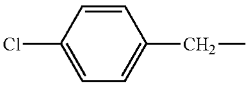 | 1 | 2 | 0 | R | H | 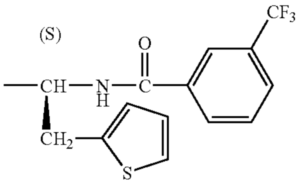 |
TABLE 1.19
| Compd. No. | 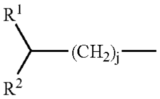 | k | m | n | chirality | $R^3$ | 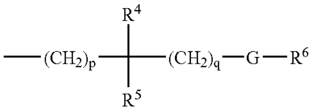 |
|---|---|---|---|---|---|---|---|
| 199 | 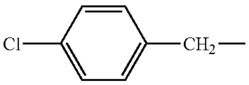 | 1 | 2 | 0 | R | H | 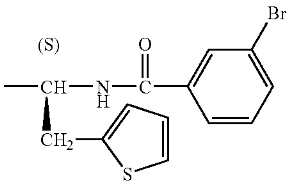 |
| 200 | 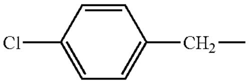 | 1 | 2 | 0 | R | H | 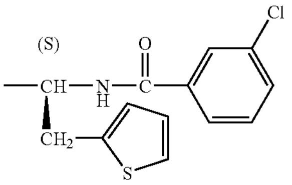 |
| 201 | 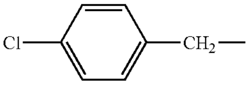 | 1 | 2 | 0 | R | H | 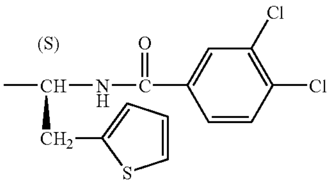 |
| 202 | 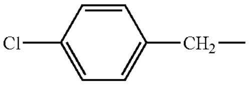 | 1 | 2 | 0 | R | H | 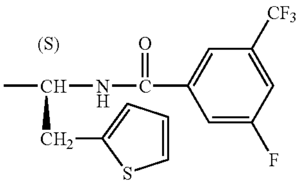 |
| 203 | 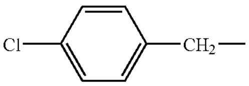 | 1 | 2 | 0 | R | H | 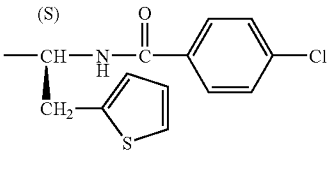 |

TABLE 1.19-continued
| Compd. No. | 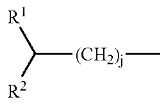 | k | m | n | chirality | $R^3$ | 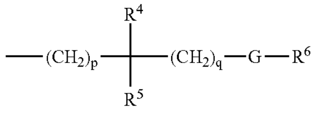 |
|---|---|---|---|---|---|---|---|
| 204 | 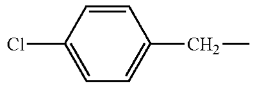 | 1 | 2 | 0 | R | H | 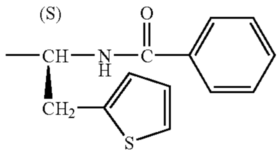 |
| 205 | 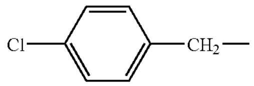 | 1 | 2 | 0 | R | H | 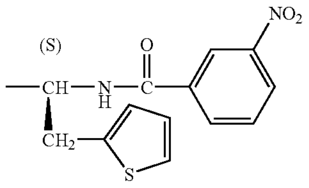 |
| 206 | 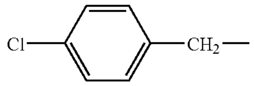 | 1 | 2 | 0 | R | H | 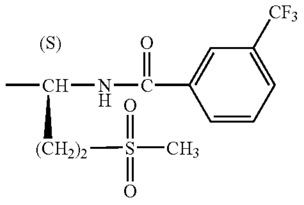 |
| 207 | 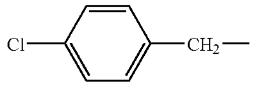 | 1 | 2 | 0 | R | H | 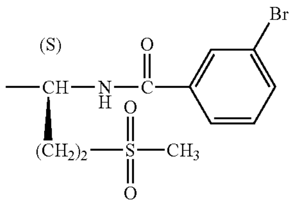 |
| 208 | 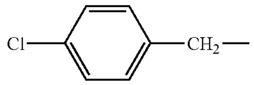 | 1 | 2 | 0 | R | H | 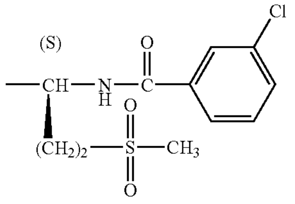 |
| 209 | 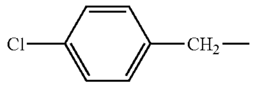 | 1 | 2 | 0 | R | H | 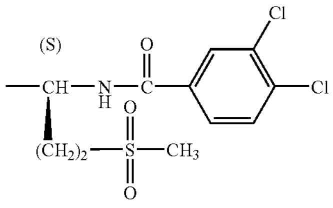 |

TABLE 1.20
| Compd. No. | 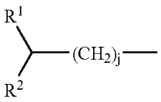 | k | m | n | chirality | $R^3$ | 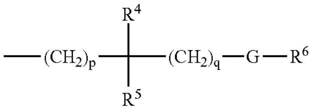 |
|---|---|---|---|---|---|---|---|
| 210 | 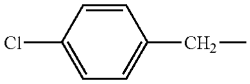 | 1 | 2 | 0 | R | H | 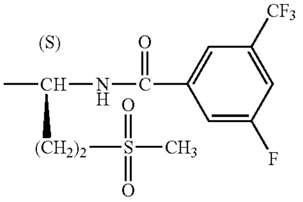 |
| 211 | 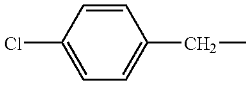 | 1 | 2 | 0 | R | H | 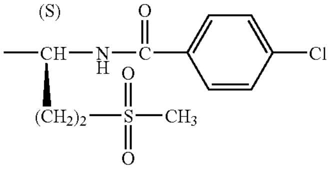 |
| 212 | 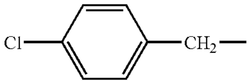 | 1 | 2 | 0 | R | H | 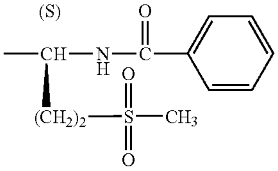 |
| 213 | 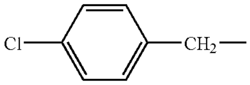 | 1 | 2 | 0 | R | H | 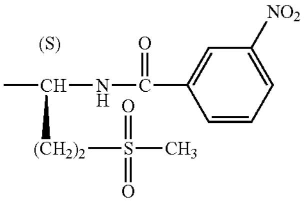 |
| 214 | 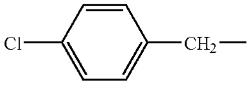 | 1 | 2 | 0 | — | H | 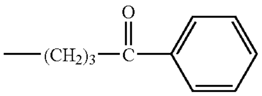 |
| 215 | 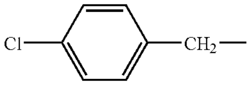 | 1 | 2 | 0 | — | H | 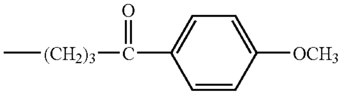 |
| 216 | 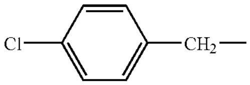 | 1 | 2 | 0 | — | H | 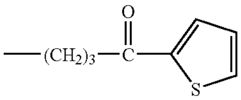 |
| 217 | 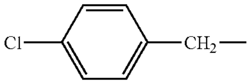 | 1 | 2 | 0 | — | H | 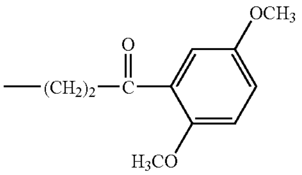 |
| 218 | 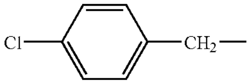 | 1 | 2 | 0 | — | H | 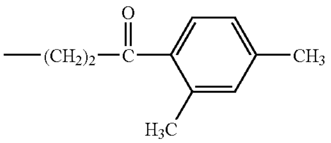 |

TABLE 1.20-continued
| Compd. No. | 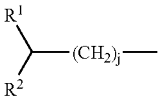 | k | m | n | chirality | $R^3$ | 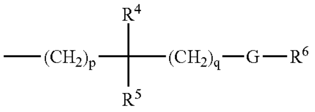 |
|---|---|---|---|---|---|---|---|
| 219 | 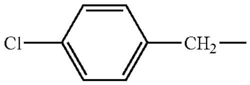 | 1 | 2 | 0 | — | H | 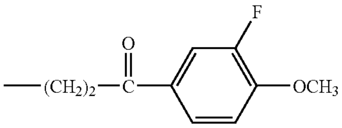 |
| 220 | 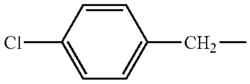 | 1 | 2 | 0 | — | H | 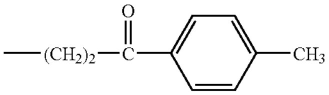 |
TABLE 1.21
| Compd. No. | 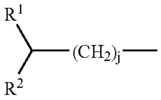 | k | m | n | chirality | $R^3$ | 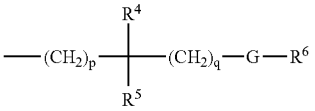 |
|---|---|---|---|---|---|---|---|
| 221 | 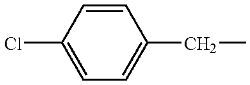 | 1 | 2 | 0 | — | H | 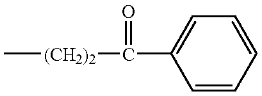 |
| 222 | 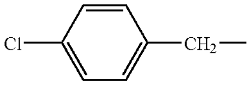 | 1 | 2 | 0 | — | H | 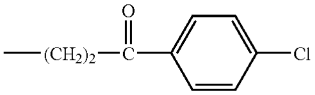 |
| 223 | 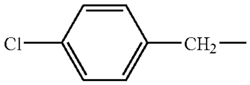 | 1 | 2 | 0 | — | H | 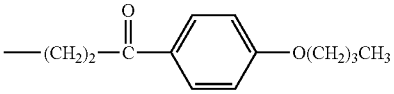 |
| 224 | 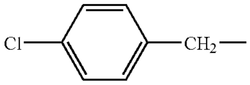 | 1 | 2 | 0 | — | H | 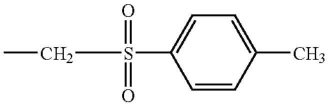 |
| 225 | 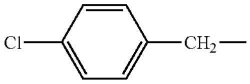 | 1 | 2 | 0 | — | H | 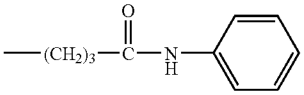 |
| 226 | 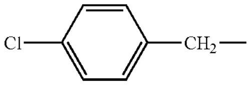 | 1 | 2 | 0 | — | H | 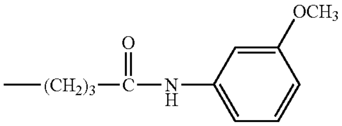 |
| 227 | 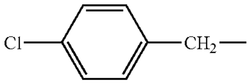 | 1 | 2 | 0 | — | H | 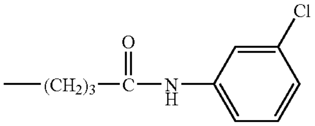 |
| 228 | 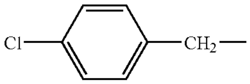 | 1 | 2 | 0 | — | H | 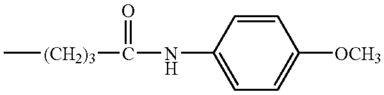 |

TABLE 1.21-continued
| Compd. No. | 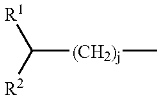 | k | m | n | chirality | $R^3$ | 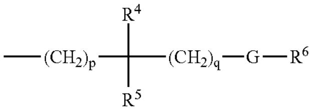 |
|---|---|---|---|---|---|---|---|
| 229 | 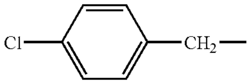 | 1 | 2 | 0 | — | H | 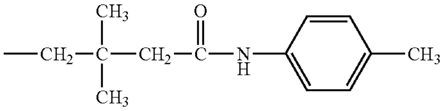 |
| 230 | 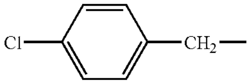 | 1 | 2 | 0 | — | H | 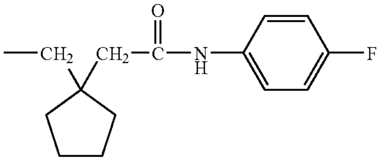 |
| 231 | 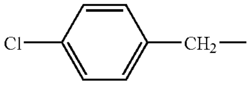 | 1 | 2 | 0 | — | H | 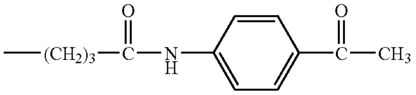 |
TABLE 1.22
| Compd. No. | 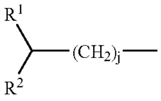 | k | m | n | chirality | $R^3$ | 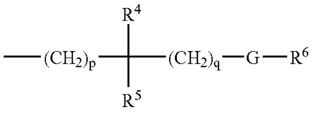 |
|---|---|---|---|---|---|---|---|
| 232 | 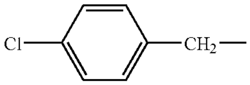 | 1 | 2 | 0 | — | H | 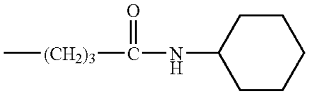 |
| 233 | 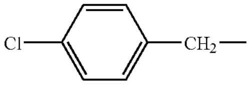 | 1 | 2 | 0 | — | H | 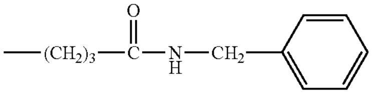 |
| 234 | 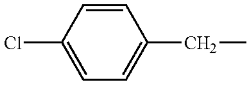 | 1 | 2 | 0 | — | H | 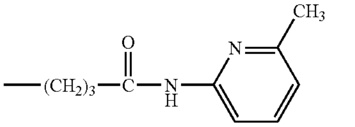 |
| 235 | 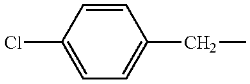 | 1 | 2 | 0 | — | H | 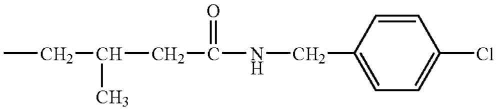 |
| 236 | 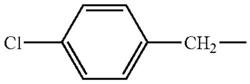 | 1 | 2 | 0 | — | H | 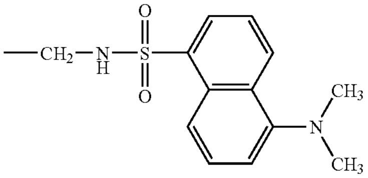 |
| 237 | 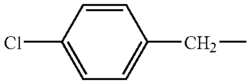 | 1 | 2 | 0 | — | H | 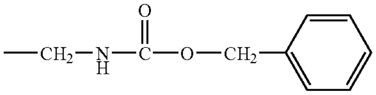 |

TABLE 1.22-continued
| Compd. No. | 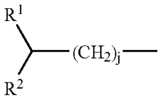 | k | m | n | chirality | $R^3$ | 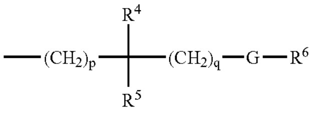 |
|---|---|---|---|---|---|---|---|
| 238 | 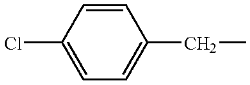 | 1 | 2 | 0 | — | H | 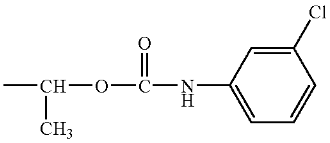 |
| 239 | 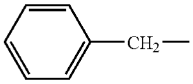 | 1 | 2 | 0 | S | H | 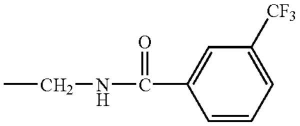 |
| 240 | 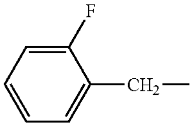 | 1 | 2 | 0 | S | H | 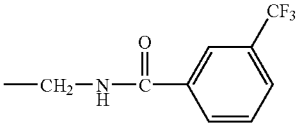 |
| 241 | 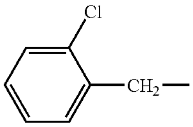 | 1 | 2 | 0 | S | H | 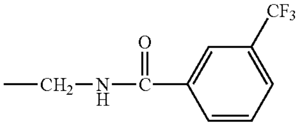 |
| 242 | 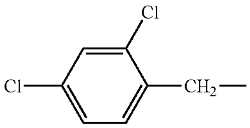 | 1 | 2 | 0 | S | H | 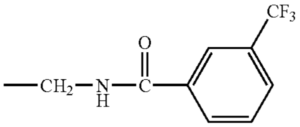 |
TABLE 1.23
| Compd. No. | 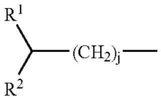 | k | m | n | chirality | $R^3$ | 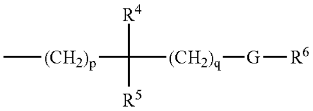 |
|---|---|---|---|---|---|---|---|
| 243 | 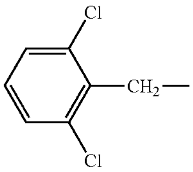 | 1 | 2 | 0 | S | H | 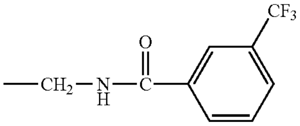 |
| 244 | 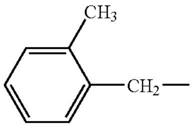 | 1 | 2 | 0 | S | H | 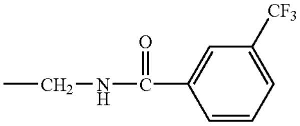 |
| 245 | 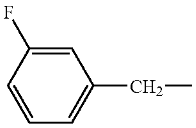 | 1 | 2 | 0 | S | H | 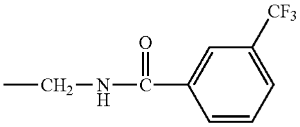 |

TABLE 1.23-continued
| Compd. No. | 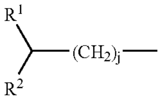 | k | m | n | chirality | $R^3$ | 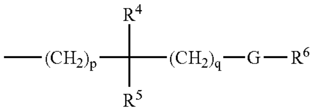 |
|---|---|---|---|---|---|---|---|
| 246 | 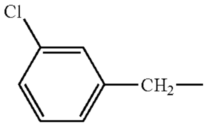 | 1 | 2 | 0 | S | H | 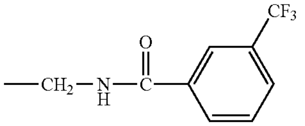 |
| 247 | 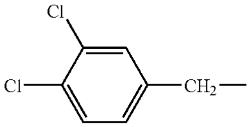 | 1 | 2 | 0 | S | H | 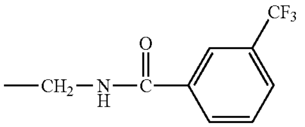 |
| 248 | 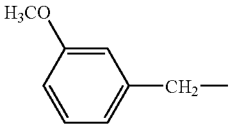 | 1 | 2 | 0 | S | H | 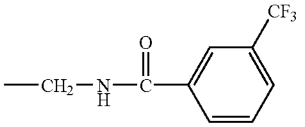 |
| 249 | 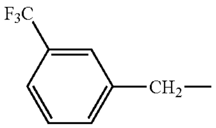 | 1 | 2 | 0 | S | H | 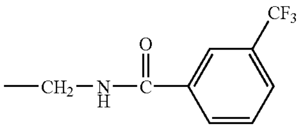 |
| 250 | 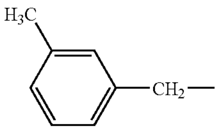 | 1 | 2 | 0 | S | H | 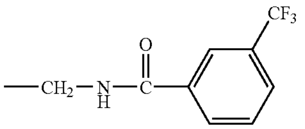 |
| 251 | 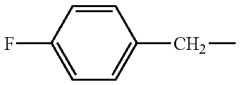 | 1 | 2 | 0 | S | H | 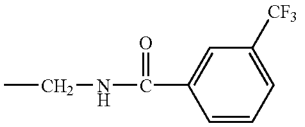 |
| 252 | 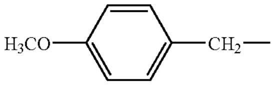 | 1 | 2 | 0 | S | H | 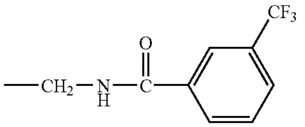 |
| 253 | 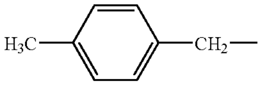 | 1 | 2 | 0 | S | H | 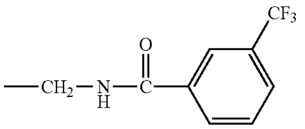 |
TABLE 1.24
| Compd. No. | 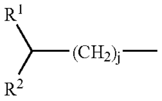 | k | m | n | chirality | $R^3$ | 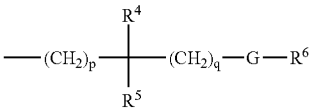 |
|---|---|---|---|---|---|---|---|
| 254 | 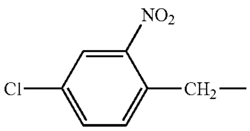 | 1 | 2 | 0 | S | H | 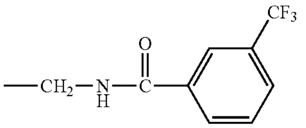 |

TABLE 1.24-continued
| Compd. No. | 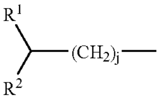 | k | m | n | chirality | $R^3$ | 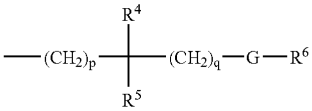 |
|---|---|---|---|---|---|---|---|
| 255 | 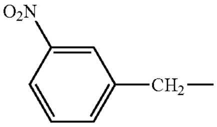 | 1 | 2 | 0 | S | H | 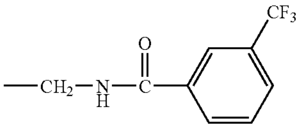 |
| 256 | 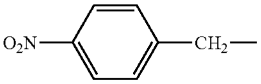 | 1 | 2 | 0 | S | H | 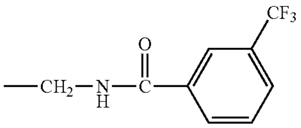 |
| 257 | 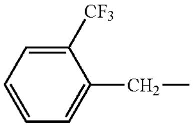 | 1 | 2 | 0 | S | H | 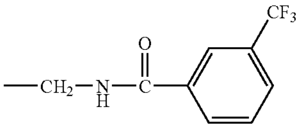 |
| 258 | 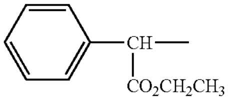 | 1 | 2 | 0 | S | H | 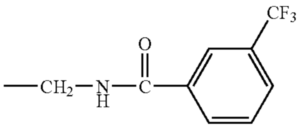 |
| 259 | 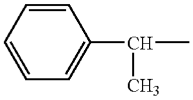 | 1 | 2 | 0 | S | H | 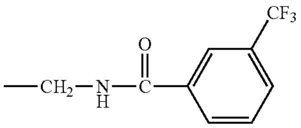 |
| 260 | 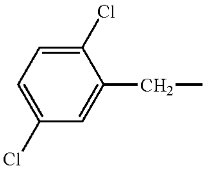 | 1 | 2 | 0 | S | H | 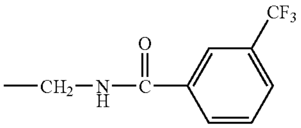 |
| 261 | 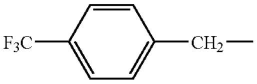 | 1 | 2 | 0 | S | H | 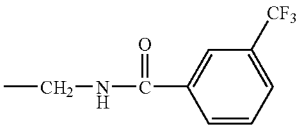 |
| 262 | 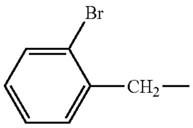 | 1 | 2 | 0 | S | H | 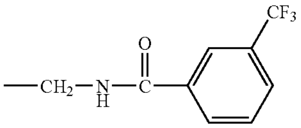 |
| 263 | 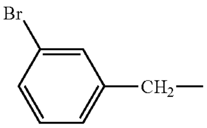 | 1 | 2 | 0 | S | H | 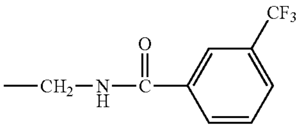 |

TABLE 1.24-continued
| Compd. No. | 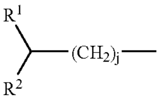 | k | m | n | chirality | $R^3$ | 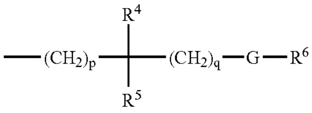 |
|---|---|---|---|---|---|---|---|
| 264 | 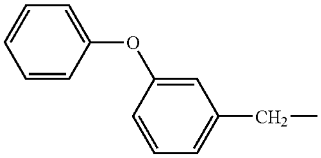 | 1 | 2 | 0 | S | H | 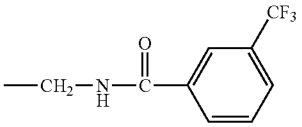 |
TABLE 1.25
| Compd. No. | 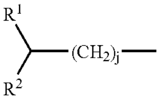 | k | m | n | chirality | $R^3$ | 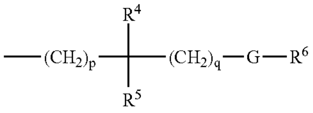 |
|---|---|---|---|---|---|---|---|
| 265 | 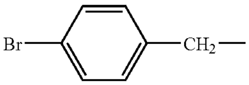 | 1 | 2 | 0 | S | H | 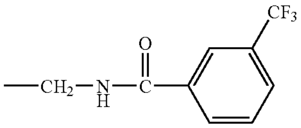 |
| 266 | 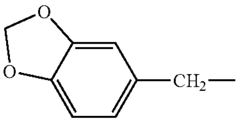 | 1 | 2 | 0 | S | H | 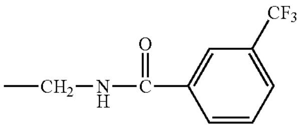 |
| 267 | 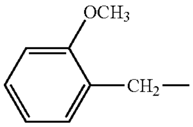 | 1 | 2 | 0 | S | H | 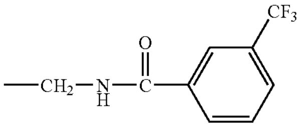 |
| 268 | 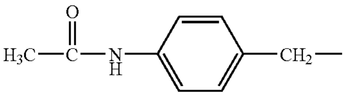 | 1 | 2 | 0 | S | H | 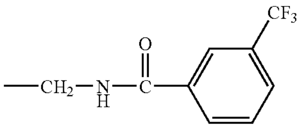 |
| 269 | 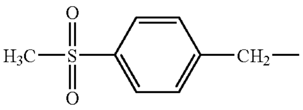 | 1 | 2 | 0 | S | H | 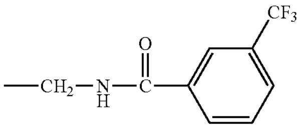 |
| 270 | 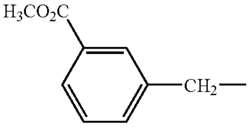 | 1 | 2 | 0 | S | H | 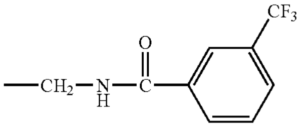 |
| 271 | 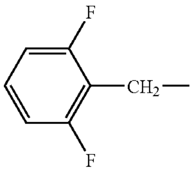 | 1 | 2 | 0 | S | H | 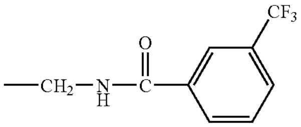 |

TABLE 1.25-continued
| Compd. No. | 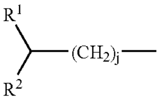 | k | m | n | chirality | $R^3$ | 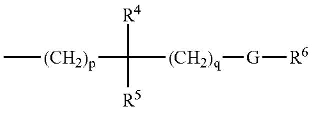 |
|---|---|---|---|---|---|---|---|
| 272 | 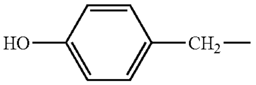 | 1 | 2 | 0 | S | H | 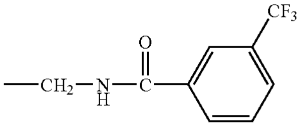 |
| 273 | 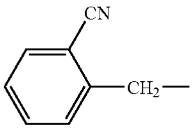 | 1 | 2 | 0 | S | H | 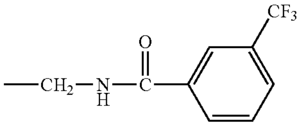 |
| 274 | 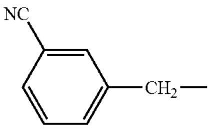 | 1 | 2 | 0 | S | H | 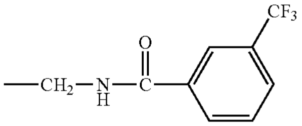 |
| 275 | 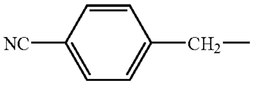 | 1 | 2 | 0 | S | H | 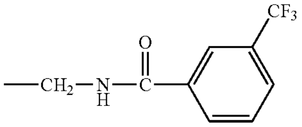 |
TABLE 1.26
| Compd. No. | 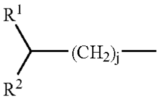 | k | m | n | chirality | $R^3$ | 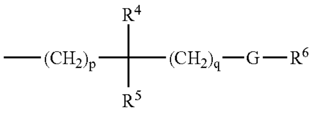 |
|---|---|---|---|---|---|---|---|
| 276 | 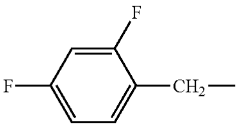 | 1 | 2 | 0 | S | H | 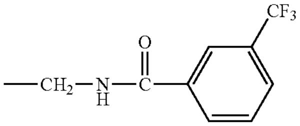 |
| 277 | 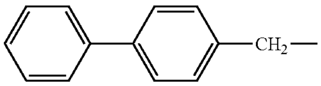 | 1 | 2 | 0 | S | H | 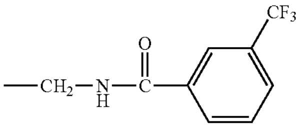 |
| 278 | 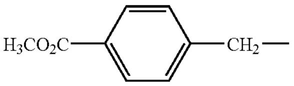 | 1 | 2 | 0 | S | H | 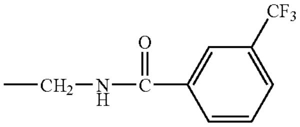 |
| 279 | 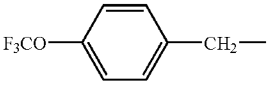 | 1 | 2 | 0 | S | H | 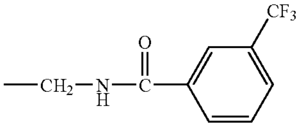 |
| 280 | 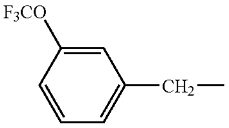 | 1 | 2 | 0 | S | H | 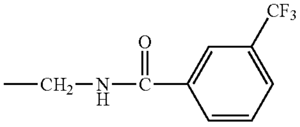 |

TABLE 1.26-continued
| Compd. No. 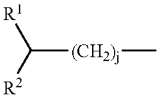 | | k | m | n | chirality | $R^3$ | 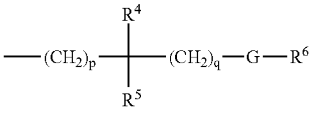 |
|---|---|---|---|---|---|---|---|
| 281 | 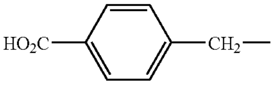 | 1 | 2 | 0 | S | H | 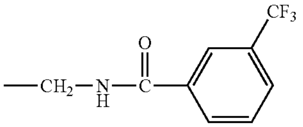 |
| 282 | 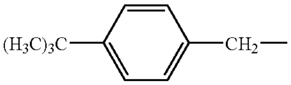 | 1 | 2 | 0 | S | H | 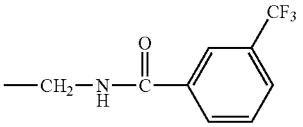 |
| 283 | 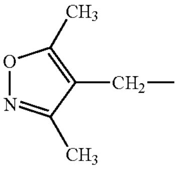 | 1 | 2 | 0 | S | H | 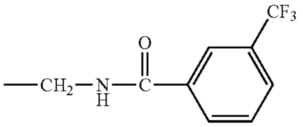 |
| 284 | 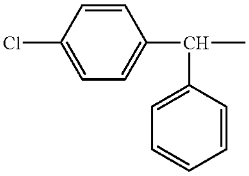 | 1 | 2 | 0 | S | H | 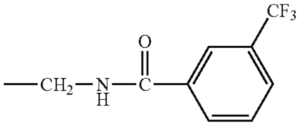 |
| 285 | 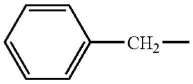 | 1 | 2 | 0 | R | H | 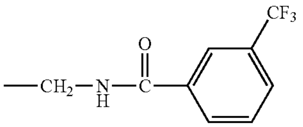 |
| 286 | 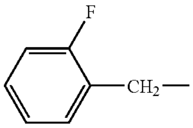 | 1 | 2 | 0 | R | H | 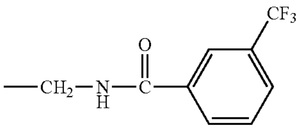 |
TABLE 1.27
| Compd. No. | 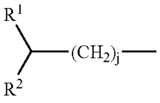 | k | m | n | chirality | $R^3$ | 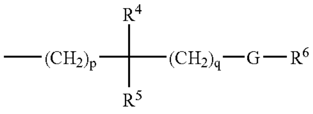 |
|---|---|---|---|---|---|---|---|
| 287 | 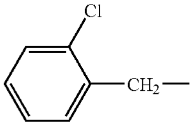 | 1 | 2 | 0 | R | H | 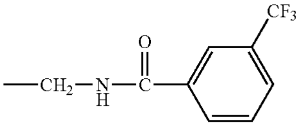 |
| 288 | 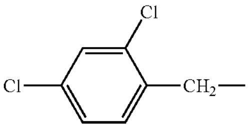 | 1 | 2 | 0 | R | H | 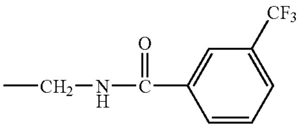 |

TABLE 1.27-continued
| Compd. No. | 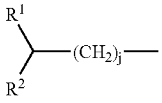 | k | m | n | chirality | $R^3$ | 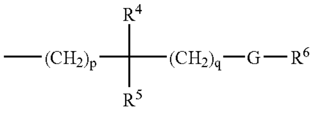 |
|---|---|---|---|---|---|---|---|
| 289 | 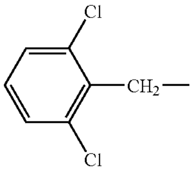 | 1 | 2 | 0 | R | H | 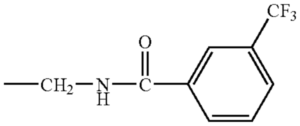 |
| 290 | 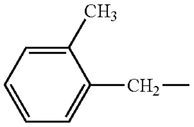 | 1 | 2 | 0 | R | H | 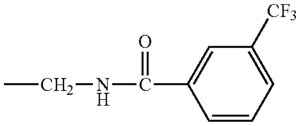 |
| 291 | 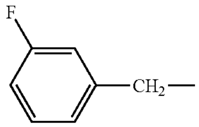 | 1 | 2 | 0 | R | H | 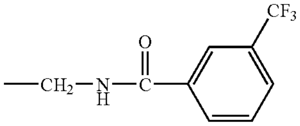 |
| 292 | 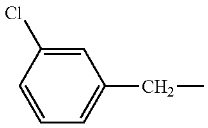 | 1 | 2 | 0 | R | H | 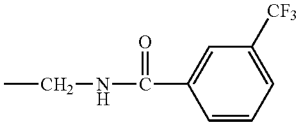 |
| 293 | 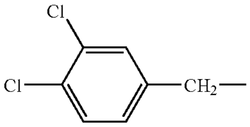 | 1 | 2 | 0 | R | H | 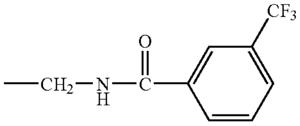 |
| 294 | 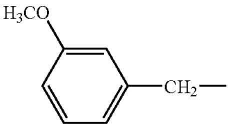 | 1 | 2 | 0 | R | H | 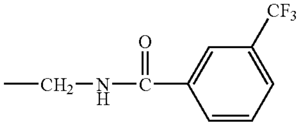 |
| 295 | 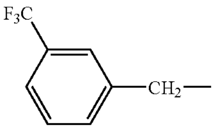 | 1 | 2 | 0 | R | H | 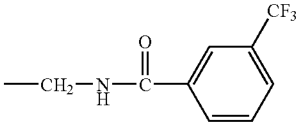 |
| 296 | 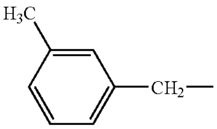 | 1 | 2 | 0 | R | H | 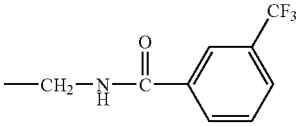 |
| 297 | 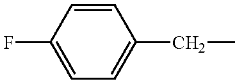 | 1 | 2 | 0 | R | H | 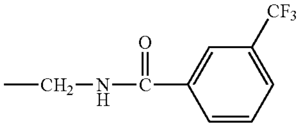 |

TABLE 1.28
| Compd. No. | 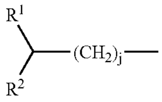 | k | m | n | chirality | $R^3$ | 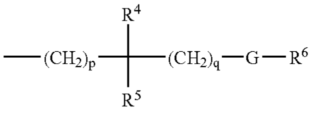 |
|---|---|---|---|---|---|---|---|
| 298 | 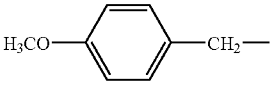 | 1 | 2 | 0 | R | H | 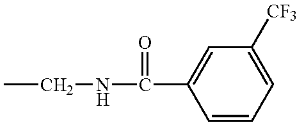 |
| 299 | 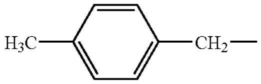 | 1 | 2 | 0 | R | H | 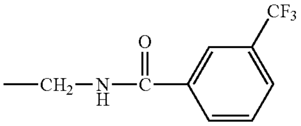 |
| 300 | 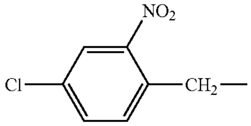 | 1 | 2 | 0 | R | H | 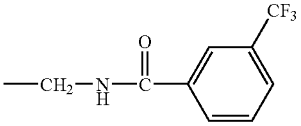 |
| 301 | 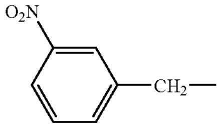 | 1 | 2 | 0 | R | H | 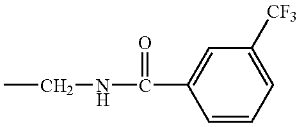 |
| 302 | 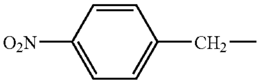 | 1 | 2 | 0 | R | H | 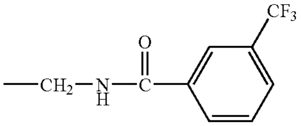 |
| 303 | 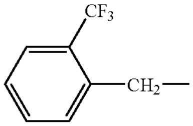 | 1 | 2 | 0 | R | H | 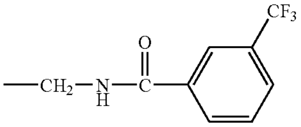 |
| 304 | 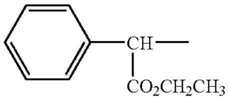 | 1 | 2 | 0 | R | H | 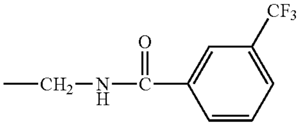 |
| 305 | 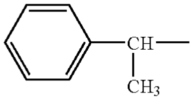 | 1 | 2 | 0 | R | H | 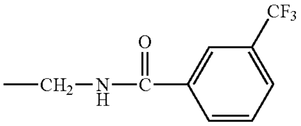 |
| 306 | 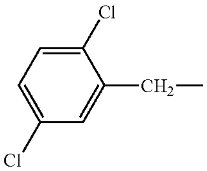 | 1 | 2 | 0 | R | H | 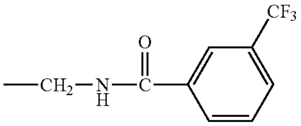 |
| 307 | 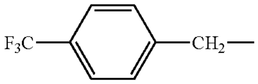 | 1 | 2 | 0 | R | H | 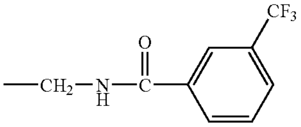 |

TABLE 1.28-continued
| Compd. No. | 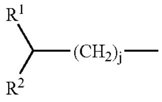 | k | m | n | chirality | $R^3$ | 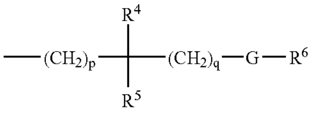 |
|---|---|---|---|---|---|---|---|
| 308 | 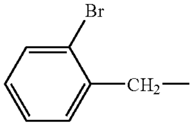 | 1 | 2 | 0 | R | H | 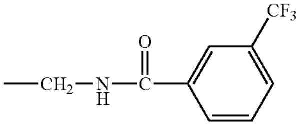 |
TABLE 1.29
| Compd. No. | 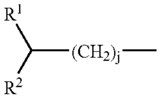 | k | m | n | chirality | $R^3$ | 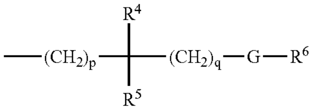 |
|---|---|---|---|---|---|---|---|
| 309 | 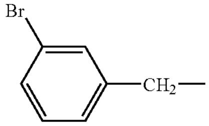 | 1 | 2 | 0 | R | H | 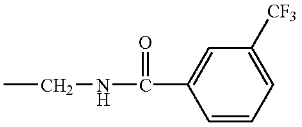 |
| 310 | 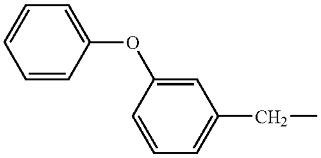 | 1 | 2 | 0 | R | H | 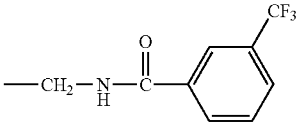 |
| 311 | 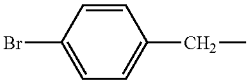 | 1 | 2 | 0 | R | H | 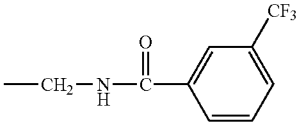 |
| 312 | 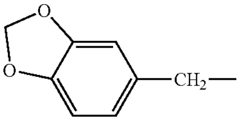 | 1 | 2 | 0 | R | H | 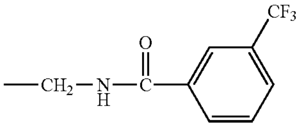 |
| 313 | 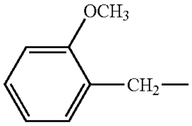 | 1 | 2 | 0 | R | H | 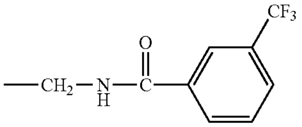 |
| 314 | 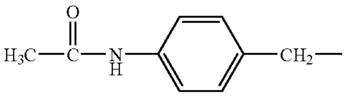 | 1 | 2 | 0 | R | H | 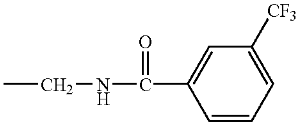 |
| 315 | 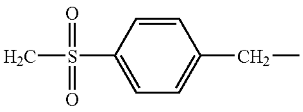 | 1 | 2 | 0 | R | H | 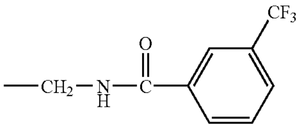 |

TABLE 1.29-continued
| Compd. No. | 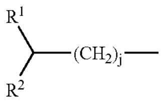 | k | m | n | chirality | $R^3$ | 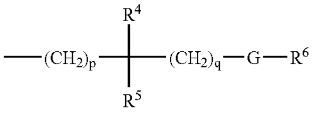 |
|---|---|---|---|---|---|---|---|
| 316 | 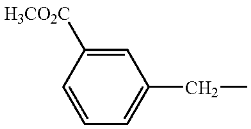 | 1 | 2 | 0 | R | H | 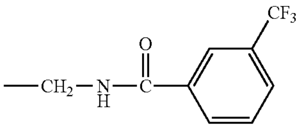 |
| 317 | 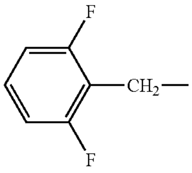 | 1 | 2 | 0 | R | H | 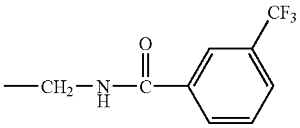 |
| 318 | 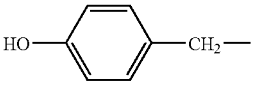 | 1 | 2 | 0 | R | H | 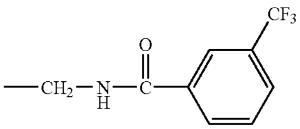 |
| 319 | 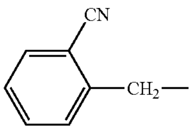 | 1 | 2 | 0 | R | H | 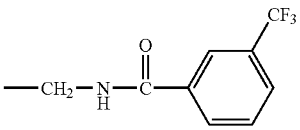 |
TABLE 1.30
| Compd. No. | 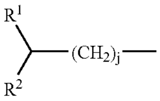 | k | m | n | chirality | $R^3$ | 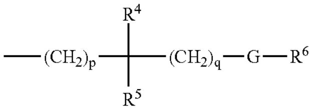 |
|---|---|---|---|---|---|---|---|
| 320 | 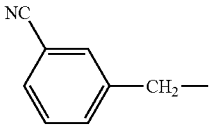 | 1 | 2 | 0 | R | H | 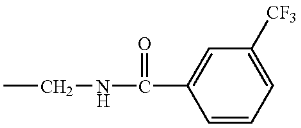 |
| 321 | 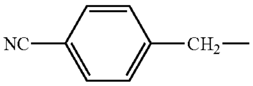 | 1 | 2 | 0 | R | H | 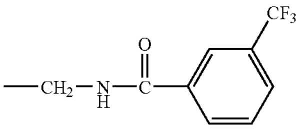 |
| 322 | 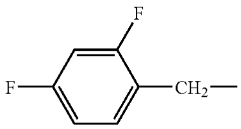 | 1 | 2 | 0 | R | H | 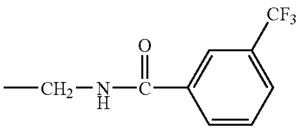 |
| 323 | 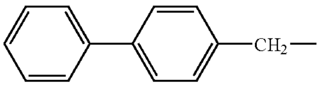 | 1 | 2 | 0 | R | H | 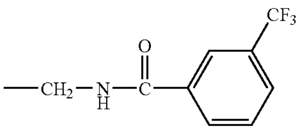 |

TABLE 1.30-continued
| Compd. No. | 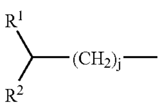 | k | m | n | chirality | $R^3$ | 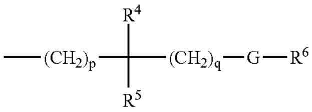 |
|---|---|---|---|---|---|---|---|
| 324 | 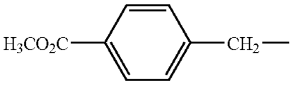 | 1 | 2 | 0 | R | H | 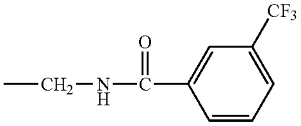 |
| 325 | 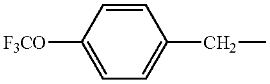 | 1 | 2 | 0 | R | H | 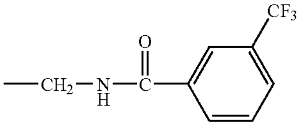 |
| 326 | 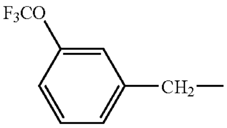 | 1 | 2 | 0 | R | H | 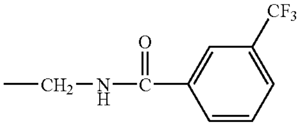 |
| 327 | 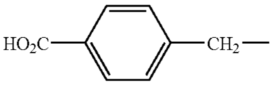 | 1 | 2 | 0 | R | H | 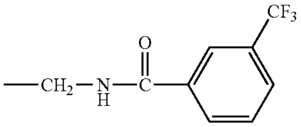 |
| 328 | 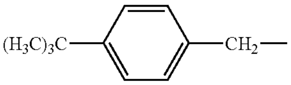 | 1 | 2 | 0 | R | H | 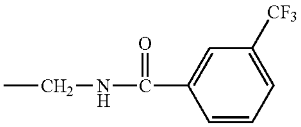 |
| 329 | 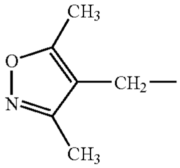 | 1 | 2 | 0 | R | H | 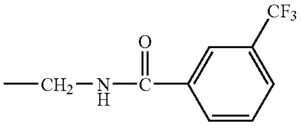 |
| 330 | 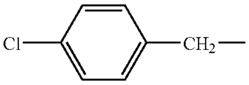 | 0 | 3 | 1 | — | H | 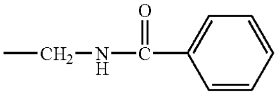 |
TABLE 1.31
| Compd. No. | 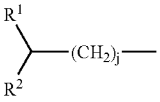 | k | m | n | chirality | $R^3$ | 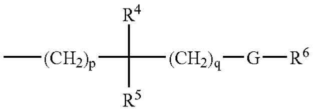 |
|---|---|---|---|---|---|---|---|
| 331 | 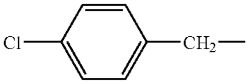 | 0 | 3 | 1 | — | H | 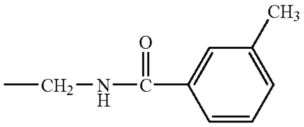 |

TABLE 1.31-continued
| Compd. No. | 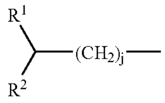 | k | m | n | chirality | $R^3$ | 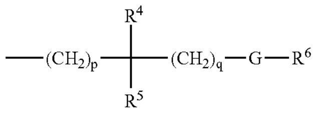 |
|---|---|---|---|---|---|---|---|
| 332 | 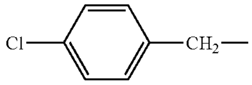 | 0 | 3 | 1 | — | H | 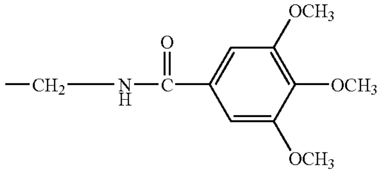 |
| 333 | 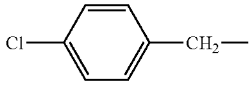 | 0 | 3 | 1 | — | H | 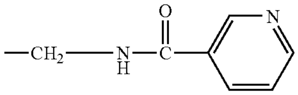 |
| 334 | 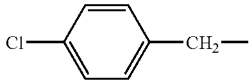 | 0 | 3 | 1 | — | H | 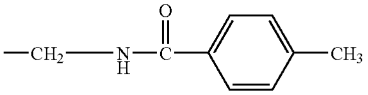 |
| 335 | 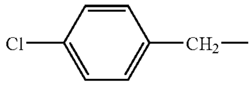 | 0 | 3 | 1 | — | H | 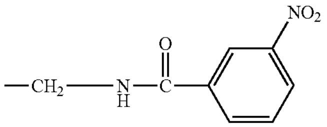 |
| 336 | 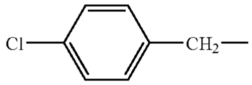 | 0 | 3 | 1 | — | H | 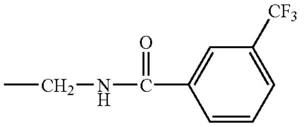 |
| 337 | 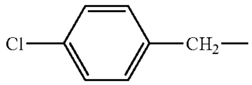 | 0 | 3 | 1 | — | H | 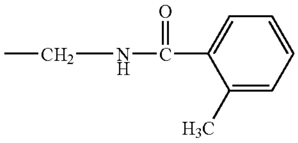 |
| 338 | 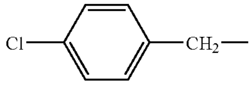 | 0 | 3 | 1 | — | H | 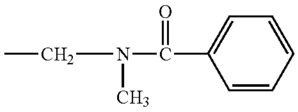 |
| 339 | 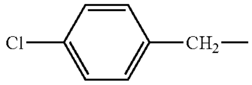 | 0 | 3 | 1 | R | H | 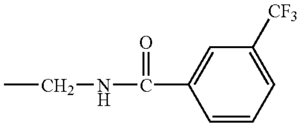 |
| 340 | 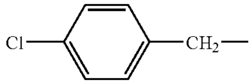 | 0 | 3 | 1 | S | H | 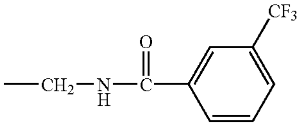 |
| 341 | 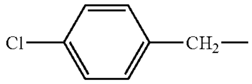 | 0 | 3 | 1 | — | H | 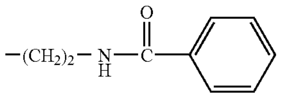 |

TABLE 1.32
| Compd. No. | 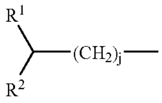 | k | m | n | chirality | $R^3$ | 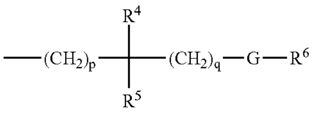 |
|---|---|---|---|---|---|---|---|
| 342 | 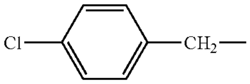 | 0 | 3 | 1 | — | H | 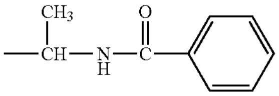 |
| 343 | 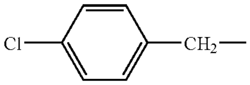 | 0 | 3 | 1 | — | H | 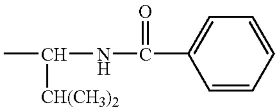 |
| 344 | 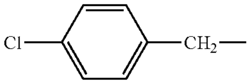 | 0 | 3 | 1 | — | H | 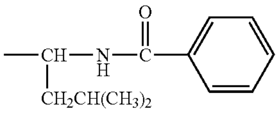 |
| 345 | 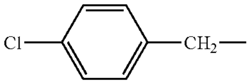 | 0 | 3 | 1 | — | H | 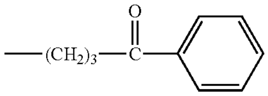 |
| 346 | 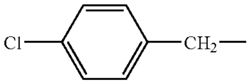 | 0 | 3 | 1 | — | H | 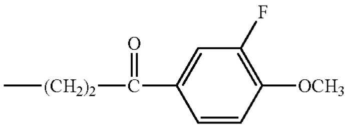 |
| 347 | 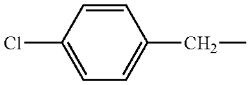 | 0 | 3 | 1 | — | H | 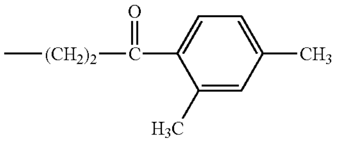 |
| 348 | 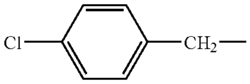 | 0 | 3 | 1 | — | H | 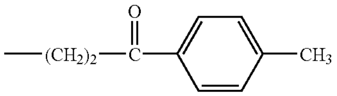 |
| 349 | 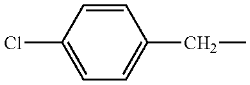 | 0 | 3 | 1 | — | H | 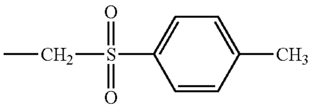 |
| 350 | 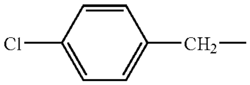 | 0 | 3 | 1 | — | H | 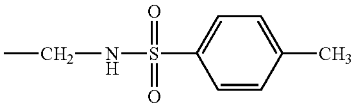 |
| 351 | 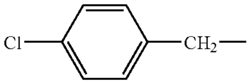 | 0 | 3 | 1 | — | H | 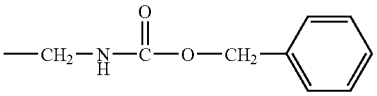 |
| 352 | 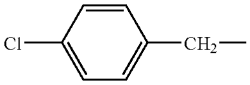 | 0 | 3 | 1 | — | H | 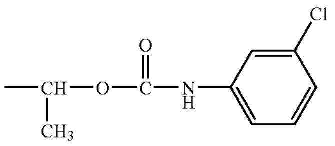 |

TABLE 1.33
| Compd. No. | 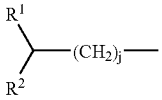 | k | m | n | chirality | $R^3$ | 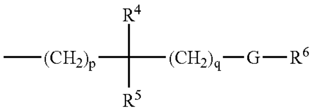 |
|---|---|---|---|---|---|---|---|
| 353 | 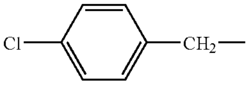 | 1 | 2 | 1 | — | H | 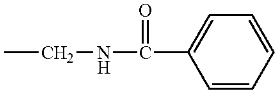 |
| 354 | 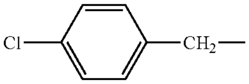 | 1 | 3 | 0 | — | H | 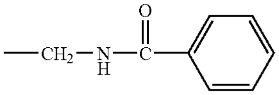 |
| 355 | 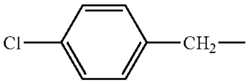 | 1 | 3 | 0 | — | H | 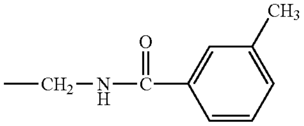 |
| 356 | 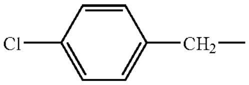 | 1 | 3 | 0 | — | H | 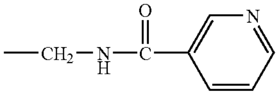 |
| 357 | 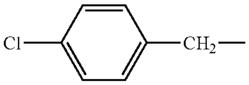 | 1 | 3 | 0 | — | H | 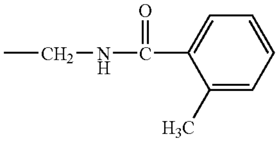 |
| 358 | 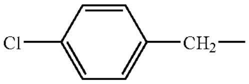 | 1 | 3 | 0 | — | H | 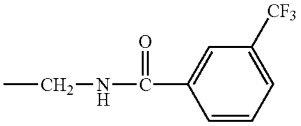 |
| 359 | 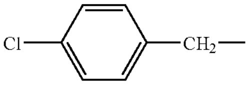 | 1 | 3 | 0 | — | H | 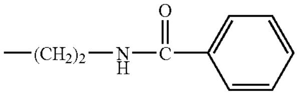 |
| 360 | 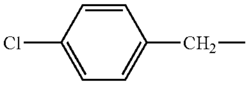 | 1 | 3 | 0 | — | H | 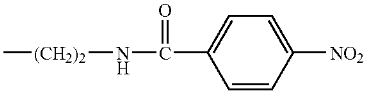 |
| 361 | 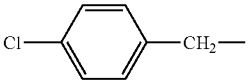 | 1 | 3 | 0 | — | H | 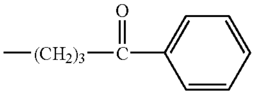 |
| 362 | 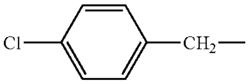 | 1 | 3 | 0 | — | H | 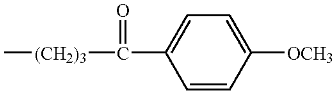 |
| 363 | 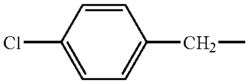 | 1 | 3 | 0 | — | H | 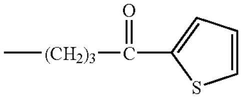 |

TABLE 1.34
| Compd. No. | 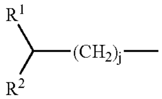 | k | m | n | chirality | $R^3$ | 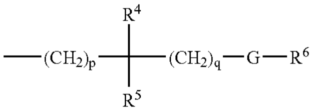 |
|---|---|---|---|---|---|---|---|
| 364 | 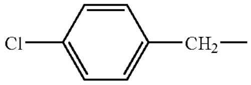 | 1 | 3 | 0 | — | H | 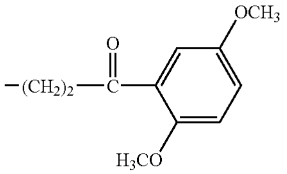 |
| 365 | 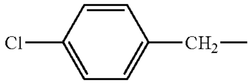 | 1 | 3 | 0 | — | H | 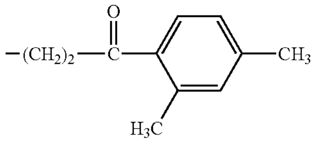 |
| 366 | 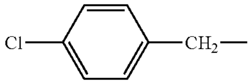 | 1 | 3 | 0 | — | H | 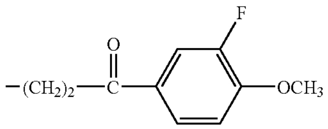 |
| 367 | 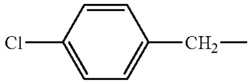 | 1 | 3 | 0 | — | H | 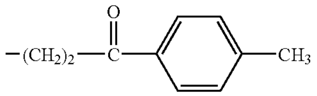 |
| 368 | 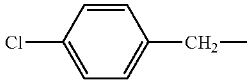 | 1 | 3 | 0 | — | H | 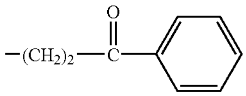 |
| 369 | 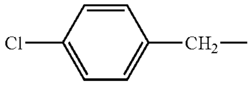 | 1 | 3 | 0 | — | H | 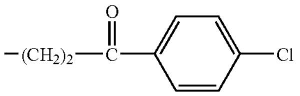 |
| 370 | 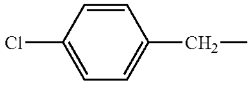 | 1 | 3 | 0 | — | H | 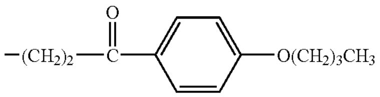 |
| 371 | 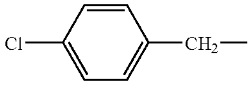 | 1 | 3 | 0 | — | H | 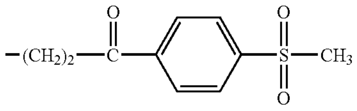 |
| 372 | 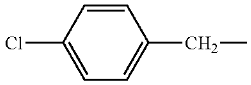 | 1 | 3 | 0 | — | H | 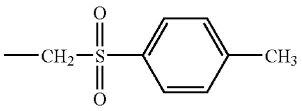 |
| 373 | 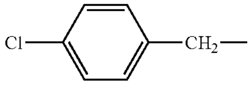 | 1 | 3 | 0 | — | H | 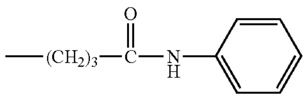 |
| 374 | 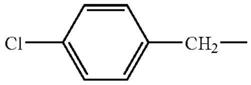 | 1 | 3 | 0 | — | H | 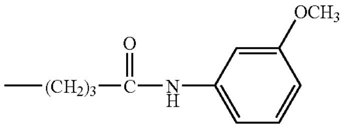 |

TABLE 1.35
| Compd. No. | 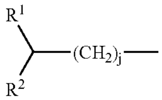 | k | m | n | chirality | R3 | 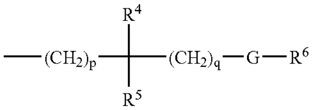 |
|---|---|---|---|---|---|---|---|
| 375 | 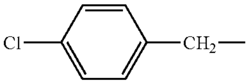 | 1 | 3 | 0 | — | H | 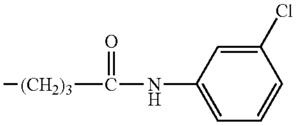 |
| 376 | 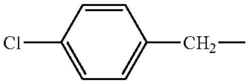 | 1 | 3 | 0 | — | H | 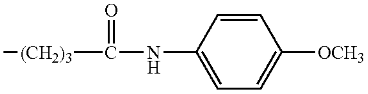 |
| 377 | 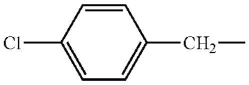 | 1 | 3 | 0 | — | H | 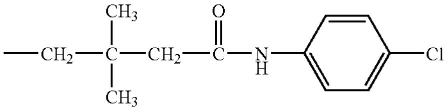 |
| 378 | 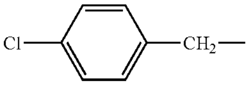 | 1 | 3 | 0 | — | H | 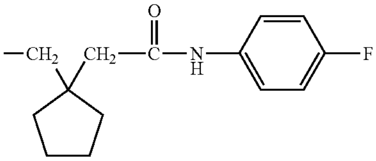 |
| 379 | 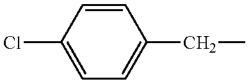 | 1 | 3 | 0 | — | H | 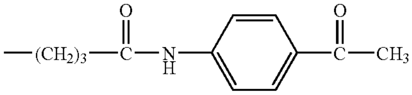 |
| 380 | 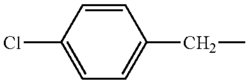 | 1 | 3 | 0 | — | H | 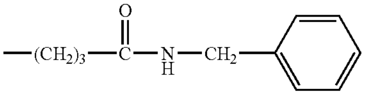 |
| 381 | 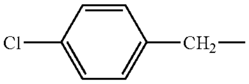 | 1 | 3 | 0 | — | H | 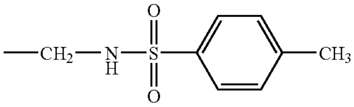 |
| 382 | 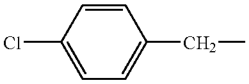 | 1 | 3 | 0 | — | H | 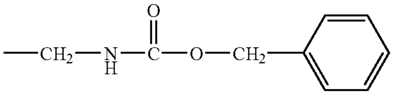 |
| 383 | 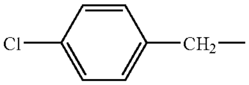 | 1 | 3 | 0 | — | H | 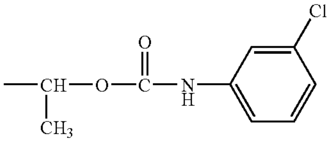 |
| 384 | 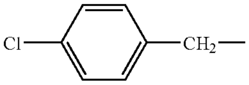 | 2 | 2 | 0 | — | H | 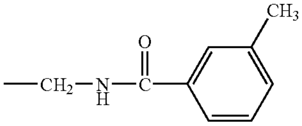 |
| 385 | 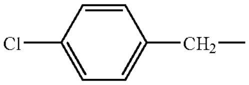 | 2 | 2 | 0 | — | H | 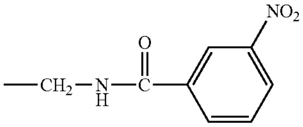 |

TABLE 1.36
| Compd. No. | 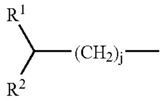 | k | m | n | chirality | $R^3$ | 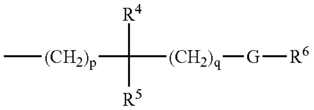 |
|---|---|---|---|---|---|---|---|
| 386 | 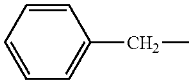 | 2 | 2 | 0 | — | H | 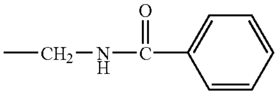 |
| 387 | 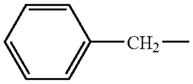 | 2 | 2 | 0 | — | H | 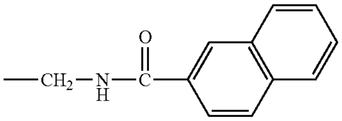 |
| 388 | 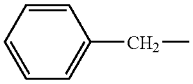 | 2 | 2 | 0 | — | H | 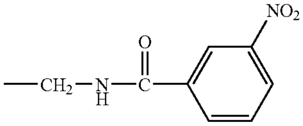 |
| 389 | 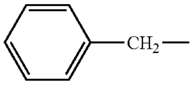 | 2 | 2 | 0 | — | H | 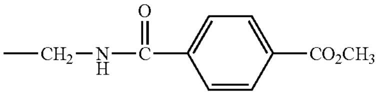 |
| 390 | 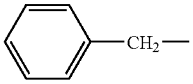 | 2 | 2 | 0 | — | H | 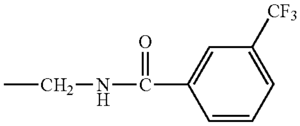 |
| 391 | 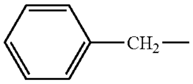 | 2 | 2 | 0 | — | H | 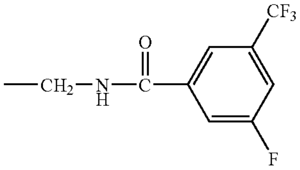 |
| 392 | 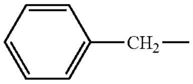 | 2 | 2 | 0 | — | H | 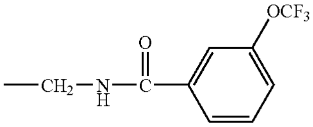 |
| 393 | 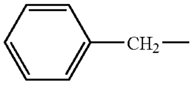 | 2 | 2 | 0 | — | H | 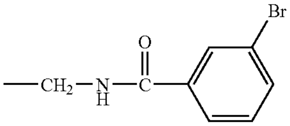 |
| 394 | 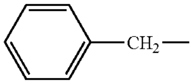 | 2 | 2 | 0 | — | H | 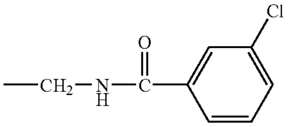 |
| 395 | 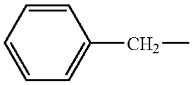 | 2 | 2 | 0 | — | H | 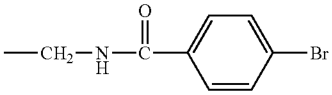 |

TABLE 1.36-continued
| Compd. No. | 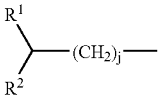 | k | m | n | chirality | $R^3$ | 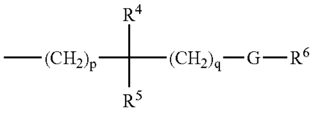 |
|---|---|---|---|---|---|---|---|
| 396 | 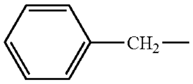 | 2 | 2 | 0 | — | H | 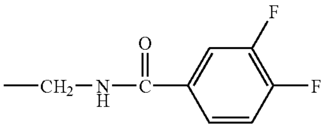 |
TABLE 1.37
| Compd. No. | 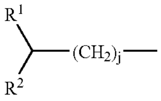 | k | m | n | chirality | $R^3$ | 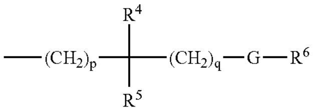 |
|---|---|---|---|---|---|---|---|
| 397 | 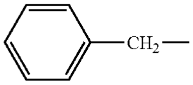 | 2 | 2 | 0 | — | H | 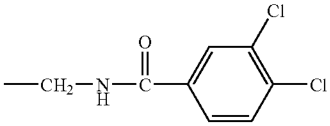 |
| 398 | 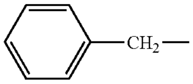 | 2 | 2 | 0 | — | H | 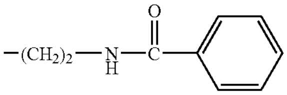 |
| 399 | 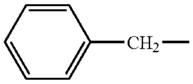 | 2 | 2 | 0 | — | H | 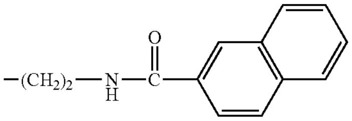 |
| 400 | 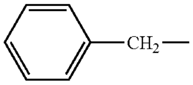 | 2 | 2 | 0 | — | H | 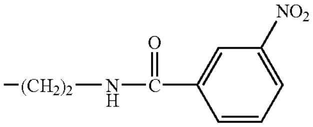 |
| 401 | 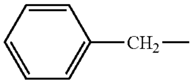 | 2 | 2 | 0 | — | H | 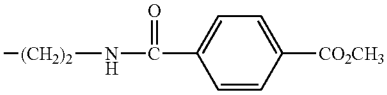 |
| 402 | 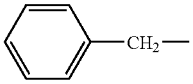 | 2 | 2 | 0 | — | H | 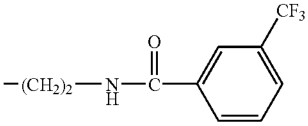 |
| 403 | 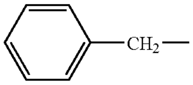 | 2 | 2 | 0 | — | H | 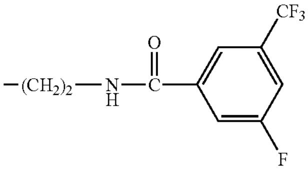 |
| 404 | 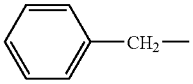 | 2 | 2 | 0 | — | H | 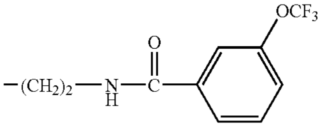 |

TABLE 1.37-continued
| Compd. No. | 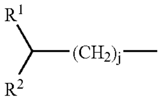 | k | m | n | chirality | $R^3$ | 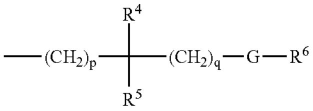 |
|---|---|---|---|---|---|---|---|
| 405 | 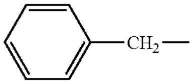 | 2 | 2 | 0 | — | H | 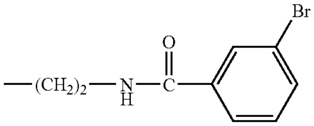 |
| 406 | 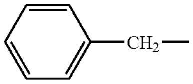 | 2 | 2 | 0 | — | H | 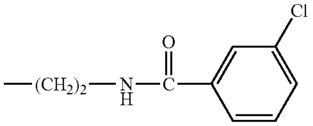 |
| 407 | 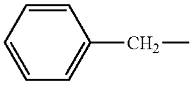 | 2 | 2 | 0 | — | H | 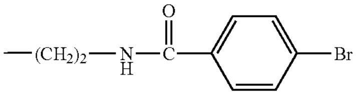 |
TABLE 1.38
| Compd. No. | 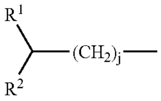 | k | m | n | chirality | $R^3$ | 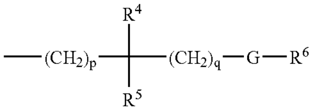 |
|---|---|---|---|---|---|---|---|
| 408 | 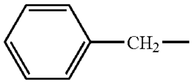 | 2 | 2 | 0 | — | H | 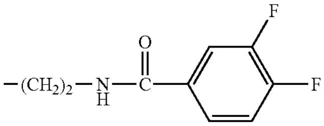 |
| 409 | 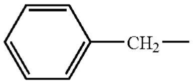 | 2 | 2 | 0 | — | H | 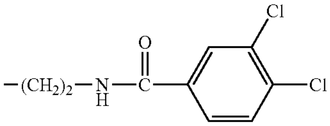 |
| 410 | 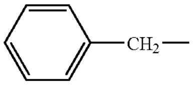 | 2 | 2 | 0 | — | H | 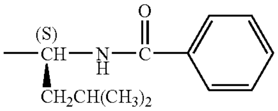 |
| 411 | 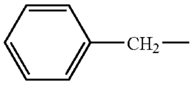 | 2 | 2 | 0 | — | H | 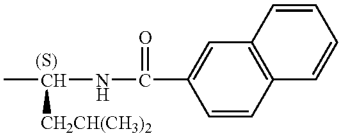 |
| 412 | 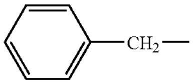 | 2 | 2 | 0 | — | H | 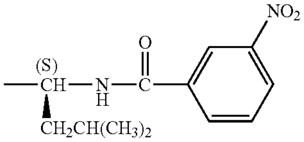 |
| 413 | 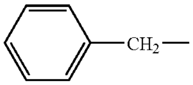 | 2 | 2 | 0 | — | H | 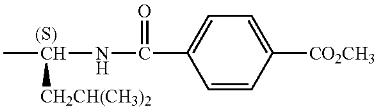 |

TABLE 1.38-continued
| Compd. No. | 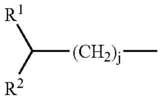 | k | m | n | chirality | $R^3$ | 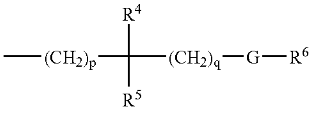 |
|---|---|---|---|---|---|---|---|
| 414 | 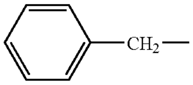 | 2 | 2 | 0 | — | H | 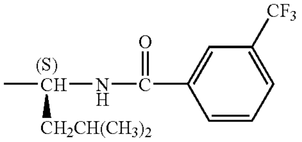 |
| 415 | 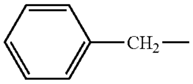 | 2 | 2 | 0 | — | H | 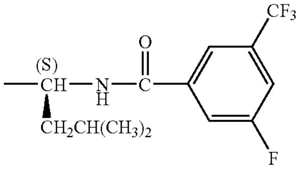 |
| 416 | 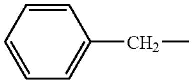 | 2 | 2 | 0 | — | H | 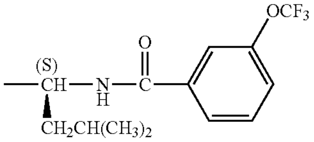 |
| 417 | 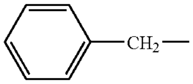 | 2 | 2 | 0 | — | H | 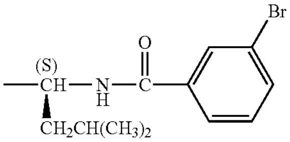 |
| 418 | 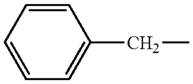 | 2 | 2 | 0 | — | H | 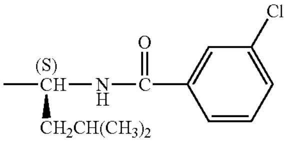 |
TABLE 1.39
| Compd. No. | 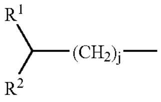 | k | m | n | chirality | $R^3$ | 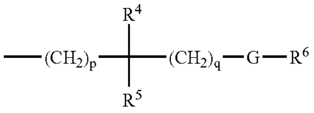 |
|---|---|---|---|---|---|---|---|
| 419 | 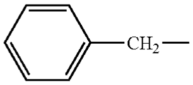 | 2 | 2 | 0 | — | H | 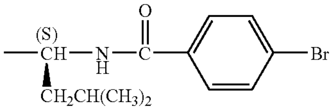 |
| 420 | 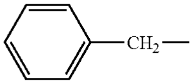 | 2 | 2 | 0 | — | H | 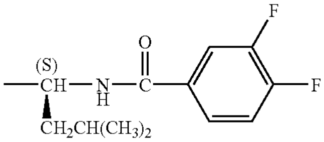 |
| 421 | 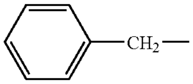 | 2 | 2 | 0 | — | H | 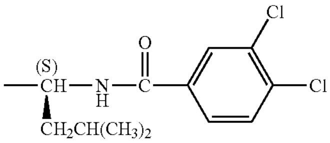 |

TABLE 1.39-continued
| Compd. No. | 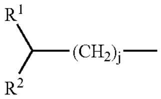 | k | m | n | chirality | $R^3$ | 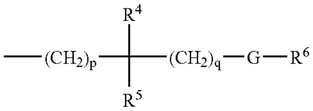 |
|---|---|---|---|---|---|---|---|
| 422 | 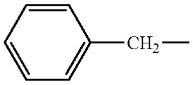 | 2 | 2 | 0 | — | H | 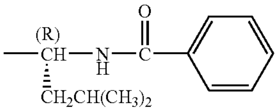 |
| 423 | 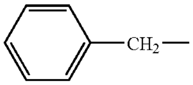 | 2 | 2 | 0 | — | H | 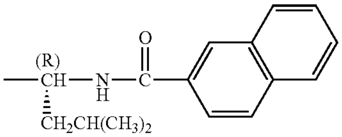 |
| 424 | 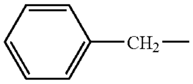 | 2 | 2 | 0 | — | H | 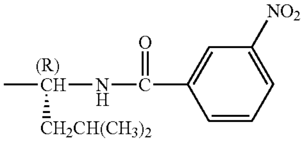 |
| 425 | 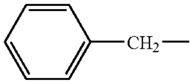 | 2 | 2 | 0 | — | H | 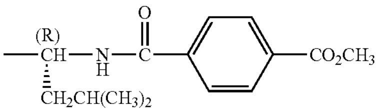 |
| 426 | 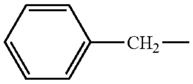 | 2 | 2 | 0 | — | H | 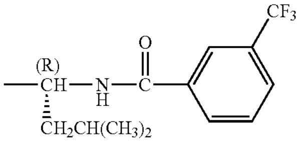 |
| 427 | 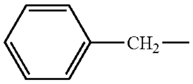 | 2 | 2 | 0 | — | H | 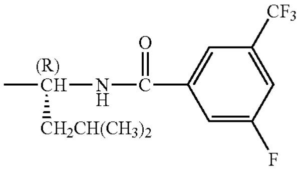 |
| 428 | 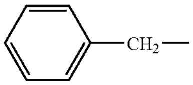 | 2 | 2 | 0 | — | H | 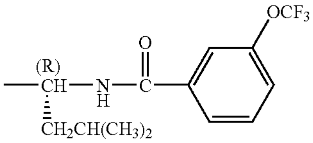 |
| 429 | 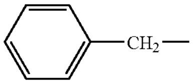 | 2 | 2 | 0 | — | H | 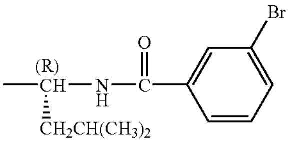 |

TABLE 1.40
| Compd. No. | 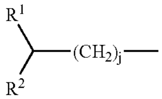 | k | m | n | chirality | R3 | 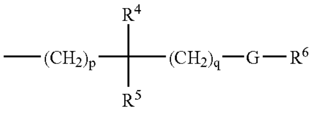 |
|---|---|---|---|---|---|---|---|
| 430 | 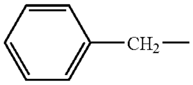 | 2 | 2 | 0 | — | H | 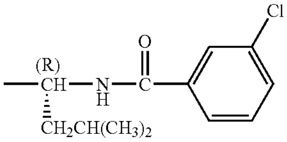 |
| 431 | 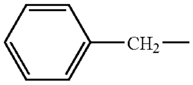 | 2 | 2 | 0 | — | H | 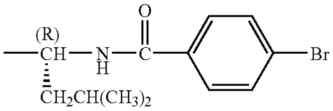 |
| 432 | 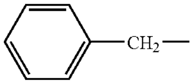 | 2 | 2 | 0 | — | H | 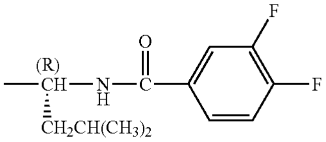 |
| 433 | 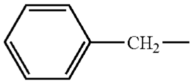 | 2 | 2 | 0 | — | H | 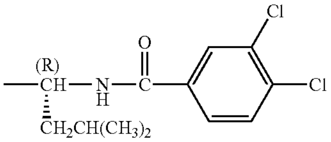 |
| 434 | 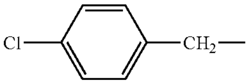 | 1 | 3 | 1 | — | H | 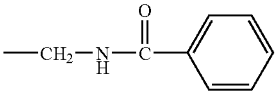 |
| 435 | 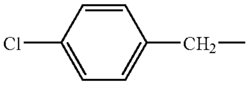 | 1 | 3 | 1 | — | H | 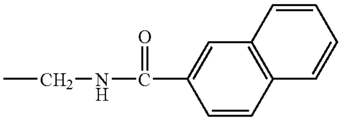 |
| 436 | 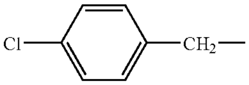 | 1 | 3 | 1 | — | H | 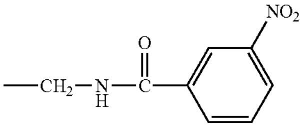 |
| 437 | 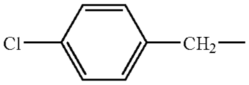 | 1 | 3 | 1 | — | H | 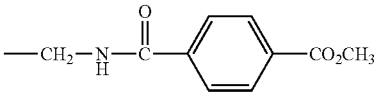 |
| 438 | 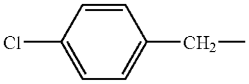 | 1 | 3 | 1 | — | H | 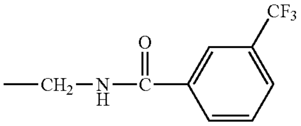 |
| 439 | 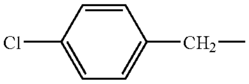 | 1 | 3 | 1 | — | H | 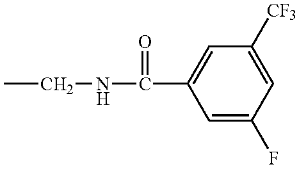 |

TABLE 1.40-continued
| Compd. No. | 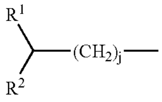 | k | m | n | chirality | $R^3$ | 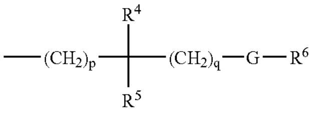 |
|---|---|---|---|---|---|---|---|
| 440 | 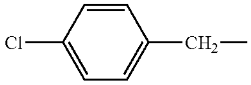 | 1 | 3 | 1 | — | H | 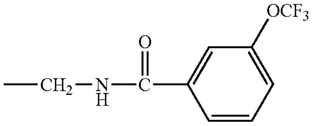 |
TABLE 1.41
| Compd. No. | 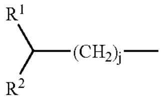 | k | m | n | chirality | $R^3$ | 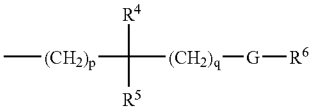 |
|---|---|---|---|---|---|---|---|
| 441 | 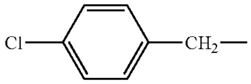 | 1 | 3 | 1 | — | H | 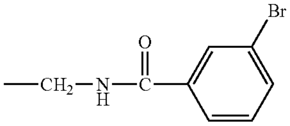 |
| 442 | 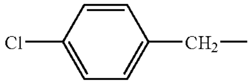 | 1 | 3 | 1 | — | H | 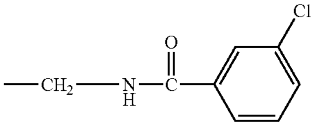 |
| 443 | 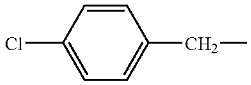 | 1 | 3 | 1 | — | H | 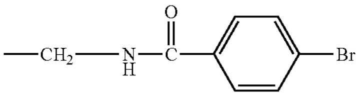 |
| 444 | 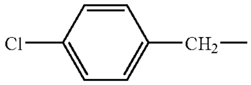 | 1 | 3 | 1 | — | H | 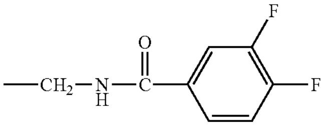 |
| 445 | 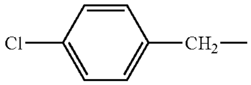 | 1 | 3 | 1 | — | H | 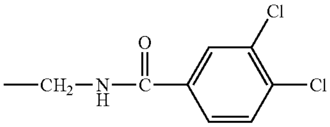 |
| 446 | 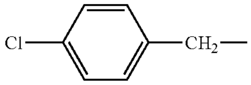 | 1 | 3 | 1 | — | H | 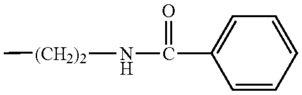 |
| 447 | 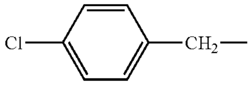 | 1 | 3 | 1 | — | H | 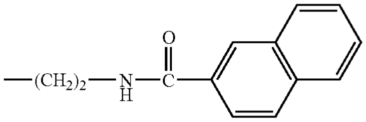 |
| 448 | 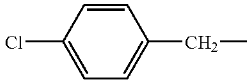 | 1 | 3 | 1 | — | H | 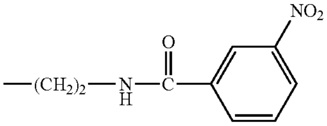 |

TABLE 1.41-continued
| Compd. No. | 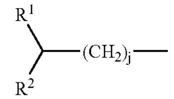 | k | m | n | chirality | $R^3$ | 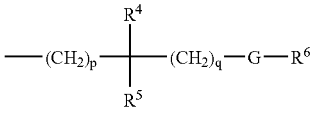 |
|---|---|---|---|---|---|---|---|
| 449 | 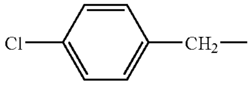 | 1 | 3 | 1 | — | H | 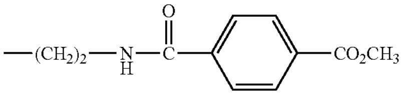 |
| 450 | 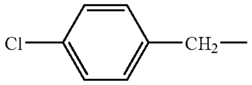 | 1 | 3 | 1 | — | H | 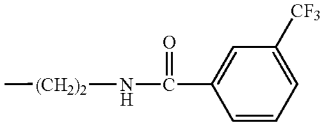 |
| 451 | 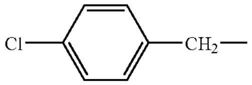 | 1 | 3 | 1 | — | H | 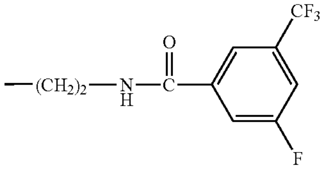 |
TABLE 1.42
| Compd. No. | 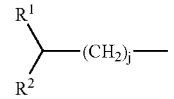 | k | m | n | chirality | $R^3$ | 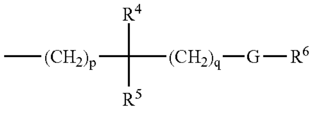 |
|---|---|---|---|---|---|---|---|
| 452 | 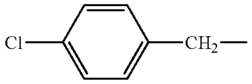 | 1 | 3 | 1 | — | H | 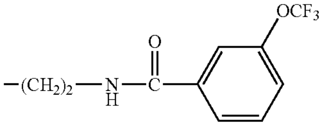 |
| 453 | 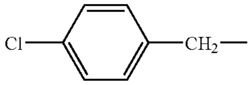 | 1 | 3 | 1 | — | H | 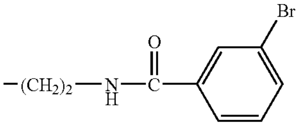 |
| 454 | 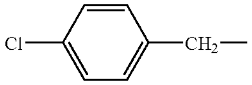 | 1 | 3 | 1 | — | H | 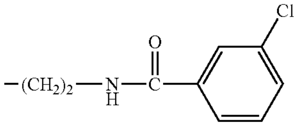 |
| 455 | 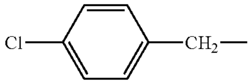 | 1 | 3 | 1 | — | H | 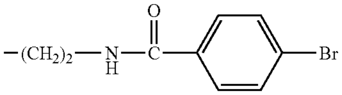 |
| 456 | 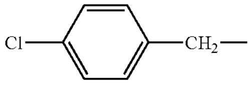 | 1 | 3 | 1 | — | H | 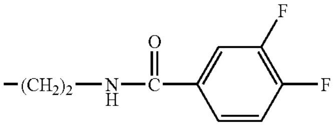 |
| 457 | 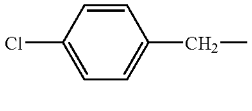 | 1 | 3 | 1 | — | H | 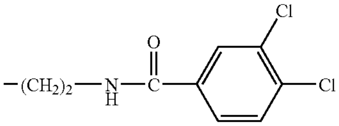 |

TABLE 1.42-continued
| Compd. No. | 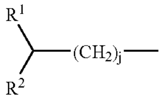 | k | m | n | chirality | $R^3$ | 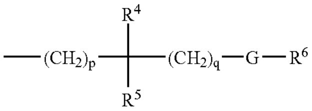 |
|---|---|---|---|---|---|---|---|
| 458 | 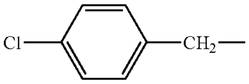 | 2 | 2 | 1 | — | H | 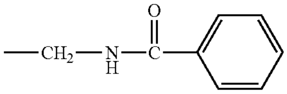 |
| 459 | 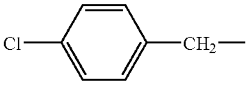 | 2 | 2 | 1 | — | H | 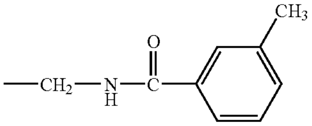 |
| 460 | 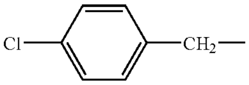 | 2 | 2 | 1 | — | H | 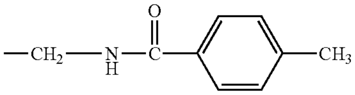 |
| 461 | 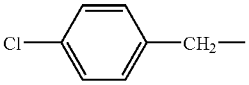 | 2 | 2 | 1 | — | H | 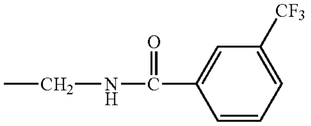 |
| 462 | 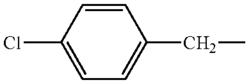 | 2 | 2 | 1 | — | H | 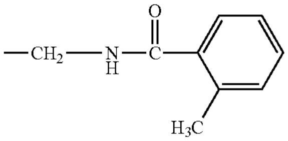 |
TABLE 1.43
| Compd. No. | 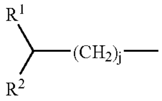 | k | m | n | chirality | $R^3$ | 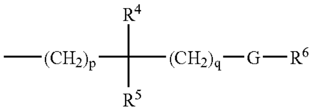 |
|---|---|---|---|---|---|---|---|
| 463 | 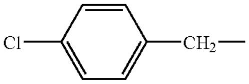 | 2 | 2 | 1 | — | H | 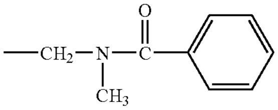 |
| 464 | 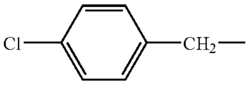 | 2 | 2 | 1 | — | H | 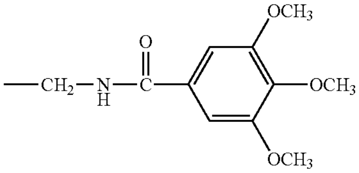 |
| 465 | 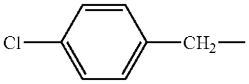 | 2 | 2 | 1 | — | H | 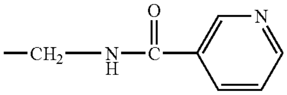 |
| 466 | 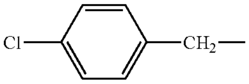 | 2 | 2 | 1 | — | H | 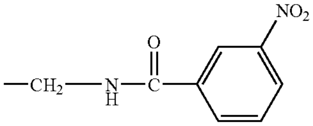 |

TABLE 1.43-continued
| Compd. No. | 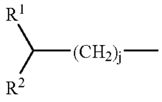 | k | m | n | chirality | $R^3$ | 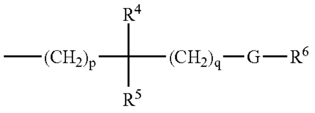 |
|---|---|---|---|---|---|---|---|
| 467 | 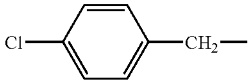 | 2 | 2 | 1 | — | H | 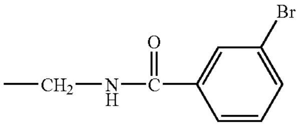 |
| 468 | 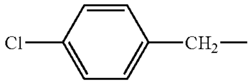 | 2 | 2 | 1 | — | H | 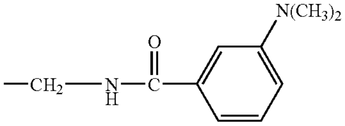 |
| 469 | 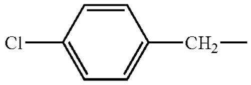 | 2 | 2 | 1 | — | H | 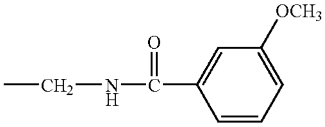 |
| 470 | 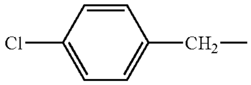 | 2 | 2 | 1 | — | H | 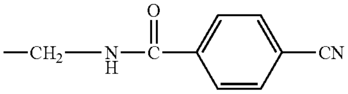 |
| 471 | 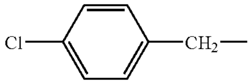 | 2 | 2 | 1 | — | H | 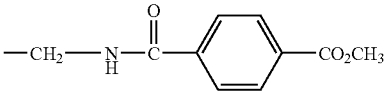 |
| 472 | 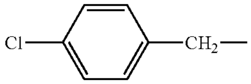 | 2 | 2 | 1 | — | H | 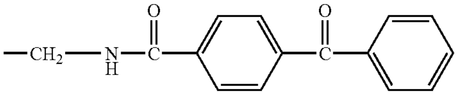 |
| 473 | 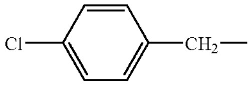 | 2 | 2 | 1 | — | H | 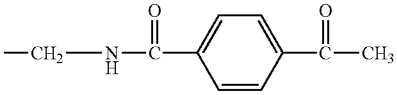 |
TABLE 1.44
| Compd. No. | 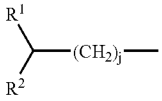 | k | m | n | chirality | $R^3$ | 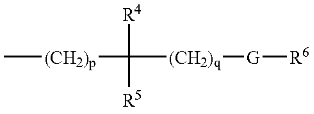 |
|---|---|---|---|---|---|---|---|
| 474 | 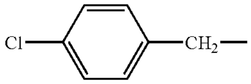 | 2 | 2 | 1 | — | H | 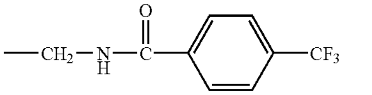 |
| 475 | 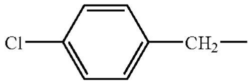 | 2 | 2 | 1 | — | H | 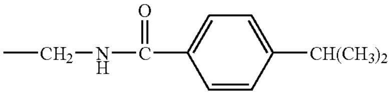 |
| 476 | 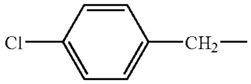 | 2 | 2 | 1 | — | H | 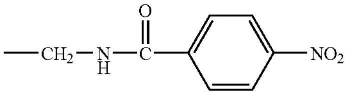 |

TABLE 1.44-continued
| Compd. No. | 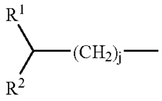 | k | m | n | chirality | $R^3$ | 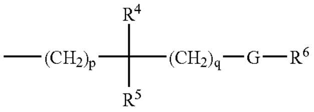 |
|---|---|---|---|---|---|---|---|
| 477 | 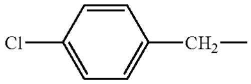 | 2 | 2 | 1 | — | H | 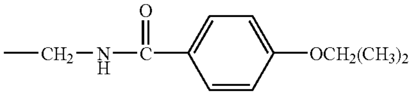 |
| 478 | 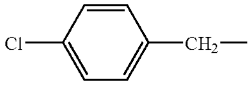 | 2 | 2 | 1 | — | H | 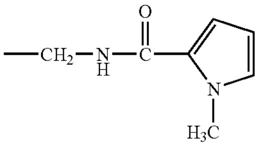 |
| 479 | 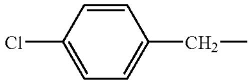 | 2 | 2 | 1 | — | H | 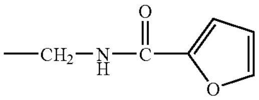 |
| 480 | 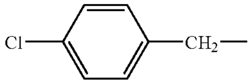 | 2 | 2 | 1 | — | H | 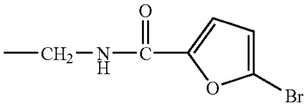 |
| 481 | 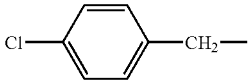 | 2 | 2 | 1 | — | H | 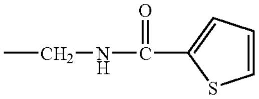 |
| 482 | 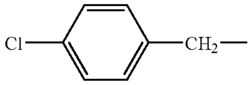 | 2 | 2 | 1 | — | H | 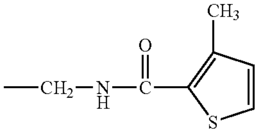 |
| 483 | 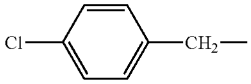 | 2 | 2 | 1 | — | H | 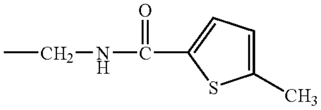 |
| 484 | 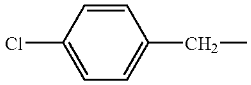 | 2 | 2 | 1 | — | H | 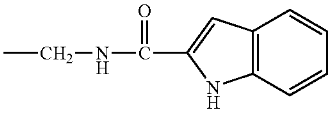 |
TABLE 1.45
| Compd. No. | 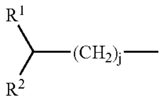 | k | m | n | chirality | $R^3$ | 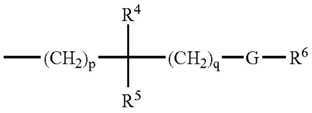 |
|---|---|---|---|---|---|---|---|
| 485 | 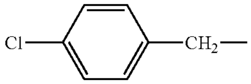 | 2 | 2 | 1 | — | H | 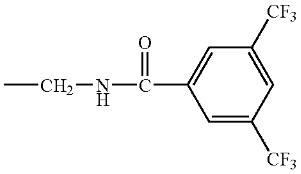 |

TABLE 1.45-continued
| Compd. No. | 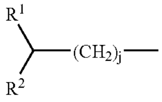 | k | m | n | chirality | $R^3$ | 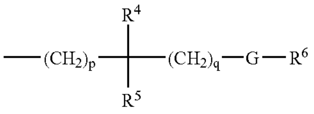 |
|---|---|---|---|---|---|---|---|
| 486 | 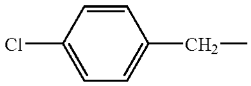 | 2 | 2 | 1 | — | H | 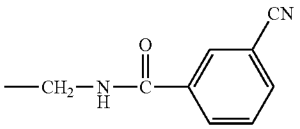 |
| 487 | 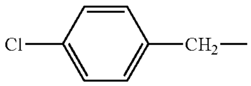 | 2 | 2 | 1 | — | H | 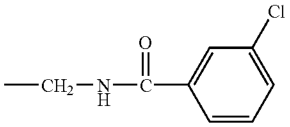 |
| 488 | 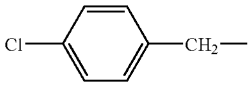 | 2 | 2 | 1 | — | H | 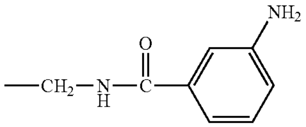 |
| 489 | 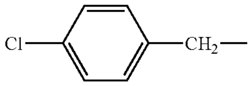 | 2 | 2 | 1 | — | H | 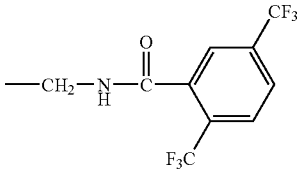 |
| 490 | 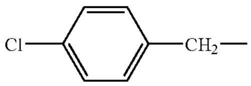 | 2 | 2 | 1 | — | H | 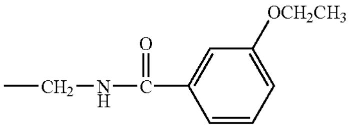 |
| 491 | 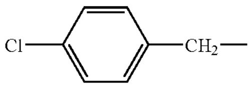 | 2 | 2 | 1 | — | H | 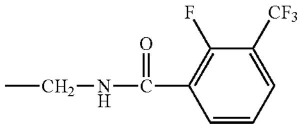 |
| 492 | 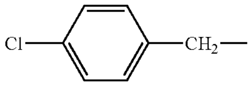 | 2 | 2 | 1 | — | H | 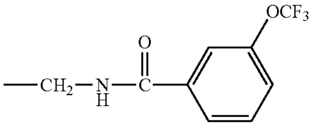 |
| 493 | 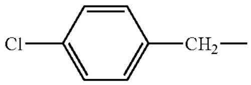 | 2 | 2 | 1 | — | H | 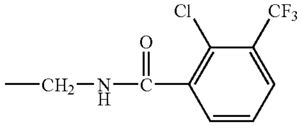 |
| 494 | 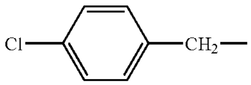 | 2 | 2 | 1 | — | H | 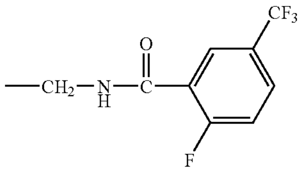 |

TABLE 1.45-continued
| Compd. No. | 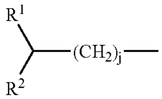 | k | m | n | chirality | $R^3$ | 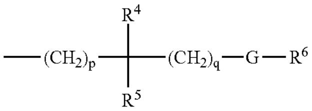 |
|---|---|---|---|---|---|---|---|
| 495 | 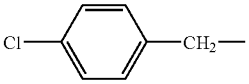 | 2 | 2 | 1 | — | H | 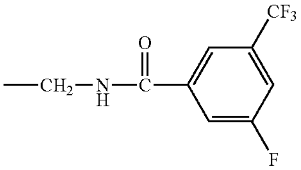 |
TABLE 1.46
| Compd. No. | 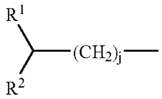 | k | m | n | chirality | $R^3$ | 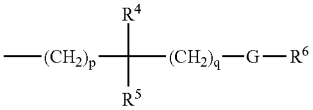 |
|---|---|---|---|---|---|---|---|
| 496 | 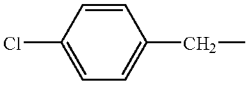 | 2 | 2 | 1 | — | H | 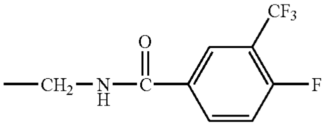 |
| 497 | 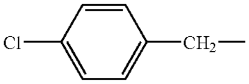 | 2 | 2 | 1 | — | H | 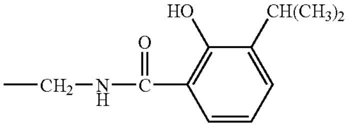 |
| 498 | 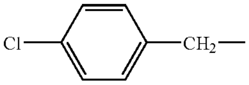 | 2 | 2 | 1 | — | H | 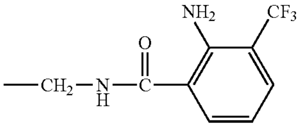 |
| 499 | 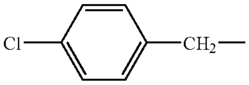 | 2 | 2 | 1 | — | H | 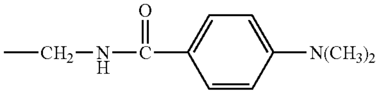 |
| 500 | 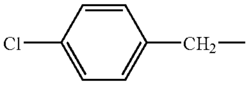 | 2 | 2 | 1 | — | H | 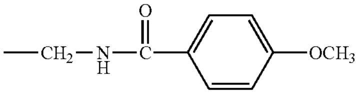 |
| 501 | 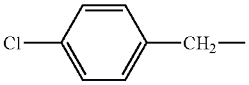 | 2 | 2 | 1 | — | H | 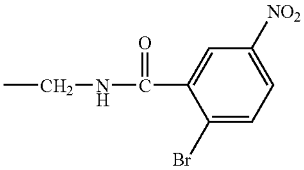 |
| 502 | 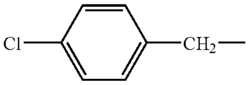 | 2 | 2 | 1 | — | H | 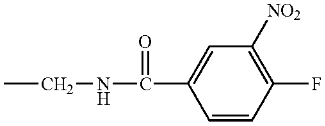 |
| 503 | 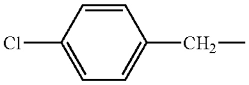 | 2 | 2 | 1 | — | H | 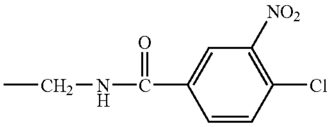 |

TABLE 1.46-continued
| Compd. No. | 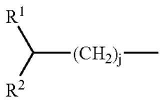 | k | m | n | chirality | $R^3$ | 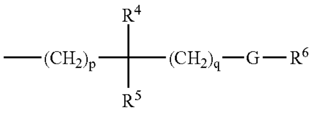 |
|---|---|---|---|---|---|---|---|
| 504 | 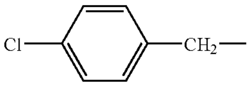 | 2 | 2 | 1 | — | H | 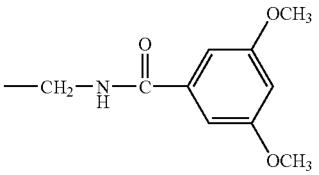 |
| 505 | 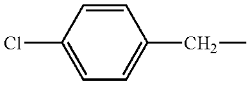 | 2 | 2 | 1 | — | H | 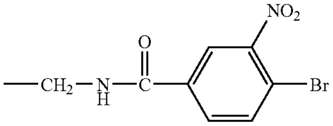 |
| 506 | 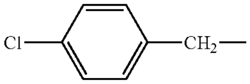 | 2 | 2 | 1 | — | H | 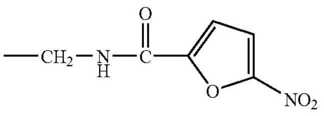 |
TABLE 1.47
| Compd. No. | 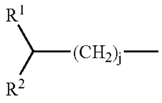 | k | m | n | chirality | $R^3$ | 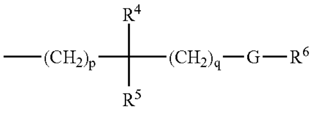 |
|---|---|---|---|---|---|---|---|
| 507 | 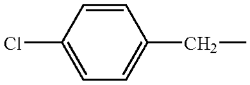 | 2 | 2 | 1 | — | H | 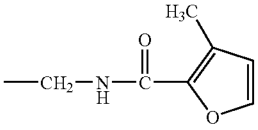 |
| 508 | 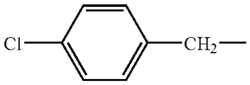 | 2 | 2 | 1 | — | H | 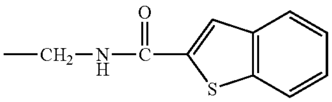 |
| 509 | 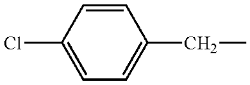 | 2 | 2 | 1 | — | H | 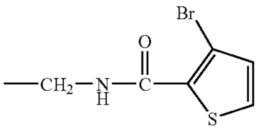 |
| 510 | 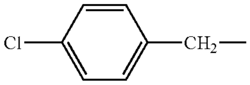 | 2 | 2 | 1 | — | H | 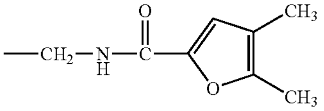 |
| 511 | 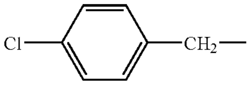 | 2 | 2 | 1 | — | H | 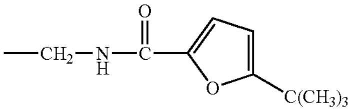 |

TABLE 1.47-continued
| Compd. No. | 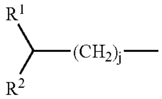 | k | m | n | chirality | $R^3$ | 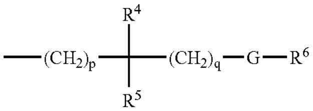 |
|---|---|---|---|---|---|---|---|
| 512 | 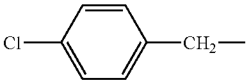 | 2 | 2 | 1 | — | H | 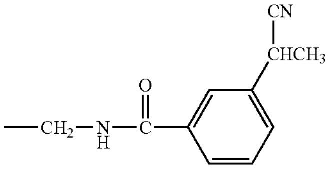 |
| 513 | 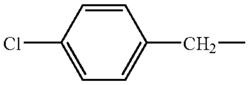 | 2 | 2 | 1 | — | H | 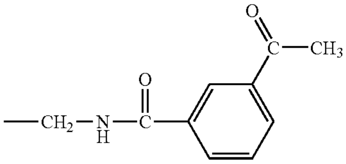 |
| 514 | 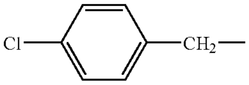 | 2 | 2 | 1 | — | H | 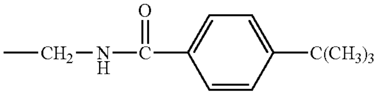 |
| 515 | 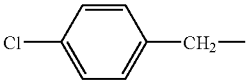 | 2 | 2 | 1 | — | H | 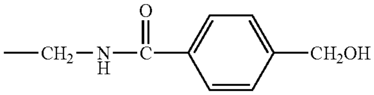 |
| 516 | 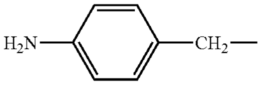 | 2 | 2 | 1 | — | H | 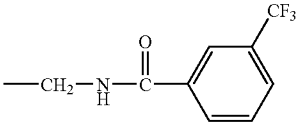 |
| 517 | 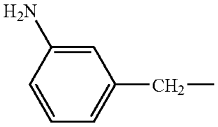 | 2 | 2 | 1 | — | H | 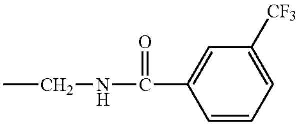 |
TABLE 1.48
| Compd. No. | 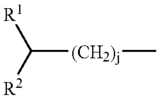 | k | m | n | chirality | $R^3$ | 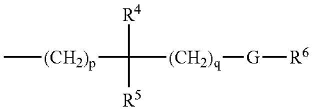 |
|---|---|---|---|---|---|---|---|
| 518 | 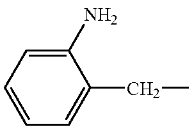 | 2 | 2 | 1 | — | H | 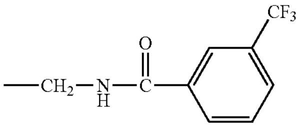 |
| 519 | 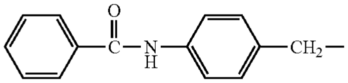 | 2 | 2 | 1 | — | H | 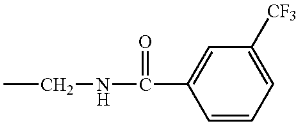 |
| 520 | 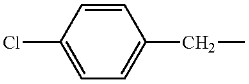 | 2 | 2 | 1 | — | —$CH_3$ | 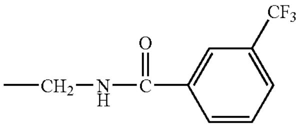 |

TABLE 1.48-continued
| Compd. No. | 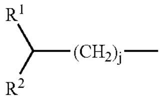 | k | m | n | chirality | $R^3$ | 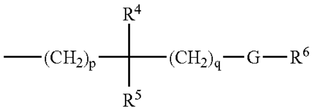 |
|---|---|---|---|---|---|---|---|
| 521 | 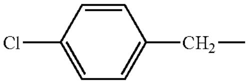 | 2 | 2 | 1 | — | 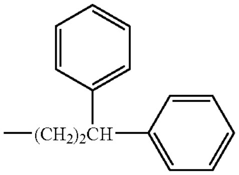 | 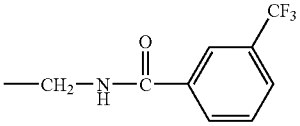 |
| 522 | 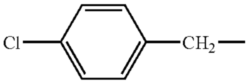 | 2 | 2 | 1 | — | 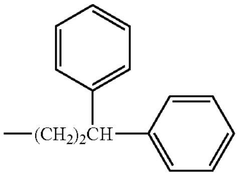 | 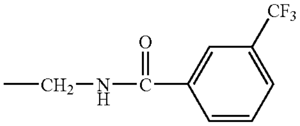 |
| 523 | 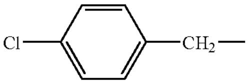 | 2 | 2 | 1 | — | 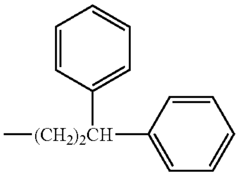 | 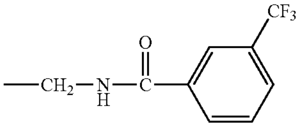 |
| 524 | 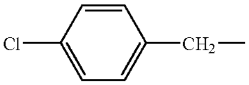 | 2 | 2 | 1 | — | 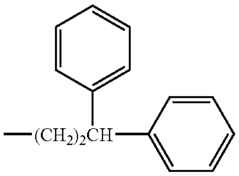 | 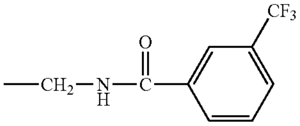 |
| 525 | 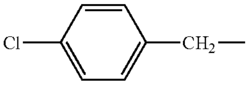 | 2 | 2 | 1 | — | H | 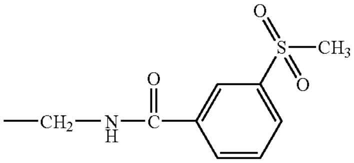 |
| 526 | 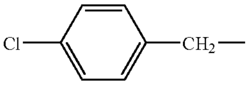 | 2 | 2 | 1 | — | H | 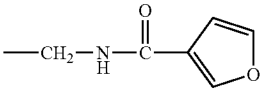 |
| 527 | 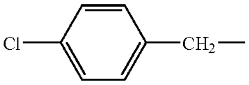 | 2 | 2 | 1 | — | H | 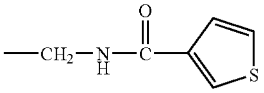 |
| 528 | 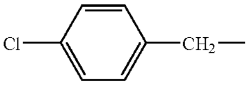 | 2 | 2 | 1 | — | H | 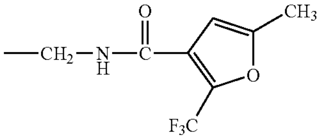 |

TABLE 1.49
| Compd. No. | 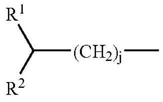 | k | m | n | chirality | $R^3$ | 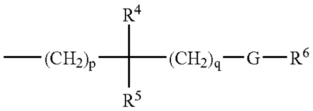 |
|---|---|---|---|---|---|---|---|
| 529 | 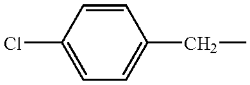 | 2 | 2 | 1 | — | H | 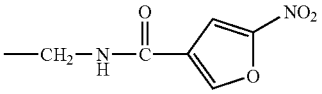 |
| 530 | 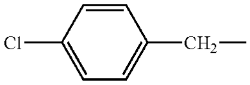 | 2 | 2 | 1 | — | H | 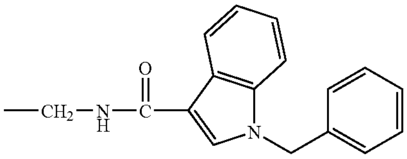 |
| 531 | 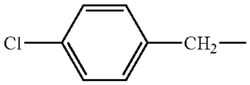 | 2 | 2 | 1 | — | H | 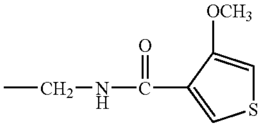 |
| 532 | 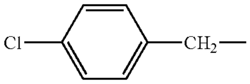 | 2 | 2 | 1 | — | H | 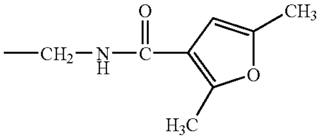 |
| 533 | 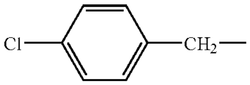 | 2 | 2 | 1 | — | H | 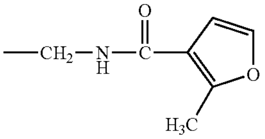 |
| 534 | 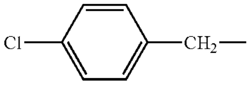 | 2 | 2 | 1 | — | H | 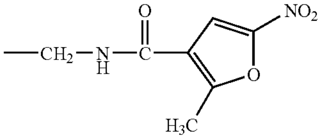 |
| 535 | 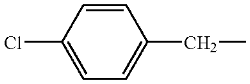 | 2 | 2 | 1 | — | H | 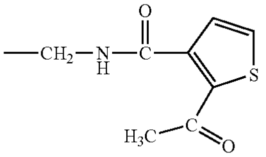 |
| 536 | 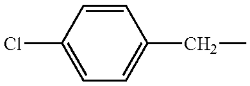 | 2 | 2 | 1 | — | H | 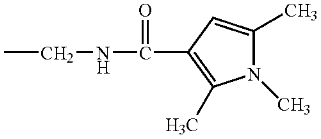 |
| 537 | 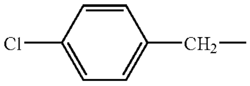 | 2 | 2 | 1 | — | H | 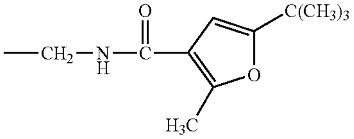 |

TABLE 1.49-continued
| Compd. No. | 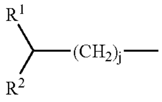 | k | m | n | chirality | $R^3$ | 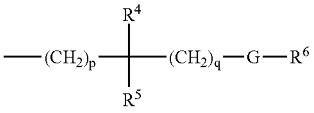 |
|---|---|---|---|---|---|---|---|
| 538 | 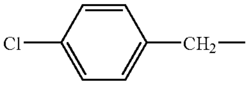 | 2 | 2 | 1 | — | H | 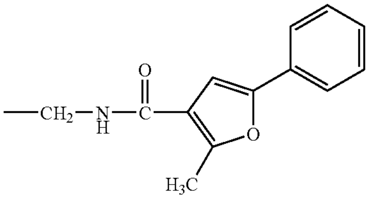 |
| 539 | 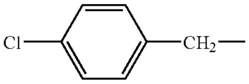 | 2 | 2 | 1 | — | H | 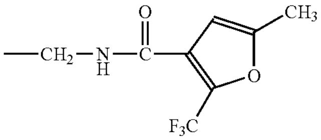 |
TABLE 1.50
| Compd. No. | 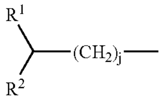 | k | m | n | chirality | $R^3$ | 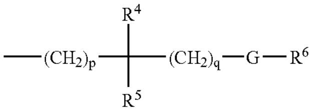 |
|---|---|---|---|---|---|---|---|
| 540 | 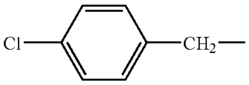 | 2 | 2 | 1 | — | H | 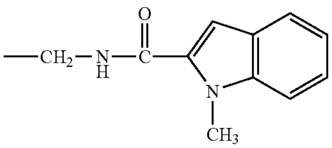 |
| 541 | 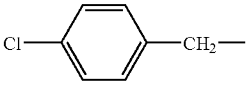 | 2 | 2 | 1 | — | H | 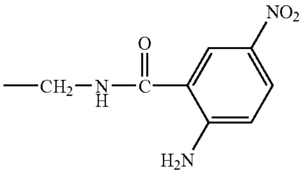 |
| 542 | 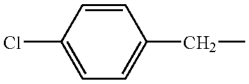 | 2 | 2 | 1 | — | H | 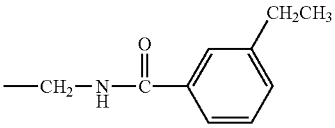 |
| 543 | 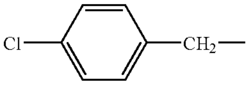 | 2 | 2 | 1 | — | H | 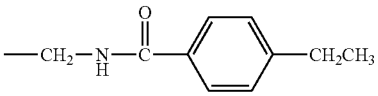 |
| 544 | 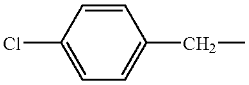 | 2 | 2 | 1 | — | H | 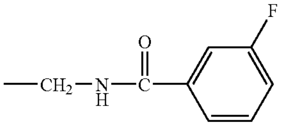 |

TABLE 1.50-continued
| Compd. No. | 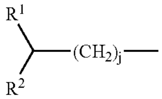 | k | m | n | chirality | $R^3$ | 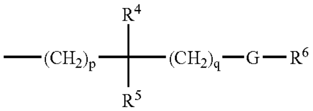 |
|---|---|---|---|---|---|---|---|
| 545 | 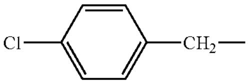 | 2 | 2 | 1 | — | H | 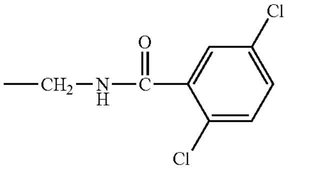 |
| 546 | 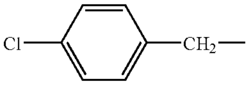 | 2 | 2 | 1 | — | H | 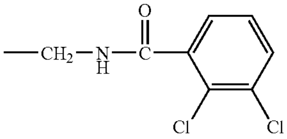 |
| 547 | 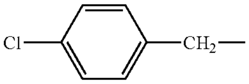 | 2 | 2 | 1 | — | H | 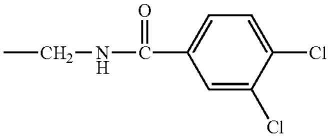 |
| 548 | 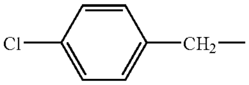 | 2 | 2 | 1 | — | H | 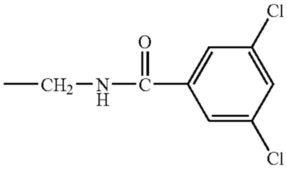 |
| 549 | 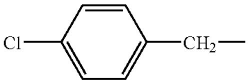 | 2 | 2 | 1 | — | H | 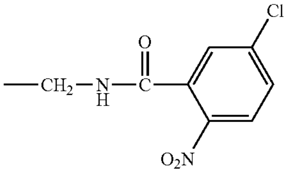 |
| 550 | 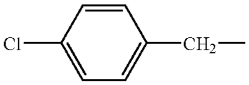 | 2 | 2 | 1 | — | H | 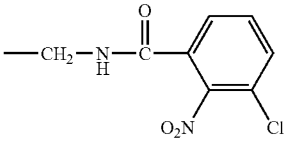 |
TABLE 1.51
| Compd. No. | 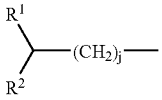 | k | m | n | chirality | $R^3$ | 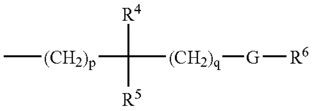 |
|---|---|---|---|---|---|---|---|
| 551 | 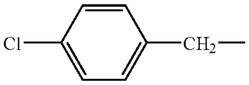 | 2 | 2 | 1 | — | H | 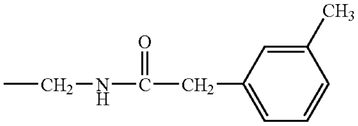 |
| 552 | 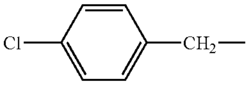 | 2 | 2 | 1 | — | H | 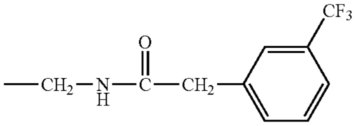 |

TABLE 1.51-continued
| Compd. No. | 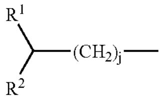 | k | m | n | chirality | $R^3$ | 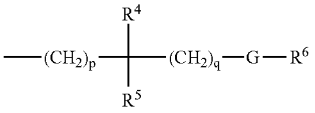 |
|---|---|---|---|---|---|---|---|
| 553 | 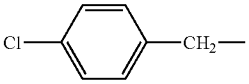 | 2 | 2 | 1 | — | H | 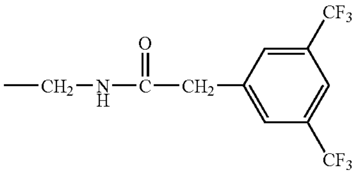 |
| 554 | 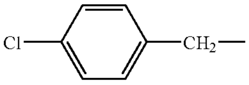 | 2 | 2 | 1 | — | H | 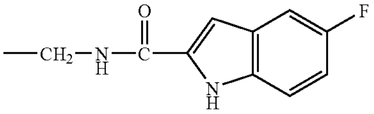 |
| 555 | 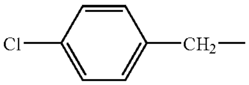 | 2 | 2 | 1 | — | H | 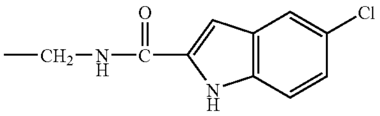 |
| 556 | 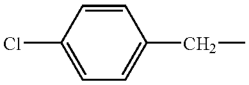 | 2 | 2 | 1 | — | H | 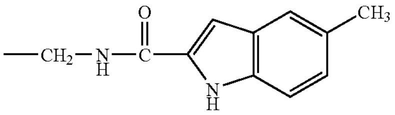 |
| 557 | 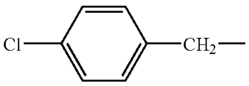 | 2 | 2 | 1 | — | H | 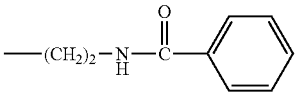 |
| 558 | 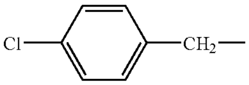 | 2 | 2 | 1 | — | H | 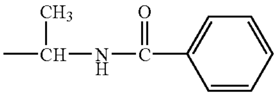 |
| 559 | 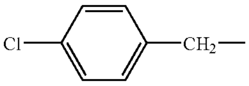 | 2 | 2 | 1 | — | H | 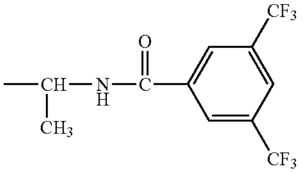 |
| 560 | 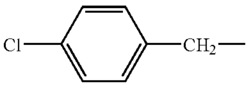 | 2 | 2 | 1 | — | H | 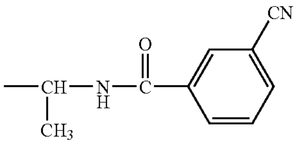 |
| 561 | 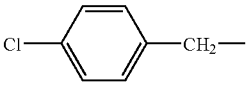 | 2 | 2 | 1 | — | H | 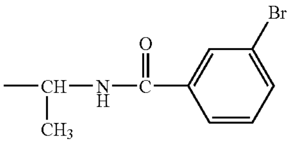 |

TABLE 1.52
| Compd. No. | 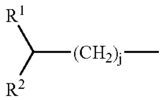 | k | m | n | chirality | $R^3$ | 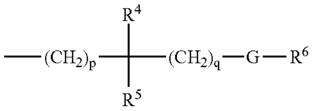 |
|---|---|---|---|---|---|---|---|
| 562 | 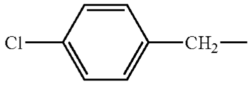 | 2 | 2 | 1 | — | H | 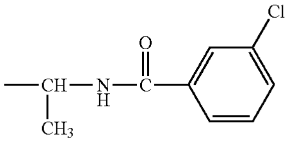 |
| 563 | 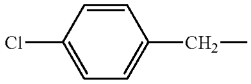 | 2 | 2 | 1 | — | H | 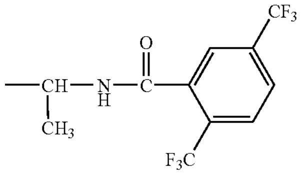 |
| 564 | 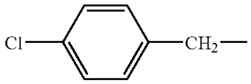 | 2 | 2 | 1 | — | H | 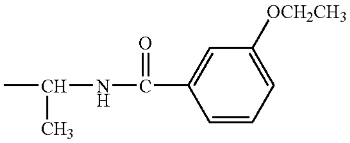 |
| 565 | 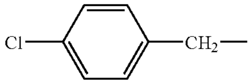 | 2 | 2 | 1 | — | H | 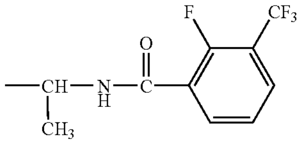 |
| 566 | 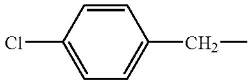 | 2 | 2 | 1 | — | H | 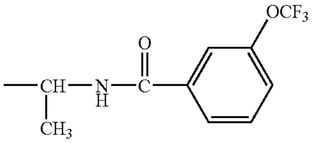 |
| 567 | 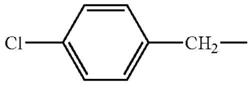 | 2 | 2 | 1 | — | H | 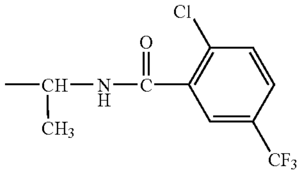 |
| 568 | 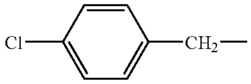 | 2 | 2 | 1 | — | H | 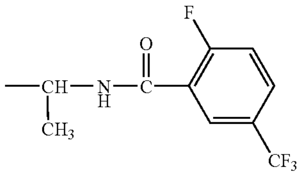 |
| 569 | 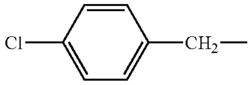 | 2 | 2 | 1 | — | H | 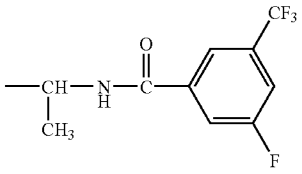 |

TABLE 1.52-continued
| Compd. No. | 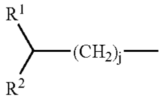 | k | m | n | chirality | $R^3$ | 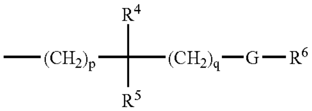 |
|---|---|---|---|---|---|---|---|
| 570 | 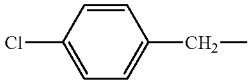 | 2 | 2 | 1 | — | H | 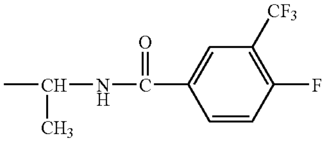 |
| 571 | 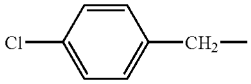 | 2 | 2 | 1 | — | H | 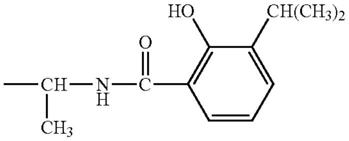 |
| 572 | 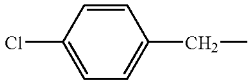 | 2 | 2 | 1 | — | H | 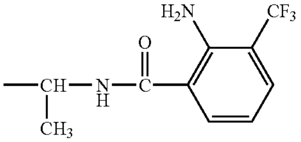 |
TABLE 1.53
| Compd. No. | 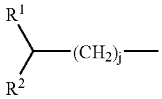 | k | m | n | chirality | $R^3$ | 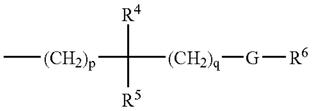 |
|---|---|---|---|---|---|---|---|
| 573 | 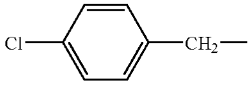 | 2 | 2 | 1 | — | H | 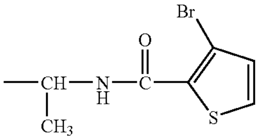 |
| 574 | 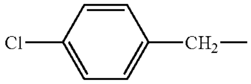 | 2 | 2 | 1 | — | H | 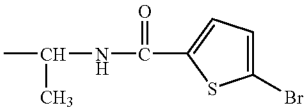 |
| 575 | 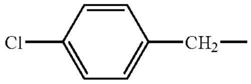 | 2 | 2 | 1 | — | H | 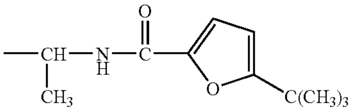 |
| 576 | 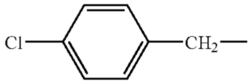 | 2 | 2 | 1 | — | H | 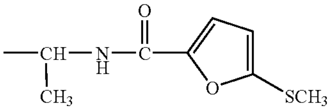 |
| 577 | 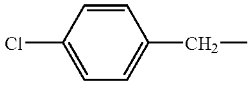 | 2 | 2 | 1 | — | H | 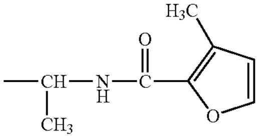 |
| 578 | 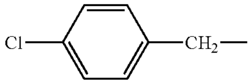 | 2 | 2 | 1 | — | H | 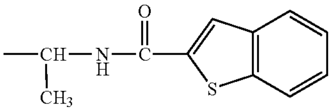 |

TABLE 1.53-continued
| Compd. No. | 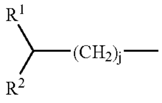 | k | m | n | chirality | $R^3$ | 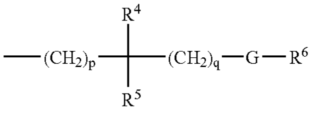 |
|---|---|---|---|---|---|---|---|
| 579 | 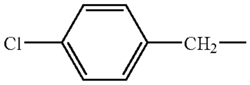 | 2 | 2 | 1 | — | H | 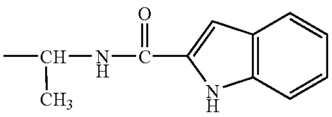 |
| 580 | 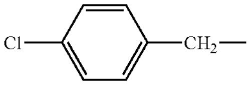 | 2 | 2 | 1 | — | H | 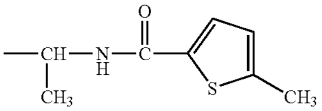 |
| 581 | 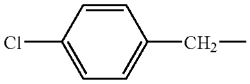 | 2 | 2 | 1 | — | H | 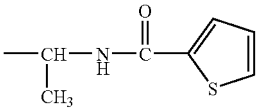 |
| 582 | 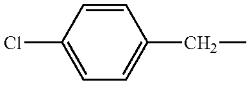 | 2 | 2 | 1 | — | H | 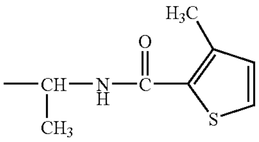 |
| 583 | 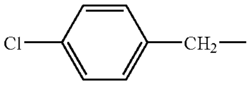 | 2 | 2 | 1 | — | H | 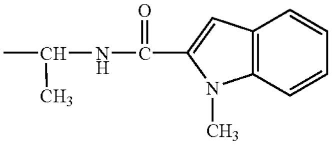 |
TABLE 1.54
| Compd. No. | 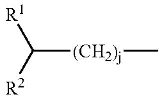 | k | m | n | chirality | $R^3$ | 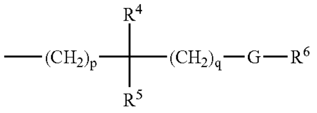 |
|---|---|---|---|---|---|---|---|
| 584 | 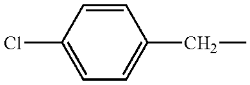 | 2 | 2 | 1 | — | H | 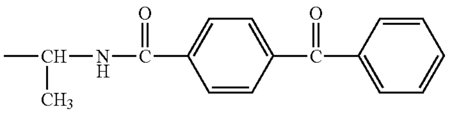 |
| 585 | 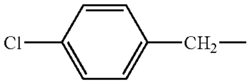 | 2 | 2 | 1 | — | H | 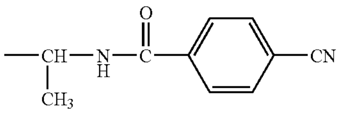 |
| 586 | 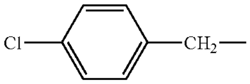 | 2 | 2 | 1 | — | H | 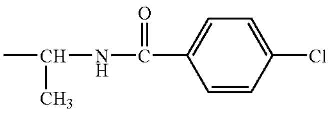 |
| 587 | 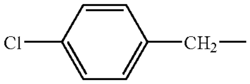 | 2 | 2 | 1 | — | H | 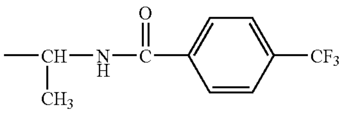 |

TABLE 1.54-continued
| Compd. No. | 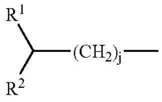 | k | m | n | chirality | $R^3$ | 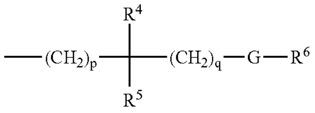 |
|---|---|---|---|---|---|---|---|
| 588 | 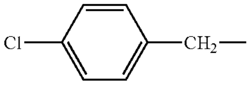 | 2 | 2 | 1 | — | H | 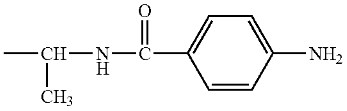 |
| 589 | 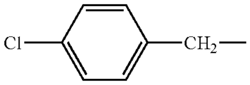 | 2 | 2 | 1 | — | H | 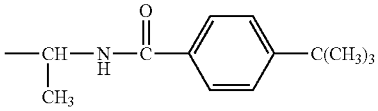 |
| 590 | 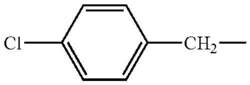 | 2 | 2 | 1 | — | H | 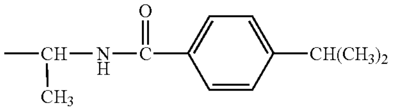 |
| 591 | 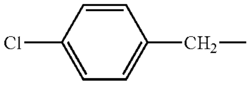 | 2 | 2 | 1 | — | H | 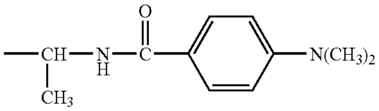 |
| 592 | 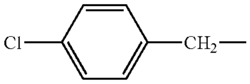 | 2 | 2 | 1 | — | H | 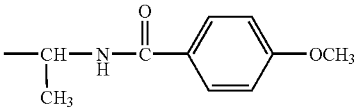 |
| 593 | 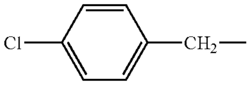 | 2 | 2 | 1 | — | H | 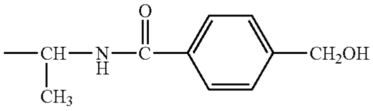 |
| 594 | 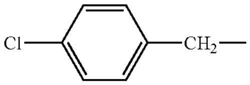 | 2 | 2 | 1 | — | H | 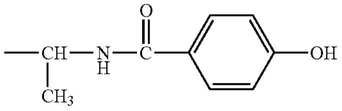 |
TABLE 1.55
| Compd. No. | 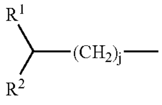 | k | m | n | chirality | $R^3$ | 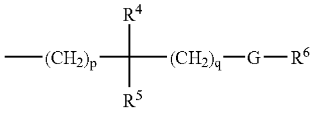 |
|---|---|---|---|---|---|---|---|
| 595 | 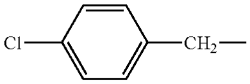 | 2 | 2 | 1 | — | H | 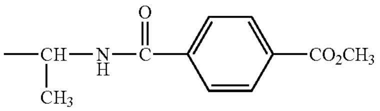 |
| 596 | 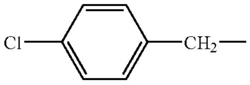 | 2 | 2 | 1 | — | H | 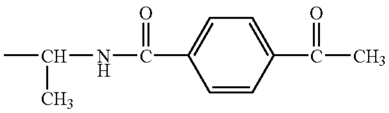 |

TABLE 1.55-continued
| Compd. No. | 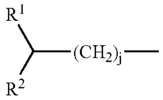 | k | m | n | chirality | $R^3$ | 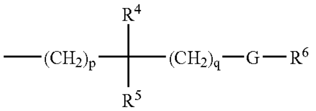 |
|---|---|---|---|---|---|---|---|
| 597 | 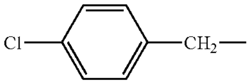 | 2 | 2 | 1 | — | H | 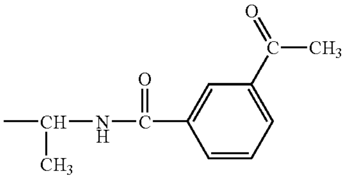 |
| 598 | 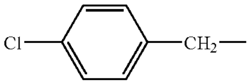 | 2 | 2 | 1 | — | H | 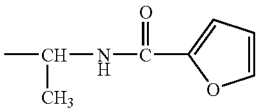 |
| 599 | 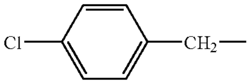 | 2 | 2 | 1 | — | H | 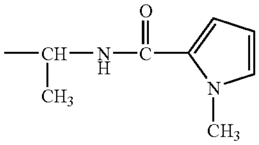 |
| 600 | 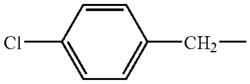 | 2 | 2 | 1 | — | H | 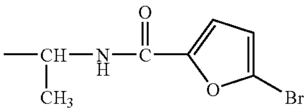 |
| 601 | 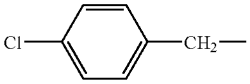 | 2 | 2 | 1 | — | H | 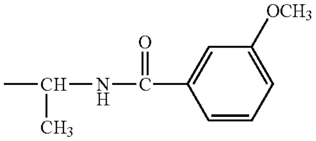 |
| 602 | 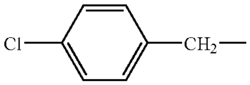 | 2 | 2 | 1 | — | H | 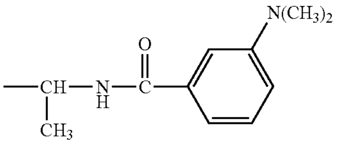 |
| 603 | 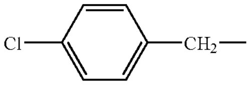 | 2 | 2 | 1 | — | H | 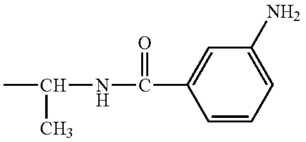 |
| 604 | 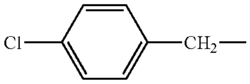 | 2 | 2 | 1 | — | H | 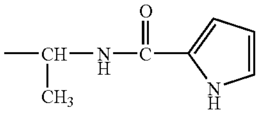 |
| 605 | 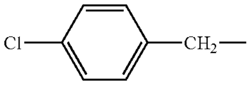 | 2 | 2 | 1 | — | H | 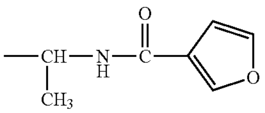 |

TABLE 1.56
| Compd. No. | 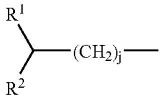 | k | m | n | chirality | $R^3$ | 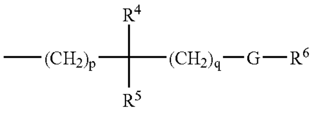 |
|---|---|---|---|---|---|---|---|
| 606 | 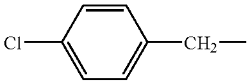 | 2 | 2 | 1 | — | H | 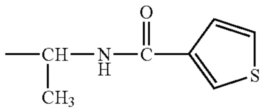 |
| 607 | 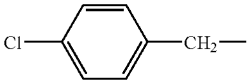 | 2 | 2 | 1 | — | H | 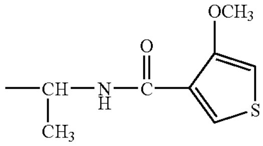 |
| 608 | 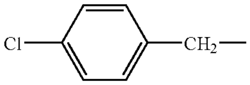 | 2 | 2 | 1 | — | H | 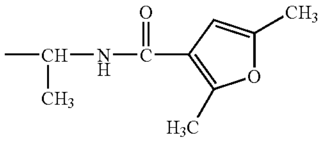 |
| 609 | 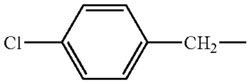 | 2 | 2 | 1 | — | H | 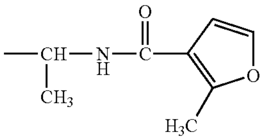 |
| 610 | 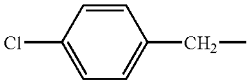 | 2 | 2 | 1 | — | H | 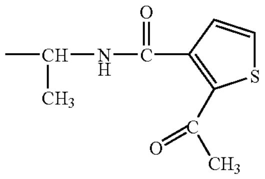 |
| 611 | 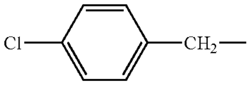 | 2 | 2 | 1 | — | H | 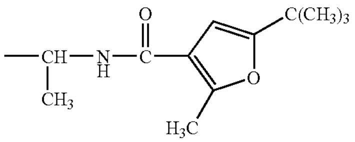 |
| 612 | 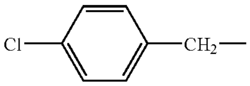 | 2 | 2 | 1 | — | H | 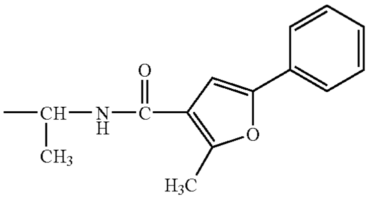 |
| 613 | 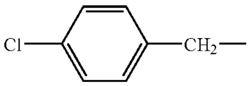 | 2 | 2 | 1 | — | H | 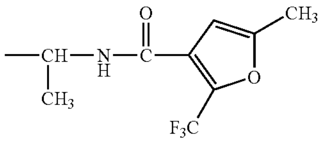 |

TABLE 1.56-continued
| Compd. No. | 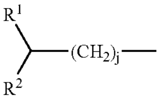 | k | m | n | chirality | $R^3$ | 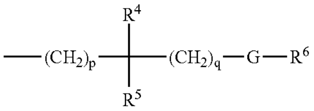 |
|---|---|---|---|---|---|---|---|
| 614 | 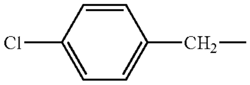 | 2 | 2 | 1 | — | H | 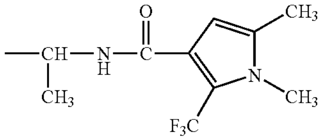 |
| 615 | 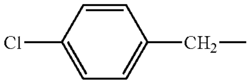 | 2 | 2 | 1 | — | H | 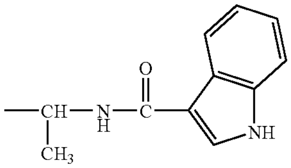 |
| 616 | 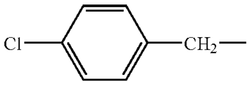 | 2 | 2 | 1 | — | H | 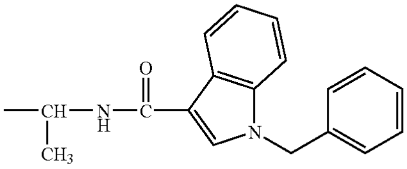 |
TABLE 1.57
| Compd. No. | 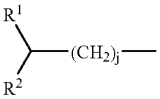 | k | m | n | chirality | $R^3$ | 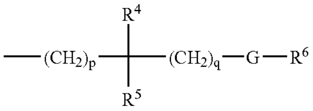 |
|---|---|---|---|---|---|---|---|
| 617 | 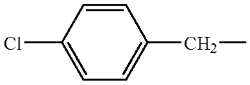 | 2 | 2 | 1 | — | H | 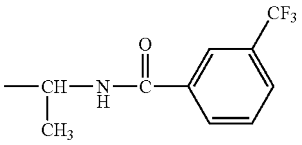 |
| 618 | 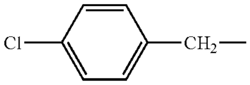 | 2 | 2 | 1 | — | H | 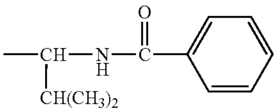 |
| 619 | 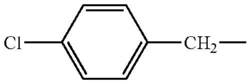 | 2 | 2 | 1 | — | H | 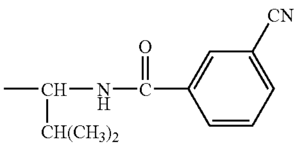 |
| 620 | 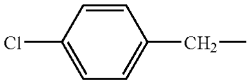 | 2 | 2 | 1 | — | H | 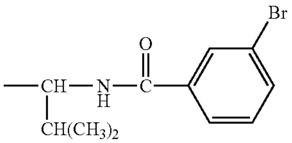 |
| 621 | 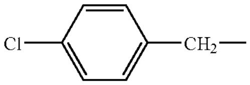 | 2 | 2 | 1 | — | H | 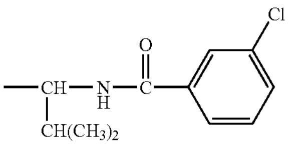 |

TABLE 1.57-continued
| Compd. No. | 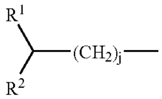 | k | m | n | chirality | $R^3$ | 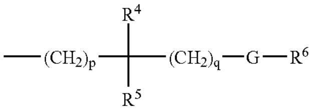 |
|---|---|---|---|---|---|---|---|
| 622 | 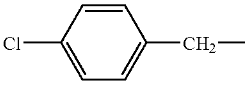 | 2 | 2 | 1 | — | H | 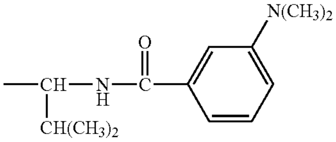 |
| 623 | 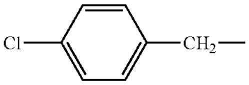 | 2 | 2 | 1 | — | H | 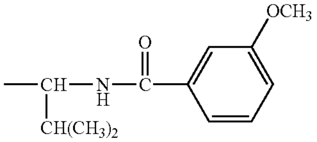 |
| 624 | 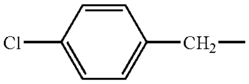 | 2 | 2 | 1 | — | H | 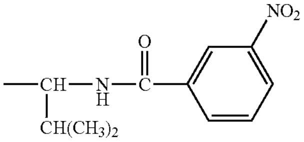 |
| 625 | 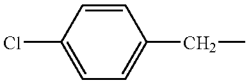 | 2 | 2 | 1 | — | H | 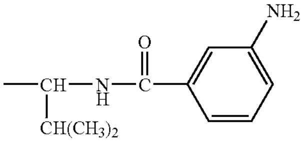 |
| 626 | 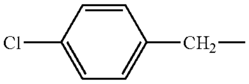 | 2 | 2 | 1 | — | H | 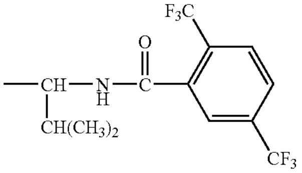 |
| 627 | 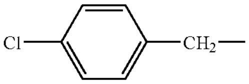 | 2 | 2 | 1 | — | H | 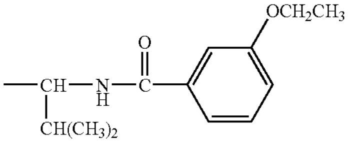 |
TABLE 1.58
| Compd. No. | 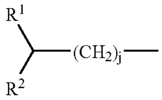 | k | m | n | chirality | $R^3$ | 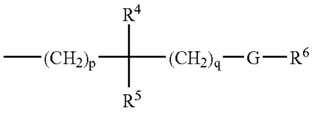 |
|---|---|---|---|---|---|---|---|
| 628 | 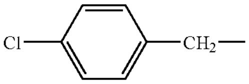 | 2 | 2 | 1 | — | H | 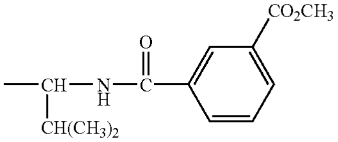 |
| 629 | 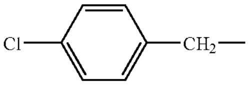 | 2 | 2 | 1 | — | H | 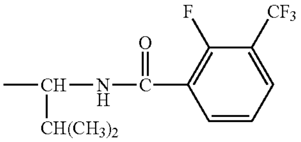 |

TABLE 1.58-continued
| Compd. No. | 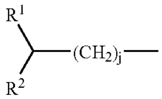 | k | m | n | chirality | $R^3$ | 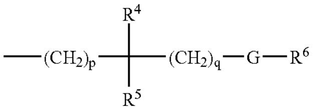 |
|---|---|---|---|---|---|---|---|
| 630 | 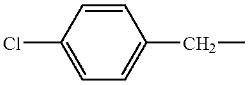 | 2 | 2 | 1 | — | H | 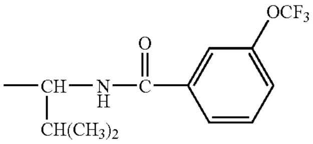 |
| 631 | 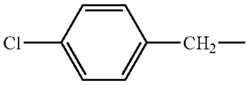 | 2 | 2 | 1 | — | H | 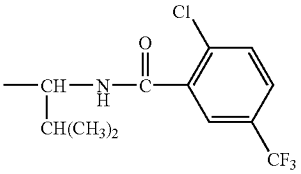 |
| 632 | 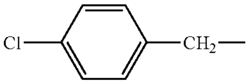 | 2 | 2 | 1 | — | H | 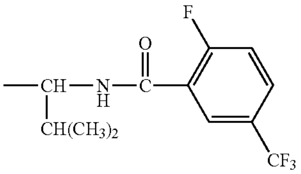 |
| 633 | 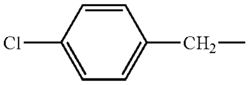 | 2 | 2 | 1 | — | H | 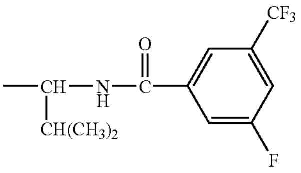 |
| 634 | 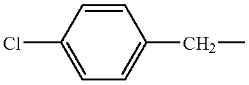 | 2 | 2 | 1 | — | H | 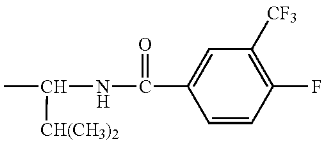 |
| 635 | 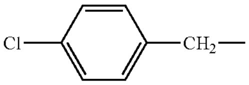 | 2 | 2 | 1 | — | H | 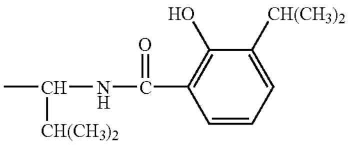 |
| 636 | 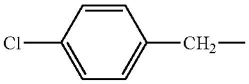 | 2 | 2 | 1 | — | H | 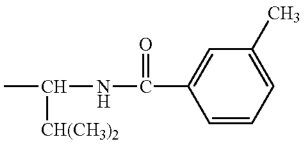 |
| 637 | 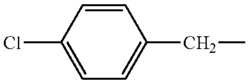 | 2 | 2 | 1 | — | H | 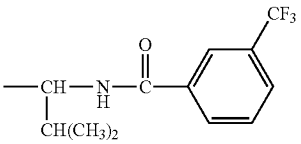 |
| 638 | 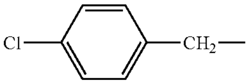 | 2 | 2 | 1 | — | H | 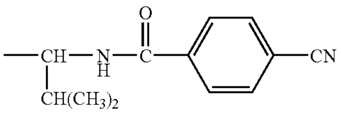 |

TABLE 1.59
| Compd. No. | 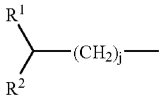 | k | m | n | chirality | $R^3$ | 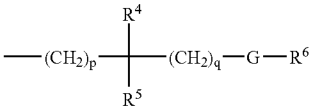 |
|---|---|---|---|---|---|---|---|
| 639 | 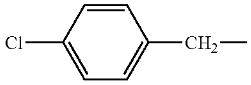 | 2 | 2 | 1 | — | H | 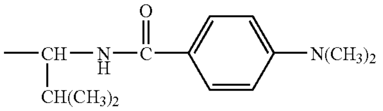 |
| 640 | 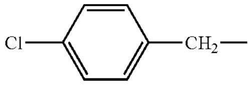 | 2 | 2 | 1 | — | H | 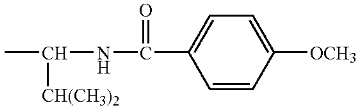 |
| 641 | 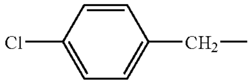 | 2 | 2 | 1 | — | H | 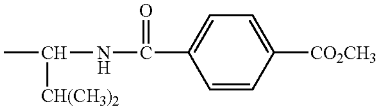 |
| 642 | 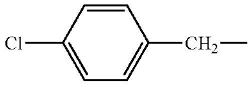 | 2 | 2 | 1 | — | H | 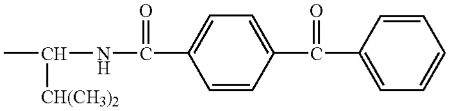 |
| 643 | 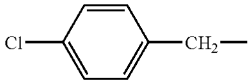 | 2 | 2 | 1 | — | H | 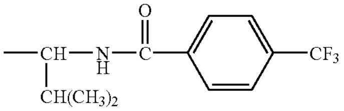 |
| 644 | 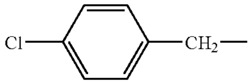 | 2 | 2 | 1 | — | H | 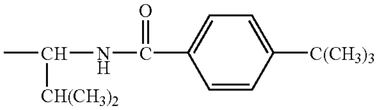 |
| 645 | 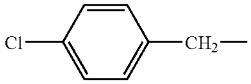 | 2 | 2 | 1 | — | H | 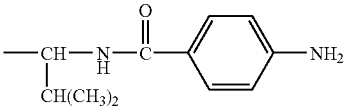 |
| 646 | 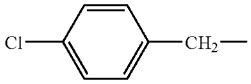 | 2 | 2 | 1 | — | H | 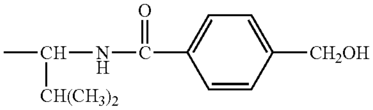 |
| 647 | 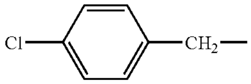 | 2 | 2 | 1 | — | H | 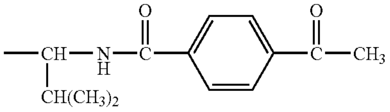 |
| 648 | 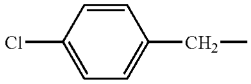 | 2 | 2 | 1 | — | H | 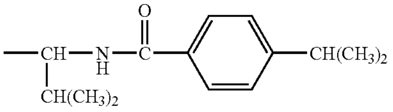 |
| 649 | 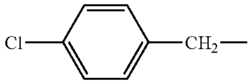 | 2 | 2 | 1 | — | H | 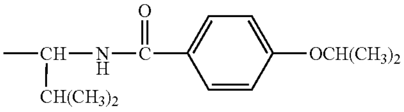 |

TABLE 1.60
| Compd. No. | 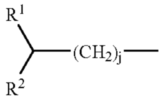 | k | m | n | chirality | R3 | 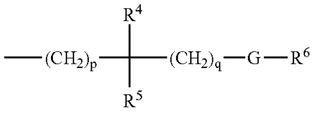 |
|---|---|---|---|---|---|---|---|
| 650 | 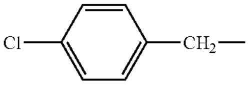 | 2 | 2 | 1 | — | H | 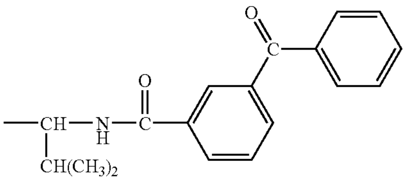 |
| 651 | 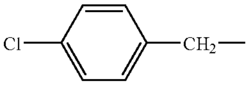 | 2 | 2 | 1 | — | H | 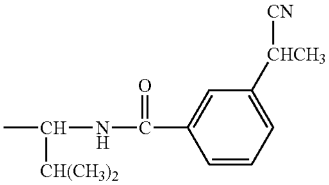 |
| 652 | 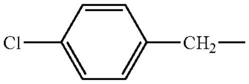 | 2 | 2 | 1 | — | H | 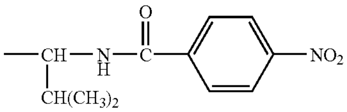 |
| 653 | 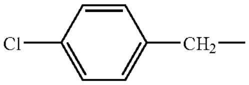 | 2 | 2 | 1 | — | H | 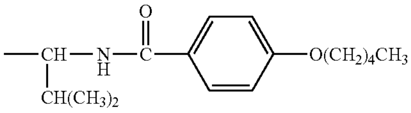 |
| 654 | 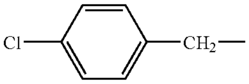 | 2 | 2 | 1 | — | H | 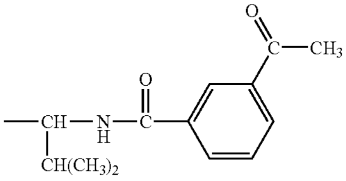 |
| 655 | 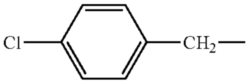 | 2 | 2 | 1 | — | H | 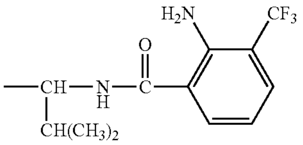 |
| 656 | 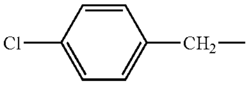 | 2 | 2 | 1 | — | H | 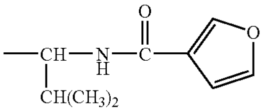 |
| 657 | 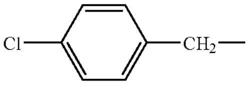 | 2 | 2 | 1 | — | H | 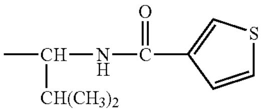 |
| 658 | 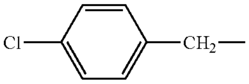 | 2 | 2 | 1 | — | H | 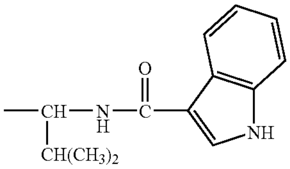 |

TABLE 1.60-continued
| Compd. No. | 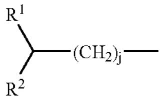 | k | m | n | chirality | $R^3$ | 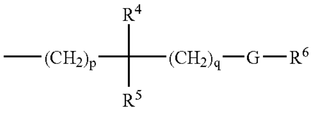 |
|---|---|---|---|---|---|---|---|
| 659 | 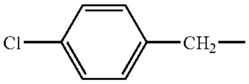 | 2 | 2 | 1 | — | H | 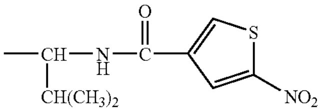 |
| 660 | 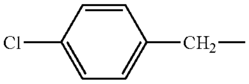 | 2 | 2 | 1 | — | H | 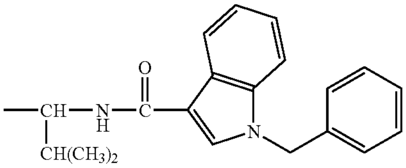 |
TABLE 1.61
| Compd. No. | 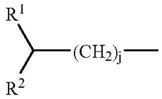 | k | m | n | chirality | $R^3$ | 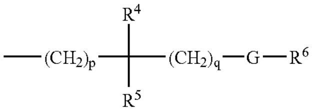 |
|---|---|---|---|---|---|---|---|
| 661 | 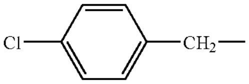 | 2 | 2 | 1 | — | H | 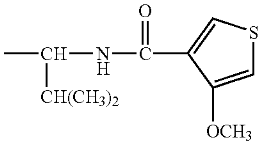 |
| 662 | 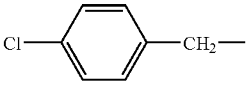 | 2 | 2 | 1 | — | H | 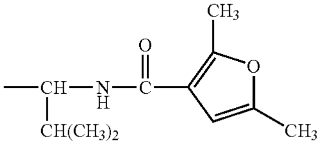 |
| 663 | 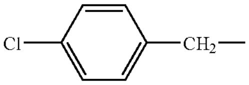 | 2 | 2 | 1 | — | H | 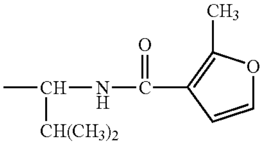 |
| 664 | 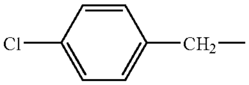 | 2 | 2 | 1 | — | H | 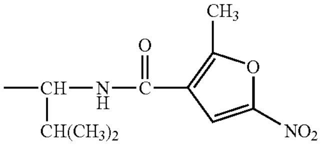 |
| 665 | 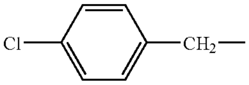 | 2 | 2 | 1 | — | H | 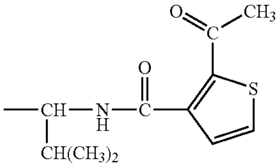 |
| 666 | 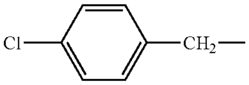 | 2 | 2 | 1 | — | H | 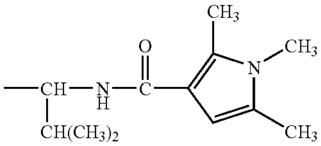 |

TABLE 1.61-continued
| Compd. No. | 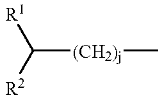 | k | m | n | chirality | $R^3$ | 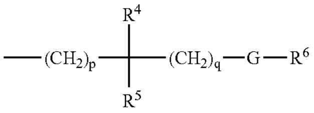 |
|---|---|---|---|---|---|---|---|
| 667 | 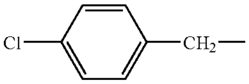 | 2 | 2 | 1 | — | H | 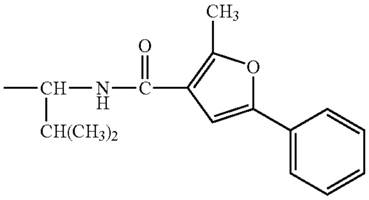 |
| 668 | 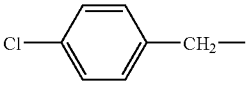 | 2 | 2 | 1 | — | H | 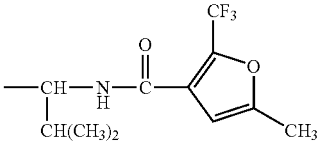 |
| 669 | 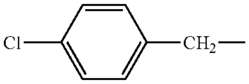 | 2 | 2 | 1 | — | H | 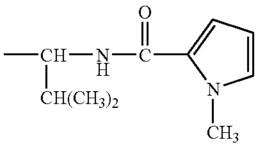 |
| 670 | 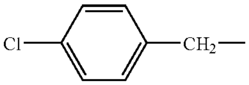 | 2 | 2 | 1 | — | H | 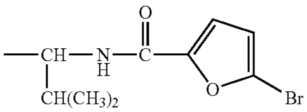 |
| 671 | 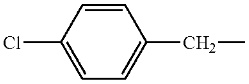 | 2 | 2 | 1 | — | H | 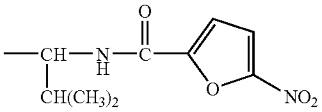 |
TABLE 1.62
| Compd. No. | 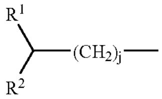 | k | m | n | chirality | $R^3$ | 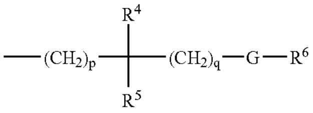 |
|---|---|---|---|---|---|---|---|
| 672 | 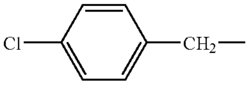 | 2 | 2 | 1 | — | H | 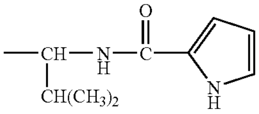 |
| 673 | 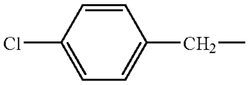 | 2 | 2 | 1 | — | H | 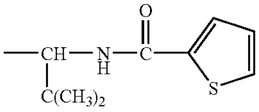 |
| 674 | 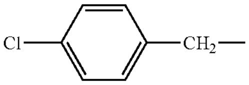 | 2 | 2 | 1 | — | H | 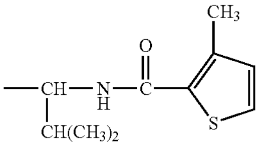 |

TABLE 1.62-continued
| Compd. No. | 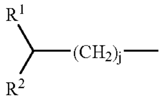 | k | m | n | chirality | $R^3$ | 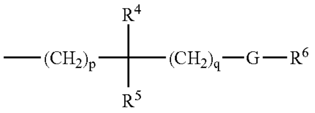 |
|---|---|---|---|---|---|---|---|
| 675 | 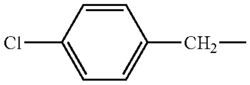 | 2 | 2 | 1 | — | H | 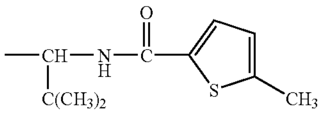 |
| 676 | 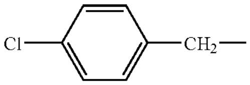 | 2 | 2 | 1 | — | H | 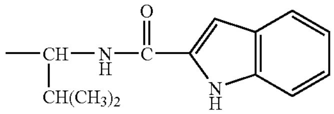 |
| 677 | 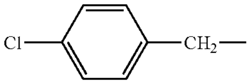 | 2 | 2 | 1 | — | H | 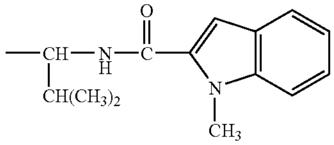 |
| 678 | 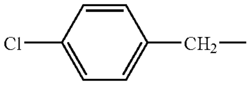 | 2 | 2 | 1 | — | H | 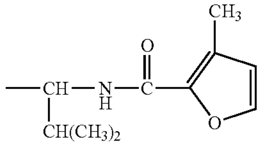 |
| 679 | 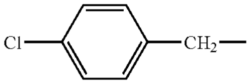 | 2 | 2 | 1 | — | H | 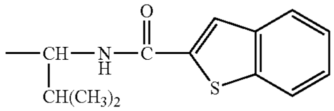 |
| 680 | 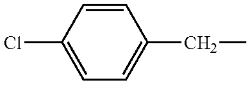 | 2 | 2 | 1 | — | H | 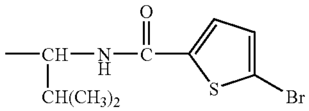 |
| 681 | 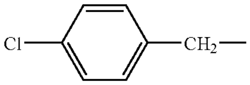 | 2 | 2 | 1 | — | H | 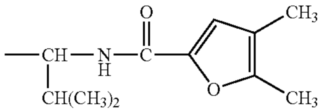 |
| 682 | 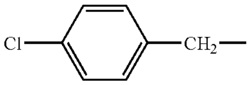 | 2 | 2 | 1 | — | H | 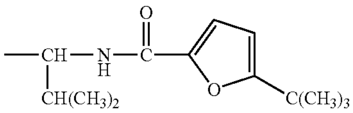 |
TABLE 1.63
| Compd. No. | 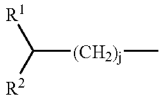 | k | m | n | chirality | $R^3$ | 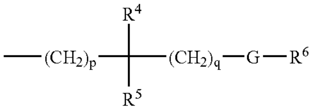 |
|---|---|---|---|---|---|---|---|
| 683 | 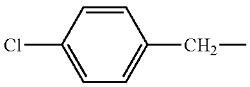 | 2 | 2 | 1 | — | H | 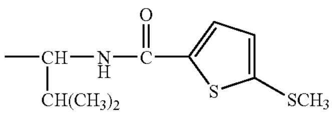 |

TABLE 1.63-continued
| Compd. No. | 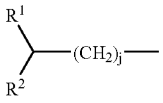 | k | m | n | chirality | $R^3$ | 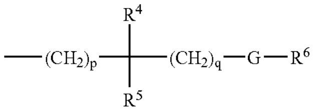 |
|---|---|---|---|---|---|---|---|
| 684 | 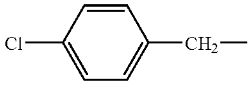 | 2 | 2 | 1 | — | H | 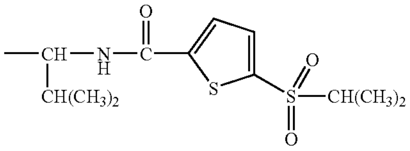 |
| 685 | 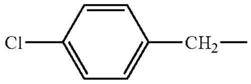 | 2 | 2 | 1 | — | H | 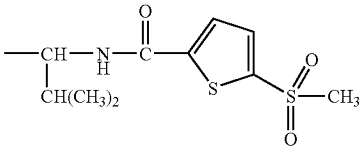 |
| 686 | 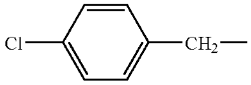 | 2 | 2 | 1 | — | H | 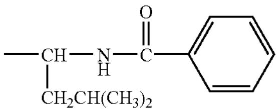 |
| 687 | 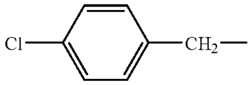 | 2 | 2 | 1 | — | H | 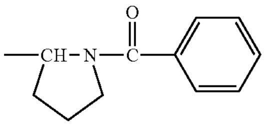 |
| 688 | 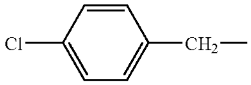 | 2 | 2 | 1 | — | H | 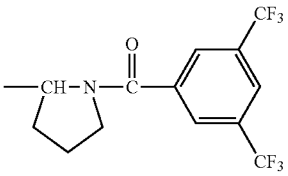 |
| 689 | 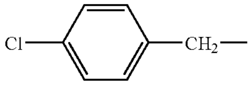 | 2 | 2 | 1 | — | H | 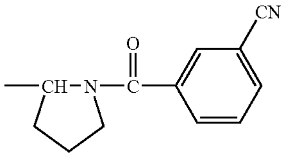 |
| 690 | 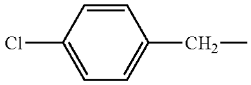 | 2 | 2 | 1 | — | H | 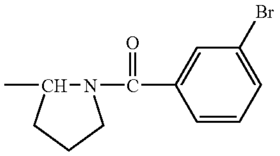 |
| 691 | 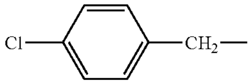 | 2 | 2 | 1 | — | H | 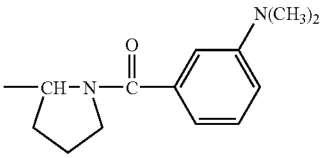 |
| 692 | 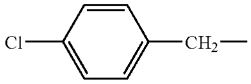 | 2 | 2 | 1 | — | H | 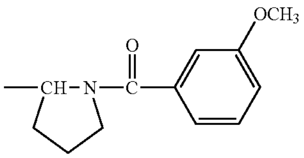 |

TABLE 1.63-continued
| Compd. No. | 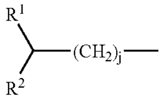 | k | m | n | chirality | $R^3$ | 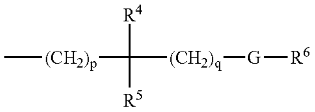 |
|---|---|---|---|---|---|---|---|
| 693 | 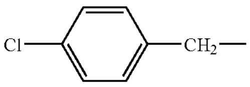 | 2 | 2 | 1 | — | H | 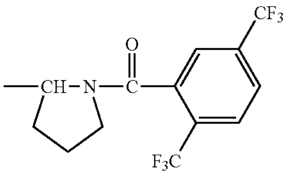 |
TABLE 1.64
| Compd. No. | 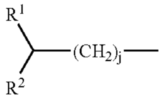 | k | m | n | chirality | $R^3$ | 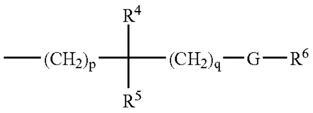 |
|---|---|---|---|---|---|---|---|
| 694 | 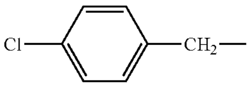 | 2 | 2 | 1 | — | H | 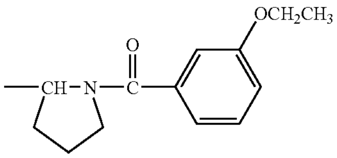 |
| 695 | 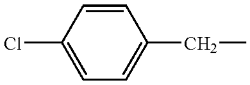 | 2 | 2 | 1 | — | H | 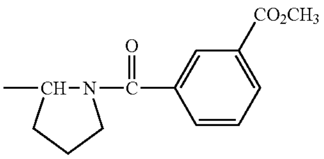 |
| 696 | 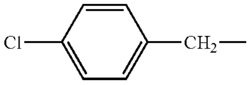 | 2 | 2 | 1 | — | H | 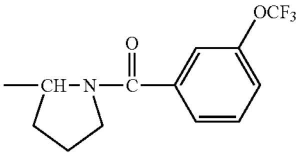 |
| 697 | 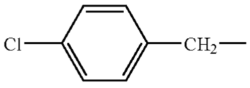 | 2 | 2 | 1 | — | H | 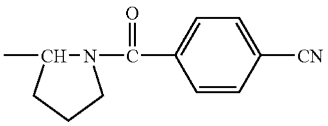 |
| 698 | 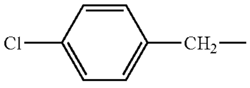 | 2 | 2 | 1 | — | H | 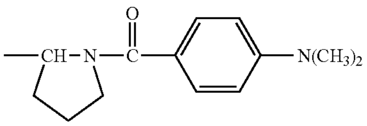 |
| 699 | 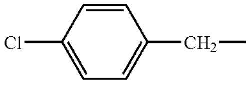 | 2 | 2 | 1 | — | H | 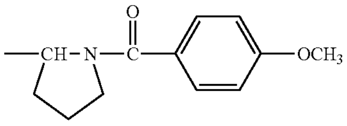 |
| 700 | 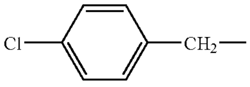 | 2 | 2 | 1 | — | H | 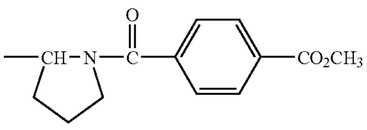 |

TABLE 1.64-continued
| Compd. No. | 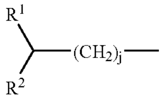 | k | m | n | chirality | $R^3$ | 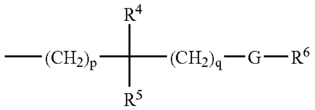 |
|---|---|---|---|---|---|---|---|
| 701 | 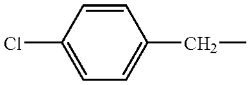 | 2 | 2 | 1 | — | H | 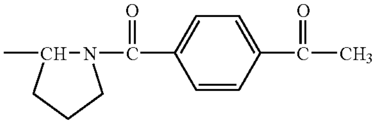 |
| 702 | 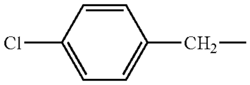 | 2 | 2 | 1 | — | H | 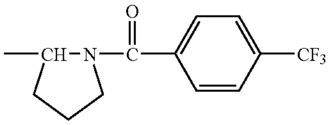 |
| 703 | 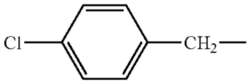 | 2 | 2 | 1 | — | H | 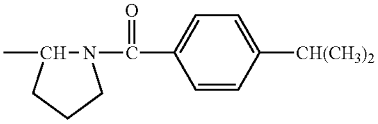 |
| 704 | 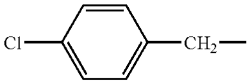 | 2 | 2 | 1 | — | H | 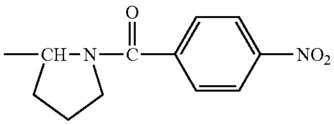 |
TABLE 1.65
| Compd. No. | 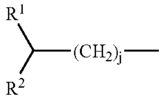 | k | m | n | chirality | $R^3$ | 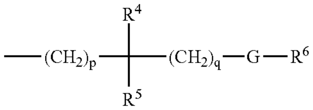 |
|---|---|---|---|---|---|---|---|
| 705 | 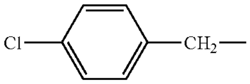 | 2 | 2 | 1 | — | H | 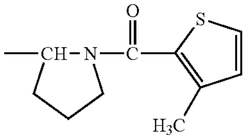 |
| 706 | 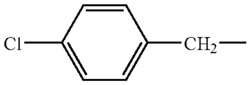 | 2 | 2 | 1 | — | H | 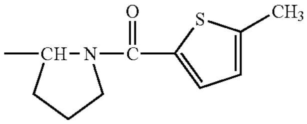 |
| 707 | 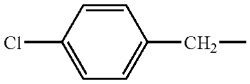 | 2 | 2 | 1 | — | H | 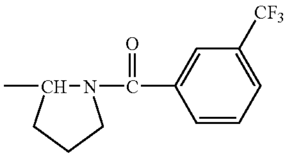 |
| 708 | 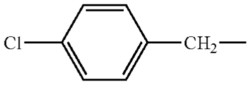 | 2 | 2 | 1 | — | H | 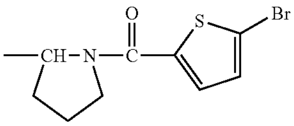 |
| 709 | 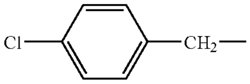 | 2 | 2 | 1 | — | H | 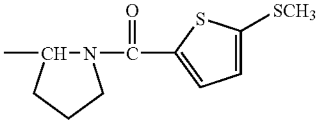 |

TABLE 1.65-continued
| Compd. No. | 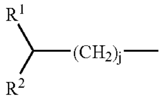 | k | m | n | chirality | $R^3$ | 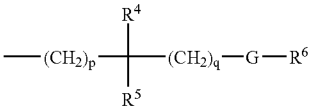 |
|---|---|---|---|---|---|---|---|
| 710 | 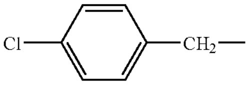 | 2 | 2 | 1 | — | H | 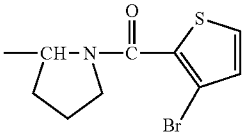 |
| 711 | 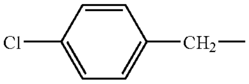 | 2 | 2 | 1 | — | H | 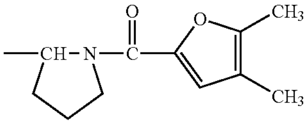 |
| 712 | 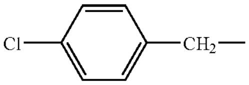 | 2 | 2 | 1 | — | H | 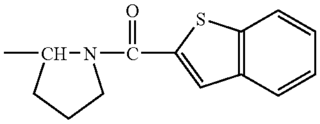 |
| 713 | 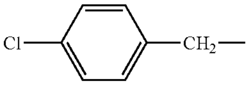 | 2 | 2 | 1 | — | H | 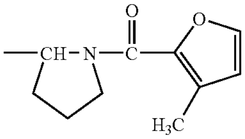 |
| 714 | 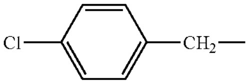 | 2 | 2 | 1 | — | H | 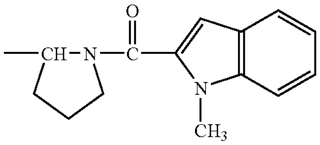 |
| 715 | 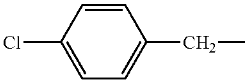 | 2 | 2 | 1 | — | H | 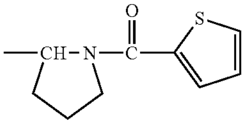 |
TABLE 1.66
| Compd. No. | 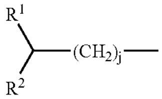 | k | m | n | chirality | $R^3$ | 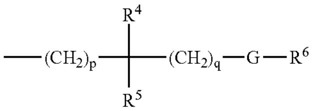 |
|---|---|---|---|---|---|---|---|
| 716 | 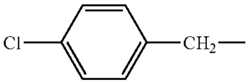 | 2 | 2 | 1 | — | H | 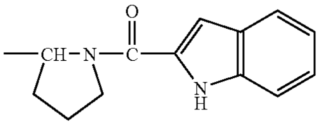 |
| 717 | 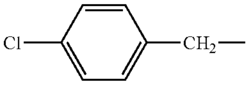 | 2 | 2 | 1 | — | H | 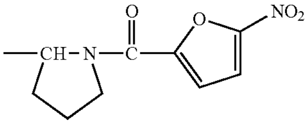 |
| 718 | 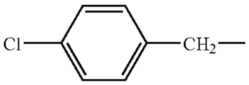 | 2 | 2 | 1 | — | H | 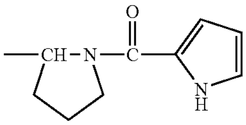 |

TABLE 1.66-continued
| Compd. No. | 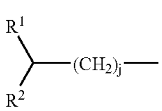 | k | m | n | chirality | $R^3$ | 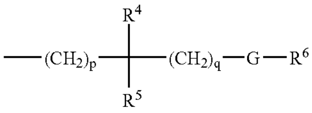 |
|---|---|---|---|---|---|---|---|
| 719 | 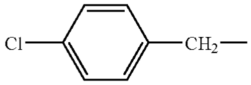 | 2 | 2 | 1 | — | H | 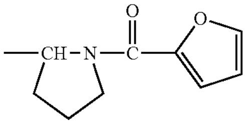 |
| 720 | 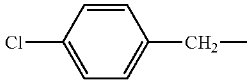 | 2 | 2 | 1 | — | H | 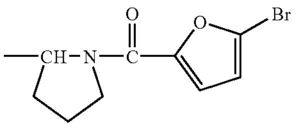 |
| 721 | 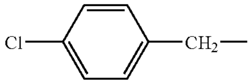 | 2 | 2 | 1 | — | H | 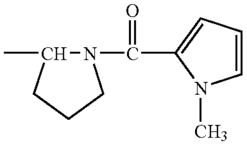 |
| 722 | 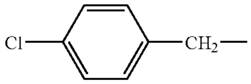 | 2 | 2 | 1 | — | H | 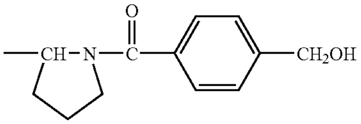 |
| 723 | 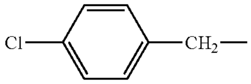 | 2 | 2 | 1 | — | H | 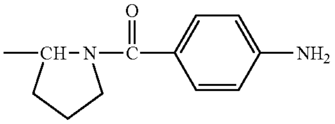 |
| 724 | 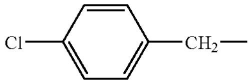 | 2 | 2 | 1 | — | H | 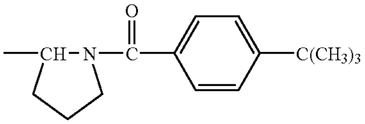 |
| 725 | 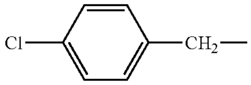 | 2 | 2 | 1 | — | H | 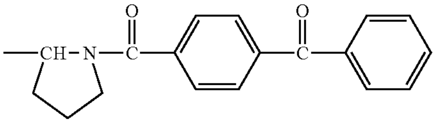 |
| 726 | 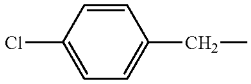 | 2 | 2 | 1 | — | H | 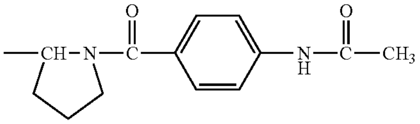 |
TABLE 1.67
| Compd. No. | 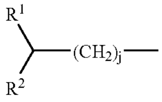 | k | m | n | chirality | $R^3$ | 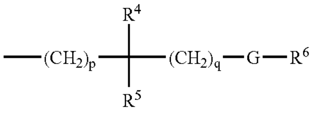 |
|---|---|---|---|---|---|---|---|
| 727 | 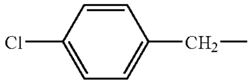 | 2 | 2 | 1 | — | H | 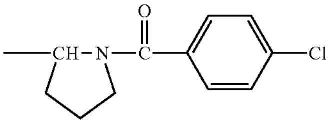 |

TABLE 1.67-continued
| Compd. No. | 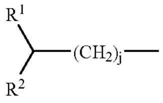 | k | m | n | chirality | $R^3$ | 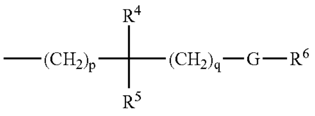 |
|---|---|---|---|---|---|---|---|
| 728 | 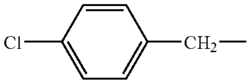 | 2 | 2 | 1 | — | H | 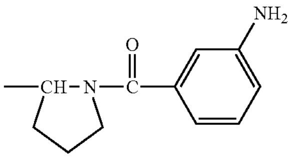 |
| 729 | 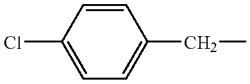 | 2 | 2 | 1 | — | H | 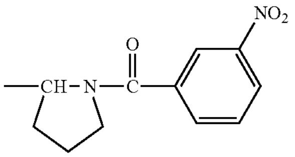 |
| 730 | 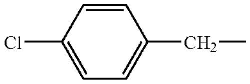 | 2 | 2 | 1 | — | H | 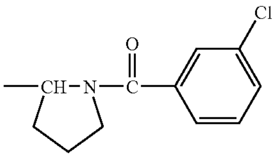 |
| 731 | 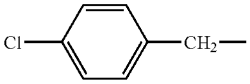 | 2 | 2 | 1 | — | H | 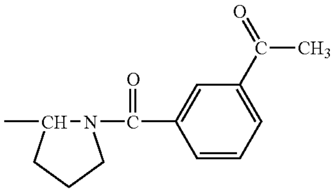 |
| 732 | 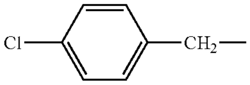 | 2 | 2 | 1 | — | H | 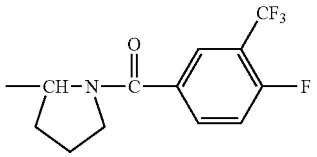 |
| 733 | 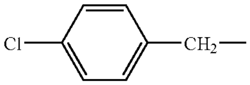 | 2 | 2 | 1 | — | H | 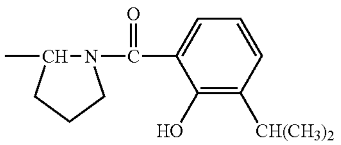 |
| 734 | 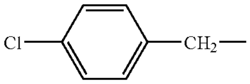 | 2 | 2 | 1 | — | H | 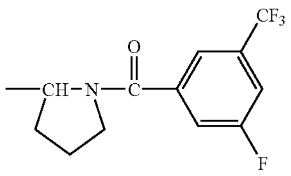 |
| 735 | 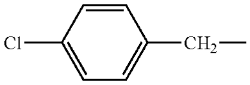 | 2 | 2 | 1 | — | H | 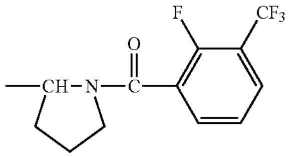 |

TABLE 1.67-continued
| Compd. No. | 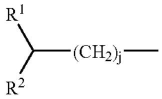 | k | m | n | chirality | $R^3$ | 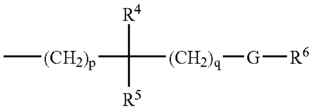 |
|---|---|---|---|---|---|---|---|
| 736 | 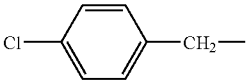 | 2 | 2 | 1 | — | H | 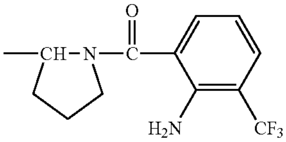 |
| 737 | 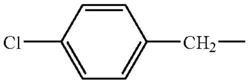 | 2 | 2 | 1 | — | H | 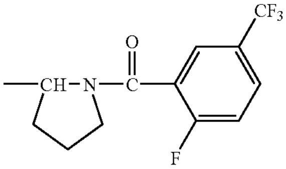 |
TABLE 1.68
| Compd. No. | 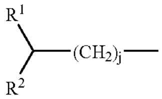 | k | m | n | chirality | $R^3$ | 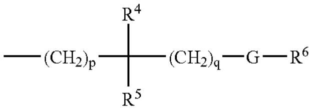 |
|---|---|---|---|---|---|---|---|
| 738 | 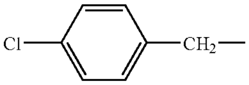 | 2 | 2 | 1 | — | H | 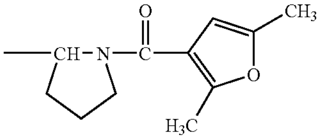 |
| 739 | 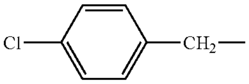 | 2 | 2 | 1 | — | H | 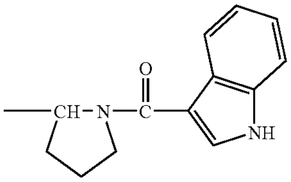 |
| 740 | 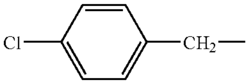 | 2 | 2 | 1 | — | H | 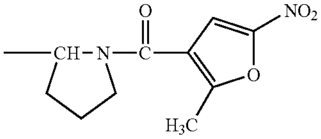 |
| 741 | 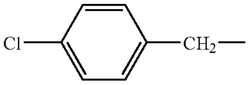 | 2 | 2 | 1 | — | H | 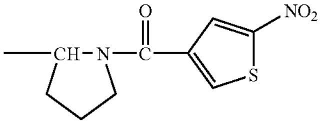 |
| 742 | 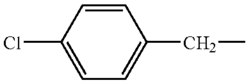 | 2 | 2 | 1 | — | H | 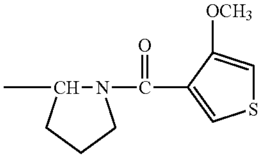 |
| 743 | 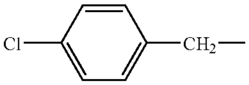 | 2 | 2 | 1 | — | H | 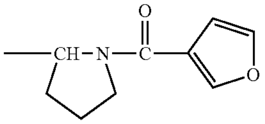 |

TABLE 1.68-continued
| Compd. No. | 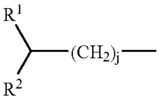 | k | m | n | chirality | $R^3$ | 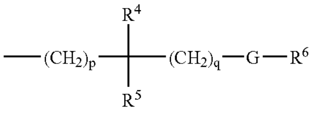 |
|---|---|---|---|---|---|---|---|
| 744 | 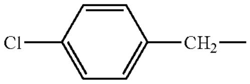 | 2 | 2 | 1 | — | H | 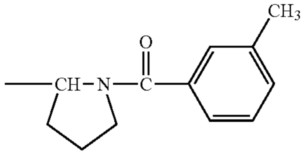 |
| 745 | 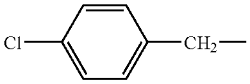 | 2 | 2 | 1 | — | H | 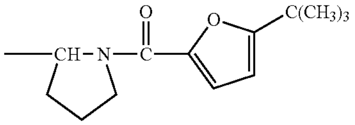 |
| 746 | 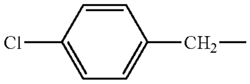 | 2 | 2 | 1 | — | H | 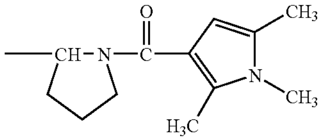 |
| 747 | 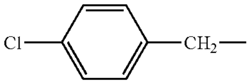 | 2 | 2 | 1 | — | H | 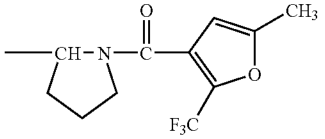 |
| 748 | 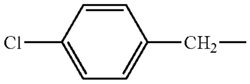 | 2 | 2 | 1 | — | H | 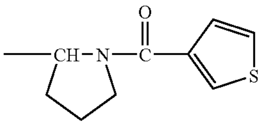 |
TABLE 1.69
| Compd. No. | 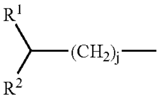 | k | m | n | chirality | $R^3$ | 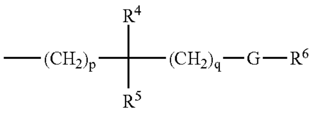 |
|---|---|---|---|---|---|---|---|
| 749 | 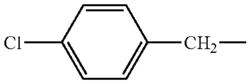 | 2 | 2 | 1 | — | H | 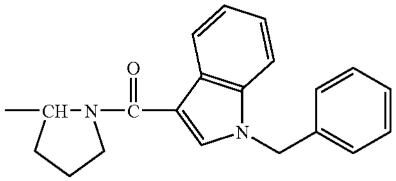 |
| 750 | 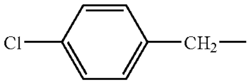 | 2 | 2 | 1 | — | H | 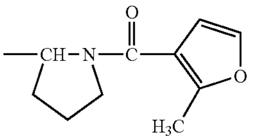 |
| 751 | 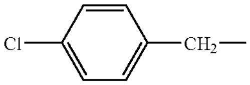 | 2 | 2 | 1 | — | H | 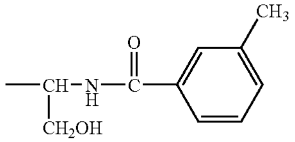 |

TABLE 1.69-continued
| Compd. No. | 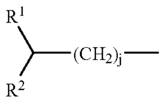 | k | m | n | chirality | R3 | 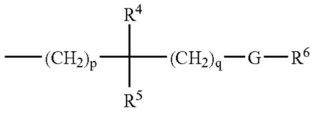 |
|---|---|---|---|---|---|---|---|
| 752 | 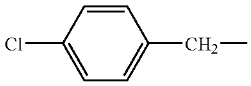 | 2 | 2 | 1 | — | H | 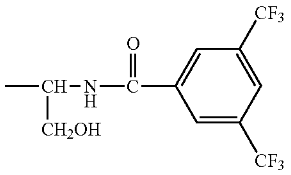 |
| 753 | 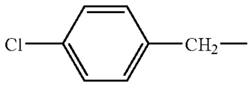 | 2 | 2 | 1 | — | H | 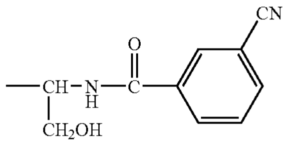 |
| 754 | 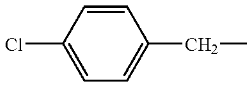 | 2 | 2 | 1 | — | H | 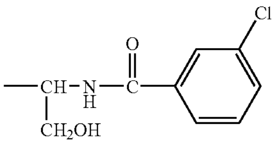 |
| 755 | 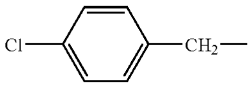 | 2 | 2 | 1 | — | H | 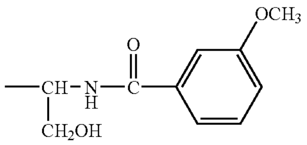 |
| 756 | 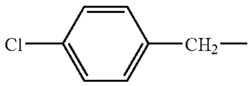 | 2 | 2 | 1 | — | H | 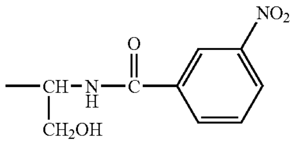 |
| 757 | 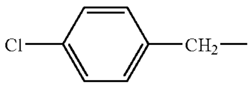 | 2 | 2 | 1 | — | H | 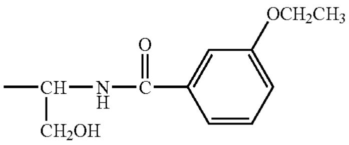 |
| 758 | 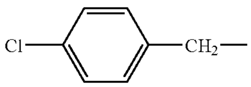 | 2 | 2 | 1 | — | H | 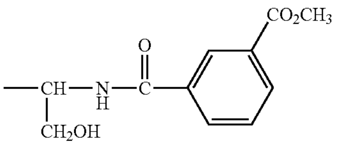 |
| 759 | 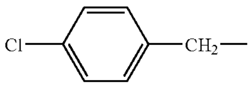 | 2 | 2 | 1 | — | H | 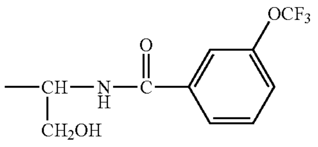 |

TABLE 1.70
| Compd. No. | 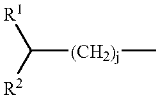 | k | m | n | chirality | $R^3$ | 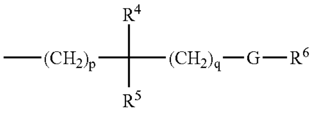 |
|---|---|---|---|---|---|---|---|
| 760 | 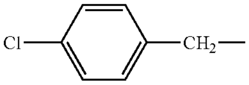 | 2 | 2 | 1 | — | H | 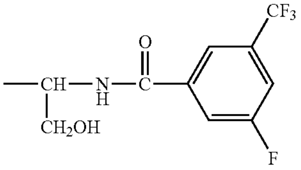 |
| 761 | 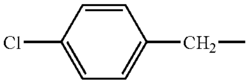 | 2 | 2 | 1 | — | H | 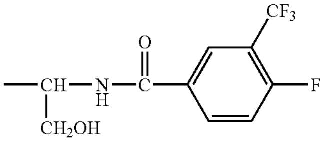 |
| 762 | 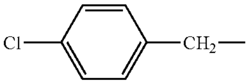 | 2 | 2 | 1 | — | H | 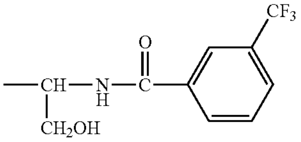 |
| 763 | 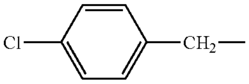 | 2 | 2 | 1 | — | H | 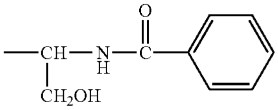 |
| 764 | 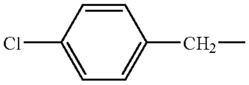 | 2 | 2 | 1 | — | H | 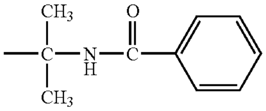 |
| 765 | 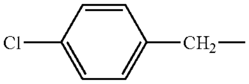 | 2 | 2 | 1 | — | H | 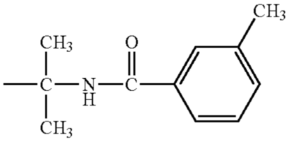 |
| 766 | 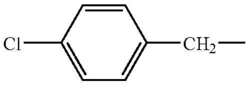 | 2 | 2 | 1 | — | H | 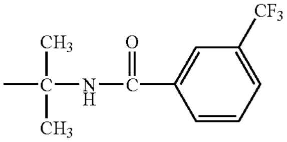 |
| 767 | 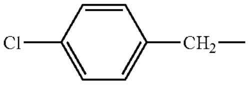 | 2 | 2 | 1 | — | H | 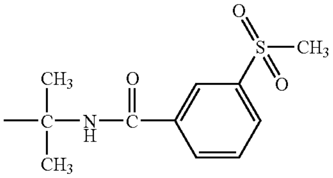 |
| 768 | 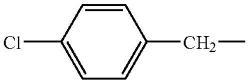 | 2 | 2 | 1 | — | H | 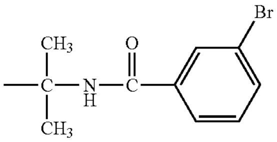 |

TABLE 1.70-continued
| Compd. No. | 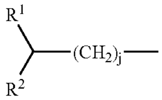 | k | m | n | chirality | $R^3$ | 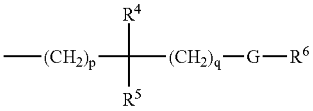 |
|---|---|---|---|---|---|---|---|
| 769 | 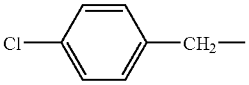 | 2 | 2 | 1 | — | H | 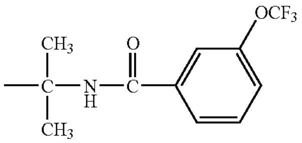 |
| 770 | 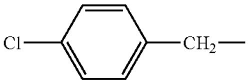 | 2 | 2 | 1 | — | H | 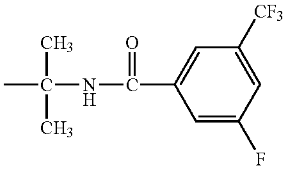 |
TABLE 1.71
| Compd. No. | 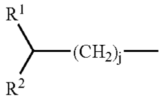 | k | m | n | chirality | $R^3$ | 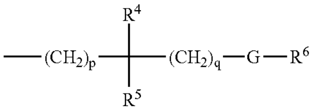 |
|---|---|---|---|---|---|---|---|
| 771 | 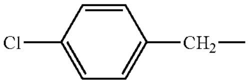 | 2 | 2 | 1 | — | H | 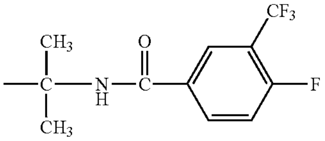 |
| 772 | 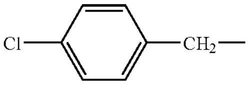 | 2 | 2 | 1 | — | H | 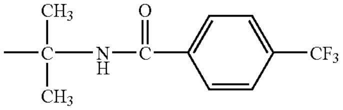 |
| 773 | 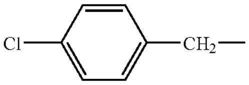 | 2 | 2 | 1 | — | H | 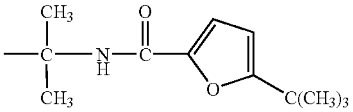 |
| 774 | 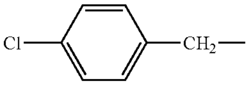 | 2 | 2 | 1 | — | H | 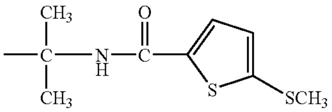 |
| 775 | 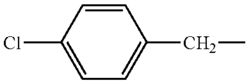 | 2 | 2 | 1 | — | H | 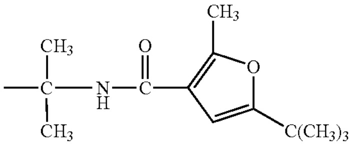 |
| 776 | 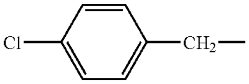 | 2 | 2 | 1 | — | H | 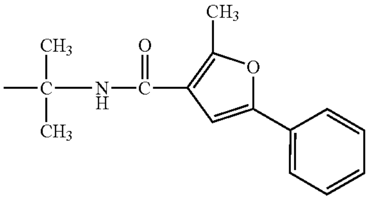 |

TABLE 1.71-continued
| Compd. No. | 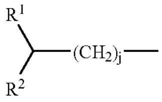 | k | m | n | chirality | $R^3$ | 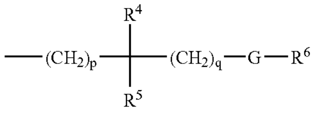 |
|---|---|---|---|---|---|---|---|
| 777 | 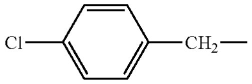 | 2 | 2 | 1 | — | H | 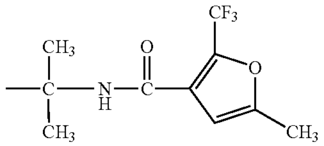 |
| 778 | 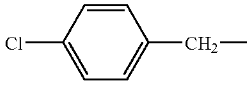 | 2 | 2 | 1 | — | H | 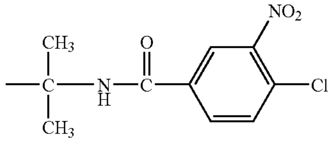 |
| 779 | 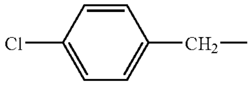 | 2 | 2 | 1 | — | H | 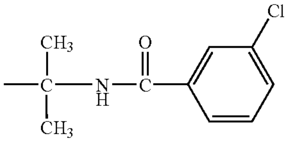 |
| 780 | 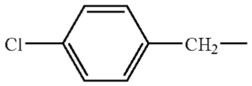 | 2 | 2 | 1 | — | H | 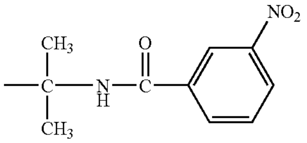 |
| 781 | 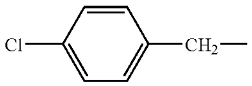 | 2 | 2 | 1 | — | H | 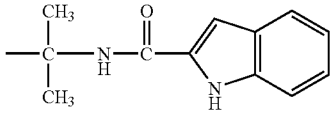 |
TABLE 1.72
| Compd. No. | 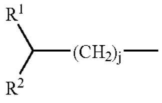 | k | m | n | chirality | $R^3$ | 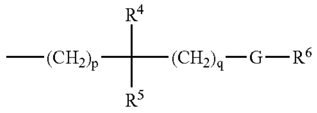 |
|---|---|---|---|---|---|---|---|
| 782 | 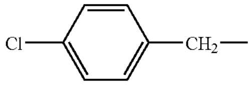 | 2 | 2 | 1 | — | H | 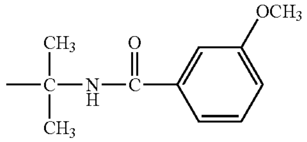 |
| 783 | 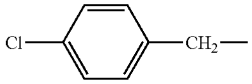 | 2 | 2 | 1 | — | H | 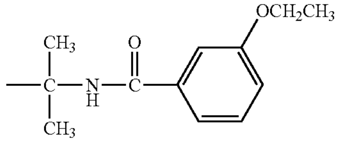 |
| 784 | 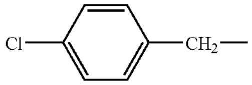 | 2 | 2 | 1 | — | H | 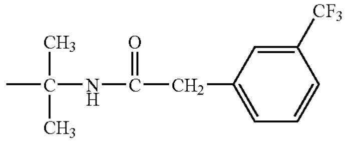 |

TABLE 1.72-continued
| Compd. No. | 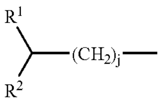 | k | m | n | chirality | $R^3$ | 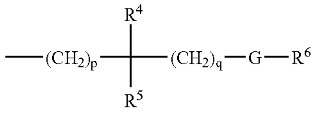 |
|---|---|---|---|---|---|---|---|
| 785 | 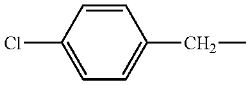 | 2 | 2 | 1 | — | H | 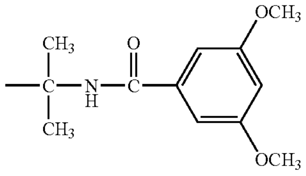 |
| 786 | 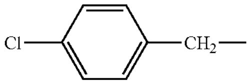 | 2 | 2 | 1 | — | H | 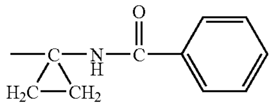 |
| 787 | 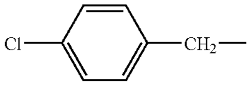 | 2 | 2 | 1 | — | H | 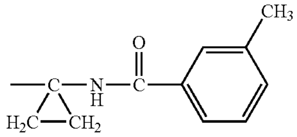 |
| 788 | 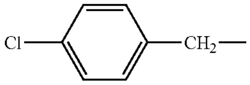 | 2 | 2 | 1 | — | H | 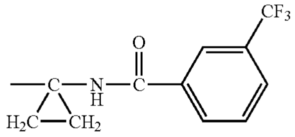 |
| 789 | 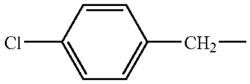 | 2 | 2 | 1 | — | H | 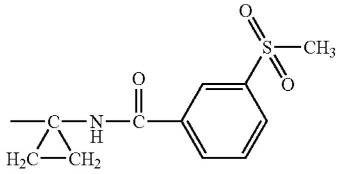 |
| 790 | 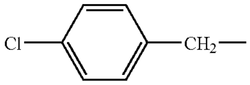 | 2 | 2 | 1 | — | H | 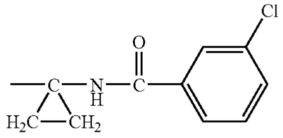 |
| 791 | 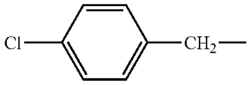 | 2 | 2 | 1 | — | H | 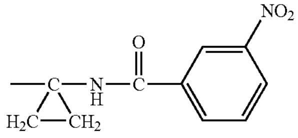 |
| 792 | 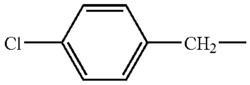 | 2 | 2 | 1 | — | H | 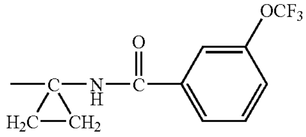 |

TABLE 1.73
| Compd. No. | 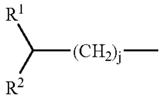 | k | m | n | chirality | $R^3$ | 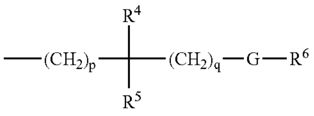 |
|---|---|---|---|---|---|---|---|
| 793 | 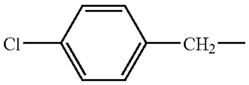 | 2 | 2 | 1 | — | H | 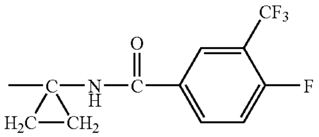 |
| 794 | 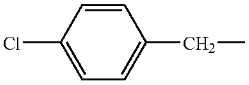 | 2 | 2 | 1 | — | H | 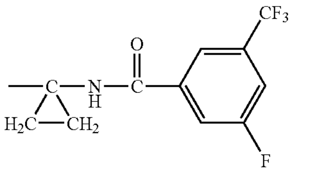 |
| 795 | 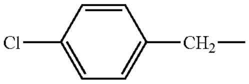 | 2 | 2 | 1 | — | H | 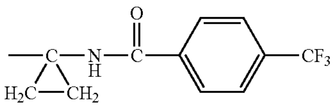 |
| 796 | 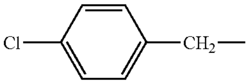 | 2 | 2 | 1 | — | H | 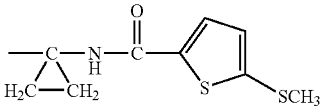 |
| 797 | 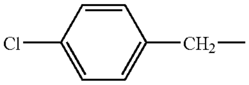 | 2 | 2 | 1 | — | H | 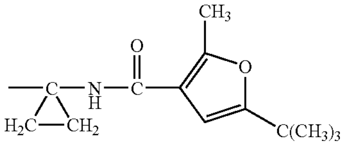 |
| 798 | 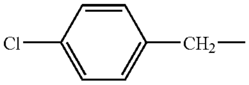 | 2 | 2 | 1 | — | H | 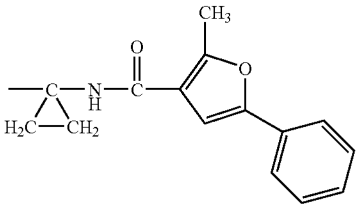 |
| 799 | 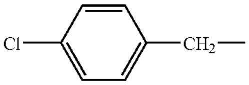 | 2 | 2 | 1 | — | H | 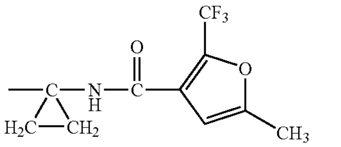 |
| 800 | 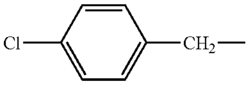 | 2 | 2 | 1 | — | H | 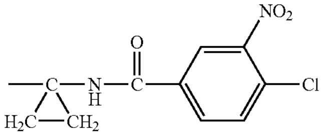 |
| 801 | 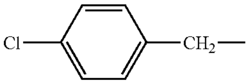 | 2 | 2 | 1 | — | H | 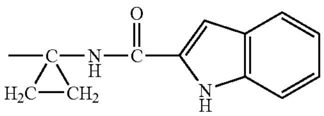 |

TABLE 1.73-continued
| Compd. No. | 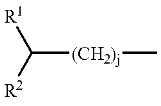 | k | m | n | chirality | $R^3$ | 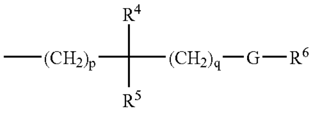 |
|---|---|---|---|---|---|---|---|
| 802 | 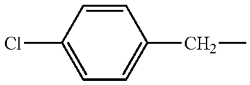 | 2 | 2 | 1 | — | H | 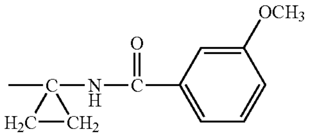 |
| 803 | 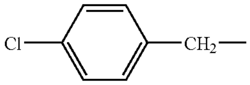 | 2 | 2 | 1 | — | H | 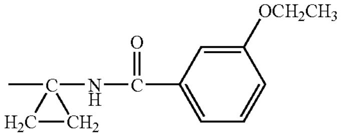 |
TABLE 1.74
| Compd. No. | 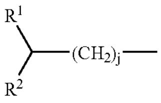 | k | m | n | chirality | $R^3$ | 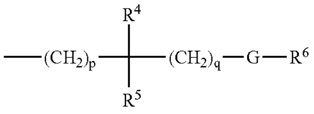 |
|---|---|---|---|---|---|---|---|
| 804 | 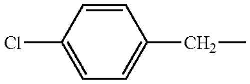 | 2 | 2 | 1 | — | H | 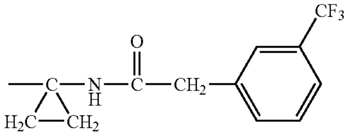 |
| 805 | 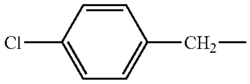 | 2 | 2 | 1 | — | H | 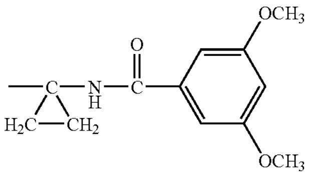 |
| 806 | 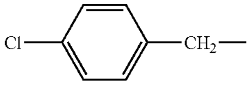 | 2 | 2 | 1 | — | H | 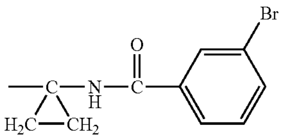 |
| 807 | 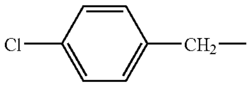 | 2 | 2 | 1 | — | H | 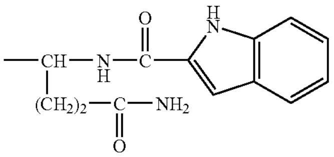 |
| 808 | 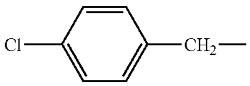 | 2 | 2 | 1 | — | H | 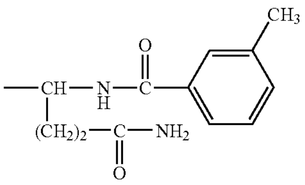 |

TABLE 1.74-continued
| Compd. No. | 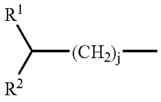 | k | m | n | chirality | $R^3$ | 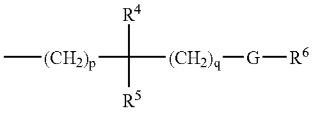 |
|---|---|---|---|---|---|---|---|
| 809 | 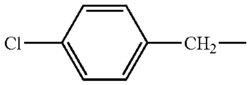 | 2 | 2 | 1 | — | H | 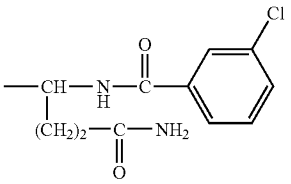 |
| 810 | 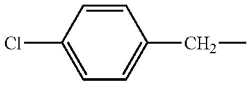 | 2 | 2 | 1 | — | H | 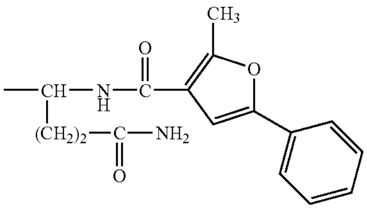 |
| 811 | 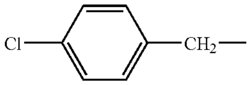 | 2 | 2 | 1 | — | H | 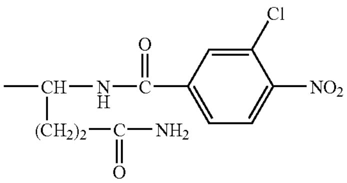 |
| 812 | 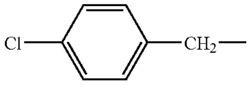 | 2 | 2 | 1 | — | H | 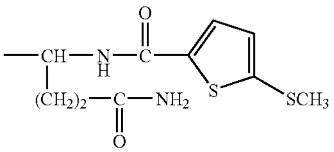 |
| 813 | 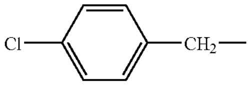 | 2 | 2 | 1 | — | H | 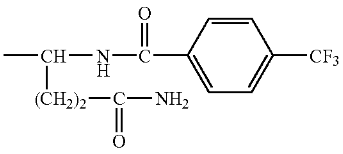 |
| 814 | 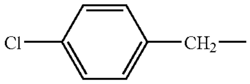 | 2 | 2 | 1 | — | H | 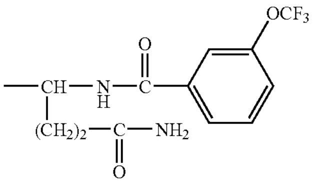 |

TABLE 1.75
| Compd. No. | 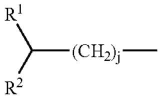 | k | m | n | chirality | $R^3$ | 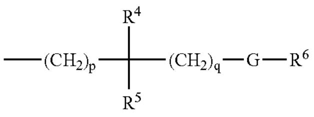 |
|---|---|---|---|---|---|---|---|
| 815 | 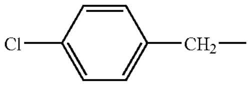 | 2 | 2 | 1 | — | H | 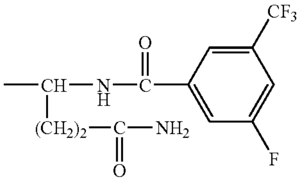 |
| 816 | 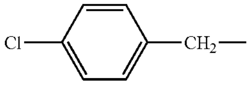 | 2 | 2 | 1 | — | H | 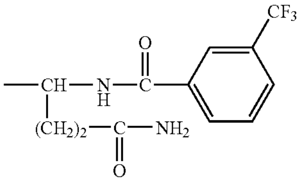 |
| 817 | 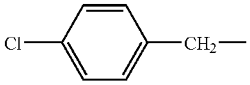 | 2 | 2 | 1 | — | H | 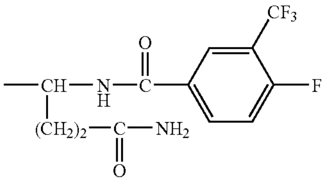 |
| 818 | 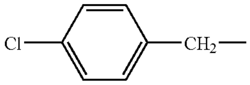 | 2 | 2 | 1 | — | H | 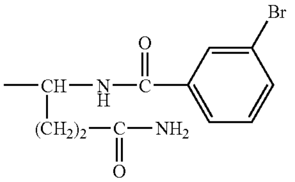 |
| 819 | 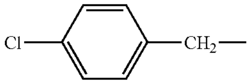 | 2 | 2 | 1 | — | H | 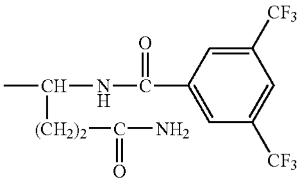 |
| 820 | 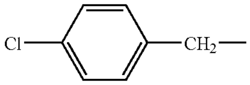 | 2 | 2 | 1 | — | H | 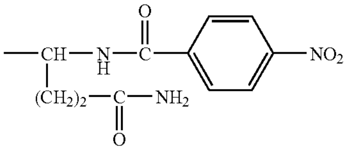 |
| 821 | 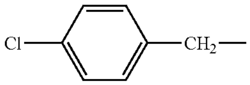 | 2 | 2 | 1 | — | H | 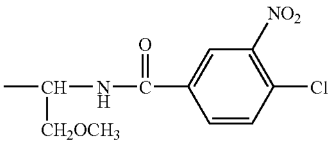 |
| 822 | 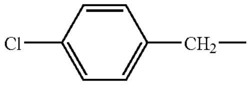 | 2 | 2 | 1 | — | H | 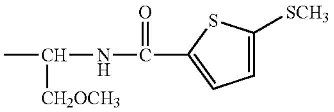 |

TABLE 1.75-continued
| Compd. No. | 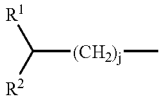 | k | m | n | chirality | $R^3$ | 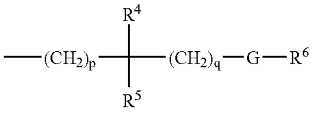 |
|---|---|---|---|---|---|---|---|
| 823 | 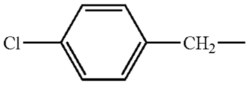 | 2 | 2 | 1 | — | H | 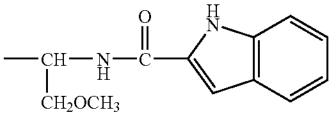 |
| 824 | 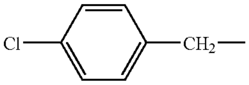 | 2 | 2 | 1 | — | H | 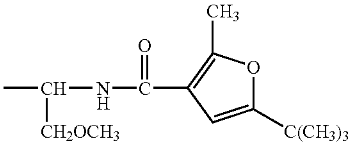 |
| 825 | 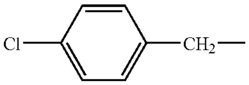 | 2 | 2 | 1 | — | H | 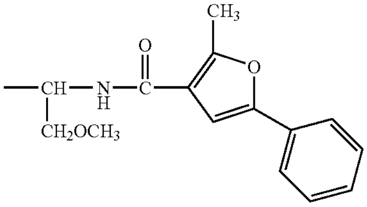 |
TABLE 1.76
| Compd. No. | 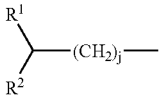 | k | m | n | chirality | $R^3$ | 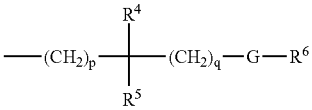 |
|---|---|---|---|---|---|---|---|
| 826 | 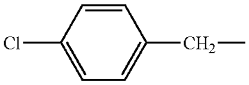 | 2 | 2 | 1 | — | H | 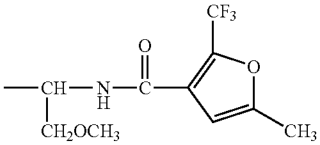 |
| 827 | 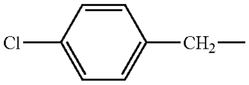 | 2 | 2 | 1 | — | H | 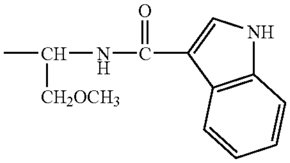 |
| 828 | 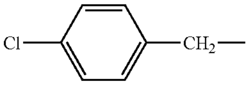 | 2 | 2 | 1 | — | H | 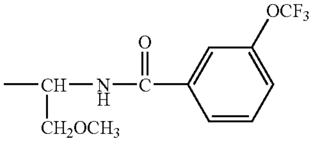 |
| 829 | 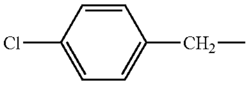 | 2 | 2 | 1 | — | H | 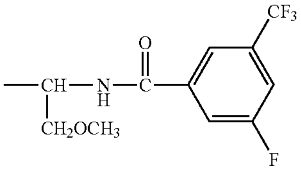 |

TABLE 1.76-continued
| Compd. No. | | k | m | n | chirality | $R^3$ | |
|---|---|---|---|---|---|---|---|
| | 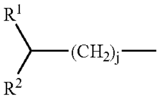 | | | | | | 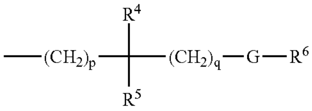 |
| 830 | 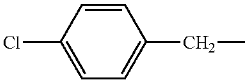 | 2 | 2 | 1 | — | H | 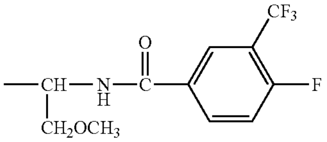 |
| 831 | 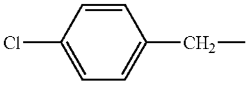 | 2 | 2 | 1 | — | H | 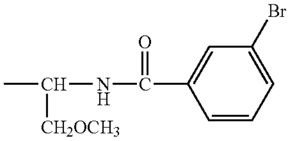 |
| 832 | 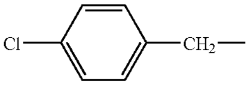 | 2 | 2 | 1 | — | H | 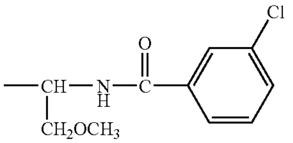 |
| 833 | 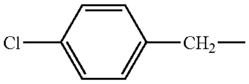 | 2 | 2 | 1 | — | H | 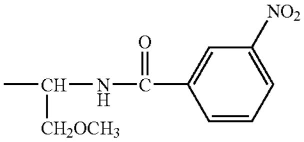 |
| 834 | 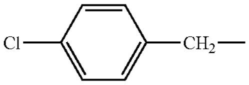 | 2 | 2 | 1 | — | H | 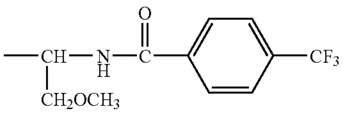 |
| 835 | 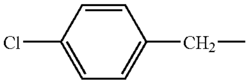 | 2 | 2 | 1 | — | H | 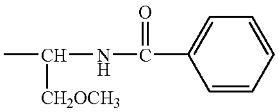 |
| 836 | 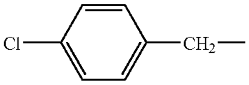 | 2 | 2 | 1 | — | H | 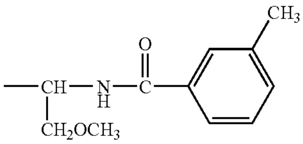 |
TABLE 1.77
| Compd. No. | | k | m | n | chirality | $R^3$ | |
|---|---|---|---|---|---|---|---|
| | 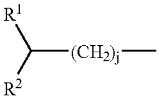 | | | | | | 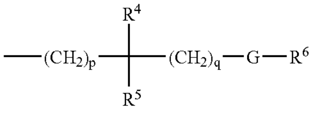 |
| 837 | 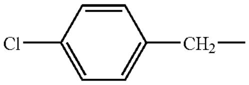 | 2 | 2 | 1 | — | H | 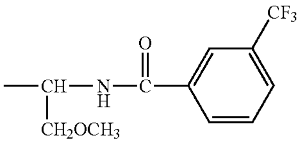 |

TABLE 1.77-continued
| Compd. No. | 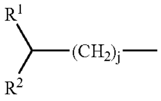 | k | m | n | chirality | $R^3$ | 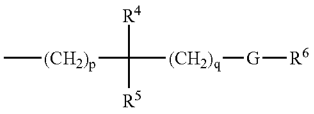 |
|---|---|---|---|---|---|---|---|
| 838 | 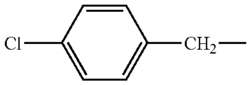 | 2 | 2 | 1 | — | H | 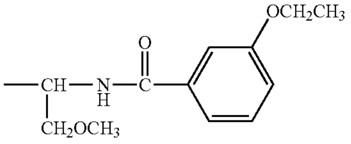 |
| 839 | 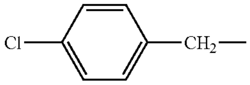 | 2 | 2 | 1 | — | H | 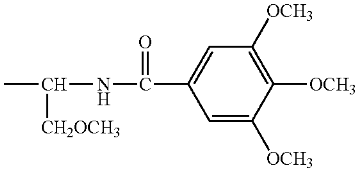 |
| 840 | 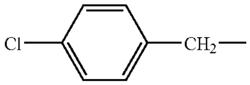 | 2 | 2 | 1 | — | H | 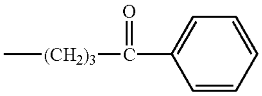 |
| 841 | 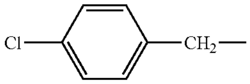 | 2 | 2 | 1 | — | H | 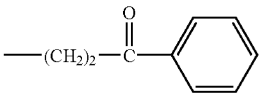 |
| 842 | 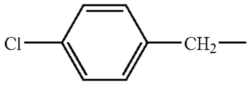 | 2 | 2 | 1 | — | H | 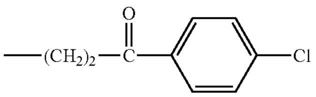 |
| 843 | 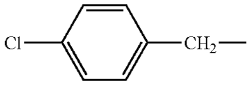 | 2 | 2 | 1 | — | H | 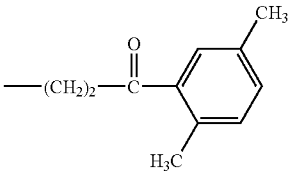 |
| 844 | 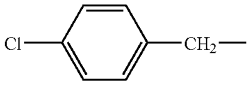 | 2 | 2 | 1 | — | H | 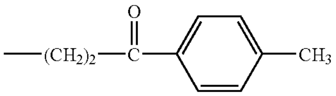 |
| 845 | 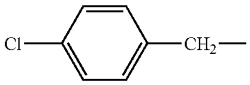 | 2 | 2 | 1 | — | H | 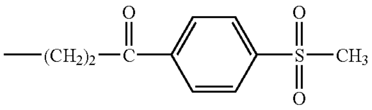 |
| 846 | 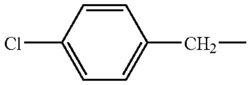 | 2 | 2 | 1 | — | H | 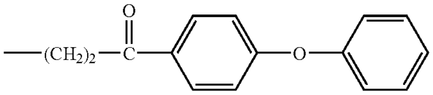 |
| 847 | 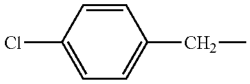 | 2 | 2 | 1 | — | H | 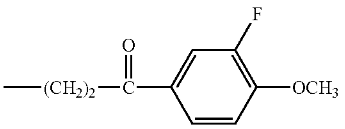 |

TABLE 1.78
| Compd. No. | 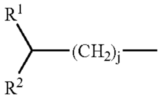 | k | m | n | chirality | $R^3$ | 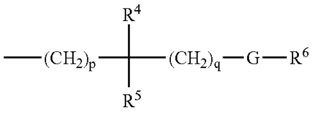 |
|---|---|---|---|---|---|---|---|
| 848 | 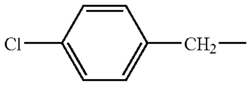 | 2 | 2 | 1 | — | H | 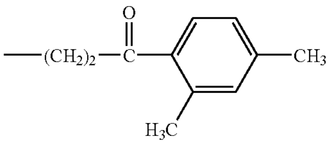 |
| 849 | 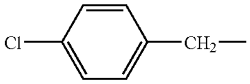 | 2 | 2 | 1 | — | H | 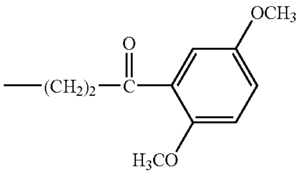 |
| 850 | 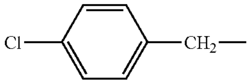 | 2 | 2 | 1 | — | H | 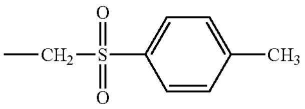 |
| 851 | 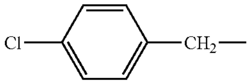 | 2 | 2 | 1 | — | H | 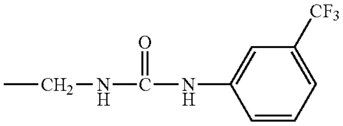 |
| 852 | 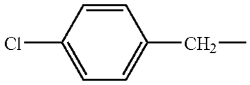 | 2 | 2 | 1 | — | H | 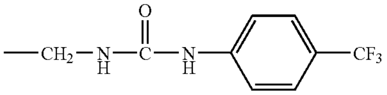 |
| 853 | 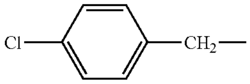 | 2 | 2 | 1 | — | H | 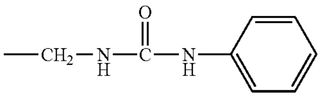 |
| 854 | 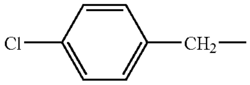 | 2 | 2 | 1 | — | H | 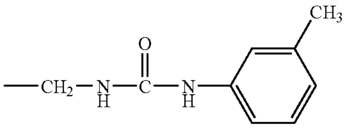 |
| 855 | 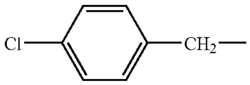 | 2 | 2 | 1 | — | H | 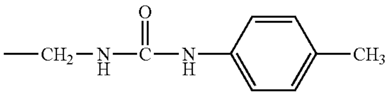 |
| 856 | 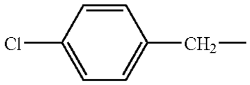 | 2 | 2 | 1 | — | H | 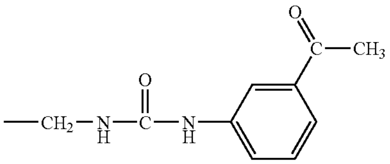 |
| 857 | 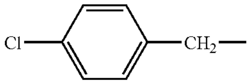 | 2 | 2 | 1 | — | H | 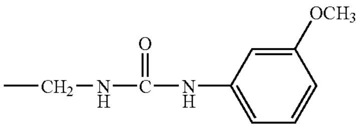 |

TABLE 1.78-continued
| Compd. No. | 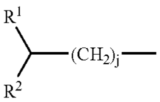 | k | m | n | chirality | $R^3$ | 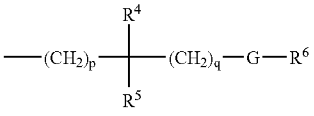 |
|---|---|---|---|---|---|---|---|
| 858 | 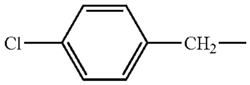 | 2 | 2 | 1 | — | H | 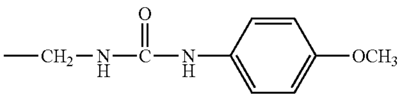 |
TABLE 1.79
| Compd. No. | 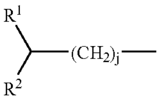 | k | m | n | chirality | $R^3$ | 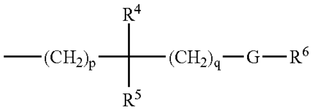 |
|---|---|---|---|---|---|---|---|
| 859 | 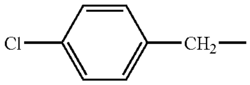 | 2 | 2 | 1 | — | H | 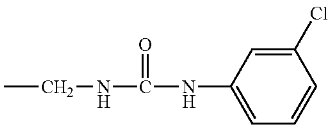 |
| 860 | 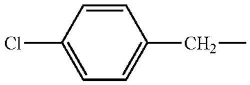 | 2 | 2 | 1 | — | H | 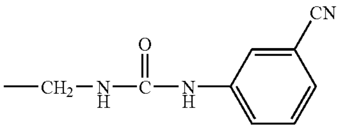 |
| 861 | 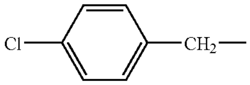 | 2 | 2 | 1 | — | H | 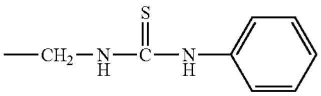 |
| 862 | 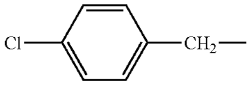 | 2 | 2 | 1 | — | H | 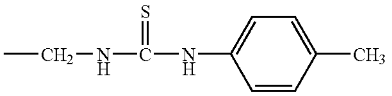 |
| 863 | 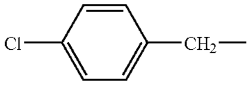 | 2 | 2 | 1 | — | H | 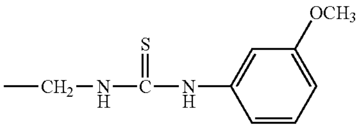 |
| 864 | 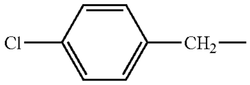 | 2 | 2 | 1 | — | H | 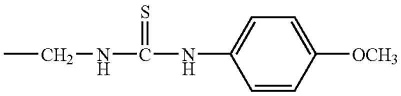 |
| 865 | 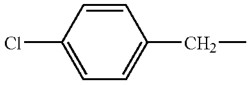 | 2 | 2 | 1 | — | H | 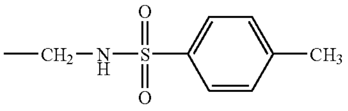 |
| 866 | 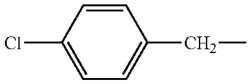 | 2 | 2 | 1 | — | H | 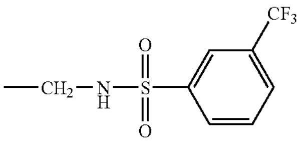 |

TABLE 1.79-continued
| Compd. No. | 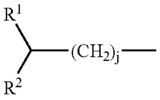 | k | m | n | chirality | $R^3$ | 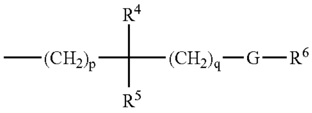 |
|---|---|---|---|---|---|---|---|
| 867 | 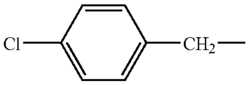 | 2 | 2 | 1 | — | H | 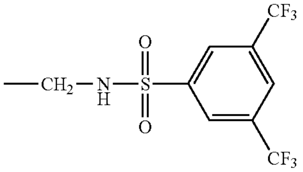 |
| 868 | 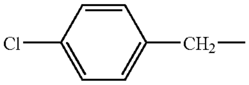 | 2 | 2 | 1 | — | H | 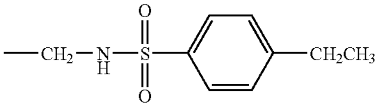 |
| 869 | 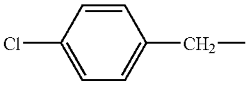 | 2 | 2 | 1 | — | H | 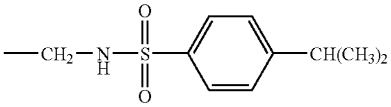 |
TABLE 1.80
| Compd. No. | 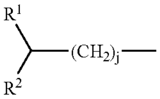 | k | m | n | chirality | $R^3$ | 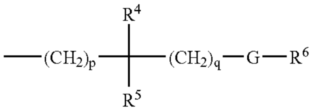 |
|---|---|---|---|---|---|---|---|
| 870 | 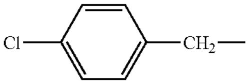 | 2 | 2 | 1 | — | H | 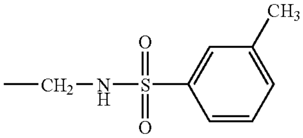 |
| 871 | 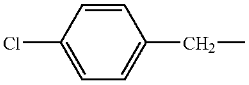 | 2 | 2 | 1 | — | H | 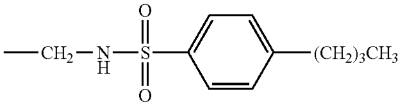 |
| 872 | 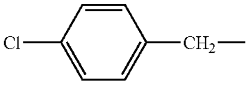 | 2 | 2 | 1 | — | H | 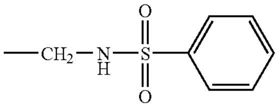 |
| 873 | 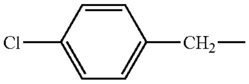 | 2 | 2 | 1 | — | H | 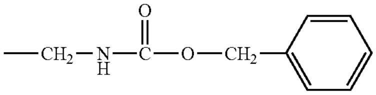 |
| 874 | 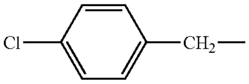 | 2 | 2 | 1 | — | H | 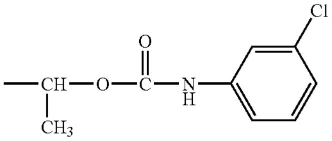 |
| 875 | 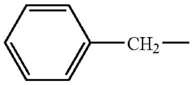 | 2 | 2 | 1 | — | H | 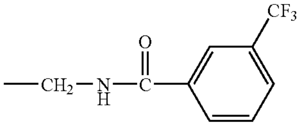 |

TABLE 1.80-continued
| Compd. No. | 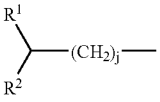 | k | m | n | chirality | $R^3$ | 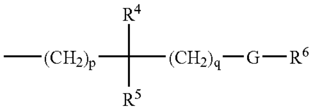 |
|---|---|---|---|---|---|---|---|
| 876 | 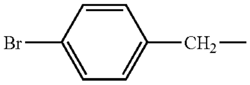 | 2 | 2 | 1 | — | H | 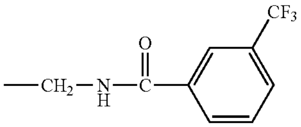 |
| 877 | 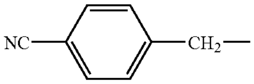 | 2 | 2 | 1 | — | H | 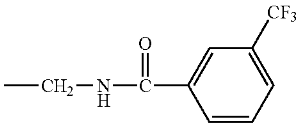 |
| 878 | 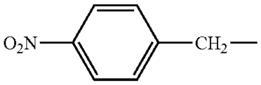 | 2 | 2 | 1 | — | H | 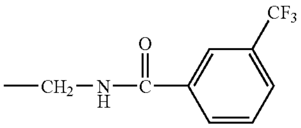 |
| 879 | 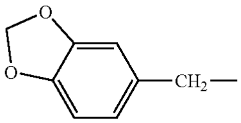 | 2 | 2 | 1 | — | H | 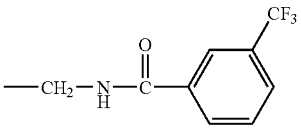 |
| 880 | 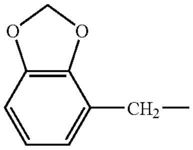 | 2 | 2 | 1 | — | H | 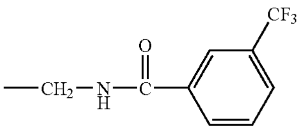 |
TABLE 1.81
| Compd. No. | 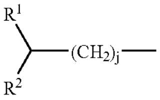 | k | m | n | chirality | $R^3$ | 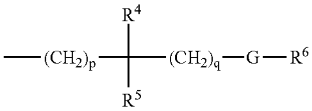 |
|---|---|---|---|---|---|---|---|
| 881 | 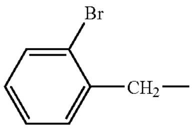 | 2 | 2 | 1 | — | H | 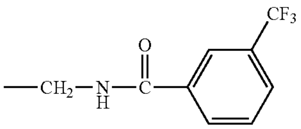 |
| 882 | 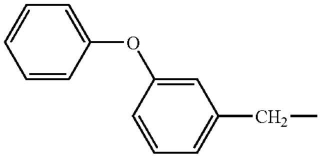 | 2 | 2 | 1 | — | H | 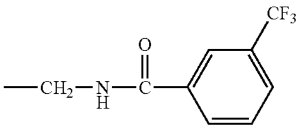 |
| 883 | 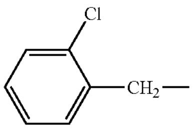 | 2 | 2 | 1 | — | H | 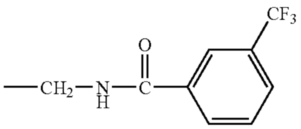 |

TABLE 1.81-continued
| Compd. No. | 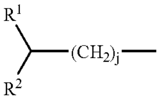 | k | m | n | chirality | $R^3$ | 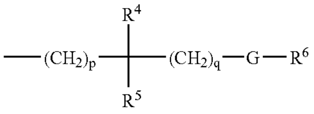 |
|---|---|---|---|---|---|---|---|
| 884 | 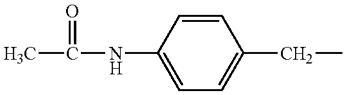 | 2 | 2 | 1 | — | H | 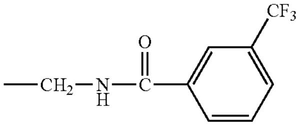 |
| 885 | 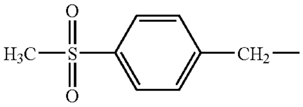 | 2 | 2 | 1 | — | H | 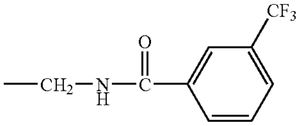 |
| 886 | 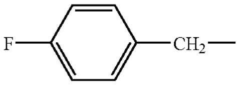 | 2 | 2 | 1 | — | H | 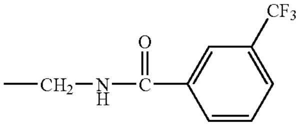 |
| 887 | 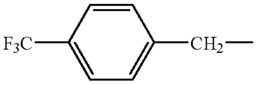 | 2 | 2 | 1 | — | H | 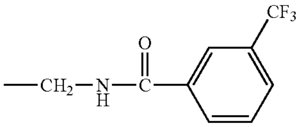 |
| 888 | 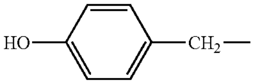 | 2 | 2 | 1 | — | H | 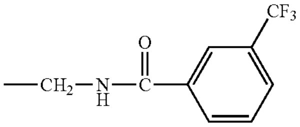 |
| 889 | 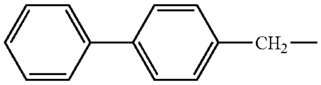 | 2 | 2 | 1 | — | H | 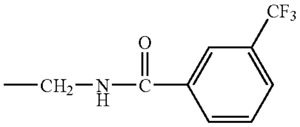 |
| 890 | 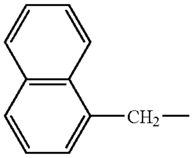 | 2 | 2 | 1 | — | H | 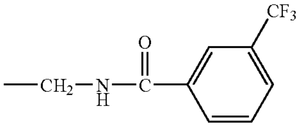 |
| 891 | 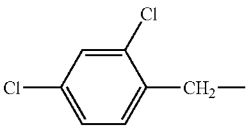 | 2 | 2 | 1 | — | H | 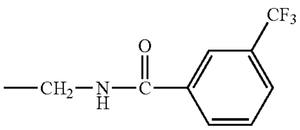 |

TABLE 1.82
| Compd. No. | 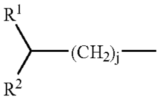 | k | m | n | chirality | $R^3$ | 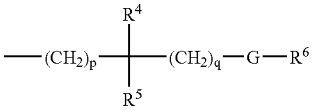 |
|---|---|---|---|---|---|---|---|
| 892 | 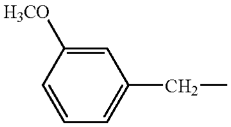 | 2 | 2 | 1 | — | H | 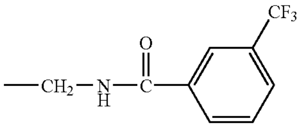 |
| 893 | 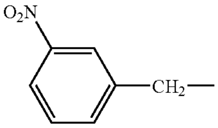 | 2 | 2 | 1 | — | H | 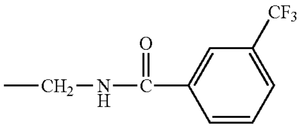 |
| 894 | 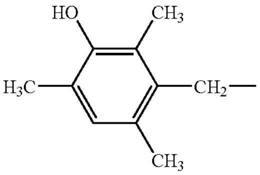 | 2 | 2 | 1 | — | H | 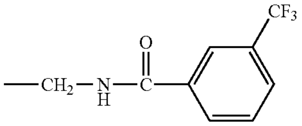 |
| 895 | 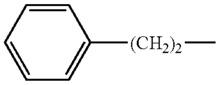 | 2 | 2 | 1 | — | H | 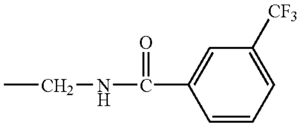 |
| 896 | 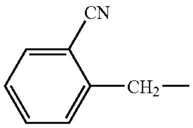 | 2 | 2 | 1 | — | H | 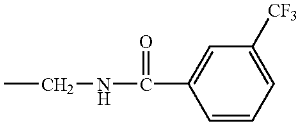 |
| 897 | 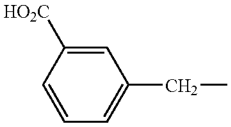 | 2 | 2 | 1 | — | H | 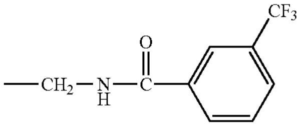 |
| 898 | 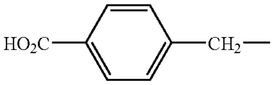 | 2 | 2 | 1 | — | H | 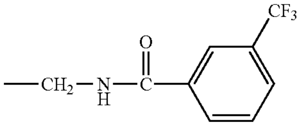 |
| 899 | 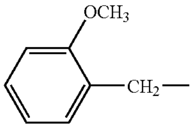 | 2 | 2 | 1 | — | H | 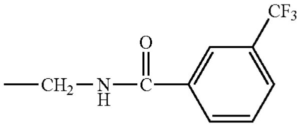 |
| 900 | 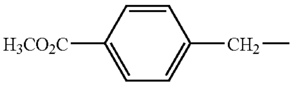 | 2 | 2 | 1 | — | H | 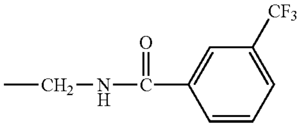 |
| 901 | 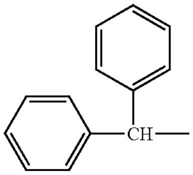 | 2 | 2 | 1 | — | H | 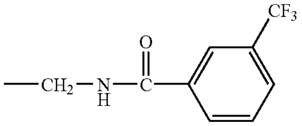 |

TABLE 1.82-continued
| Compd. No. | 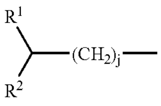 | k | m | n | chirality | $R^3$ | 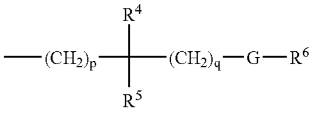 |
|---|---|---|---|---|---|---|---|
| 902 | 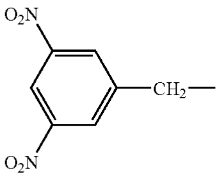 | 2 | 2 | 1 | — | H | 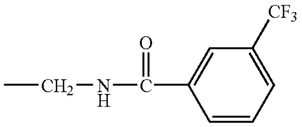 |
TABLE 1.83
| Compd. No. | 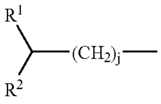 | k | m | n | chirality | $R^3$ | 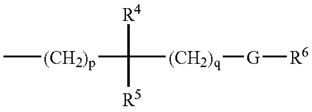 |
|---|---|---|---|---|---|---|---|
| 903 | 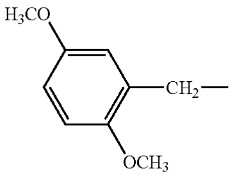 | 2 | 2 | 1 | — | H | 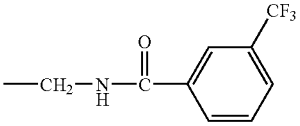 |
| 904 | 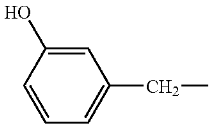 | 2 | 2 | 1 | — | H | 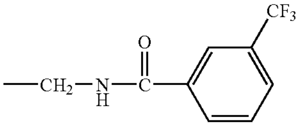 |
| 905 | 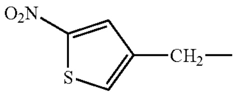 | 2 | 2 | 1 | — | H | 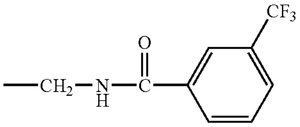 |
| 906 | 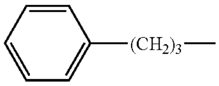 | 2 | 2 | 1 | — | H | 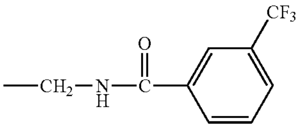 |
| 907 | 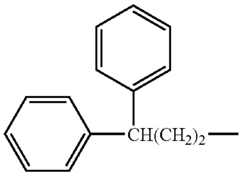 | 2 | 2 | 1 | — | H | 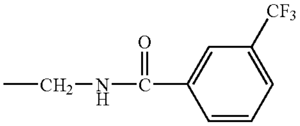 |
| 908 | 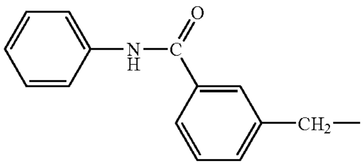 | 2 | 2 | 1 | — | H | 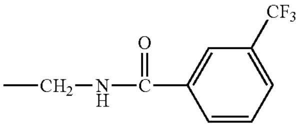 |

TABLE 1.83-continued
| Compd. No. | 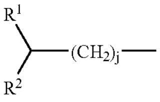 | k | m | n | chirality | $R^3$ | 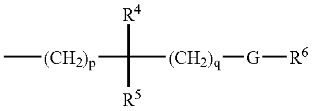 |
|---|---|---|---|---|---|---|---|
| 909 | 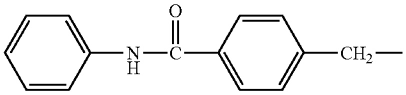 | 2 | 2 | 1 | — | H | 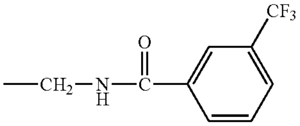 |
| 910 | 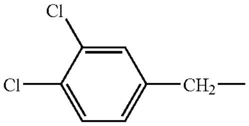 | 2 | 2 | 1 | — | H | 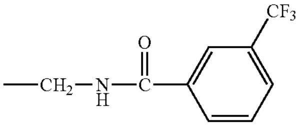 |
| 911 | 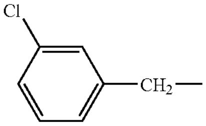 | 2 | 2 | 1 | — | H | 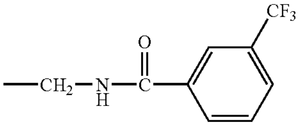 |
| 912 | 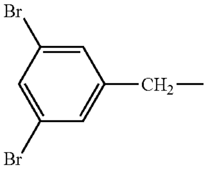 | 2 | 2 | 1 | — | H | 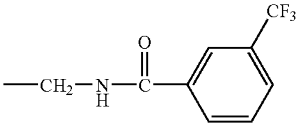 |
| 913 | 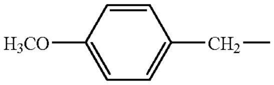 | 2 | 2 | 1 | — | H | 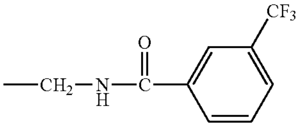 |
TABLE 1.84
| Compd. No. | 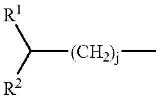 | k | m | n | chirality | $R^3$ | 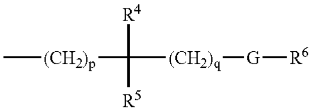 |
|---|---|---|---|---|---|---|---|
| 914 | 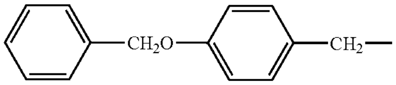 | 2 | 2 | 1 | — | H | 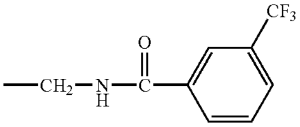 |
| 915 | 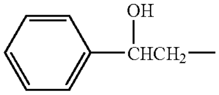 | 2 | 2 | 1 | — | H | 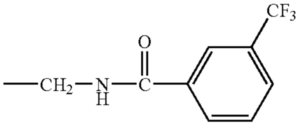 |
| 916 | 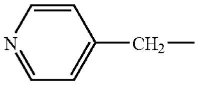 | 2 | 2 | 1 | — | H | 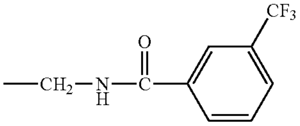 |

TABLE 1.84-continued
| Compd. No. | 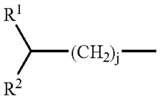 | k | m | n | chirality | $R^3$ | 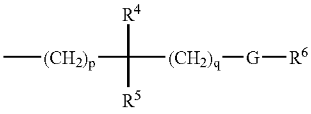 |
|---|---|---|---|---|---|---|---|
| 917 | 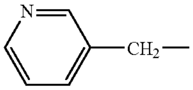 | 2 | 2 | 1 | — | H | 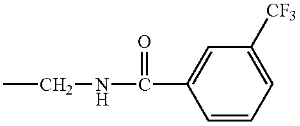 |
| 918 | 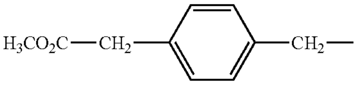 | 2 | 2 | 1 | — | H | 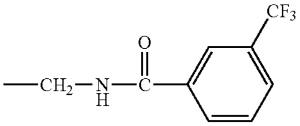 |
| 919 | 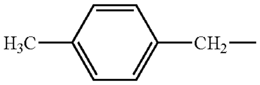 | 2 | 2 | 1 | — | H | 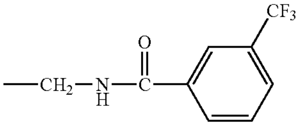 |
| 920 | 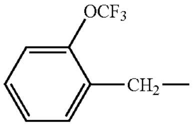 | 2 | 2 | 1 | — | H | 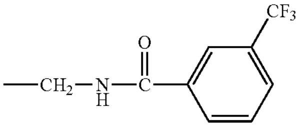 |
| 921 | 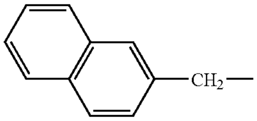 | 2 | 2 | 1 | — | H | 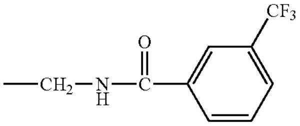 |
| 922 | 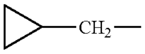 | 2 | 2 | 1 | — | H | 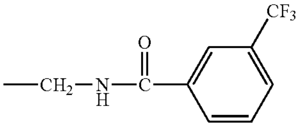 |
| 923 | 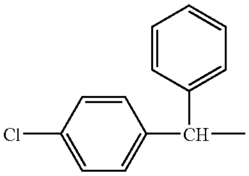 | 2 | 2 | 1 | — | H | 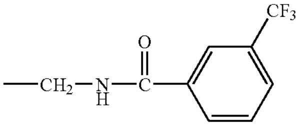 |
| 924 | 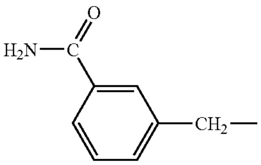 | 2 | 2 | 1 | — | H | 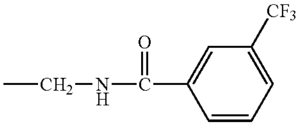 |

TABLE 1.85
| Compd. No. | 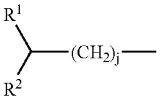 | k | m | n | chirality | $R^3$ | 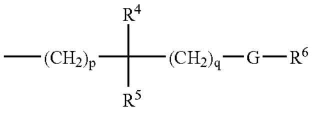 |
|---|---|---|---|---|---|---|---|
| 925 | 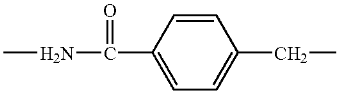 | 2 | 2 | 1 | — | H | 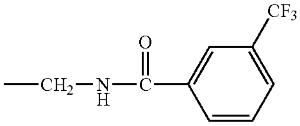 |
| 926 | 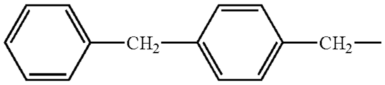 | 2 | 2 | 1 | — | H | 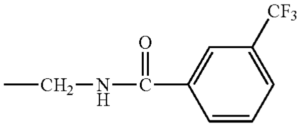 |
| 927 | 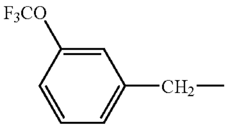 | 2 | 2 | 1 | — | H | 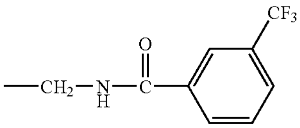 |
| 928 | 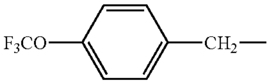 | 2 | 2 | 1 | — | H | 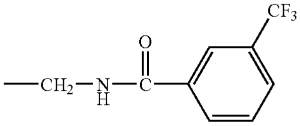 |
| 929 | 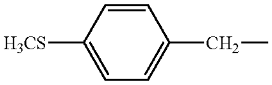 | 2 | 2 | 1 | — | H | 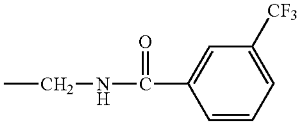 |
| 930 | 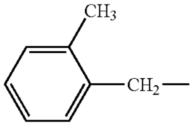 | 2 | 2 | 1 | — | H | 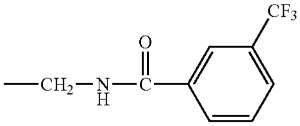 |
| 931 | 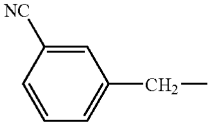 | 2 | 2 | 1 | — | H | 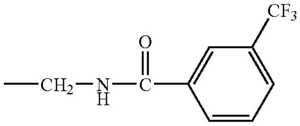 |
| 932 | 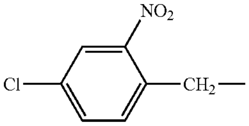 | 2 | 2 | 1 | — | H | 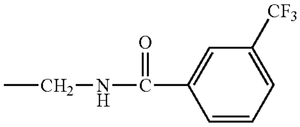 |
| 933 | 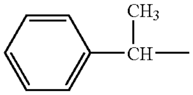 | 2 | 2 | 1 | — | H | 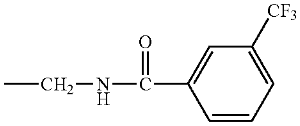 |
| 934 | 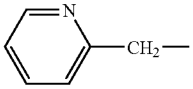 | 2 | 2 | 1 | — | H | 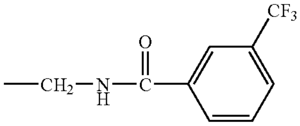 |

TABLE 1.85-continued
| Compd. No. | 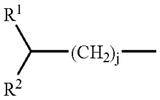 | k | m | n | chirality | $R^3$ | 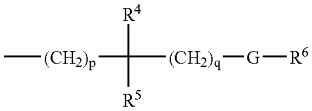 |
|---|---|---|---|---|---|---|---|
| 935 | 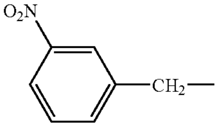 | 2 | 2 | 1 | — | H | 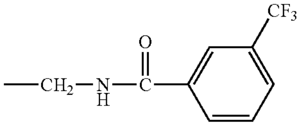 |
TABLE 1.86
| Compd. No. | 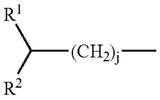 | k | m | n | chirality | $R^3$ | 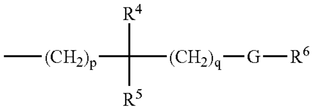 |
|---|---|---|---|---|---|---|---|
| 936 | 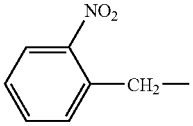 | 2 | 2 | 1 | — | H | 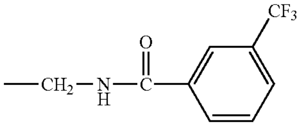 |
| 937 | 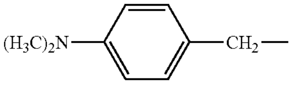 | 2 | 2 | 1 | — | H | 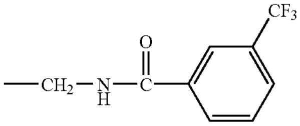 |
| 938 | 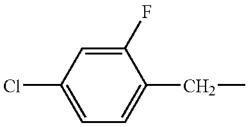 | 2 | 2 | 1 | — | H | 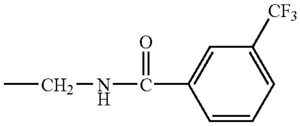 |
| 939 | 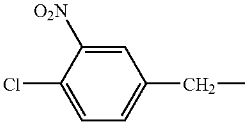 | 2 | 2 | 1 | — | H | 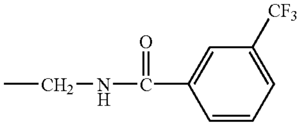 |
| 940 | 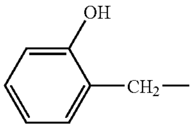 | 2 | 2 | 1 | — | H | 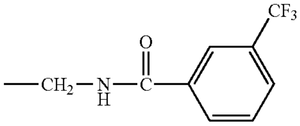 |
| 941 | 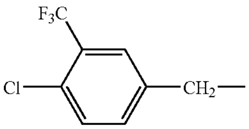 | 2 | 2 | 1 | — | H | 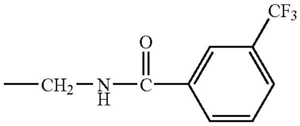 |
| 942 | 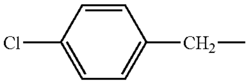 | 2 | 2 | 1 | — | H | 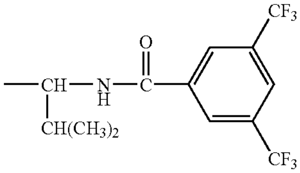 |

TABLE 1.86-continued
| Compd. No. | 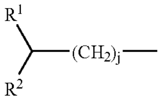 | k | m | n | chirality | $R^3$ | 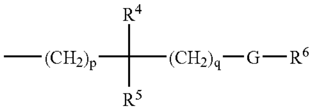 |
|---|---|---|---|---|---|---|---|
| 943 | 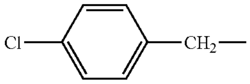 | 1 | 4 | 0 | — | H | 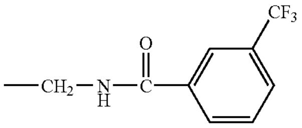 |
| 944 | 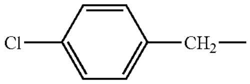 | 1 | 4 | 0 | — | H | 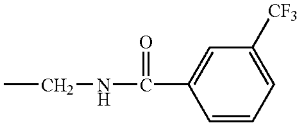 |
| 945 | 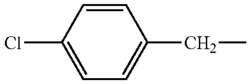 | 1 | 4 | 0 | — | H | 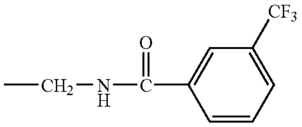 |
| 946 | 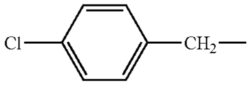 | 1 | 4 | 0 | — | H | 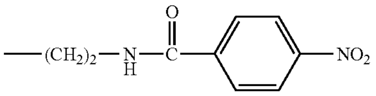 |
TABLE 1.87
| Compd. No. | 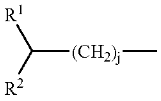 | k | m | n | chirality | $R^3$ | 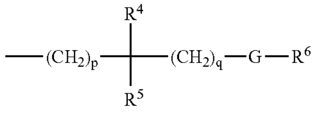 |
|---|---|---|---|---|---|---|---|
| 947 | 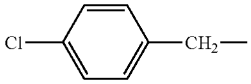 | 1 | 4 | 0 | — | H | 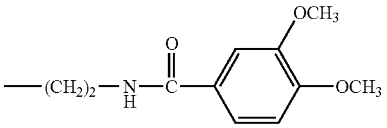 |
| 948 | 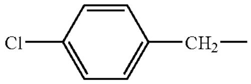 | 1 | 4 | 0 | — | H | 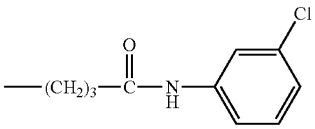 |
| 949 | 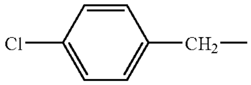 | 1 | 4 | 0 | — | H | 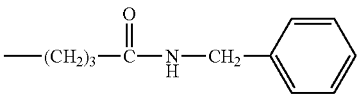 |
| 950 | 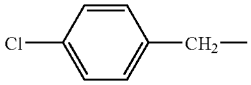 | 0 | 4 | 1 | — | H | 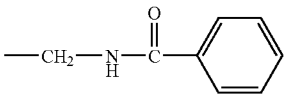 |
| 951 | 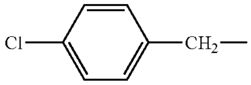 | 1 | 2 | 0 | R | H | 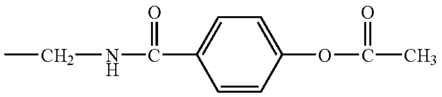 |
| 952 | 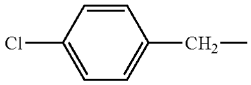 | 1 | 2 | 0 | R | H | 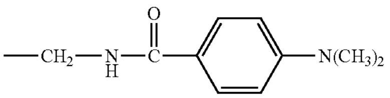 |

TABLE 1.87-continued
| Compd. No. | 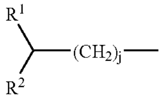 | k | m | n | chirality | $R^3$ | 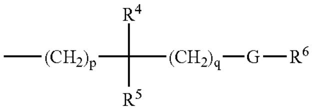 |
|---|---|---|---|---|---|---|---|
| 953 | 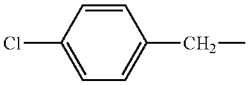 | 1 | 2 | 0 | R | H | 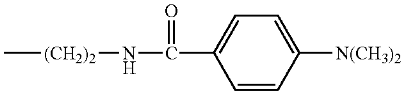 |
| 954 | 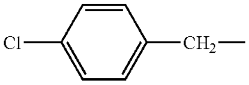 | 1 | 2 | 0 | R | H | 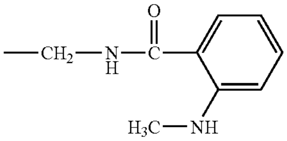 |
| 955 | 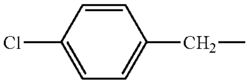 | 1 | 2 | 0 | R | H | 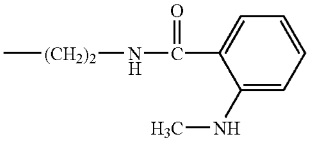 |
| 956 | 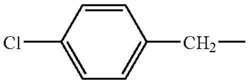 | 1 | 2 | 0 | R | H | 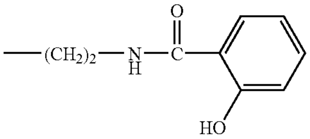 |
| 957 | 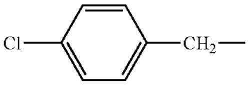 | 1 | 2 | 0 | R | H | 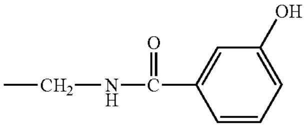 |
TABLE 1.88
| Compd. No. | 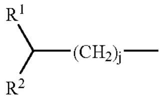 | k | m | n | chirality | $R^3$ | 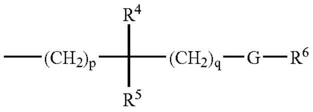 |
|---|---|---|---|---|---|---|---|
| 958 | 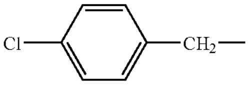 | 1 | 2 | 0 | R | H | 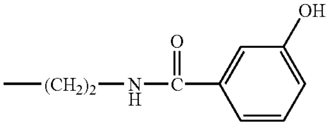 |
| 959 | 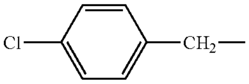 | 1 | 2 | 0 | R | H | 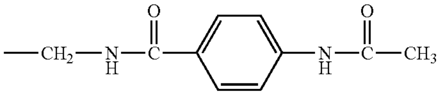 |
| 960 | 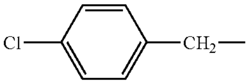 | 1 | 2 | 0 | R | H | 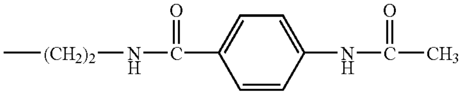 |
| 961 | 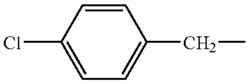 | 1 | 2 | 0 | R | H | 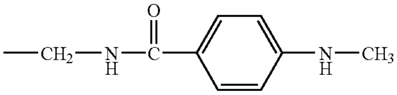 |
| 962 | 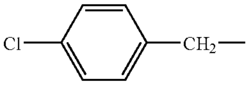 | 1 | 2 | 0 | R | H | 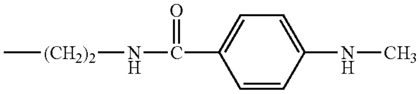 |

TABLE 1.88-continued
| Compd. No. | 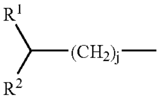 | k | m | n | chirality | $R^3$ | 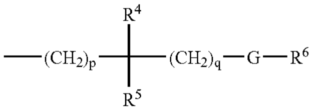 |
|---|---|---|---|---|---|---|---|
| 963 | 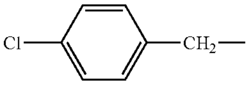 | 1 | 2 | 0 | R | H | 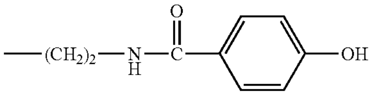 |
| 964 | 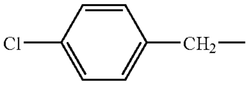 | 1 | 2 | 0 | R | H | 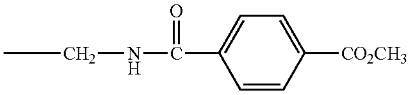 |
| 965 | 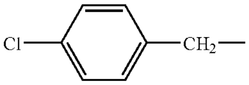 | 1 | 2 | 0 | R | H | 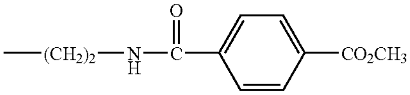 |
| 966 | 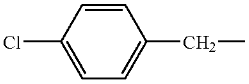 | 1 | 2 | 0 | R | H | 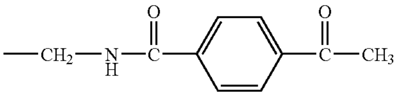 |
| 967 | 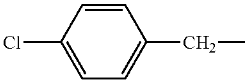 | 1 | 2 | 0 | R | H | 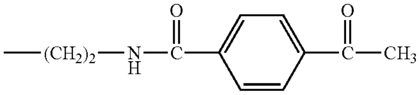 |
| 968 | 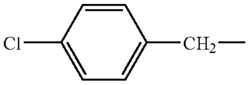 | 1 | 2 | 0 | R | H | 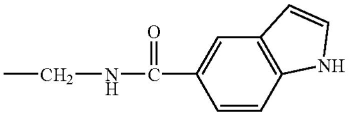 |
TABLE 1.89
| Compd. No. | 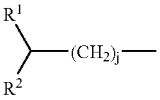 | k | m | n | chirality | $R^3$ | 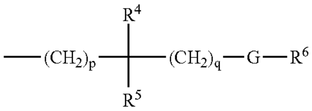 |
|---|---|---|---|---|---|---|---|
| 969 | 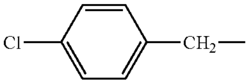 | 1 | 2 | 0 | R | H | 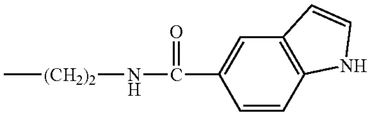 |
| 970 | 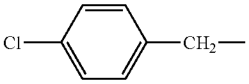 | 1 | 2 | 0 | R | H | 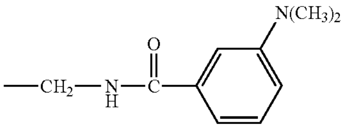 |
| 971 | 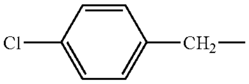 | 1 | 2 | 0 | R | H | 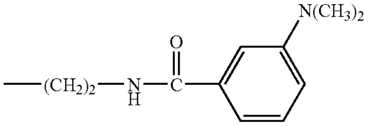 |
| 972 | 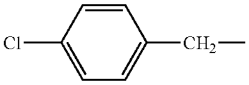 | 1 | 2 | 0 | R | H | 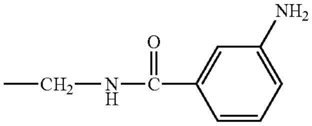 |

TABLE 1.89-continued
| Compd. No. | 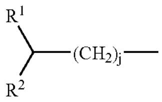 | k | m | n | chirality | $R^3$ | 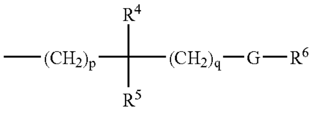 |
|---|---|---|---|---|---|---|---|
| 973 | 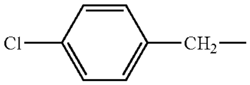 | 1 | 2 | 0 | R | H | 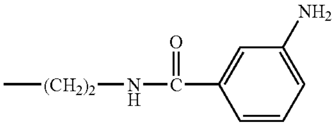 |
| 974 | 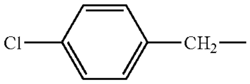 | 1 | 2 | 0 | R | H | 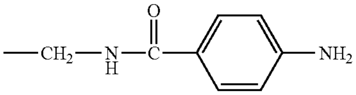 |
| 975 | 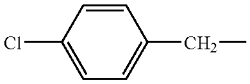 | 1 | 2 | 0 | R | H | 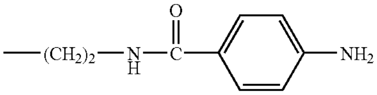 |
| 976 | 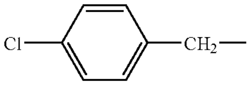 | 1 | 2 | 0 | R | H | 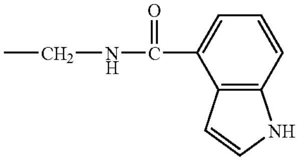 |
| 977 | 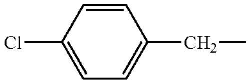 | 1 | 2 | 0 | R | H | 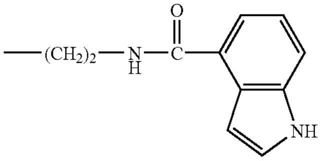 |
| 978 | 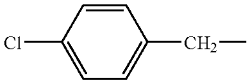 | 1 | 2 | 0 | R | H | 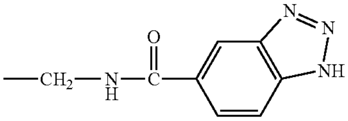 |
| 979 | 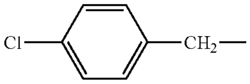 | 1 | 2 | 0 | R | H | 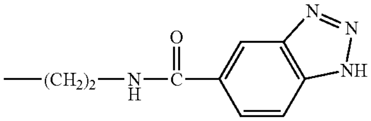 |

TABLE 1.90
| Compd. No. | 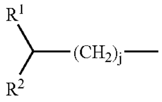 | k | m | n | chirality | $R^3$ | 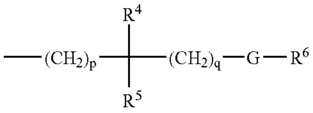 |
|---|---|---|---|---|---|---|---|
| 980 | 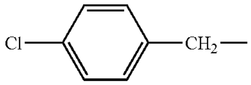 | 1 | 2 | 0 | R | H | 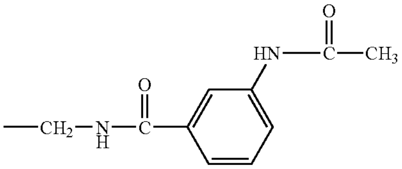 |
| 981 | 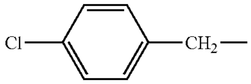 | 1 | 2 | 0 | R | H | 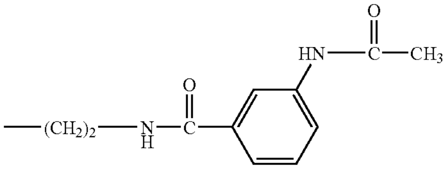 |
| 982 | 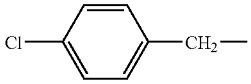 | 1 | 2 | 0 | R | H | 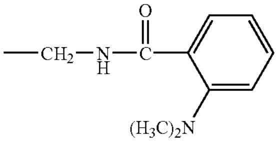 |
| 983 | 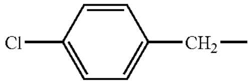 | 1 | 2 | 0 | R | H | 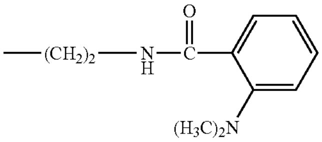 |
| 984 | 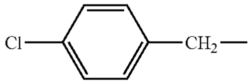 | 1 | 2 | 0 | R | H | 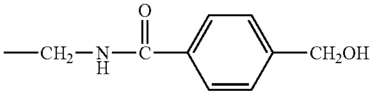 |
| 985 | 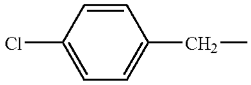 | 1 | 2 | 0 | R | H | 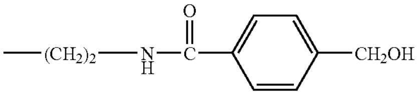 |
| 986 | 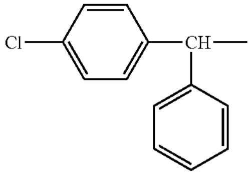 | 1 | 2 | 0 | R | H | 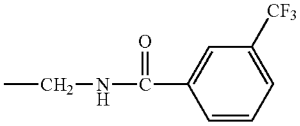 |
| 987 | 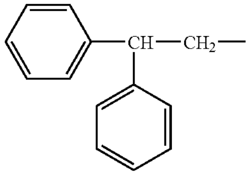 | 2 | 2 | 1 | — | H | 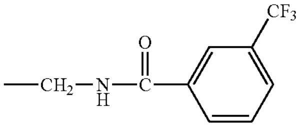 |
| 988 | 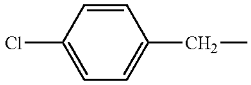 | 1 | 4 | 0 | — | H | 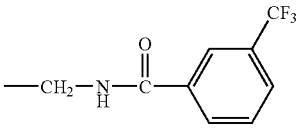 |

TABLE 1.90-continued
| Compd. No. | 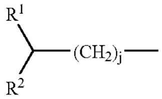 | k | m | n | chirality | $R^3$ | 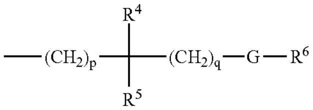 |
|---|---|---|---|---|---|---|---|
| 989 | 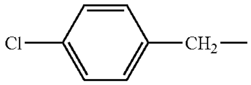 | 1 | 4 | 0 | — | H | 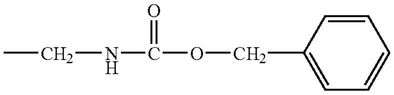 |
| 990 | 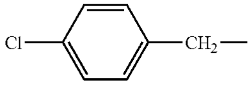 | 1 | 4 | 0 | — | H | 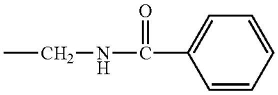 |
TABLE 1.91
| Compd. No. | 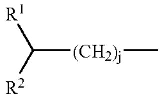 | k | m | n | chirality | $R^3$ | 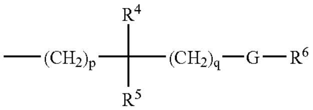 |
|---|---|---|---|---|---|---|---|
| 991 | 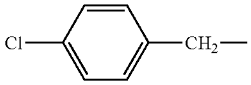 | 1 | 4 | 0 | — | H | 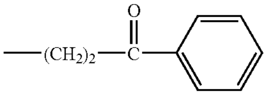 |
| 992 | 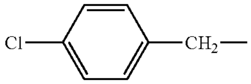 | 1 | 4 | 0 | — | H | 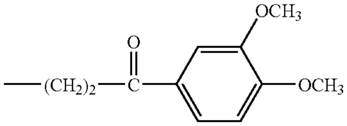 |
| 993 | 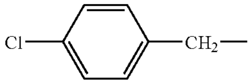 | 1 | 4 | 0 | — | H | 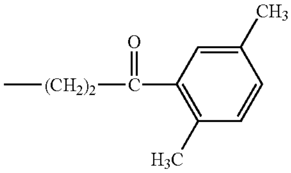 |
| 994 | 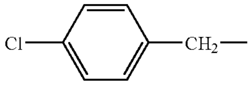 | 1 | 4 | 0 | — | H | 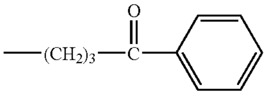 |
| 995 | 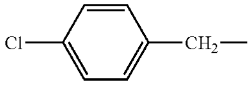 | 1 | 4 | 0 | — | H | 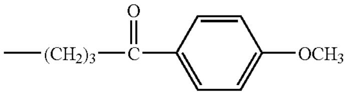 |
| 996 | 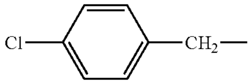 | 1 | 4 | 0 | — | H | 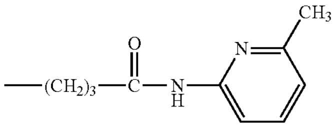 |
| 997 | 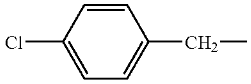 | 2 | 2 | 1 | — | H | 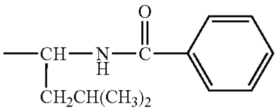 |
| 998 | 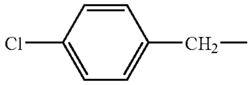 | 2 | 2 | 1 | — | H | 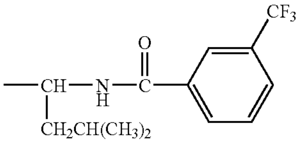 |

TABLE 1.91-continued
| Compd. No. | 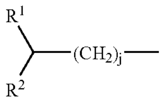 | k | m | n | chirality | R3 | 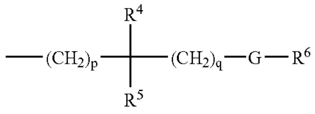 |
|---|---|---|---|---|---|---|---|
| 999 | 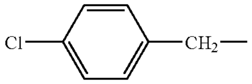 | 2 | 2 | 1 | — | H | 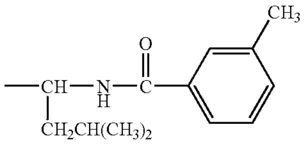 |
| 1000 | 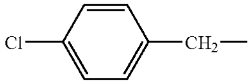 | 2 | 2 | 1 | — | H | 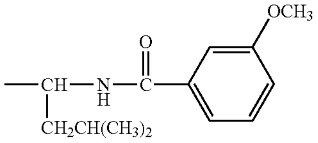 |
| 1001 | 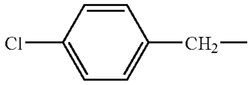 | 2 | 2 | 1 | — | H | 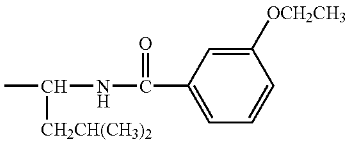 |
TABLE 1.92
| Compd. No. | 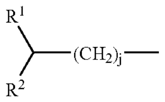 | k | m | n | chirality | R3 | 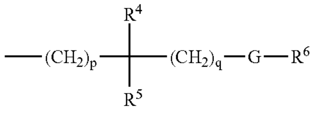 |
|---|---|---|---|---|---|---|---|
| 1002 | 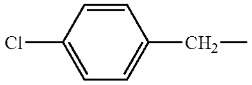 | 2 | 2 | 1 | — | H | 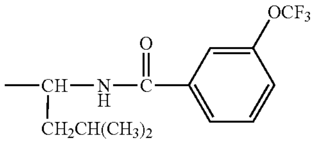 |
| 1003 | 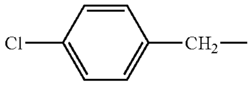 | 2 | 2 | 1 | — | H | 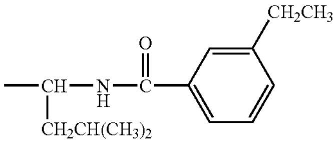 |
| 1004 | 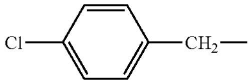 | 2 | 2 | 1 | — | H | 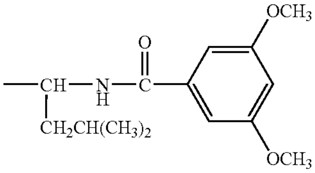 |
| 1005 | 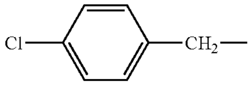 | 2 | 2 | 1 | — | H | 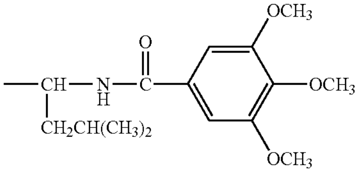 |

TABLE 1.92-continued
| Compd. No. | 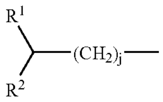 | k | m | n | chirality | $R^3$ | 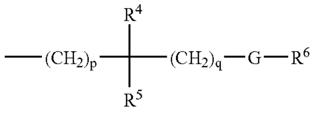 |
|---|---|---|---|---|---|---|---|
| 1006 | 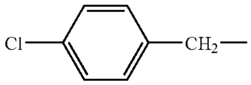 | 2 | 2 | 1 | — | H | 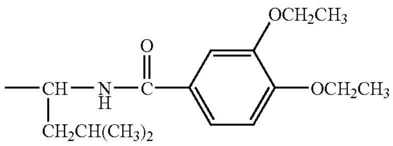 |
| 1007 | 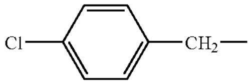 | 2 | 2 | 1 | — | H | 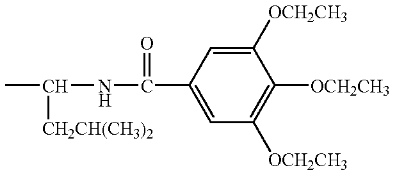 |
| 1008 | 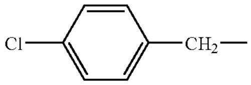 | 2 | 2 | 1 | — | H | 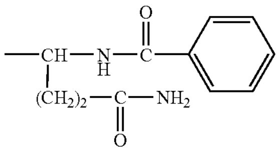 |
| 1009 | 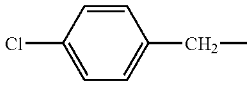 | 2 | 2 | 1 | — | H | 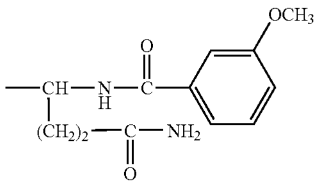 |
| 1010 | 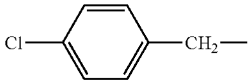 | 2 | 2 | 1 | — | H | 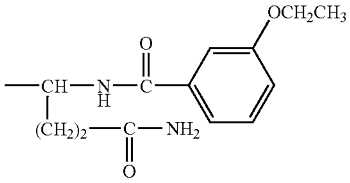 |
| 1011 | 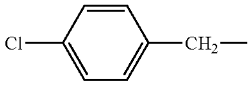 | 2 | 2 | 1 | — | H | 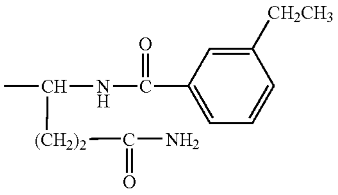 |
| 1012 | 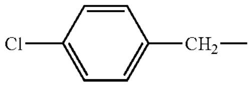 | 2 | 2 | 1 | — | H | 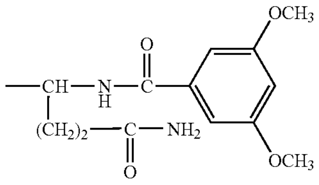 |

TABLE 1.93
| Compd. No. | 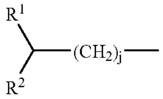 | k | m | n | chirality | $R^3$ | 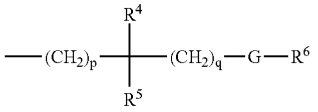 |
|---|---|---|---|---|---|---|---|
| 1013 | 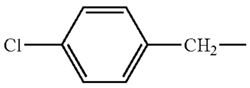 | 2 | 2 | 1 | — | H | 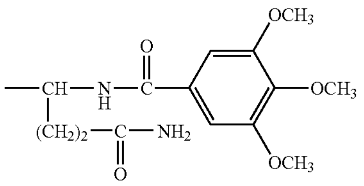 |
| 1014 | 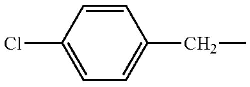 | 2 | 2 | 1 | — | H | 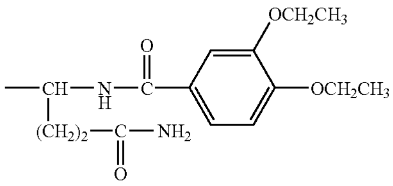 |
| 1015 | 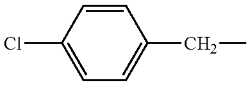 | 2 | 2 | 1 | — | H | 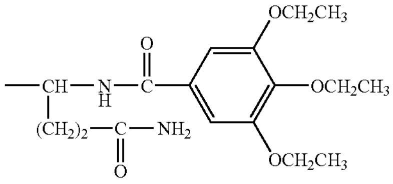 |
| 1016 | 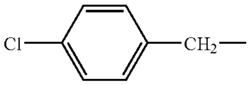 | 2 | 2 | 0 | — | H | 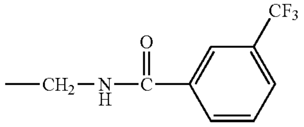 |
| 1017 | 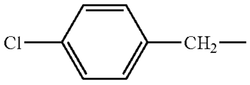 | 2 | 2 | 0 | — | H | 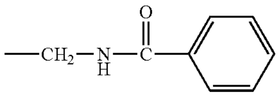 |
| 1018 | 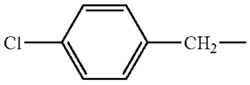 | 2 | 2 | 1 | — | H | 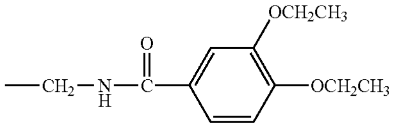 |
| 1019 | 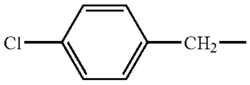 | 2 | 2 | 1 | — | H | 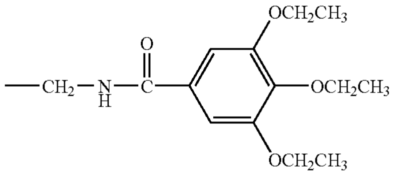 |
| 1020 | 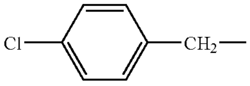 | 2 | 2 | 1 | — | H | 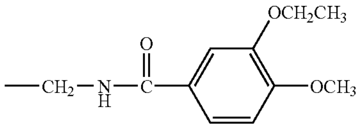 |
| 1021 | 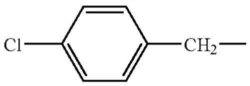 | 2 | 2 | 1 | — | H | 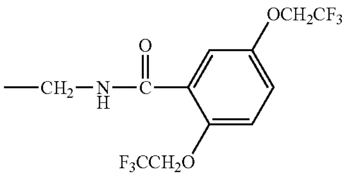 |

TABLE 1.93-continued
| Compd. No. | 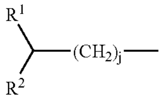 | k | m | n | chirality | $R^3$ | 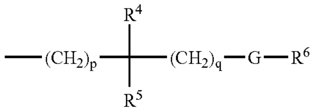 |
|---|---|---|---|---|---|---|---|
| 1022 | 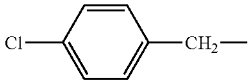 | 2 | 2 | 1 | — | H | 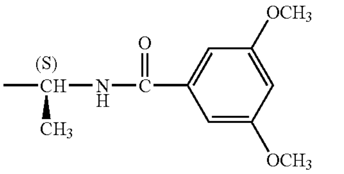 |
| 1023 | 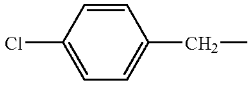 | 2 | 2 | 1 | — | H | 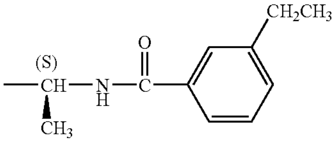 |
TABLE 1.94
| Compd. No. | 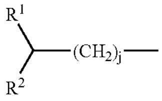 | k | m | n | chirality | $R^3$ | 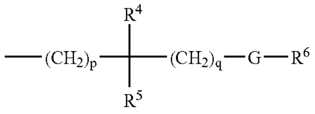 |
|---|---|---|---|---|---|---|---|
| 1024 | 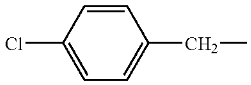 | 2 | 2 | 1 | — | H | 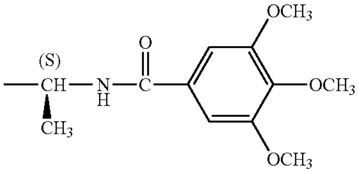 |
| 1025 | 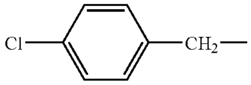 | 2 | 2 | 1 | — | H | 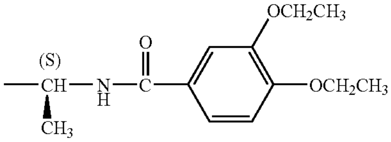 |
| 1026 | 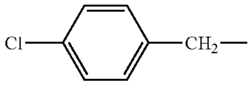 | 2 | 2 | 1 | — | H | 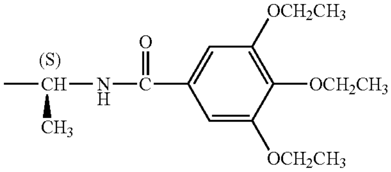 |
| 1027 | 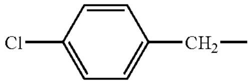 | 2 | 2 | 1 | — | H | 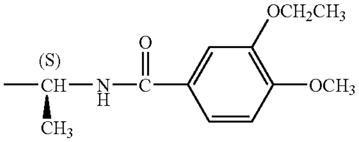 |
| 1028 | 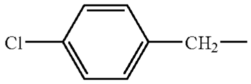 | 2 | 2 | 1 | — | H | 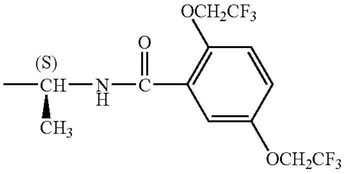 |

TABLE 1.94-continued
| Compd. No. | 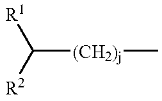 | k | m | n | chirality | $R^3$ | 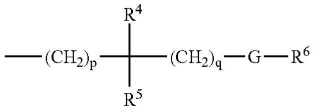 |
|---|---|---|---|---|---|---|---|
| 1029 | 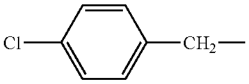 | 2 | 2 | 1 | — | H | 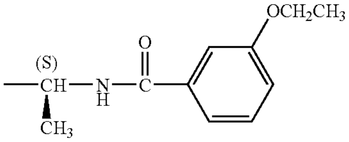 |
| 1030 | 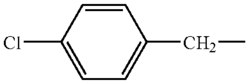 | 2 | 2 | 1 | — | H | 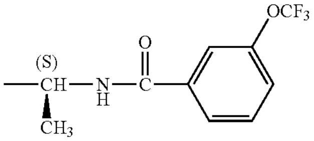 |
| 1031 | 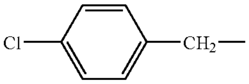 | 2 | 2 | 1 | — | H | 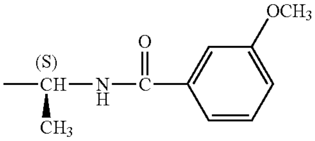 |
| 1032 | 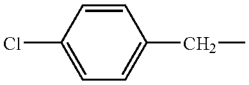 | 2 | 2 | 1 | — | H | 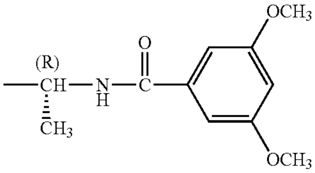 |
| 1033 | 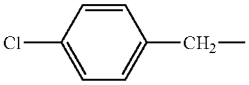 | 2 | 2 | 1 | — | H | 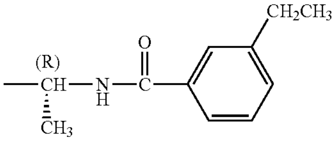 |
| 1034 | 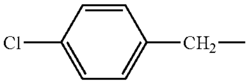 | 2 | 2 | 1 | — | H | 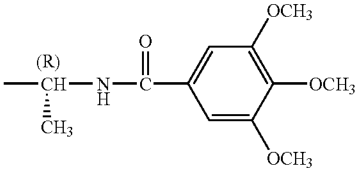 |
TABLE 1.95
| Compd. No. | 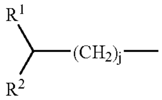 | k | m | n | chirality | $R^3$ | 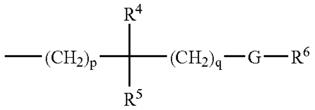 |
|---|---|---|---|---|---|---|---|
| 1035 | 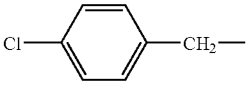 | 2 | 2 | 1 | — | H | 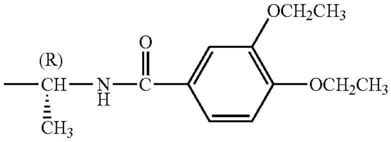 |

TABLE 1.95-continued
| Compd. No. | 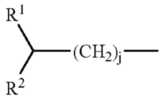 | k | m | n | chirality | $R^3$ | 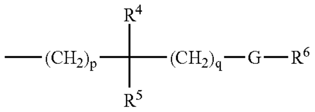 |
|---|---|---|---|---|---|---|---|
| 1036 | 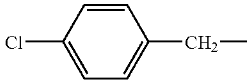 | 2 | 2 | 1 | — | H | 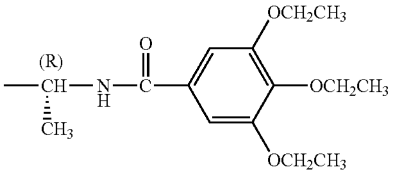 |
| 1037 | 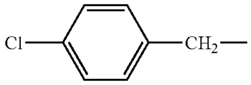 | 2 | 2 | 1 | — | H | 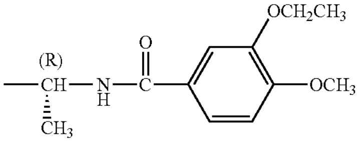 |
| 1038 | 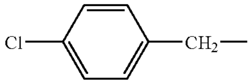 | 2 | 2 | 1 | — | H | 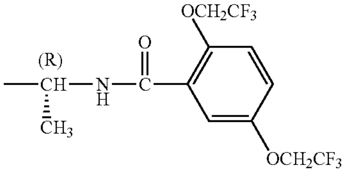 |
| 1039 | 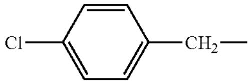 | 2 | 2 | 1 | — | H | 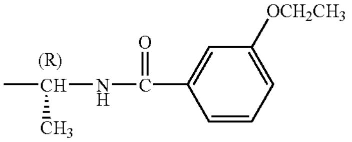 |
| 1040 | 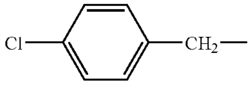 | 2 | 2 | 1 | — | H | 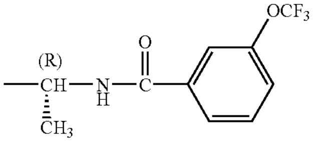 |
| 1041 | 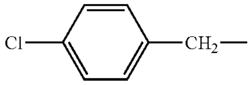 | 2 | 2 | 1 | — | H | 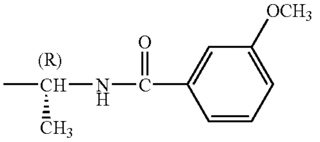 |
| 1042 | 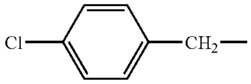 | 2 | 2 | 1 | — | H | 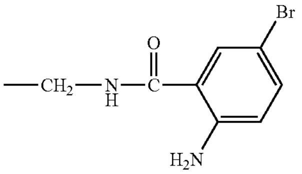 |
| 1043 | 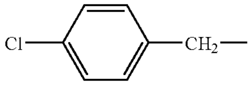 | 2 | 2 | 1 | — | H | 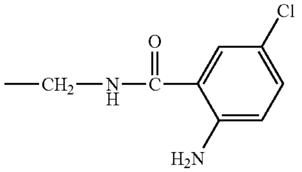 |

TABLE 1.95-continued
| Compd. No. | 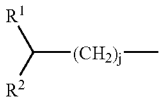 | k | m | n | chirality | $R^3$ | 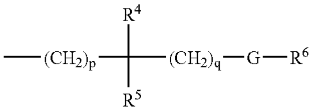 |
|---|---|---|---|---|---|---|---|
| 1044 | 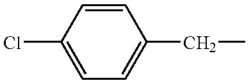 | 2 | 2 | 1 | — | H | 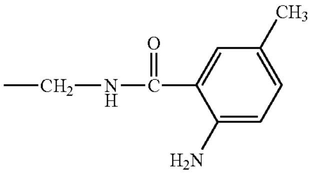 |
| 1045 | 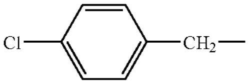 | 2 | 2 | 1 | — | H | 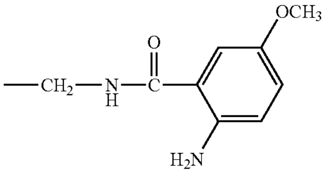 |
TABLE 1.96
| Compd. No. | 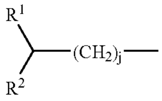 | k | m | n | chirality | $R^3$ | 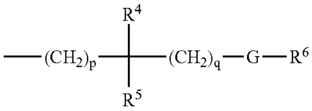 |
|---|---|---|---|---|---|---|---|
| 1046 | 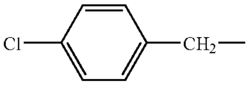 | 2 | 2 | 1 | — | H | 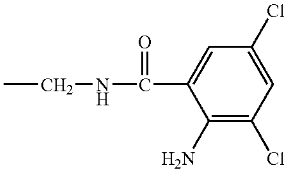 |
| 1047 | 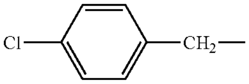 | 2 | 2 | 1 | — | H | 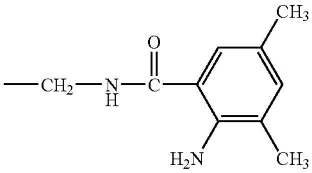 |
| 1048 | 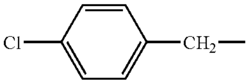 | 2 | 2 | 1 | — | H | 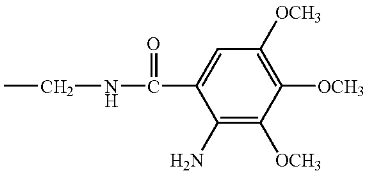 |
| 1049 | 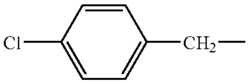 | 2 | 2 | 1 | — | H | 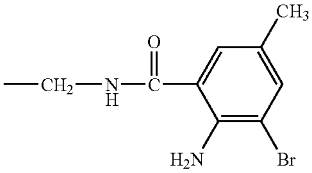 |

TABLE 1.96-continued
| Compd. No. | 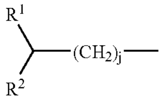 | k | m | n | chirality | $R^3$ | 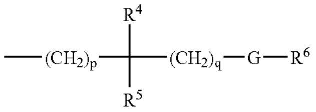 |
|---|---|---|---|---|---|---|---|
| 1050 | 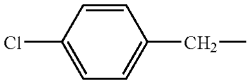 | 2 | 2 | 1 | — | H | 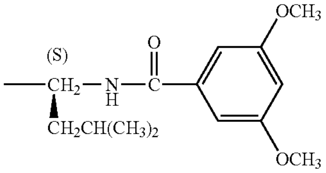 |
| 1051 | 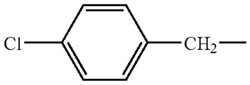 | 2 | 2 | 1 | — | H | 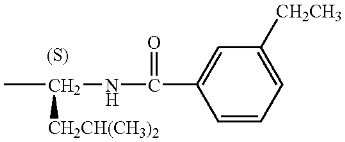 |
| 1052 | 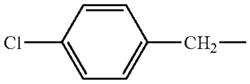 | 2 | 2 | 1 | — | H | 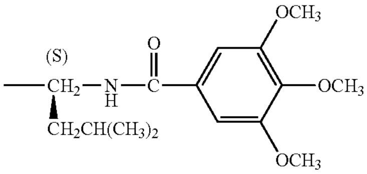 |
| 1053 | 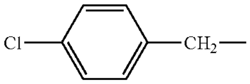 | 2 | 2 | 1 | — | H | 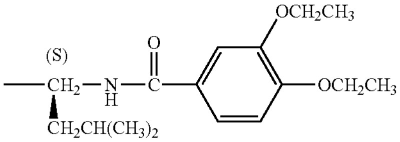 |
| 1054 | 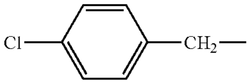 | 2 | 2 | 1 | — | H | 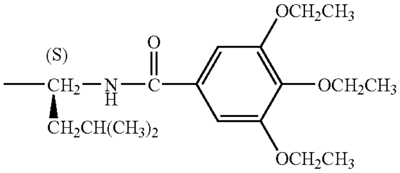 |
| 1055 | 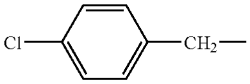 | 2 | 2 | 1 | — | H | 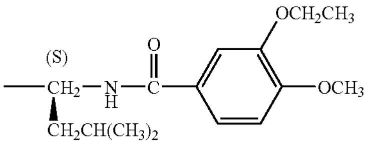 |
| 1056 | 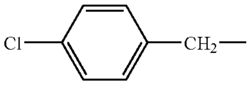 | 2 | 2 | 1 | — | H | 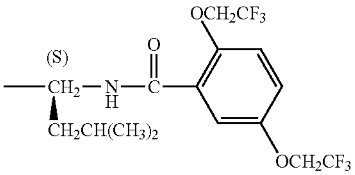 |

TABLE 1.97
| Compd. No. | 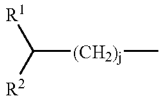 | k | m | n | chirality | $R^3$ | 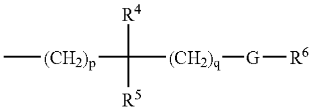 |
|---|---|---|---|---|---|---|---|
| 1057 | 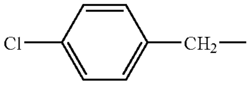 | 2 | 2 | 1 | — | H | 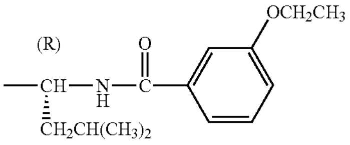 |
| 1058 | 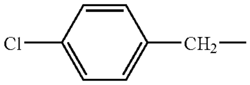 | 2 | 2 | 1 | — | H | 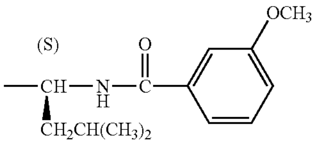 |
| 1059 | 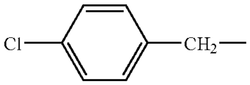 | 2 | 2 | 1 | — | H | 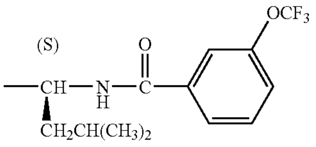 |
| 1060 | 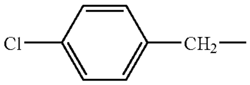 | 2 | 2 | 1 | — | H | 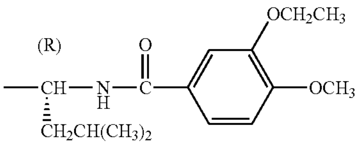 |
| 1061 | 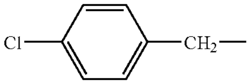 | 2 | 2 | 1 | — | H | 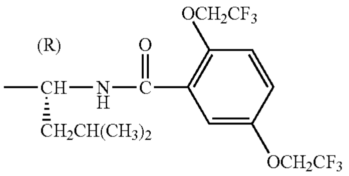 |
| 1062 | 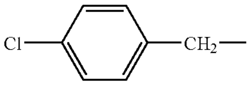 | 2 | 2 | 1 | — | H | 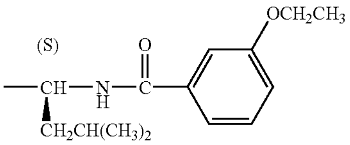 |
| 1063 | 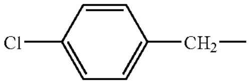 | 2 | 2 | 1 | — | H | 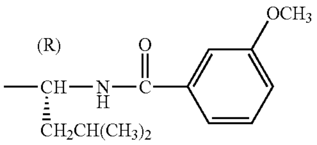 |
| 1064 | 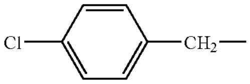 | 2 | 2 | 1 | — | H | 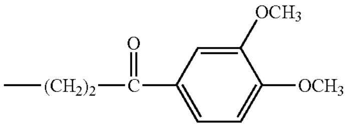 |
| 1065 | 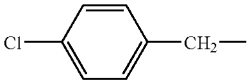 | 2 | 2 | 1 | — | H | 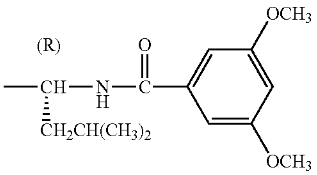 |

TABLE 1.97-continued
| Compd. No. | 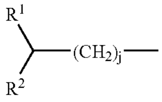 | k | m | n | chirality | $R^3$ | 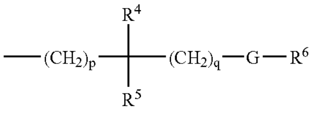 |
|---|---|---|---|---|---|---|---|
| 1066 | 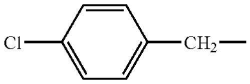 | 2 | 2 | 1 | — | H | 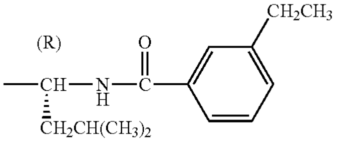 |
| 1067 | 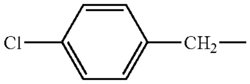 | 2 | 2 | 1 | — | H | 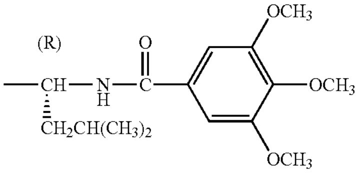 |
TABLE 1.98
| Compd. No. | 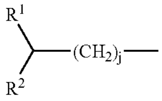 | k | m | n | chirality | $R^3$ | 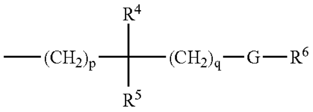 |
|---|---|---|---|---|---|---|---|
| 1068 | 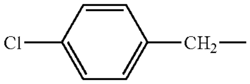 | 2 | 2 | 1 | — | H | 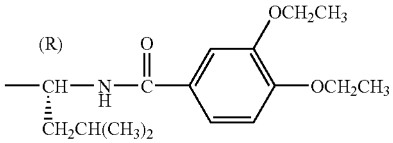 |
| 1069 | 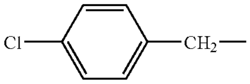 | 2 | 2 | 1 | — | H | 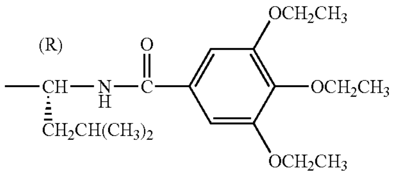 |
| 1070 | 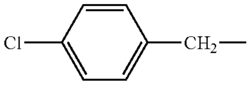 | 2 | 2 | 1 | — | H | 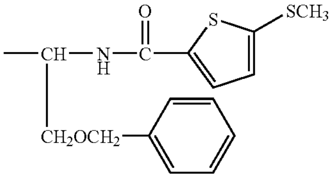 |
| 1071 | 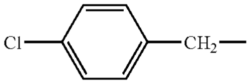 | 2 | 2 | 1 | — | H | 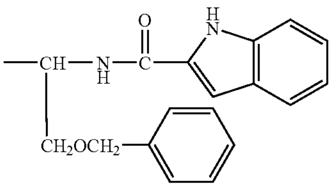 |
| 1072 | 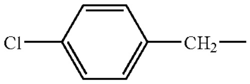 | 2 | 2 | 1 | — | H | 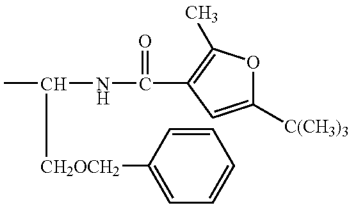 |

TABLE 1.98-continued
| Compd. No. | 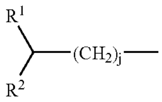 | k | m | n | chirality | $R^3$ | 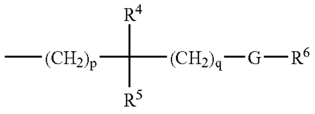 |
|---|---|---|---|---|---|---|---|
| 1073 | 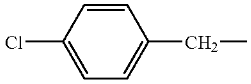 | 2 | 2 | 1 | — | H | 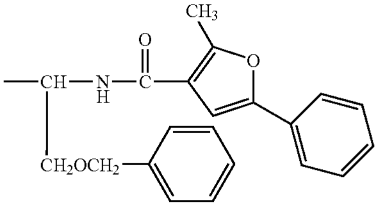 |
| 1074 | 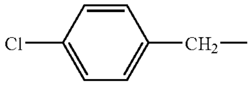 | 2 | 2 | 1 | — | H | 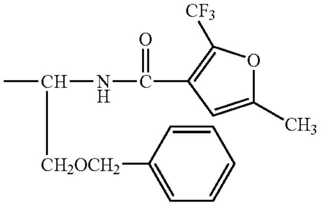 |
| 1075 | 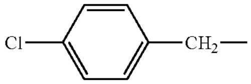 | 2 | 2 | 1 | — | H | 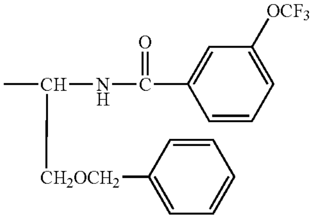 |
| 1076 | 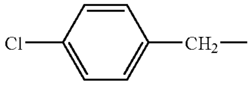 | 2 | 2 | 1 | — | H | 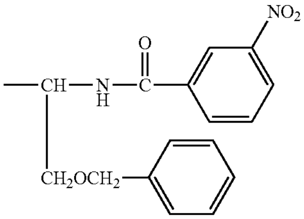 |
| 1077 | 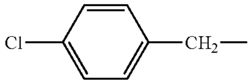 | 2 | 2 | 1 | — | H | 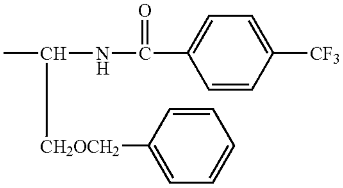 |
| 1078 | 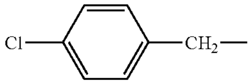 | 2 | 2 | 1 | — | H | 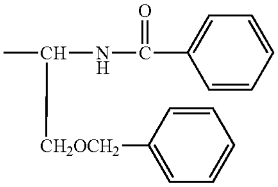 |

TABLE 1.99
| Compd. No. | 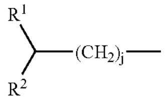 | k | m | n | chirality | $R^3$ | 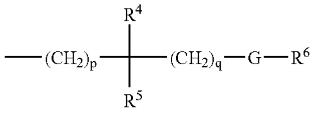 |
|---|---|---|---|---|---|---|---|
| 1079 | 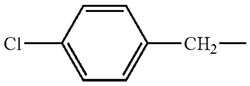 | 2 | 2 | 1 | — | H | 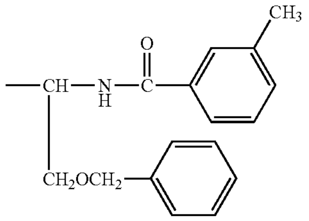 |
| 1080 | 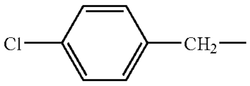 | 2 | 2 | 1 | — | H | 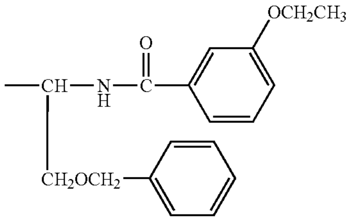 |
| 1081 | 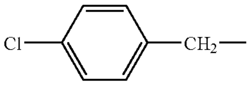 | 2 | 2 | 1 | — | H | 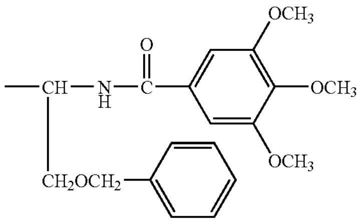 |
| 1082 | 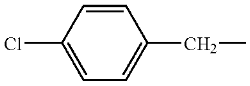 | 2 | 2 | 1 | — | H | 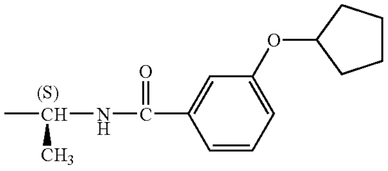 |
| 1083 | 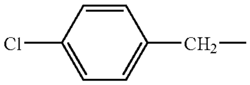 | 2 | 2 | 1 | — | H | 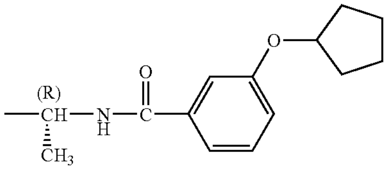 |
| 1084 | 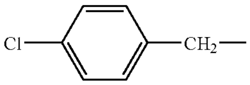 | 1 | 2 | 0 | R | H | 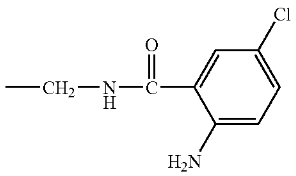 |
| 1085 | 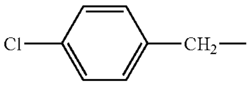 | 1 | 2 | 0 | R | H | 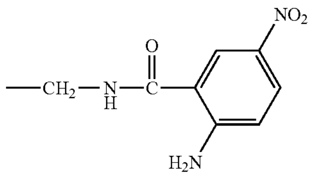 |

TABLE 1.99-continued
| Compd. No. | 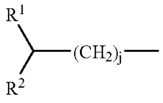 | k | m | n | chirality | $R^3$ | 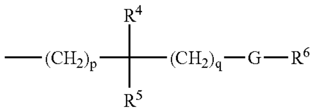 |
|---|---|---|---|---|---|---|---|
| 1086 | 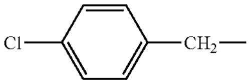 | 1 | 2 | 0 | R | H | 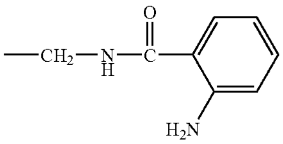 |
| 1087 | 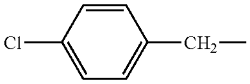 | 1 | 2 | 0 | R | H | 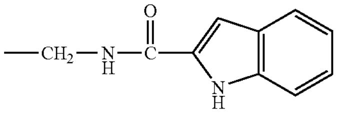 |
| 1088 | 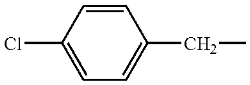 | 1 | 2 | 0 | R | H | 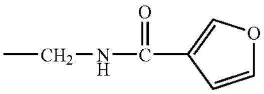 |
| 1089 | 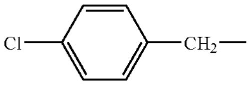 | 1 | 2 | 0 | R | H | 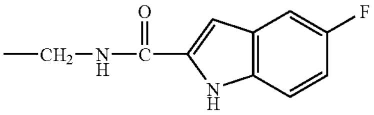 |
TABLE 1.100
| Compd. No. | 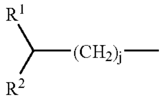 | k | m | n | chirality | $R^3$ | 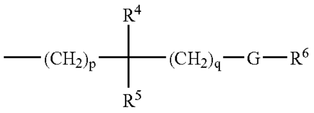 |
|---|---|---|---|---|---|---|---|
| 1090 | 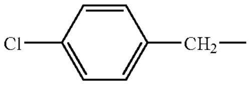 | 1 | 2 | 0 | R | H | 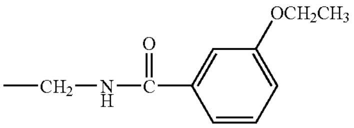 |
| 1091 | 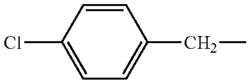 | 1 | 2 | 0 | R | H | 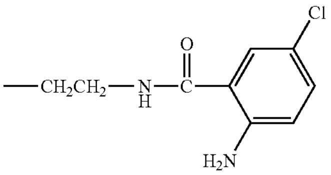 |
| 1092 | 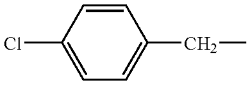 | 1 | 2 | 0 | R | H | 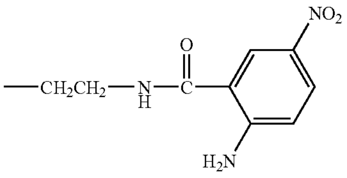 |
| 1093 | 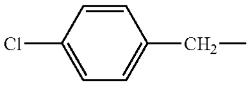 | 1 | 2 | 0 | R | H | 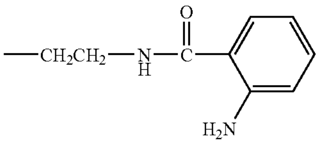 |

TABLE 1.100-continued
| Compd. No. | 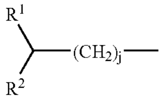 | k | m | n | chirality | $R^3$ | 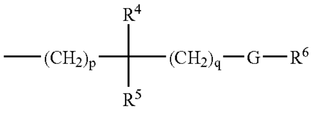 |
|---|---|---|---|---|---|---|---|
| 1094 | 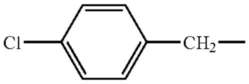 | 1 | 2 | 0 | R | H | 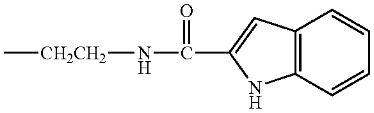 |
| 1095 | 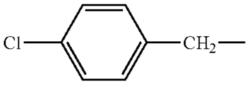 | 1 | 2 | 0 | R | H | 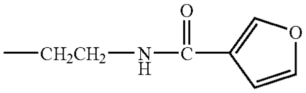 |
| 1096 | 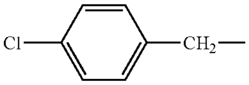 | 1 | 2 | 0 | R | H | 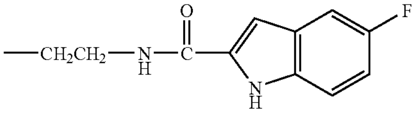 |
| 1097 | 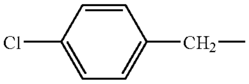 | 1 | 2 | 0 | R | H | 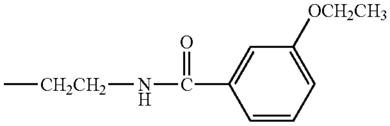 |
| 1098 | 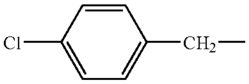 | 1 | 2 | 0 | R | H | 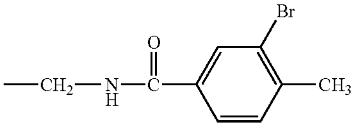 |
| 1099 | 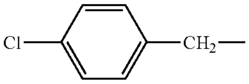 | 1 | 2 | 0 | R | H | 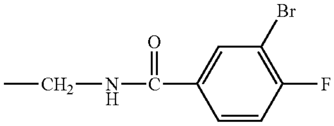 |
| 1100 | 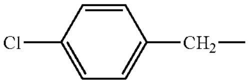 | 1 | 2 | 0 | R | H | 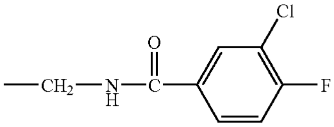 |
TABLE 1.101
| Compd. No. | 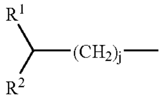 | k | m | n | chirality | $R^3$ | 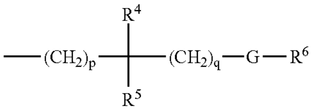 |
|---|---|---|---|---|---|---|---|
| 1101 | 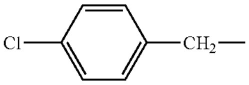 | 1 | 2 | 0 | R | H | 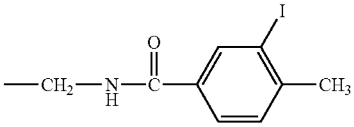 |
| 1102 | 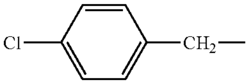 | 1 | 2 | 0 | R | H | 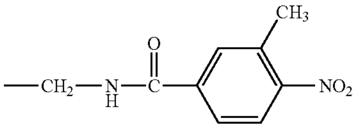 |

TABLE 1.101-continued
| Compd. No. | 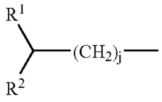 | k | m | n | chirality | $R^3$ | 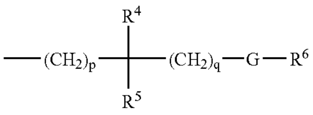 |
|---|---|---|---|---|---|---|---|
| 1103 | 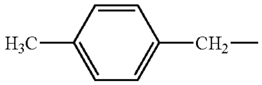 | 1 | 2 | 0 | R | H | 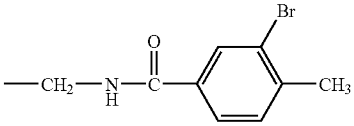 |
| 1104 | 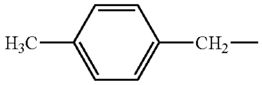 | 1 | 2 | 0 | R | H | 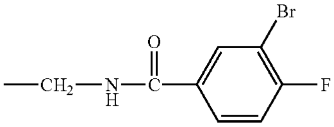 |
| 1105 | 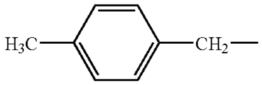 | 1 | 2 | 0 | R | H | 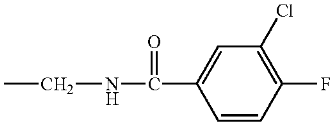 |
| 1106 | 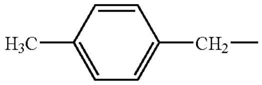 | 1 | 2 | 0 | R | H | 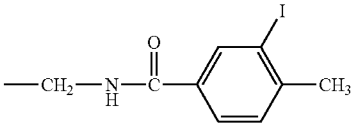 |
| 1107 | 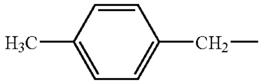 | 1 | 2 | 0 | R | H | 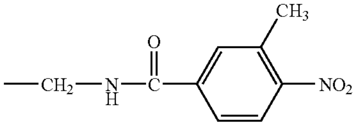 |
| 1108 | 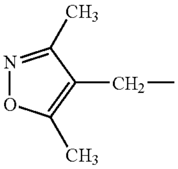 | 1 | 2 | 0 | R | H | 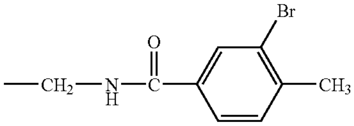 |
| 1109 | 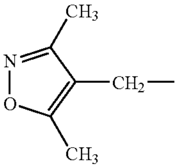 | 1 | 2 | 0 | R | H | 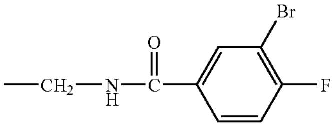 |
| 1110 | 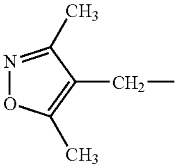 | 1 | 2 | 0 | R | H | 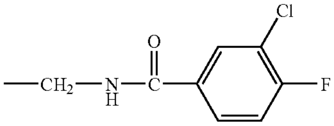 |
| 1111 | 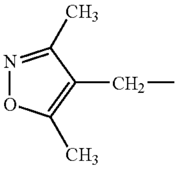 | 1 | 2 | 0 | R | H | 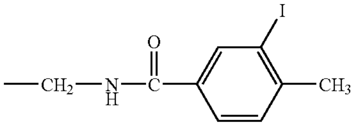 |

TABLE 1.102
| Compd. No. | 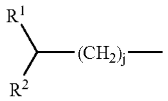 | k | m | n | chirality | $R^3$ | 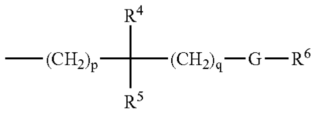 |
|---|---|---|---|---|---|---|---|
| 1112 | 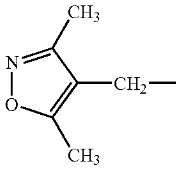 | 1 | 2 | 0 | R | H | 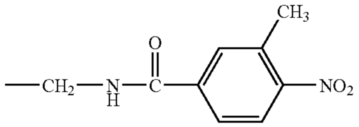 |
| 1113 | 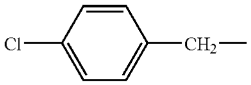 | 2 | 2 | 1 | — | H | 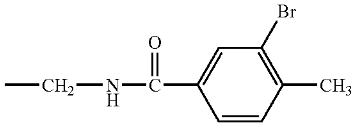 |
| 1114 | 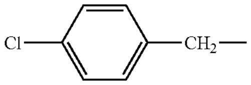 | 2 | 2 | 1 | — | H | 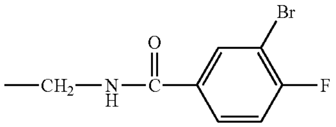 |
| 1115 | 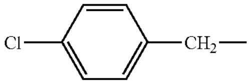 | 2 | 2 | 1 | — | H | 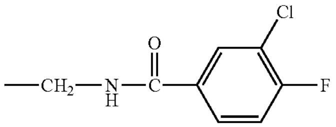 |
| 1116 | 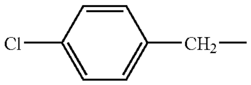 | 2 | 2 | 1 | — | H | 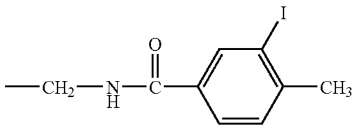 |
| 1117 | 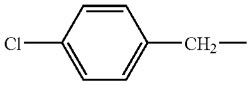 | 2 | 2 | 1 | — | H | 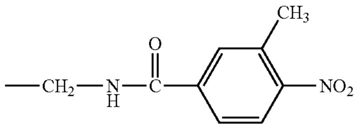 |
| 1118 | 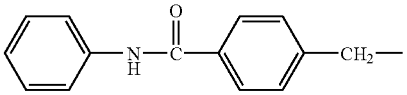 | 1 | 2 | 0 | R | H | 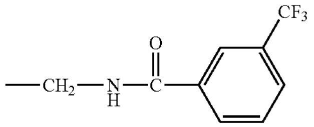 |
| 1119 | 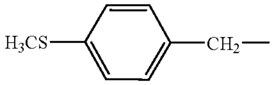 | 1 | 2 | 0 | R | H | 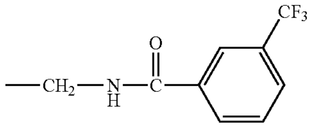 |
| 1120 | 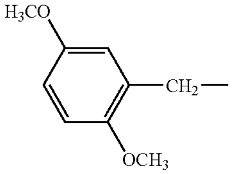 | 1 | 2 | 0 | R | H | 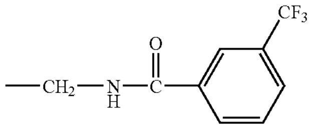 |
| 1121 | 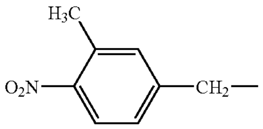 | 1 | 2 | 0 | R | H | 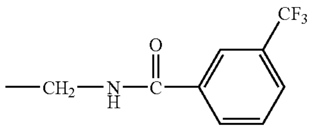 |

TABLE 1.102-continued
| Compd. No. | 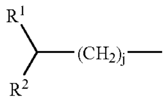 | k | m | n | chirality | $R^3$ | 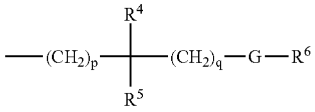 |
|---|---|---|---|---|---|---|---|
| 1122 | 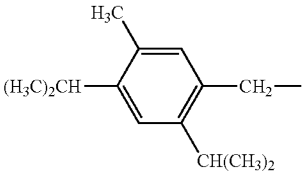 | 1 | 2 | 0 | R | H | 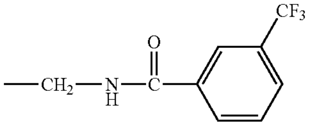 |
TABLE 1.103
| Compd. No. | 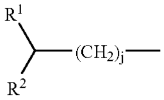 | k | m | n | chirality | $R^3$ | 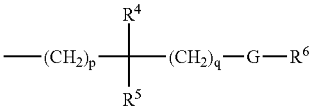 |
|---|---|---|---|---|---|---|---|
| 1123 | 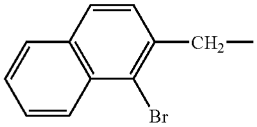 | 1 | 2 | 0 | R | H | 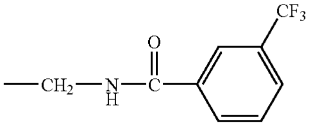 |
| 1124 | 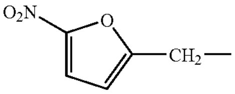 | 1 | 2 | 0 | R | H | 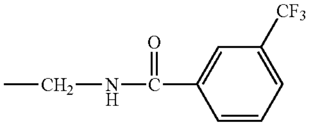 |
| 1125 | 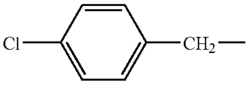 | 2 | 2 | 1 | — | H | 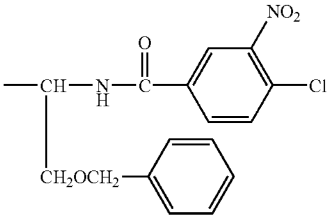 |
| 1126 | 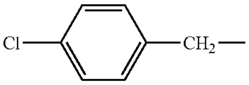 | 2 | 2 | 1 | — | H | 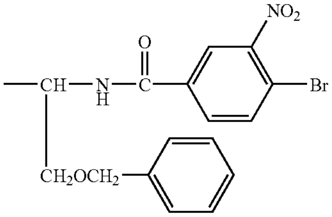 |
| 1127 | 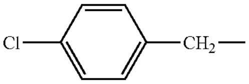 | 2 | 2 | 1 | — | H | 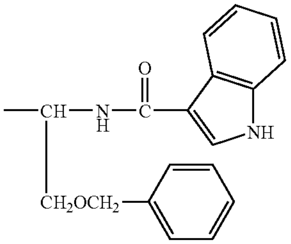 |

TABLE 1.103-continued
| Compd. No. | 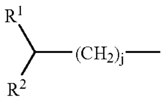 | k | m | n | chirality | $R^3$ | 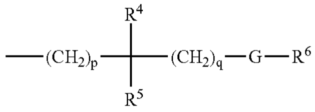 |
|---|---|---|---|---|---|---|---|
| 1128 | 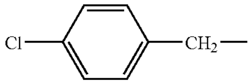 | 2 | 2 | 1 | — | H | 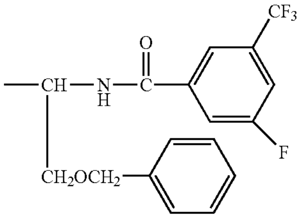 |
| 1129 | 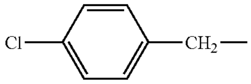 | 2 | 2 | 1 | — | H | 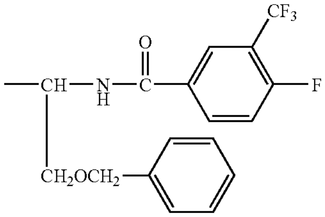 |
| 1130 | 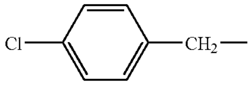 | 2 | 2 | 1 | — | H | 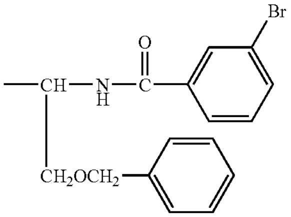 |
| 1131 | 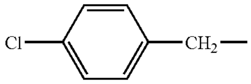 | 2 | 2 | 1 | — | H | 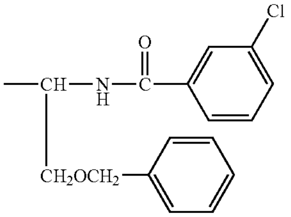 |
| 1132 | 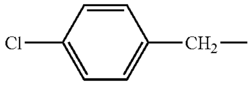 | 2 | 2 | 1 | — | H | 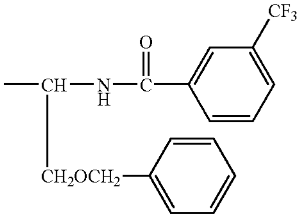 |
| 1133 | 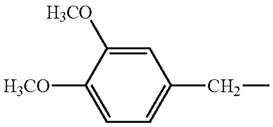 | 1 | 2 | 0 | R | H | 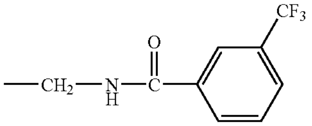 |

TABLE 1.104
| Compd. No. | 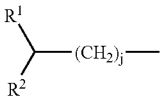 | k | m | n | chirality | $R^3$ | 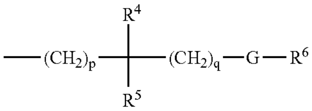 |
|---|---|---|---|---|---|---|---|
| 1134 | 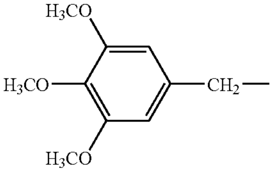 | 1 | 2 | 0 | R | H | 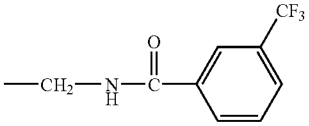 |
| 1135 | 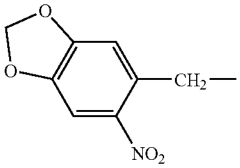 | 1 | 2 | 0 | R | H | 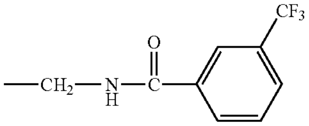 |
| 1136 | 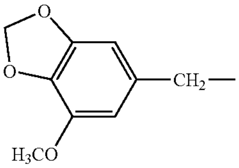 | 1 | 2 | 0 | R | H | 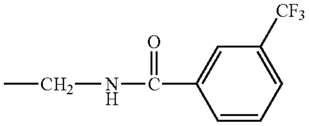 |
| 1137 | 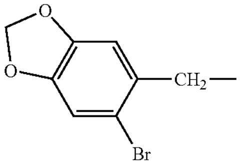 | 1 | 2 | 0 | R | H | 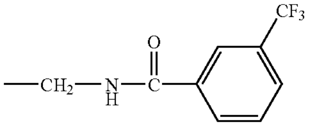 |
| 1138 | 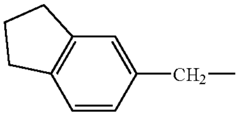 | 1 | 2 | 0 | R | H | 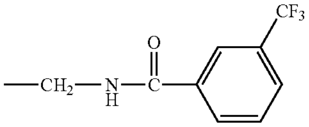 |
| 1139 | 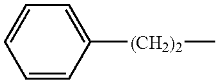 | 1 | 2 | 0 | R | H | 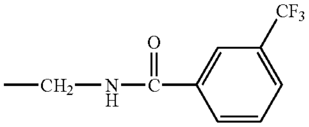 |
| 1140 | 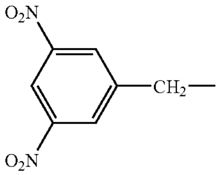 | 1 | 2 | 0 | R | H | 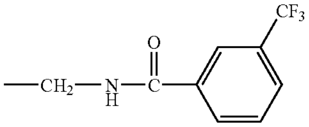 |
| 1141 | 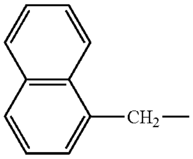 | 1 | 2 | 0 | R | H | 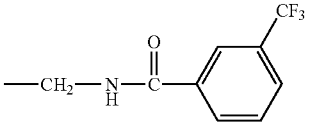 |
| 1142 | 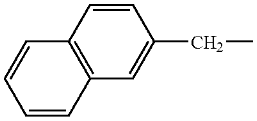 | 1 | 2 | 0 | R | H | 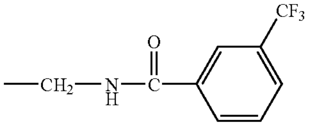 |

TABLE 1.104-continued
| Compd. No. | 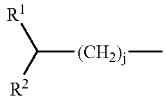 | k | m | n | chirality | $R^3$ | 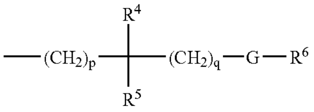 |
|---|---|---|---|---|---|---|---|
| 1143 | 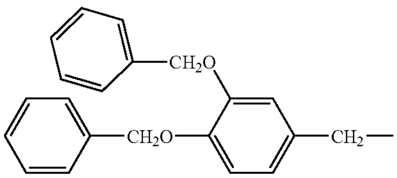 | 1 | 2 | 0 | R | H | 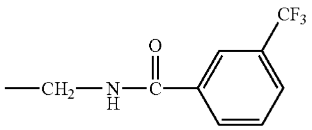 |
| 1144 | 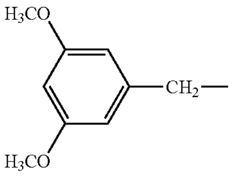 | 1 | 2 | 0 | R | H | 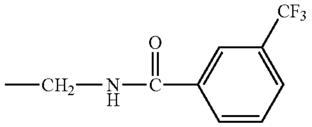 |
TABLE 1.105
| Compd. No. | 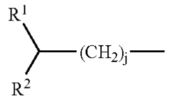 | k | m | n | chirality | $R^3$ | 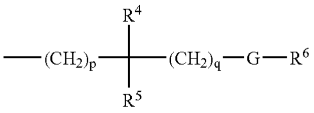 |
|---|---|---|---|---|---|---|---|
| 1145 | 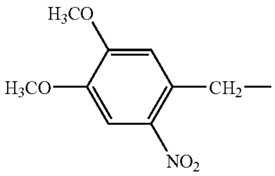 | 1 | 2 | 0 | R | H | 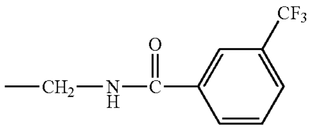 |
| 1146 | 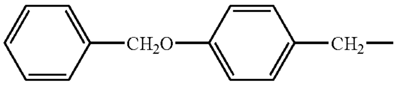 | 1 | 2 | 0 | R | H | 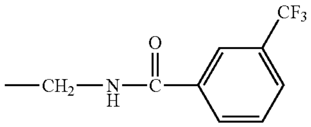 |
| 1147 | 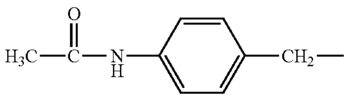 | 1 | 2 | 0 | R | H | 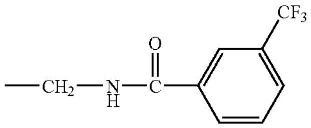 |
| 1148 | 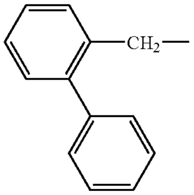 | 1 | 2 | 0 | R | H | 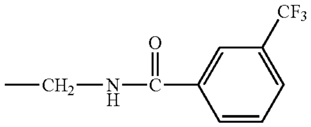 |
| 1149 | 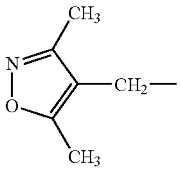 | 1 | 2 | 0 | R | H | 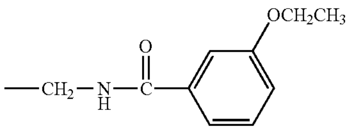 |

TABLE 1.105-continued
| Compd. No. | 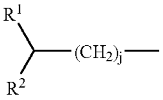 | k | m | n | chirality | $R^3$ | 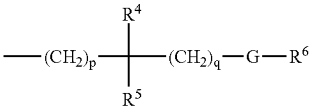 |
|---|---|---|---|---|---|---|---|
| 1150 | 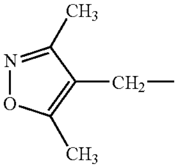 | 1 | 2 | 0 | R | H | 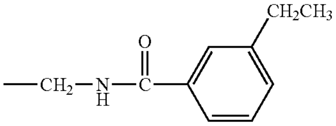 |
| 1151 | 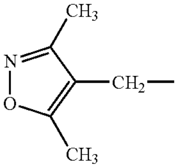 | 1 | 2 | 0 | R | H | 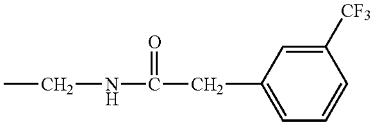 |
| 1152 | 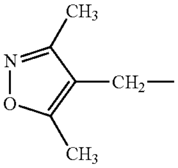 | 1 | 2 | 0 | R | H | 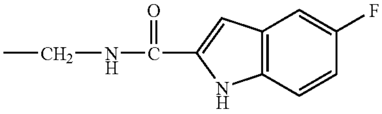 |
| 1153 | 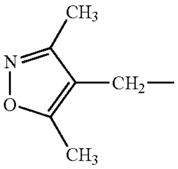 | 1 | 2 | 0 | R | H | 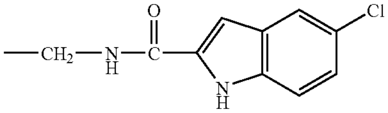 |
| 1154 | 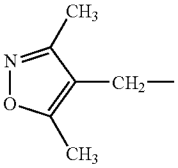 | 1 | 2 | 0 | R | H | 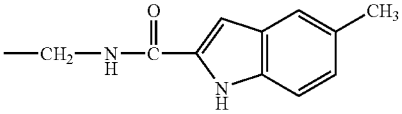 |
| 1155 | 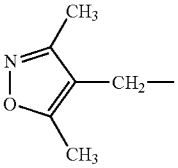 | 1 | 2 | 0 | R | H | 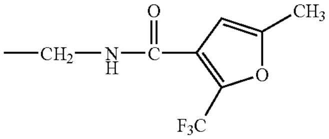 |
TABLE 1.106
| Compd. No. | 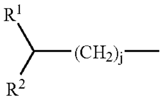 | k | m | n | chirality | $R^3$ | 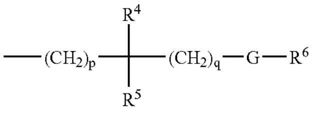 |
|---|---|---|---|---|---|---|---|
| 1156 | 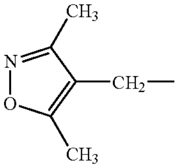 | 1 | 2 | 0 | R | H | 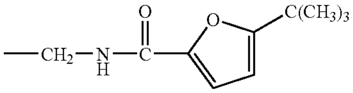 |

TABLE 1.106-continued
| Compd. No. | 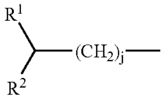 | k | m | n | chirality | $R^3$ | 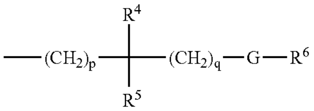 |
|---|---|---|---|---|---|---|---|
| 1157 | 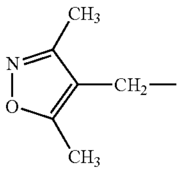 | 1 | 2 | 0 | R | H | 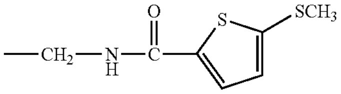 |
| 1158 | 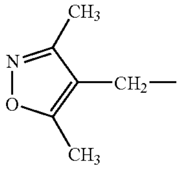 | 1 | 2 | 0 | R | H | 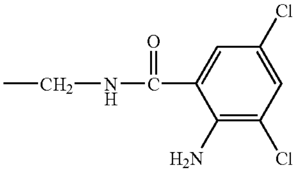 |
| 1159 | 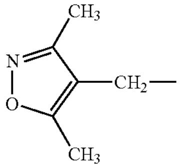 | 1 | 2 | 0 | R | H | 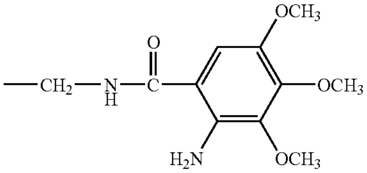 |
| 1160 | 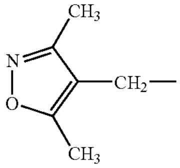 | 1 | 2 | 0 | R | H | 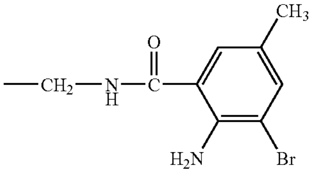 |
| 1161 | 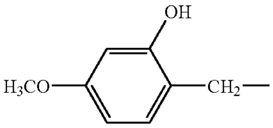 | 1 | 2 | 0 | R | H | 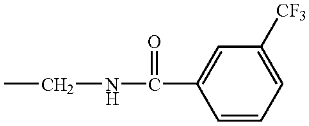 |
| 1162 | 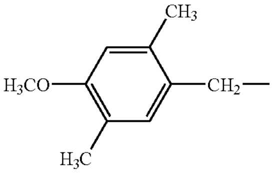 | 1 | 2 | 0 | R | H | 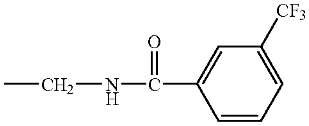 |
| 1163 | 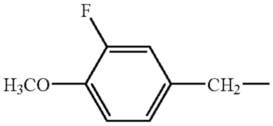 | 1 | 2 | 0 | R | H | 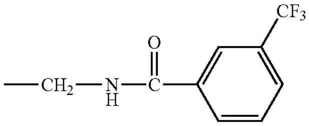 |
| 1164 | 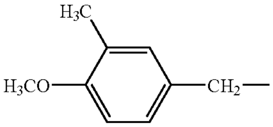 | 1 | 2 | 0 | R | H | 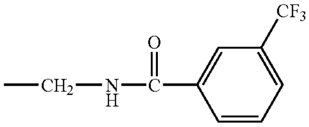 |
| 1165 | 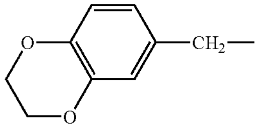 | 1 | 2 | 0 | R | H | 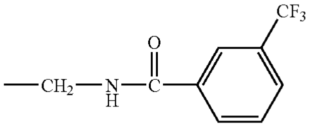 |

TABLE 1.106-continued
| Compd. No. | 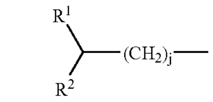 | k | m | n | chirality | $R^3$ | 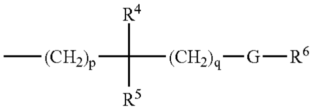 |
|---|---|---|---|---|---|---|---|
| 1166 | 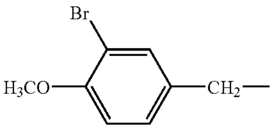 | 1 | 2 | 0 | R | H | 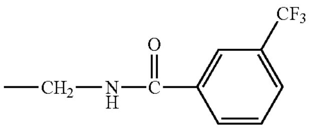 |
TABLE 1.107
| Compd. No. | 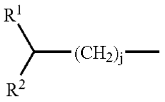 | k | m | n | chirality | $R^3$ | 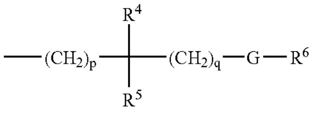 |
|---|---|---|---|---|---|---|---|
| 1167 | 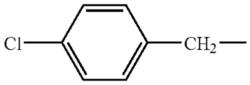 | 2 | 2 | 1 | — | H | 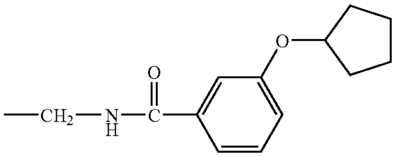 |
| 1168 | 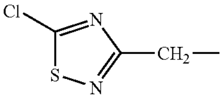 | 1 | 2 | 0 | R | H | 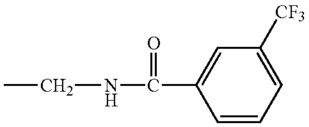 |
| 1169 | 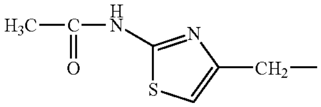 | 1 | 2 | 0 | R | H | 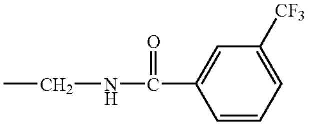 |
| 1170 | 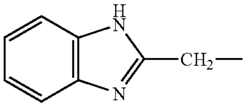 | 1 | 2 | 0 | R | H | 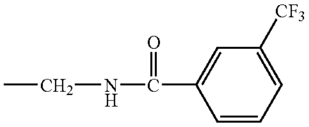 |
| 1171 | 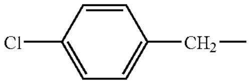 | 1 | 2 | 0 | R | H | 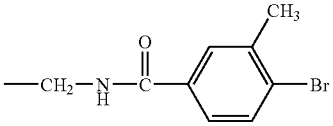 |
| 1172 | 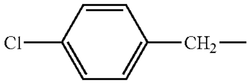 | 1 | 2 | 0 | R | H | 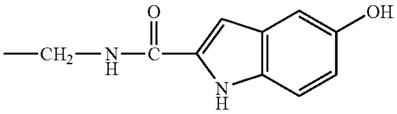 |
| 1173 | 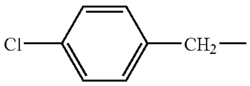 | 1 | 2 | 0 | R | H | 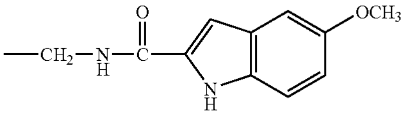 |

TABLE 1.107-continued
| Compd. No. | 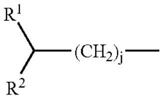 | k | m | n | chirality | $R^3$ | 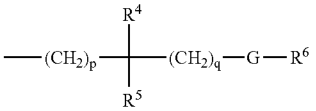 |
|---|---|---|---|---|---|---|---|
| 1174 | 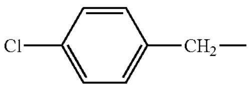 | 1 | 2 | 0 | R | H | 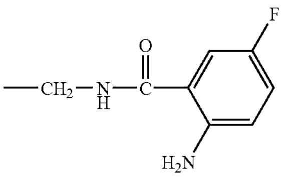 |
| 1175 | 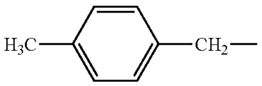 | 1 | 2 | 0 | R | H | 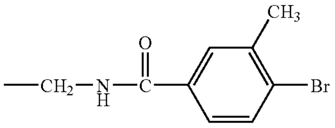 |
| 1176 | 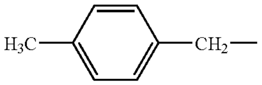 | 1 | 2 | 0 | R | H | 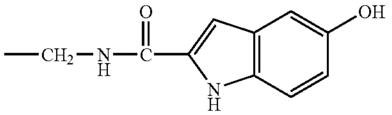 |
| 1177 | 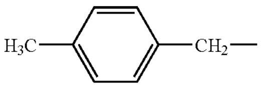 | 1 | 2 | 0 | R | H | 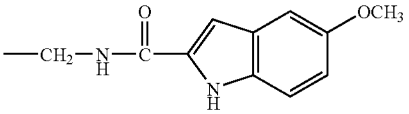 |
TABLE 1.108
| Compd. No. | 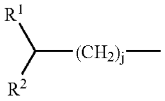 | k | m | n | chirality | $R^3$ | 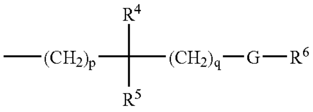 |
|---|---|---|---|---|---|---|---|
| 1178 | 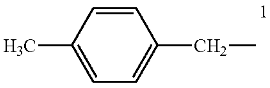 | 1 | 2 | 0 | R | H | 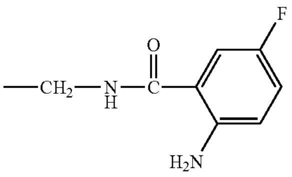 |
| 1179 | 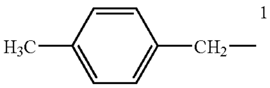 | 1 | 2 | 0 | R | H | 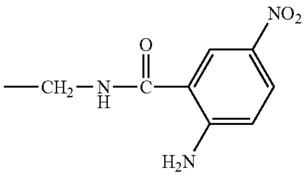 |
| 1180 | 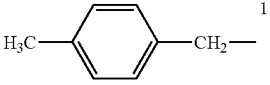 | 1 | 2 | 0 | R | H | 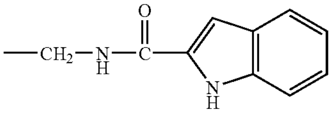 |
| 1181 | 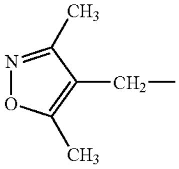 | 1 | 2 | 0 | R | H | 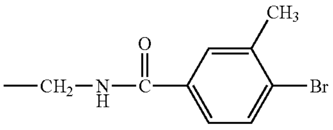 |

TABLE 1.108-continued
| Compd. No. | 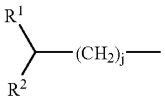 | k | m | n | chirality | $R^3$ | 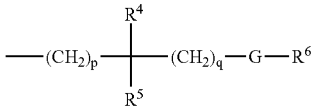 |
|---|---|---|---|---|---|---|---|
| 1182 | 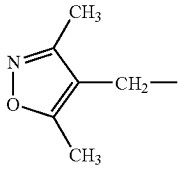 | 1 | 2 | 0 | R | H | 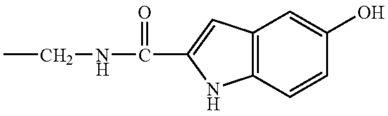 |
| 1183 | 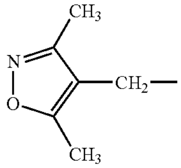 | 1 | 2 | 0 | R | H | 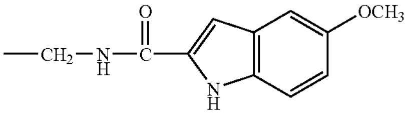 |
| 1184 | 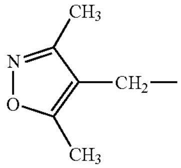 | 1 | 2 | 0 | R | H | 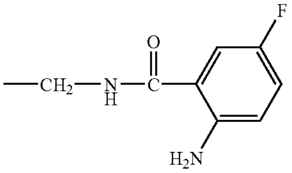 |
| 1185 | 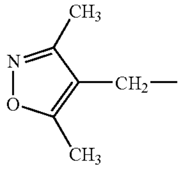 | 1 | 2 | 0 | R | H | 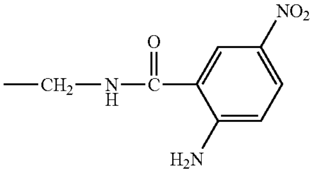 |
| 1186 | 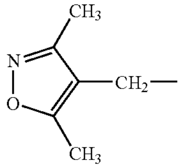 | 1 | 2 | 0 | R | H | 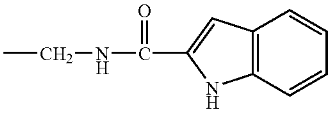 |
| 1187 | 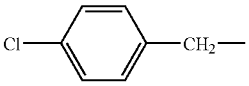 | 2 | 2 | 1 | — | H | 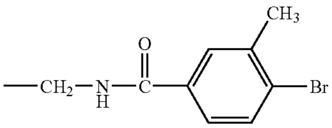 |
| 1188 | 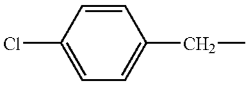 | 2 | 2 | 1 | — | H | 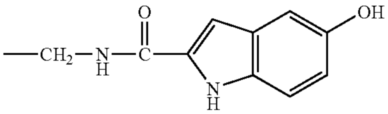 |

TABLE 1.109
| Compd. No. | 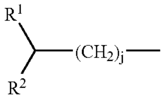 | k | m | n | chirality | $R^3$ | 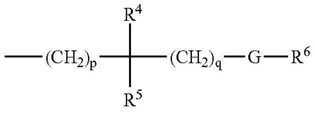 |
|---|---|---|---|---|---|---|---|
| 1189 | 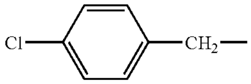 | 2 | 2 | 1 | — | H | 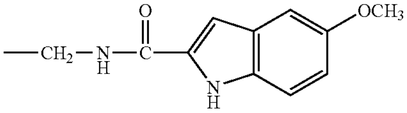 |
| 1190 | 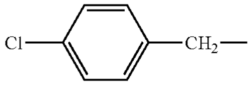 | 2 | 2 | 1 | — | H | 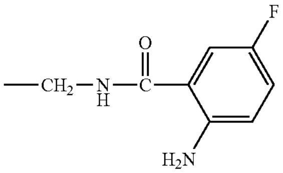 |
| 1191 | 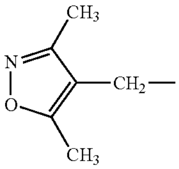 | 1 | 2 | 0 | R | H | 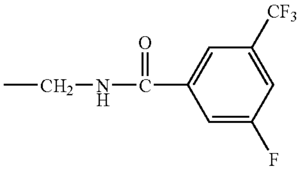 |
| 1192 | 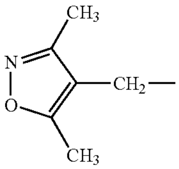 | 1 | 2 | 0 | R | H | 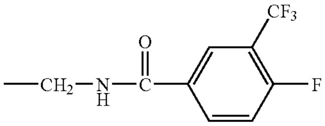 |
| 1193 | 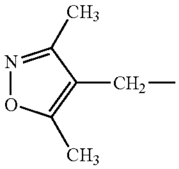 | 1 | 2 | 0 | R | H | 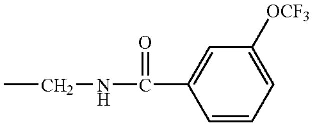 |
| 1194 | 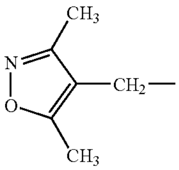 | 1 | 2 | 0 | R | H | 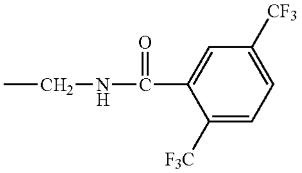 |
| 1195 | 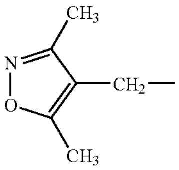 | 1 | 2 | 0 | R | H | 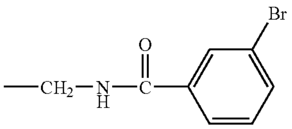 |
| 1196 | 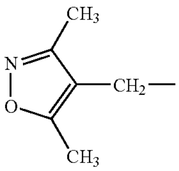 | 1 | 2 | 0 | R | H | 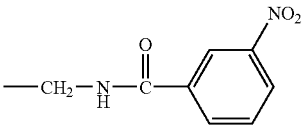 |

TABLE 1.109-continued
| Compd. No. | 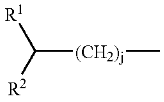 | k | m | n | chirality | $R^3$ | 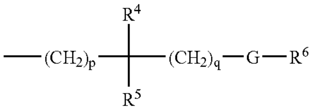 |
|---|---|---|---|---|---|---|---|
| 1197 | 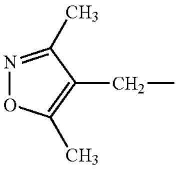 | 1 | 2 | 0 | R | H | 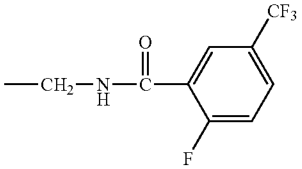 |
| 1198 | 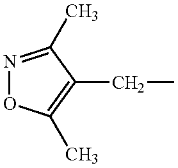 | 1 | 2 | 0 | R | H | 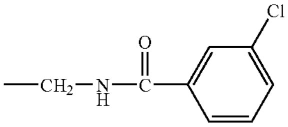 |
| 1199 | 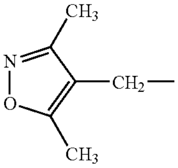 | 1 | 2 | 0 | R | H | 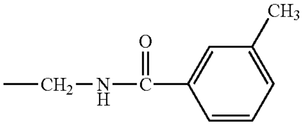 |
TABLE 1.110
| Compd. No. | 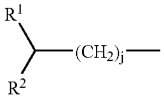 | k | m | n | chirality | $R^3$ | 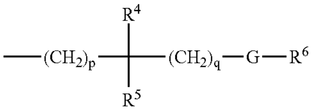 |
|---|---|---|---|---|---|---|---|
| 1200 | 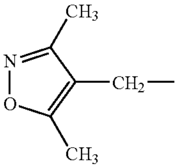 | 1 | 2 | 0 | R | H | 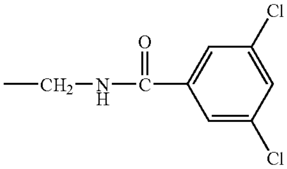 |
| 1201 | 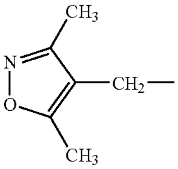 | 1 | 2 | 0 | R | H | 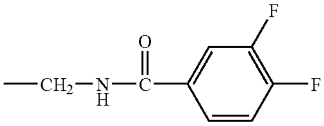 |
| 1202 | 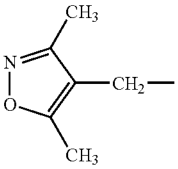 | 1 | 2 | 0 | R | H | 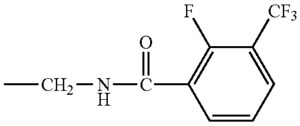 |
| 1203 | 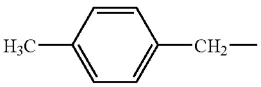 | 1 | 2 | 0 | R | H | 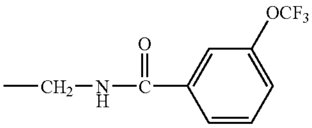 |

TABLE 1.110-continued
| Compd. No. | 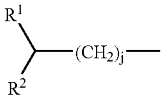 | k | m | n | chirality | R3 | 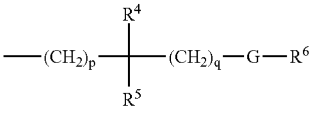 |
|---|---|---|---|---|---|---|---|
| 1204 | 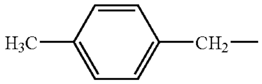 | 1 | 2 | 0 | R | H | 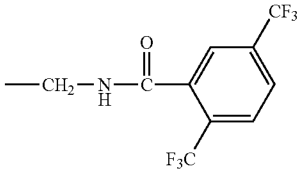 |
| 1205 | 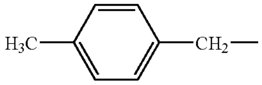 | 1 | 2 | 0 | R | H | 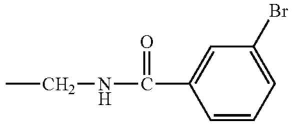 |
| 1206 | 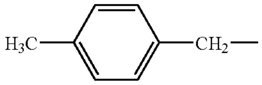 | 1 | 2 | 0 | R | H | 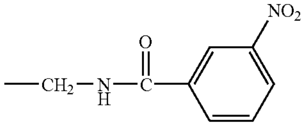 |
| 1207 | 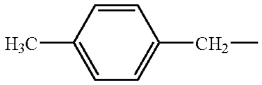 | 1 | 2 | 0 | R | H | 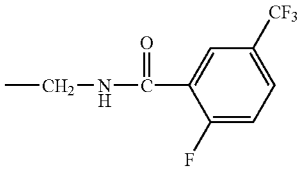 |
| 1208 | 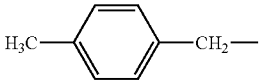 | 1 | 2 | 0 | R | H | 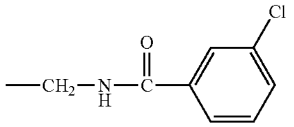 |
| 1209 | 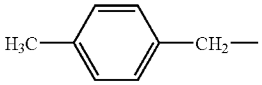 | 1 | 2 | 0 | R | H | 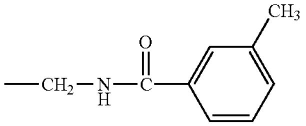 |
| 1210 | 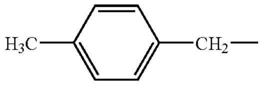 | 1 | 2 | 0 | R | H | 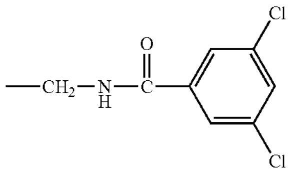 |
TABLE 1.111
| Compd. No. | 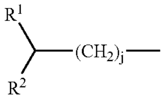 | k | m | n | chirality | R3 | 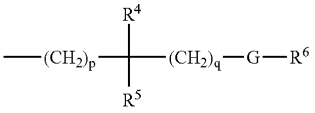 |
|---|---|---|---|---|---|---|---|
| 1211 | 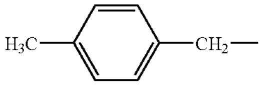 | 1 | 2 | 0 | R | H | 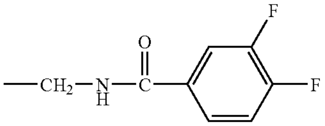 |

TABLE 1.111-continued
| Compd. No. | 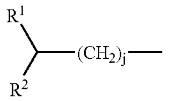 | k | m | n | chirality | $R^3$ | 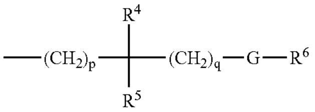 |
|---|---|---|---|---|---|---|---|
| 1212 | 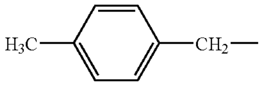 | 1 | 2 | 0 | R | H | 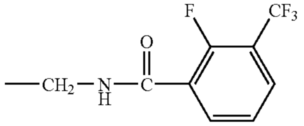 |
| 1213 | 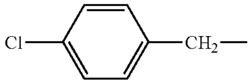 | 2 | 2 | 1 | — | H | 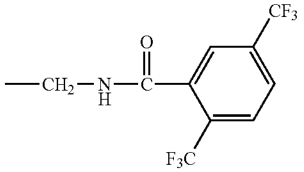 |
| 1214 | 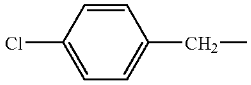 | 2 | 2 | 1 | — | H | 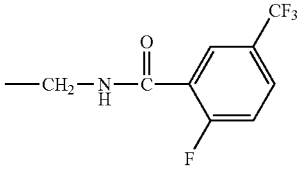 |
| 1215 | 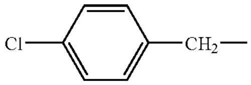 | 2 | 2 | 1 | — | H | 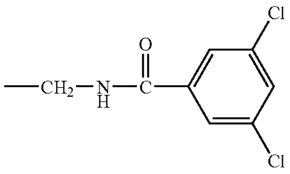 |
| 1216 | 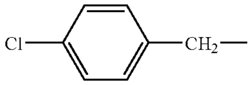 | 2 | 2 | 1 | — | H | 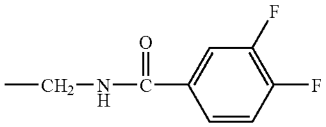 |
| 1217 | 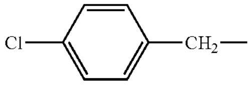 | 1 | 2 | 0 | R | H | 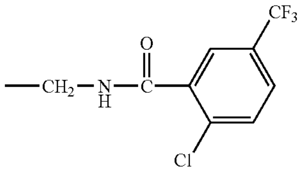 |
| 1218 | 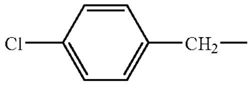 | 1 | 2 | 0 | R | H | 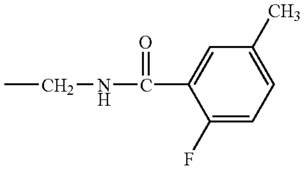 |
| 1219 | 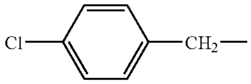 | 1 | 2 | 0 | R | H | 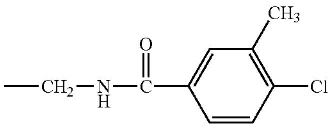 |
| 1220 | 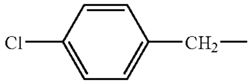 | 1 | 2 | 0 | R | H | 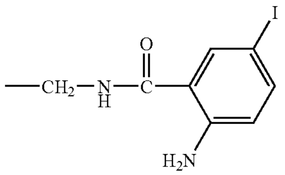 |

TABLE 1.111-continued
| Compd. No. | 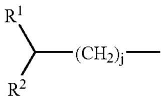 | k | m | n | chirality | $R^3$ | 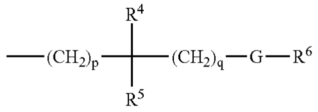 |
|---|---|---|---|---|---|---|---|
| 1221 | 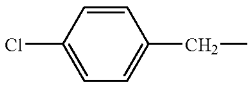 | 1 | 2 | 0 | R | H | 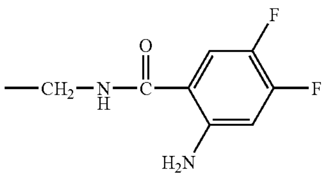 |
TABLE 1.112
| Compd. No. | 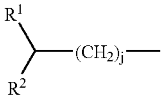 | k | m | n | chirality | $R^3$ | 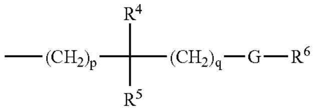 |
|---|---|---|---|---|---|---|---|
| 1222 | 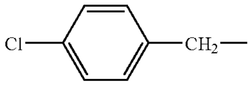 | 1 | 2 | 0 | R | H | 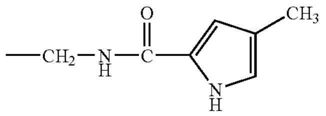 |
| 1223 | 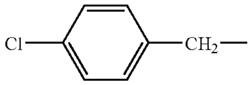 | 1 | 2 | 0 | R | H | 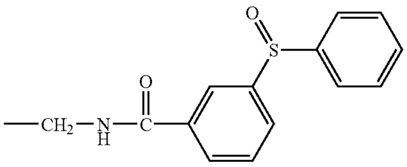 |
| 1224 | 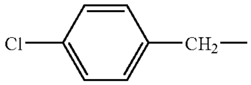 | 1 | 2 | 0 | R | H | 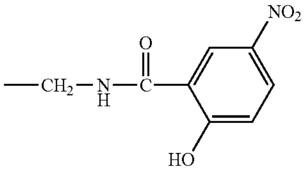 |
| 1225 | 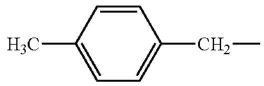 | 1 | 2 | 0 | R | H | 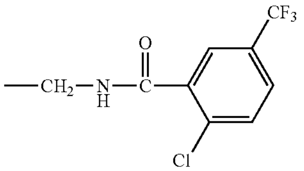 |
| 1226 | 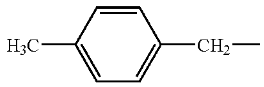 | 1 | 2 | 0 | R | H | 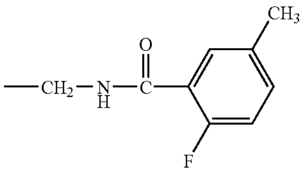 |
| 1227 | 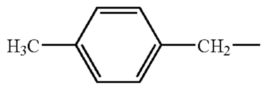 | 1 | 2 | 0 | R | H | 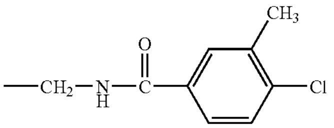 |

TABLE 1.112-continued
| Compd. No. | 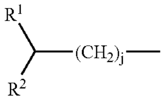 | k | m | n | chirality | $R^3$ | 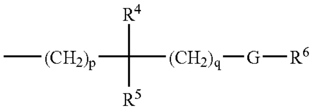 |
|---|---|---|---|---|---|---|---|
| 1228 | 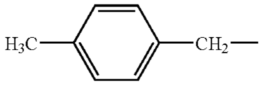 | 1 | 2 | 0 | R | H | 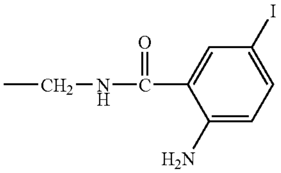 |
| 1229 | 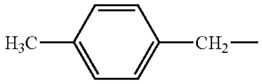 | 1 | 2 | 0 | R | H | 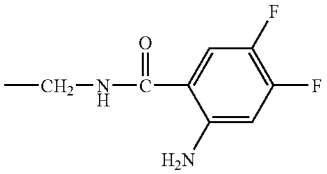 |
| 1230 | 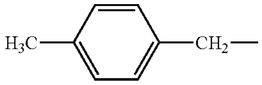 | 1 | 2 | 0 | R | H | 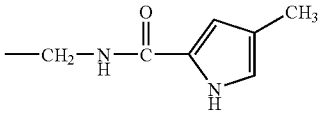 |
| 1231 | 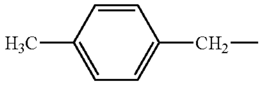 | 1 | 2 | 0 | R | H | 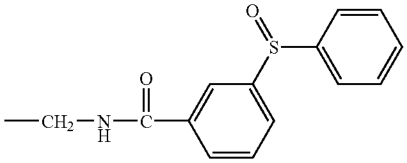 |
| 1232 | 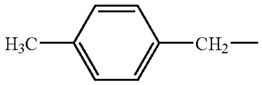 | 1 | 2 | 0 | R | H | 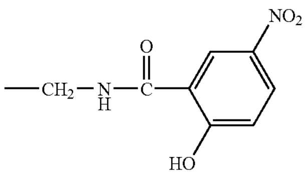 |
TABLE 1.113
| Compd. No. | 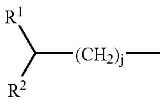 | k | m | n | chirality | $R^3$ | 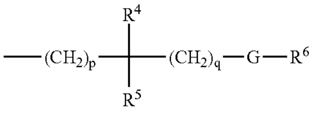 |
|---|---|---|---|---|---|---|---|
| 1233 | 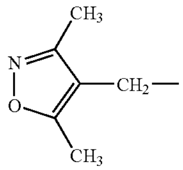 | 1 | 2 | 0 | R | H | 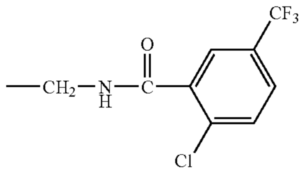 |
| 1234 | 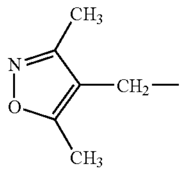 | 1 | 2 | 0 | R | H | 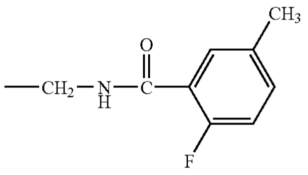 |

TABLE 1.113-continued
| Compd. No. | 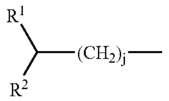 | k | m | n | chirality | $R^3$ | 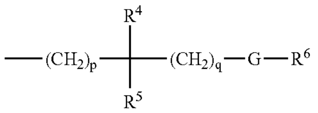 |
|---|---|---|---|---|---|---|---|
| 1235 | 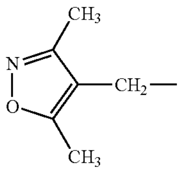 | 1 | 2 | 0 | R | H | 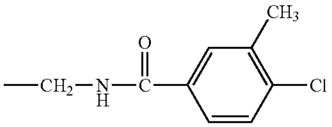 |
| 1236 | 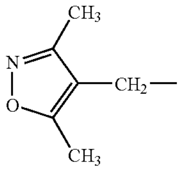 | 1 | 2 | 0 | R | H | 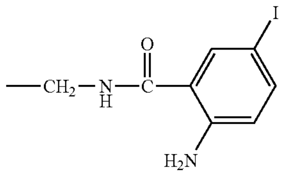 |
| 1237 | 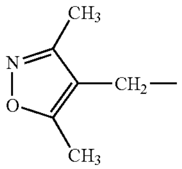 | 1 | 2 | 0 | R | H | 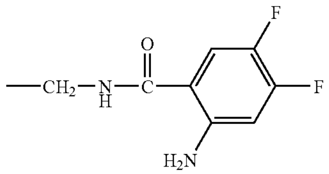 |
| 1238 | 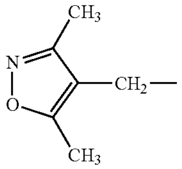 | 1 | 2 | 0 | R | H | 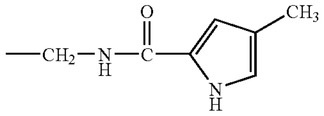 |
| 1239 | 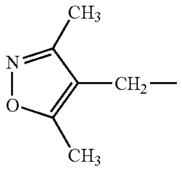 | 1 | 2 | 0 | R | H | 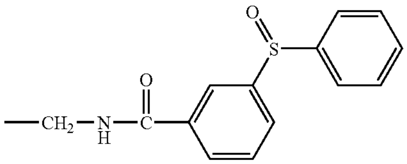 |
| 1240 | 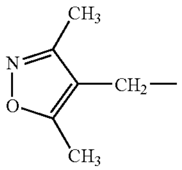 | 1 | 2 | 0 | R | H | 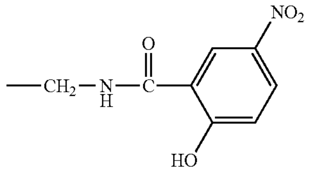 |
| 1241 | 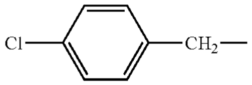 | 2 | 2 | 1 | — | H | 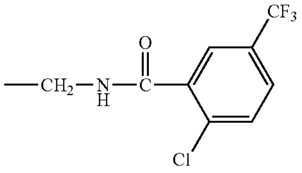 |
| 1242 | 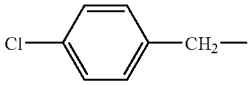 | 2 | 2 | 1 | — | H | 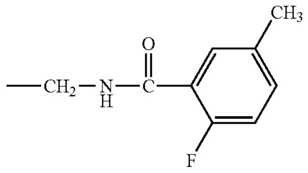 |

TABLE 1.113-continued
| Compd. No. | 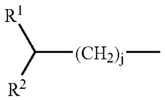 | k | m | n | chirality | $R^3$ | 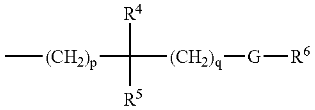 |
|---|---|---|---|---|---|---|---|
| 1243 | 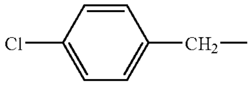 | 2 | 2 | 1 | — | H | 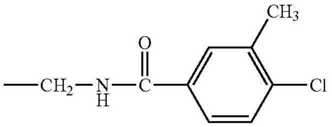 |
TABLE 1.114
| Compd. No. | 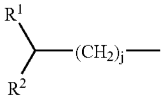 | k | m | n | chirality | $R^3$ | 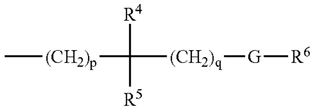 |
|---|---|---|---|---|---|---|---|
| 1244 | 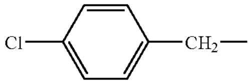 | 2 | 2 | 1 | — | H | 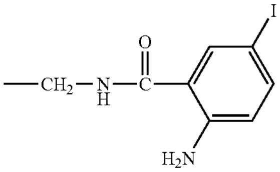 |
| 1245 | 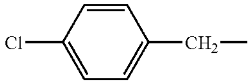 | 2 | 2 | 1 | — | H | 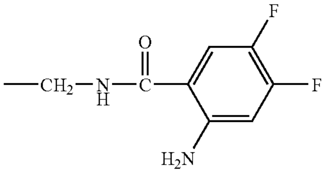 |
| 1246 | 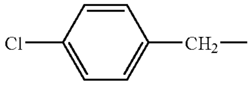 | 2 | 2 | 1 | — | H | 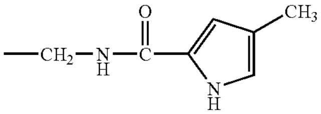 |
| 1247 | 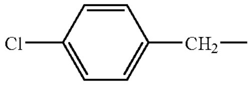 | 2 | 2 | 1 | — | H | 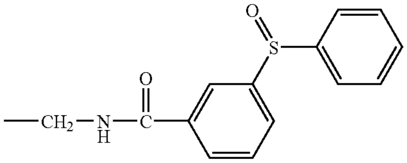 |
| 1248 | 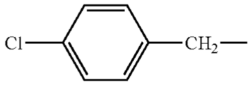 | 2 | 2 | 1 | — | H | 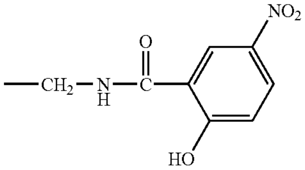 |
| 1249 | 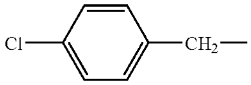 | 1 | 2 | 0 | R | H | 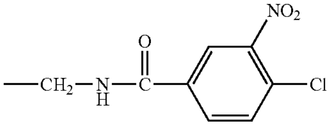 |
| 1250 | 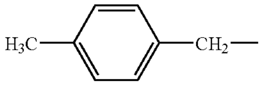 | 1 | 2 | 0 | R | H | 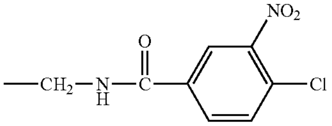 |

TABLE 1.114-continued
| Compd. No. | 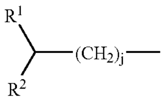 | k | m | n | chirality | $R^3$ | 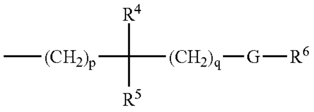 |
|---|---|---|---|---|---|---|---|
| 1251 | 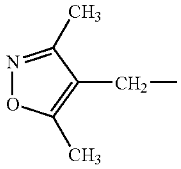 | 1 | 2 | 0 | R | H | 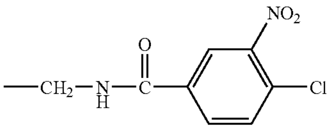 |
| 1252 | 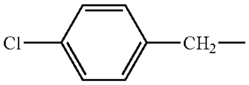 | 1 | 2 | 0 | R | H | 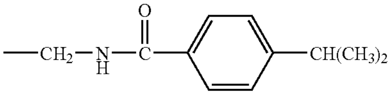 |
| 1253 | 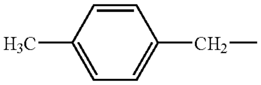 | 1 | 2 | 0 | R | H | 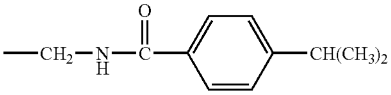 |
| 1254 | 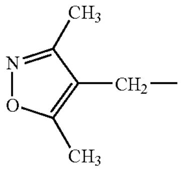 | 1 | 2 | 0 | R | H | 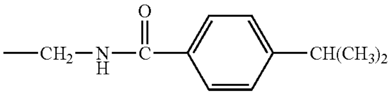 |
TABLE 1.115
| Compd. No. | 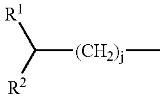 | k | m | n | chirality | $R^3$ | 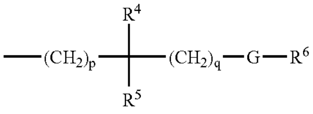 |
|---|---|---|---|---|---|---|---|
| 1255 | 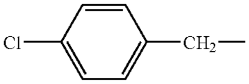 | 1 | 2 | 0 | R | H | 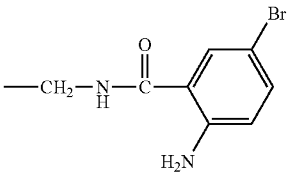 |
| 1256 | 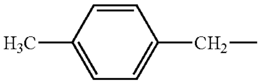 | 1 | 2 | 0 | R | H | 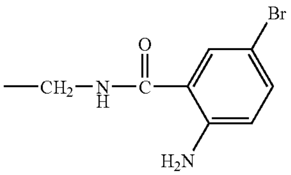 |
| 1257 | 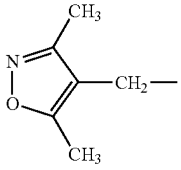 | 1 | 2 | 0 | R | H | 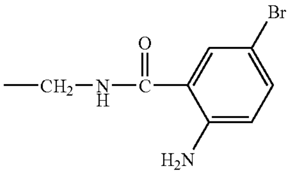 |

TABLE 1.115-continued
| Compd. No. | 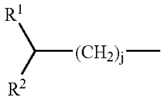 | k | m | n | chirality | $R^3$ | 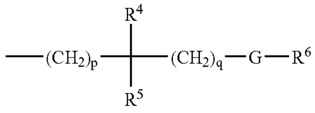 |
|---|---|---|---|---|---|---|---|
| 1258 | 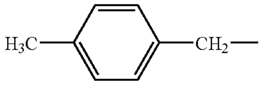 | 1 | 2 | 0 | R | H | 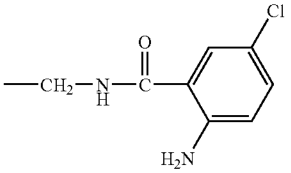 |
| 1259 | 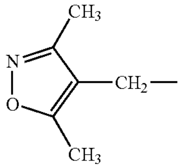 | 1 | 2 | 0 | R | H | 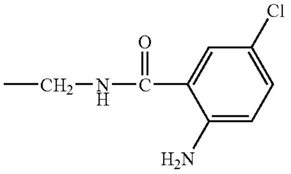 |
| 1260 | 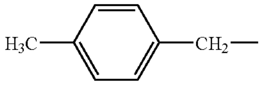 | 1 | 2 | 0 | R | H | 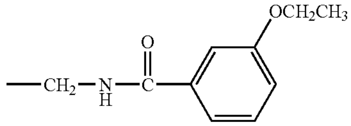 |
| 1261 | 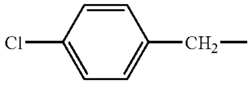 | 1 | 2 | 0 | R | H | 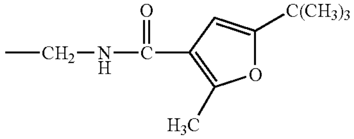 |
| 1262 | 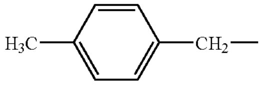 | 1 | 2 | 0 | R | H | 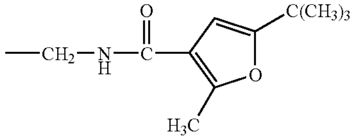 |
| 1263 | 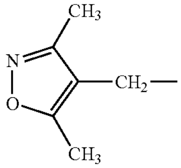 | 1 | 2 | 0 | R | H | 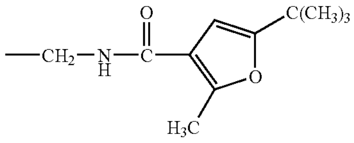 |
| 1264 | 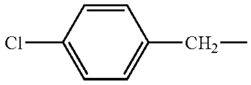 | 1 | 2 | 0 | R | H | 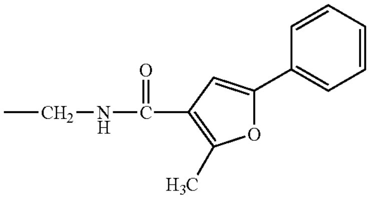 |
| 1265 | 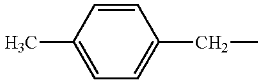 | 1 | 2 | 0 | R | H | 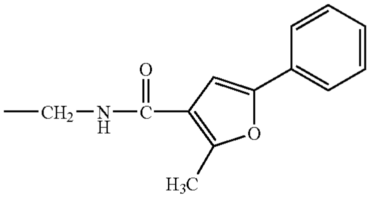 |

TABLE 1.116
| Compd. No. | 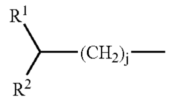 | k | m | n | chirality | $R^3$ | 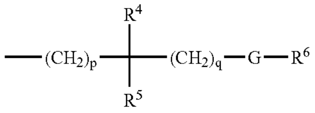 |
|---|---|---|---|---|---|---|---|
| 1266 | 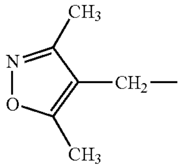 | 1 | 2 | 0 | R | H | 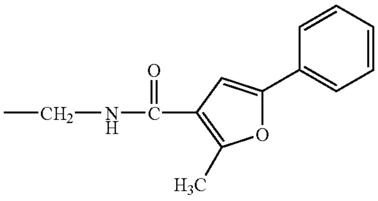 |
| 1267 | 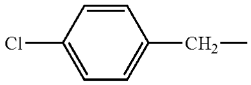 | 1 | 2 | 0 | R | H | 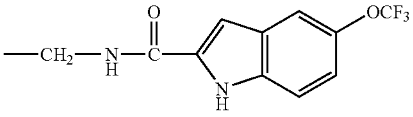 |
| 1268 | 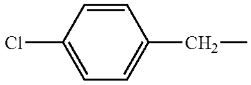 | 1 | 2 | 0 | R | H | 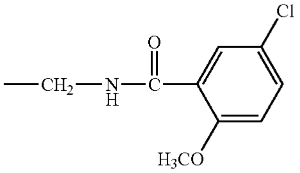 |
| 1269 | 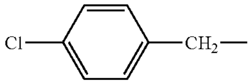 | 1 | 2 | 0 | R | H | 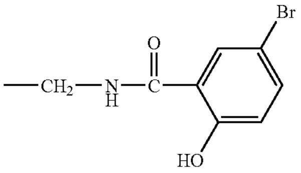 |
| 1270 | 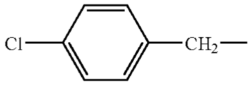 | 1 | 2 | 0 | R | H | 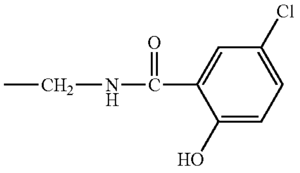 |
| 1271 | 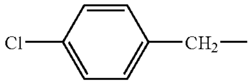 | 1 | 2 | 0 | R | H | 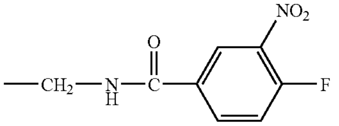 |
| 1272 | 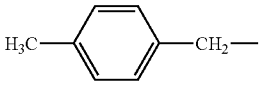 | 1 | 2 | 0 | R | H | 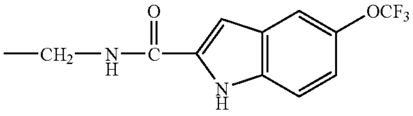 |
| 1273 | 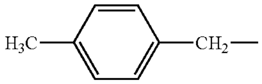 | 1 | 2 | 0 | R | H | 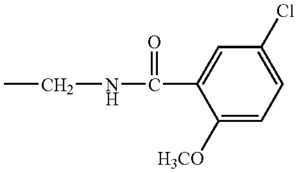 |

TABLE 1.116-continued
| Compd. No. | 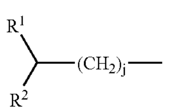 | k | m | n | chirality | $R^3$ | 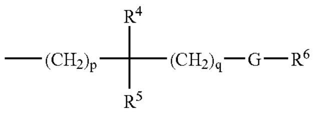 |
|---|---|---|---|---|---|---|---|
| 1274 | 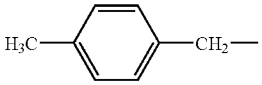 | 1 | 2 | 0 | R | H | 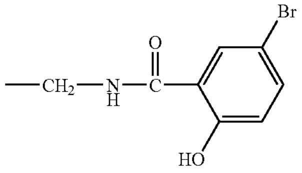 |
| 1275 | 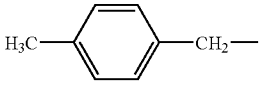 | 1 | 2 | 0 | R | H | 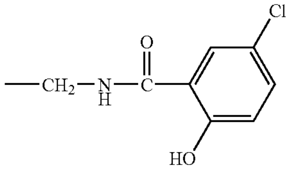 |
| 1276 | 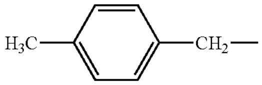 | 1 | 2 | 0 | R | H | 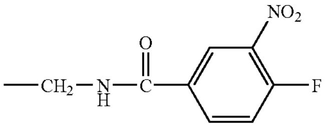 |
TABLE 1.117
| Compd. No. | 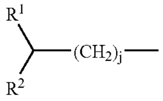 | k | m | n | chirality | $R^3$ | 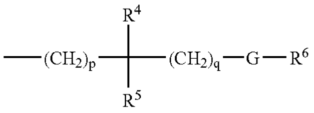 |
|---|---|---|---|---|---|---|---|
| 1277 | 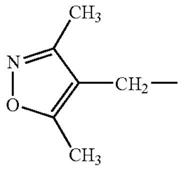 | 1 | 2 | 0 | R | H | 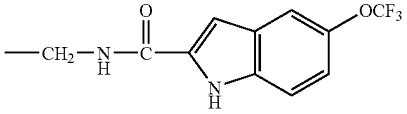 |
| 1278 | 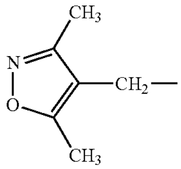 | 1 | 2 | 0 | R | H | 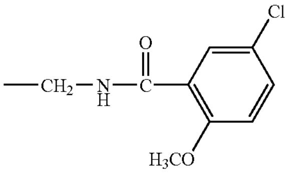 |
| 1279 | 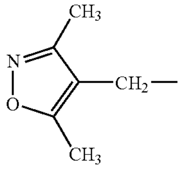 | 1 | 2 | 0 | R | H | 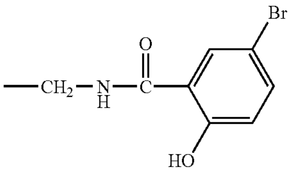 |
| 1280 | 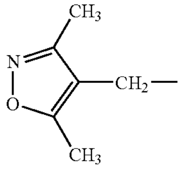 | 1 | 2 | 0 | R | H | 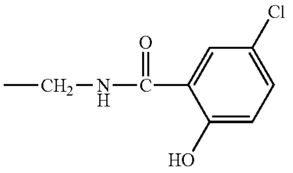 |

TABLE 1.117-continued
| Compd. No. | 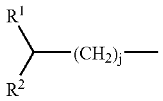 | k | m | n | chirality | $R^3$ | 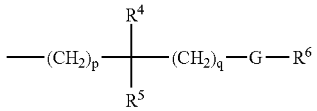 |
|---|---|---|---|---|---|---|---|
| 1281 | 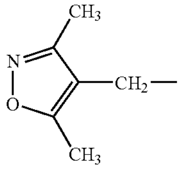 | 1 | 2 | 0 | R | H | 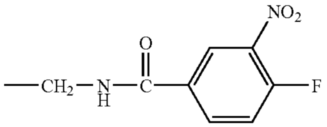 |
| 1282 | 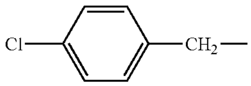 | 2 | 2 | 1 | — | H | 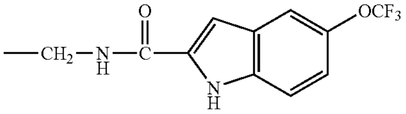 |
| 1283 | 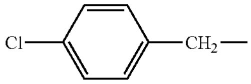 | 2 | 2 | 1 | — | H | 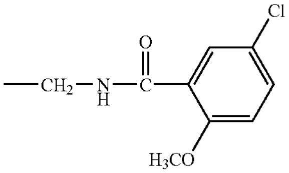 |
| 1284 | 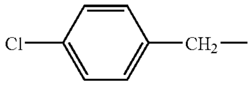 | 2 | 2 | 1 | — | H | 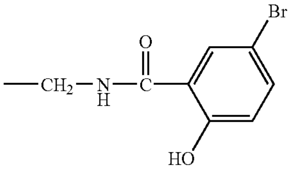 |
| 1285 | 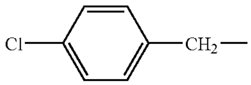 | 2 | 2 | 1 | — | H | 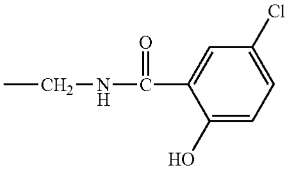 |
| 1286 | 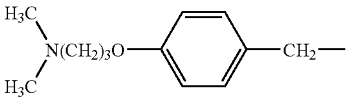 | 1 | 2 | 0 | R | H | 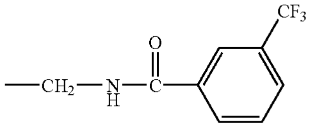 |
| 1287 | 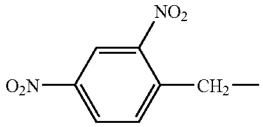 | 1 | 2 | 0 | R | H | 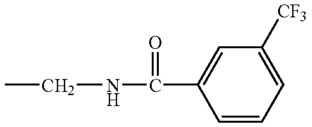 |
TABLE 1.118
| Compd. No. | 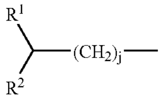 | k | m | n | chirality | $R^3$ | 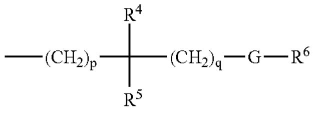 |
|---|---|---|---|---|---|---|---|
| 1288 | 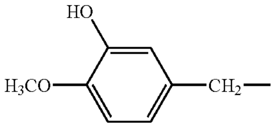 | 1 | 2 | 0 | R | H | 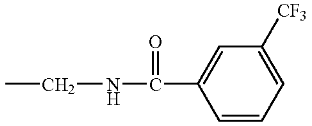 |

TABLE 1.118-continued
| Compd. No. | 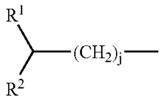 | k | m | n | chirality | $R^3$ | 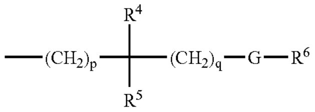 |
|---|---|---|---|---|---|---|---|
| 1289 | 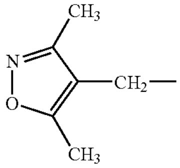 | 1 | 2 | 0 | R | H | 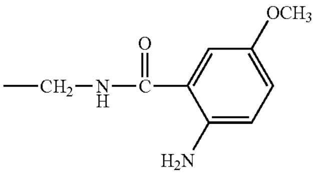 |
| 1290 | 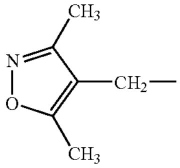 | 1 | 2 | 0 | R | H | 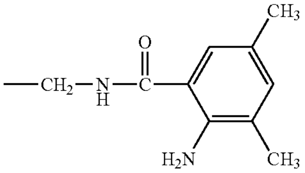 |
| 1291 | 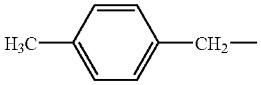 | 1 | 2 | 0 | R | H | 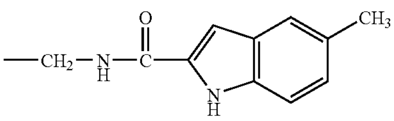 |
| 1292 | 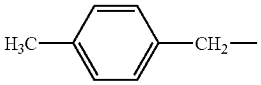 | 1 | 2 | 0 | R | H | 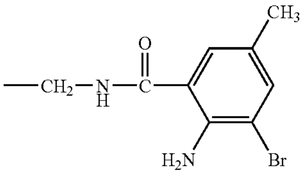 |
| 1293 | 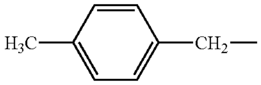 | 1 | 2 | 0 | R | H | 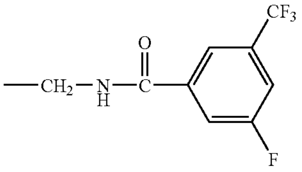 |
| 1294 | 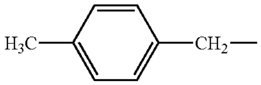 | 1 | 2 | 0 | R | H | 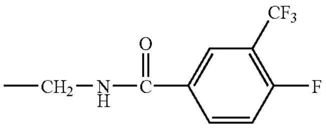 |
| 1295 | 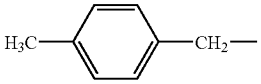 | 1 | 2 | 0 | R | H | 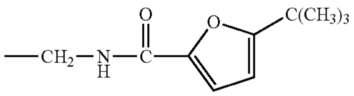 |
| 1296 | 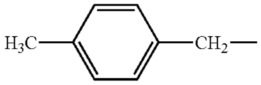 | 1 | 2 | 0 | R | H | 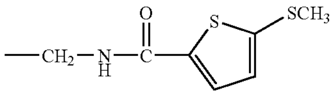 |
| 1297 | 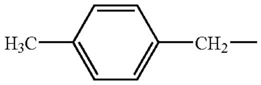 | 1 | 2 | 0 | R | H | 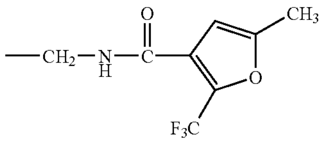 |

TABLE 1.118-continued
| Compd. No. | 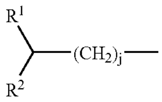 | k | m | n | chirality | $R^3$ | 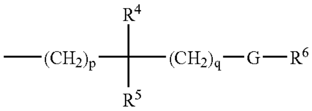 |
|---|---|---|---|---|---|---|---|
| 1298 | 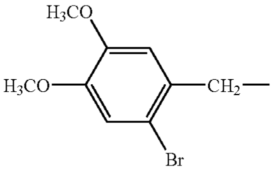 | 1 | 2 | 0 | R | H | 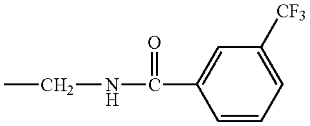 |
TABLE 1.119
| Compd. No. | 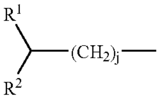 | k | m | n | chirality | $R^3$ | 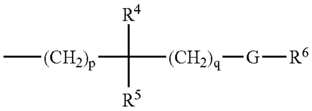 |
|---|---|---|---|---|---|---|---|
| 1299 | 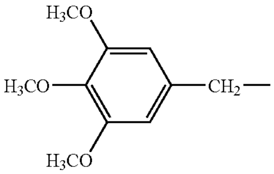 | 1 | 2 | 0 | R | H | 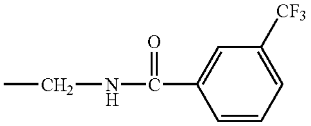 |
| 1300 | 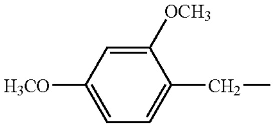 | 1 | 2 | 0 | R | H | 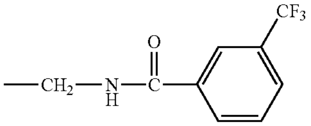 |
| 1301 | 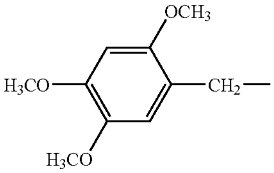 | 1 | 2 | 0 | R | H | 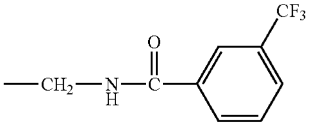 |
| 1302 | 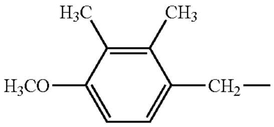 | 1 | 2 | 0 | R | H | 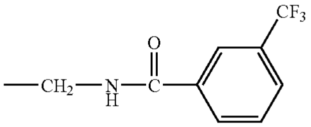 |
| 1303 | 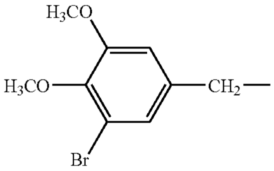 | 1 | 2 | 0 | R | H | 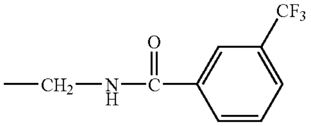 |
| 1304 | 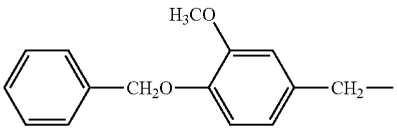 | 1 | 2 | 0 | R | H | 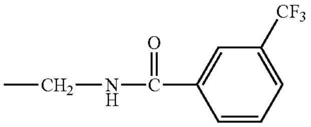 |

TABLE 1.119-continued
| Compd. No. | 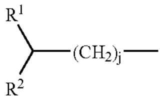 | k | m | n | chirality | $R^3$ | 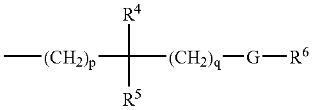 |
|---|---|---|---|---|---|---|---|
| 1305 | 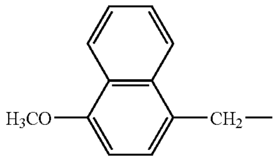 | 1 | 2 | 0 | R | H | 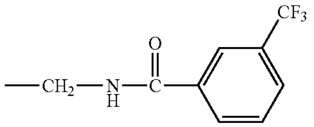 |
| 1306 | 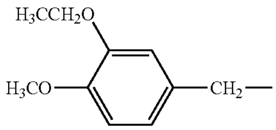 | 1 | 2 | 0 | R | H | 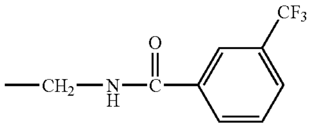 |
| 1307 | 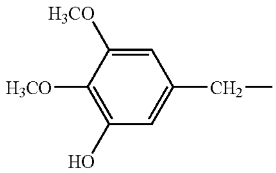 | 1 | 2 | 0 | R | H | 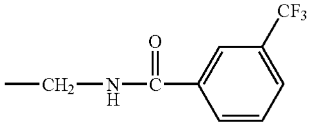 |
| 1308 | 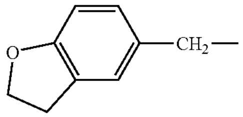 | 1 | 2 | 0 | R | H | 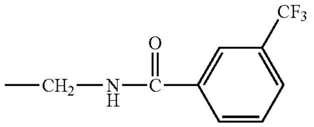 |
| 1309 | 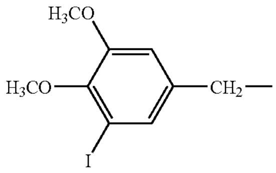 | 1 | 2 | 0 | R | H | 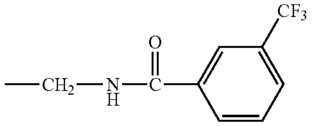 |
TABLE 1.120
| Compd. No. | 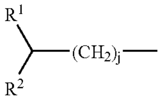 | k | m | n | chirality | $R^3$ | 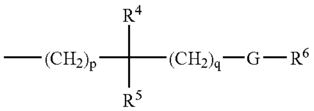 |
|---|---|---|---|---|---|---|---|
| 1310 | 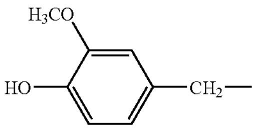 | 1 | 2 | 0 | R | H | 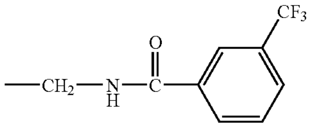 |
| 1311 | 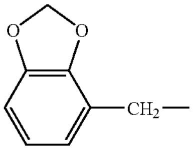 | 1 | 2 | 0 | R | H | 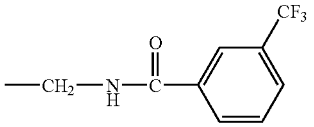 |
| 1312 | 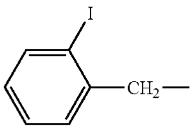 | 1 | 2 | 0 | R | H | 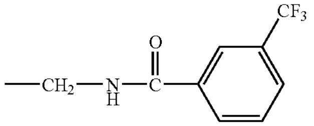 |

TABLE 1.120-continued
| Compd. No. | 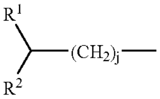 | k | m | n | chirality | $R^3$ | 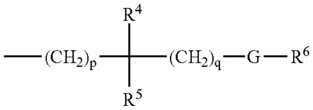 |
|---|---|---|---|---|---|---|---|
| 1313 | 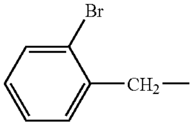 | 1 | 2 | 0 | R | H | 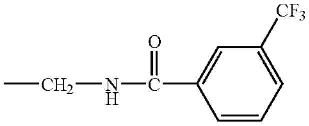 |
| 1314 | 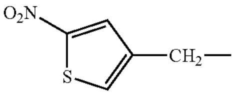 | 1 | 2 | 0 | R | H | 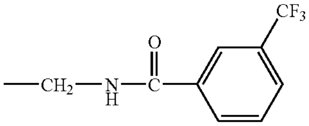 |
| 1315 | 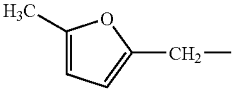 | 1 | 2 | 0 | R | H | 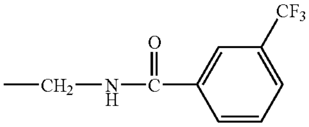 |
| 1316 | 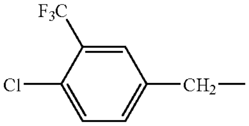 | 1 | 2 | 0 | R | H | 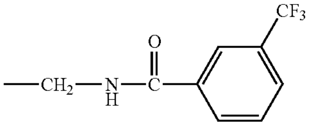 |
| 1317 | 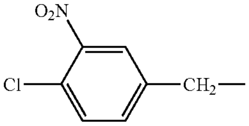 | 1 | 2 | 0 | R | H | 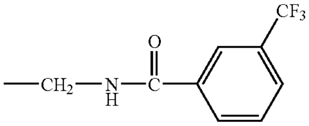 |
| 1318 | 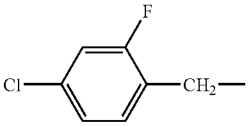 | 1 | 2 | 0 | R | H | 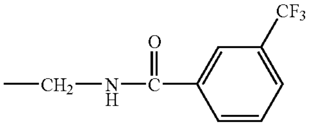 |
| 1319 | 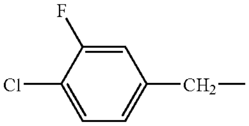 | 1 | 2 | 0 | R | H | 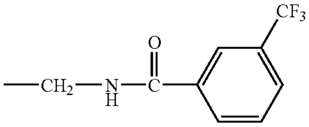 |
| 1320 | 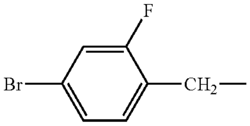 | 1 | 2 | 0 | R | H | 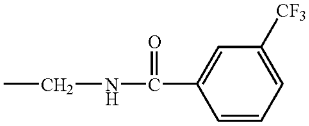 |
TABLE 1.121
| Compd. No. | 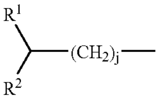 | k | m | n | chirality | $R^3$ | 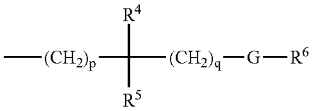 |
|---|---|---|---|---|---|---|---|
| 1321 | 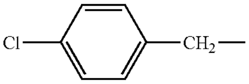 | 1 | 2 | 0 | R | H | 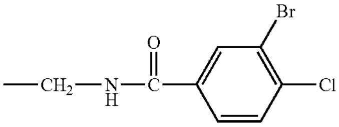 |

TABLE 1.121-continued
| Compd. No. | 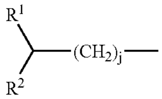 | k | m | n | chirality | $R^3$ | 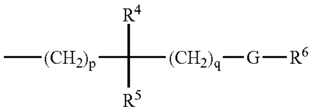 |
|---|---|---|---|---|---|---|---|
| 1322 | 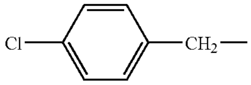 | 1 | 2 | 0 | R | H | 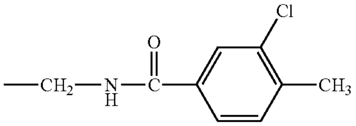 |
| 1323 | 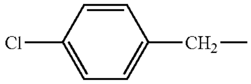 | 1 | 2 | 0 | R | H | 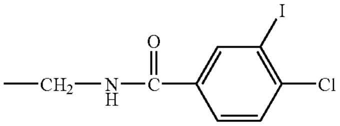 |
| 1324 | 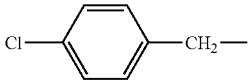 | 1 | 2 | 0 | R | H | 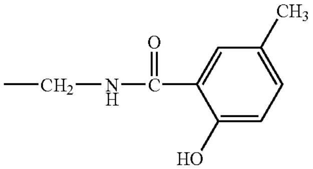 |
| 1325 | 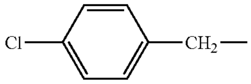 | 1 | 2 | 0 | R | H | 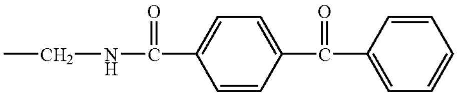 |
| 1326 | 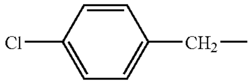 | 1 | 2 | 0 | R | H | 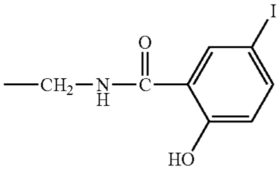 |
| 1327 | 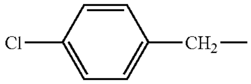 | 1 | 2 | 0 | R | H | 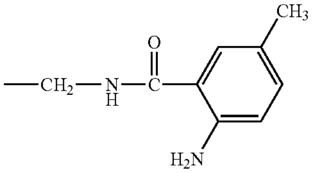 |
| 1328 | 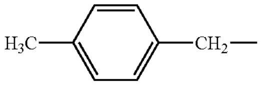 | 1 | 2 | 0 | R | H | 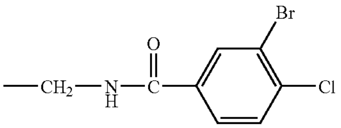 |
| 1329 | 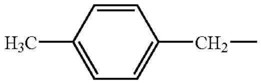 | 1 | 2 | 0 | R | H | 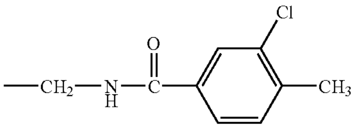 |
| 1330 | 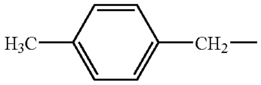 | 1 | 2 | 0 | R | H | 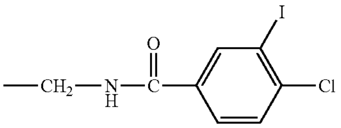 |

TABLE 1.121-continued
| Compd. No. | 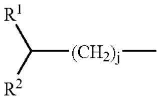 | k | m | n | chirality | $R^3$ | 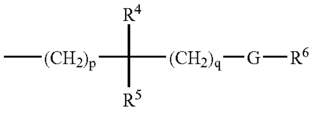 |
|---|---|---|---|---|---|---|---|
| 1331 | 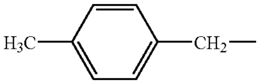 | 1 | 2 | 0 | R | H | 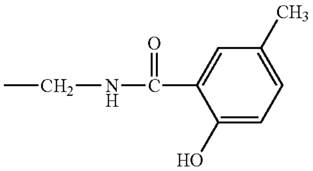 |
TABLE 1.122
| Compd. No. | 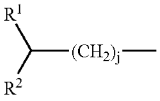 | k | m | n | chirality | $R^3$ | 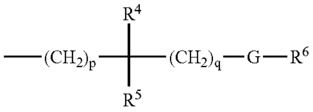 |
|---|---|---|---|---|---|---|---|
| 1332 | 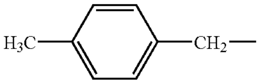 | 1 | 2 | 0 | R | H | 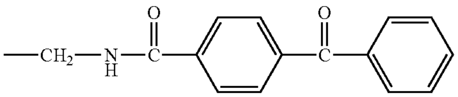 |
| 1333 | 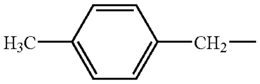 | 1 | 2 | 0 | R | H | 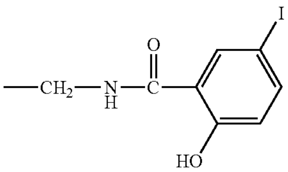 |
| 1334 | 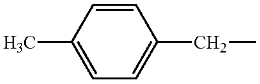 | 1 | 2 | 0 | R | H | 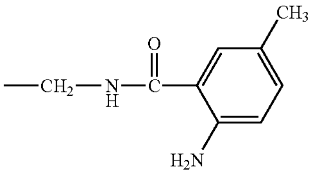 |
| 1335 | 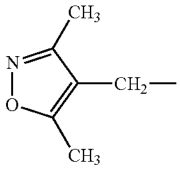 | 1 | 2 | 0 | R | H | 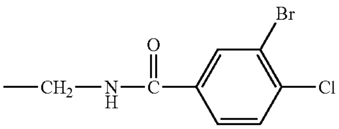 |
| 1336 | 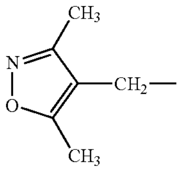 | 1 | 2 | 0 | R | H | 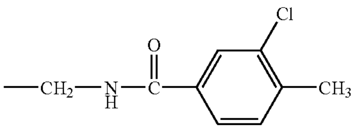 |
| 1337 | 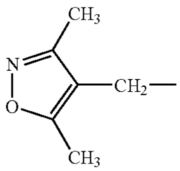 | 1 | 2 | 0 | R | H | 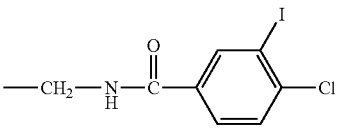 |

TABLE 1.122-continued
| Compd. No. | 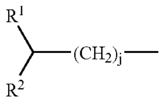 | k | m | n | chirality | $R^3$ | 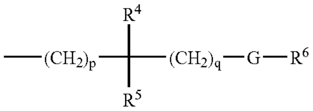 |
|---|---|---|---|---|---|---|---|
| 1338 | 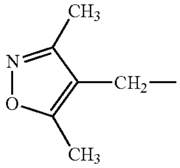 | 1 | 2 | 0 | R | H | 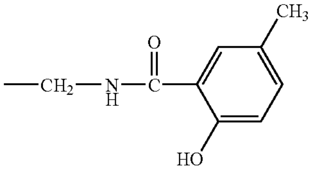 |
| 1339 | 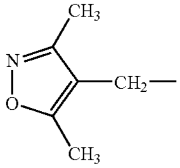 | 1 | 2 | 0 | R | H | 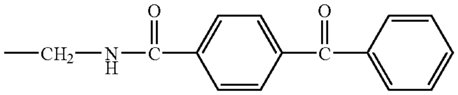 |
| 1340 | 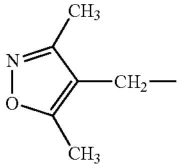 | 1 | 2 | 0 | R | H | 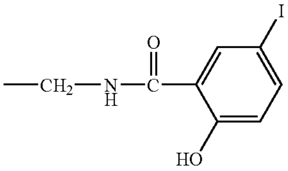 |
| 1341 | 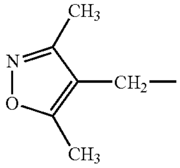 | 1 | 2 | 0 | R | H | 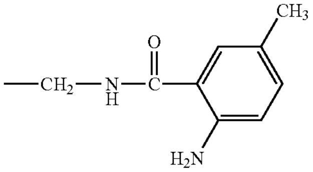 |
| 1342 | 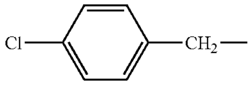 | 2 | 2 | 1 | — | H | 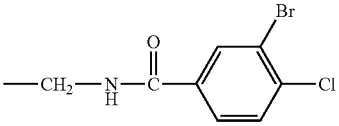 |
TABLE 1.123
| Compd. No. | 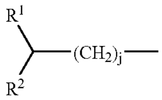 | k | m | n | chirality | $R^3$ | 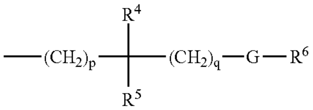 |
|---|---|---|---|---|---|---|---|
| 1343 | 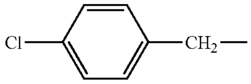 | 2 | 2 | 1 | — | H | 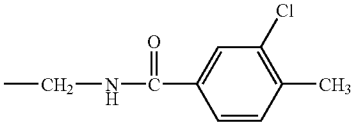 |
| 1344 | 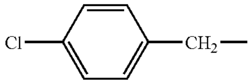 | 2 | 2 | 1 | — | H | 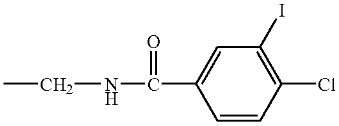 |

TABLE 1.123-continued
| Compd. No. | 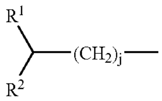 | k | m | n | chirality | $R^3$ | 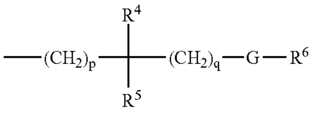 |
|---|---|---|---|---|---|---|---|
| 1345 | 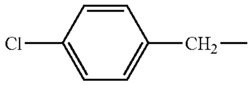 | 2 | 2 | 1 | — | H | 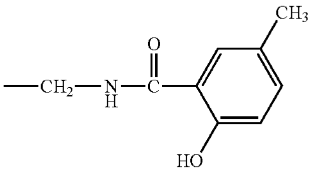 |
| 1346 | 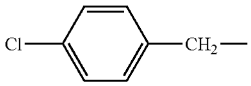 | 2 | 2 | 1 | — | H | 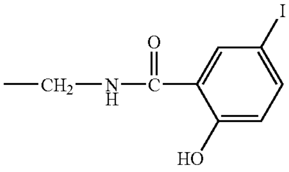 |
| 1347 | 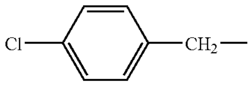 | 1 | 2 | 0 | R | H | 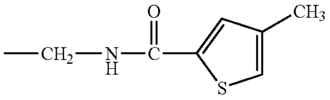 |
| 1348 | 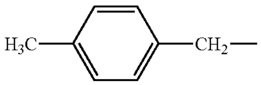 | 1 | 2 | 0 | R | H | 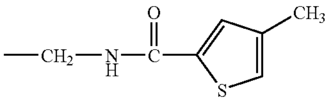 |
| 1349 | 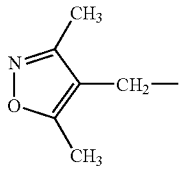 | 1 | 2 | 0 | R | H | 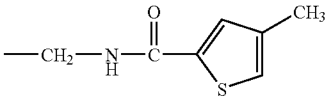 |
| 1350 | 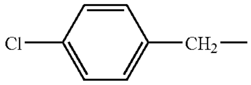 | 2 | 2 | 1 | — | H | 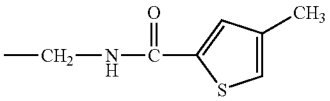 |
| 1351 | 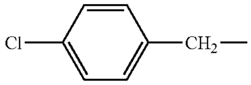 | 1 | 2 | 0 | R | H | 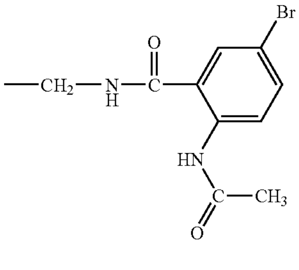 |
| 1352 | 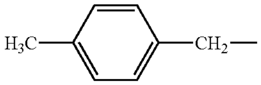 | 1 | 2 | 0 | R | H | 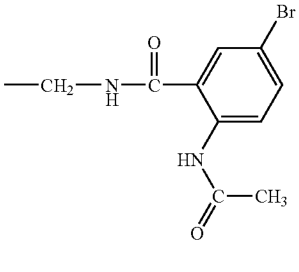 |

TABLE 1.123-continued
| Compd. No. | 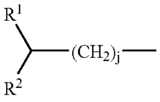 | k | m | n | chirality | $R^3$ | 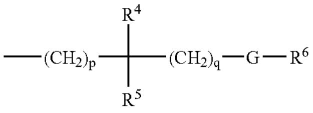 |
|---|---|---|---|---|---|---|---|
| 1353 | 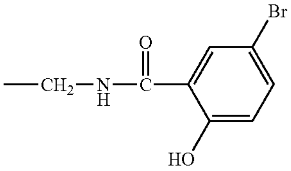 | 1 | 2 | 0 | R | H | 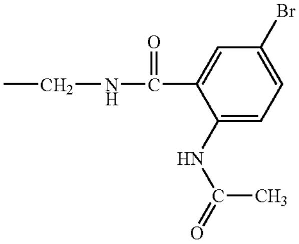 |
TABLE 1.124
| Compd. No. | 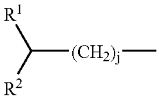 | k | m | n | chirality | $R^3$ | 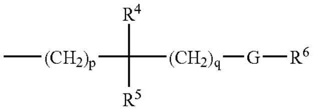 |
|---|---|---|---|---|---|---|---|
| 1354 | 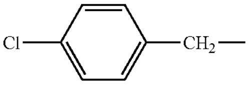 | 2 | 2 | 1 | — | H | 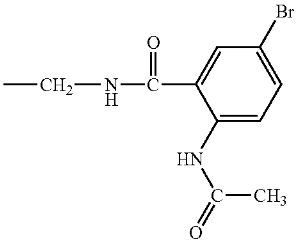 |
| 1355 | 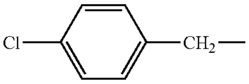 | 1 | 2 | 0 | R | H | 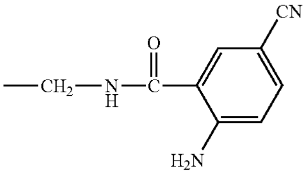 |
| 1356 | 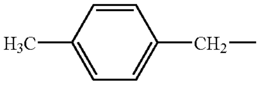 | 1 | 2 | 0 | R | H | 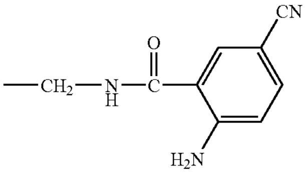 |
| 1357 | 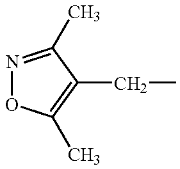 | 1 | 2 | 0 | R | H | 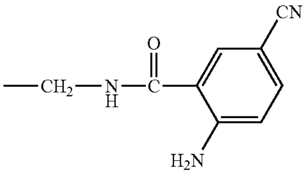 |
| 1358 | 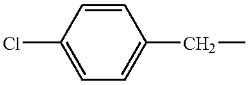 | 2 | 2 | 1 | — | H | 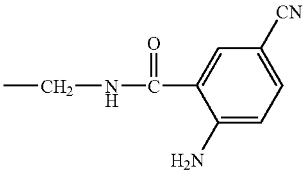 |

TABLE 1.124-continued
| Compd. No. | 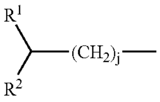 | k | m | n | chirality | $R^3$ | 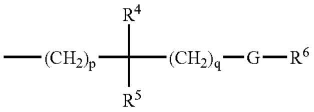 |
|---|---|---|---|---|---|---|---|
| 1359 | 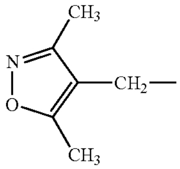 | 1 | 2 | 0 | R | H | 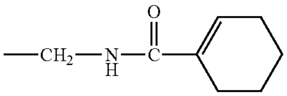 |
| 1360 | 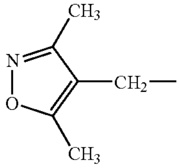 | 1 | 2 | 0 | R | H | 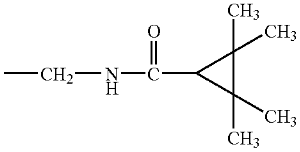 |
| 1361 | 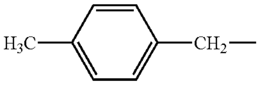 | 1 | 2 | 0 | R | H | 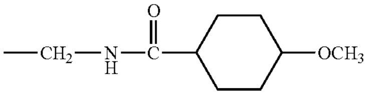 |
| 1362 | 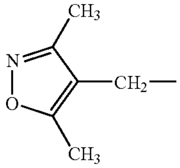 | 1 | 2 | 0 | R | H | 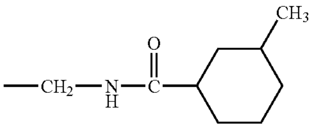 |
| 1363 | 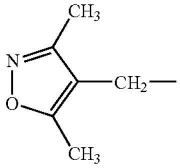 | 1 | 2 | 0 | R | H | 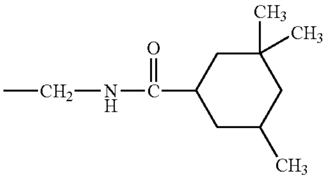 |
| 1364 | 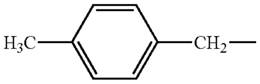 | 1 | 2 | 0 | R | H | 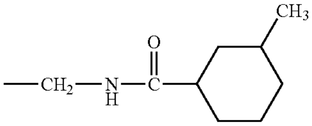 |
TABLE 1.125
| Compd. No. | 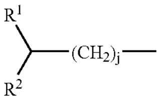 | k | m | n | chirality | $R^3$ | 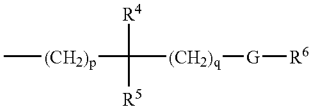 |
|---|---|---|---|---|---|---|---|
| 1365 | 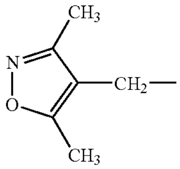 | 1 | 2 | 0 | R | H | 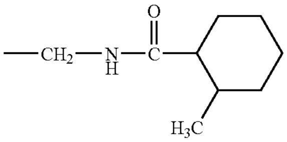 |

TABLE 1.125-continued
| Compd. No. | 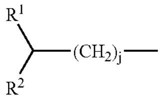 | k | m | n | chirality | $R^3$ | 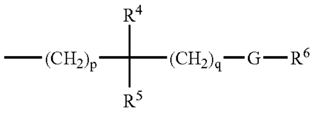 |
|---|---|---|---|---|---|---|---|
| 1366 | 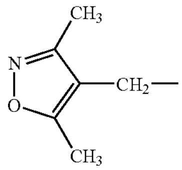 | 1 | 2 | 0 | R | H | 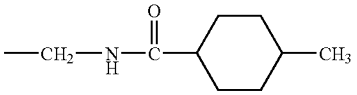 |
| 1367 | 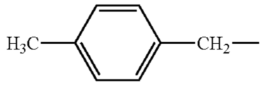 | 1 | 2 | 0 | R | H | 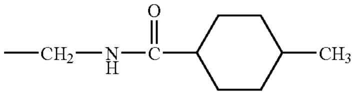 |
| 1368 | 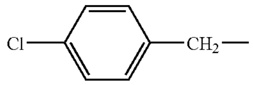 | 1 | 2 | 0 | R | H | 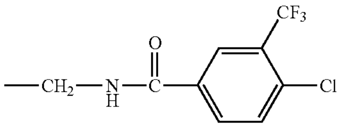 |
| 1369 | 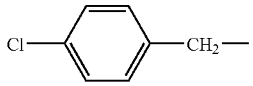 | 1 | 2 | 0 | R | H | 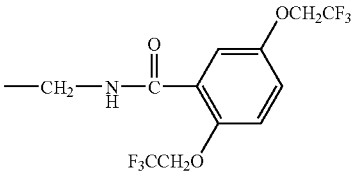 |
| 1370 | 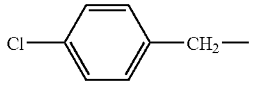 | 1 | 2 | 0 | R | H | 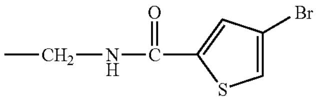 |
| 1371 | 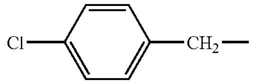 | 1 | 2 | 0 | R | H | 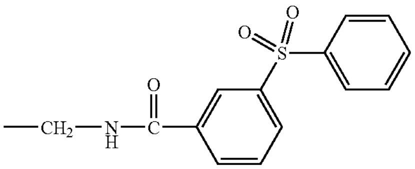 |
| 1372 | 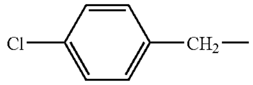 | 1 | 2 | 0 | R | H | 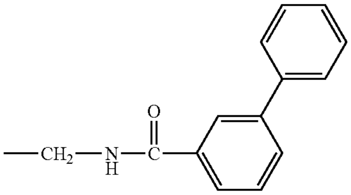 |
| 1373 | 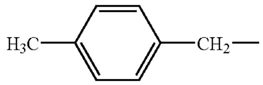 | 1 | 2 | 0 | R | H | 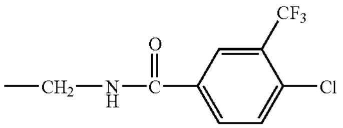 |

TABLE 1.125-continued
| Compd. No. | 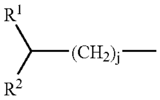 | k | m | n | chirality | $R^3$ | 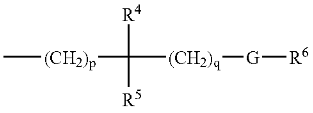 |
|---|---|---|---|---|---|---|---|
| 1374 | 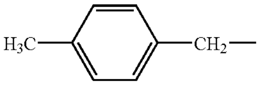 | 1 | 2 | 0 | R | H | 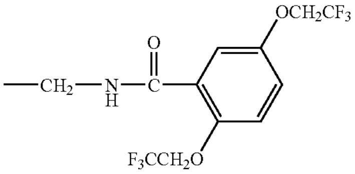 |
| 1375 | 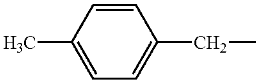 | 1 | 2 | 0 | R | H | 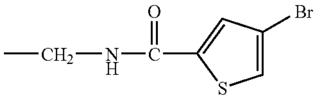 |
TABLE 1.126
| Compd. No. | 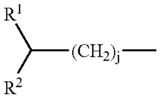 | k | m | n | chirality | $R^3$ | 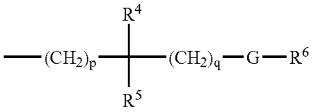 |
|---|---|---|---|---|---|---|---|
| 1376 | 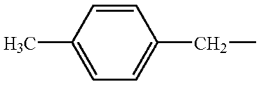 | 1 | 2 | 0 | R | H | 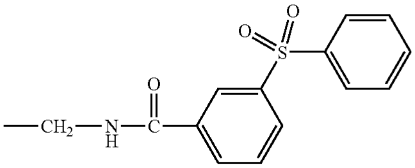 |
| 1377 | 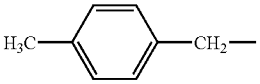 | 1 | 2 | 0 | R | H | 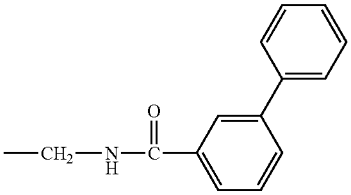 |
| 1378 | 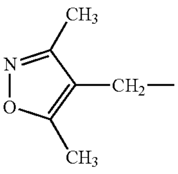 | 1 | 2 | 0 | R | H | 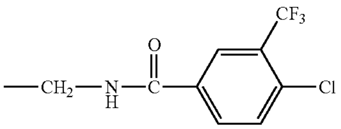 |
| 1379 | 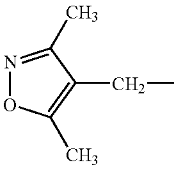 | 1 | 2 | 0 | R | H | 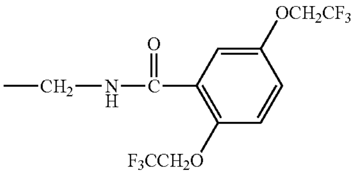 |
| 1380 | 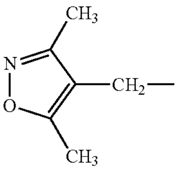 | 1 | 2 | 0 | R | H | 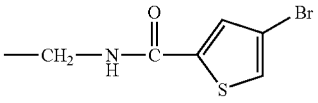 |

TABLE 1.126-continued
| Compd. No. | 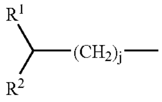 | k | m | n | chirality | $R^3$ | 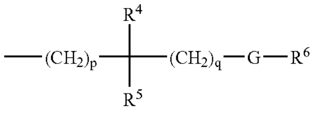 |
|---|---|---|---|---|---|---|---|
| 1381 | 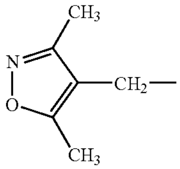 | 1 | 2 | 0 | R | H | 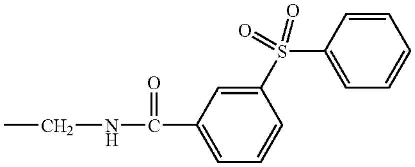 |
| 1382 | 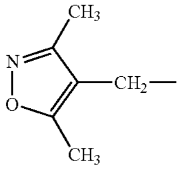 | 1 | 2 | 0 | R | H | 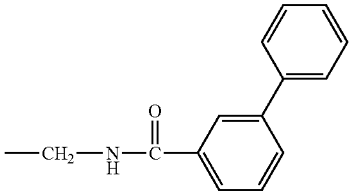 |
| 1383 | 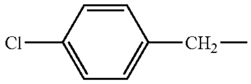 | 2 | 2 | 1 | — | H | 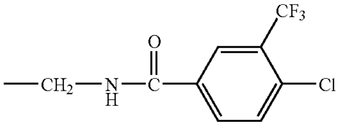 |
| 1384 | 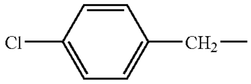 | 2 | 2 | 1 | — | H | 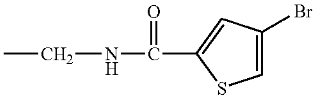 |
| 1385 | 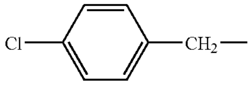 | 2 | 2 | 1 | — | H | 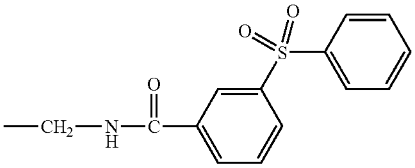 |
| 1386 | 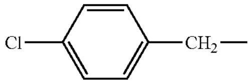 | 2 | 2 | 1 | — | H | 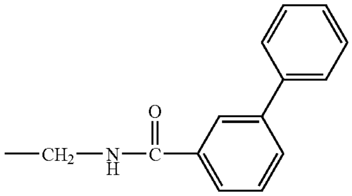 |
TABLE 1.127
| Compd. No. | 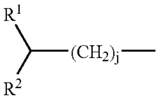 | k | m | n | chirality | $R^3$ | 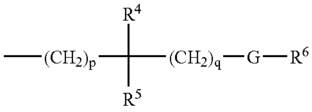 |
|---|---|---|---|---|---|---|---|
| 1387 | 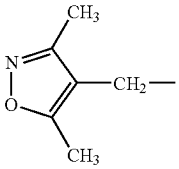 | 1 | 2 | 0 | R | H | 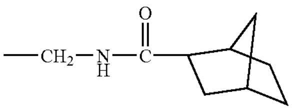 |

TABLE 1.127-continued
| Compd. No. | 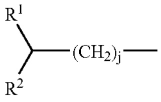 | k | m | n | chirality | $R^3$ | 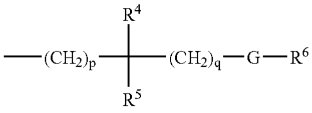 |
|---|---|---|---|---|---|---|---|
| 1388 | 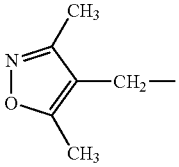 | 1 | 2 | 0 | R | H | 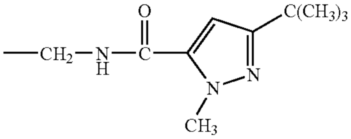 |
| 1389 | 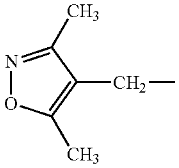 | 1 | 2 | 0 | R | H | 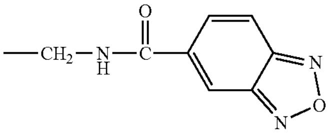 |
| 1390 | 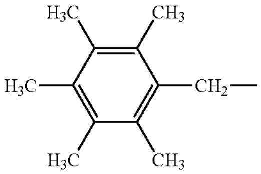 | 1 | 2 | 0 | R | H | 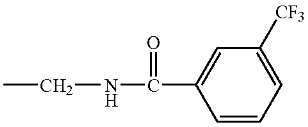 |
| 1391 | 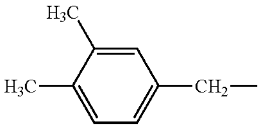 | 1 | 2 | 0 | R | H | 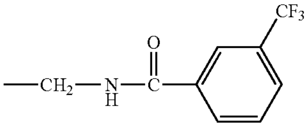 |
| 1392 | 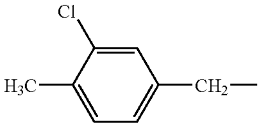 | 1 | 2 | 0 | R | H | 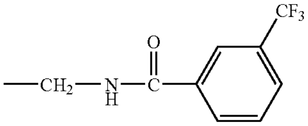 |
| 1393 | 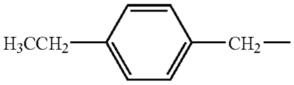 | 1 | 2 | 0 | R | H | 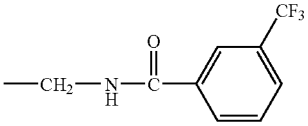 |
| 1394 | 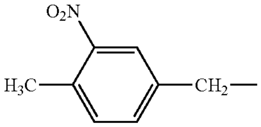 | 1 | 2 | 0 | R | H | 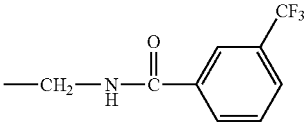 |
| 1395 | 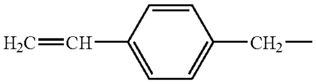 | 1 | 2 | 0 | R | H | 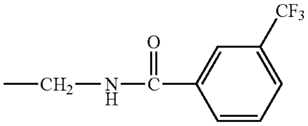 |
| 1396 | 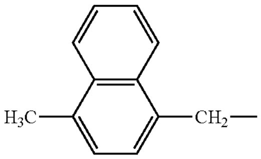 | 1 | 2 | 0 | R | H | 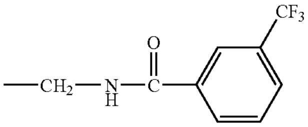 |

TABLE 1.127-continued
| Compd. No. | 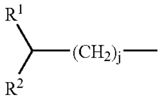 | k | m | n | chirality | $R^3$ | 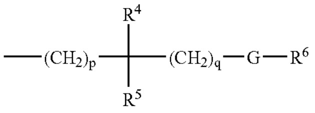 |
|---|---|---|---|---|---|---|---|
| 1397 | 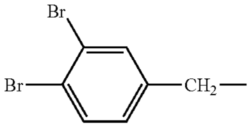 | 1 | 2 | 0 | R | H | 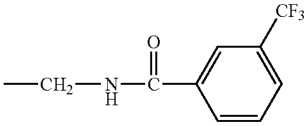 |
TABLE 1.127
| Compd. No. | 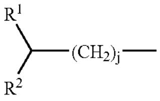 | k | m | n | chirality | $R^3$ | 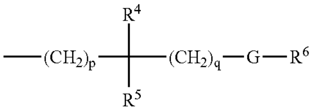 |
|---|---|---|---|---|---|---|---|
| 1398 | 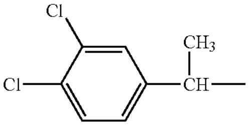 | 1 | 2 | 0 | R | H | 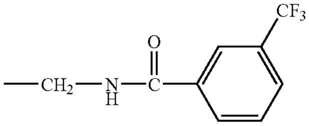 |
| 1399 | 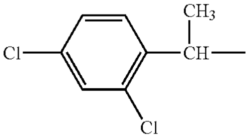 | 1 | 2 | 0 | R | H | 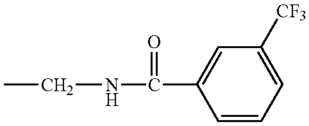 |
| 1400 | 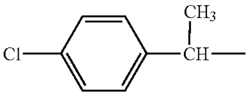 | 1 | 2 | 0 | R | H | 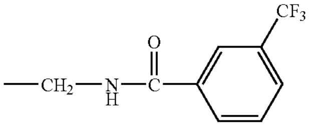 |
| 1401 | 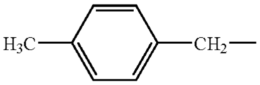 | 1 | 2 | 0 | R | H | 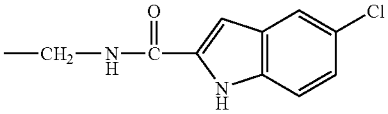 |
| 1402 | 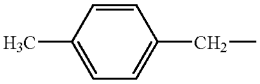 | 1 | 2 | 0 | R | H | 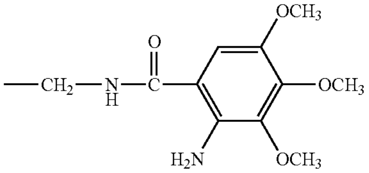 |
| 1403 | 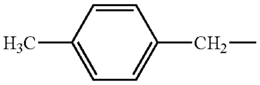 | 1 | 2 | 0 | R | H | 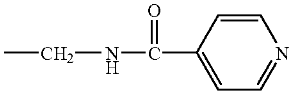 |
| 1404 | 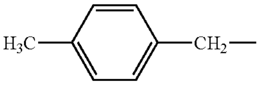 | 1 | 2 | 0 | R | H | 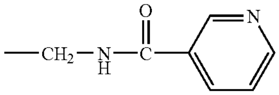 |
| 1405 | 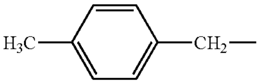 | 1 | 2 | 0 | R | H | 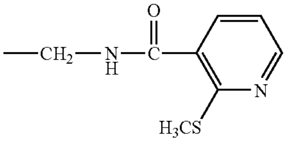 |

TABLE 1.127-continued
| Compd. No. | 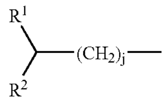 | k | m | n | chirality | $R^3$ | 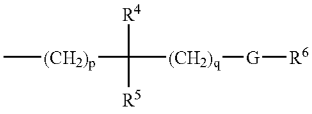 |
|---|---|---|---|---|---|---|---|
| 1406 | 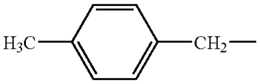 | 1 | 2 | 0 | R | H | 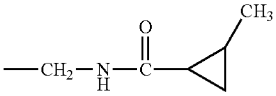 |
| 1407 | 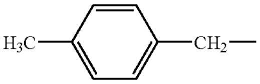 | 1 | 2 | 0 | R | H | 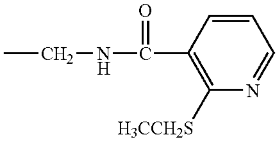 |
| 1408 | 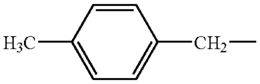 | 1 | 2 | 0 | R | H | 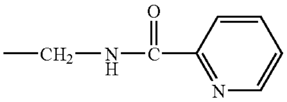 |
TABLE 1.129
| Compd. No. | 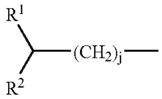 | k | m | n | chirality | $R^3$ | 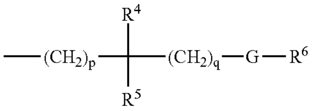 |
|---|---|---|---|---|---|---|---|
| 1409 | 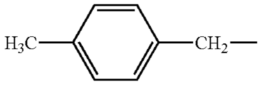 | 1 | 2 | 0 | R | H | 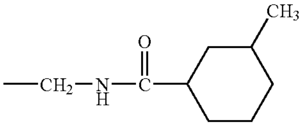 |
| 1410 | 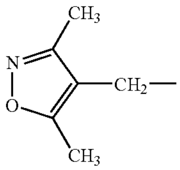 | 1 | 2 | 0 | R | H | 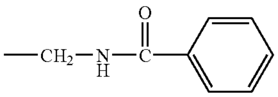 |
| 1411 | 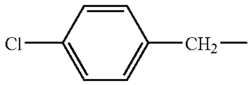 | 1 | 2 | 0 | R | H | 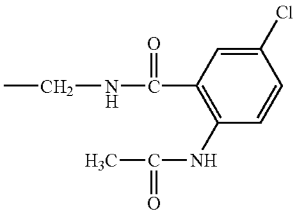 |
| 1412 | 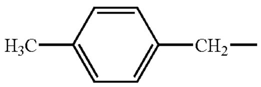 | 1 | 2 | 0 | R | H | 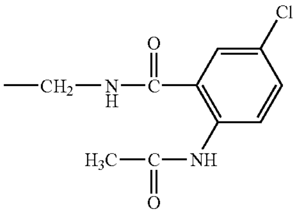 |

TABLE 1.129-continued
| Compd. No. | 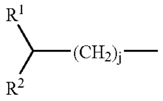 | k | m | n | chirality | $R^3$ | 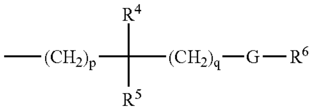 |
|---|---|---|---|---|---|---|---|
| 1413 | 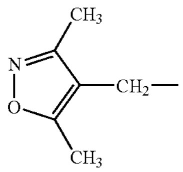 | 1 | 2 | 0 | R | H | 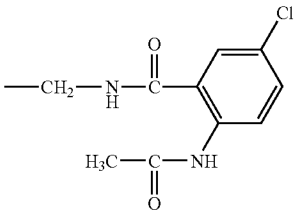 |
| 1414 | 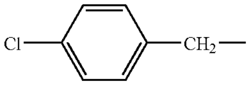 | 2 | 2 | 1 | — | H | 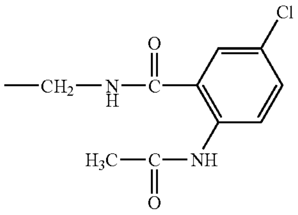 |
| 1415 | 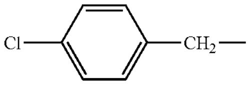 | 1 | 2 | 0 | R | H | 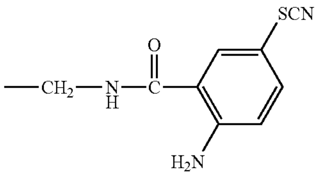 |
| 1416 | 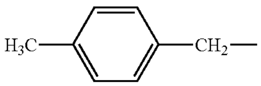 | 1 | 2 | 0 | R | H | 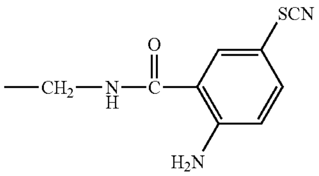 |
| 1417 | 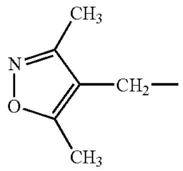 | 1 | 2 | 0 | R | H | 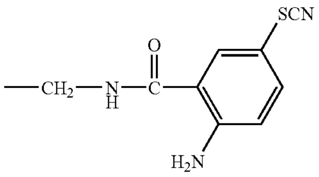 |
| 1418 | 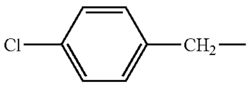 | 2 | 2 | 1 | — | H | 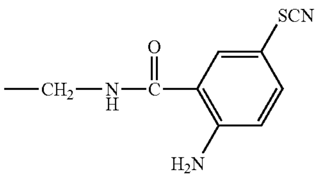 |
| 1419 | 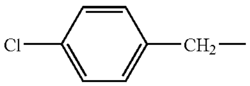 | 1 | 2 | 0 | R | H | 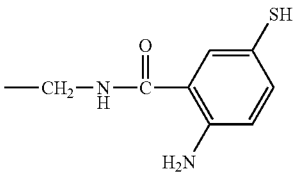 |

TABLE 1.130
| Compd. No. | 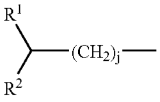 | k | m | n | chirality | $R^3$ | 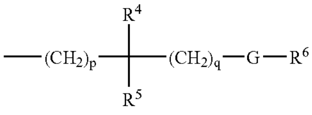 |
|---|---|---|---|---|---|---|---|
| 1420 | 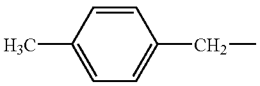 | 1 | 2 | 0 | R | H | 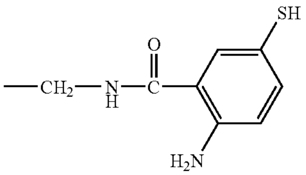 |
| 1421 | 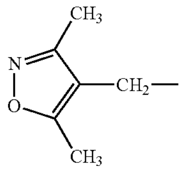 | 1 | 2 | 0 | R | H | 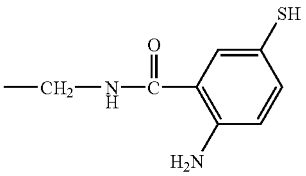 |
| 1422 | 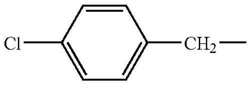 | 2 | 2 | 1 | — | H | 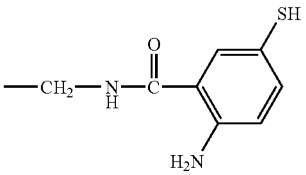 |
| 1423 | 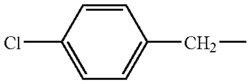 | 1 | 2 | 0 | R | H | 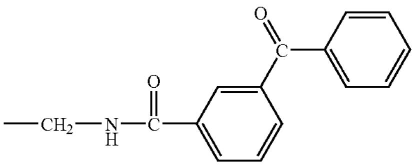 |
| 1424 | 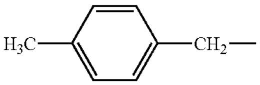 | 1 | 2 | 0 | R | H | 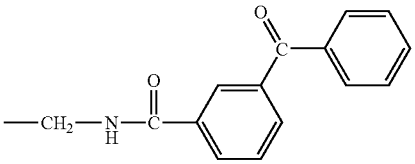 |
| 1425 | 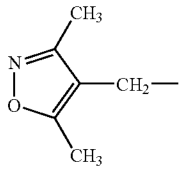 | 1 | 2 | 0 | R | H | 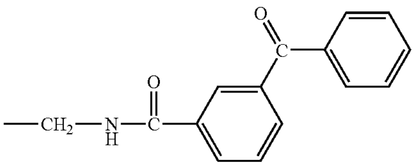 |
| 1426 | 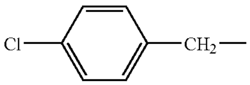 | 2 | 2 | 1 | — | H | 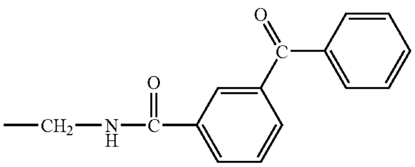 |
| 1427 | 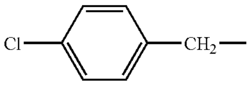 | 2 | 2 | 1 | — | H | 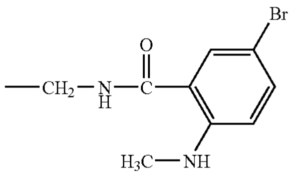 |

TABLE 1.130-continued
| Compd. No. | 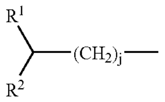 | k | m | n | chirality | $R^3$ | 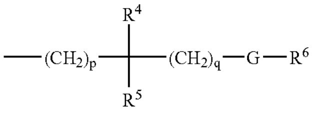 |
|---|---|---|---|---|---|---|---|
| 1428 | 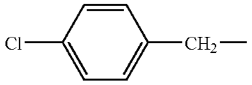 | 2 | 2 | 1 | — | H | 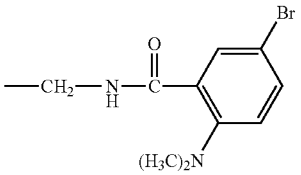 |
| 1429 | 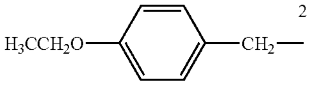 | 2 | 2 | 1 | — | H | 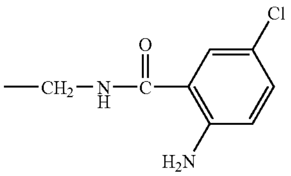 |
| 1430 | 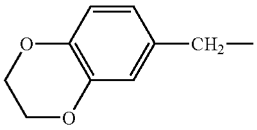 | 2 | 2 | 1 | — | H | 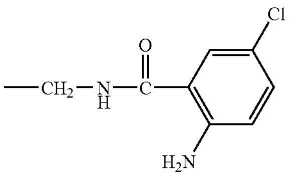 |
TABLE 1.131
| Compd. No. | 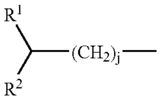 | k | m | n | chirality | $R^3$ | 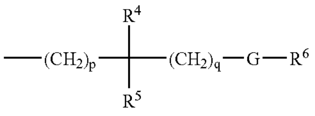 |
|---|---|---|---|---|---|---|---|
| 1431 | 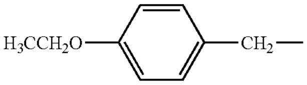 | 2 | 2 | 1 | — | H | 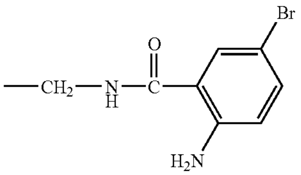 |
| 1432 | 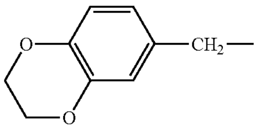 | 2 | 2 | 1 | — | H | 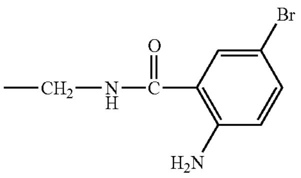 |
| 1433 | 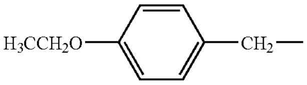 | 2 | 2 | 1 | — | H | 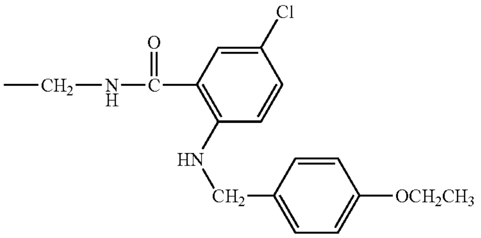 |

TABLE 1.131-continued
| Compd. No. | 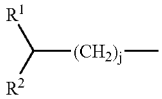 | k | m | n | chirality | $R^3$ | 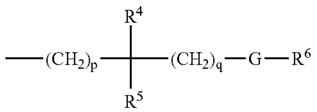 |
|---|---|---|---|---|---|---|---|
| 1434 | 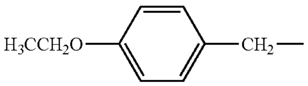 | 2 | 2 | 1 | — | H | 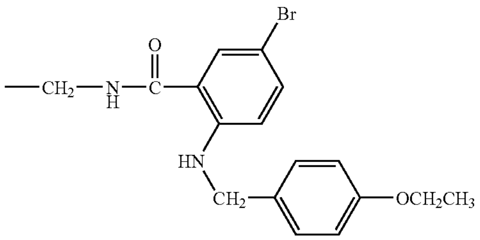 |
| 1435 | 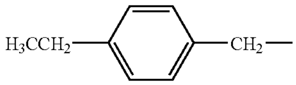 | 2 | 2 | 1 | — | H | 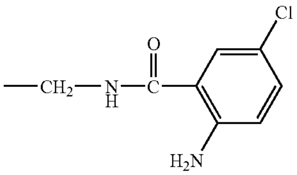 |
| 1436 | 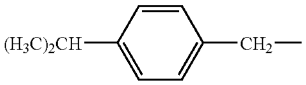 | 2 | 2 | 1 | — | H | 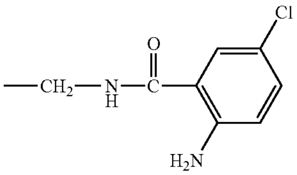 |
| 1437 | 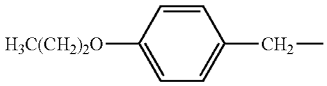 | 2 | 2 | 1 | — | H | 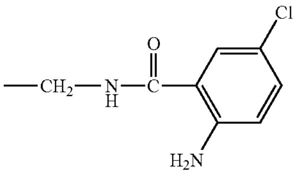 |
| 1438 | 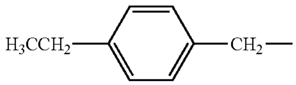 | 2 | 2 | 1 | — | H | 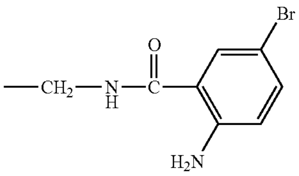 |
| 1439 | 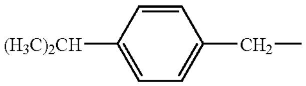 | 2 | 2 | 1 | — | H | 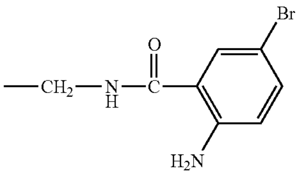 |

TABLE 1.131-continued
| Compd. No. | 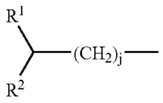 | k | m | n | chirality | $R^3$ | 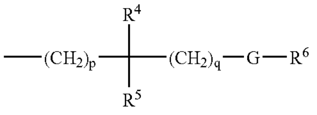 |
|---|---|---|---|---|---|---|---|
| 1440 | 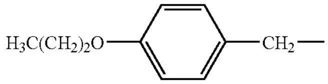 | 2 | 2 | 1 | — | H | 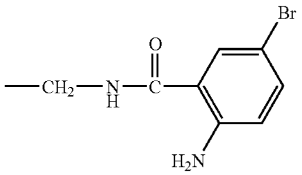 |
| 1441 | 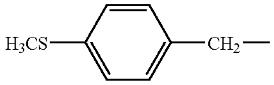 | 2 | 2 | 1 | — | H | 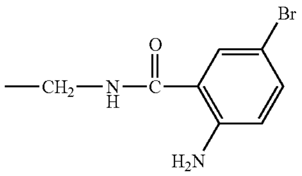 |
TABLE 1.132
| Compd. No. | 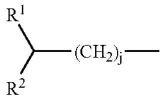 | k | m | n | chirality | $R^3$ | 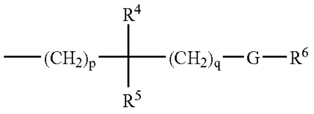 |
|---|---|---|---|---|---|---|---|
| 1442 | 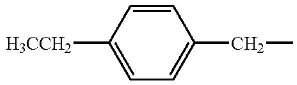 | 2 | 2 | 1 | — | H | 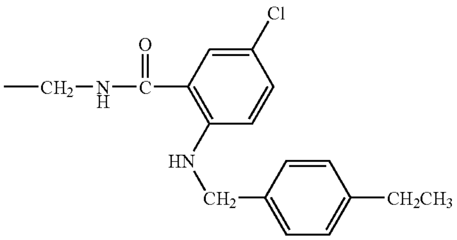 |
| 1443 | 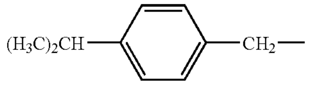 | 2 | 2 | 1 | — | H | 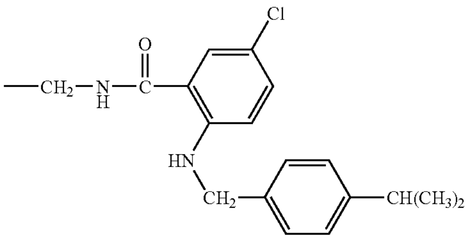 |
| 1444 | 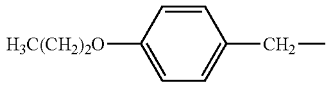 | 2 | 2 | 1 | — | H | 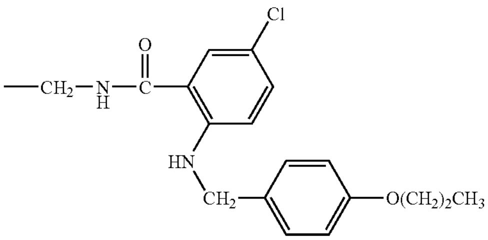 |

TABLE 1.132-continued
| Compd. No. | 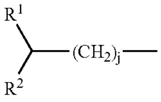 | k | m | n | chirality | $R^3$ | 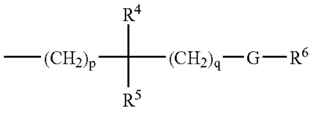 |
|---|---|---|---|---|---|---|---|
| 1445 | 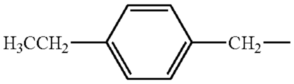 | 2 | 2 | 1 | — | H | 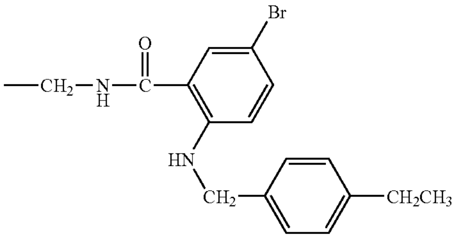 |
| 1446 | 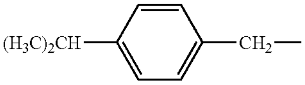 | 2 | 2 | 1 | — | H | 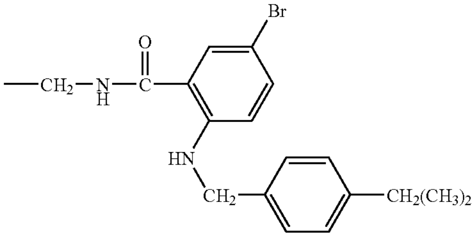 |
| 1447 | 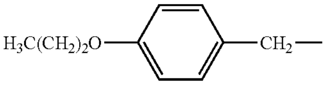 | 2 | 2 | 1 | — | H | 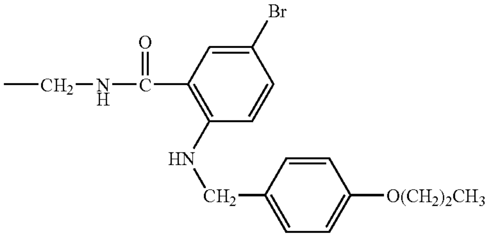 |
| 1448 | 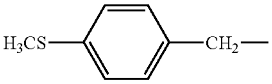 | 2 | 2 | 1 | — | H | 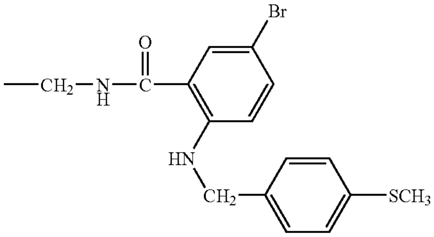 |
| 1449 | 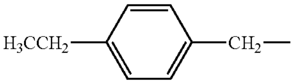 | 2 | 2 | 1 | — | H | 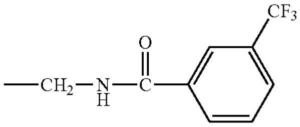 |
| 1450 | 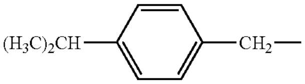 | 2 | 2 | 1 | — | H | 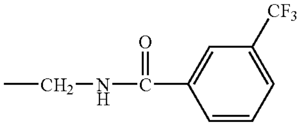 |
| 1451 | 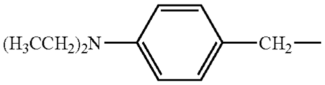 | 2 | 2 | 1 | — | H | 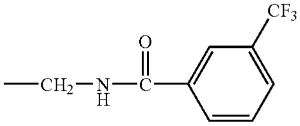 |

TABLE 1.132-continued
| Compd. No. | 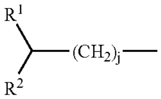 | k | m | n | chirality | $R^3$ | 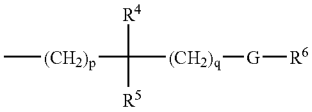 |
|---|---|---|---|---|---|---|---|
| 1452 | 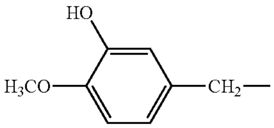 | 2 | 2 | 1 | — | H | 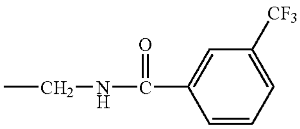 |
TABLE 1.133
| Compd. No. | 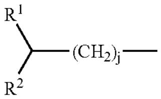 | k | m | n | chirality | $R^3$ | 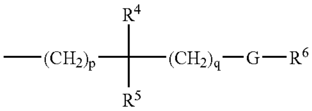 |
|---|---|---|---|---|---|---|---|
| 1453 | 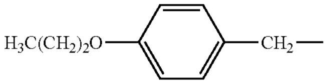 | 2 | 2 | 1 | — | H | 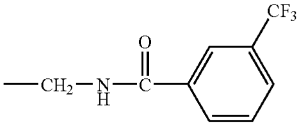 |
| 1454 | 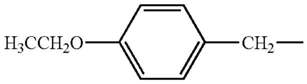 | 2 | 2 | 1 | — | H | 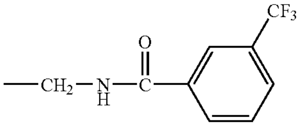 |
| 1455 | 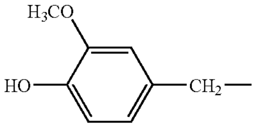 | 2 | 2 | 1 | — | H | 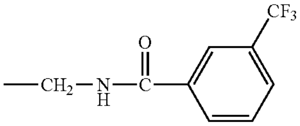 |
| 1456 | 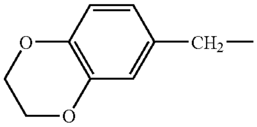 | 2 | 2 | 1 | — | H | 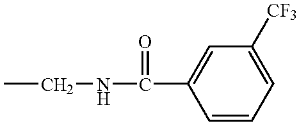 |
| 1457 | 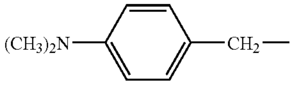 | 2 | 2 | 1 | — | H | 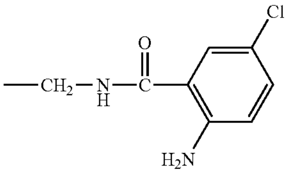 |
| 1458 | 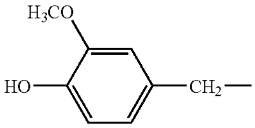 | 2 | 2 | 1 | — | H | 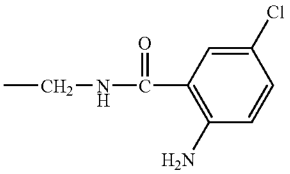 |
| 1459 | 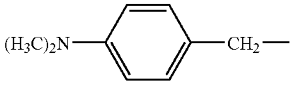 | 2 | 2 | 1 | — | H | 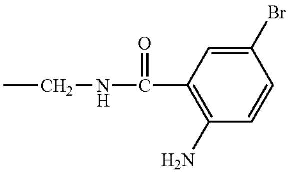 |

TABLE 1.133-continued
| Compd. No. 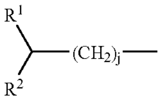 | k | m | n | chirality | $R^3$ | 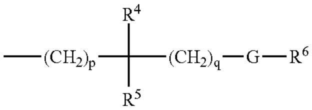 |
|---|---|---|---|---|---|---|
| 1460 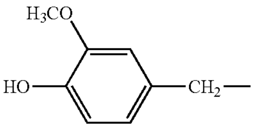 | 2 | 2 | 1 | — | H | 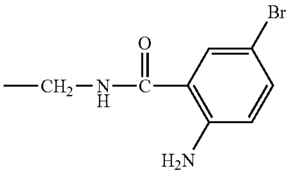 |
| 1461 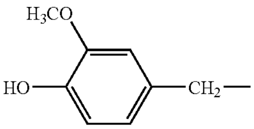 | 2 | 2 | 1 | — | H | 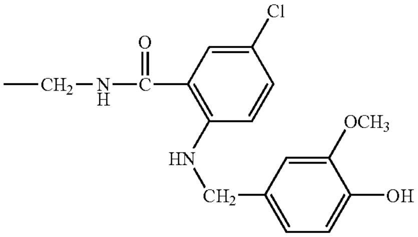 |
| 1462 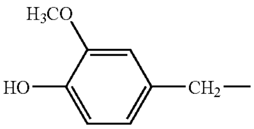 | 2 | 2 | 1 | — | H | 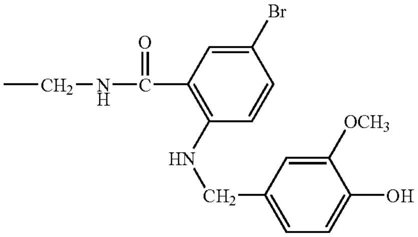 |
| 1463 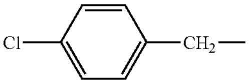 | 2 | 1 | 1 | — | H | 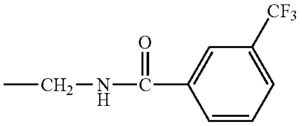 |
TABLE 1.134
| Compd. No. 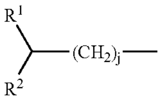 | k | m | n | chirality | $R^3$ | 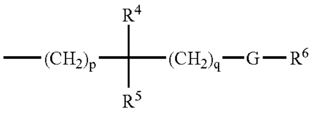 |
|---|---|---|---|---|---|---|
| 1464 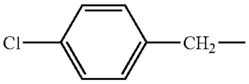 | 2 | 1 | 1 | — | H | 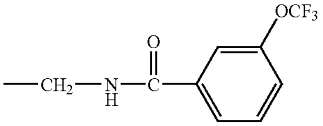 |
| 1465 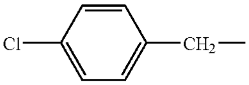 | 2 | 1 | 1 | — | H | 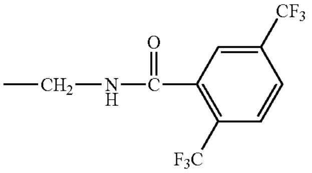 |
| 1466 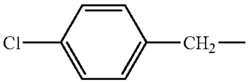 | 2 | 1 | 1 | — | H | 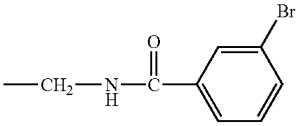 |

TABLE 1.134-continued
| Compd. No. | 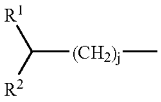 | k | m | n | chirality | $R^3$ | 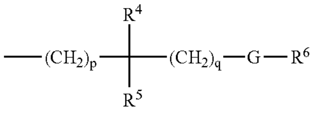 |
|---|---|---|---|---|---|---|---|
| 1467 | 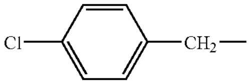 | 2 | 1 | 1 | — | H | 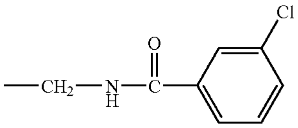 |
| 1468 | 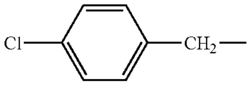 | 2 | 1 | 1 | — | H | 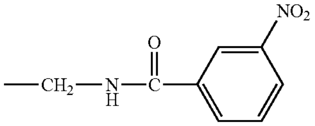 |
| 1469 | 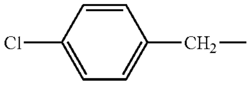 | 2 | 1 | 1 | — | H | 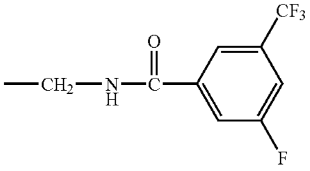 |
| 1470 | 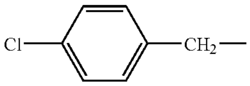 | 2 | 1 | 1 | — | H | 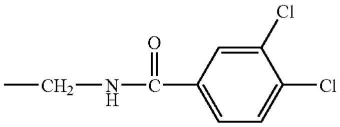 |
| 1471 | 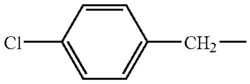 | 2 | 1 | 1 | — | H | 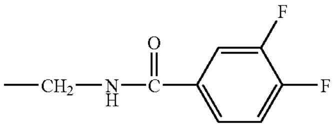 |
| 1472 | 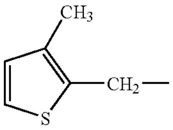 | 1 | 2 | 0 | R | H | 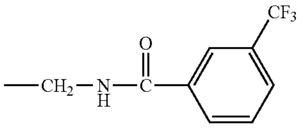 |
| 1473 | 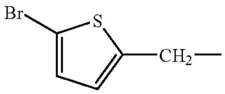 | 1 | 2 | 0 | R | H | 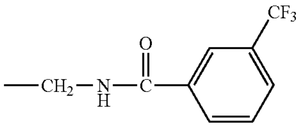 |
| 1474 | 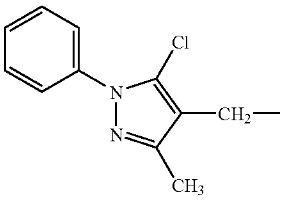 | 1 | 2 | 0 | R | H | 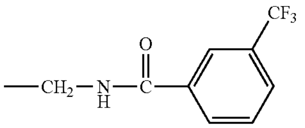 |

TABLE 1.135
| Compd. No. | 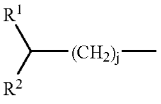 | k | m | n | chirality | $R^3$ | 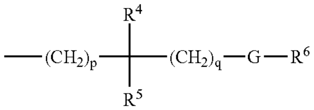 |
|---|---|---|---|---|---|---|---|
| 1475 | 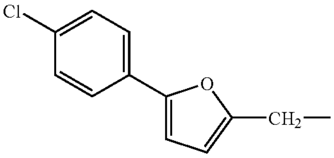 | 1 | 2 | 0 | R | H | 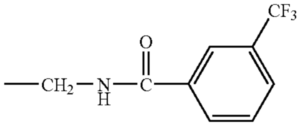 |
| 1476 | 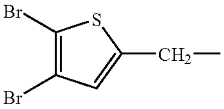 | 1 | 2 | 0 | R | H | 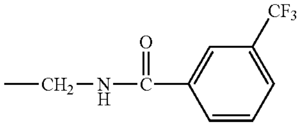 |
| 1477 | 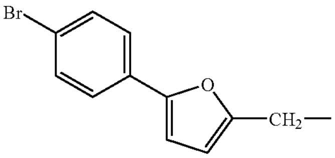 | 1 | 2 | 0 | R | H | 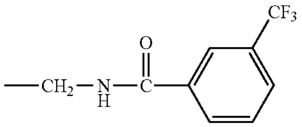 |
| 1478 | 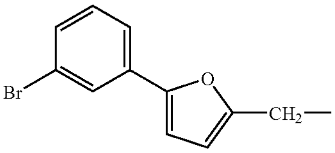 | 1 | 2 | 0 | R | H | 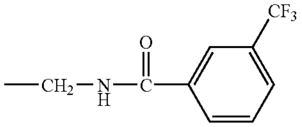 |
| 1479 | 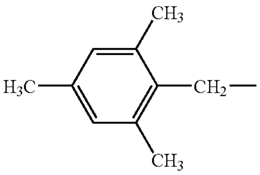 | 1 | 2 | 0 | R | H | 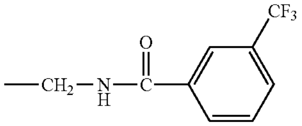 |
| 1480 | 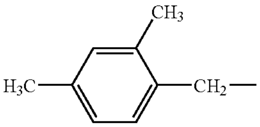 | 1 | 2 | 0 | R | H | 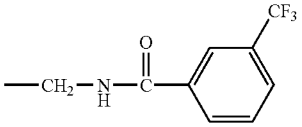 |
| 1481 | 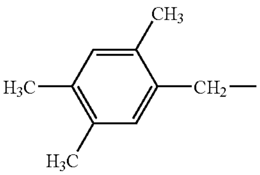 | 1 | 2 | 0 | R | H | 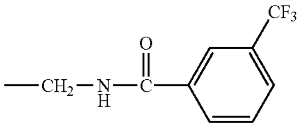 |
| 1482 | 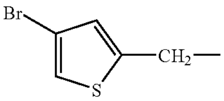 | 1 | 2 | 0 | R | H | 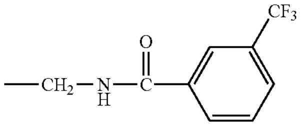 |
| 1483 | 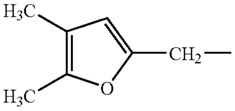 | 1 | 2 | 0 | R | H | 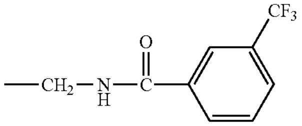 |

TABLE 1.135-continued
| Compd. No. | 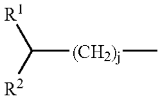 | k | m | n | chirality | $R^3$ | 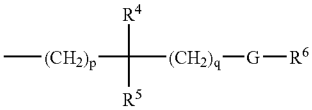 |
|---|---|---|---|---|---|---|---|
| 1484 | 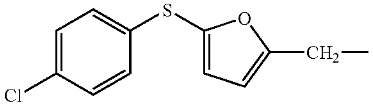 | 1 | 2 | 0 | R | H | 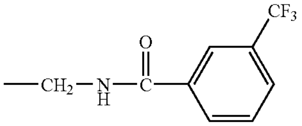 |
| 1485 | 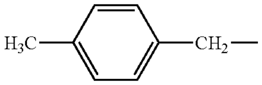 | 1 | 2 | 0 | R | H | 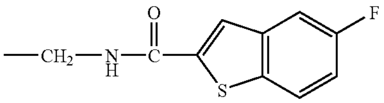 |
TABLE 1.136
| Compd. No. | 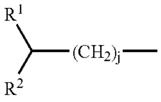 | k | m | n | chirality | $R^3$ | 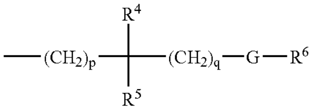 |
|---|---|---|---|---|---|---|---|
| 1486 | 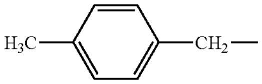 | 1 | 2 | 0 | R | H | 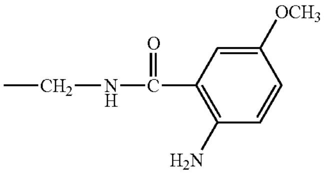 |
| 1487 | 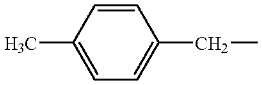 | 1 | 2 | 0 | R | H | 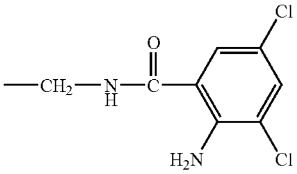 |
| 1488 | 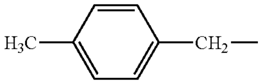 | 1 | 2 | 0 | R | H | 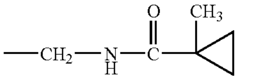 |
| 1489 | 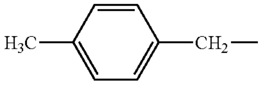 | 1 | 2 | 0 | R | H | 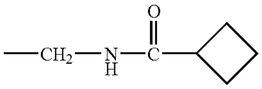 |
| 1490 | 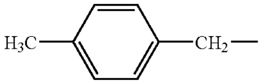 | 1 | 2 | 0 | R | H | 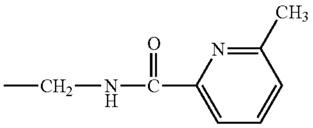 |
| 1491 | 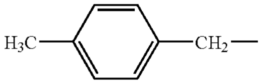 | 1 | 2 | 0 | R | H | 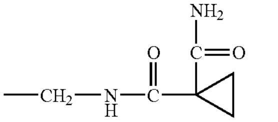 |
| 1492 | 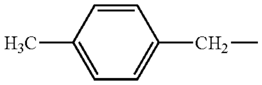 | 1 | 2 | 0 | R | H | 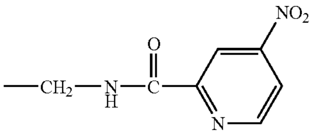 |

TABLE 1.136-continued
| Compd. No. | 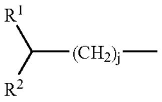 | k | m | n | chirality | $R^3$ | 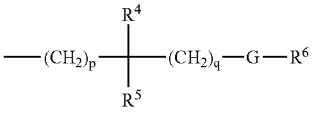 |
|---|---|---|---|---|---|---|---|
| 1493 | 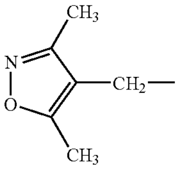 | 1 | 2 | 0 | R | H | 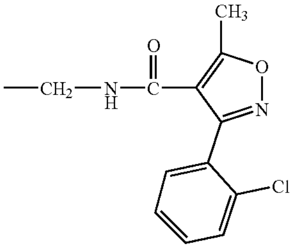 |
| 1494 | 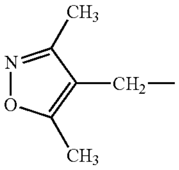 | 1 | 2 | 0 | R | H | 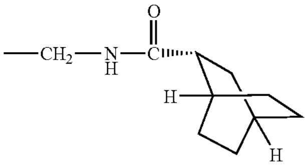 |
| 1495 | 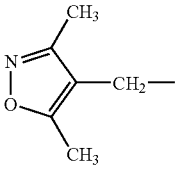 | 1 | 2 | 0 | R | H | 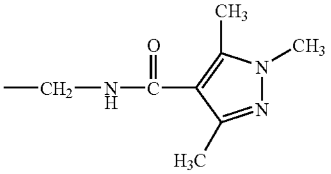 |
| 1496 | 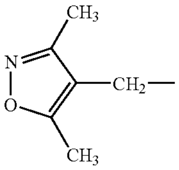 | 1 | 2 | 0 | R | H | 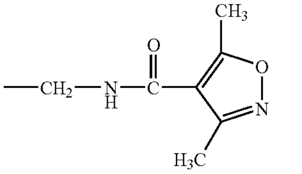 |
TABLE 1.137
| Compd. No. | 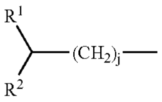 | k | m | n | chirality | $R^3$ | 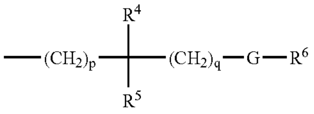 |
|---|---|---|---|---|---|---|---|
| 1497 | 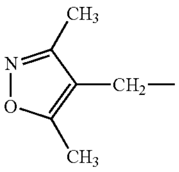 | 1 | 2 | 0 | R | H | 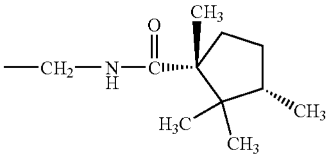 |
| 1498 | 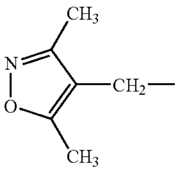 | 1 | 2 | 0 | R | H | 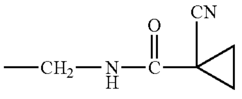 |

TABLE 1.137-continued
| Compd. No. | 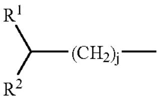 | k | m | n | chirality | $R^3$ | 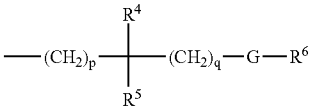 |
|---|---|---|---|---|---|---|---|
| 1499 | 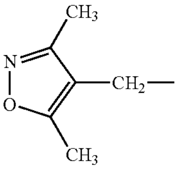 | 1 | 2 | 0 | R | H | 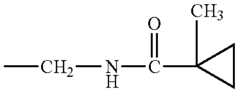 |
| 1500 | 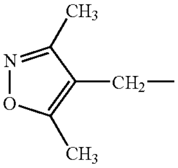 | 1 | 2 | 0 | R | H | 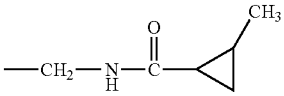 |
| 1501 | 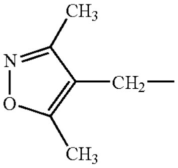 | 1 | 2 | 0 | R | H | 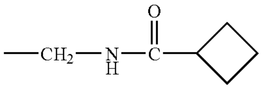 |
| 1502 | 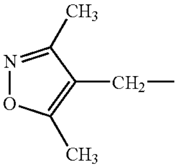 | 1 | 2 | 0 | R | H | 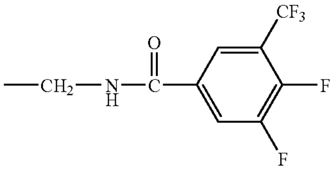 |
| 1503 | 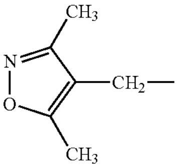 | 1 | 2 | 0 | R | H | 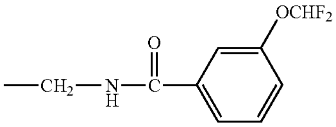 |
| 1504 | 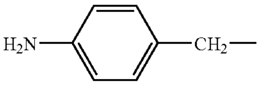 | 1 | 2 | 0 | R | H | 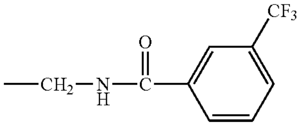 |
| 1505 | 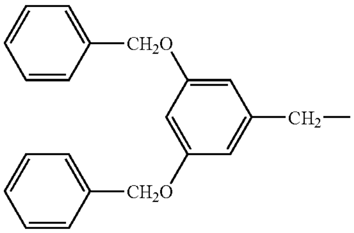 | 1 | 2 | 0 | R | H | 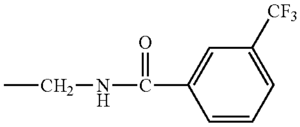 |
| 1506 | 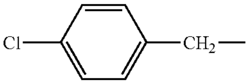 | 2 | 1 | 1 | — | H | 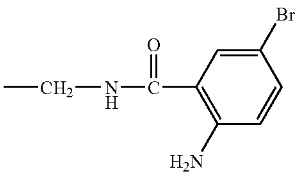 |

TABLE 1.137-continued
| Compd. No. | 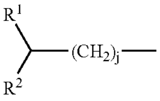 | k | m | n | chirality | $R^3$ | 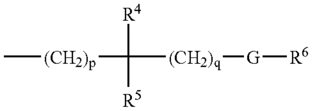 |
|---|---|---|---|---|---|---|---|
| 1507 | 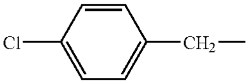 | 2 | 1 | 1 | — | H | 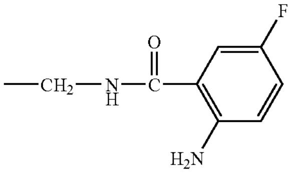 |
TABLE 1.138
| Compd. No. | 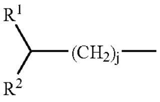 | k | m | n | chirality | $R^3$ | 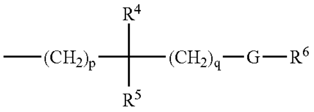 |
|---|---|---|---|---|---|---|---|
| 1508 | 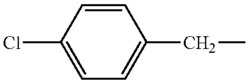 | 2 | 1 | 1 | — | H | 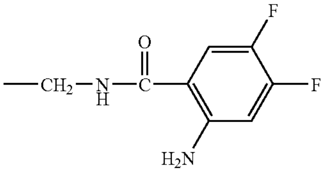 |
| 1509 | 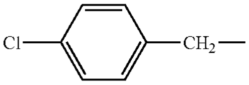 | 2 | 1 | 1 | — | H | 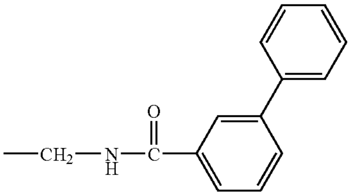 |
| 1510 | 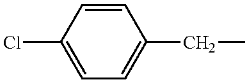 | 2 | 1 | 1 | — | H | 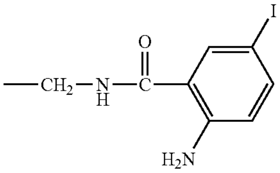 |
| 1511 | 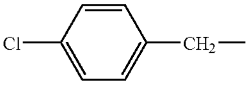 | 2 | 1 | 1 | — | H | 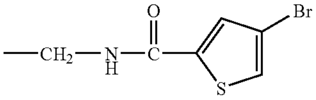 |
| 1512 | 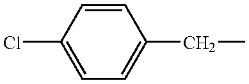 | 2 | 1 | 1 | — | H | 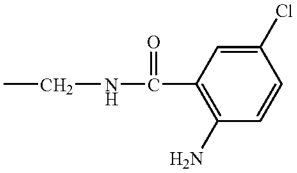 |
| 1513 | 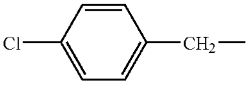 | 2 | 1 | 1 | — | H | 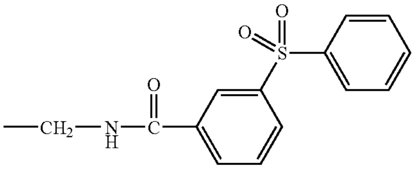 |

TABLE 1.138-continued
| Compd. No. | 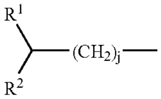 | k | m | n | chirality | $R^3$ | 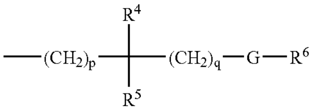 |
|---|---|---|---|---|---|---|---|
| 1514 | 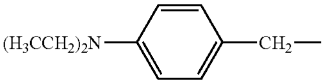 | 2 | 2 | 1 | — | H | 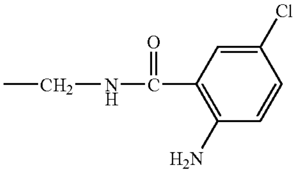 |
| 1515 | 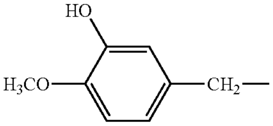 | 2 | 2 | 1 | — | H | 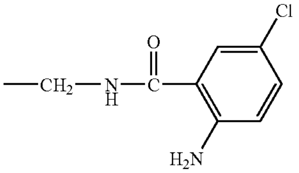 |
| 1516 | 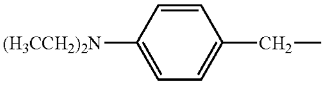 | 2 | 2 | 1 | — | H | 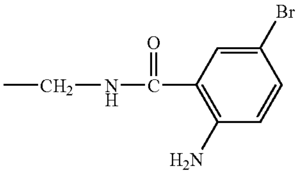 |
| 1517 | 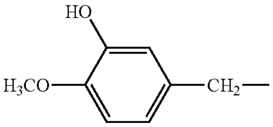 | 2 | 2 | 1 | — | H | 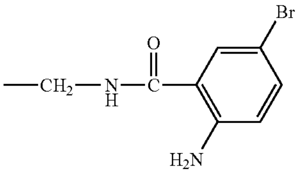 |
| 1518 | 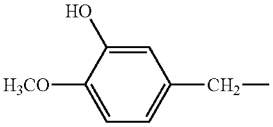 | 2 | 2 | 1 | — | H | 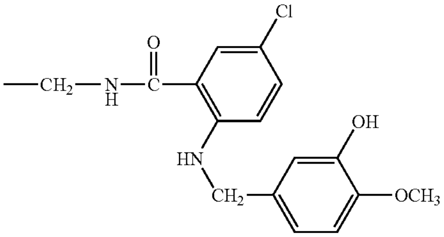 |
TABLE 1.139
| Compd. No. | 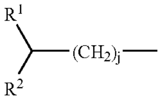 | k | m | n | chirality | $R^3$ | 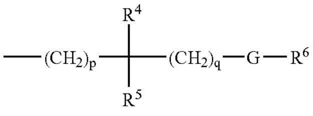 |
|---|---|---|---|---|---|---|---|
| 1519 | 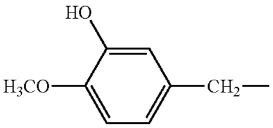 | 2 | 2 | 1 | — | H | 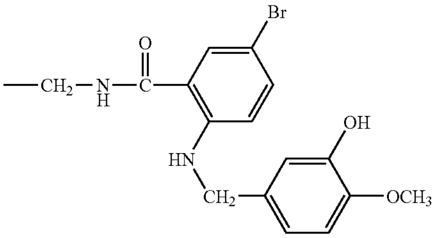 |

TABLE 1.139-continued
| Compd. No. | 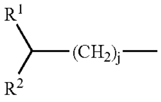 | k | m | n | chirality | $R^3$ | 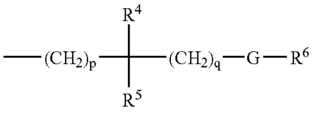 |
|---|---|---|---|---|---|---|---|
| 1520 | 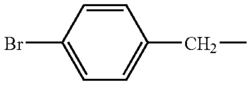 | 1 | 2 | 0 | R | H | 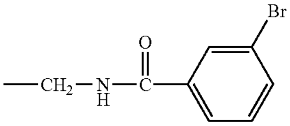 |
| 1521 | 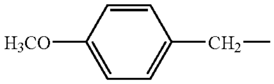 | 1 | 2 | 0 | R | H | 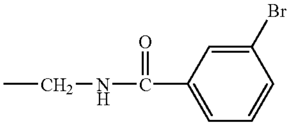 |
| 1522 | 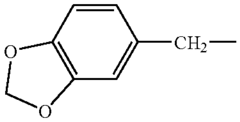 | 1 | 2 | 0 | R | H | 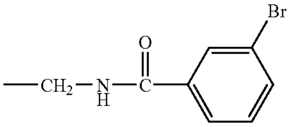 |
| 1523 | 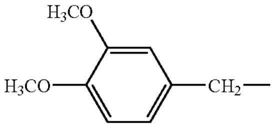 | 1 | 2 | 0 | R | H | 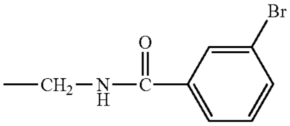 |
| 1524 | 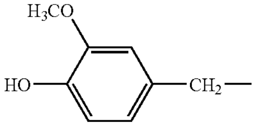 | 1 | 2 | 0 | R | H | 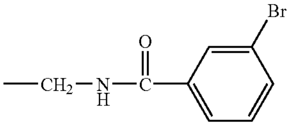 |
| 1525 | 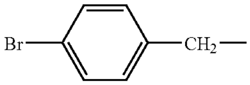 | 1 | 2 | 0 | R | H | 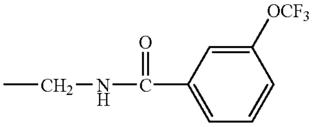 |
| 1526 | 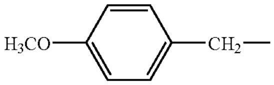 | 1 | 2 | 0 | R | H | 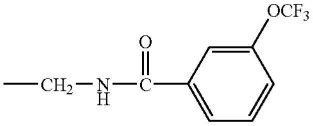 |
| 1527 | 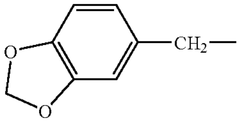 | 1 | 2 | 0 | R | H | 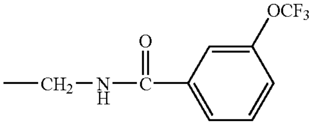 |
| 1528 | 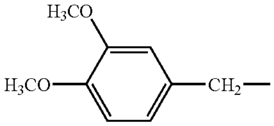 | 1 | 2 | 0 | R | H | 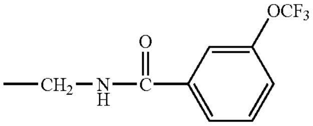 |
| 1529 | 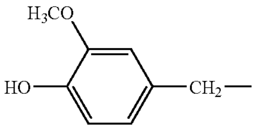 | 1 | 2 | 0 | R | H | 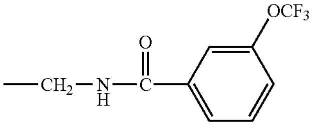 |

TABLE 1.140
| Compd. No. | 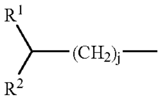 | k | m | n | chirality | $R^3$ | 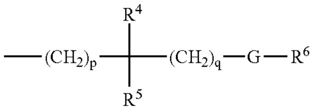 |
|---|---|---|---|---|---|---|---|
| 1530 | 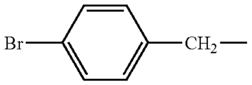 | 1 | 2 | 0 | R | H | 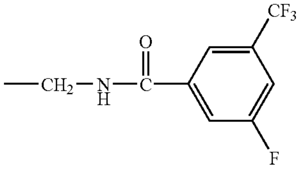 |
| 1531 | 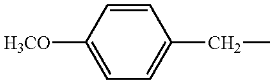 | 1 | 2 | 0 | R | H | 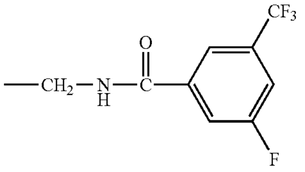 |
| 1532 | 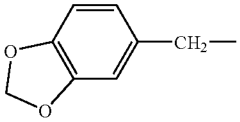 | 1 | 2 | 0 | R | H | 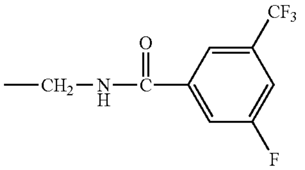 |
| 1533 | 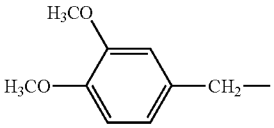 | 1 | 2 | 0 | R | H | 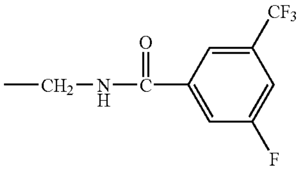 |
| 1534 | 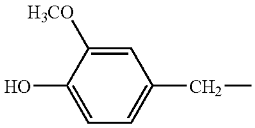 | 1 | 2 | 0 | R | H | 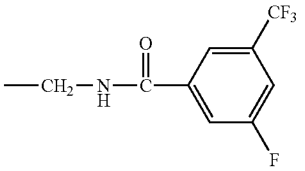 |
| 1535 | 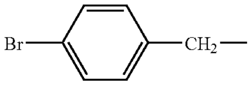 | 1 | 2 | 0 | R | H | 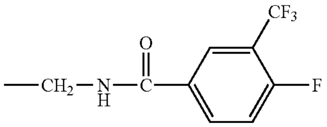 |
| 1536 | 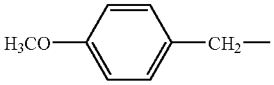 | 1 | 2 | 0 | R | H | 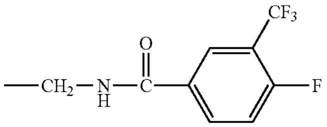 |
| 1537 | 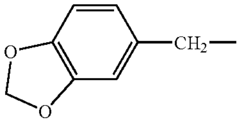 | 1 | 2 | 0 | R | H | 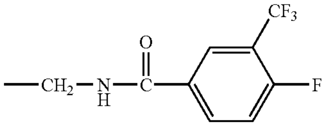 |
| 1538 | 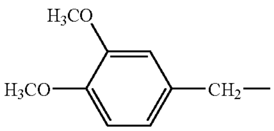 | 1 | 2 | 0 | R | H | 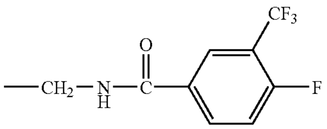 |

TABLE 1.140-continued
| Compd. No. | 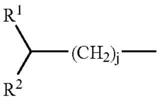 | k | m | n | chirality | $R^3$ | 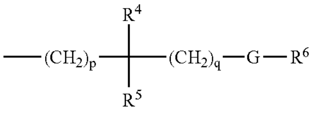 |
|---|---|---|---|---|---|---|---|
| 1539 | 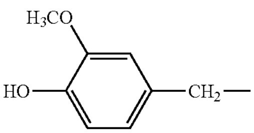 | 1 | 2 | 0 | R | H | 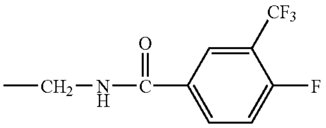 |
| 1540 | 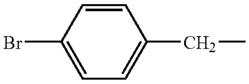 | 1 | 2 | 0 | R | H | 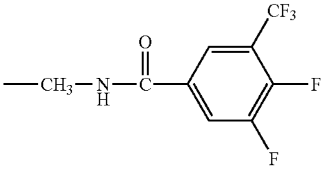 |
TABLE 1.141
| Compd. No. | 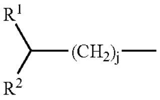 | k | m | n | chirality | $R^3$ | 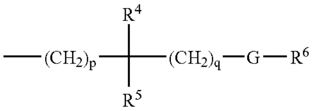 |
|---|---|---|---|---|---|---|---|
| 1541 | 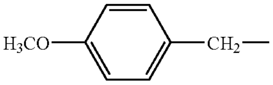 | 1 | 2 | 0 | R | H | 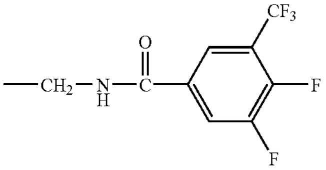 |
| 1542 | 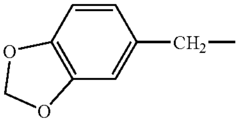 | 1 | 2 | 0 | R | H | 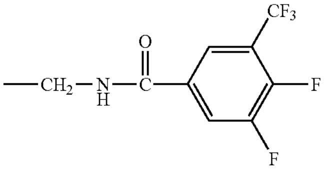 |
| 1543 | 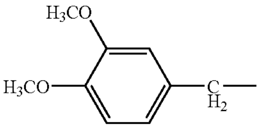 | 1 | 2 | 0 | R | H | 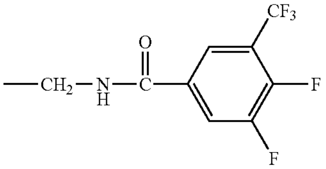 |
| 1544 | 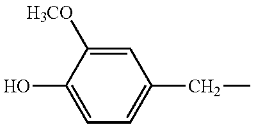 | 1 | 2 | 0 | R | H | 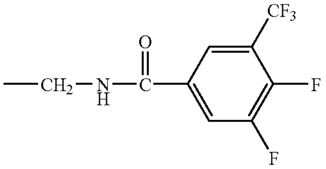 |
| 1545 | 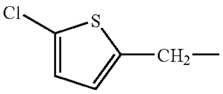 | 1 | 2 | 0 | R | H | 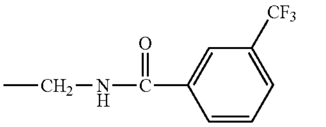 |

TABLE 1.141-continued
| Compd. No. | 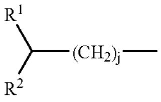 | k | m | n | chirality | $R^3$ | 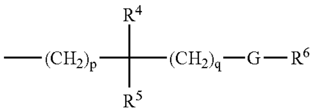 |
|---|---|---|---|---|---|---|---|
| 1546 | 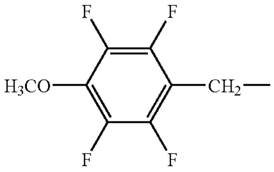 | 1 | 2 | 0 | R | H | 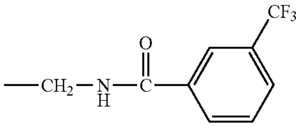 |
| 1547 | 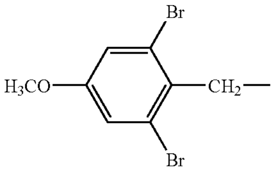 | 1 | 2 | 0 | R | H | 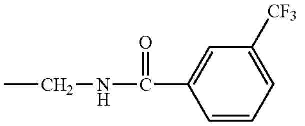 |
| 1548 | 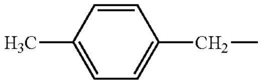 | 1 | 2 | 0 | R | H | 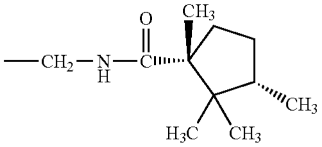 |
| 1549 | 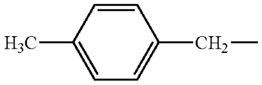 | 1 | 2 | 0 | R | H | 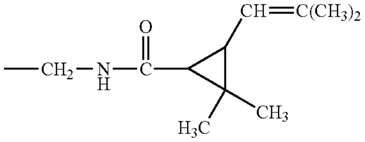 |
| 1550 | 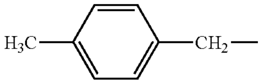 | 1 | 2 | 0 | R | H | 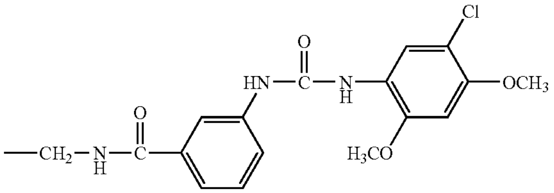 |
| 1551 | 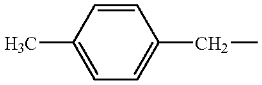 | 1 | 2 | 0 | R | H | 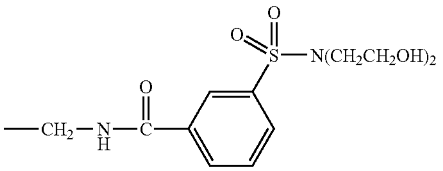 |
TABLE 1.142
| Compd. No. | 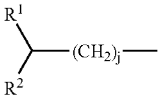 | k | m | n | chirality | $R^3$ | 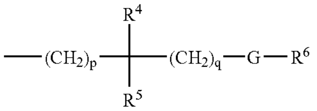 |
|---|---|---|---|---|---|---|---|
| 1552 | 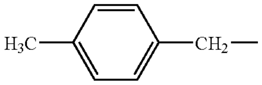 | 1 | 2 | 0 | R | H | 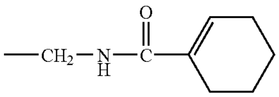 |

TABLE 1.142-continued
| Compd. No. | 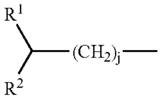 | k | m | n | chirality | $R^3$ | 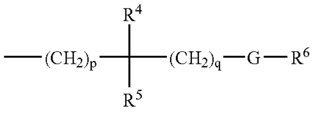 |
|---|---|---|---|---|---|---|---|
| 1553 | 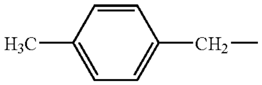 | 1 | 2 | 0 | R | H | 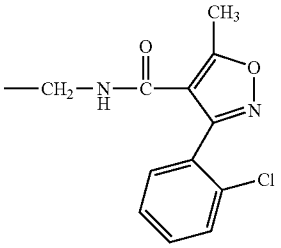 |
| 1554 | 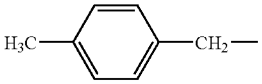 | 1 | 2 | 0 | R | H | 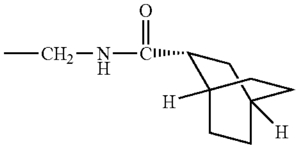 |
| 1555 | 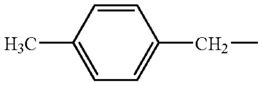 | 1 | 2 | 0 | R | H | 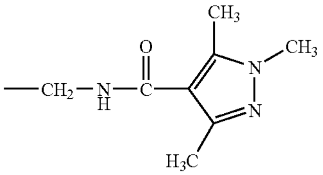 |
| 1556 | 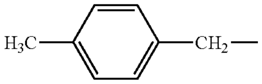 | 1 | 2 | 0 | R | H | 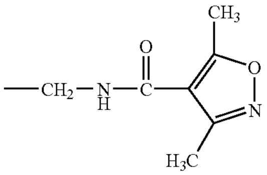 |
| 1557 | 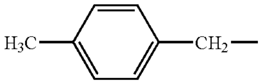 | 1 | 2 | 0 | R | H | 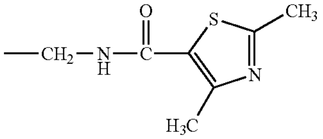 |
| 1558 | 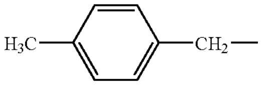 | 1 | 2 | 0 | R | H | 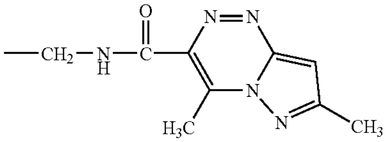 |
| 1559 | 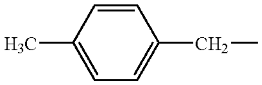 | 1 | 2 | 0 | R | H | 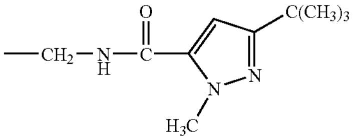 |

TABLE 1.142-continued
| Compd. No. 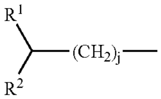 | k | m | n | chirality | $R^3$ | 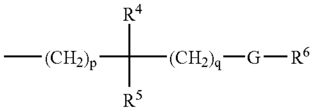 |
|---|---|---|---|---|---|---|
| 1560 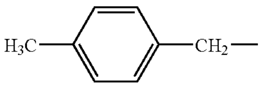 | 1 | 2 | 0 | R | H | 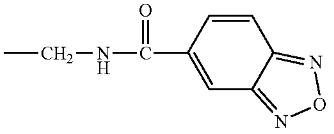 |
| 1561 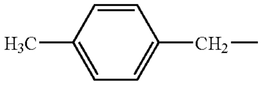 | 1 | 2 | 0 | R | H | 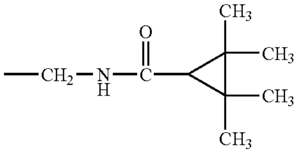 |
| 1562 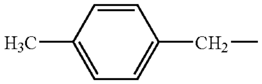 | 1 | 2 | 0 | R | H | 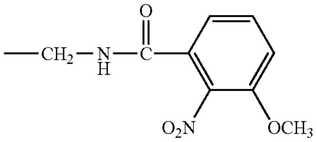 |
TABLE 1.143
| Compd. No. 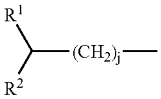 | k | m | n | chirality | $R^3$ | 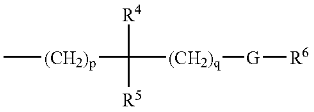 |
|---|---|---|---|---|---|---|
| 1563 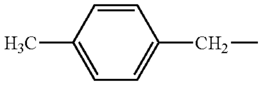 | 1 | 2 | 0 | R | H | 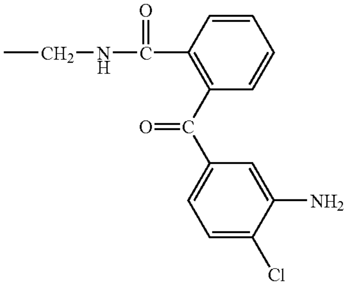 |
| 1564 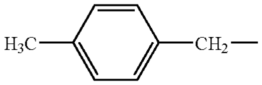 | 1 | 2 | 0 | R | H | 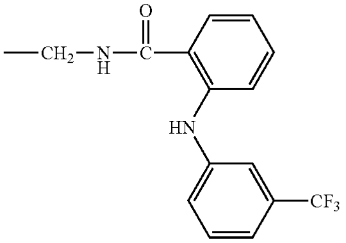 |
| 1565 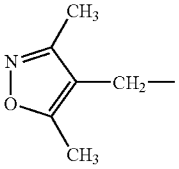 | 1 | 2 | 0 | R | H | 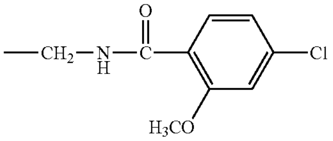 |

TABLE 1.143-continued
| Compd. No. | 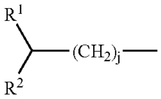 | k | m | n | chirality | $R^3$ | 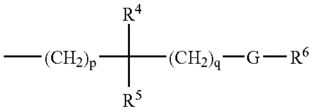 |
|---|---|---|---|---|---|---|---|
| 1566 | 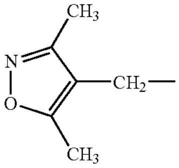 | 1 | 2 | 0 | R | H | 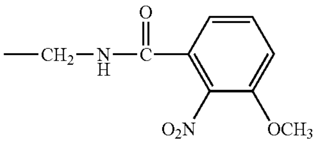 |
| 1567 | 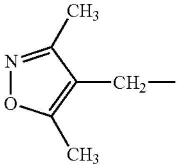 | 1 | 2 | 0 | R | H | 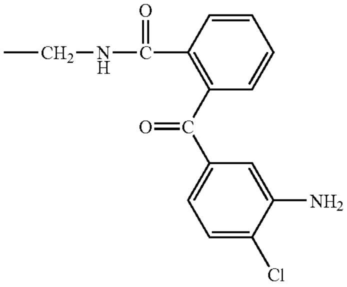 |
| 1568 | 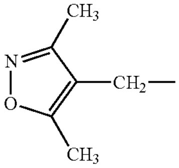 | 1 | 2 | 0 | R | H | 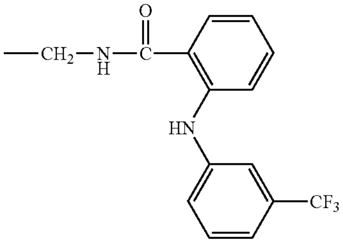 |
| 1569 | 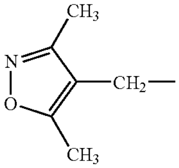 | 1 | 2 | 0 | R | H | 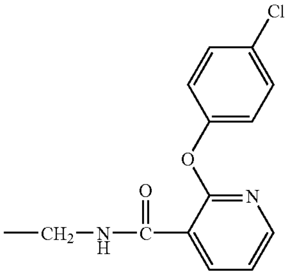 |
| 1570 | 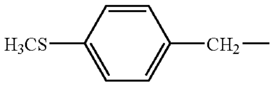 | 2 | 2 | 1 | — | H | 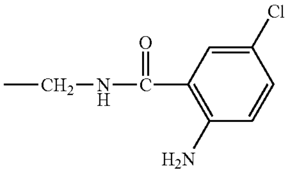 |
| 1571 | 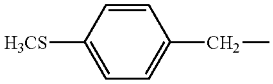 | 2 | 2 | 1 | — | H | 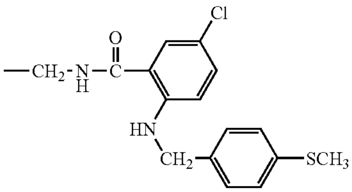 |

TABLE 1.143-continued
| Compd. No. | 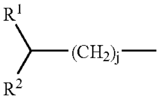 | k | m | n | chirality | $R^3$ | 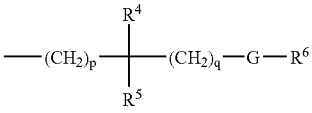 |
|---|---|---|---|---|---|---|---|
| 1572 | 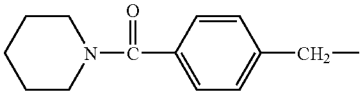 | 2 | 2 | 1 | — | H | 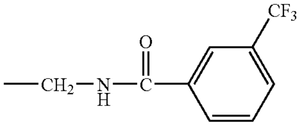 |
| 1573 | 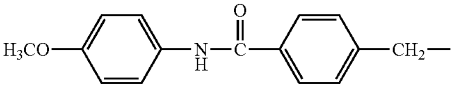 | 2 | 2 | 1 | — | H | 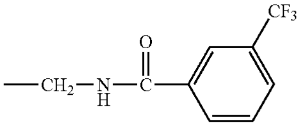 |
TABLE 1.144
| Compd. No. | 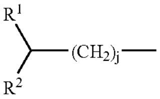 | k | m | n | chirality | $R^3$ | 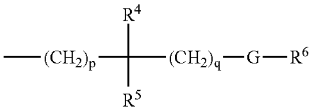 |
|---|---|---|---|---|---|---|---|
| 1574 | 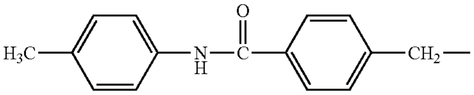 | 2 | 2 | 1 | — | H | 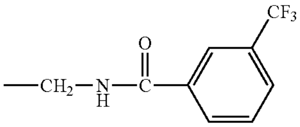 |
| 1575 | 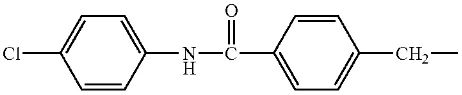 | 2 | 2 | 1 | — | H | 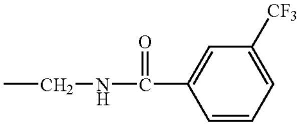 |
| 1576 | 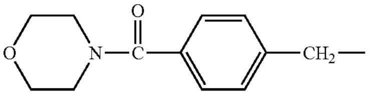 | 2 | 2 | 1 | — | H | 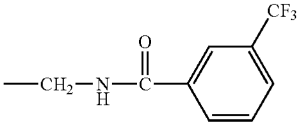 |
| 1577 | 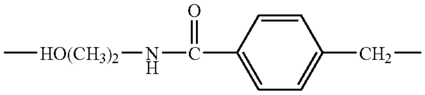 | 2 | 2 | 1 | — | H | 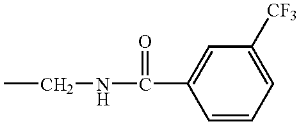 |
| 1578 | 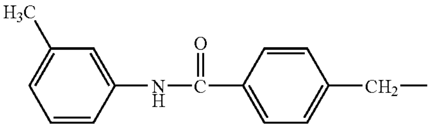 | 2 | 2 | 1 | — | H | 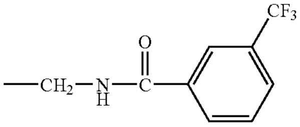 |
| 1579 | 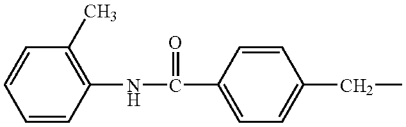 | 2 | 2 | 1 | — | H | 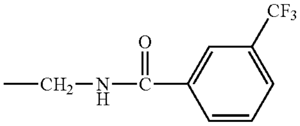 |
| 1580 | 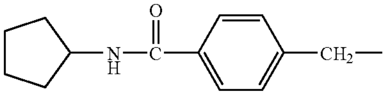 | 2 | 2 | 1 | — | H | 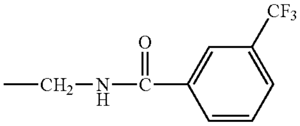 |

TABLE 1.144-continued
| Compd. No. 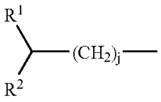 | k | m | n | chirality | $R^3$ | 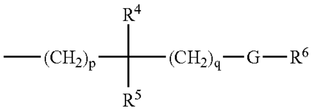 |
|---|---|---|---|---|---|---|
| 1581 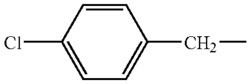 | 2 | 2 | 1 | — | H | 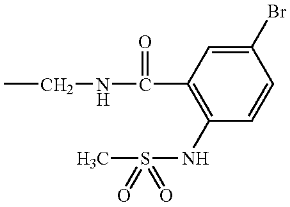 |
| 1582 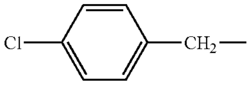 | 2 | 2 | 1 | — | H | 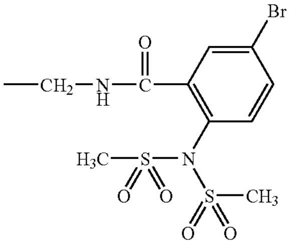 |
| 1583 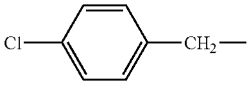 | 1 | 2 | 0 | R | H | 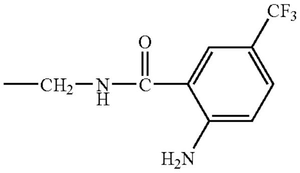 |
| 1584 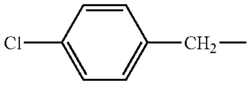 | 1 | 2 | 0 | R | H | 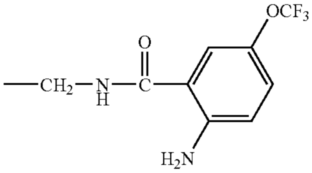 |
TABLE 1.145
| Compd. No. 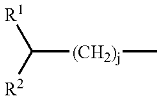 | k | m | n | chirality | $R^3$ | 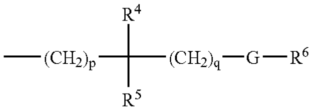 |
|---|---|---|---|---|---|---|
| 1585 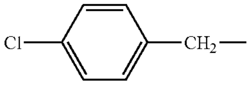 | 1 | 2 | 0 | R | H | 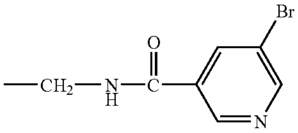 |
| 1586 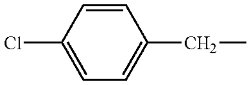 | 1 | 2 | 0 | R | H | 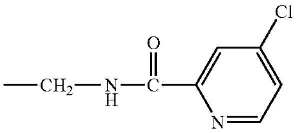 |

TABLE 1.145-continued
| Compd. No. | 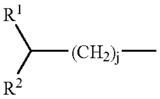 | k | m | n | chirality | $R^3$ | 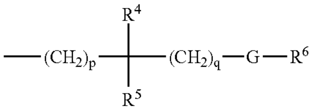 |
|---|---|---|---|---|---|---|---|
| 1587 | 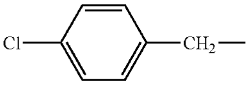 | 1 | 2 | 0 | R | H | 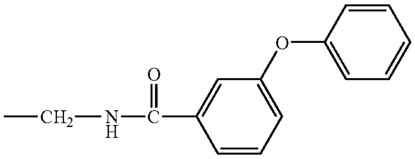 |
| 1588 | 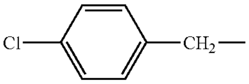 | 1 | 2 | 0 | R | H | 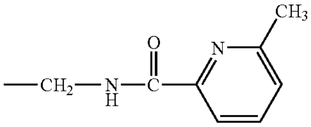 |
| 1589 | 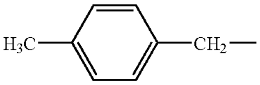 | 1 | 2 | 0 | R | H | 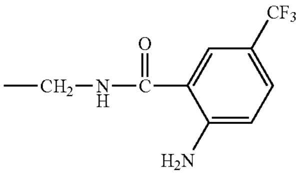 |
| 1590 | 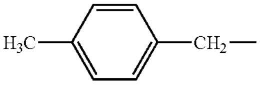 | 1 | 2 | 0 | R | H | 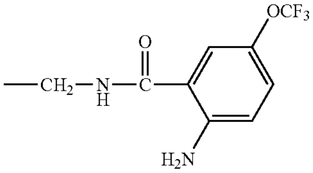 |
| 1591 | 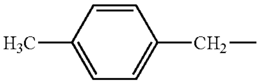 | 1 | 2 | 0 | R | H | 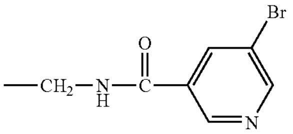 |
| 1592 | 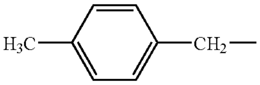 | 1 | 2 | 0 | R | H | 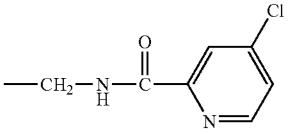 |
| 1593 | 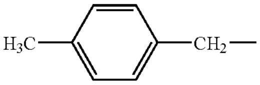 | 1 | 2 | 0 | R | H | 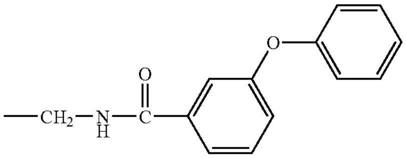 |
| 1594 | 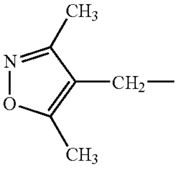 | 1 | 2 | 0 | R | H | 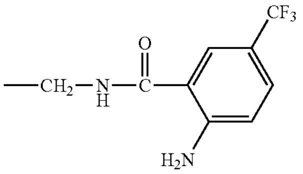 |

TABLE 1.145-continued
| Compd. No. 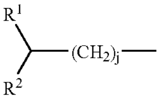 | k | m | n | chirality | $R^3$ | 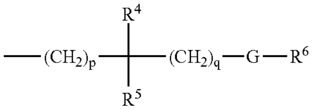 |
|---|---|---|---|---|---|---|
| 1595 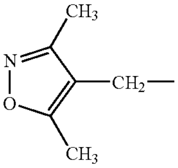 | 1 | 2 | 0 | R | H | 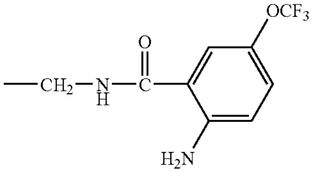 |
TABLE 1.146
| Compd. No. 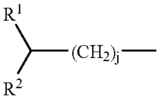 | k | m | n | chirality | $R^3$ | 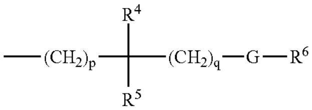 |
|---|---|---|---|---|---|---|
| 1596 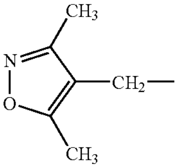 | 1 | 2 | 0 | R | H | 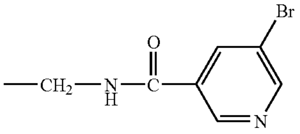 |
| 1597 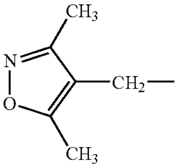 | 1 | 2 | 0 | R | H | 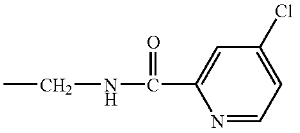 |
| 1598 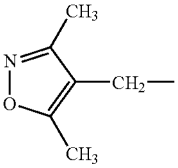 | 1 | 2 | 0 | R | H | 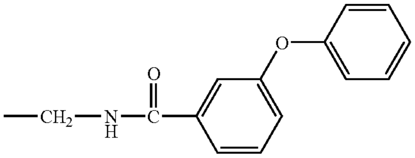 |
| 1599 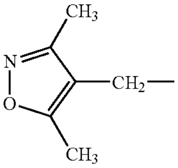 | 1 | 2 | 0 | R | H | 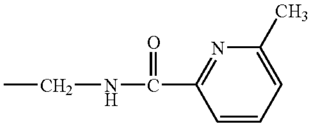 |
| 1600 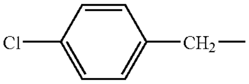 | 2 | 2 | 1 | — | H | 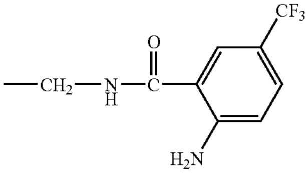 |
| 1601 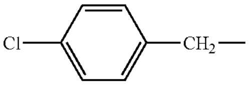 | 2 | 2 | 1 | — | H | 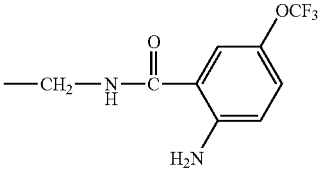 |

TABLE 1.146-continued
| Compd. No. | 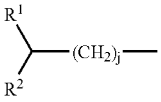 | k | m | n | chirality | $R^3$ | 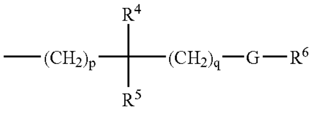 |
|---|---|---|---|---|---|---|---|
| 1602 | 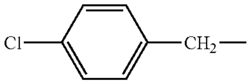 | 2 | 2 | 1 | — | H | 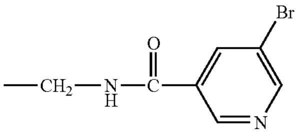 |
| 1603 | 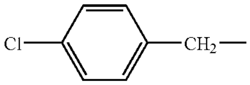 | 2 | 2 | 1 | — | H | 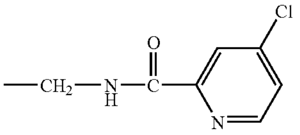 |
| 1604 | 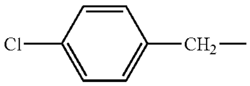 | 2 | 2 | 1 | — | H | 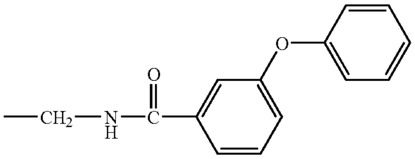 |
| 1605 | 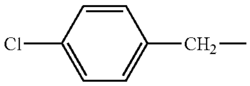 | 2 | 2 | 1 | — | H | 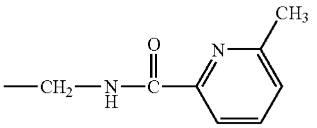 |
| 1606 | 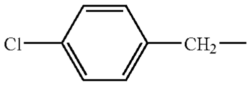 | 1 | 2 | 0 | R | H | 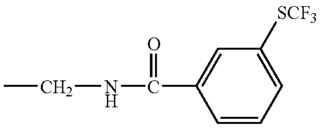 |
TABLE 1.147
| Compd. No. | 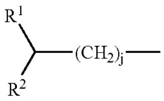 | k | m | n | chirality | $R^3$ | 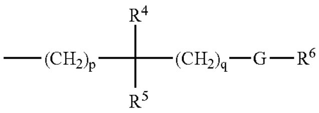 |
|---|---|---|---|---|---|---|---|
| 1607 | 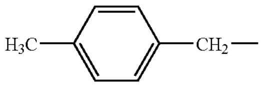 | 1 | 2 | 0 | R | H | 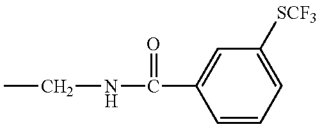 |
| 1608 | 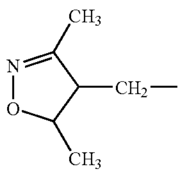 | 1 | 2 | 0 | R | H | 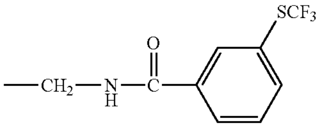 |
| 1609 | 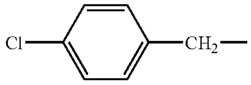 | 2 | 2 | 1 | — | H | 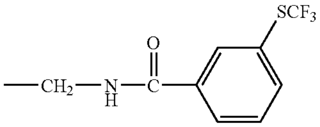 |

TABLE 1.147-continued
| Compd. No. | 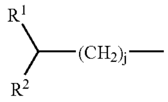 | k | m | n | chirality | $R^3$ | 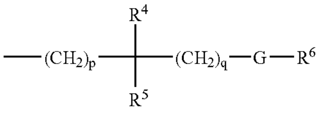 |
|---|---|---|---|---|---|---|---|
| 1610 | 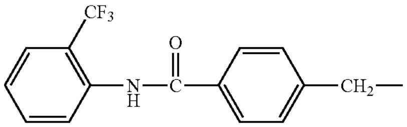 | 2 | 2 | 1 | — | H | 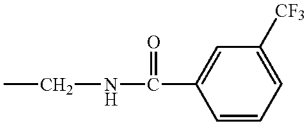 |
| 1611 | 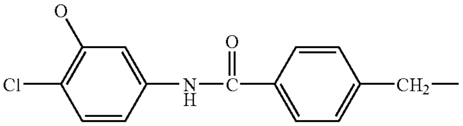 | 2 | 2 | 1 | — | H | 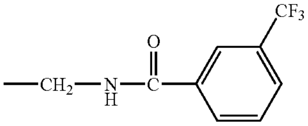 |
| 1612 | 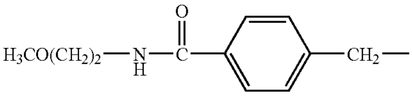 | 2 | 2 | 1 | — | H | 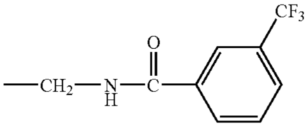 |
| 1613 | 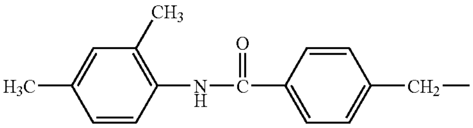 | 2 | 2 | 1 | — | H | 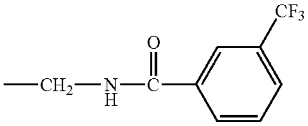 |
| 1614 | 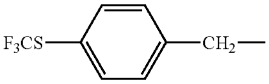 | 1 | 2 | 0 | R | H | 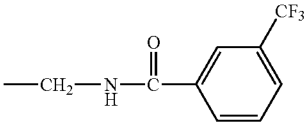 |
| 1615 | 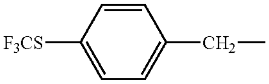 | 2 | 2 | 1 | — | H | 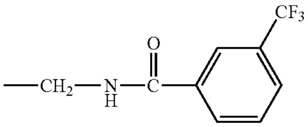 |
| 1616 | 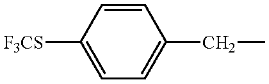 | 2 | 2 | 1 | — | H | 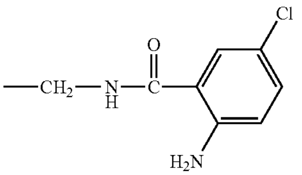 |
| 1617 | 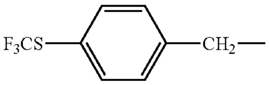 | 2 | 2 | 1 | — | H | 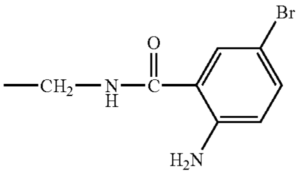 |

TABLE 1.148
| Compd. No. | 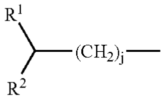 | k | m | n | chirality | $R^3$ | 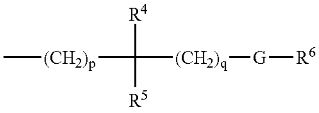 |
|---|---|---|---|---|---|---|---|
| 1618 | 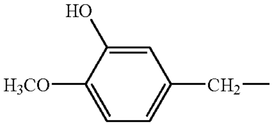 | 1 | 2 | 0 | R | H | 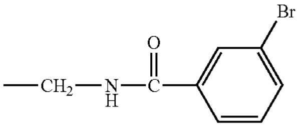 |
| 1619 | 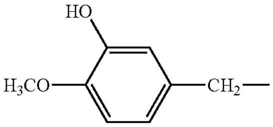 | 1 | 2 | 0 | R | H | 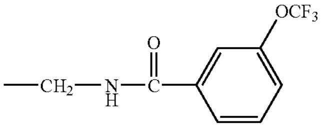 |
| 1620 | 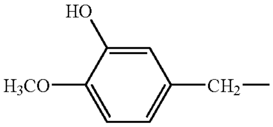 | 1 | 2 | 0 | R | H | 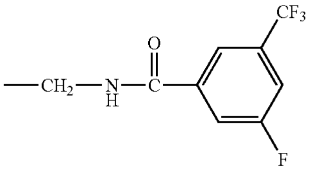 |
| 1621 | 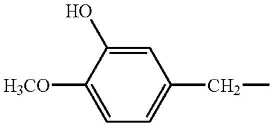 | 1 | 2 | 0 | R | H | 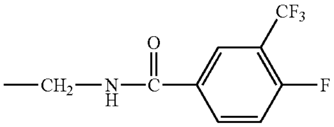 |
| 1622 | 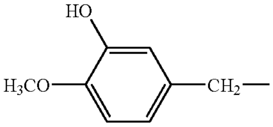 | 1 | 2 | 0 | R | H | 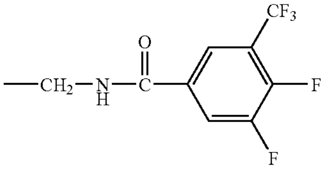 |
| 1623 | 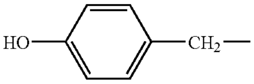 | 1 | 2 | 0 | R | H | 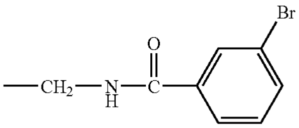 |
| 1624 | 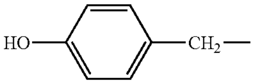 | 1 | 2 | 0 | R | H | 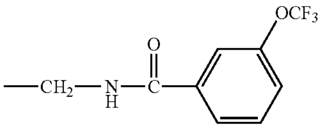 |
| 1625 | 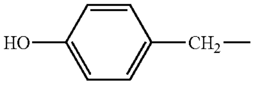 | 1 | 2 | 0 | R | H | 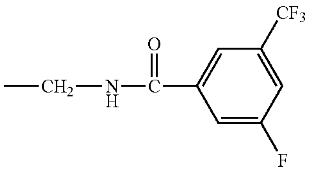 |

TABLE 1.148-continued
| Compd. No. | 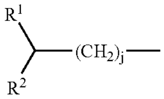 | k | m | n | chirality | $R^3$ | 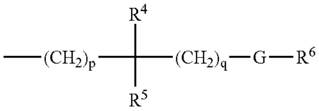 |
|---|---|---|---|---|---|---|---|
| 1626 | 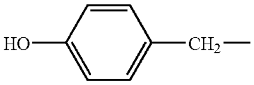 | 1 | 2 | 0 | R | H | 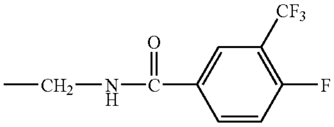 |
| 1627 | 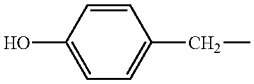 | 1 | 2 | 0 | R | H | 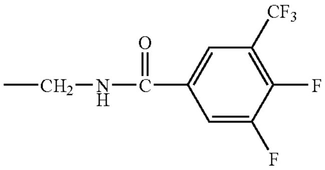 |
| 1628 | 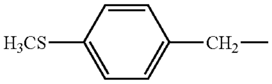 | 1 | 2 | 0 | R | H | 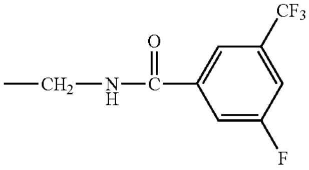 |
TABLE 1.149
| Compd. No. | 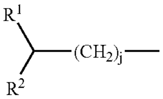 | k | m | n | chirality | $R^3$ | 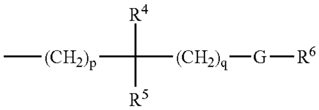 |
|---|---|---|---|---|---|---|---|
| 1629 | 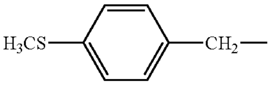 | 1 | 2 | 0 | R | H | 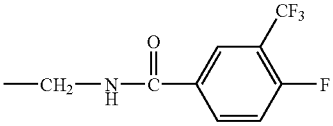 |
| 1630 | 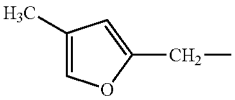 | 1 | 2 | 0 | R | H | 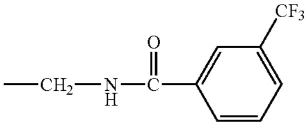 |
| 1631 | 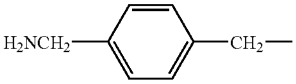 | 1 | 2 | 0 | R | H | 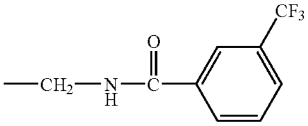 |
| 1632 | 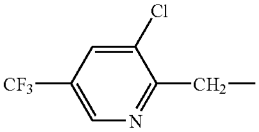 | 1 | 2 | 0 | R | H | 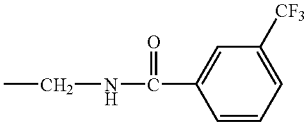 |
| 1633 | 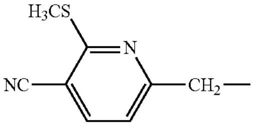 | 1 | 2 | 0 | R | H | 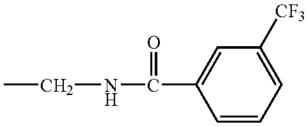 |

TABLE 1.149-continued
| Compd. No. | 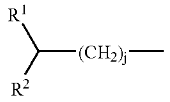 | k | m | n | chirality | $R^3$ | 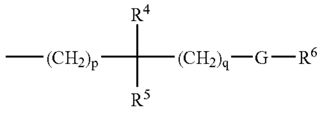 |
|---|---|---|---|---|---|---|---|
| 1634 | 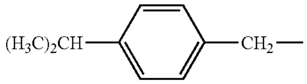 | 1 | 2 | 0 | R | H | 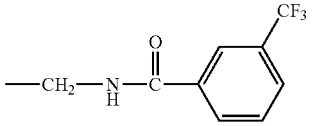 |
| 1635 | 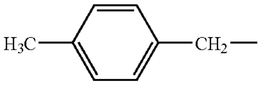 | 1 | 2 | 0 | R | H | 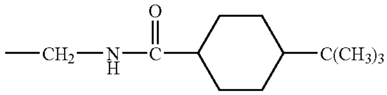 |
| 1636 | 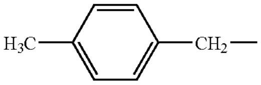 | 1 | 2 | 0 | R | H | 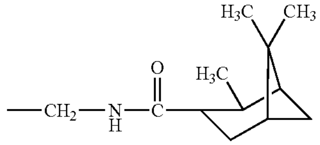 |
| 1637 | 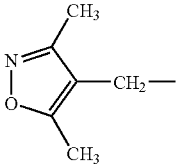 | 1 | 2 | 0 | R | H | 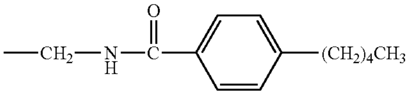 |
| 1638 | 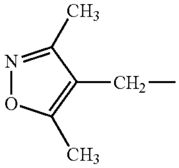 | 1 | 2 | 0 | R | H | 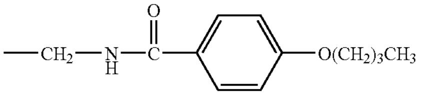 |
| 1639 | 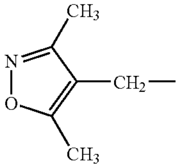 | 1 | 2 | 0 | R | H | 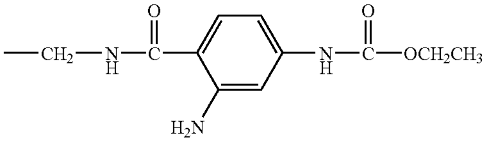 |
TABLE 1.150
| Compd. No. | 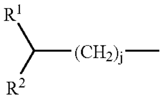 | k | m | n | chirality | $R^3$ | 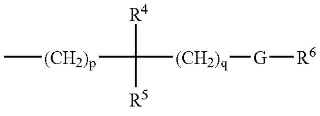 |
|---|---|---|---|---|---|---|---|
| 1640 | 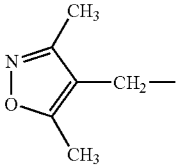 | 1 | 2 | 0 | R | H | 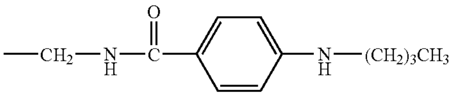 |

TABLE 1.150-continued
| Compd. No. | 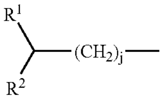 | k | m | n | chirality | $R^3$ | 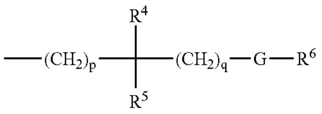 |
|---|---|---|---|---|---|---|---|
| 1641 | 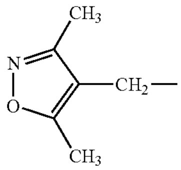 | 1 | 2 | 0 | R | H | 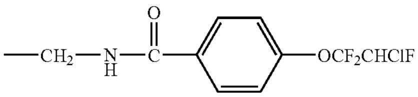 |
| 1642 | 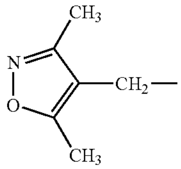 | 1 | 2 | 0 | R | H | 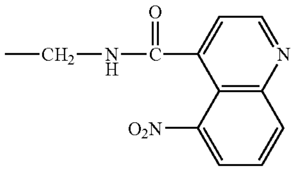 |
| 1643 | 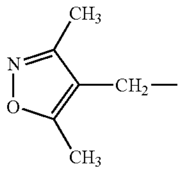 | 1 | 2 | 0 | R | H | 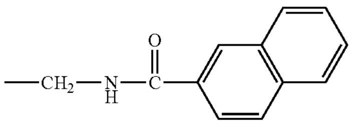 |
| 1644 | 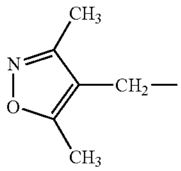 | 1 | 2 | 0 | R | H | 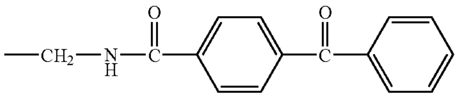 |
| 1645 | 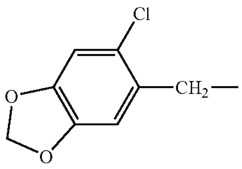 | 1 | 2 | 0 | R | H | 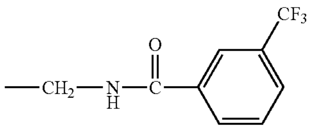 |
| 1646 | 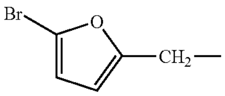 | 1 | 2 | 0 | R | H | 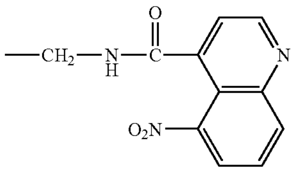 |
| 1647 | 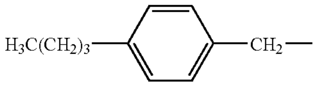 | 2 | 2 | 1 | — | H | 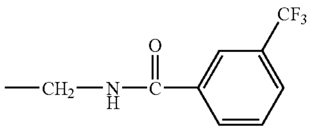 |
| 1648 | 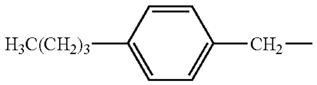 | 1 | 2 | 0 | R | H | 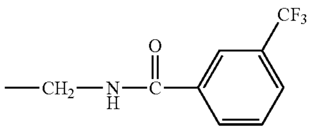 |

TABLE 1.150-continued
| Compd. No. | 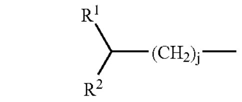 | k | m | n | chirality | $R^3$ | 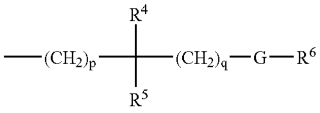 |
|---|---|---|---|---|---|---|---|
| 1649 | 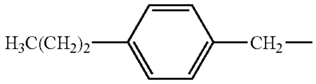 | 2 | 2 | 1 | — | H | 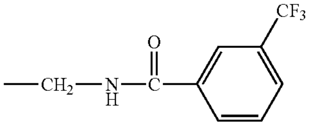 |
| 1650 | 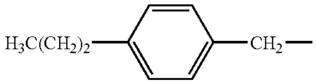 | 1 | 2 | 0 | R | H | 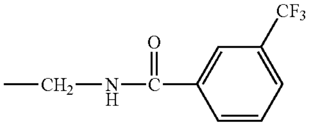 |
TABLE 1.151
| Compd. No. | 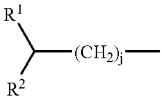 | k | m | n | chirality | $R^3$ | 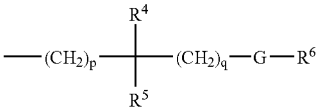 |
|---|---|---|---|---|---|---|---|
| 1651 | 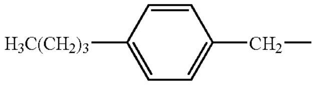 | 2 | 2 | 1 | — | H | 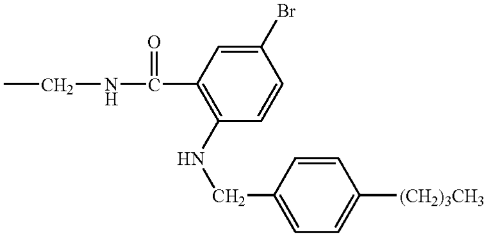 |
| 1652 | 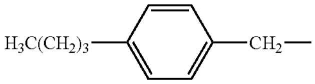 | 2 | 2 | 1 | — | H | 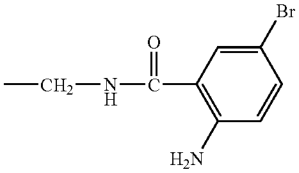 |
| 1653 | 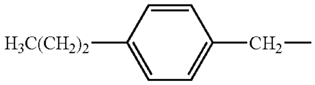 | 2 | 2 | 1 | — | H | 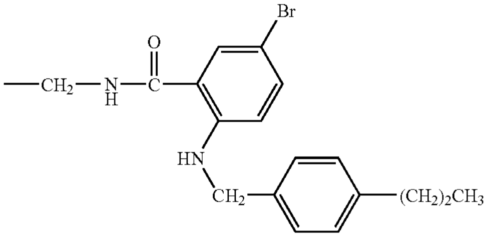 |
| 1654 | 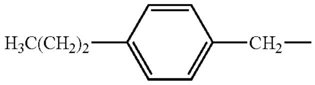 | 2 | 2 | 1 | — | H | 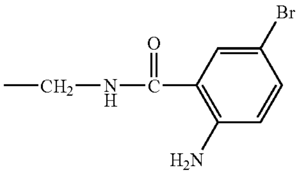 |

TABLE 1.151-continued
| Compd. No. | 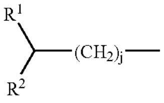 | k | m | n | chirality | $R^3$ | 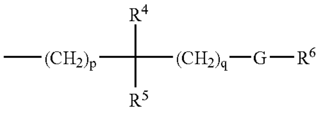 |
|---|---|---|---|---|---|---|---|
| 1655 | 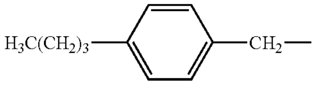 | 2 | 2 | 1 | — | H | 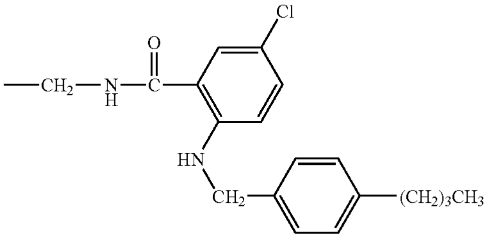 |
| 1656 | 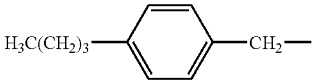 | 2 | 2 | 1 | — | H | 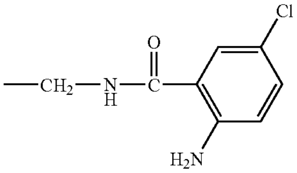 |
| 1657 | 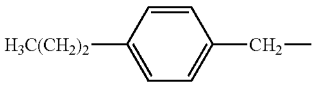 | 2 | 2 | 1 | — | H | 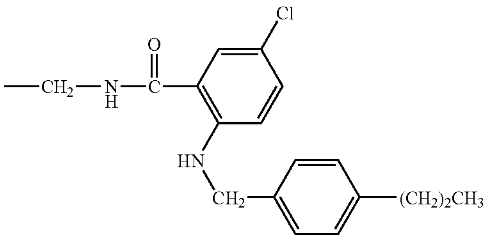 |
| 1658 | 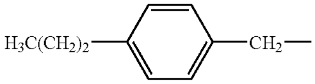 | 2 | 2 | 1 | — | H | 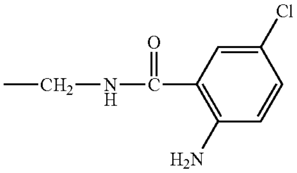 |
| 1659 | 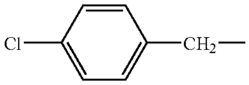 | 2 | 2 | 1 | — | H | 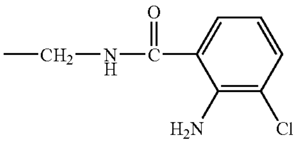 |
| 1660 | 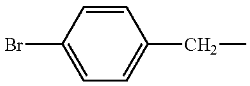 | 1 | 2 | 0 | R | H | 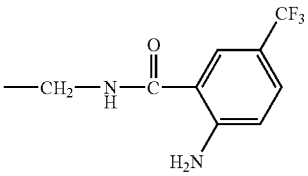 |
| 1661 | 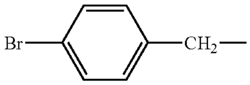 | 1 | 2 | 0 | R | H | 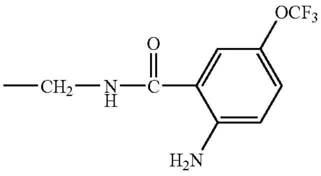 |

TABLE 1.152
| Compd. No. | 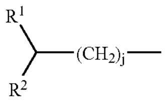 | k | m | n | chirality | $R^3$ | 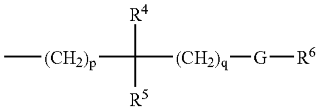 |
|---|---|---|---|---|---|---|---|
| 1662 | 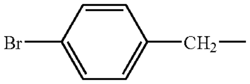 | 1 | 2 | 0 | R | H | 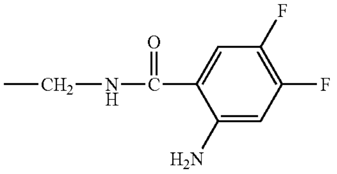 |
| 1663 | 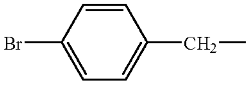 | 1 | 2 | 0 | R | H | 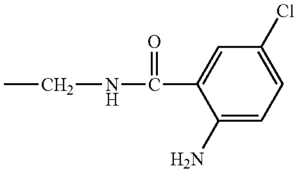 |
| 1664 | 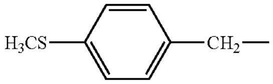 | 2 | 2 | 1 | R | H | 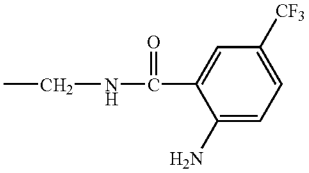 |
| 1665 | 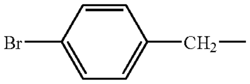 | 2 | 2 | 1 | R | H | 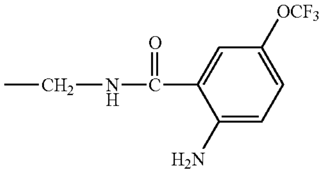 |
| 1666 | 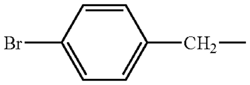 | 2 | 2 | 1 | R | H | 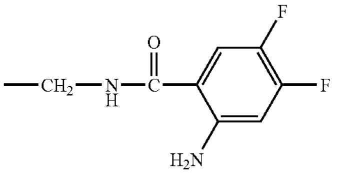 |
| 1667 | 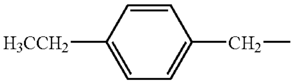 | 2 | 2 | 1 | R | H | 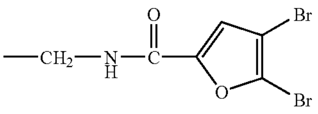 |
| 1668 | 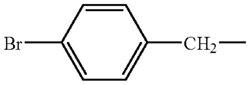 | 2 | 2 | 1 | R | H | 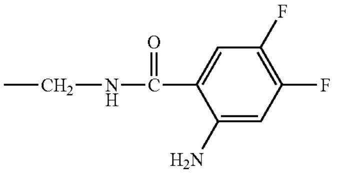 |
| 1669 | 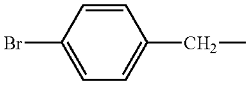 | 2 | 2 | 1 | R | H | 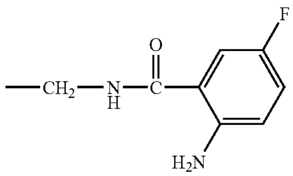 |

TABLE 1.152-continued
| Compd. No. | 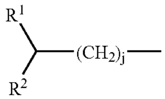 | k | m | n | chirality | $R^3$ | 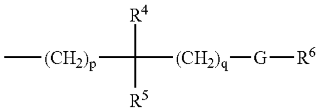 |
|---|---|---|---|---|---|---|---|
| 1670 | 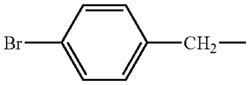 | 2 | 2 | 1 | R | H | 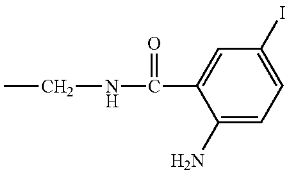 |
| 1671 | 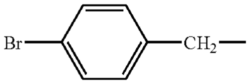 | 2 | 2 | 1 | R | H | 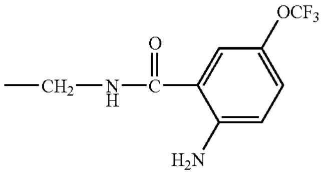 |
| 1672 | 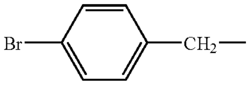 | 2 | 2 | 1 | R | H | 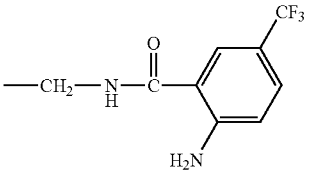 |
TABLE 1.153
| Compd. No. | 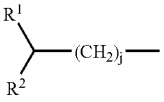 | k | m | n | chirality | $R^3$ | 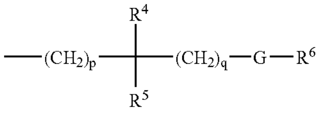 |
|---|---|---|---|---|---|---|---|
| 1673 | 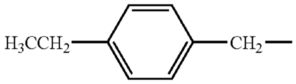 | 2 | 2 | 1 | — | H | 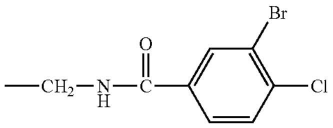 |
| 1674 | 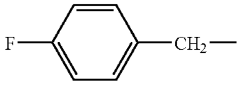 | 2 | 2 | 1 | — | H | 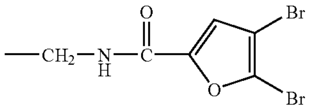 |
| 1675 | 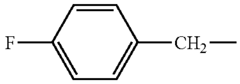 | 2 | 2 | 1 | — | H | 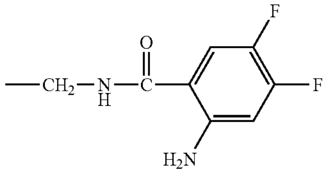 |
| 1676 | 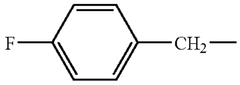 | 2 | 2 | 1 | — | H | 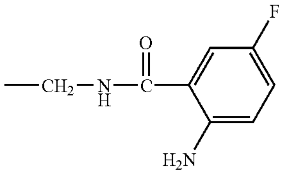 |

TABLE 1.153-continued
| Compd. No. | 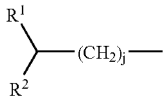 | k | m | n | chirality | $R^3$ | 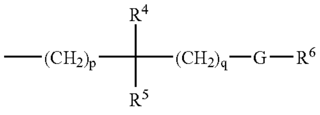 |
|---|---|---|---|---|---|---|---|
| 1677 | 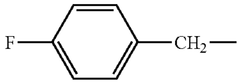 | 2 | 2 | 1 | — | H | 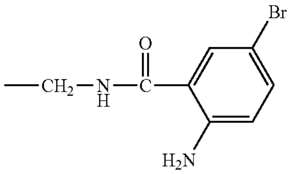 |
| 1678 | 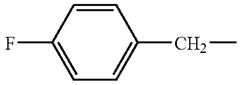 | 2 | 2 | 1 | — | H | 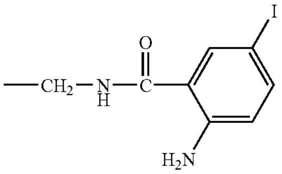 |
| 1679 | 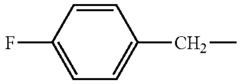 | 2 | 2 | 1 | — | H | 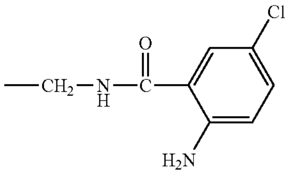 |
| 1680 | 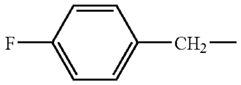 | 2 | 2 | 1 | — | H | 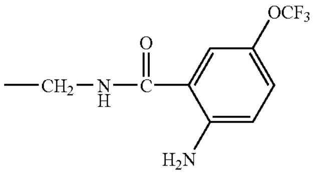 |
| 1681 | 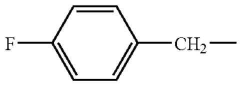 | 2 | 2 | 1 | — | H | 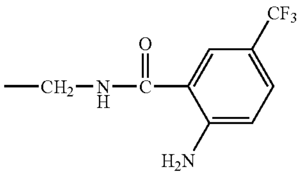 |
| 1682 | 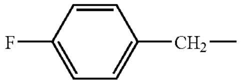 | 2 | 2 | 1 | — | H | 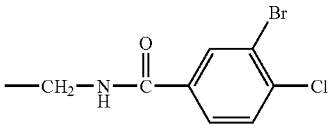 |
| 1683 | 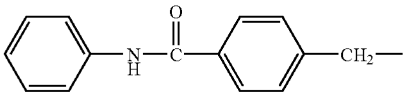 | 2 | 2 | 1 | — | H | 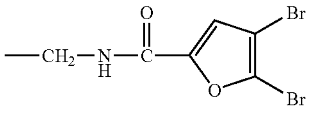 |

TABLE 1.154
| Compd. No. | 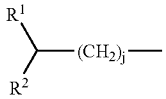 | k | m | n | chirality | $R^3$ | 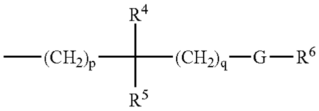 |
|---|---|---|---|---|---|---|---|
| 1684 | 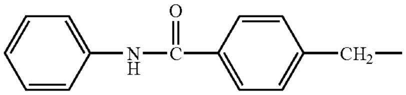 | 2 | 2 | 1 | — | H | 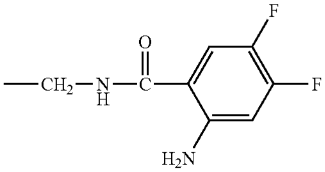 |
| 1685 | 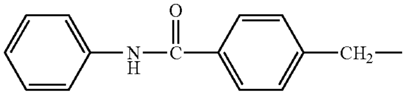 | 2 | 2 | 1 | — | H | 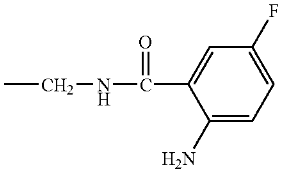 |
| 1686 | 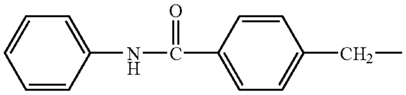 | 2 | 2 | 1 | — | H | 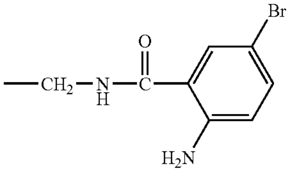 |
| 1687 | 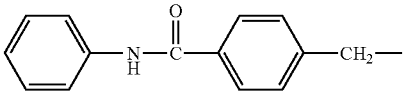 | 2 | 2 | 1 | — | H | 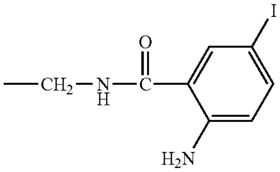 |
| 1688 | 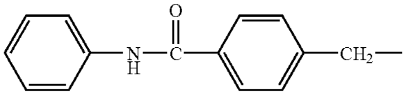 | 2 | 2 | 1 | — | H | 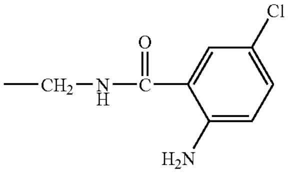 |
| 1689 | 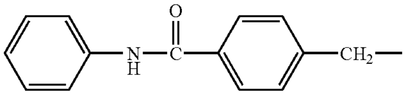 | 2 | 2 | 1 | — | H | 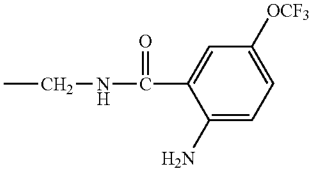 |
| 1690 | 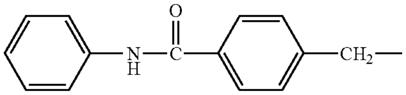 | 2 | 2 | 1 | — | H | 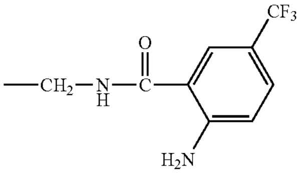 |

TABLE 1.154-continued
| Compd. No. | 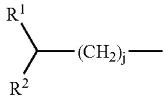 | k | m | n | chirality | $R^3$ | 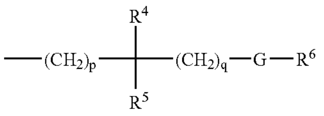 |
|---|---|---|---|---|---|---|---|
| 1691 | 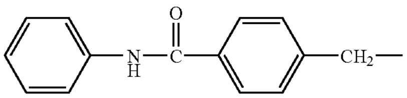 | 2 | 2 | 1 | — | H | 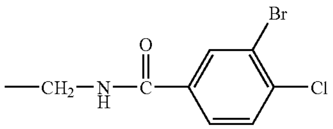 |
| 1692 | 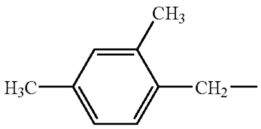 | 1 | 2 | 0 | R | H | 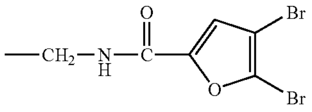 |
| 1693 | 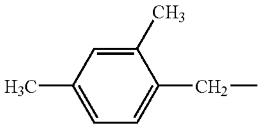 | 1 | 2 | 0 | R | H | 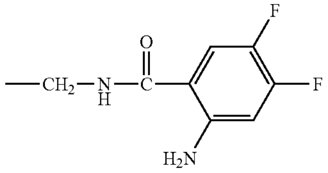 |
| 1694 | 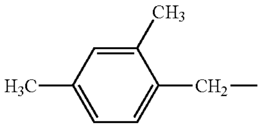 | 1 | 2 | 0 | R | H | 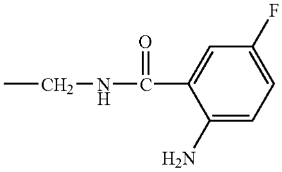 |
TABLE 1.155
| Compd. No. | 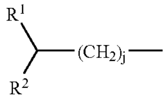 | k | m | n | chirality | $R^3$ | 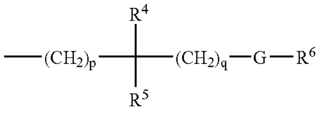 |
|---|---|---|---|---|---|---|---|
| 1695 | 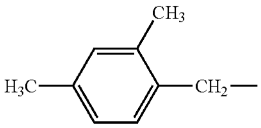 | 2 | 2 | 1 | R | H | 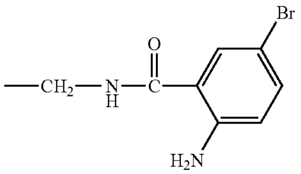 |
| 1696 | 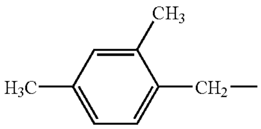 | 2 | 2 | 1 | R | H | 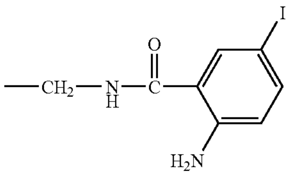 |
| 1697 | 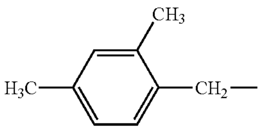 | 2 | 2 | 1 | R | H | 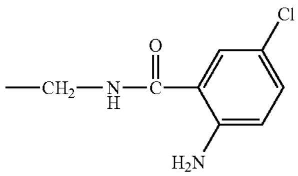 |

TABLE 1.155-continued
| Compd. No. | 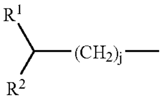 | k | m | n | chirality | $R^3$ | 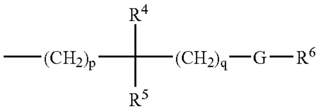 |
|---|---|---|---|---|---|---|---|
| 1698 | 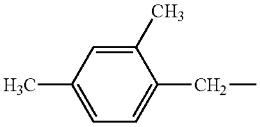 | 2 | 2 | 1 | R | H | 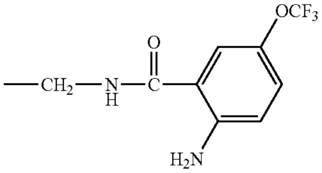 |
| 1699 | 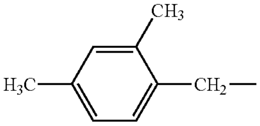 | 2 | 2 | 1 | R | H | 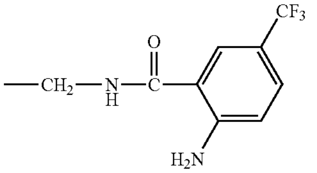 |
| 1700 | 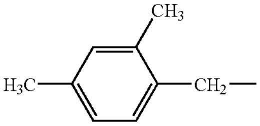 | 2 | 2 | 1 | R | H | 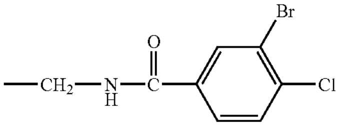 |
| 1701 | 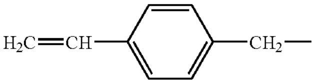 | 2 | 2 | 1 | R | H | 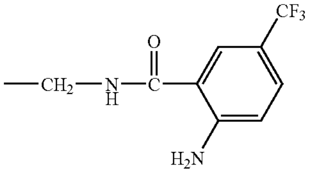 |
| 1702 | 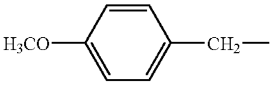 | 2 | 2 | 1 | R | H | 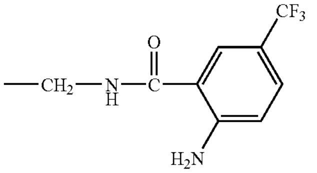 |
| 1703 | 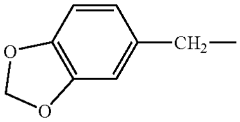 | 1 | 2 | 0 | R | H | 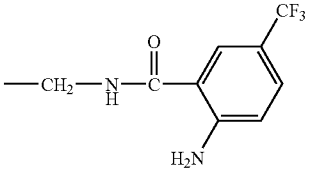 |
| 1704 | 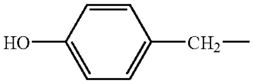 | 1 | 2 | 0 | R | H | 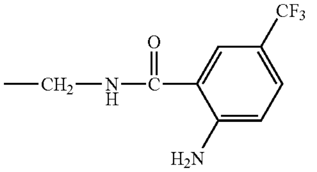 |
| 1705 | 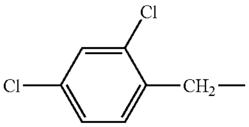 | 1 | 2 | 0 | R | H | 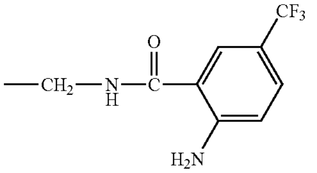 |

TABLE 1.156
| Compd. No. | 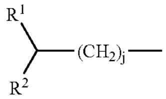 | k | m | n | chirality | $R^3$ | 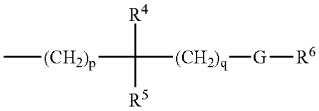 |
|---|---|---|---|---|---|---|---|
| 1706 | 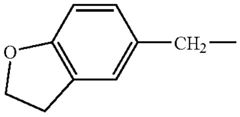 | 1 | 2 | 0 | R | H | 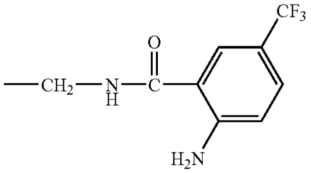 |
| 1707 | 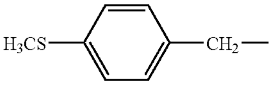 | 1 | 2 | 0 | R | H | 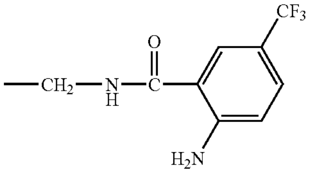 |
| 1708 | 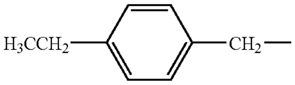 | 1 | 2 | 0 | R | H | 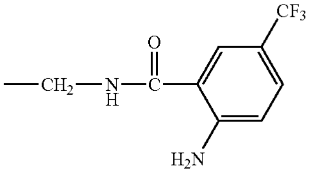 |
| 1709 | 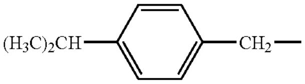 | 1 | 2 | 0 | R | H | 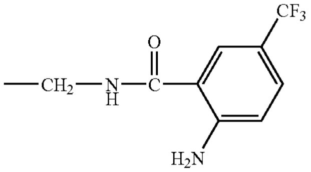 |
| 1710 | 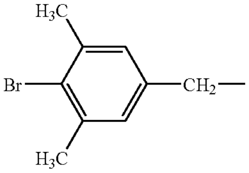 | 1 | 2 | 0 | R | H | 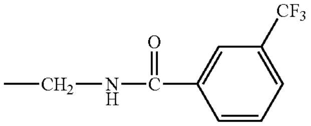 |
| 1711 | 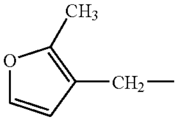 | 1 | 2 | 0 | R | H | 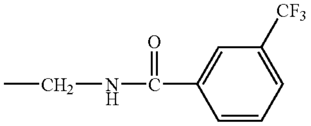 |
| 1712 | 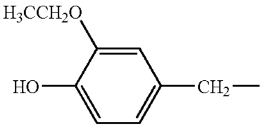 | 1 | 2 | 0 | R | H | 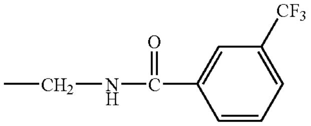 |
| 1713 | 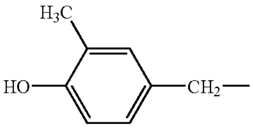 | 1 | 2 | 0 | R | H | 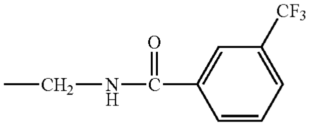 |

TABLE 1.156-continued
| Compd. No. | 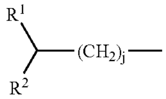 | k | m | n | chirality | $R^3$ | 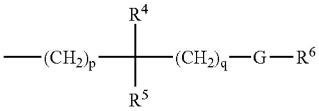 |
|---|---|---|---|---|---|---|---|
| 1714 | 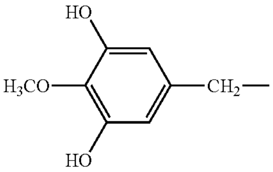 | 1 | 2 | 0 | R | H | 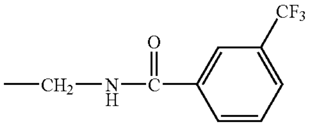 |
| 1715 | 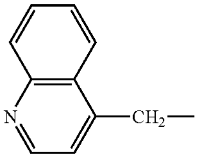 | 1 | 2 | 0 | R | H | 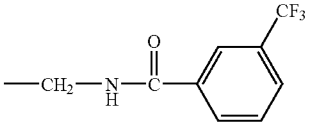 |
| 1716 | 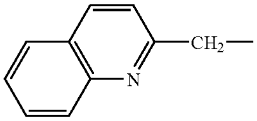 | 1 | 2 | 0 | R | H | 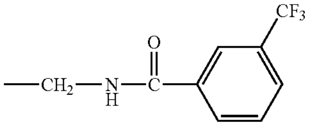 |
TABLE 1.157
| Compd. No. | 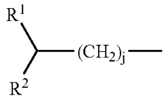 | k | m | n | chirality | $R^3$ | 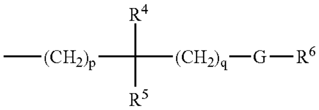 |
|---|---|---|---|---|---|---|---|
| 1717 | 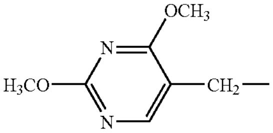 | 1 | 2 | 0 | R | H | 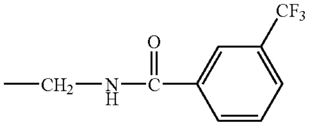 |
| 1718 | 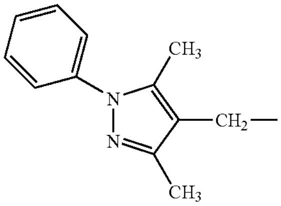 | 1 | 2 | 0 | R | H | 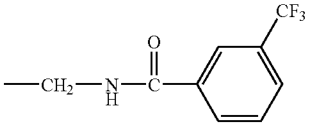 |
| 1719 | 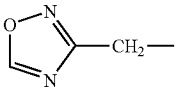 | 1 | 2 | 0 | R | H | 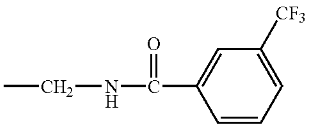 |
| 1720 | 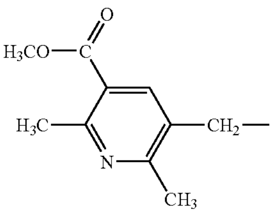 | 1 | 2 | 0 | R | H | 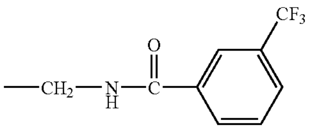 |

TABLE 1.157-continued
| Compd. No. | 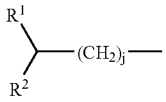 | k | m | n | chirality | $R^3$ | 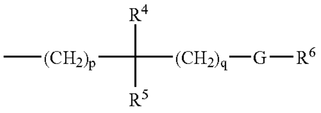 |
|---|---|---|---|---|---|---|---|
| 1721 | 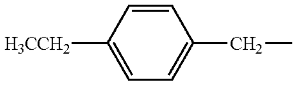 | 1 | 2 | 0 | R | H | 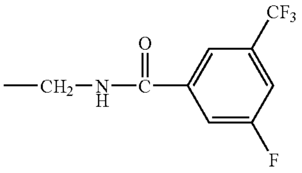 |
| 1722 | 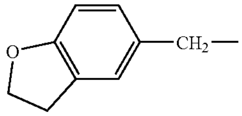 | 1 | 2 | 0 | R | H | 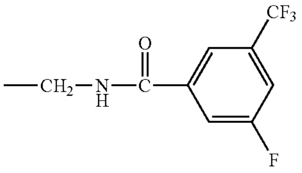 |
| 1723 | 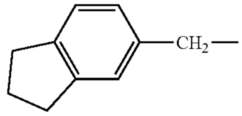 | 1 | 2 | 0 | R | H | 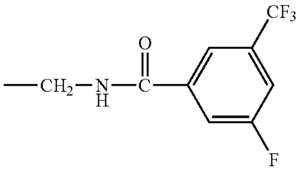 |
| 1724 | 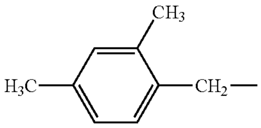 | 1 | 2 | 0 | R | H | 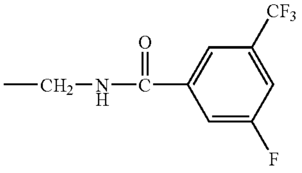 |
| 1725 | 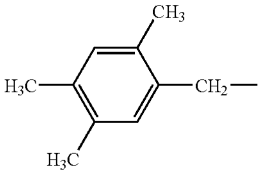 | 1 | 2 | 0 | R | H | 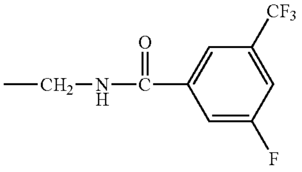 |
| 1726 | 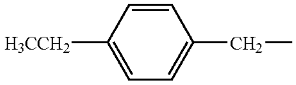 | 1 | 2 | 0 | R | H | 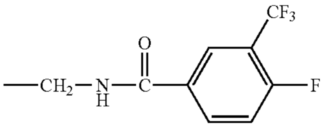 |
| 1727 | 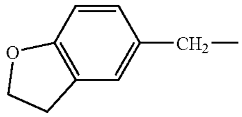 | 1 | 2 | 0 | R | H | 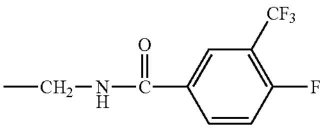 |

TABLE 1.158
| Compd. No. | 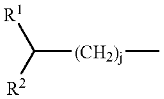 | k | m | n | chirality | $R^3$ | 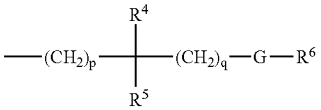 |
|---|---|---|---|---|---|---|---|
| 1728 | 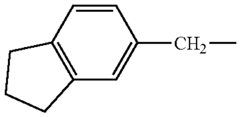 | 1 | 2 | 0 | R | H | 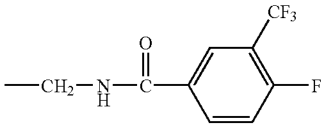 |
| 1729 | 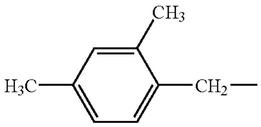 | 1 | 2 | 0 | R | H | 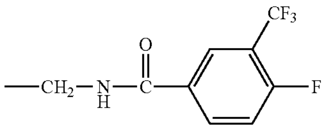 |
| 1730 | 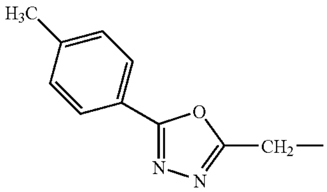 | 1 | 2 | 0 | R | H | 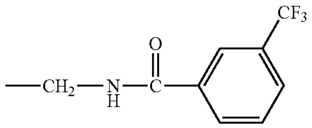 |
| 1731 | 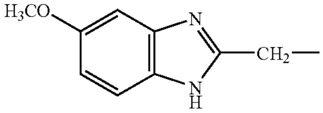 | 1 | 2 | 0 | R | H | 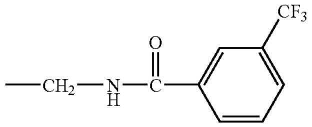 |
| 1732 | 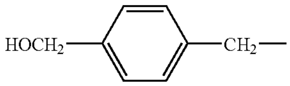 | 1 | 2 | 0 | R | H | 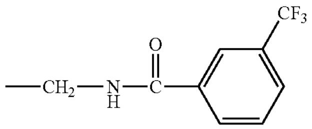 |
| 1733 | 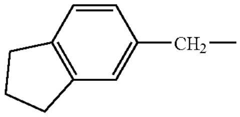 | 1 | 2 | 0 | R | H | 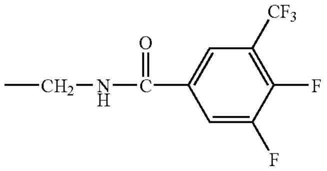 |
| 1734 | 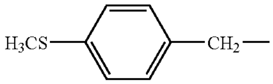 | 1 | 2 | 0 | R | H | 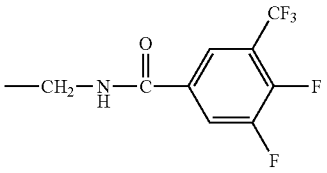 |
| 1735 | 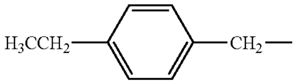 | 1 | 2 | 0 | R | H | 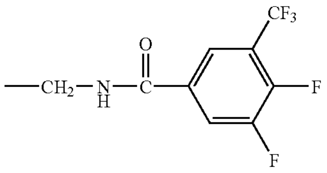 |
| 1736 | 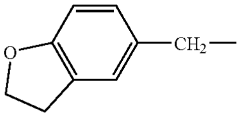 | 1 | 2 | 0 | R | H | 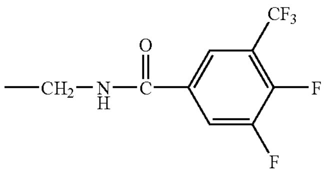 |

TABLE 1.158-continued
| Compd. No. | 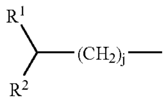 | k | m | n | chirality | $R^3$ | 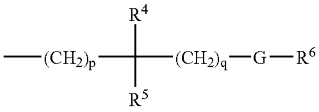 |
|---|---|---|---|---|---|---|---|
| 1737 | 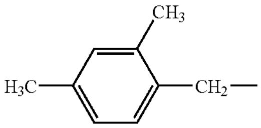 | 1 | 2 | 0 | R | H | 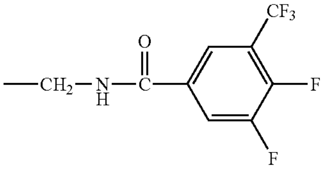 |
| 1738 | 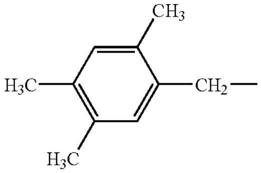 | 1 | 2 | 0 | R | H | 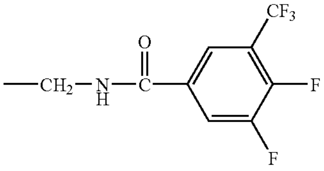 |
TABLE 1.159
| Compd. No. | 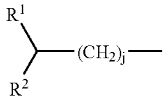 | k | m | n | chirality | $R^3$ | 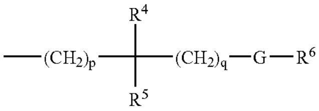 |
|---|---|---|---|---|---|---|---|
| 1739 | 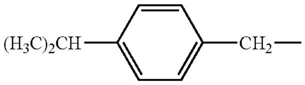 | 1 | 2 | 0 | R | H | 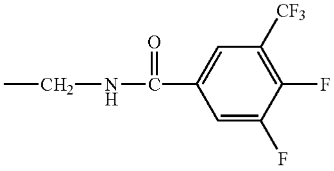 |
| 1740 | 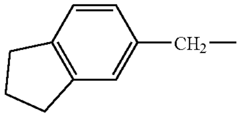 | 1 | 2 | 0 | R | H | 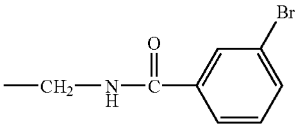 |
| 1741 | 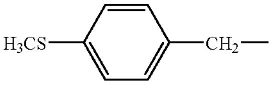 | 1 | 2 | 0 | R | H | 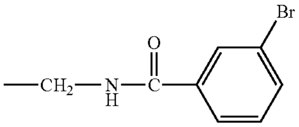 |
| 1742 | 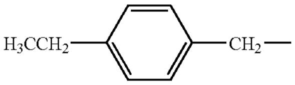 | 1 | 2 | 0 | R | H | 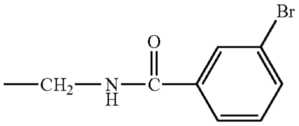 |
| 1743 | 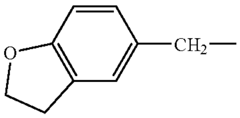 | 1 | 2 | 0 | R | H | 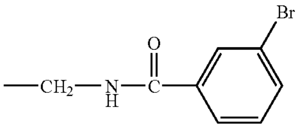 |
| 1744 | 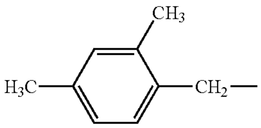 | 1 | 2 | 0 | R | H | 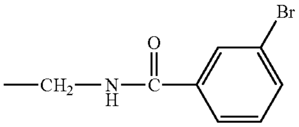 |

TABLE 1.159-continued
| Compd. No. | 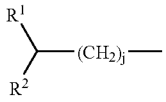 | k | m | n | chirality | R3 | 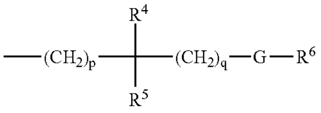 |
|---|---|---|---|---|---|---|---|
| 1745 | 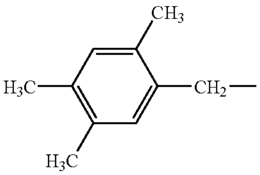 | 1 | 2 | 0 | R | H | 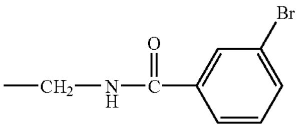 |
| 1746 | 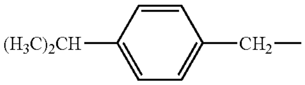 | 1 | 2 | 0 | R | H | 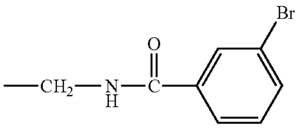 |
| 1747 | 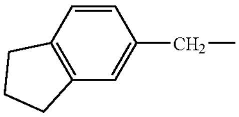 | 1 | 2 | 0 | R | H | 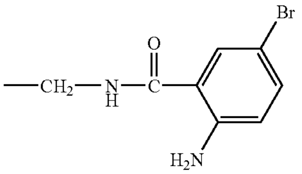 |
| 1748 | 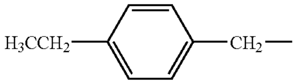 | 1 | 2 | 0 | R | H | 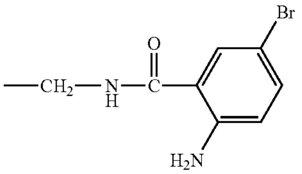 |
| 1749 | 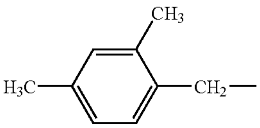 | 1 | 2 | 0 | R | H | 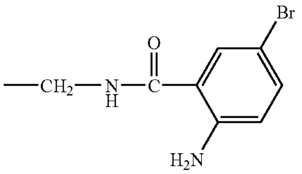 |
TABLE 1.160
| Compd. No. | 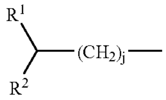 | k | m | n | chirality | R3 | 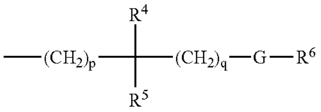 |
|---|---|---|---|---|---|---|---|
| 1750 | 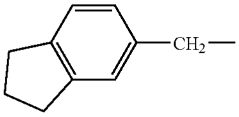 | 1 | 2 | 0 | R | H | 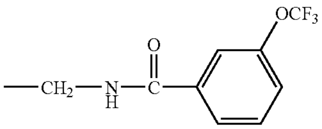 |
| 1751 | 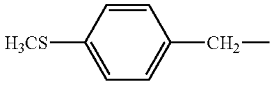 | 1 | 2 | 0 | R | H | 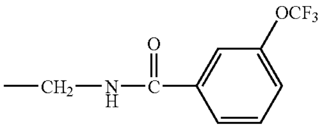 |

TABLE 1.160-continued
| Compd. No. | 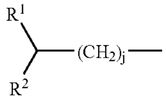 | k | m | n | chirality | $R^3$ | 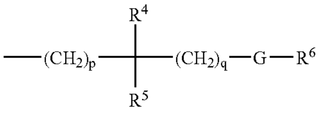 |
|---|---|---|---|---|---|---|---|
| 1752 | 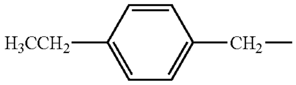 | 1 | 2 | 0 | R | H | 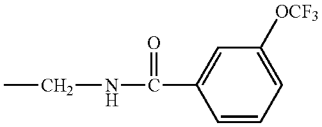 |
| 1753 | 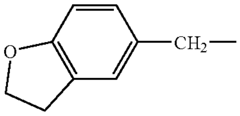 | 1 | 2 | 0 | R | H | 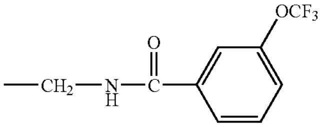 |
| 1754 | 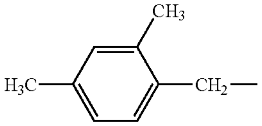 | 1 | 2 | 0 | R | H | 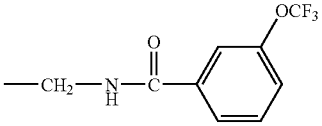 |
| 1755 | 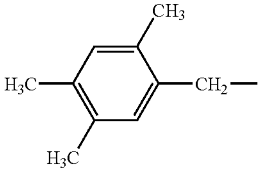 | 1 | 2 | 0 | R | H | 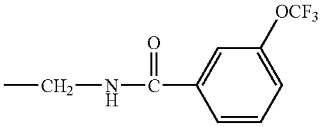 |
| 1756 | 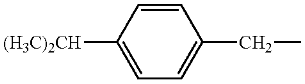 | 1 | 2 | 0 | R | H | 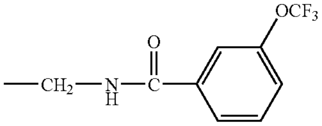 |
| 1757 | 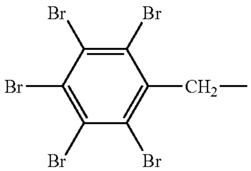 | 1 | 2 | 0 | R | H | 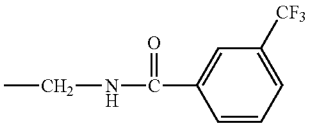 |
| 1758 | 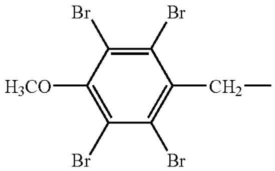 | 1 | 2 | 0 | R | H | 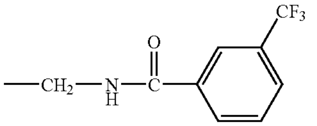 |
| 1759 | 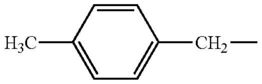 | 1 | 2 | 0 | R | H | 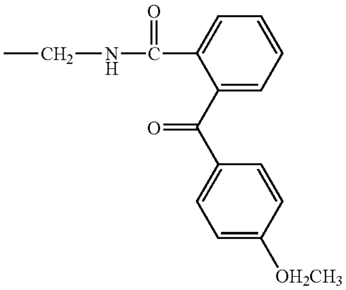 |

TABLE 1.160-continued
| Compd. No. | 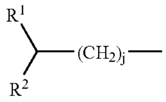 | k | m | n | chirality | $R^3$ | 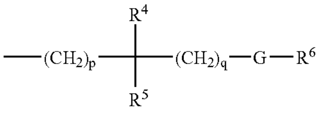 |
|---|---|---|---|---|---|---|---|
| 1760 | 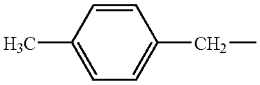 | 1 | 2 | 0 | R | H | 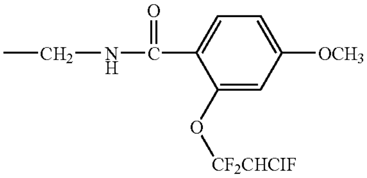 |
TABLE 1.161
| Compd. No. | 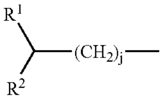 | k | m | n | chirality | $R^3$ | 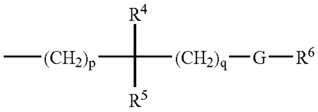 |
|---|---|---|---|---|---|---|---|
| 1761 | 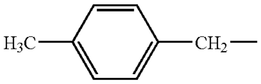 | 1 | 2 | 0 | R | H | 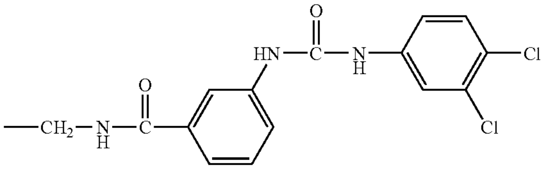 |
| 1762 | 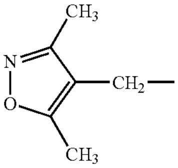 | 1 | 2 | 0 | R | H | 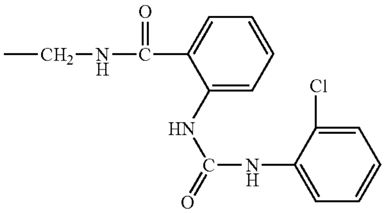 |
| 1763 | 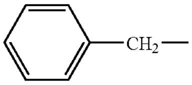 | 1 | 2 | 0 | R | H | 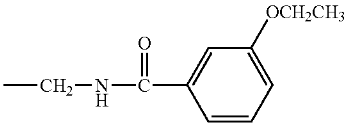 |
| 1764 | 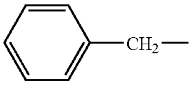 | 1 | 2 | 0 | R | H | 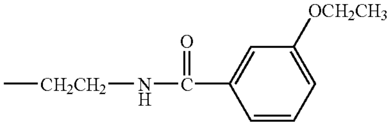 |
| 1765 | 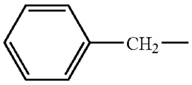 | 1 | 2 | 0 | R | H | 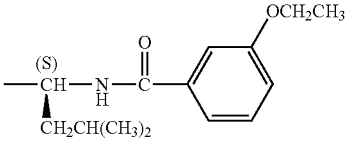 |
| 1766 | 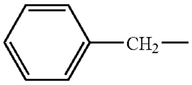 | 1 | 2 | 0 | R | H | 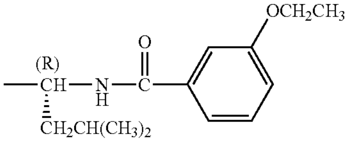 |

TABLE 1.161-continued
| Compd. No. | 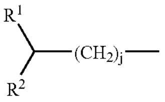 | k | m | n | chirality | $R^3$ | 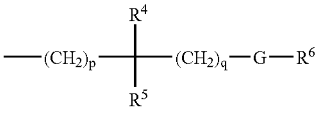 |
|---|---|---|---|---|---|---|---|
| 1767 | 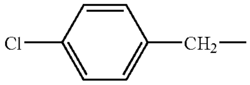 | 1 | 2 | 0 | R | H | 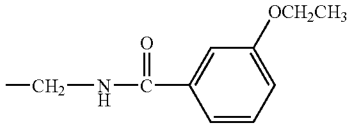 |
| 1768 | 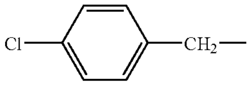 | 1 | 2 | 0 | R | H | 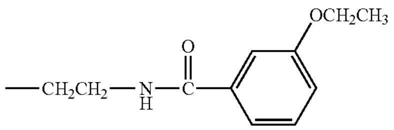 |
| 1769 | 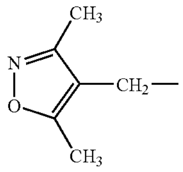 | 1 | 2 | 0 | R | H | 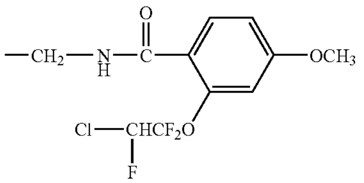 |
| 1770 | 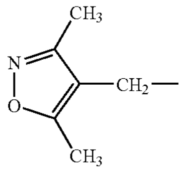 | 1 | 2 | 0 | R | H | 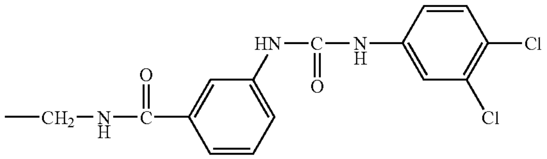 |
| 1771 | 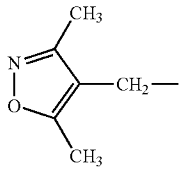 | 1 | 2 | 0 | R | H | 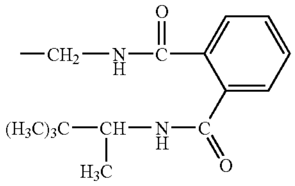 |
TABLE 1.162
| Compd. No. | 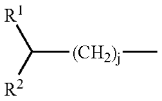 | k | m | n | chirality | $R^3$ | 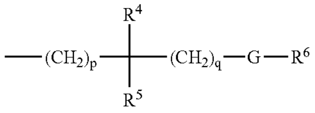 |
|---|---|---|---|---|---|---|---|
| 1772 | 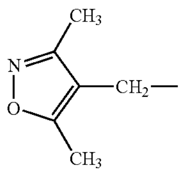 | 1 | 2 | 0 | R | H | 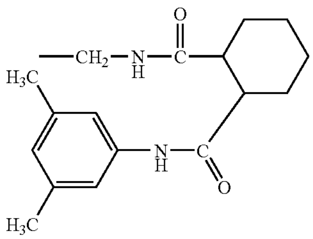 |

TABLE 1.162-continued
| Compd. No. | 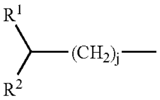 | k | m | n | chirality | $R^3$ | 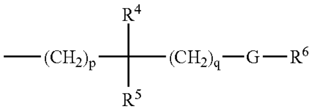 |
|---|---|---|---|---|---|---|---|
| 1773 | 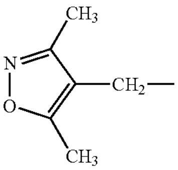 | 1 | 2 | 0 | R | H | 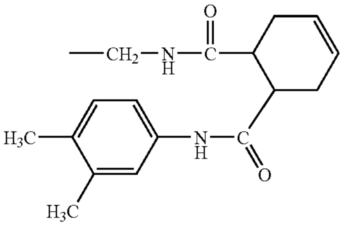 |
| 1774 | 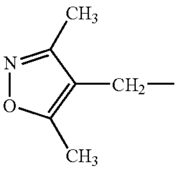 | 1 | 2 | 0 | R | H | 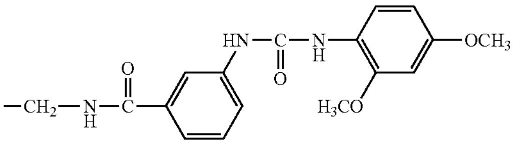 |
| 1775 | 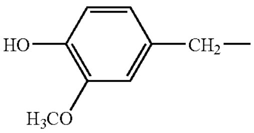 | 1 | 2 | 0 | R | H | 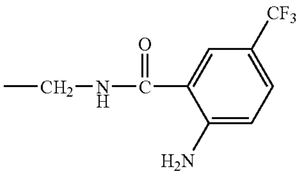 |
| 1776 | 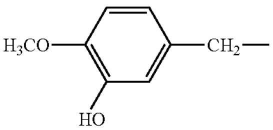 | 1 | 2 | 0 | R | H | 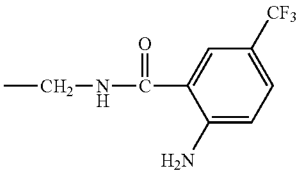 |
| 1777 | 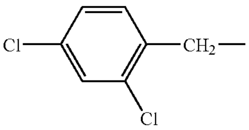 | 2 | 2 | 1 | — | H | 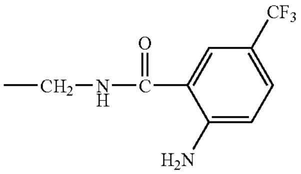 |
| 1778 | 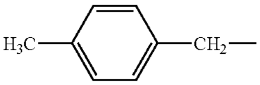 | 2 | 2 | 1 | — | H | 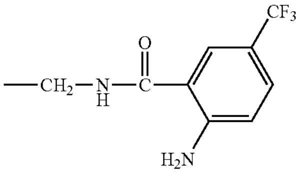 |
| 1779 | 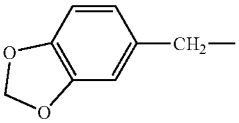 | 2 | 2 | 1 | — | H | 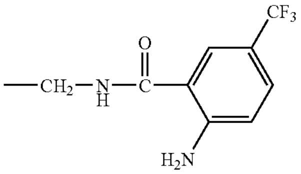 |

TABLE 1.162-continued
| Compd. No. | 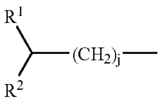 | k | m | n | chirality | $R^3$ | 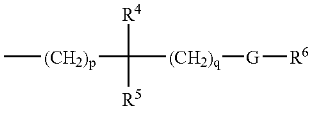 |
|---|---|---|---|---|---|---|---|
| 1780 | 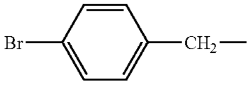 | 2 | 2 | 1 | — | H | 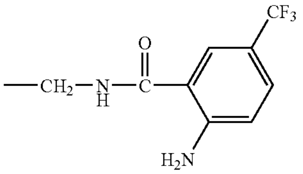 |
| 1781 | 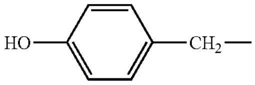 | 2 | 2 | 1 | — | H | 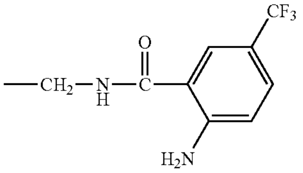 |
| 1782 | 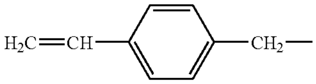 | 2 | 2 | 1 | — | H | 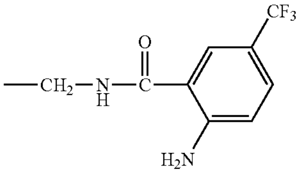 |
TABLE 1.163
| Compd. No. | 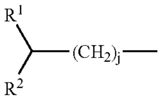 | k | m | n | chirality | $R^3$ | 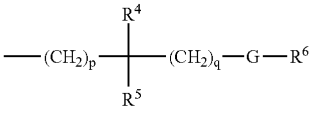 |
|---|---|---|---|---|---|---|---|
| 1783 | 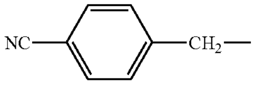 | 2 | 2 | 1 | — | H | 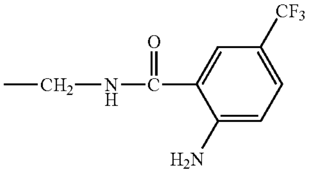 |
| 1784 | 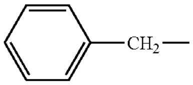 | 2 | 2 | 1 | — | H | 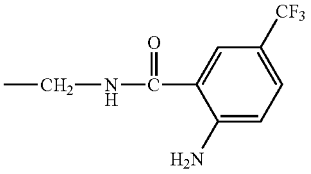 |
| 1785 | 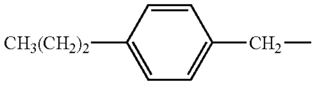 | 2 | 2 | 1 | — | H | 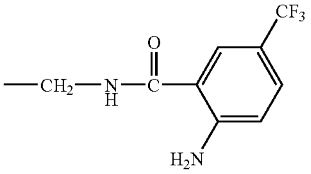 |

TABLE 1.163-continued
| Compd. No. 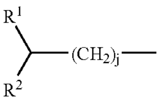 | k | m | n | chirality | $R^3$ | 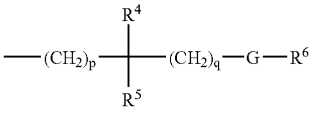 |
|---|---|---|---|---|---|---|
| 1786 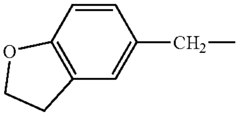 | 2 | 2 | 1 | — | H | 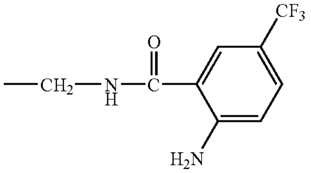 |
| 1787 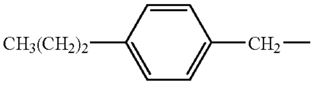 | 1 | 2 | 0 | R | H | 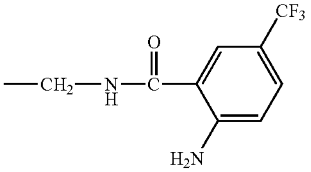 |
| 1788 | | | | | | |
| 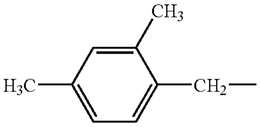 | 2 | 2 | 1 | — | H | 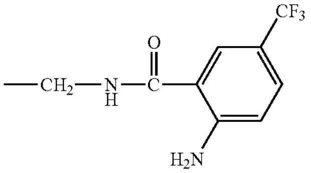 |
| 1789 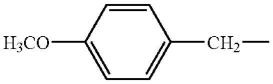 | 2 | 2 | 1 | — | H | 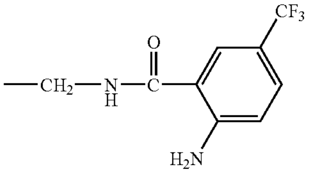 |
| 1790 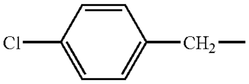 | 1 | 2 | 0 | S | H | 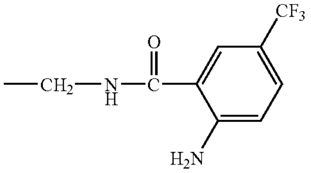 |
| 1791 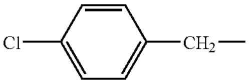 | 1 | 2 | 0 | S | H | 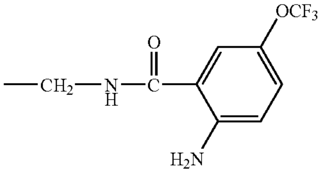 |
| 1792 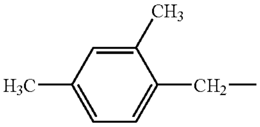 | 2 | 2 | 1 | — | H | 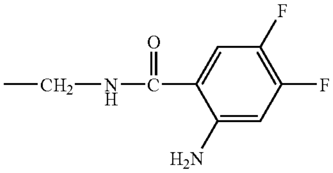 |

TABLE 1.163-continued
| Compd. No. | 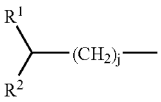 | k | m | n | chirality | $R^3$ | 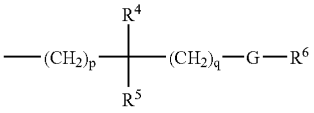 |
|---|---|---|---|---|---|---|---|
| 1793 | 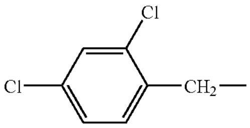 | 2 | 2 | 1 | — | H | 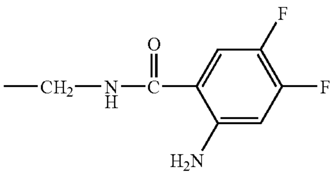 |
TABLE 1.164
| Compd. No. | 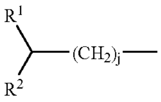 | k | m | n | chirality | $R^3$ | 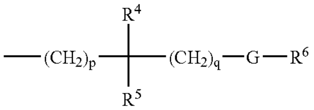 |
|---|---|---|---|---|---|---|---|
| 1794 | 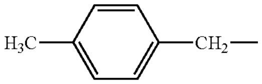 | 2 | 2 | 1 | — | H | 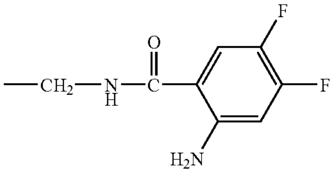 |
| 1795 | 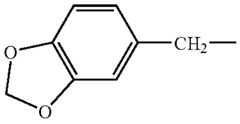 | 2 | 2 | 1 | — | H | 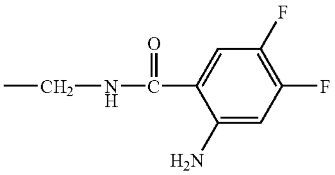 |
| 1796 | 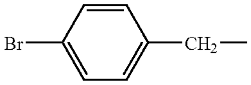 | 2 | 2 | 1 | — | H | 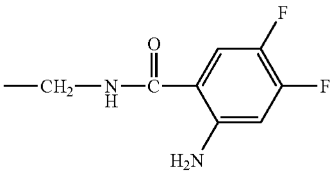 |
| 1797 | 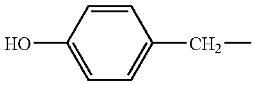 | 2 | 2 | 1 | — | H | 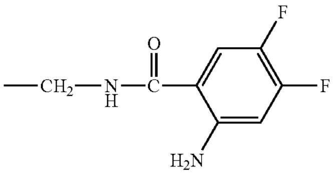 |
| 1798 | 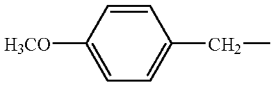 | 2 | 2 | 1 | — | H | 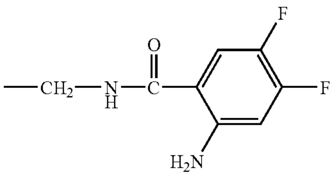 |

TABLE 1.164-continued
| Compd. No. 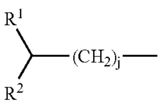 | | k | m | n | chirality | $R^3$ | 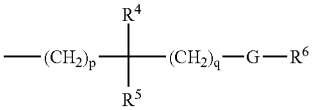 |
|---|---|---|---|---|---|---|---|
| 1799 | 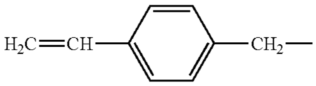 | 2 | 2 | 1 | — | H | 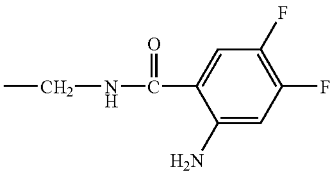 |
| 1800 | 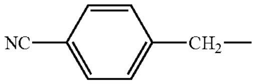 | 2 | 2 | 1 | — | H | 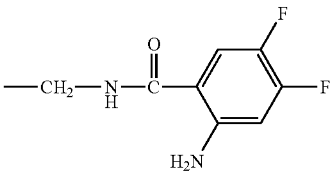 |
| 1801 | 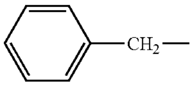 | 2 | 2 | 1 | — | H | 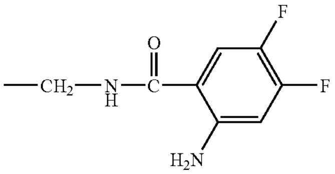 |
| 1802 | 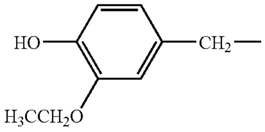 | 1 | 2 | 0 | R | H | 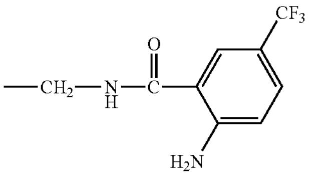 |
| 1803 | 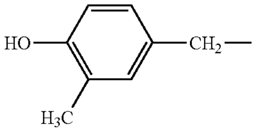 | 1 | 2 | 0 | R | H | 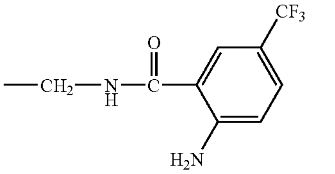 |
| 1804 | 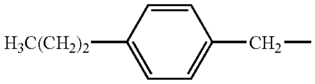 | 2 | 2 | 1 | — | H | 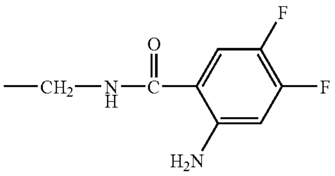 |
TABLE 1.165
| Compd. No. 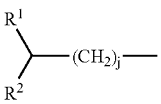 | | k | m | n | chirality | $R^3$ | 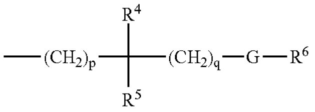 |
|---|---|---|---|---|---|---|---|
| 1805 | 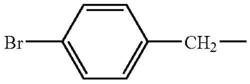 | 1 | 2 | 0 | R | H | 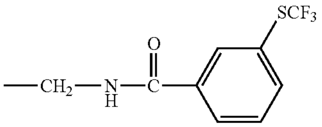 |

TABLE 1.165-continued
| Compd. No. | 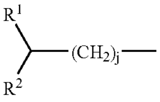 | k | m | n | chirality | $R^3$ | 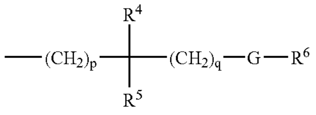 |
|---|---|---|---|---|---|---|---|
| 1806 | 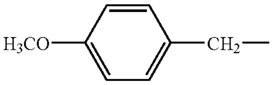 | 1 | 2 | 0 | R | H | 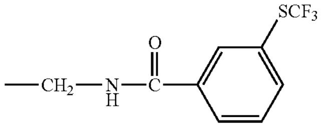 |
| 1807 | 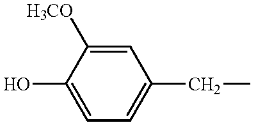 | 1 | 2 | 0 | R | H | 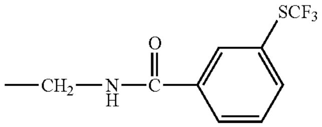 |
| 1808 | 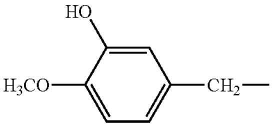 | 1 | 2 | 0 | R | H | 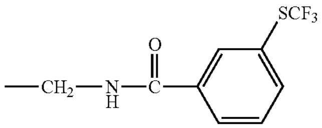 |
| 1809 | 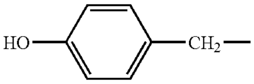 | 1 | 2 | 0 | R | H | 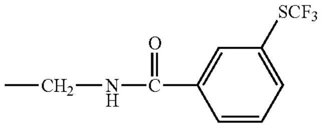 |
| 1810 | 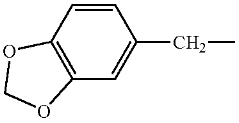 | 1 | 2 | 0 | R | H | 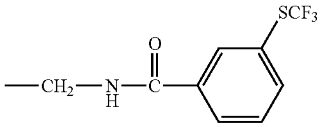 |
| 1811 | 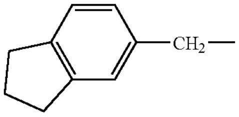 | 1 | 2 | 0 | R | H | 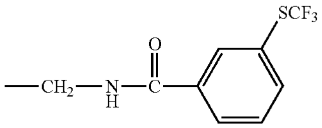 |
| 1812 | 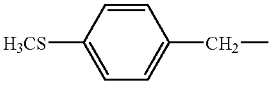 | 1 | 2 | 0 | R | H | 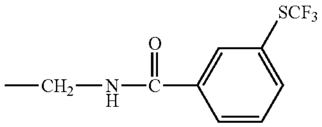 |
| 1813 | 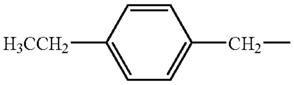 | 1 | 2 | 0 | R | H | 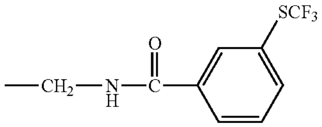 |
| 1814 | 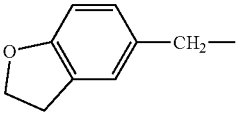 | 1 | 2 | 0 | R | H | 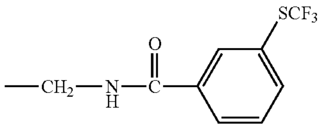 |
| 1815 | 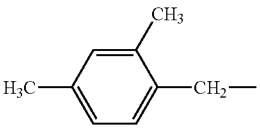 | 1 | 2 | 0 | R | H | 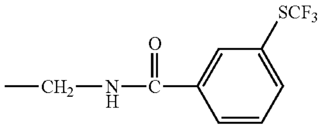 |

TABLE 1.166
| Compd. No. | 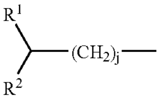 | k | m | n | chirality | $R^3$ | 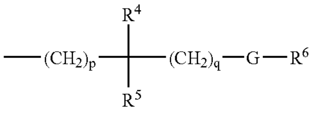 |
|---|---|---|---|---|---|---|---|
| 1816 | 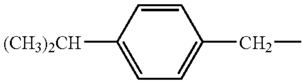 | 1 | 2 | 0 | R | H | 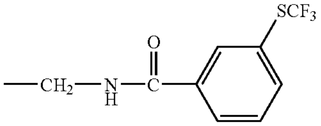 |
| 1817 | 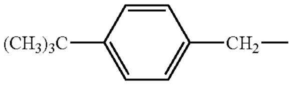 | 1 | 2 | 0 | R | H | 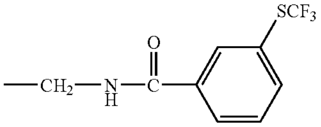 |
| 1818 | 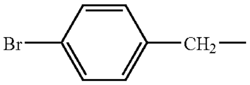 | 1 | 2 | 0 | R | H | 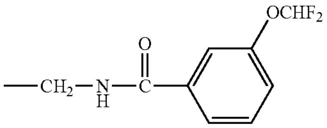 |
| 1819 | 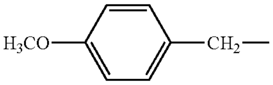 | 1 | 2 | 0 | R | H | 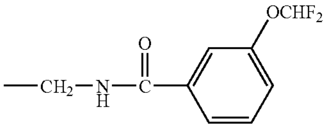 |
| 1820 | 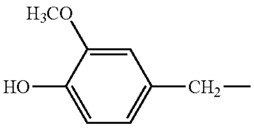 | 1 | 2 | 0 | R | H | 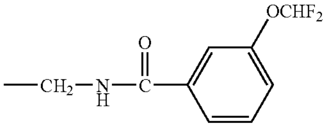 |
| 1821 | 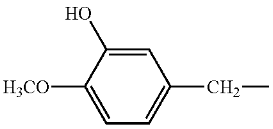 | 1 | 2 | 0 | R | H | 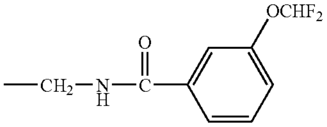 |
| 1822 | 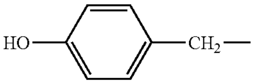 | 1 | 2 | 0 | R | H | 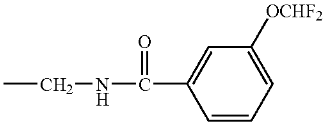 |
| 1823 | 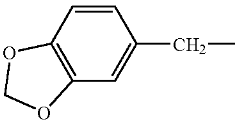 | 1 | 2 | 0 | R | H | 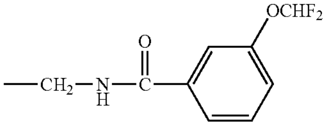 |
| 1824 | 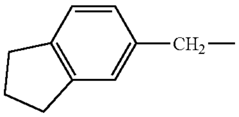 | 1 | 2 | 0 | R | H | 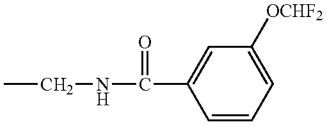 |
| 1825 | 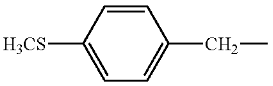 | 1 | 2 | 0 | R | H | 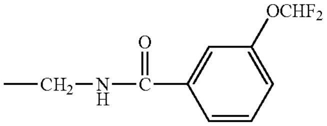 |

TABLE 1.166-continued
| Compd. No. 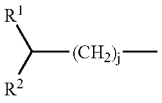 | | k | m | n | chirality | $R^3$ | 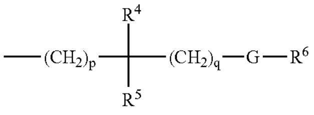 |
|---|---|---|---|---|---|---|---|
| 1826 | 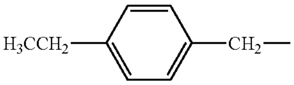 | 1 | 2 | 0 | R | H | 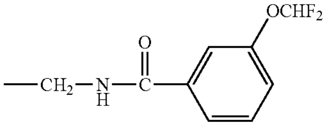 |
TABLE 1.167
| Compd. No. 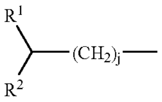 | | k | m | n | chirality | $R^3$ | 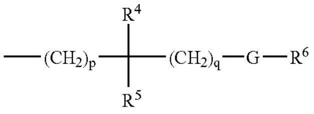 |
|---|---|---|---|---|---|---|---|
| 1827 | 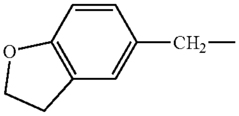 | 1 | 2 | 0 | R | H | 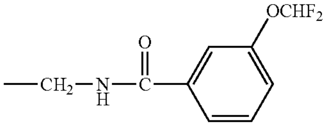 |
| 1828 | 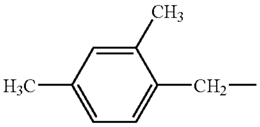 | 1 | 2 | 0 | R | H | 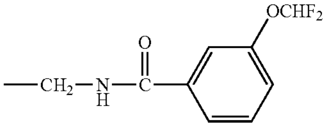 |
| 1829 | 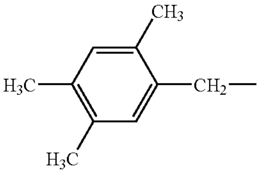 | 1 | 2 | 0 | R | H | 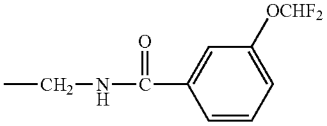 |
| 1830 | 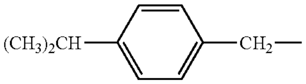 | 1 | 2 | 0 | R | H | 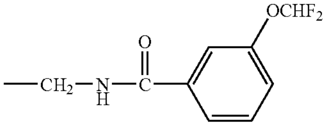 |
| 1831 | 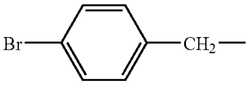 | 1 | 2 | 0 | R | H | 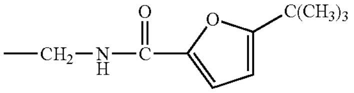 |
| 1832 | 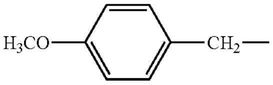 | 1 | 2 | 0 | R | H | 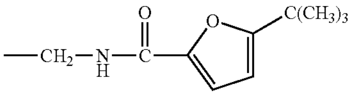 |
| 1833 | 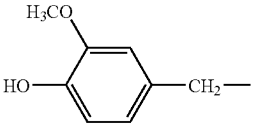 | 1 | 2 | 0 | R | H | 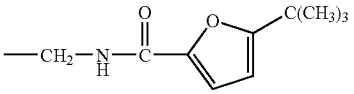 |
| 1834 | 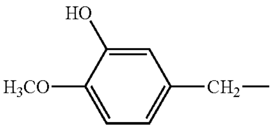 | 1 | 2 | 0 | R | H | 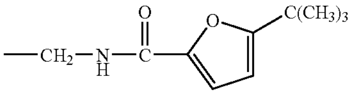 |

TABLE 1.167-continued
| Compd. No. 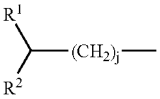 | | k | m | n | chirality | $R^3$ | 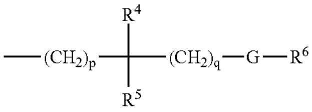 |
|---|---|---|---|---|---|---|---|
| 1835 | 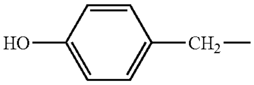 | 1 | 2 | 0 | R | H | 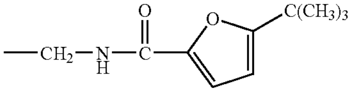 |
| 1836 | 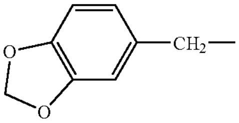 | 1 | 2 | 0 | R | H | 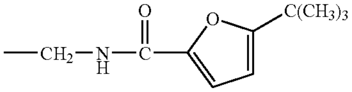 |
| 1837 | 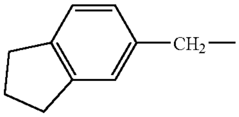 | 1 | 2 | 0 | R | H | 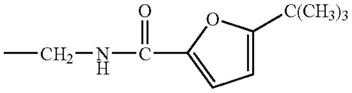 |
TABLE 1.168
| Compd. No. 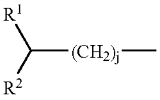 | | k | m | n | chirality | $R^3$ | 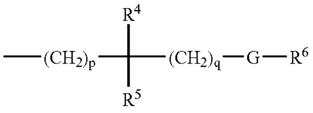 |
|---|---|---|---|---|---|---|---|
| 1838 | 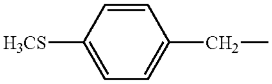 | 1 | 2 | 0 | R | H | 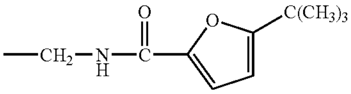 |
| 1839 | 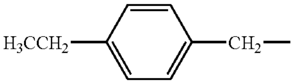 | 1 | 2 | 0 | R | H | 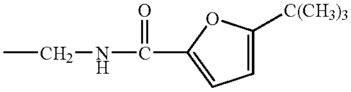 |
| 1840 | 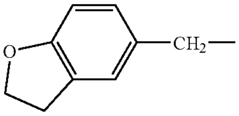 | 1 | 2 | 0 | R | H | 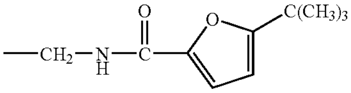 |
| 1841 | 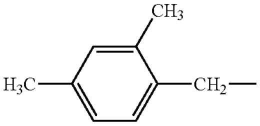 | 1 | 2 | 0 | R | H | 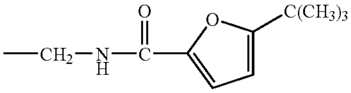 |
| 1842 | 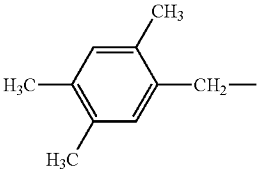 | 1 | 2 | 0 | R | H | 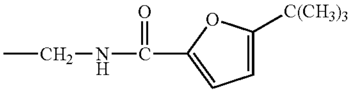 |
| 1843 | 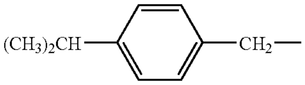 | 1 | 2 | 0 | R | H | 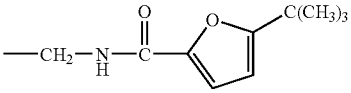 |
| 1844 | 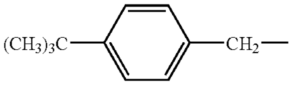 | 1 | 2 | 0 | R | H | 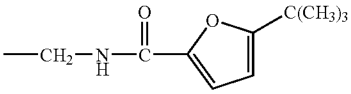 |

TABLE 1.168-continued
| Compd. No. 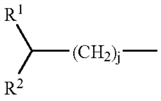 | | k | m | n | chirality | R3 | 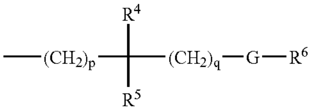 |
|---|---|---|---|---|---|---|---|
| 1845 | 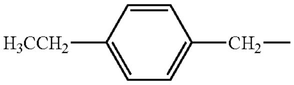 | 1 | 2 | 0 | R | H | 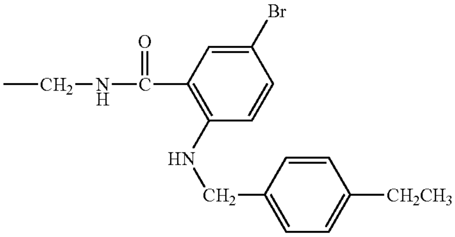 |
| 1846 | 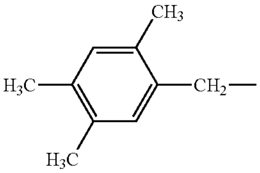 | 1 | 2 | 0 | R | H | 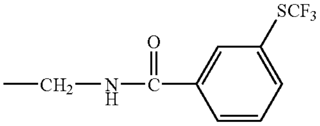 |
| 1847 | 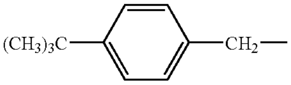 | 1 | 2 | 0 | R | H | 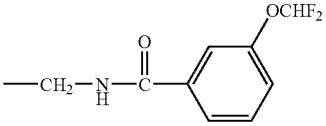 |
| 1848 | 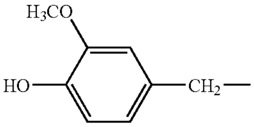 | 1 | 2 | 0 | R | H | 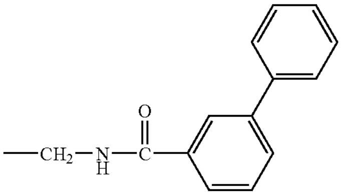 |
TABLE 1.169
| Compd. No. 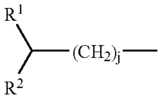 | | k | m | n | chirality | R3 | 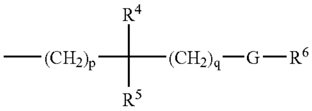 |
|---|---|---|---|---|---|---|---|
| 1849 | 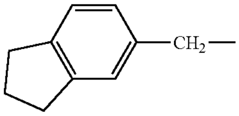 | 1 | 2 | 0 | R | H | 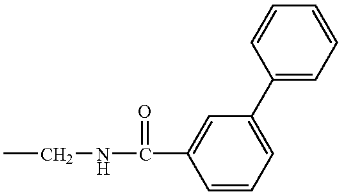 |
| 1850 | 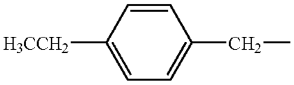 | 1 | 2 | 0 | R | H | 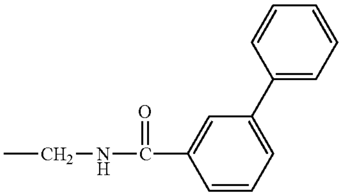 |

TABLE 1.169-continued
| Compd. No. | 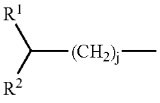 | k | m | n | chirality | $R^3$ | 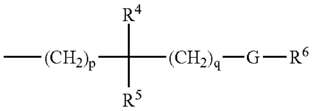 |
|---|---|---|---|---|---|---|---|
| 1851 | 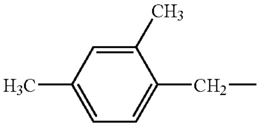 | 1 | 2 | 0 | R | H | 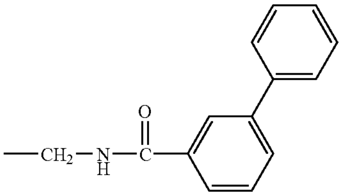 |
| 1852 | 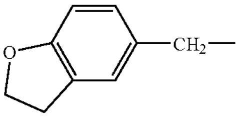 | 1 | 2 | 0 | R | H | 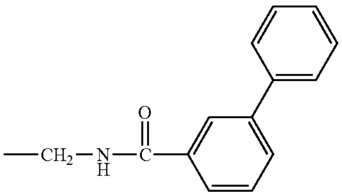 |
| 1853 | 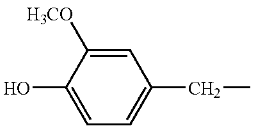 | 1 | 2 | 0 | R | H | 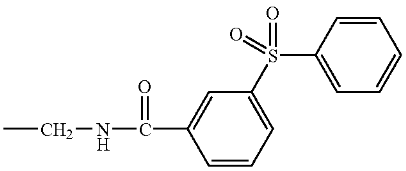 |
| 1854 | 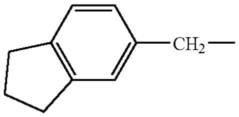 | 1 | 2 | 0 | R | H | 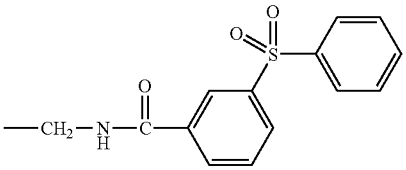 |
| 1855 | 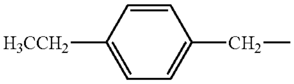 | 1 | 2 | 0 | R | H | 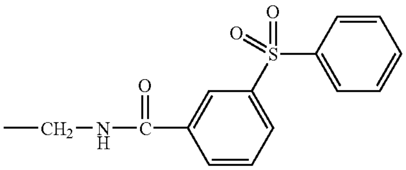 |
| 1856 | 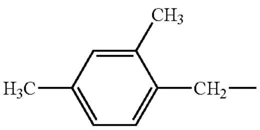 | 1 | 2 | 0 | R | H | 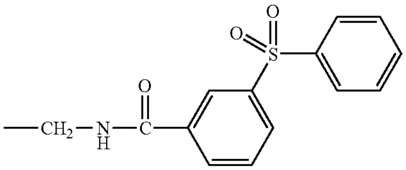 |
| 1857 | 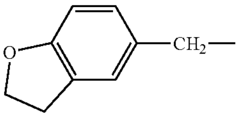 | 1 | 2 | 0 | R | H | 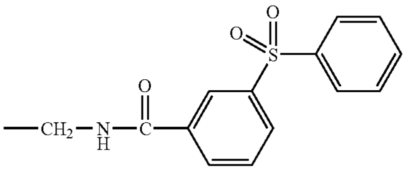 |

TABLE 1.169-continued
| Compd. No. | 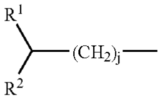 | k | m | n | chirality | $R^3$ | 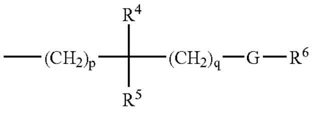 |
|---|---|---|---|---|---|---|---|
| 1858 | 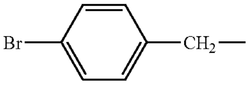 | 1 | 2 | 0 | R | H | 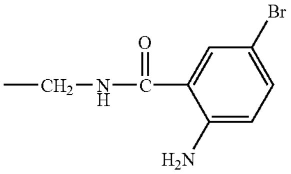 |
| 1859 | 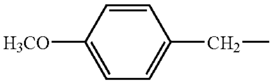 | 1 | 2 | 0 | R | H | 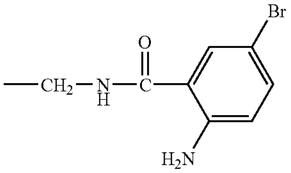 |
TABLE 1.170
| Compd. No. | 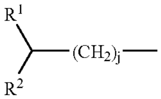 | k | m | n | chirality | $R^3$ | 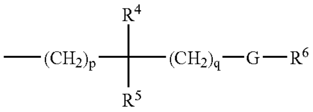 |
|---|---|---|---|---|---|---|---|
| 1860 | 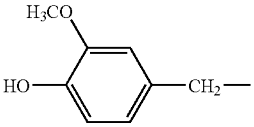 | 1 | 2 | 0 | R | H | 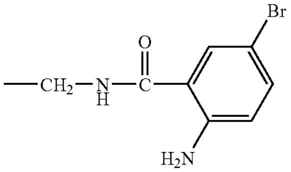 |
| 1861 | 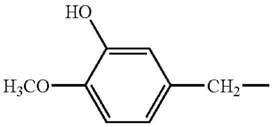 | 1 | 2 | 0 | R | H | 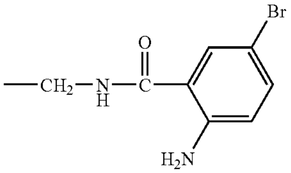 |
| 1862 | 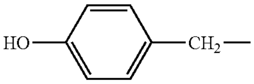 | 1 | 2 | 0 | R | H | 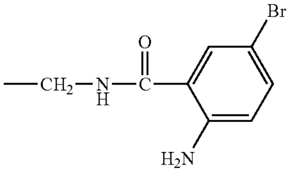 |
| 1863 | 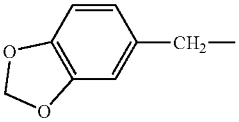 | 1 | 2 | 0 | R | H | 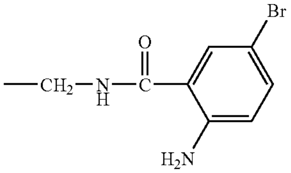 |

TABLE 1.170-continued
| Compd. No. | 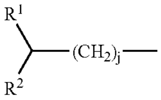 | k | m | n | chirality | $R^3$ | 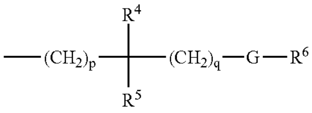 |
|---|---|---|---|---|---|---|---|
| 1864 | 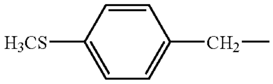 | 1 | 2 | 0 | R | H | 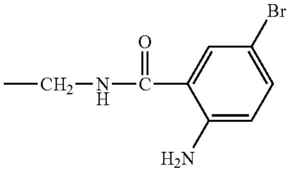 |
| 1865 | 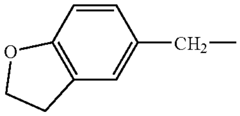 | 1 | 2 | 0 | R | H | 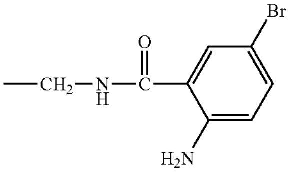 |
| 1866 | 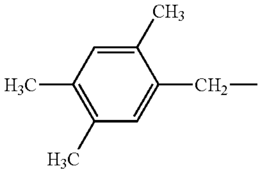 | 1 | 2 | 0 | R | H | 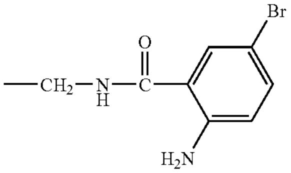 |
| 1867 | 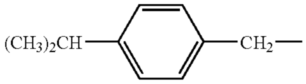 | 1 | 2 | 0 | R | H | 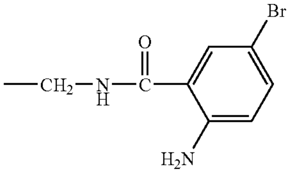 |
| 1868 | 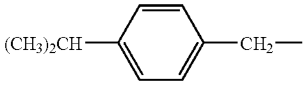 | 1 | 2 | 0 | R | H | 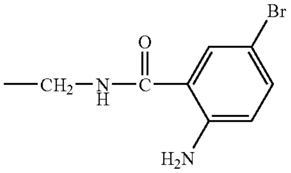 |
| 1869 | 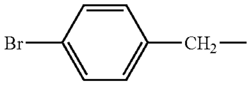 | 1 | 2 | 0 | R | H | 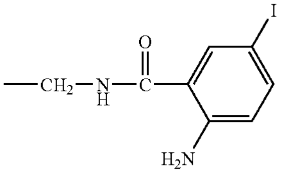 |
| 1870 | 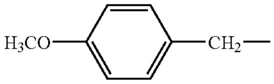 | 1 | 2 | 0 | R | H | 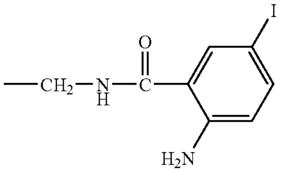 |

TABLE 1.171
| Compd. No. 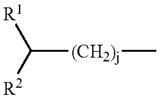 | | k | m | n | chirality | $R^3$ | 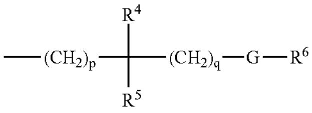 |
|---|---|---|---|---|---|---|---|
| 1871 | 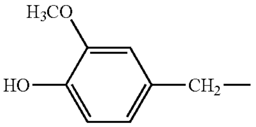 | 1 | 2 | 0 | R | H | 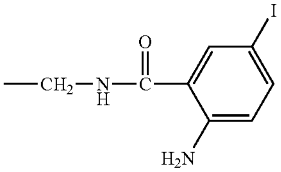 |
| 1872 | 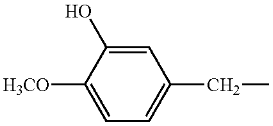 | 1 | 2 | 0 | R | H | 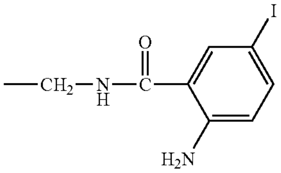 |
| 1873 | 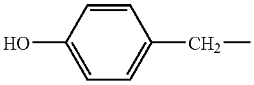 | 1 | 2 | 0 | R | H | 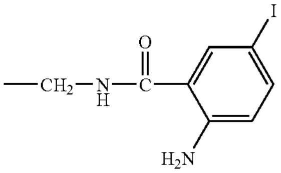 |
| 1874 | 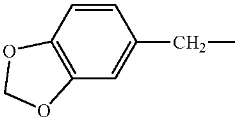 | 1 | 2 | 0 | R | H | 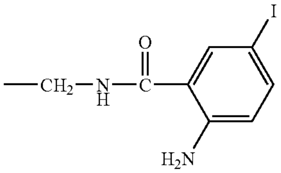 |
| 18751 | 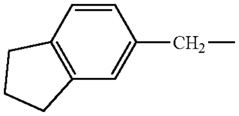 | 1 | 2 | 0 | R | H | 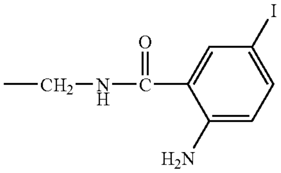 |
| 1876 | 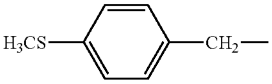 | 1 | 2 | 0 | R | H | 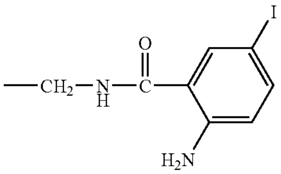 |
| 1877 | 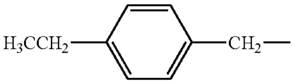 | 1 | 2 | 0 | R | H | 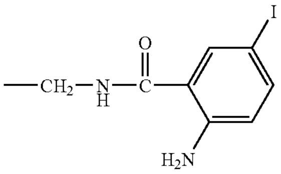 |

TABLE 1.171-continued
| Compd. No. | 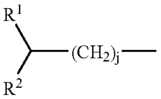 | k | m | n | chirality | $R^3$ | 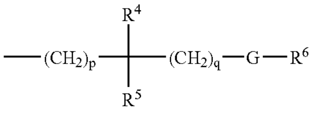 |
|---|---|---|---|---|---|---|---|
| 1878 | 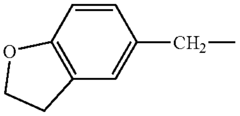 | 1 | 2 | 0 | R | H | 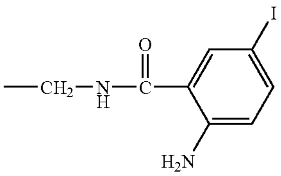 |
| 1879 | 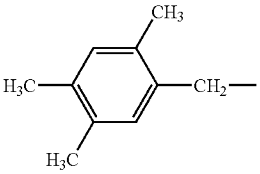 | 1 | 2 | 0 | R | H | 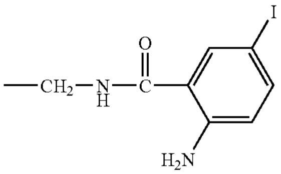 |
| 1880 | 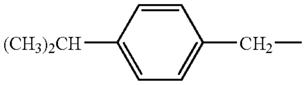 | 1 | 2 | 0 | R | H | 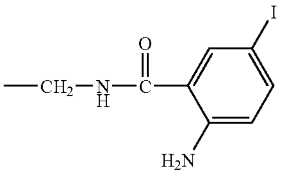 |
| 1881 | 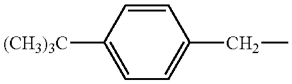 | 1 | 2 | 0 | R | H | 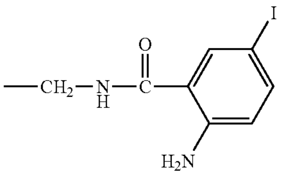 |
TABLE 1.172
| Compd. No. | 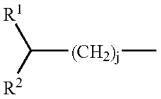 | k | m | n | chirality | $R^3$ | 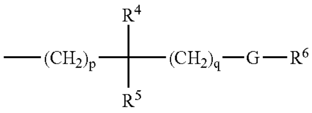 |
|---|---|---|---|---|---|---|---|
| 1882 | 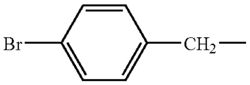 | 1 | 2 | 0 | R | H | 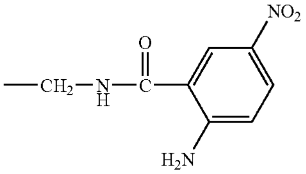 |
| 1883 | 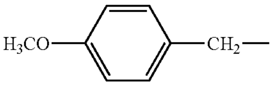 | 1 | 2 | 0 | R | H | 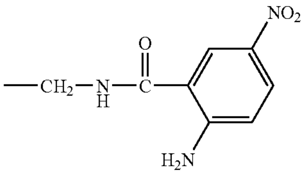 |

TABLE 1.172-continued
| Compd. No. | 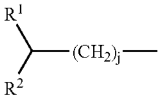 | k | m | n | chirality | $R^3$ | 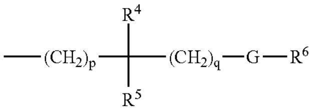 |
|---|---|---|---|---|---|---|---|
| 1884 | 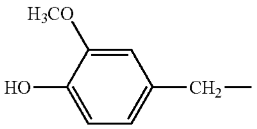 | 1 | 2 | 0 | R | H | 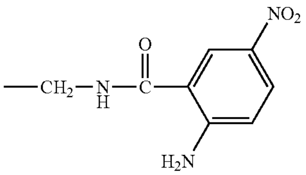 |
| 1885 | 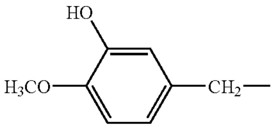 | 1 | 2 | 0 | R | H | 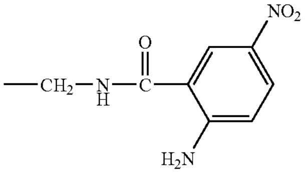 |
| 1886 | 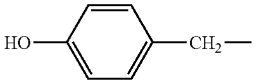 | 1 | 2 | 0 | R | H | 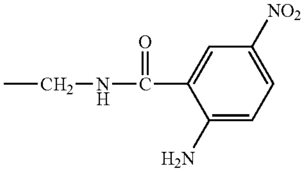 |
| 1887 | 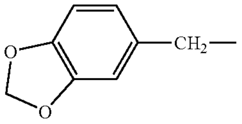 | 1 | 2 | 0 | R | H | 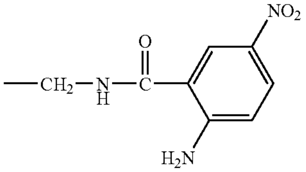 |
| 1888 | 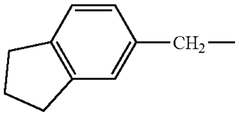 | 1 | 2 | 0 | R | H | 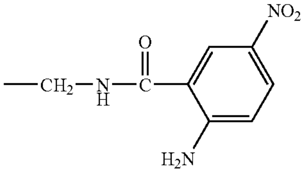 |
| 1889 | 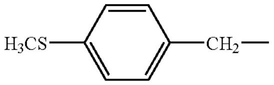 | 1 | 2 | 0 | R | H | 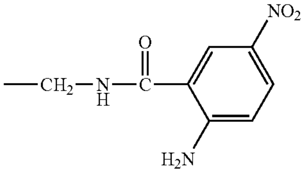 |
| 1890 | 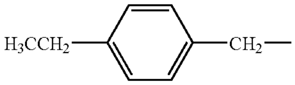 | 1 | 2 | 0 | R | H | 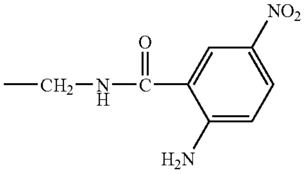 |
| 1891 | 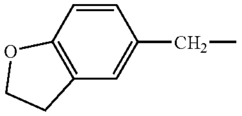 | 1 | 2 | 0 | R | H | 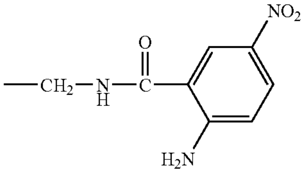 |

TABLE 1.172-continued
| Compd. No. | 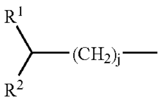 | k | m | n | chirality | $R^3$ | 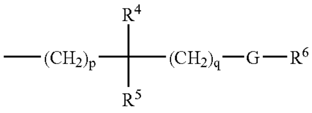 |
|---|---|---|---|---|---|---|---|
| 1892 | 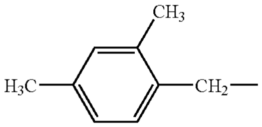 | 1 | 2 | 0 | R | H | 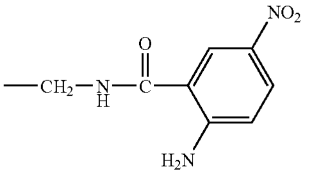 |
TABLE 1.173
| Compd. No. | 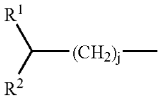 | k | m | n | chirality | $R^3$ | 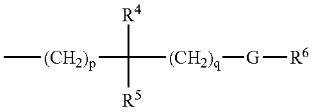 |
|---|---|---|---|---|---|---|---|
| 1893 | 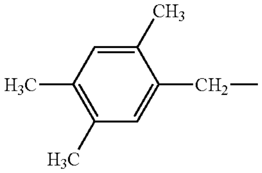 | 1 | 2 | 0 | R | H | 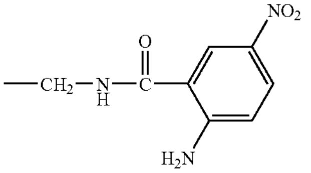 |
| 1894 | 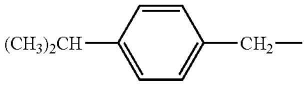 | 1 | 2 | 0 | R | H | 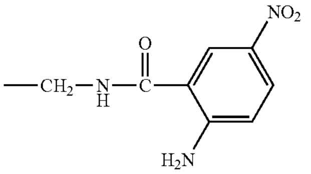 |
| 1895 | 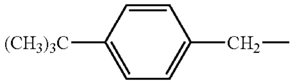 | 1 | 2 | 0 | R | H | 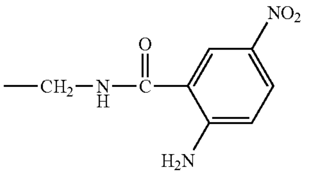 |
| 1896 | 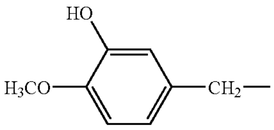 | 1 | 2 | 0 | R | H | 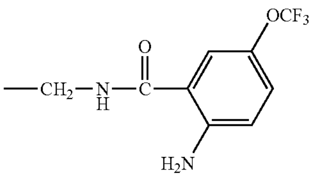 |
| 1897 | 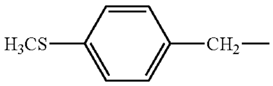 | 1 | 2 | 0 | R | H | 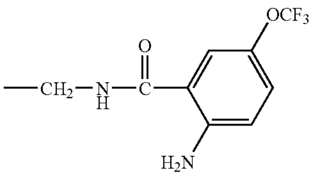 |

TABLE 1.173-continued
| Compd. No. | 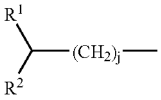 | k | m | n | chirality | $R^3$ | 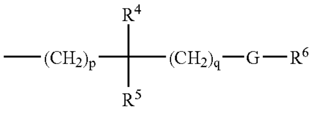 |
|---|---|---|---|---|---|---|---|
| 1898 | 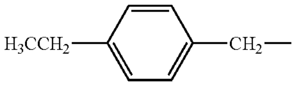 | 1 | 2 | 0 | R | H | 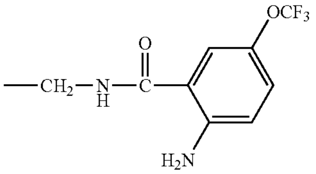 |
| 1899 | 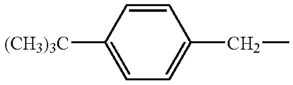 | 1 | 2 | 0 | R | H | 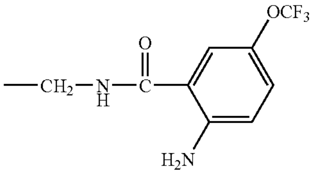 |
| 1900 | 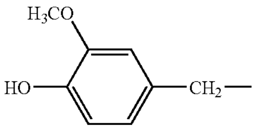 | 1 | 2 | 0 | R | H | 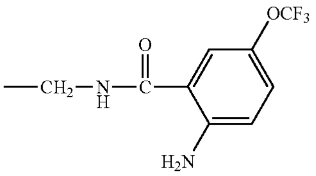 |
| 1901 | 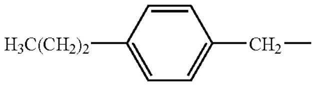 | 1 | 2 | 0 | R | H | 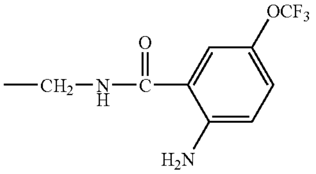 |
| 1902 | 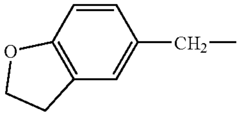 | 1 | 2 | 0 | R | H | 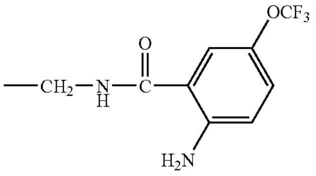 |
| 1903 | 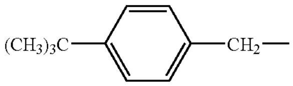 | 2 | 2 | 1 | — | H | 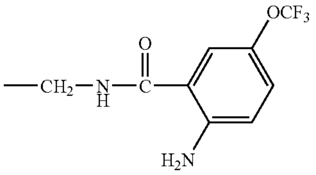 |

TABLE 1.174
| Compd. No. 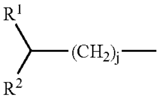 | k | m | n | chirality | $R^3$ | 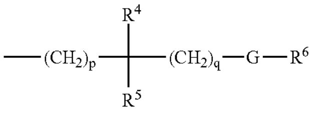 |
|---|---|---|---|---|---|---|
| 1904 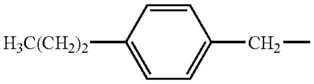 | 2 | 2 | 1 | — | H | 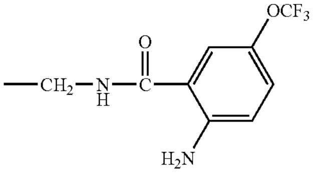 |
| 1905 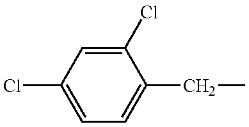 | 1 | 2 | 0 | R | H | 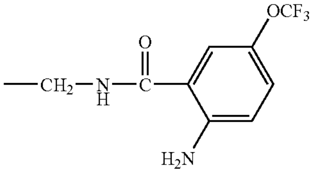 |
| 1906 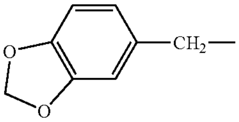 | 1 | 2 | 0 | R | H | 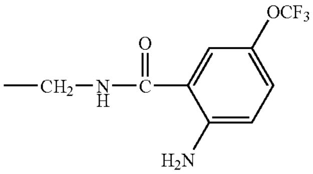 |
| 1907 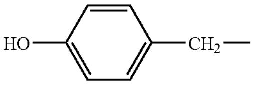 | 1 | 2 | 0 | R | H | 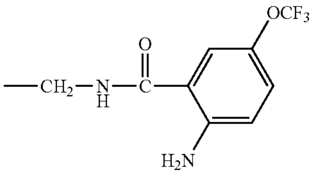 |
| 1908 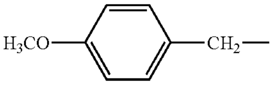 | 1 | 2 | 0 | R | H | 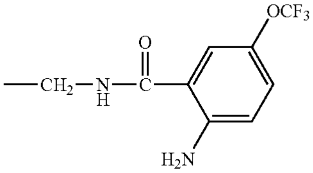 |
| 1909 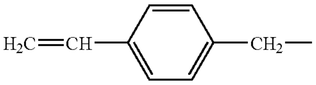 | 1 | 2 | 0 | R | H | 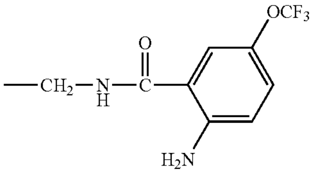 |
| 1910 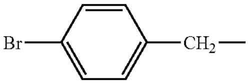 | 2 | 2 | 1 | — | H | 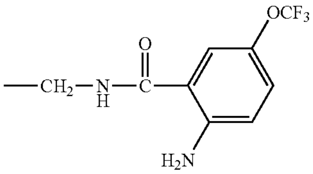 |

TABLE 1.174-continued
| Compd. No. | 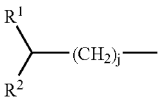 | k | m | n | chirality | $R^3$ | 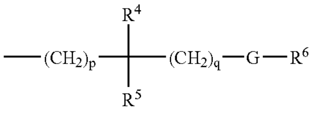 |
|---|---|---|---|---|---|---|---|
| 1911 | 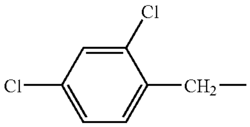 | 2 | 2 | 1 | — | H | 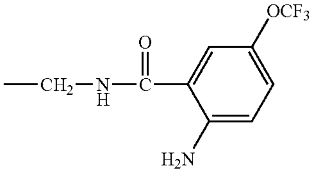 |
| 1912 | 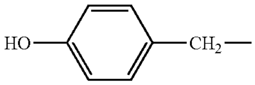 | 2 | 2 | 1 | — | H | 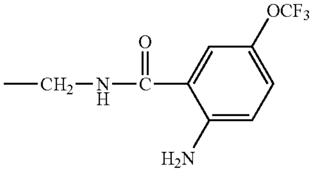 |
| 1913 | 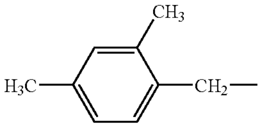 | 2 | 2 | 1 | — | H | 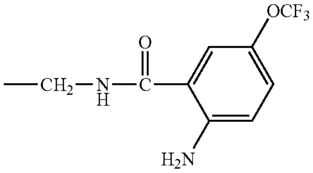 |
| 1914 | 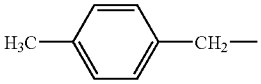 | 2 | 2 | 1 | — | H | 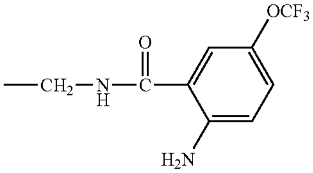 |
TABLE 1.175
| Compd. No. | 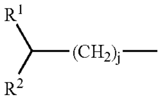 | k | m | n | chirality | $R^3$ | 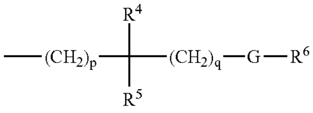 |
|---|---|---|---|---|---|---|---|
| 1915 | 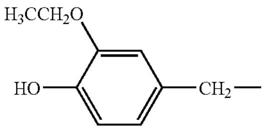 | 1 | 2 | 0 | R | H | 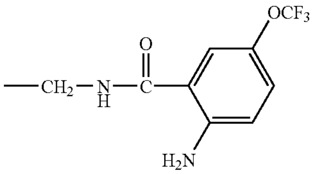 |
| 1916 | 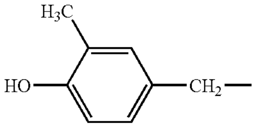 | 1 | 2 | 0 | R | H | 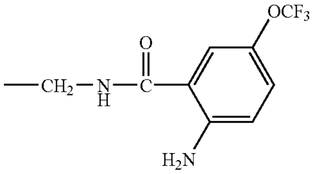 |

TABLE 1.175-continued
| Compd. No. | 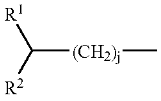 | k | m | n | chirality | $R^3$ | 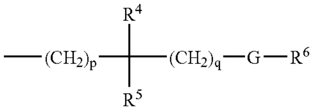 |
|---|---|---|---|---|---|---|---|
| 1917 | 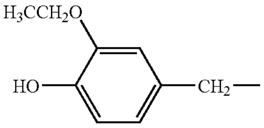 | 2 | 2 | 1 | — | H | 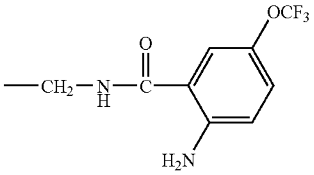 |
| 1918 | 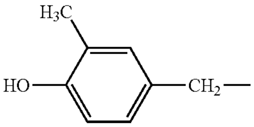 | 2 | 2 | 1 | — | H | 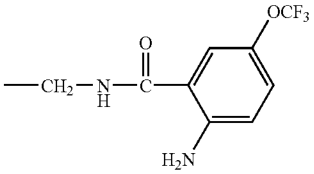 |
| 1919 | 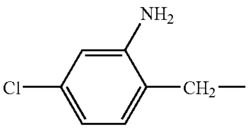 | 2 | 2 | 1 | — | H | 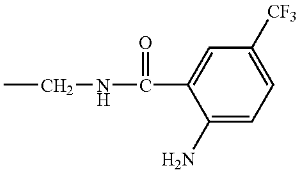 |
| 1920 | 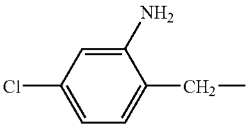 | 2 | 2 | 1 | — | H | 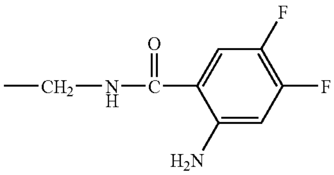 |
| 1921 | 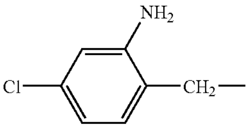 | 1 | 2 | 0 | R | H | 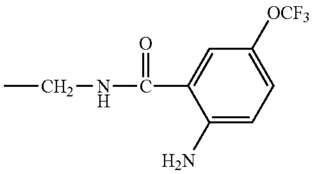 |
| 1922 | 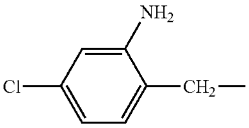 | 2 | 2 | 1 | — | H | 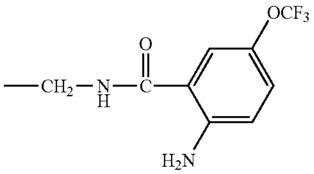 |
| 1923 | 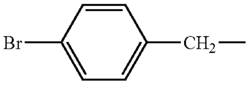 | 2 | 2 | 1 | — | H | 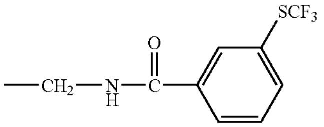 |
| 1924 | 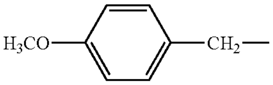 | 2 | 2 | 1 | — | H | 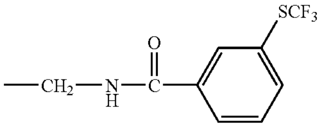 |

TABLE 1.175-continued
| Compd. No. | 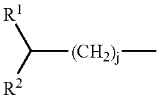 | k | m | n | chirality | $R^3$ | 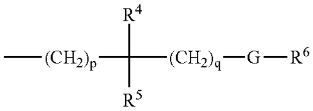 |
|---|---|---|---|---|---|---|---|
| 1925 | 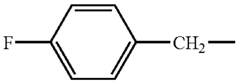 | 2 | 2 | 1 | — | H | 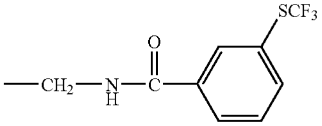 |
TABLE 1.176
| Compd. No. | 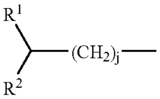 | k | m | n | chirality | $R^3$ | 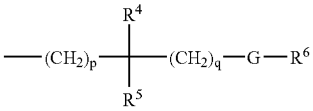 |
|---|---|---|---|---|---|---|---|
| 1926 | 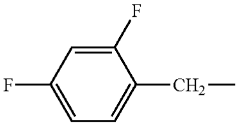 | 2 | 2 | 1 | — | H | 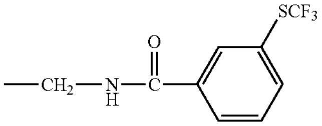 |
| 1927 | 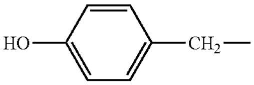 | 2 | 2 | 1 | — | H | 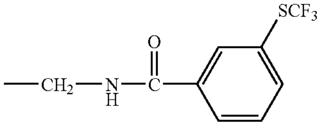 |
| 1928 | 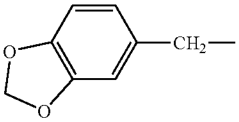 | 2 | 2 | 1 | — | H | 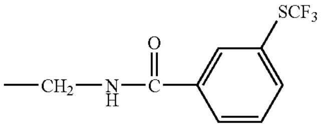 |
| 1929 | 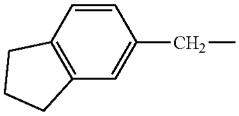 | 2 | 2 | 1 | — | H | 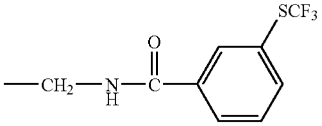 |
| 1930 | 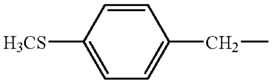 | 2 | 2 | 1 | — | H | 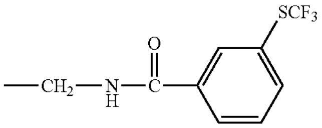 |
| 1931 | 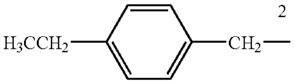 | 2 | 2 | 1 | — | H | 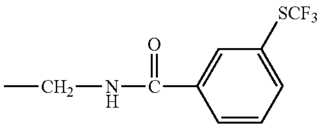 |
| 1932 | 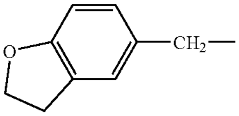 | 2 | 2 | 1 | — | H | 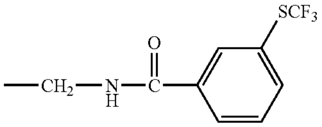 |
| 1933 | 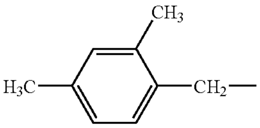 | 2 | 2 | 1 | — | H | 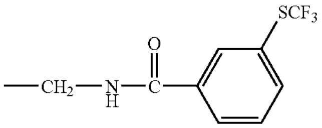 |

TABLE 1.176-continued
| Compd. No. | 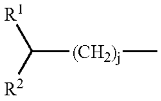 | k | m | n | chirality | R3 | 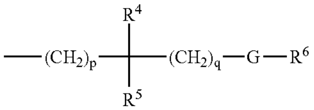 |
|---|---|---|---|---|---|---|---|
| 1934 | 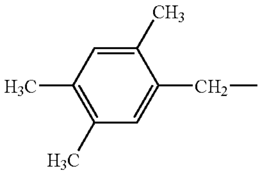 | 2 | 2 | 1 | — | H | 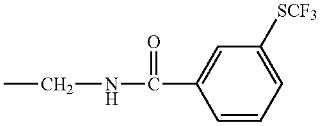 |
| 1935 | 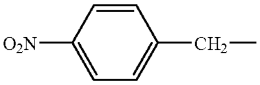 | 2 | 2 | 1 | — | H | 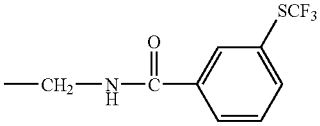 |
| 1936 | 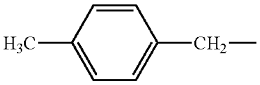 | 2 | 2 | 1 | — | H | 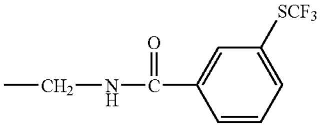 |
TABLE 1.177
| Compd. No. | 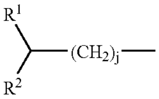 | k | m | n | chirality | R3 | 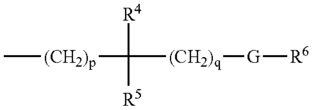 |
|---|---|---|---|---|---|---|---|
| 1937 | 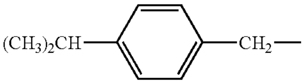 | 2 | 2 | 1 | — | H | 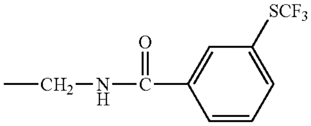 |
| 1938 | 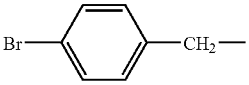 | 2 | 2 | 1 | — | H | 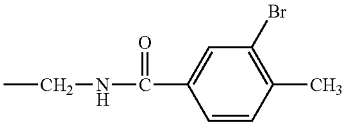 |
| 1939 | 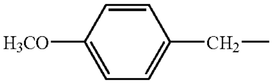 | 2 | 2 | 1 | — | H | 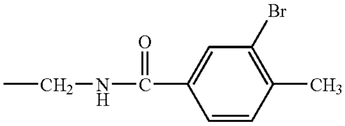 |
| 1940 | 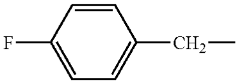 | 2 | 2 | 1 | — | H | 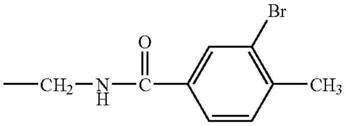 |
| 1941 | 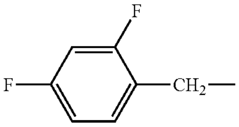 | 2 | 2 | 1 | — | H | 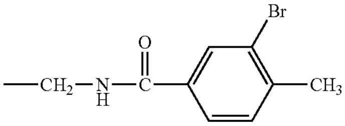 |

TABLE 1.177-continued
| Compd. No. | 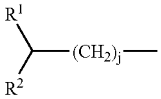 | k | m | n | chirality | $R^3$ | 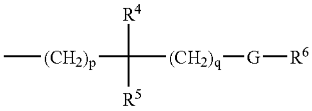 |
|---|---|---|---|---|---|---|---|
| 1942 | 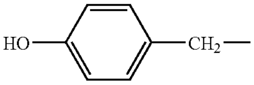 | 2 | 2 | 1 | — | H | 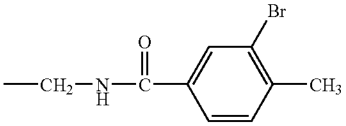 |
| 1943 | 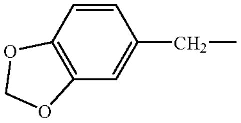 | 2 | 2 | 1 | — | H | 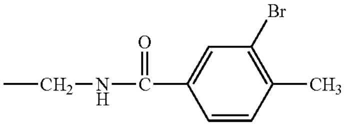 |
| 1944 | 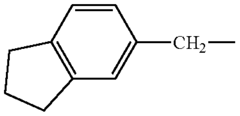 | 2 | 2 | 1 | — | H | 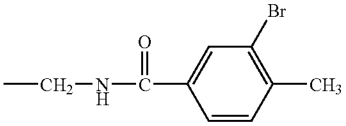 |
| 1945 | 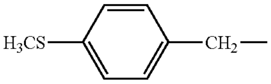 | 2 | 2 | 1 | — | H | 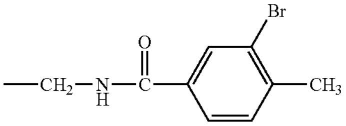 |
| 1946 | 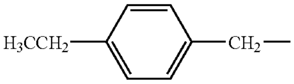 | 2 | 2 | 1 | — | H | 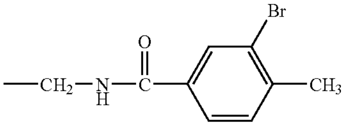 |
| 1947 | 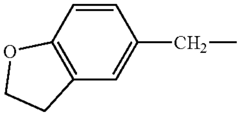 | 2 | 2 | 1 | — | H | 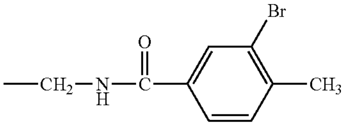 |
TABLE 1.178
| Compd. No. | 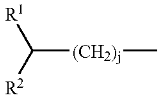 | k | m | n | chirality | $R^3$ | 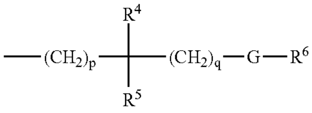 |
|---|---|---|---|---|---|---|---|
| 1948 | 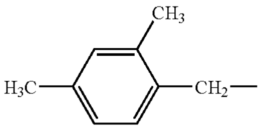 | 2 | 2 | 1 | — | H | 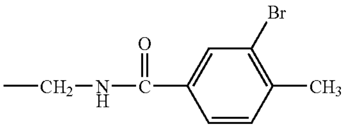 |
| 1949 | 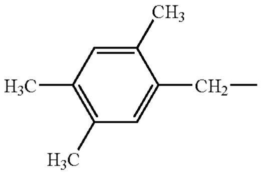 | 2 | 2 | 1 | — | H | 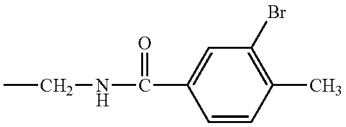 |

TABLE 1.178-continued
| Compd. No. | 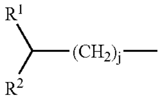 | k | m | n | chirality | $R^3$ | 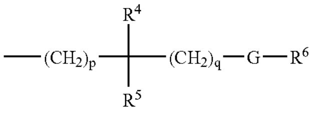 |
|---|---|---|---|---|---|---|---|
| 1950 | 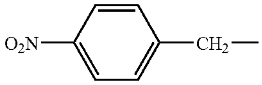 | 2 | 2 | 1 | — | H | 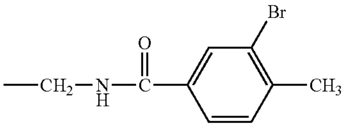 |
| 1951 | 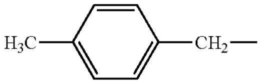 | 2 | 2 | 1 | — | H | 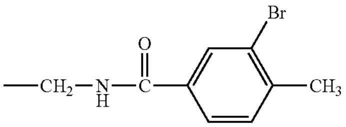 |
| 1952 | 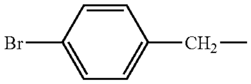 | 2 | 2 | 1 | — | H | 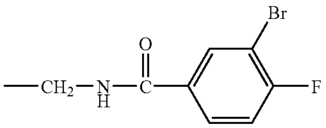 |
| 1953 | 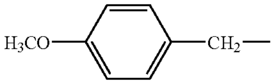 | 2 | 2 | 1 | — | H | 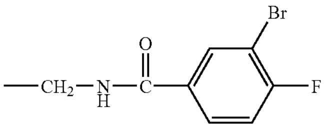 |
| 1954 | 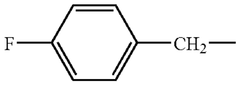 | 2 | 2 | 1 | — | H | 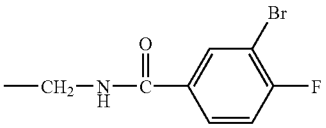 |
| 1955 | 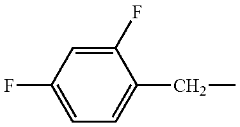 | 2 | 2 | 1 | — | H | 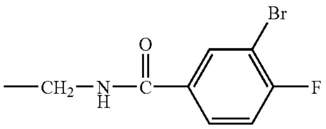 |
| 1956 | 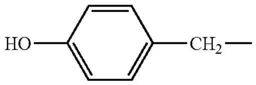 | 2 | 2 | 1 | — | H | 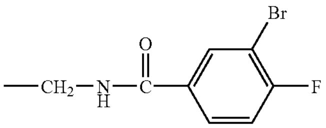 |
| 1957 | 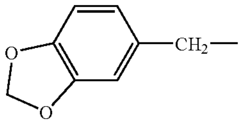 | 2 | 2 | 1 | — | H | 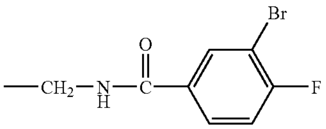 |
| 1958 | 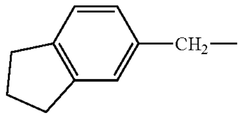 | 2 | 2 | 1 | — | H | 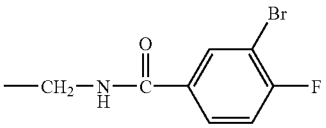 |

TABLE 1.179
| Compd. No. | 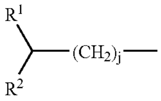 | k | m | n | chirality | $R^3$ | 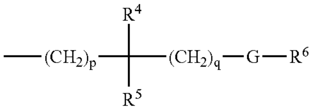 |
|---|---|---|---|---|---|---|---|
| 1959 | 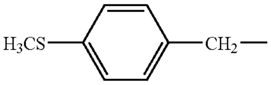 | 2 | 2 | 1 | — | H | 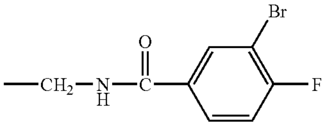 |
| 1960 | 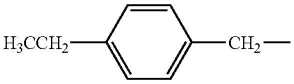 | 2 | 2 | 1 | — | H | 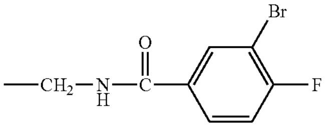 |
| 1961 | 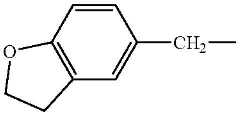 | 2 | 2 | 1 | — | H | 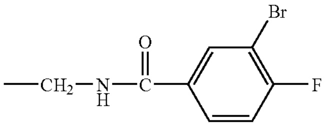 |
| 1962 | 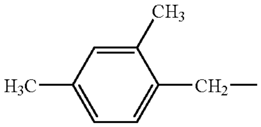 | 2 | 2 | 1 | — | H | 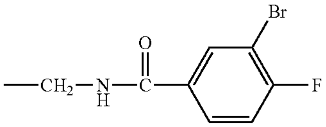 |
| 1963 | 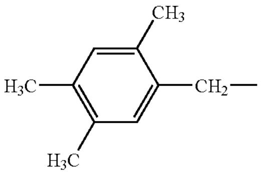 | 2 | 2 | 1 | — | H | 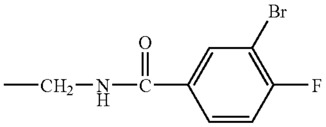 |
| 1964 | 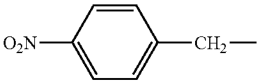 | 2 | 2 | 1 | — | H | 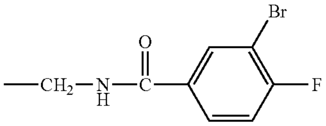 |
| 1965 | 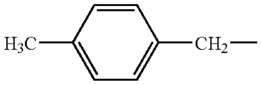 | 2 | 2 | 1 | — | H | 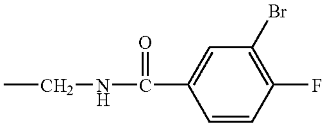 |
| 1966 | 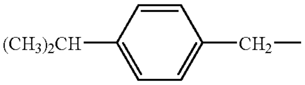 | 2 | 2 | 1 | — | H | 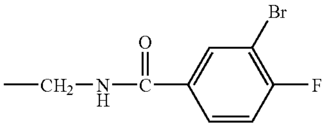 |
| 1967 | 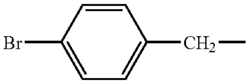 | 2 | 2 | 1 | — | H | 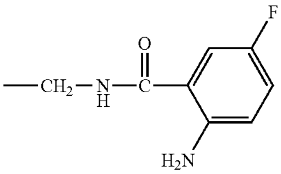 |

TABLE 1.179-continued
| Compd. No. | 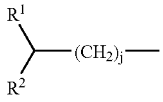 | k | m | n | chirality | $R^3$ | 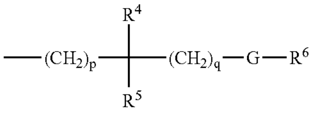 |
|---|---|---|---|---|---|---|---|
| 1968 | 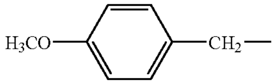 | 2 | 2 | 1 | — | H | 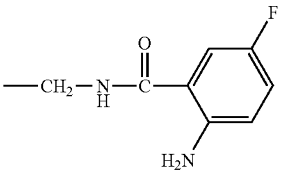 |
| 1969 | 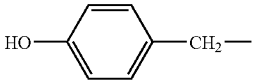 | 2 | 2 | 1 | — | H | 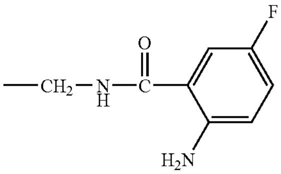 |
TABLE 1.180
| Compd. No. | 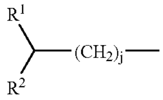 | k | m | n | chirality | $R^3$ | 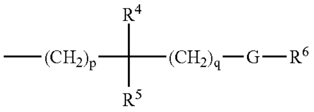 |
|---|---|---|---|---|---|---|---|
| 1970 | 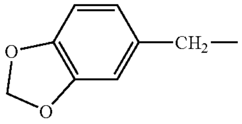 | 2 | 2 | 1 | — | H | 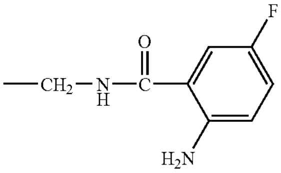 |
| 1971 | 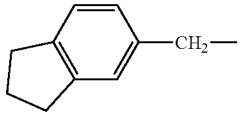 | 2 | 2 | 1 | — | H | 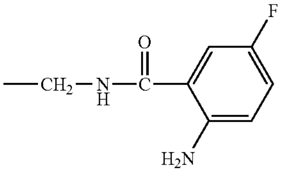 |
| 1972 | 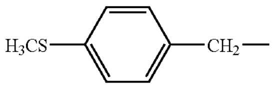 | 2 | 2 | 1 | — | H | 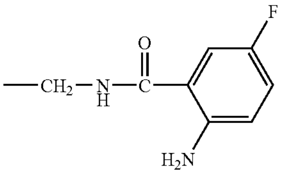 |
| 1973 | 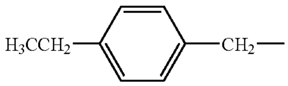 | 2 | 2 | 1 | — | H | 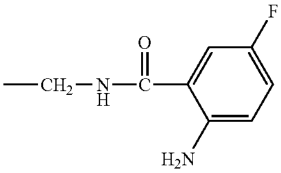 |

TABLE 1.180-continued
| Compd. No. | 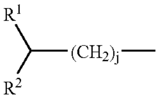 | k | m | n | chirality | $R^3$ | 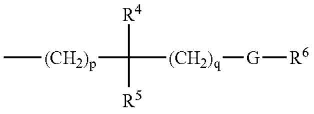 |
|---|---|---|---|---|---|---|---|
| 1974 | 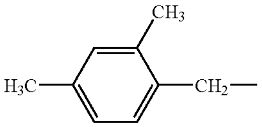 | 2 | 2 | 1 | — | H | 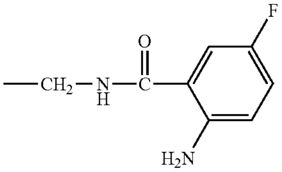 |
| 1975 | 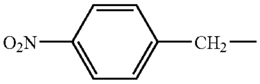 | 2 | 2 | 1 | — | H | 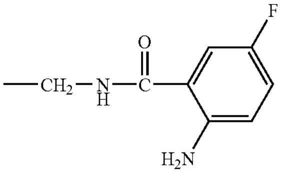 |
| 1976 | 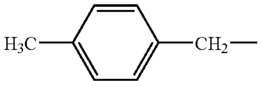 | 2 | 2 | 1 | — | H | 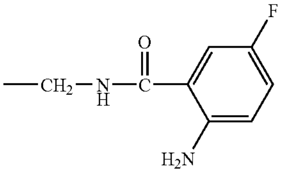 |
| 1977 | 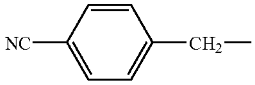 | 2 | 2 | 1 | — | H | 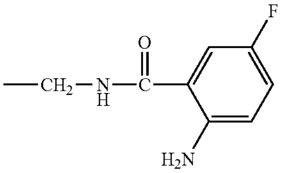 |
| 1978 | 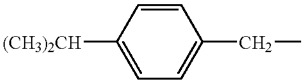 | 2 | 2 | 1 | — | H | 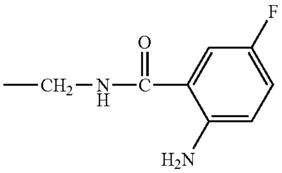 |
| 1979 | 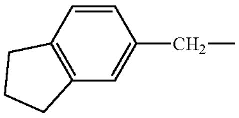 | 2 | 2 | 1 | — | H | 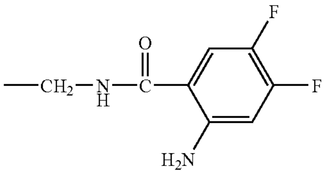 |
| 1980 | 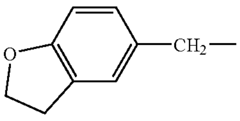 | 2 | 2 | 1 | — | H | 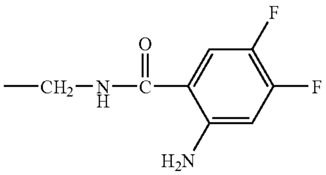 |

TABLE 1.181
| Compd. No. | 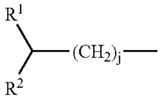 | k | m | n | chirality | $R^3$ | 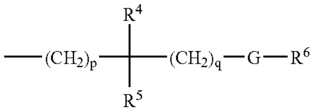 |
|---|---|---|---|---|---|---|---|
| 1981 | 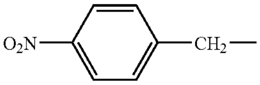 | 2 | 2 | 1 | — | H | 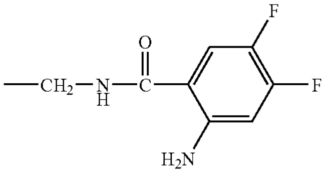 |
| 1982 | 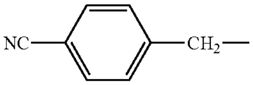 | 2 | 2 | 1 | — | H | 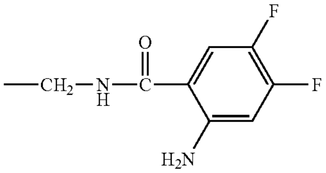 |
| 1983 | 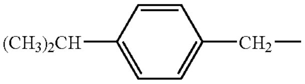 | 2 | 2 | 1 | — | H | 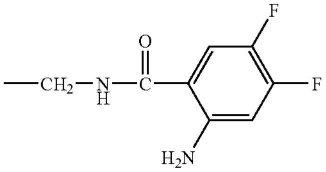 |
| 1984 | 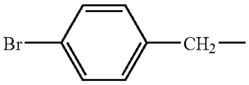 | 2 | 2 | 1 | — | H | 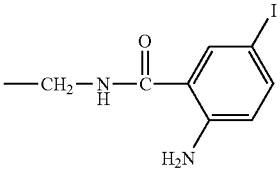 |
| 1985 | 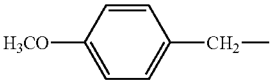 | 2 | 2 | 1 | — | H | 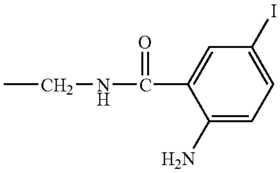 |
| 1986 | 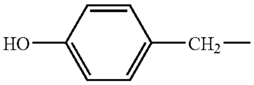 | 2 | 2 | 1 | — | H | 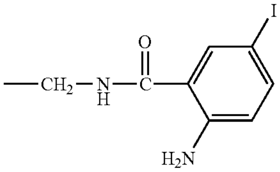 |
| 1987 | 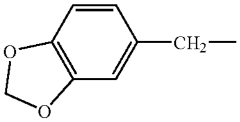 | 2 | 2 | 1 | — | H | 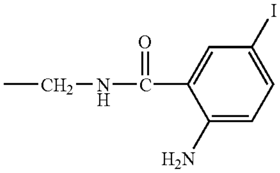 |
| 1988 | 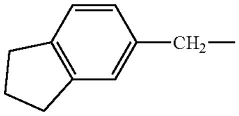 | 2 | 2 | 1 | — | H | 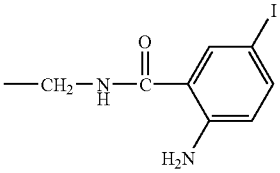 |

TABLE 1.181-continued
| Compd. No. | 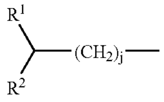 | k | m | n | chirality | $R^3$ | 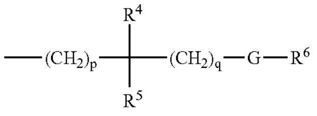 |
|---|---|---|---|---|---|---|---|
| 1989 | 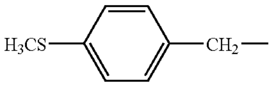 | 2 | 2 | 1 | — | H | 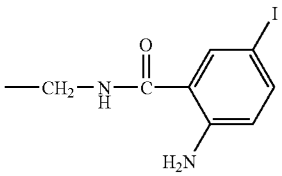 |
| 1990 | 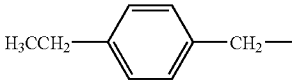 | 2 | 2 | 1 | — | H | 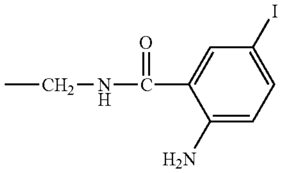 |
| 1991 | 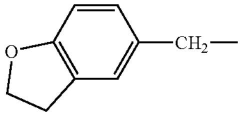 | 2 | 2 | 1 | — | H | 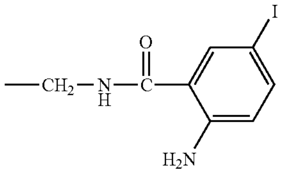 |
TABLE 1.182
| Compd. No. | 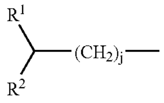 | k | m | n | chirality | $R^3$ | 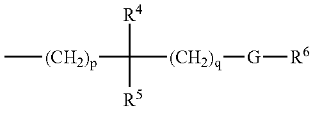 |
|---|---|---|---|---|---|---|---|
| 1992 | 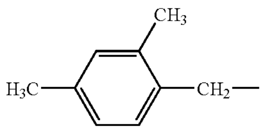 | 2 | 2 | 1 | — | H | 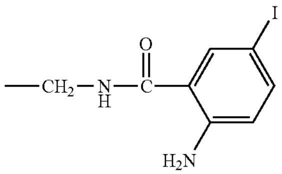 |
| 1993 | 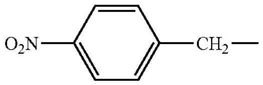 | 2 | 2 | 1 | — | H | 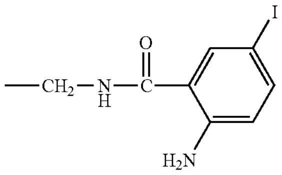 |
| 1994 | 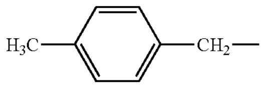 | 2 | 2 | 1 | — | H | 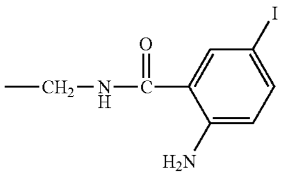 |

TABLE 1.182-continued
| Compd. No. | 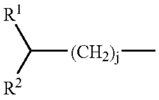 | k | m | n | chirality | $R^3$ | 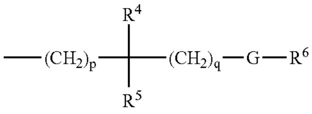 |
|---|---|---|---|---|---|---|---|
| 1995 | 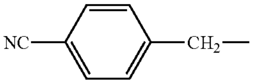 | 2 | 2 | 1 | — | H | 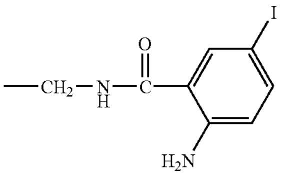 |
| 1996 | 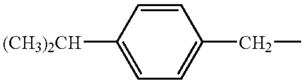 | 2 | 2 | 1 | — | H | 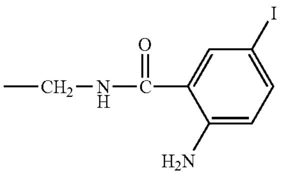 |
| 1997 | 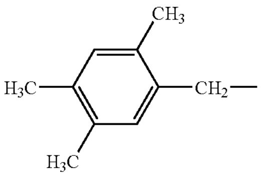 | 2 | 2 | 1 | — | H | 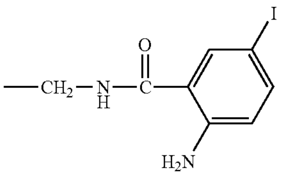 |
| 1998 | 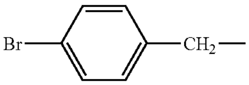 | 2 | 2 | 1 | — | H | 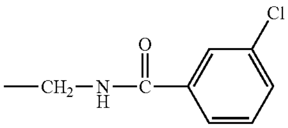 |
| 1999 | 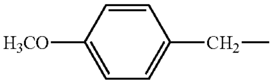 | 2 | 2 | 1 | — | H | 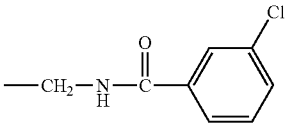 |
| 2000 | 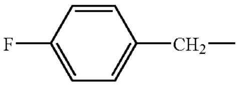 | 2 | 2 | 1 | — | H | 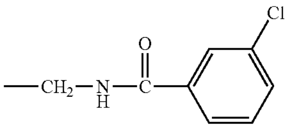 |
| 2001 | 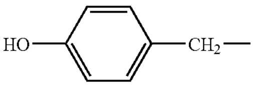 | 2 | 2 | 1 | — | H | 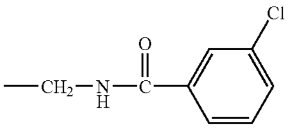 |
| 2002 | 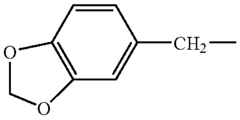 | 2 | 2 | 1 | — | H | 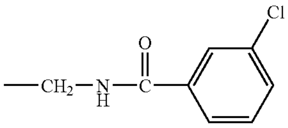 |

TABLE 1.183
| Compd. No. | 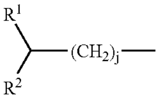 | k | m | n | chirality | $R^3$ | 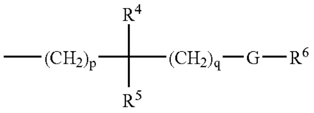 |
|---|---|---|---|---|---|---|---|
| 2003 | 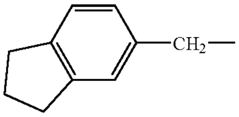 | 2 | 2 | 1 | — | H | 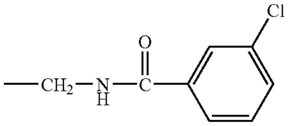 |
| 2004 | 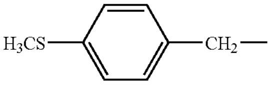 | 2 | 2 | 1 | — | H | 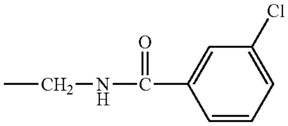 |
| 2005 | 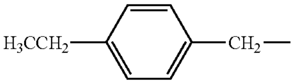 | 2 | 2 | 1 | — | H | 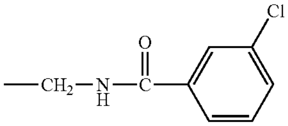 |
| 2006 | 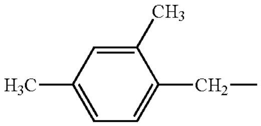 | 2 | 2 | 1 | — | H | 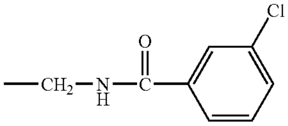 |
| 2007 | 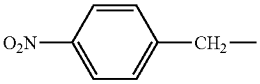 | 2 | 2 | 1 | — | H | 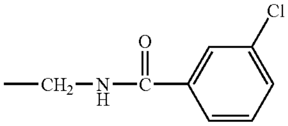 |
| 2008 | 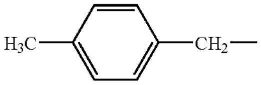 | 2 | 2 | 1 | — | H | 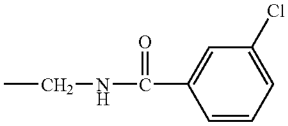 |
| 2009 | 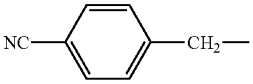 | 2 | 2 | 1 | — | H | 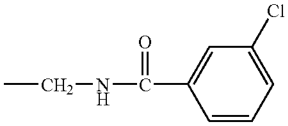 |
| 2010 | 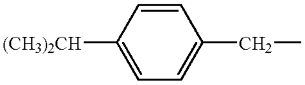 | 2 | 2 | 1 | — | H | 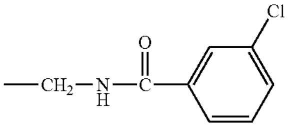 |
| 2011 | 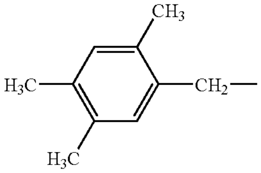 | 2 | 2 | 1 | — | H | 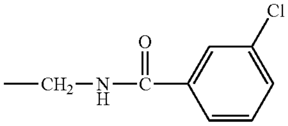 |
| 2012 | 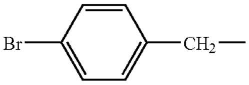 | 2 | 2 | 1 | — | H | 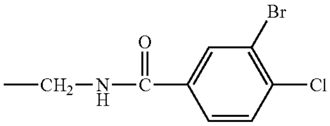 |

TABLE 1.183-continued
| Compd. No. | 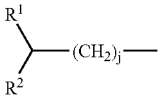 | k | m | n | chirality | $R^3$ | 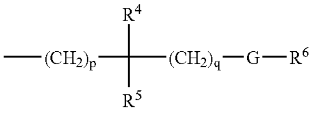 |
|---|---|---|---|---|---|---|---|
| 2013 | 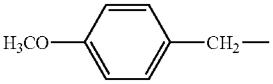 | 2 | 2 | 1 | — | H | 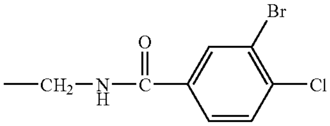 |
TABLE 1.184
| Compd. No. | 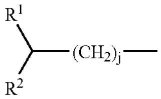 | k | m | n | chirality | $R^3$ | 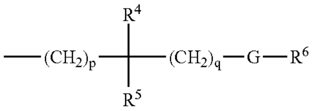 |
|---|---|---|---|---|---|---|---|
| 2014 | 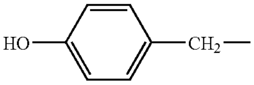 | 2 | 2 | 1 | — | H | 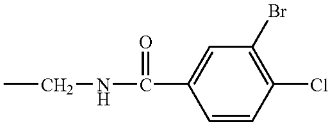 |
| 2015 | 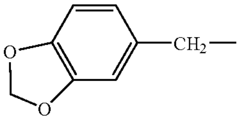 | 2 | 2 | 1 | — | H | 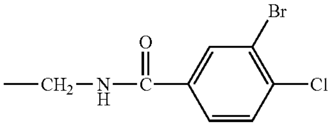 |
| 2016 | 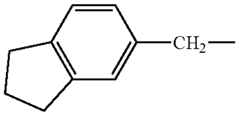 | 2 | 2 | 1 | — | H | 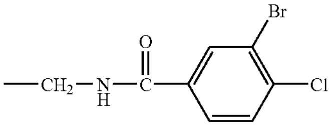 |
| 2017 | 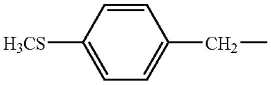 | 2 | 2 | 1 | — | H | 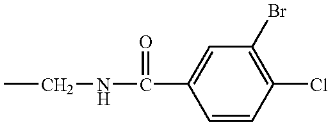 |
| 2018 | 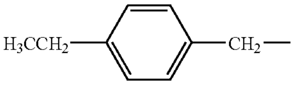 | 2 | 2 | 1 | — | H | 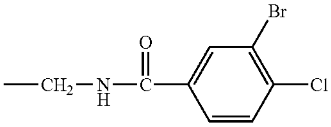 |
| 2019 | 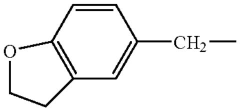 | 2 | 2 | 1 | — | H | 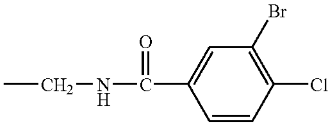 |
| 2020 | 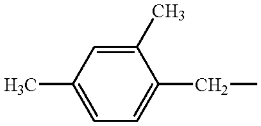 | 2 | 2 | 1 | — | H | 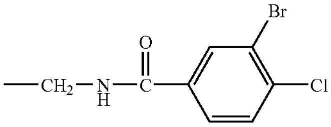 |
| 2021 | 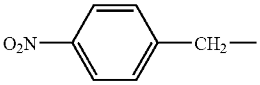 | 2 | 2 | 1 | — | H | 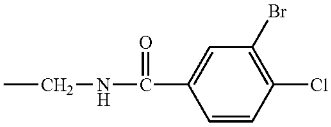 |

TABLE 1.184-continued
| Compd. No. | 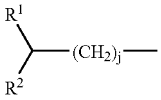 | k | m | n | chirality | $R^3$ | 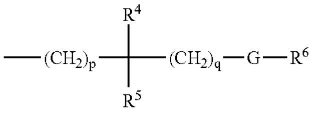 |
|---|---|---|---|---|---|---|---|
| 2022 | 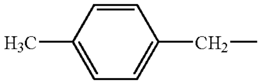 | 2 | 2 | 1 | — | H | 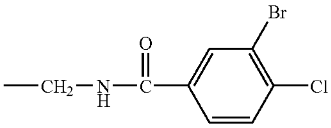 |
| 2023 | 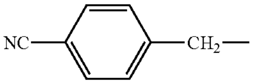 | 2 | 2 | 1 | — | H | 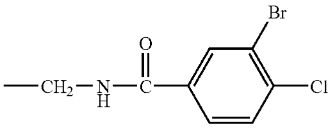 |
| 2024 | 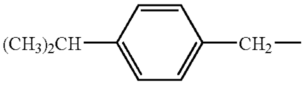 | 2 | 2 | 1 | — | H | 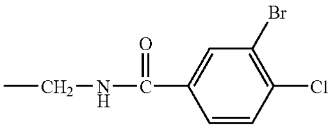 |
TABEL 1.185
| Compd. No. | 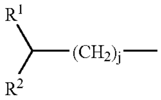 | k | m | n | chirality | $R^3$ | 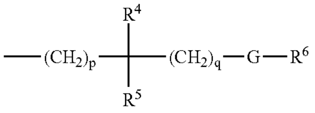 |
|---|---|---|---|---|---|---|---|
| 2025 | 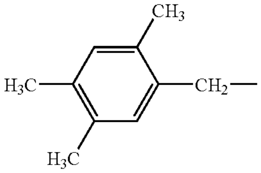 | 2 | 2 | 1 | — | H | 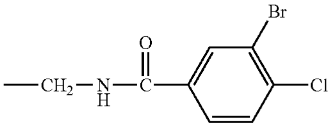 |
| 2026 | 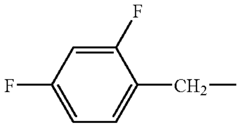 | 2 | 2 | 1 | — | H | 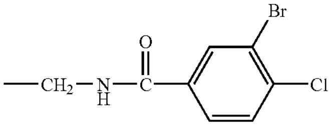 |
| 2027 | 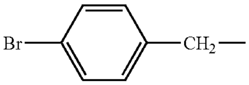 | 2 | 2 | 1 | — | H | 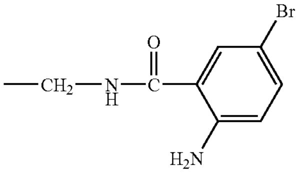 |
| 2028 | 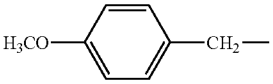 | 2 | 2 | 1 | — | H | 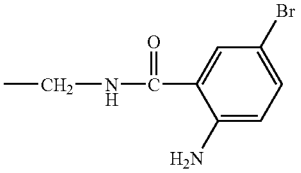 |

TABEL 1.185-continued
| Compd. No. | 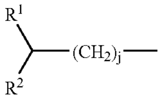 | k | m | n | chirality | $R^3$ | 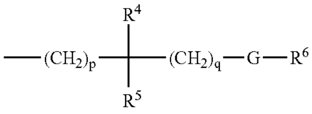 |
|---|---|---|---|---|---|---|---|
| 2029 | 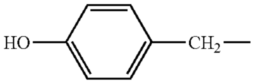 | 2 | 2 | 1 | — | H | 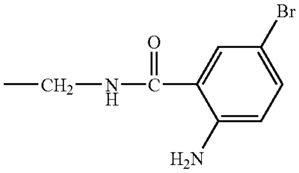 |
| 2030 | 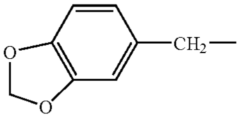 | 2 | 2 | 1 | — | H | 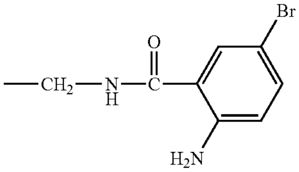 |
| 2031 | 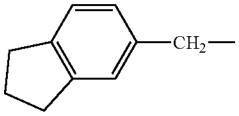 | 2 | 2 | 1 | — | H | 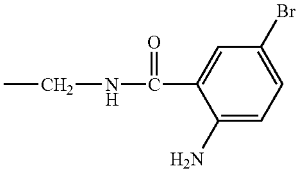 |
| 2032 | 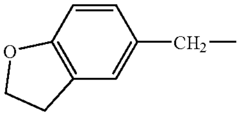 | 2 | 2 | 1 | — | H | 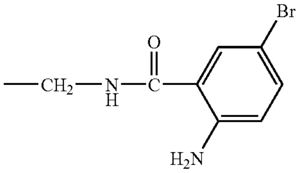 |
| 2033 | 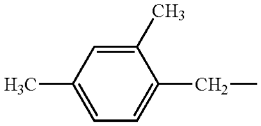 | 2 | 2 | 1 | — | H | 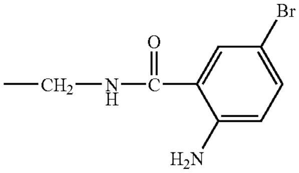 |
| 2034 | 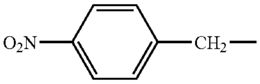 | 2 | 2 | 1 | — | H | 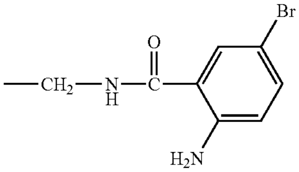 |
| 2035 | 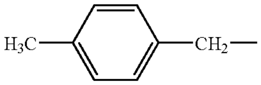 | 2 | 2 | 1 | — | H | 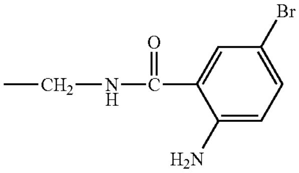 |

TABLE 1.186
| Compd. No. | 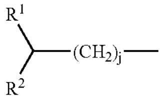 | k | m | n | chirality | $R^3$ | 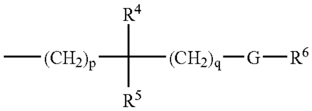 |
|---|---|---|---|---|---|---|---|
| 2036 | 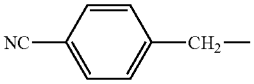 | 2 | 2 | 1 | — | H | 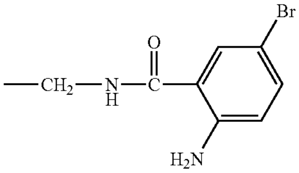 |
| 2037 | 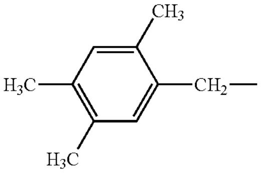 | 2 | 2 | 1 | — | H | 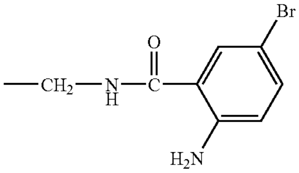 |
| 2038 | 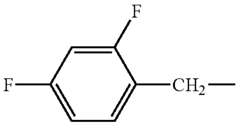 | 2 | 2 | 1 | — | H | 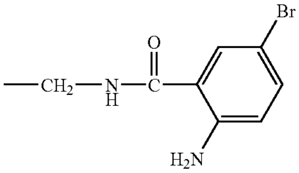 |
| 2039 | 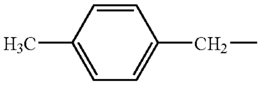 | 2 | 2 | 1 | — | H | 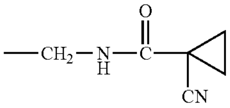 |
| 2040 | 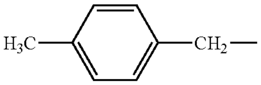 | 1 | 2 | 0 | R | H | 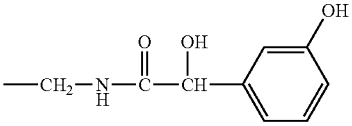 |
| 2041 | 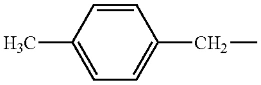 | 1 | 2 | 0 | R | H | 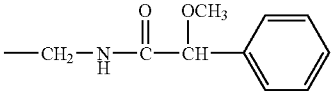 |
| 2042 | 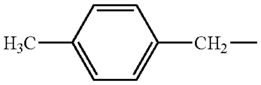 | 1 | 2 | 0 | R | H | 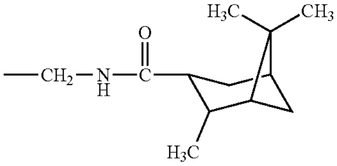 |
| 2043 | 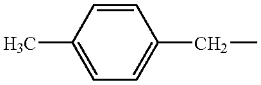 | 1 | 2 | 0 | R | H | 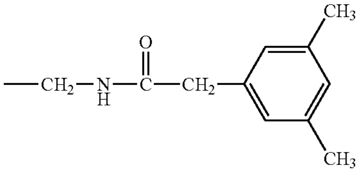 |
| 2044 | 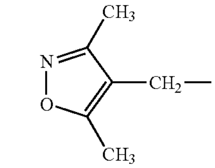 | 1 | 2 | 0 | R | H | 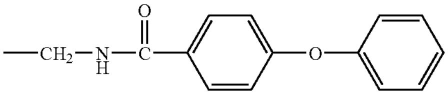 |

TABLE 1.186-continued
| Compd. No. | 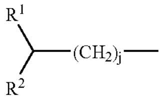 | k | m | n | chirality | $R^3$ | 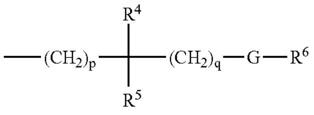 |
|---|---|---|---|---|---|---|---|
| 2045 | 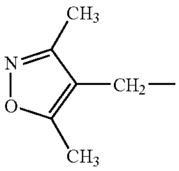 | 1 | 2 | 0 | R | H | 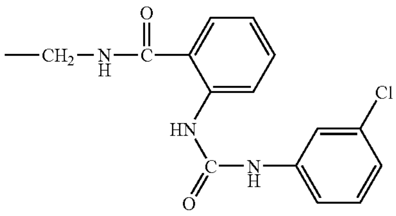 |
| 2046 | 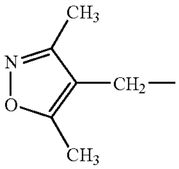 | 1 | 2 | 0 | R | H | 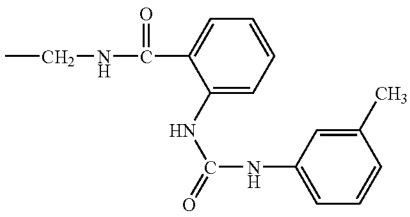 |
TABLE 1.187
| Compd. No. | 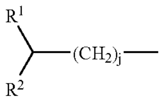 | k | m | n | chirality | $R^3$ | 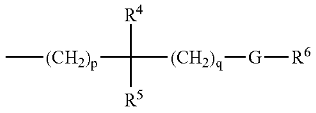 |
|---|---|---|---|---|---|---|---|
| 2047 | 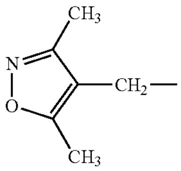 | 1 | 2 | 0 | R | H | 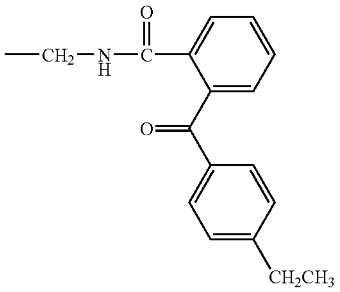 |
| 2048 | 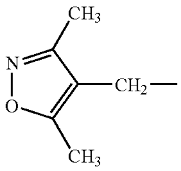 | 1 | 2 | 0 | R | H | 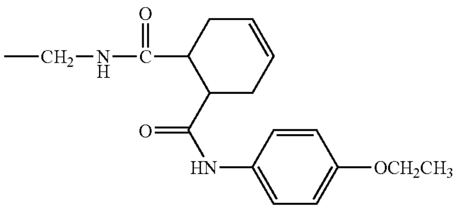 |
| 2049 | 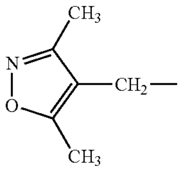 | 1 | 2 | 0 | R | H | 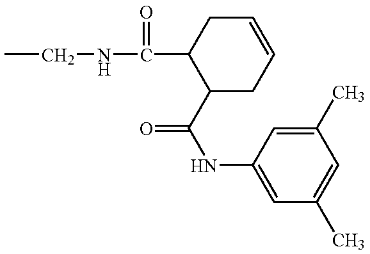 |

TABLE 1.187-continued
| Compd. No. | 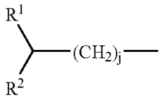 | k | m | n | chirality | $R^3$ | 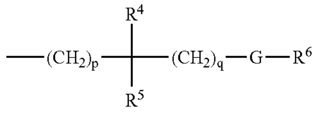 |
|---|---|---|---|---|---|---|---|
| 2050 | 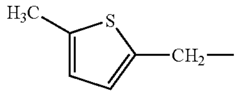 | 1 | 2 | 0 | R | H | 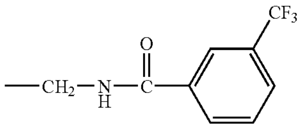 |
| 2051 | 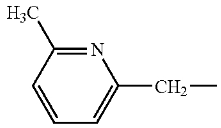 | 1 | 2 | 0 | R | H | 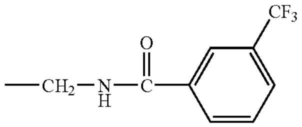 |
| 2052 | 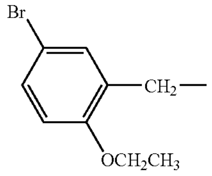 | 2 | 2 | 1 | — | H | 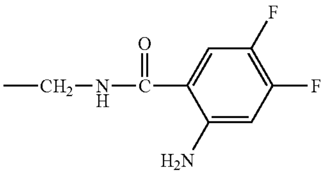 |
| 2053 | 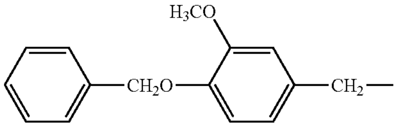 | 2 | 2 | 1 | — | H | 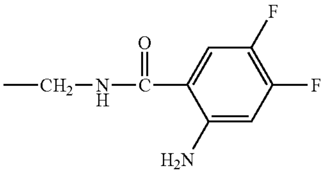 |
| 2054 | 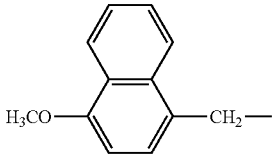 | 2 | 2 | 1 | — | H | 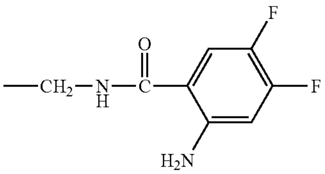 |
| 2055 | 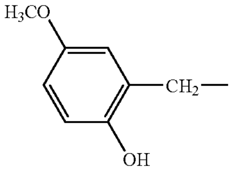 | 2 | 2 | 1 | — | H | 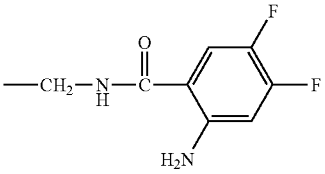 |
| 2056 | 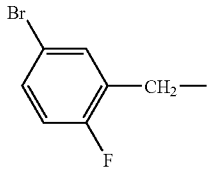 | 2 | 2 | 1 | — | H | 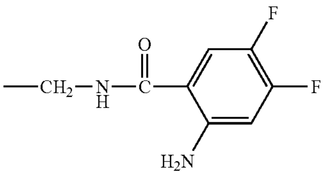 |
| 2057 | 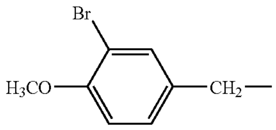 | 2 | 2 | 1 | — | H | 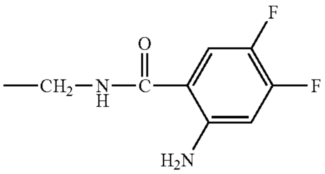 |

TABLE 1.188
| Compd. No. | 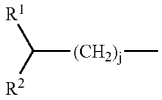 | k | m | n | chirality | $R^3$ | 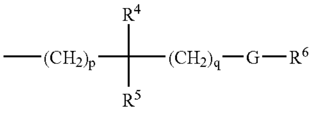 |
|---|---|---|---|---|---|---|---|
| 2058 | 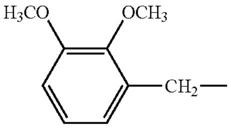 | 2 | 2 | 1 | — | H | 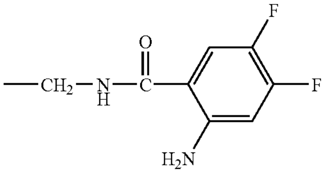 |
| 2059 | 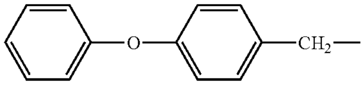 | 2 | 2 | 1 | — | H | 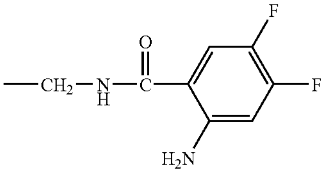 |
| 2060 | 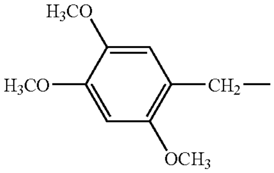 | 2 | 2 | 1 | — | H | 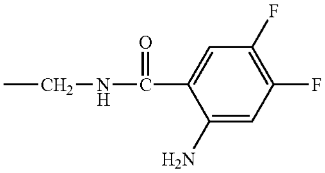 |
| 2061 | 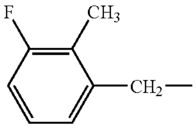 | 2 | 2 | 1 | — | H | 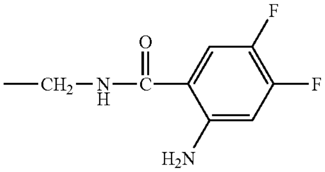 |
| 2062 | 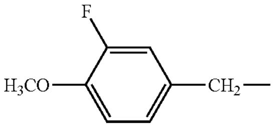 | 2 | 2 | 1 | — | H | 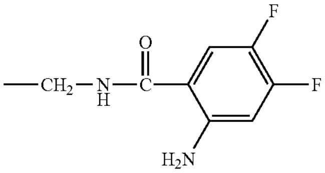 |
| 2063 | 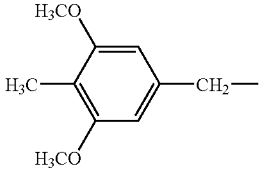 | 2 | 2 | 1 | — | H | 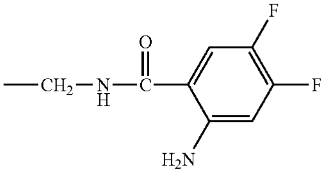 |
| 2064 | 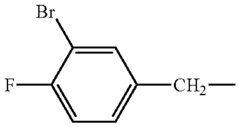 | 2 | 2 | 1 | — | H | 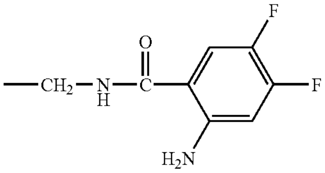 |

TABLE 1.188-continued
| Compd. No. | 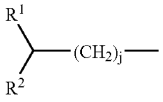 | k | m | n | chirality | $R^3$ | 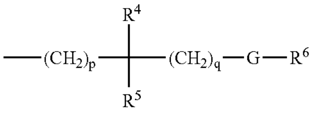 |
|---|---|---|---|---|---|---|---|
| 2065 | 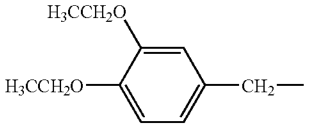 | 2 | 2 | 1 | — | H | 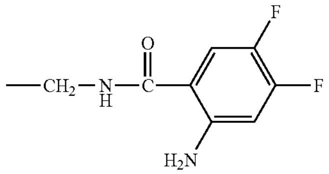 |
| 2066 | 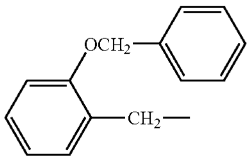 | 2 | 2 | 1 | — | H | 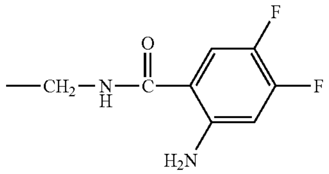 |
| 2067 | 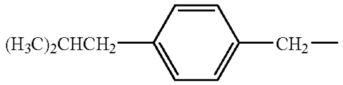 | 2 | 2 | 1 | — | H | 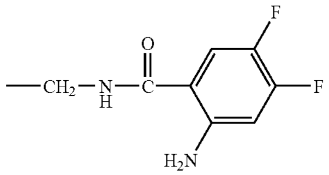 |
| 2068 | 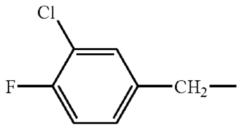 | 2 | 2 | 1 | — | H | 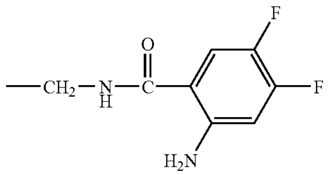 |
TABLE 1.189
| Compd. No. | 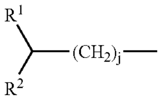 | k | m | n | chirality | $R^3$ | 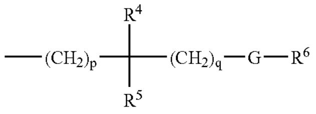 |
|---|---|---|---|---|---|---|---|
| 2069 | 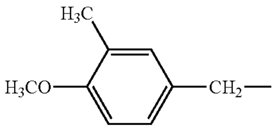 | 2 | 2 | 1 | — | H | 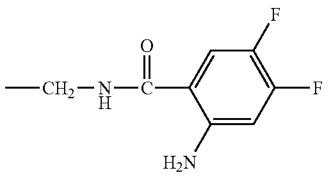 |
| 2070 | 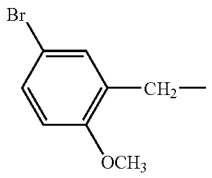 | 2 | 2 | 1 | — | H | 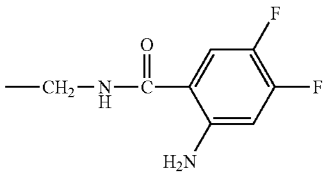 |

TABLE 1.189-continued
| Compd. No. | 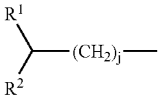 | k | m | n | chirality | $R^3$ | 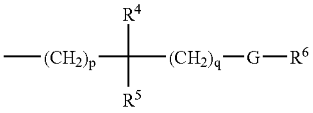 |
|---|---|---|---|---|---|---|---|
| 2071 | 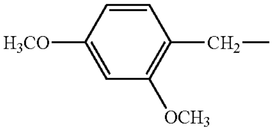 | 2 | 2 | 1 | — | H | 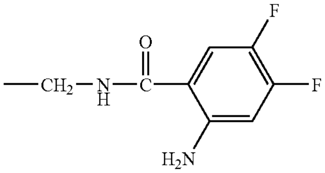 |
| 2072 | 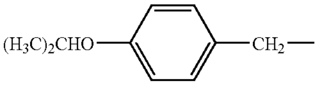 | 2 | 2 | 1 | — | H | 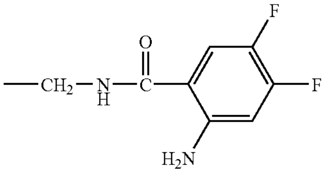 |
| 2073 | 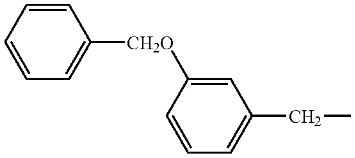 | 2 | 2 | 1 | — | H | 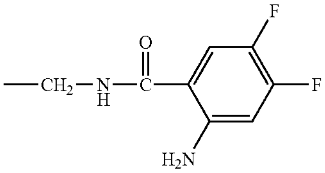 |
| 2074 | 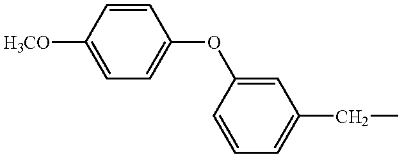 | 2 | 2 | 1 | — | H | 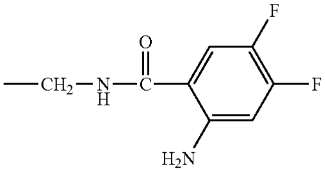 |
| 2075 | 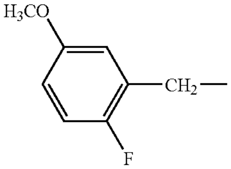 | 2 | 2 | 1 | — | H | 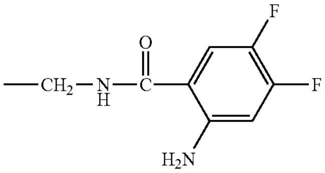 |
| 2076 | 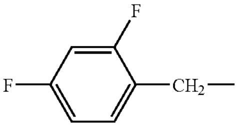 | 2 | 2 | 1 | — | H | 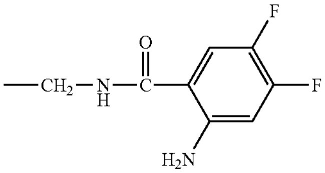 |
| 2077 | 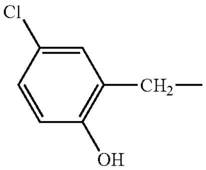 | 2 | 2 | 1 | — | H | 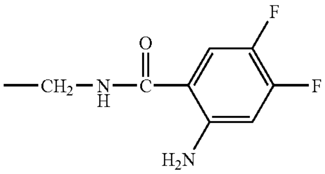 |

TABLE 1.189-continued
| Compd. No. | 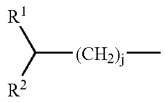 | k | m | n | chirality | $R^3$ | 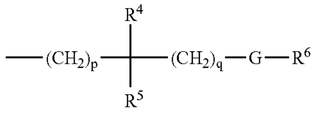 |
|---|---|---|---|---|---|---|---|
| 2078 | 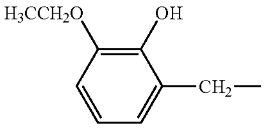 | 2 | 2 | 1 | — | H | 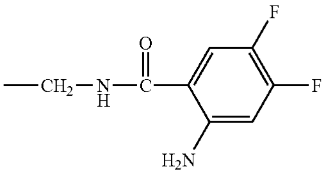 |
| 2079 | 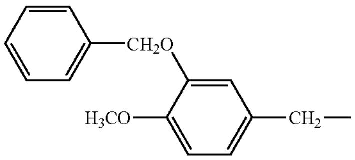 | 2 | 2 | 1 | — | H | 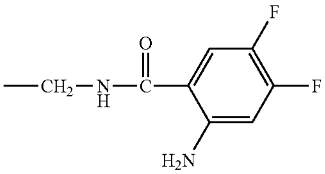 |
TABLE 1.190
| Compd. No. | 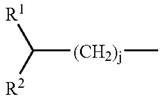 | k | m | n | chirality | $R^3$ | 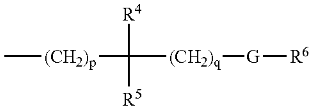 |
|---|---|---|---|---|---|---|---|
| 2080 | 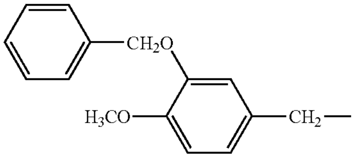 | 2 | 2 | 1 | — | H | 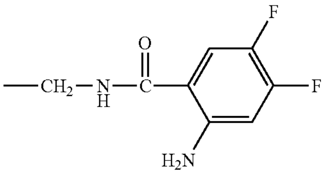 |
| 2081 | 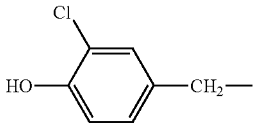 | 2 | 2 | 1 | — | H | 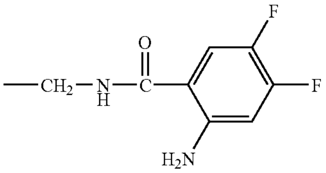 |
| 2082 | 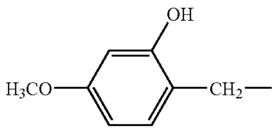 | 2 | 2 | 1 | — | H | 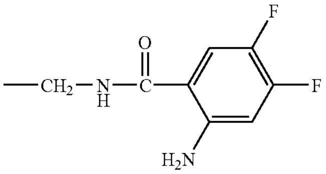 |
| 2083 | 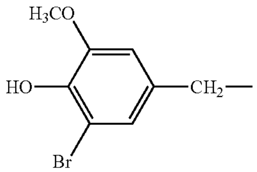 | 1 | 2 | 0 | R | H | 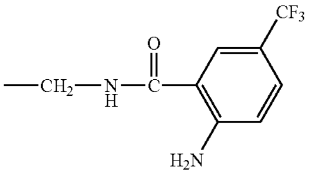 |

TABLE 1.190-continued
| Compd. No. | 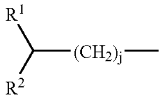 | k | m | n | chirality | $R^3$ | 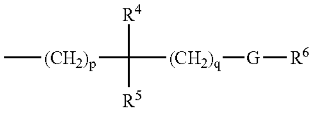 |
|---|---|---|---|---|---|---|---|
| 2084 | 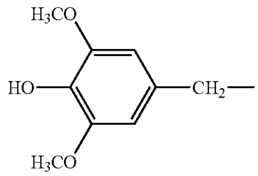 | 1 | 2 | 0 | R | H | 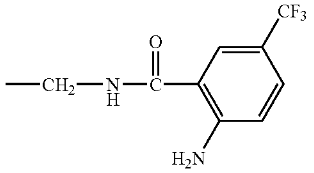 |
| 2085 | 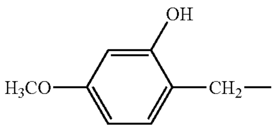 | 1 | 2 | 0 | R | H | 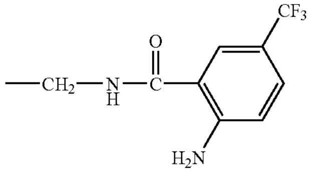 |
| 2086 | 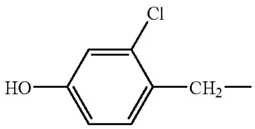 | 1 | 2 | 0 | R | H | 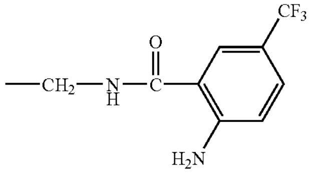 |
| 2087 | 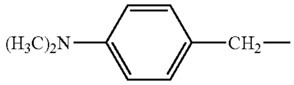 | 1 | 2 | 0 | R | H | 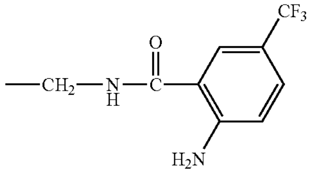 |
| 2088 | 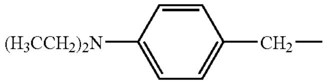 | 1 | 2 | 0 | R | H | 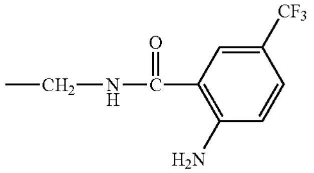 |
| 2089 | 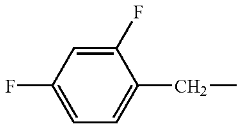 | 1 | 2 | 0 | R | H | 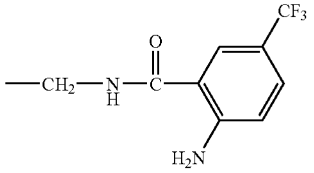 |
| 2090 | 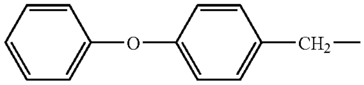 | 1 | 2 | 0 | R | H | 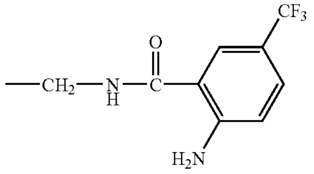 |

TABLE 1.191
| Compd. No. | 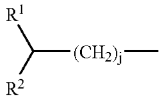 | k | m | n | chirality | $R^3$ | 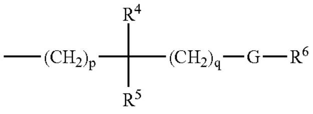 |
|---|---|---|---|---|---|---|---|
| 2091 | 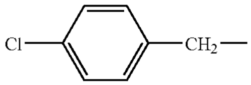 | 2 | 2 | 1 | — | H | 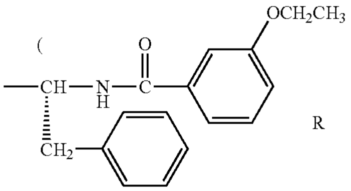 |
| 2092 | 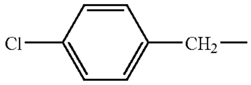 | 2 | 2 | 1 | — | H | 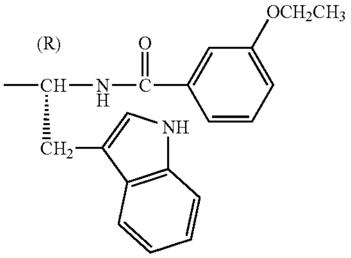 |
| 2093 | 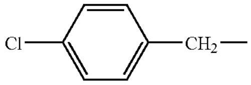 | 2 | 2 | 1 | — | H | 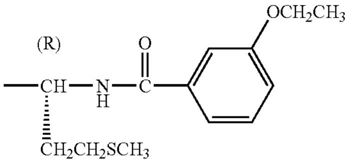 |
| 2094 | 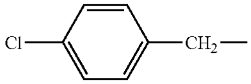 | 2 | 2 | 1 | — | H | 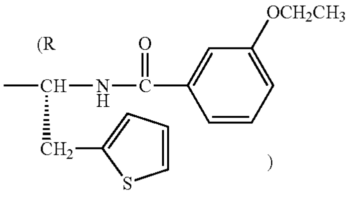 |
| 2095 | 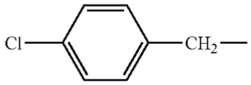 | 2 | 2 | 1 | — | H | 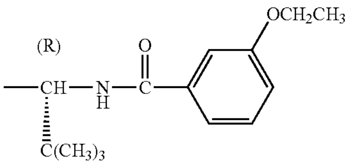 |
| 2096 | 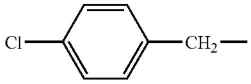 | 2 | 2 | 1 | — | H | 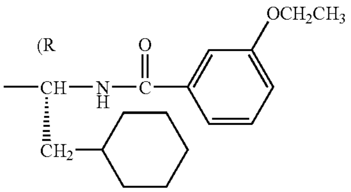 |
| 2097 | 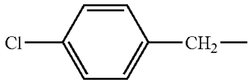 | 2 | 2 | 1 | — | H | 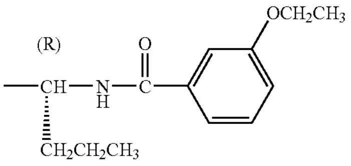 |

TABLE 1.191-continued
| Compd. No. | 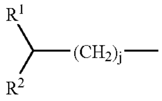 | k | m | n | chirality | $R^3$ | 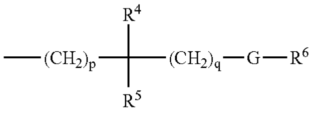 |
|---|---|---|---|---|---|---|---|
| 2098 | 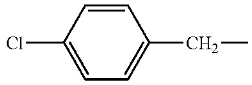 | 2 | 2 | 1 | — | H | 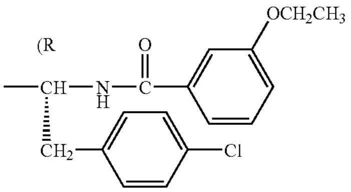 |
| 2099 | 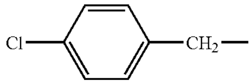 | 2 | 2 | 1 | — | H | 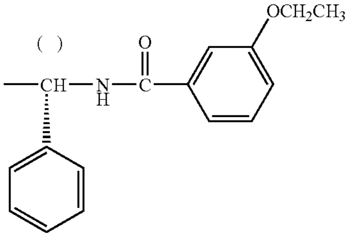 |
| 2100 | 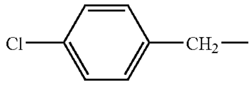 | 2 | 2 | 1 | — | H | 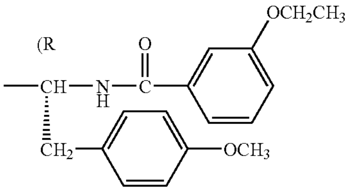 |
| 2101 | 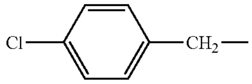 | 2 | 2 | 1 | — | H | 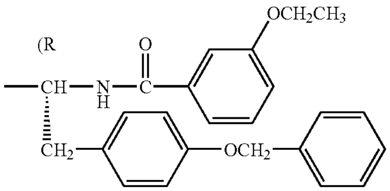 |
TABLE 1.192
| Compd. No. | 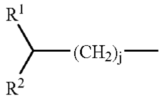 | k | m | n | chirality | $R^3$ | 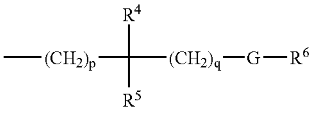 |
|---|---|---|---|---|---|---|---|
| 2102 | 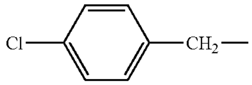 | 2 | 2 | 1 | — | H | 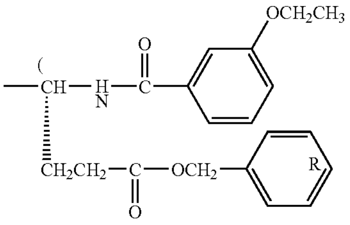 |

TABLE 1.192-continued
| Compd. No. | 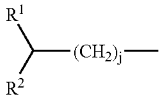 | k | m | n | chirality | $R^3$ | 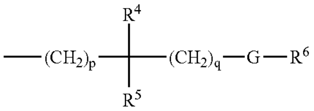 |
|---|---|---|---|---|---|---|---|
| 2103 | 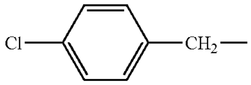 | 2 | 2 | 1 | — | H | 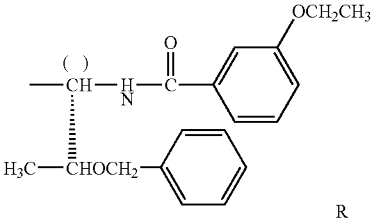 R |
| 2104 | 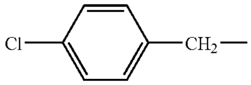 | 2 | 2 | 1 | — | H | 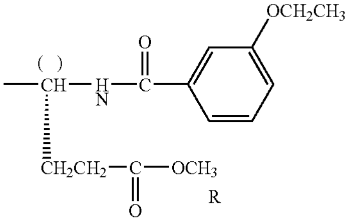 R |
| 2105 | 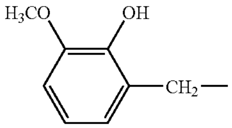 | 2 | 2 | 1 | — | H | 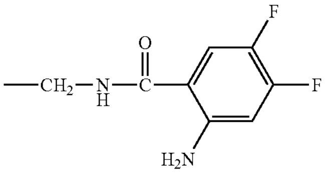 |
| 2106 | 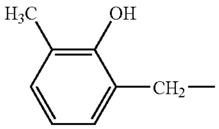 | 2 | 2 | 1 | — | H | 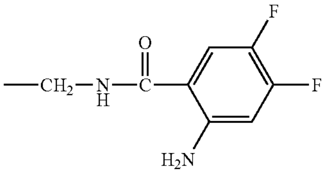 |
| 2107 | 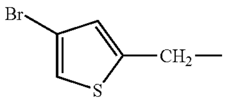 | 2 | 2 | 1 | — | H | 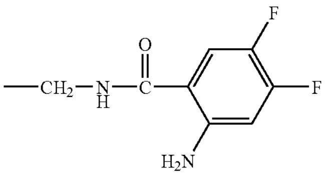 |
| 2108 | 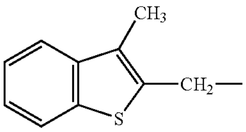 | 2 | 2 | 1 | — | H | 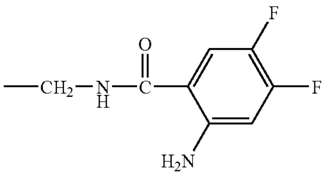 |
| 2109 | 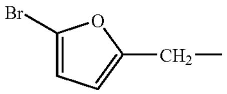 | 2 | 2 | 1 | — | H | 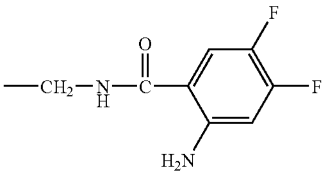 |

TABLE 1.192-continued
| Compd. No. | 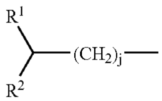 | k | m | n | chirality | $R^3$ | 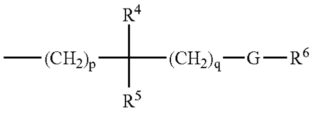 |
|---|---|---|---|---|---|---|---|
| 2110 | 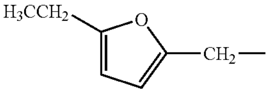 | 2 | 2 | 1 | — | H | 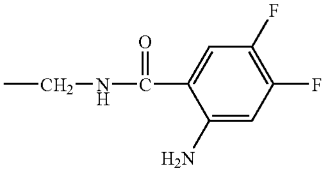 |
| 2111 | 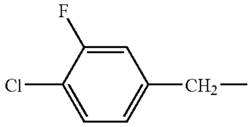 | 2 | 2 | 1 | — | H | 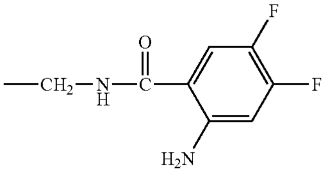 |
| 2112 | 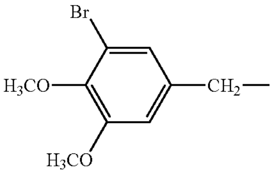 | 2 | 2 | 1 | — | H | 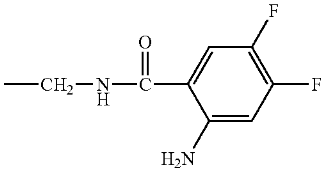 |
TABLE 1.193
| Compd. No. | 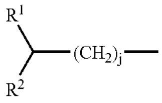 | k | m | n | chirality | $R^3$ | 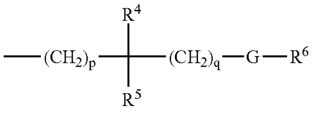 |
|---|---|---|---|---|---|---|---|
| 2113 | 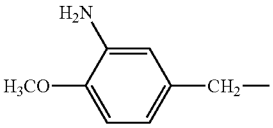 | 2 | 2 | 1 | — | H | 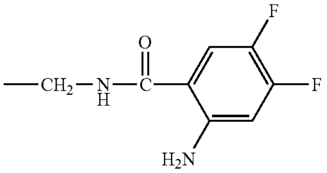 |
| 2114 | 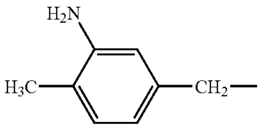 | 2 | 2 | 1 | — | H | 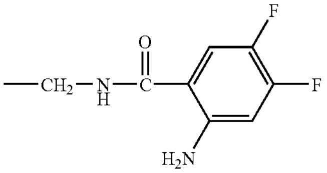 |
| 2115 | 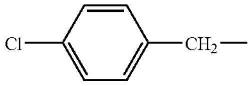 | 2 | 2 | 1 | — | H | 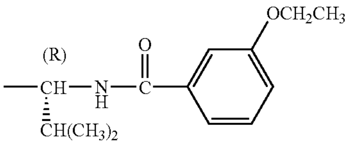 |
| 2116 | 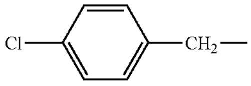 | 2 | 2 | 1 | — | H | 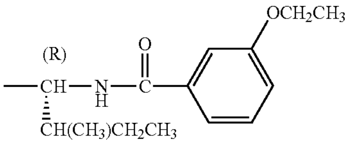 |

TABLE 1.193-continued
| Compd. No. | 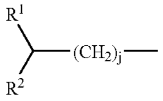 | k | m | n | chirality | $R^3$ | 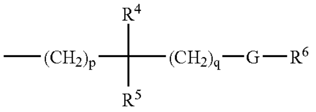 |
|---|---|---|---|---|---|---|---|
| 2117 | 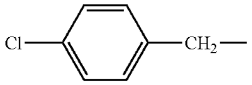 | 2 | 2 | 1 | — | H | 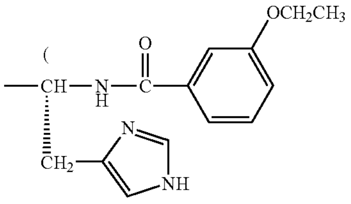 |
| 2118 | 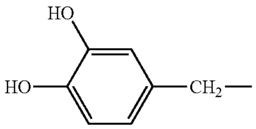 | 1 | 2 | 0 | R | H | 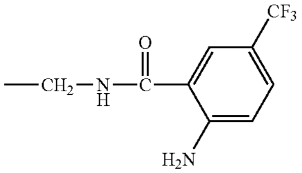 |
| 2119 | 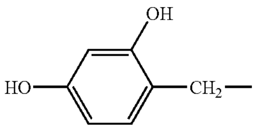 | 1 | 2 | 0 | R | H | 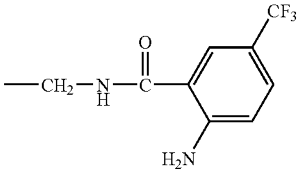 |
| 2120 | 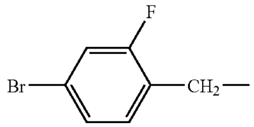 | 1 | 2 | 0 | R | H | 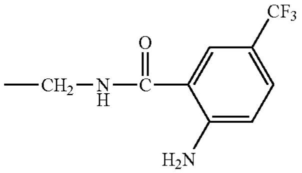 |
| 2121 | 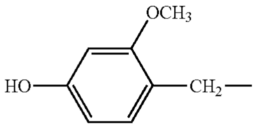 | 1 | 2 | 0 | R | H | 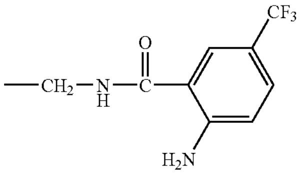 |
| 2122 | 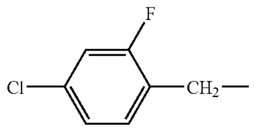 | 1 | 2 | 0 | R | H | 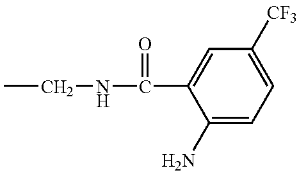 |
| 2123 | 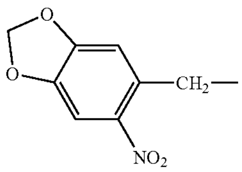 | 1 | 2 | 0 | R | H | 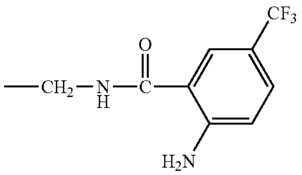 |

TABLE 1.194
| Compd. No. | 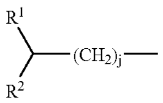 | k | m | n | chirality | $R^3$ | 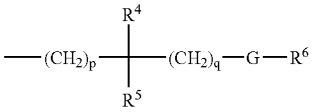 |
|---|---|---|---|---|---|---|---|
| 2124 | 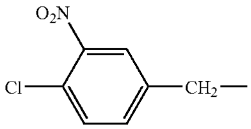 | 1 | 2 | 0 | R | H | 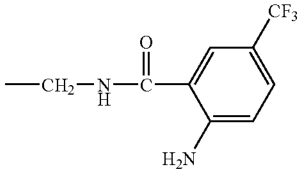 |
| 2125 | 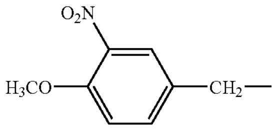 | 1 | 2 | 0 | R | H | 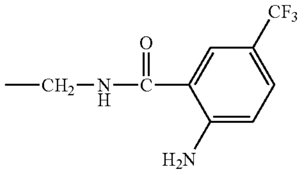 |
| 2126 | 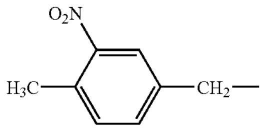 | 1 | 2 | 0 | R | H | 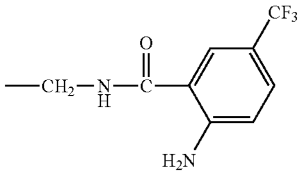 |
| 2127 | 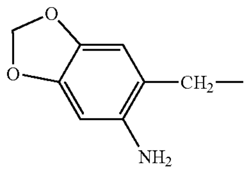 | 1 | 2 | 0 | R | H | 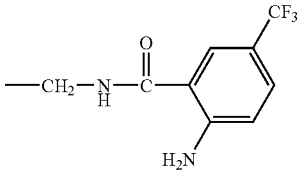 |
| 2128 | 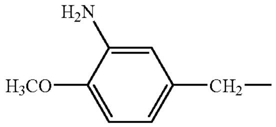 | 1 | 2 | 0 | R | H | 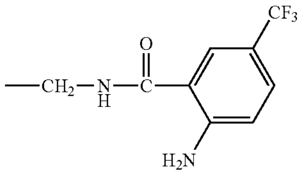 |
| 2129 | 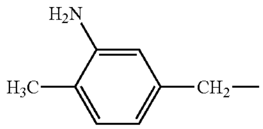 | 1 | 2 | 0 | R | H | 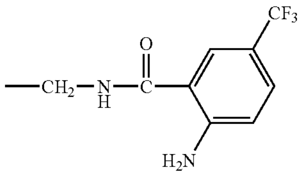 |
| 2130 | 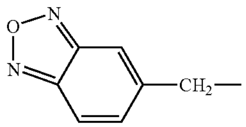 | 2 | 2 | 1 | — | H | 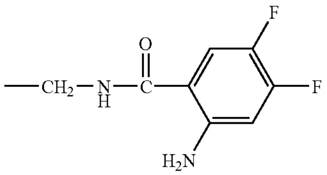 |
| 2131 | 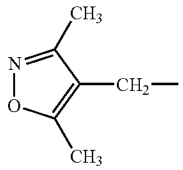 | 2 | 2 | 1 | — | H | 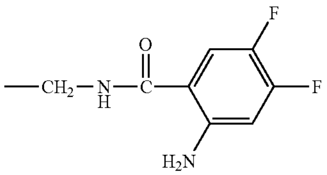 |

TABLE 1.194-continued
| Compd. No. | 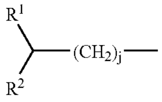 | k | m | n | chirality | $R^3$ | 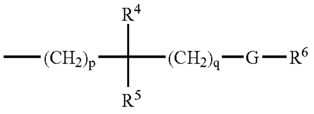 |
|---|---|---|---|---|---|---|---|
| 2132 | 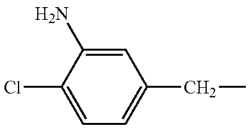 | 1 | 2 | 0 | R | H | 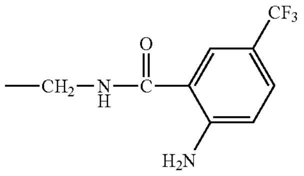 |
| 2133 | 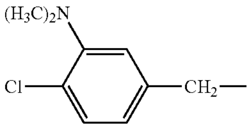 | 1 | 2 | 0 | R | H | 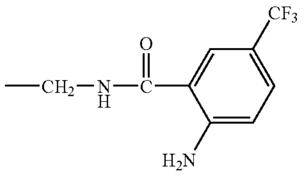 |
| 2134 | 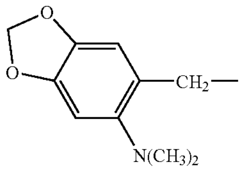 | 1 | 2 | 0 | R | H | 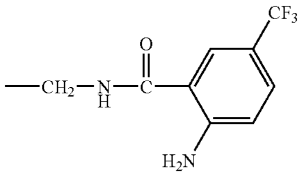 |
TABLE 1.195
| Compd. No. | 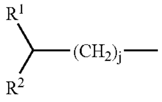 | k | m | n | chirality | $R^3$ | 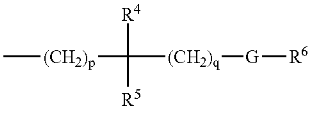 |
|---|---|---|---|---|---|---|---|
| 2135 | 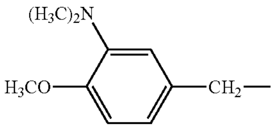 | 1 | 2 | 0 | R | H | 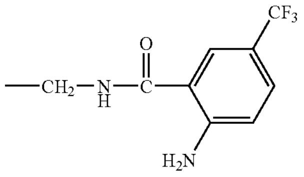 |
| 2136 | 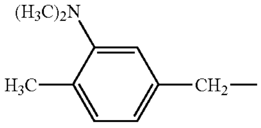 | 1 | 2 | 0 | R | H | 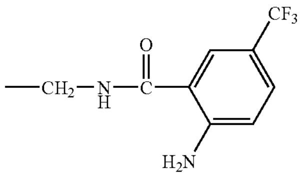 |
| 2137 | 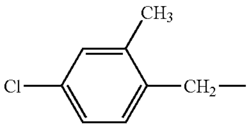 | 1 | 2 | 0 | R | H | 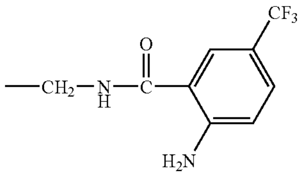 |

TABLE 1.195-continued
| Compd. No. | 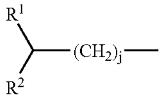 | k | m | n | chirality | $R^3$ | 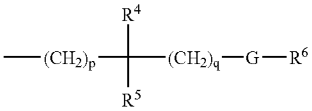 |
|---|---|---|---|---|---|---|---|
| 2138 | 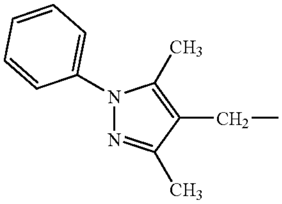 | 1 | 2 | 0 | R | H | 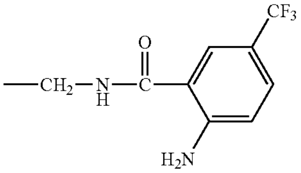 |
| 2139 | 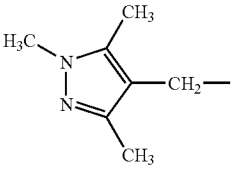 | 1 | 2 | 0 | R | H | 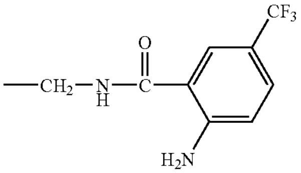 |
| 2140 | 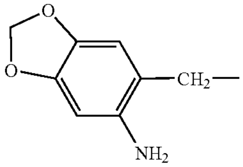 | 2 | 2 | 1 | — | H | 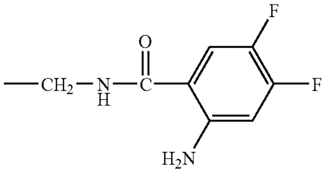 |
| 2141 | 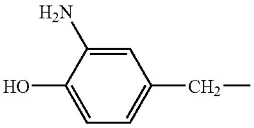 | 2 | 2 | 1 | — | H | 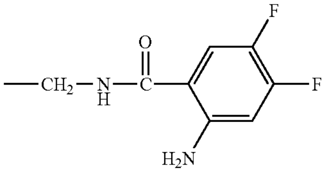 |
| 2142 | 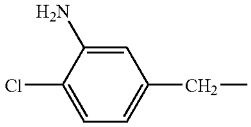 | 2 | 2 | 1 | — | H | 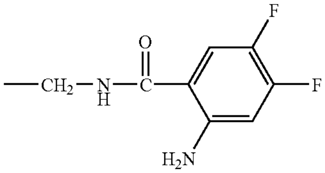 |
| 2143 | 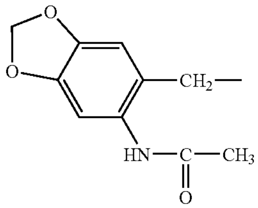 | 2 | 2 | 1 | — | H | 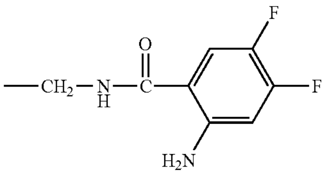 |
| 2144 | 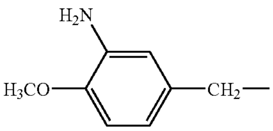 | 2 | 2 | 1 | — | H | 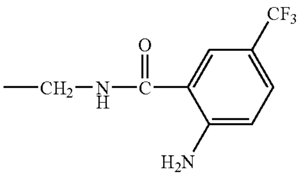 |

TABLE 1.195-continued
| Compd. No. | 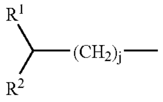 | k | m | n | chirality | $R^3$ | 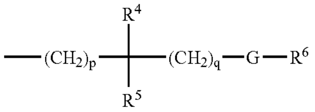 |
|---|---|---|---|---|---|---|---|
| 2145 | 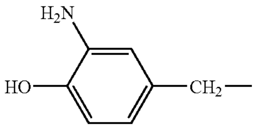 | 2 | 2 | 1 | — | H | 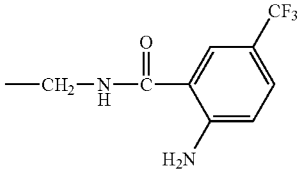 |
TABLE 1.196
| Compd. No. | 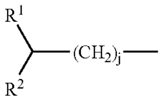 | k | m | n | chirality | $R^3$ | 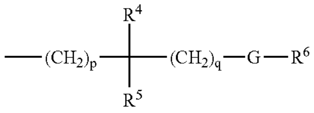 |
|---|---|---|---|---|---|---|---|
| 2146 | 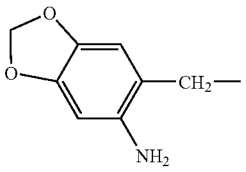 | 2 | 2 | 1 | — | H | 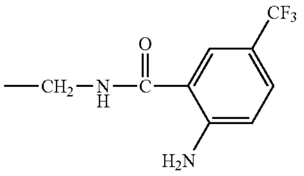 |
| 2147 | 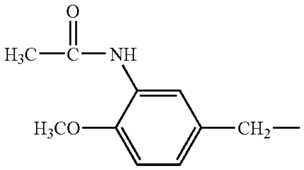 | 2 | 2 | 1 | — | H | 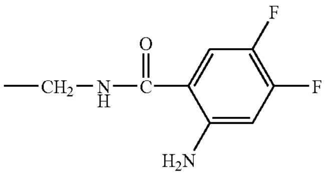 |
| 2148 | 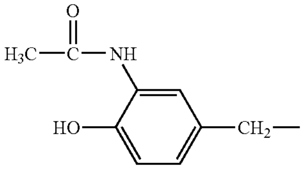 | 2 | 2 | 1 | — | H | 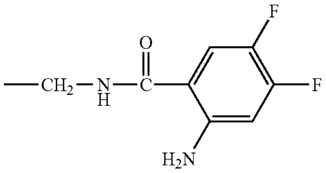 |
| 2149 | 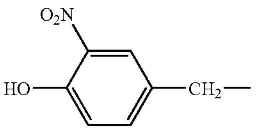 | 1 | 2 | 0 | R | H | 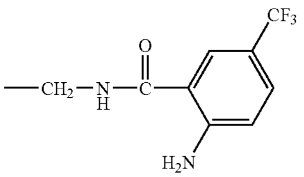 |
| 2150 | 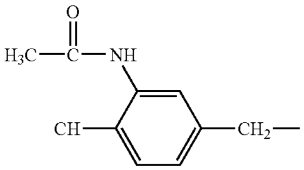 | 1 | 2 | 0 | R | H | 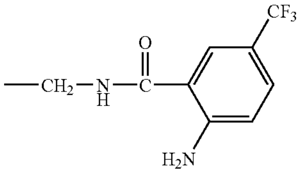 |

TABLE 1.196-continued
| Compd. No. | 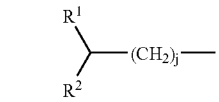 | k | m | n | chirality | $R^3$ | 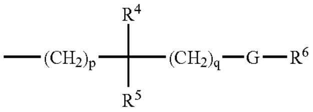 |
|---|---|---|---|---|---|---|---|
| 2151 | 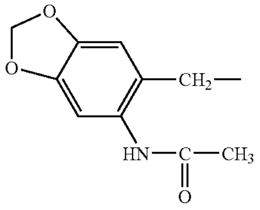 | 1 | 2 | 0 | R | H | 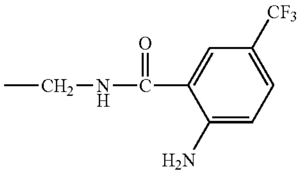 |
| 2152 | 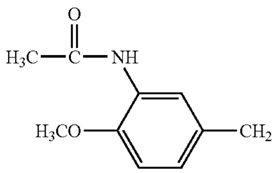 | 1 | 2 | 0 | R | H | 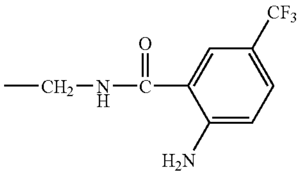 |
| 2153 | 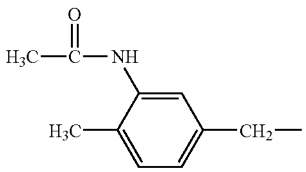 | 1 | 2 | 0 | R | H | 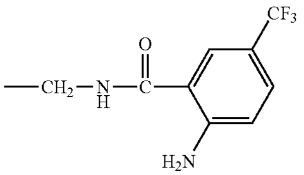 |
| 2154 | 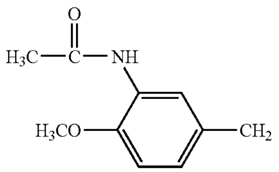 | 2 | 2 | 1 | — | H | 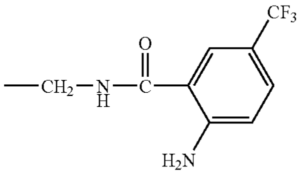 |
| 2155 | 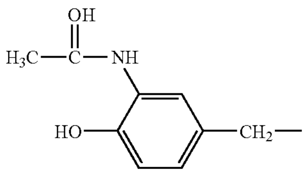 | 2 | 2 | 1 | — | H | 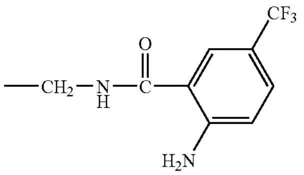 |
| 2156 | 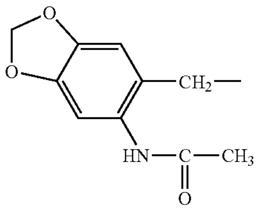 | 2 | 2 | 1 | — | H | 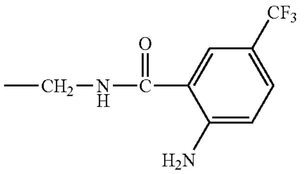 |

TABLE 1.197
| Compd. No. | 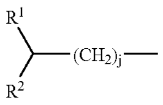 | k | m | n | chirality | $R^3$ | 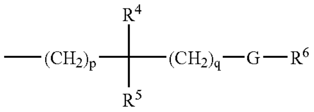 |
|---|---|---|---|---|---|---|---|
| 2157 | 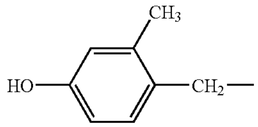 | 1 | 2 | 0 | R | H | 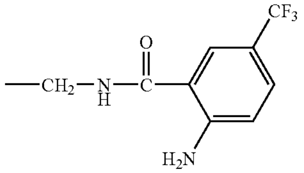 |
| 2158 | 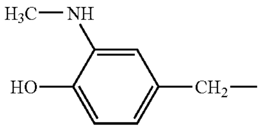 | 1 | 2 | 0 | R | H | 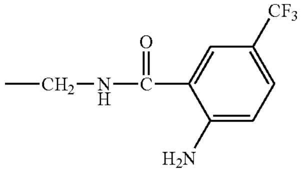 |
| 2159 | 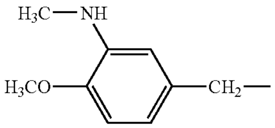 | 2 | 2 | 1 | — | H | 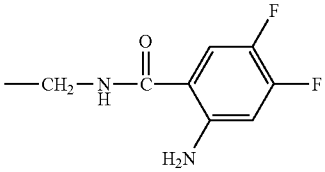 |
| 2160 | 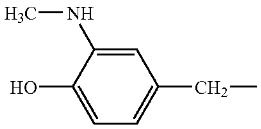 | 2 | 2 | 1 | — | H | 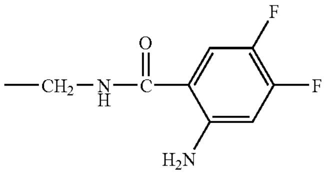 |
| 2161 | 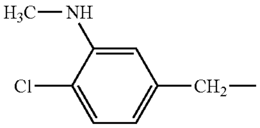 | 2 | 2 | 1 | — | H | 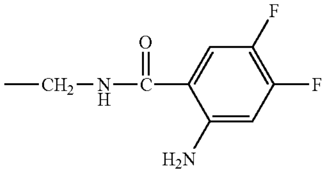 |
| 2162 | 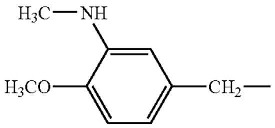 | 2 | 2 | 1 | — | H | 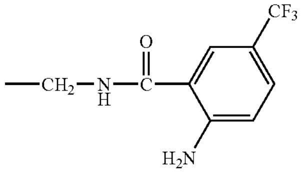 |
| 2163 | 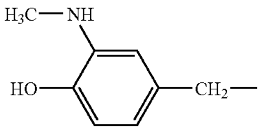 | 2 | 2 | 1 | — | H | 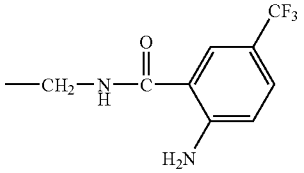 |
| 2164 | 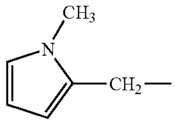 | 1 | 2 | 0 | R | H | 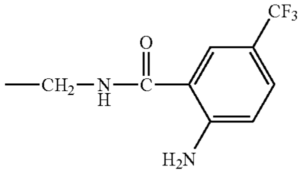 |

TABLE 1.197-continued
| Compd. No. | 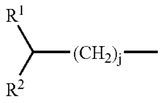 | k | m | n | chirality | $R^3$ | 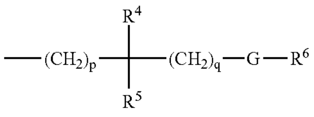 |
|---|---|---|---|---|---|---|---|
| 2165 | 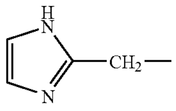 | 1 | 2 | 0 | R | H | 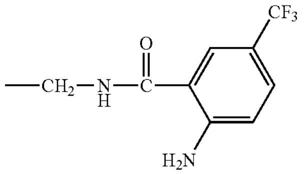 |
| 2166 | 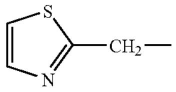 | 1 | 2 | 0 | R | H | 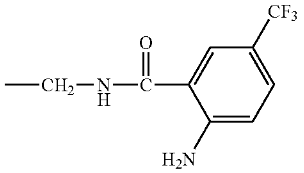 |
| 2167 | 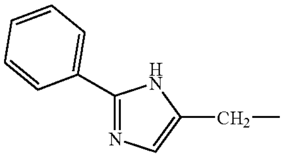 | 1 | 2 | 0 | R | H | 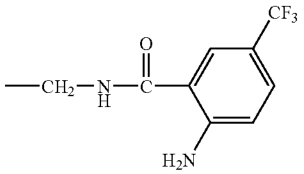 |
TABLE 1.198
| Compd. No. | 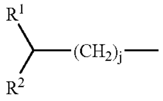 | k | m | n | chirality | $R^3$ | 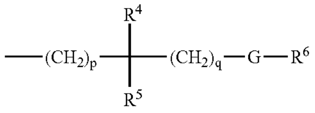 |
|---|---|---|---|---|---|---|---|
| 2168 | 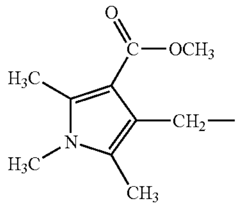 | 1 | 2 | 0 | R | H | 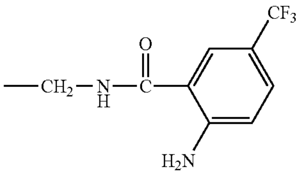 |
| 2169 | 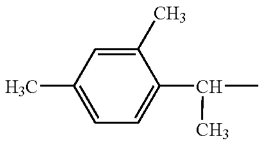 | 1 | 2 | 0 | R | H | 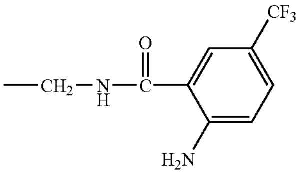 |
| 2170 | 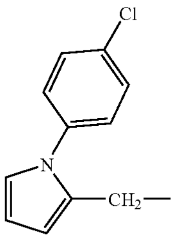 | 1 | 2 | 0 | R | H | 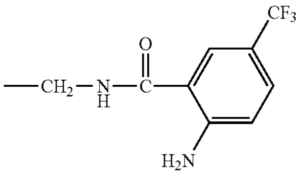 |

TABLE 1.198-continued
| Compd. No. | 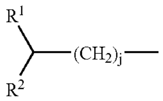 | k | m | n | chirality | $R^3$ | 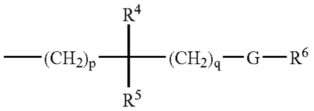 |
|---|---|---|---|---|---|---|---|
| 2171 | 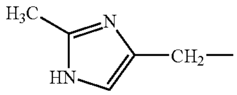 | 1 | 2 | 0 | R | H | 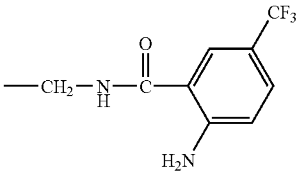 |
| 2172 | 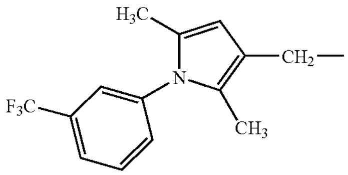 | 1 | 2 | 0 | R | H | 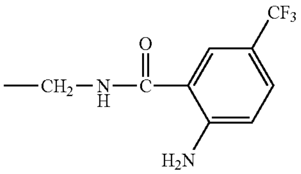 |
| 2173 | 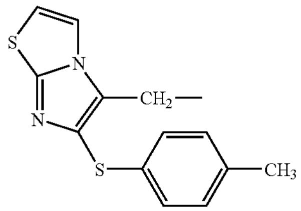 | 1 | 2 | 0 | R | H | 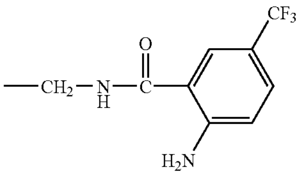 |
| 2174 | 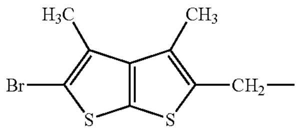 | 1 | 2 | 0 | R | H | 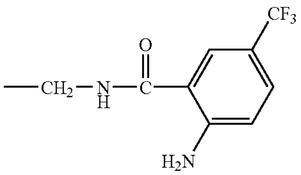 |
| 2175 | 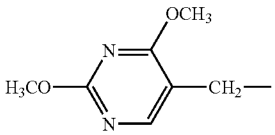 | 1 | 2 | 0 | R | H | 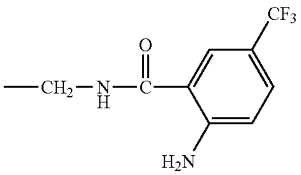 |
| 2176 | 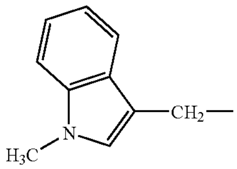 | 1 | 2 | 0 | R | H | 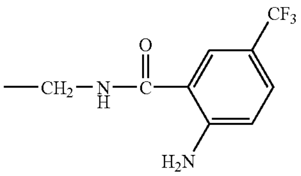 |
| 2177 | 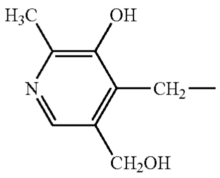 | 1 | 2 | 0 | R | H | 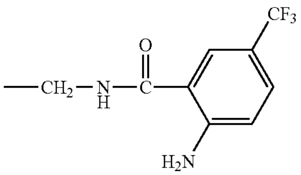 |

TABLE 1.198-continued
| Compd. No. | 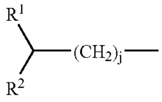 | k | m | n | chirality | $R^3$ | 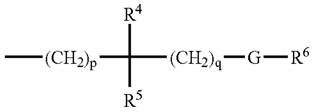 |
|---|---|---|---|---|---|---|---|
| 2178 | 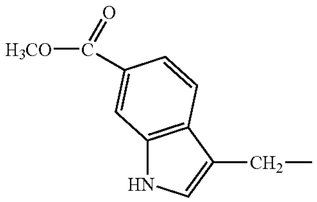 | 1 | 2 | 0 | R | H | 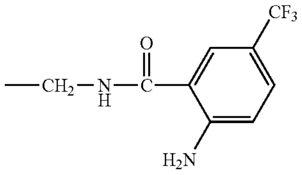 |
TABLE 1.199
| Compd. No. | 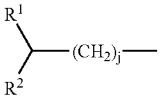 | k | m | n | chirality | $R^3$ | 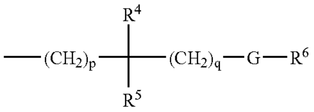 |
|---|---|---|---|---|---|---|---|
| 2179 | 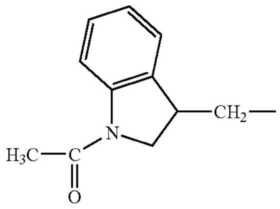 | 1 | 2 | 0 | R | H | 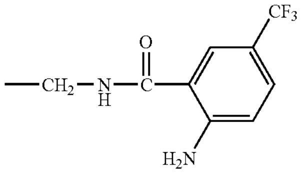 |
| 2180 | 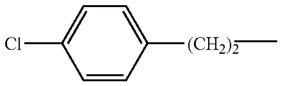 | 1 | 2 | 0 | R | H | 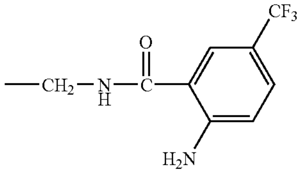 |
| 2181 | 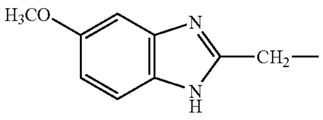 | 1 | 2 | 0 | R | H | 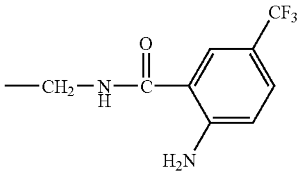 |
| 2182 | 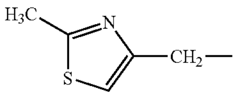 | 1 | 2 | 0 | R | H | 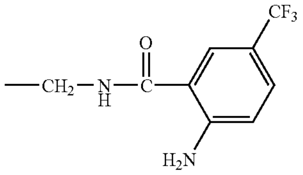 |
| 2183 | 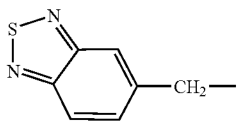 | 1 | 2 | 0 | R | H | 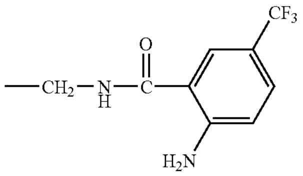 |

TABLE 1.199-continued
| Compd. No. | 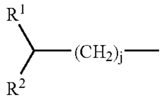 | k | m | n | chirality | $R^3$ | 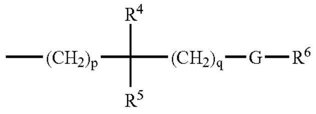 |
|---|---|---|---|---|---|---|---|
| 2184 | 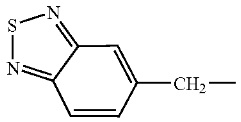 | 2 | 2 | 1 | — | H | 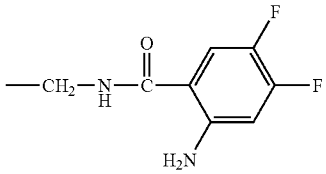 |
| 2185 | 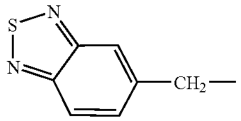 | 2 | 2 | 1 | — | H | 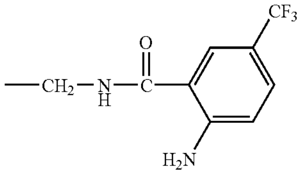 |
| 2186 | 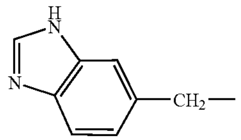 | 2 | 2 | 1 | — | H | 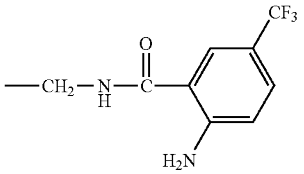 |
| 2187 | 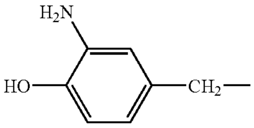 | 1 | 2 | 0 | R | H | 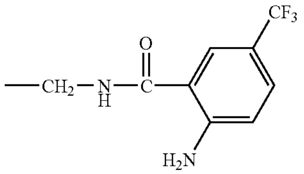 |
| 2188 | 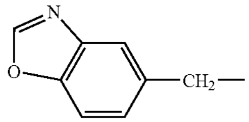 | 2 | 2 | 1 | — | H | 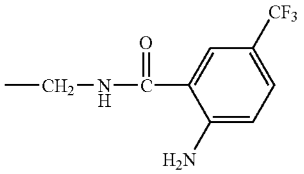 |
| 2189 | 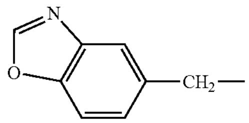 | 1 | 2 | 0 | R | H | 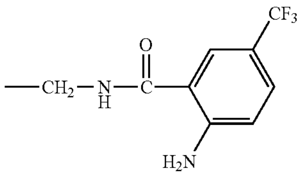 |

TABLE 1.200
| Compd. No. | 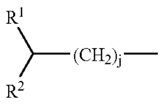 | k | m | n | chirality | $R^3$ | 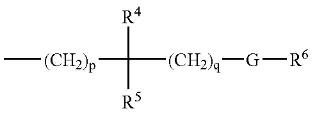 |
|---|---|---|---|---|---|---|---|
| 2190 | 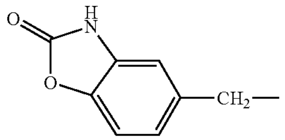 | 2 | 2 | 1 | — | H | 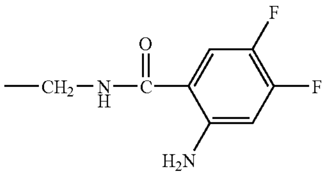 |
| 2191 | 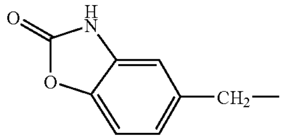 | 2 | 2 | 1 | — | H | 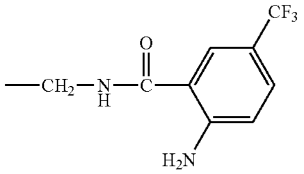 |
| 2192 | 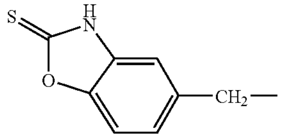 | 2 | 2 | 1 | — | H | 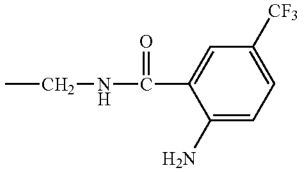 |
| 2193 | 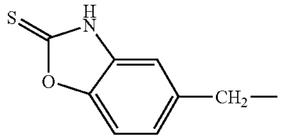 | 2 | 2 | 1 | — | H | 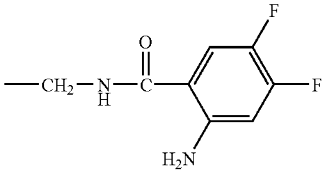 |
| 2194 | 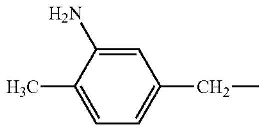 | 2 | 2 | 1 | — | H | 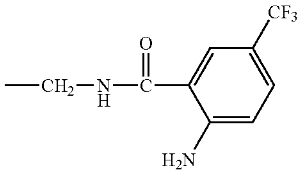 |
| 2195 | 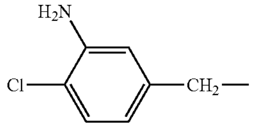 | 2 | 2 | 1 | — | H | 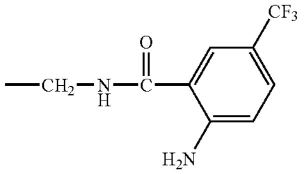 |
| 2196 | 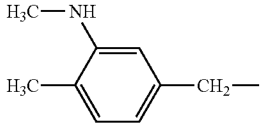 | 1 | 2 | 0 | R | H | 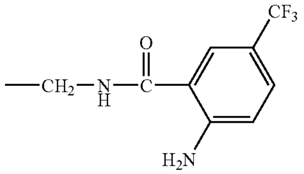 |
| 2197 | 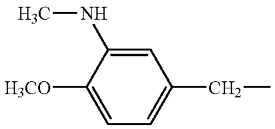 | 1 | 2 | 0 | R | H | 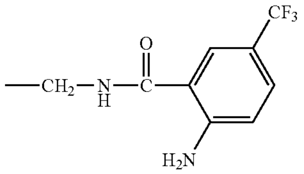 |

TABLE 1.200-continued
| Compd. No. | 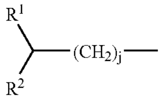 | k | m | n | chirality | $R^3$ | 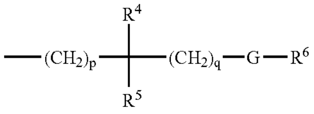 |
|---|---|---|---|---|---|---|---|
| 2198 | 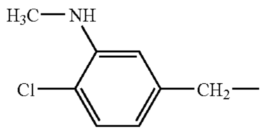 | 1 | 2 | 0 | R | H | 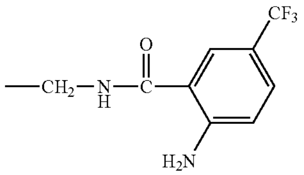 |
| 2199 | 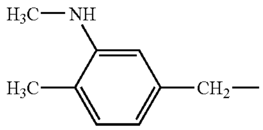 | 2 | 2 | 1 | — | H | 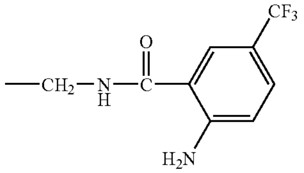 |
| 2200 | 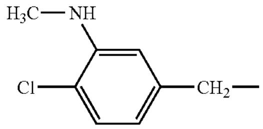 | 2 | 2 | 1 | — | H | 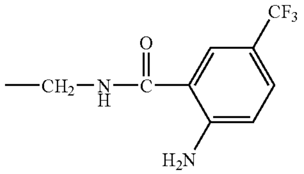 |
TABLE 1.201
| Compd. No. | 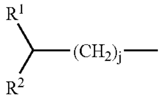 | k | m | n | chirality | $R^3$ | 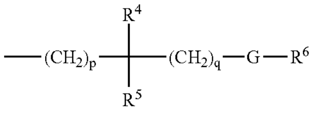 |
|---|---|---|---|---|---|---|---|
| 2201 | 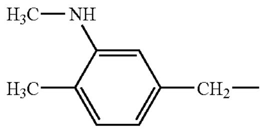 | 2 | 2 | 1 | — | H | 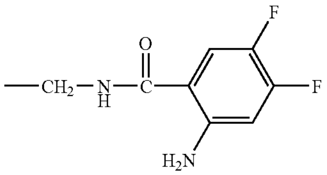 |
| 2202 | 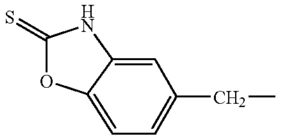 | 1 | 2 | 0 | R | H | 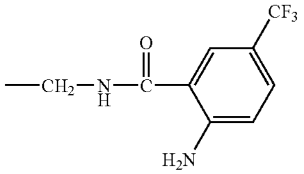 |
| 2203 | 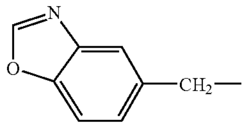 | 2 | 2 | 1 | — | H | 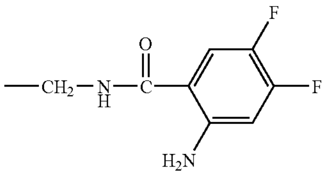 |

TABLE 1.201-continued
| Compd. No. | 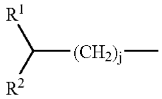 | k | m | n | chirality | $R^3$ | 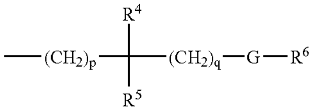 |
|---|---|---|---|---|---|---|---|
| 2204 | 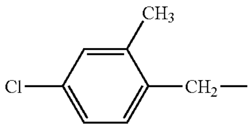 | 2 | 2 | 1 | — | H | 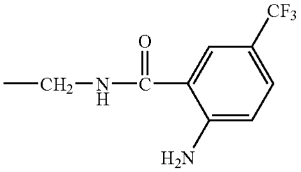 |
| 2205 | 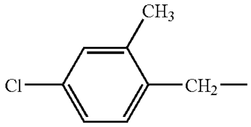 | 2 | 2 | 1 | — | H | 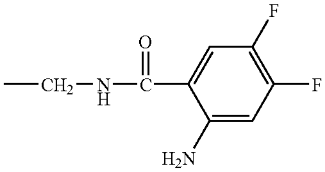 |
| 2206 | 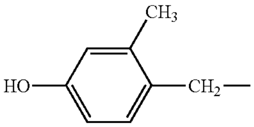 | 2 | 2 | 1 | — | H | 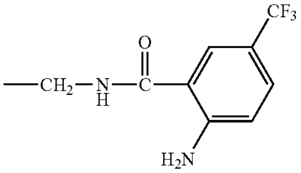 |
| 2207 | 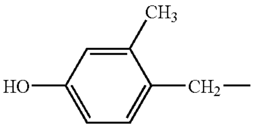 | 2 | 2 | 1 | — | H | 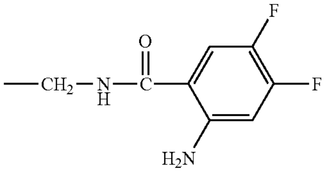 |
| 2208 | 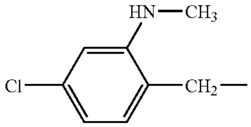 | 2 | 2 | 1 | — | H | 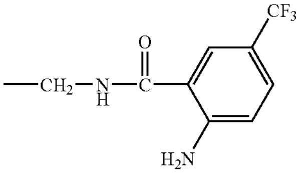 |
| 2209 | 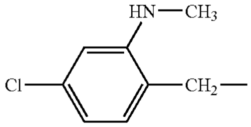 | 2 | 2 | 1 | — | H | 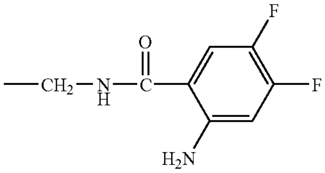 |
| 2210 | 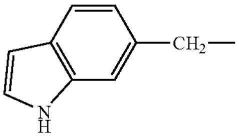 | 1 | 2 | 0 | R | H | 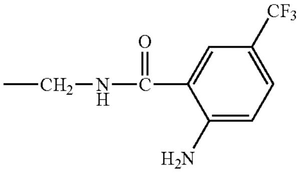 |

TABLE 1.201-continued
| Compd. No. | 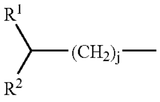 | k | m | n | chirality | $R^3$ | 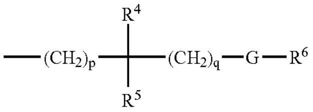 |
|---|---|---|---|---|---|---|---|
| 2211 | 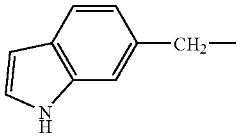 | 2 | 2 | 1 | — | H | 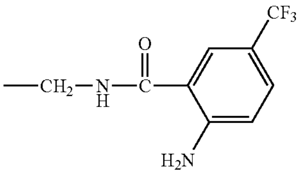 |
TABLE 1.202
| Compd. No. | 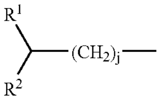 | k | m | n | chirality | $R^3$ | 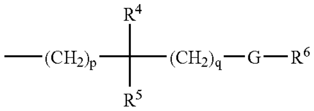 |
|---|---|---|---|---|---|---|---|
| 2212 | 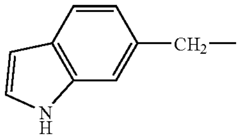 | 2 | 2 | 1 | — | H | 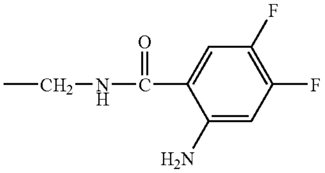 |
| 2213 | 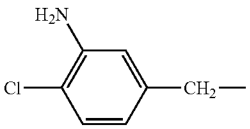 | 2 | 2 | 1 | — | H | 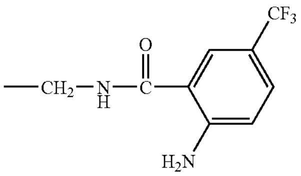 |
| 2214 | 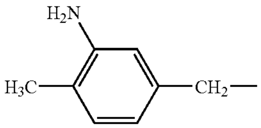 | 2 | 2 | 1 | — | H | 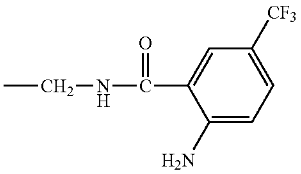 |
| 2215 | 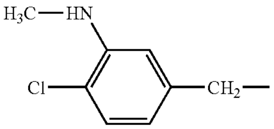 | 1 | 2 | 0 | R | H | 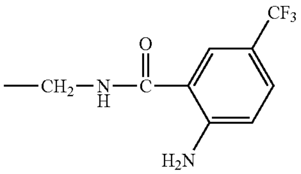 |
| 2216 | 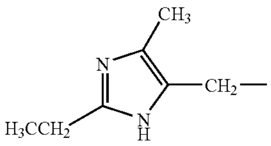 | 1 | 2 | 0 | R | H | 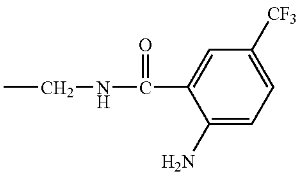 |

TABLE 1.202-continued
| Compd. No. | 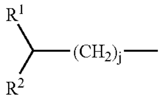 | k | m | n | chirality | $R^3$ | 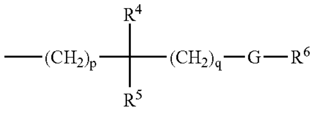 |
|---|---|---|---|---|---|---|---|
| 2217 | 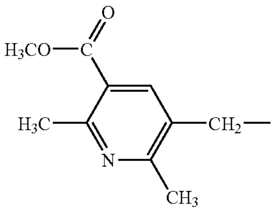 | 1 | 2 | 0 | R | H | 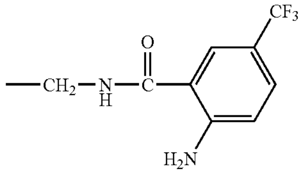 |
| 2218 | 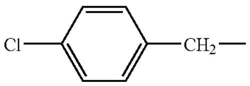 | 1 | 2 | 0 | R | H | 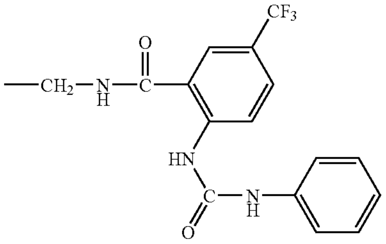 |
| 2219 | 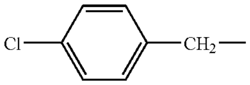 | 1 | 2 | 0 | R | H | 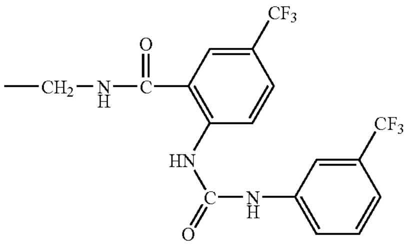 |
| 2220 | 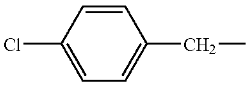 | 1 | 2 | 0 | R | H | 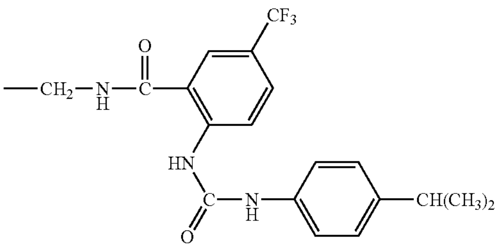 |
| 2221 | 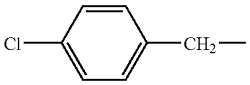 | 1 | 2 | 0 | R | H | 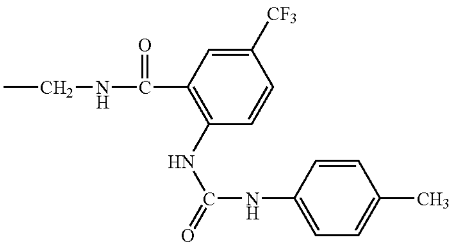 |

TABLE 1.202-continued
| Compd. No. | 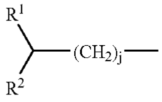 | k | m | n | chirality | $R^3$ | 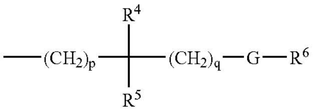 |
|---|---|---|---|---|---|---|---|
| 2222 | 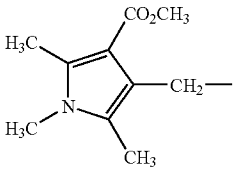 | 1 | 2 | 0 | R | H | 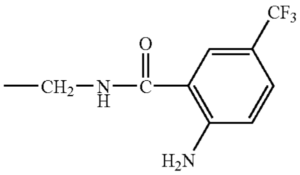 |
TABLE 1.203
| Compd. No. | 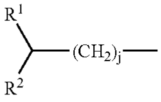 | k | m | n | chirality | $R^3$ | 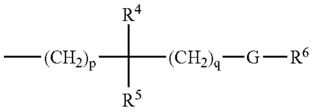 |
|---|---|---|---|---|---|---|---|
| 2223 | 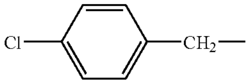 | 1 | 2 | 0 | R | H | 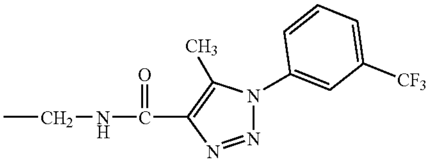 |
| 2224 | 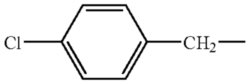 | 1 | 2 | 0 | R | H | 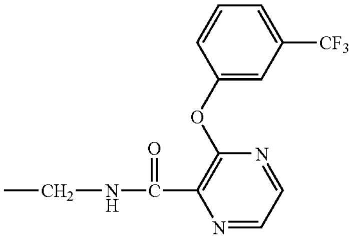 |
| 2225 | 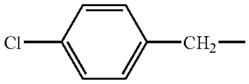 | 1 | 2 | 0 | R | H | 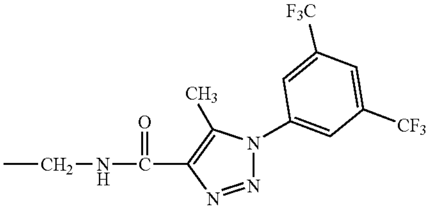 |
| 2226 | 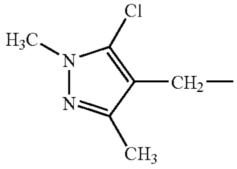 | 1 | 2 | 0 | R | H | 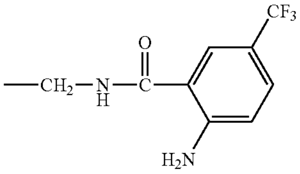 |
| 2227 | 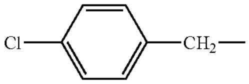 | 1 | 2 | 0 | R | H | 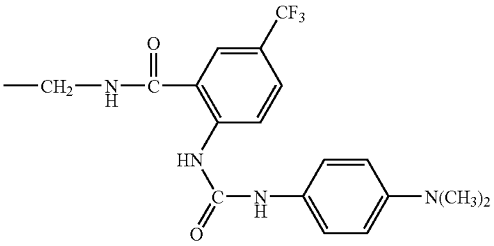 |

TABLE 1.203-continued
| Compd. No. | 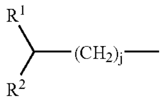 | k | m | n | chirality | $R^3$ | 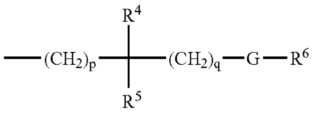 |
|---|---|---|---|---|---|---|---|
| 2228 | 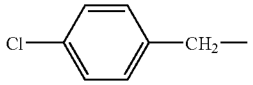 | 1 | 2 | 0 | R | H | 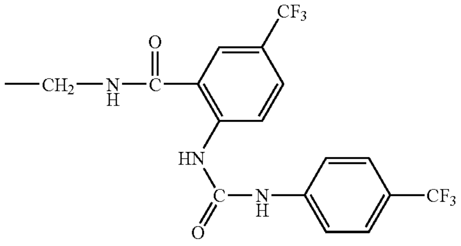 |
| 2229 | 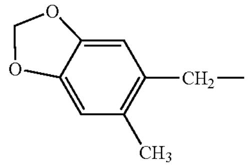 | 1 | 2 | 0 | R | H | 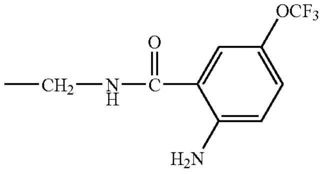 |
| 2230 | 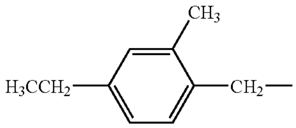 | 1 | 2 | 0 | R | H | 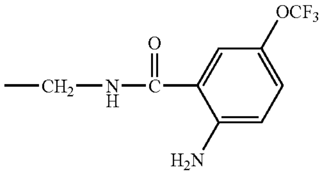 |
| 2231 | 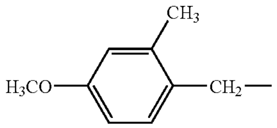 | 1 | 2 | 0 | R | H | 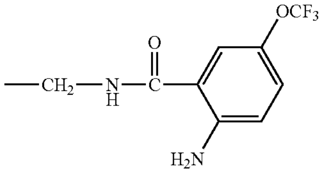 |
| 2232 | 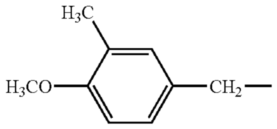 | 1 | 2 | 0 | R | H | 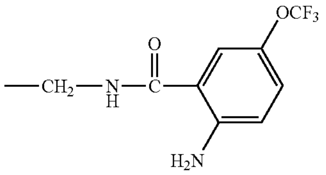 |
| 2233 | 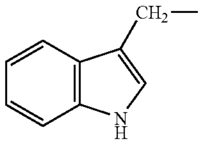 | 1 | 2 | 0 | R | H | 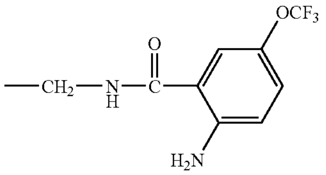 |

TABLE 1.204
| Compd. No. | 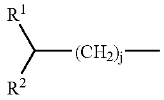 | k | m | n | chirality | $R^3$ | 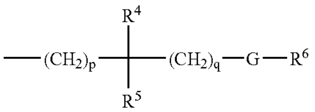 |
|---|---|---|---|---|---|---|---|
| 2234 | 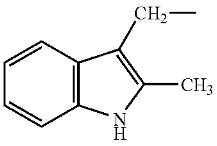 | 1 | 2 | 0 | R | H | 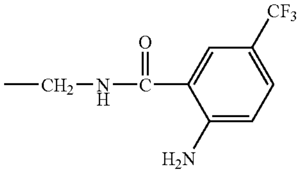 |
| 2235 | 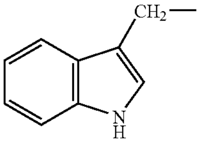 | 1 | 2 | 0 | R | H | 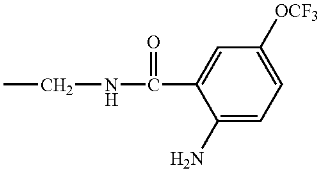 |
| 2236 | 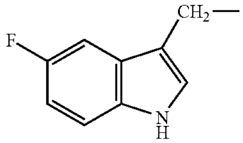 | 1 | 2 | 0 | R | H | 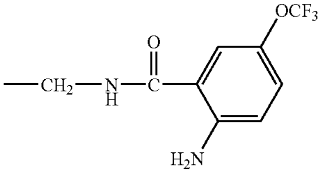 |
| 2237 | 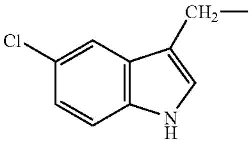 | 1 | 2 | 0 | R | H | 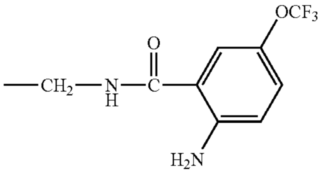 |
| 2238 | 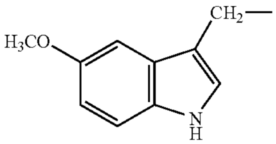 | 1 | 2 | 0 | R | H | 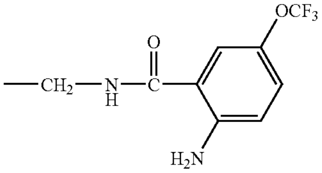 |
| 2239 | 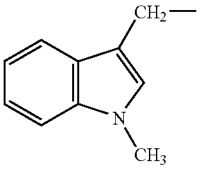 | 1 | 2 | 0 | R | H | 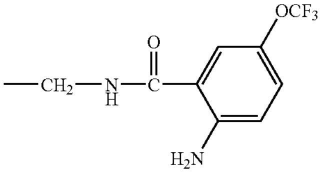 |
| 2240 | 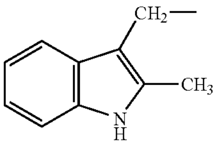 | 1 | 2 | 0 | R | H | 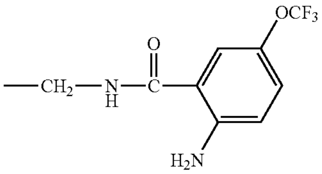 |
| 2241 | 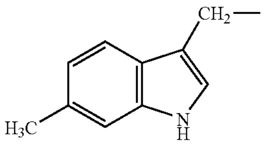 | 1 | 2 | 0 | R | H | 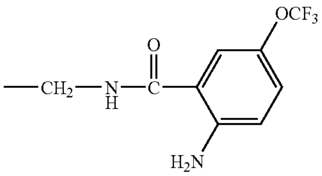 |

TABLE 1.204-continued
| Compd. No. | 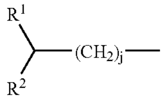 | k | m | n | chirality | $R^3$ | 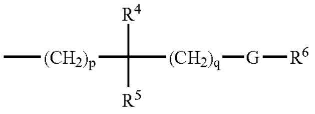 |
|---|---|---|---|---|---|---|---|
| 2242 | 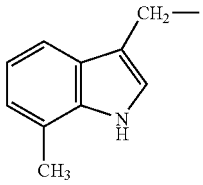 | 1 | 2 | 0 | R | H | 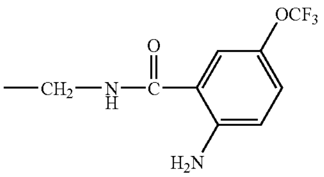 |
| 2243 | 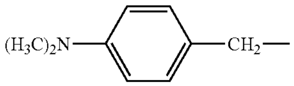 | 1 | 2 | 0 | R | H | 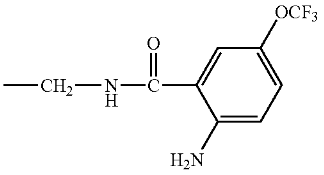 |
| 2244 | 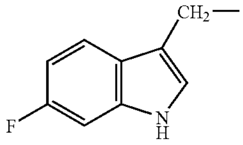 | 1 | 2 | 0 | R | H | 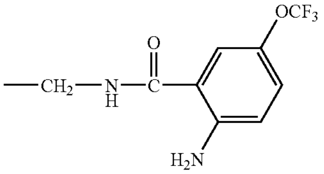 |
TABLE 1.205
| Compd. No. | 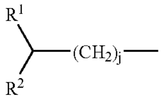 | k | m | n | chirality | $R^3$ | 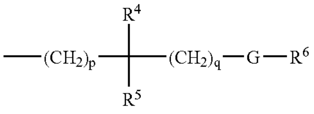 |
|---|---|---|---|---|---|---|---|
| 2245 | 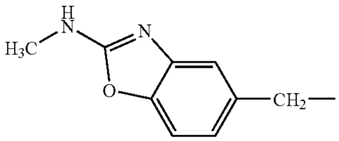 | 1 | 2 | 0 | R | H | 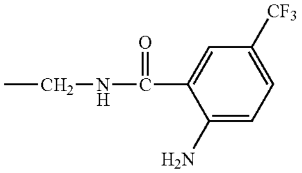 |
| 2246 | 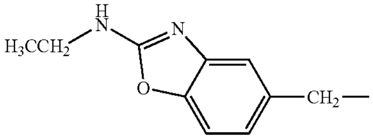 | 1 | 2 | 0 | R | H | 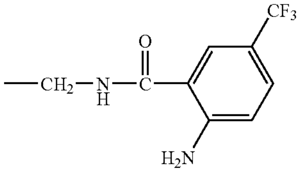 |
| 2247 | 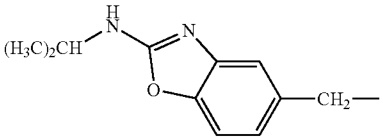 | 1 | 2 | 0 | R | H | 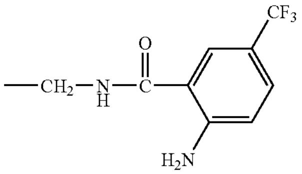 |

TABLE 1.205-continued
| Compd. No. | 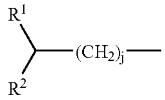 | k | m | n | chirality | $R^3$ | 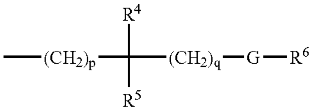 |
|---|---|---|---|---|---|---|---|
| 2248 | 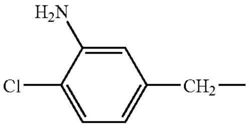 | 1 | 2 | 0 | R | H | 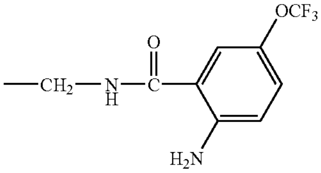 |
| 2249 | 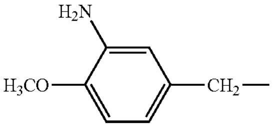 | 1 | 2 | 0 | R | H | 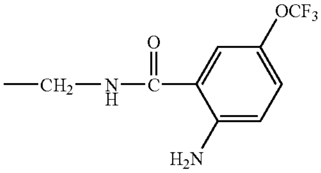 |
| 2250 | 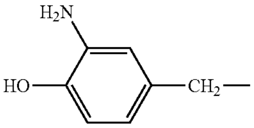 | 1 | 2 | 0 | R | H | 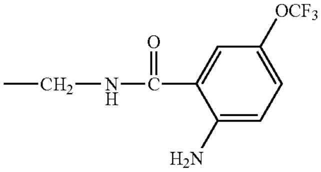 |
| 2251 | 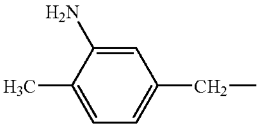 | 1 | 2 | 0 | R | H | 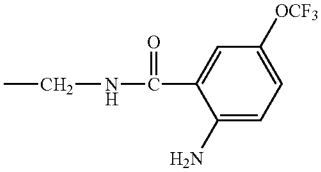 |
| 2252 | 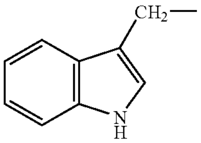 | 2 | 2 | 1 | — | H | 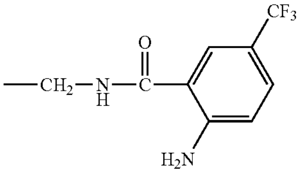 |
| 2253 | 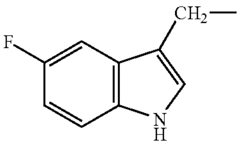 | 2 | 2 | 1 | — | H | 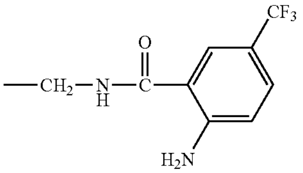 |
| 2254 | 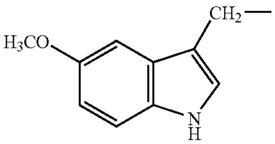 | 2 | 2 | 1 | — | H | 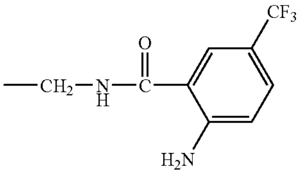 |

TABLE 1.205-continued

| Compd. No. | 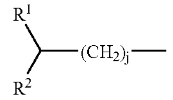 | k | m | n | chirality | $R^3$ | 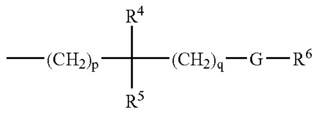 |
|---|---|---|---|---|---|---|---|
| 2255 | 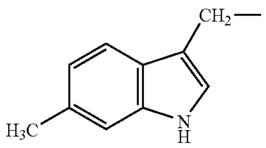 | 2 | 2 | 1 | — | H | 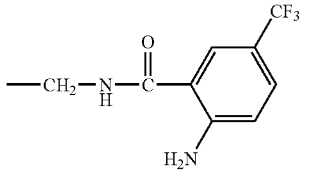 |

TABLE 1.206

| Compd. No. | 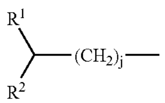 | k | m | n | chirality | $R^3$ | 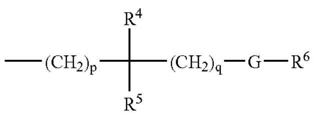 |
|---|---|---|---|---|---|---|---|
| 2256 | 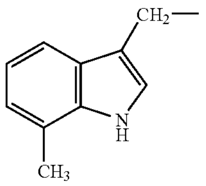 | 2 | 2 | 1 | — | H | 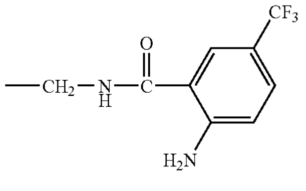 |
| 2257 | 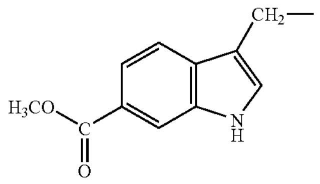 | 2 | 2 | 1 | — | H | 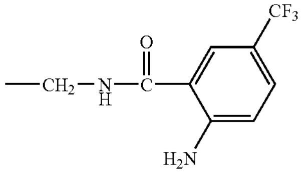 |

The acid addition salts of the cyclic amine compounds are also used in the present invention. Examples of the acid include a mineral acid such as hydrochloric acid, hydrobromic acid, sulfuric acid, phosphoric acid or carbonic acid and an organic acid such as maleic acid, citric acid, malic acid, tartaric acid, fumaric acid, methanesulfonic acid, trifluoroacetic acid or formic acid.

Furthermore, $C_1$-$C_6$ alkyl addition salts of the cyclic amine compounds, for example, 1-(4-chlorobenzyl)-1-methyl-4-[{N-(3-trifluoromethylbenzoyl)glycyl}aminomethyl]piperidinium iodide are also used in the present invention. The alkyl group preferably includes methyl, ethyl, n-propyl, n-butyl, n-pentyl, n-hexyl, n-heptyl, n-octyl, isopropyl, isobutyl, sec-butyl, tert-butyl, isopentyl, neopentyl, tert-pentyl, 2-methylpentyl and 1-ethylbutyl herein; however, methyl group, ethyl group or the like is especially preferable. A halide anion such as fluoride, chloride, bromide or iodide is preferable for a counter anion of an ammonium cation.

In the present invention, a racemate and all the possible optically active forms of the compounds represented by the above formula (I) can also be used.

The compounds represented by the above formula (I) can be synthesized by using any of the following general preparation processes described in WO9925686:

(Preparation Process 1)

A preparation process comprises reacting one equivalent of a compound represented by the following formula (II):

(II)

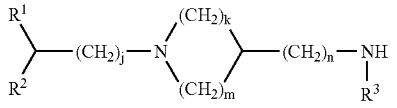

wherein $R^1$, $R^2$, $R^3$, j, k, m and n are each the same as defined in the above formula (I), with 0.1 to 10 equivalents of a carboxylic acid represented by the following formula (III):

(III)

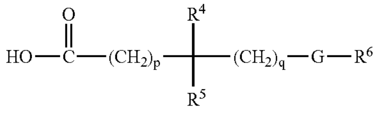

wherein $R^4$, $R^5$, $R^6$, G, p and q are each the same as defined in the above formula (I), or a reactive derivative thereof in the absence or presence of a solvent.

The "reactive derivative" of the carboxylic acid represented by the above formula (III) mean a carboxylic acid derivative, for example, an acid halide, an acid anhydride or a mixed acid anhydride usually used in the synthetic organic chemistry field and having high reactivity.

The reaction can more smoothly be made to proceed by suitably using an adequate amount of a dehydrating agent such as molecular sieve; a coupling reagent such as dicyclohexylcarbodiimide (DCC), N-ethyl-N'-(3-dimethylaminopropyl)carbodiimide (EDCI or WSC), carbonyldiimidazole (CDI), N-hydroxysuccinimide (HOSu), N-hydroxybenzotriazole (HOBt), benzotriazol-1-yloxytris(pyrrolidinol) phosphonium hexafluorophosphate (PyBOP), 2-(1H-benzotriazol-1-yl)-1,1,3,3-tetramethyluronium hexafluorophosphate (HBTU), 2-=(1H-benzotriazol-1-yl)-1,1,3,3-tetramethyluronium tetrafluoroborate (TBTU), 2-(5-norbornene-2,3-dicarboxylmide)-1,1,3,3-tetramethyluronium tetrafluorobonite (TNTU), O-(N-succinimidyl)-1,1,3,3-tetramethyluronium hexafluorophosphate (TSTU) or bromotris(pyrrolidino) phosphonium hexafluorophosphate (PyBroP); a base such as an inorganic base such as potassium carbonate, calcium carbonate or sodium hydrogencarbonate; amines such as triethylamine, diisoproylethylamine or pyridine or a polymer supported base such as (piperidinomethyl)polystyrene, (morpholinomethyl)polystyrene, (dimethylaminomethyl) polystyrene or poly(4-vinylpyridine).

(Preparation process 2)

A preparation process comprises reacting one equivalent of an alkylating reagent represented by the following formula (IV):

(IV)

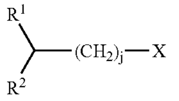

wherein $R^1$, $R^2$ and j are each the same as defined in the above formula (I); X is a halogen atom, an alkylsulfonyloxy group or an arylsulfonyloxy group, with 0.1 to 10 equivalents of a compound represented by the following formula (V):

(V)

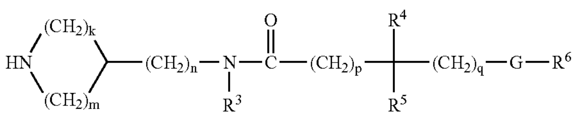

wherein $R^3$, $R^4$, $R^5$, $R^6$, G, k, m, n, p and q are each the same as defined in the above formula (I), in the absence or presence of a solvent.

The reaction can more smoothly be made to proceed by suitably using a base similar to that in the preparation process 1. Furthermore, the reaction sometimes can be promoted by the presence of an iodide such as potassium iodide or sodium iodide.

In the above formula (IV), X is a halogen atom, an alkylsulfonyloxy group or an arylsulfonyloxy group. Examples of the halogen atom preferably include a chlorine atom, a bromine atom and an iodine atom. Specific examples of the alkylsulfonyloxy group preferably include a methylsulfonyloxy group, a trifluoromethylsulfonyloxy group and the like, and the specific example of the arylsulfonyloxy group preferably includes tosyloxy group.

(Preparation process 3)

A preparation process comprises reacting one equivalent of an aldehyde represented by the following formula (VI):

(VI)

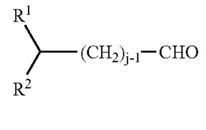

wherein $R^1$ and $R^2$ are each the same as defined in the above formula (I); j is 1 or 2, or an aldehyde represented by the following formula (VII):

$R^1$—CHO (VII)

wherein $R^1$ is the same as defined for $R^1$ in the above formula (I); the compound corresponds to the case where j is 0, with 0.1 to 10 equivalents of a compound represented by the above formula (V) in the absence or presence of a solvent.

The reaction is usually called a reductive amination reaction and a catalytic hydrogenation reaction using a catalyst containing a metal such as palladium, platinum, nickel or rhodium, a hydrogenation reaction using a complex hydride such as lithium aluminum hydride, sodium borohydride, sodium cyanoborohydride or sodium triacetoxyborohydride and borane, an electrolytic reducing reaction or the like can be used as reductive conditions.

(Preparation process 4)

A preparation process comprises reacting one equivalent of a compound represented by the following formula (VIII):

(VIII)

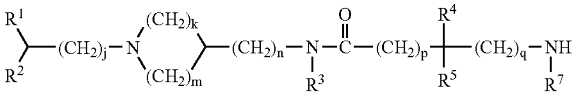

wherein $R^1$, $R^2$, $R^3$, $R^4$, $R^5$, $R^7$, j, k, m, n, p and q are each the same as defined in the above formula (I), with 0.1 to 10 equivalents of a carboxylic acid or a sulfonic acid represented by the following formula (IX):

HO—A—$R^6$ (IX)

wherein $R^6$ is the same as defined in the above formula (I); A is a carbonyl group or a sulfonyl group, or a reactive derivative thereof in the absence or presence of a solvent.

The reactive derivative of the carboxylic acid or sulfonic acid represented by the above formula (IX) means a carboxylic acid derivative or sulfonic acid derivative, for example, an acid halide, an acid anhydride or a mixed acid anhydride usually used in the synthetic organic chemistry field and having high reactivity. The reaction can more smoothly be made to proceed by suitably using a dehydrating agent, a coupling reagent or a base similar to that in the above preparation process 1.

(Preparation Process 5)

A preparation process comprises reacting one equivalent of a compound represented by the above formula (VIII) with 0.1 to 10 equivalents of an isocyanate or an isothiocyanate represented by the following formula (X):

$$Z{=}C{=}N{-}R^6 \qquad (X)$$

wherein $R^6$ is the same as defined in the above formula (I); Z is an oxygen atom or a sulfur atom, in the absence or presence of a solvent.

(Preparation process 6)

A preparation process comprises reacting one equivalent of a compound represented by the following formula (XI):

(XI)

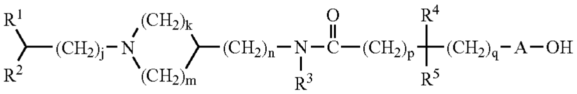

wherein $R^1$, $R^2$, $R^3$, $R^4$, $R^5$, j, k, m, n, p and q are each the same as defined in the above formula (I); A is a carbonyl group or a sulfonyl group, with 0.1 to 10 equivalents of an amine represented by the following formula (XII):

$$R^6{-}NH_2 \qquad (XII)$$

wherein $R^6$ is the same as defined for $R^6$ in the above formula (I), in the absence or presence of a solvent.

The reaction can more smoothly be made to proceed by suitably using a dehydrating agent, a coupling reagent or a base similar to that in the above preparation process 1.

In the above preparation processes 1 to 6, when a substrate used for each reaction has substitutents regarded as usually reacting under respective reaction conditions in the organic synthetic chemistry or having adverse effects on the reaction, the functional groups can be protected with a known suitable protecting group, and the substrate can be used for the reaction and then deprotected by a conventional known method to afford the objective compound.

In addition, the compounds used in the present invention can be obtained by further converting (single or plural) substituents of the compound produced by the above preparation process 1-6 using a known reaction usually used in the organic-synthetic chemistry, for example, an alkylation reaction, an acylation reaction or a reduction reaction.

In the above respective preparation processes, a halogenated hydrocarbon such as dichloromethane or chloroform, an aromatic hydrocarbon such as benzene or toluene, ethers such as diethyl ether or tetrahydrofuran, esters such as ethyl acetate, an aprotic polar solvent such as dimethylformamide, dimethyl sulfoxide or acetonitrile and alcohols such as methanol, ethanol or isopropyl alcohol are suitably used as a reaction solvent according to the reaction.

In each of the preparation processes, the reaction temperature is within the range of −78 to +150° C., preferably within the range of 0 to 100° C. After completing the reaction, the objective cyclic amine compounds represented by the above formula (I) can be isolated by carrying out usual isolating and purifying operations, i.e., concentration, filtration, extraction, solid-phase extraction, recrystallization or chromatography.

The compounds can be converted into their pharmaceutically acceptable acid addition salts thereof or their $C_1$-$C_6$ alkyl addition salts thereof according to a usual method.

EXAMPLES

The present invention is detailed specifically based on Examples; however, the present invention is not restricted to compounds described in the Examples. The Compound number (Compd. No.) assigned to each compound in the following Examples corresponds to the Compd. No. assigned to each compound cited as a preferred specific example in Tables 1.1 to 1.206.

Reference Example 1

Synthesis of 3-amino-1-(4-chlorobenzyl)pyrrolidine dihydrochloride

4-Chlorobenzyl chloride (4.15 g, 25.8 mmol) and $^iPr_2NEt$ (6.67 g, 51.6 mmol) were added to a DMF (50 mL) solution of 3-[(tert-butoxycarbonyl)amino]pyrrolidine (4.81 g, 25.8 mmol). The reaction mixture was stirred at 70° C. for 15 hours, and the solvent was removed under reduced pressure. The objective 3-[(tert-butoxycarbonyl)amino]-1-(4-chlorobenzyl)pyrrolidine (6.43 g, 80%) was obtained as an off-white solid by recrystallization (acetonitrile, 50 mL). $^1H$ NMR ($CDCl_3$, 300 MHz) δ 1.37 (s, 9H), 1.5-1.7 (br, 1H), 2.1-2.4 (m, 2H), 2.5-2.7 (m, 2H), 2.83 (br, 1H), 3.57 (s, 2H), 4.1-4.3 (br, 1H), 4.9-5.1 (br, 1H), 7.15-7.35 (br, 4H); the purity was determined by RPLC/MS (98%). ESI/MS m/e 311.0 ($M^+$+H, $C_{16}H_{24}ClN_2O_2$).

To a methanol solution (80 mL) of the 3-[(tert-butoxycarbonyl)amino]-1-(4-chlorobenzyl)pyrrolidine (6.38 g, 20.5 mmol), was added 1 M HCl-$Et_2O$ (100 mL). The resulting mixture was stirred at 25° C. for 15 hours. The solvent was removed under reduced pressure to provide a solid, which was purified by recrystallization (methanol/acetonitrile=1:2, 130 mL) to thereby afford 3-amino-1-(4-chlorobenzyl)pyrrolidine dihydrochloride (4.939 g, 85%) as a white powder. $^1H$ NMR ($d_6$-DMSO, 300 MHz) δ 3.15 (br, 1H), 3.3-3.75 (br-m, 4H), 3.9 (br, 1H), 4.05 (br, 1H), 4.44 (br, 1H), 4.54 (br, 1H), 7.5-7.7 (m, 4H), 8.45 (br, 1H), 8.60 (br, 1H); the purity was determined by RPLC/MS (>99%). ESI/MS m/e 211.0 ($M^+$+H, $C_{11}H_{16}ClN_2$).

Optically active (R)-3-amino-1-(4-chlorobenzyl)pyrrolidine dihydrochloride and (S)-3-amino-1-(4-chlorobenzyl)pyrrolidine dihydrochloride were synthesized by using the respective corresponding starting materials according to the above method. The products exhibited the same $^1H$ NMR as that of the above racemate.

Example 1

Synthesis of 3-(N-benzoylglycyl)amino-1-(4-chlorobenzyl)pyrrolidine (Compd. No. 1)

N-Benzoylglycine (9.3 mg, 0.055 mmol), 3-ethyl-1-[3-(dimethylamino)propyl]carbodiimide hydrochloride (EDCI) (1.05 mg) and 1-hydroxybenzotriazole hydrate (HOBt) (7.4 mg) were added to a chloroform (2.5 mL) solution of 3-amino-1-(4-chlorobenzyl)pyrrolidine dihydrochloride (14.2 mg, 0.050 mmol) and triethylamine (15.2 mg). The resulting reaction mixture was stirred at 25° C. for 16 hours and then washed with a 2 M aqueous solution of NaOH (2 mL×2) and brine. After filtration through a PTFE membrane filter, the solvent was removed under reduced pressure to provide 3-(N-benzoylglycyl)amino-1-(4-chlorobenzyl)pyrrolidine (Compd. No. 1) as an off-white oil (17.7 mg, 95%). The purity was determined by RPLC/MS (95%). ESI/MS m/e 372.0 ($M^+$+H, $C_{20}H_{22}ClN_3O_2$).

Examples 2 to 32

The compounds used in the present invention were synthesized by using the respective corresponding starting materials and reactants according to the method in Example 1. The data of ESI/MS, yields (mg) and yields (%) are collectively shown in Table 2.

TABLE 2

| Example | Compd. No. | Molecular Formula | ESI/MS m/e | Yield (mg) | Yield (%) |
|---|---|---|---|---|---|
| 2 | 2 | $C_{21}H_{24}ClN_3O_2$ | 386 | 16.4 | 85 |
| 3 | 3 | $C_{19}H_{21}ClN_4O_2$ | 373 | 18.7 | 100 |
| 4 | 4 | $C_{21}H_{21}ClF_3N_3O_2$ | 440 | 57.2 | 69 |
| 5 | 82 | $C_{22}H_{23}ClF_3N_3O_2$ | 454 | 5.6 | 11 |
| 6 | 85 | $C_{21}H_{24}ClN_3O_2$ | 386 | 22.6 | 59 |
| 7 | 86 | $C_{21}H_{23}ClN_4O_4$ | 431 | 21.2 | 98 |
| 8 | 214 | $C_{22}H_{25}ClN_2O_2$ | 385 | 23.9 | 62 |
| 9 | 215 | $C_{23}H_{27}ClN_2O_3$ | 415 | 17.4 | 84 |
| 10 | 216 | $C_{20}H_{23}ClN_2O_2S$ | 391 | 21.6 | Q |
| 11 | 217 | $C_{23}H_{27}ClN_2O_4$ | 431 | 15.3 | 66 |
| 12 | 218 | $C_{23}H_{27}ClN_2O_2$ | 399 | 12.8 | 64 |
| 13 | 219 | $C_{22}H_{24}ClFN_2O_3$ | 419 | 18.1 | 86 |
| 14 | 220 | $C_{22}H_{25}ClN_2O_2$ | 385 | 16.4 | 85 |
| 15 | 221 | $C_{21}H_{23}ClN_2O_2$ | 371 | 14.9 | 80 |
| 16 | 222 | $C_{21}H_{22}Cl_2N_2O_2$ | 405 | 13.3 | 65 |
| 17 | 223 | $C_{25}H_{31}ClN_2O_3$ | 443 | 18.4* | 63 |
| 18 | 224 | $C_{20}H_{23}ClN_2O_3S$ | 407 | 11.2 | 28 |
| 19 | 225 | $C_{22}H_{26}ClN_3O_2$ | 400 | 22.7 | Q |
| 20 | 226 | $C_{23}H_{28}ClN_3O_3$ | 430 | 21.0 | 98 |
| 21 | 227 | $C_{22}H_{25}Cl_2N_3O_2$ | 434 | 21.9 | 100 |
| 22 | 228 | $C_{23}H_{28}ClN_3O_3$ | 430 | 20.8 | 97 |
| 23 | 229 | $C_{25}H_{32}ClN_3O_2$ | 462 | 25.4 | Q |
| 24 | 230 | $C_{26}H_{31}ClFN_3O_2$ | 472 | 26.0 | Q |
| 25 | 231 | $C_{24}H_{28}ClN_3O_3$ | 442 | 30.3* | Q |
| 26 | 232 | $C_{22}H_{32}ClN_3O_2$ | 406 | 3.9 | 19 |
| 27 | 233 | $C_{23}H_{28}ClN_3O_2$ | 414 | 8.5 | 41 |
| 28 | 234 | $C_{22}H_{27}ClN_4O_2$ | 415 | 7.3 | 35 |
| 29 | 235 | $C_{24}H_{29}Cl_2N_3O_2$ | 462 | 9.0 | 39 |
| 30 | 236 | $C_{25}H_{29}ClN_4O_3S$ | 501 | 17.4 | 69 |
| 31 | 237 | $C_{21}H_{24}ClN_3O_3$ | 402 | 14.2 | 71 |
| 32 | 238 | $C_{21}H_{23}Cl_2N_3O_3$ | 436 | 23.4 | Q |

Notes:
*indicates "yield (mg) of trifluoroacetate".
Q means "Quantitative".

Reference Example 2

Synthesis of (R)-3-[(N-tert-butoxycarbonyl)glycyl]amino-1-(4 chlorobenzyl)pyrrolidine A mixture of (R)-3-amino-1-(4-chlorobenzyl)pyrrolidine dihydrochloride (4.54 g, 16.0 mmol) with a 2 M solution (80 mL) of NaOH and ethyl acetate (80 mL) was stirred, and the organic layer was separated to extract the aqueous layer with ethyl acetate (80 mL×2). The organic layers were combined, dried over anhydrous sodium sulfate, then filtered and concentrated to thereby afford free (R)-3-amino-1-(4-chlorobenzyl)pyrrolidine (3.35 g, 99%).

To a dichloromethane (80 mL) solution of the (R)-3-amino-1-(4-chlorobenzyl)pyrrolidine (3.35 g, 16 mmol), were added triethylamine (2.5 mL, 17.6 mmol), N-tert-butoxycarbonylglycine (2.79 g, 16.0 mmol), EDCI (3.07 g, 16.0 mmol) and HOBt (12.16 g, 16 mmol). The resulting reaction mixture was stirred at 25° C. for 16 hours, and a 2 M solution (80 mL) of NaOH was then added thereto. The organic layer was separated, and the aqueous layer was extracted with dichloromethane (100 mL×3). The organic layers were combined, washed with water (100 mL×2) and brine (100 mL), dried over anhydrous sodium sulfate, filtered, concentrated and purified by column chromatography ($SiO_2$, ethyl acetate) to thereby provide the objective (R)-3-[N-(tert-butoxycarbonyl)glycyl]amino-1-(4-chlorobenzyl)pyrrolidine (5.40 g, 92%).

Reference Example 3

Synthesis of (R)-1-(4-chlorobenzyl)-3-(glycylamino) pyrrolidine

A 4 M HCl dioxane (38 mL) solution was added to a methanol (60 mL) solution of (R)-3-[N-(tert-butoxycarbonyl)glycyl]amino-1-(4-chlorobenzyl)pyrrolidine (5.39 g, 14.7 mmol). The resulting solution was stirred at room temperature for 2 hours. The reaction mixture was concentrated, and a 2 M solution (80 mL) of NaOH was added. The mixture solution was extracted with dichloromethane (80 mL×3), and the extracts were combined, dried over anhydrous sodium sulfate, concentrated and purified by column chromatography ($SiO_2$, ethyl acetate/ethanol/triethylamine=90:5:5) to afford (R)-3-(glycylamino)-1-(4-chlorobenzyl)pyrrolidine (3.374 g, 86%) $^1$H NMR ($CDCl_3$, 270 MHz) δ 1.77 (dd, J=1.3 and 6.9 Hz, 1H), 2.20-3.39 (m, 2H), 2.53 (dd, J=3.3 and 9.6 Hz, 1H), 2.62 (dd, J=6.6 and 9.6 Hz, 1H), 2.78-2.87 (m, 1H), 3.31 (s, 2H), 3.57 (s, 2H), 4.38-4.53 (br, 1H), 7.18-7.32 (m, 4H), 7.39 (br, s, 1H).

Other 3-acylamino-1-(4-chlorobenzyl)pyrrolidines were synthesized by using the respective corresponding starting materials and reactants according to the methods of Reference Examples 2 and 3.

(S)-1-(4-chlorobenzyl)-3-(glycylamino)pyrrolidine: 3.45 g, 79% (two steps).

(R)-3-(β-alanylamino)-1-(4-chlorobenzyl)pyrrolidine: 3.79 g, 85% (two steps).

(S)-3-(β-alanylamino)-1-(4-chlorobenzyl)pyrrolidine: 3.72 g, 86% (two steps)

(R)-3-[(S)-alanylamino]-1-(4-chlorobenzyl)pyrrolidine: 368 mg, 65% (two steps).

(R)-3-[(R)-alanylamino]-1-(4-chlorobenzyl)pyrrolidine: 425 mg, 75% (two steps).

(R)-3-[(2S)-2-amino-3-thienylpropanoyl]amino-1-(4-chlorobenzyl)pyrrolidine:

566 mg, 78% (two step).

(R)-3-[(2R)-2-amino-3-thienylpropanoyl]amino-1-(4-chlorobenzyl)pyrrolidine: 5.85 mg, 81% (two steps).

(R)-3-(2-amino-2-methylpropanoyl)amino-1-(4-chlorobenzyl)pyrrolidine: 404 mg, 66% (two steps).

(R)-3-[(2S)-2-amino-4-(methylsulfonyl)butanoyl]amino-1-(4-chlorobenzyl)pyrrolidine: 535 mg, 72% (two steps).

Furthermore, (R)-3-(glycylamino)-1-(4-methylbenzyl) pyrrolidine, (R)-1-(4-bromobenzyl)-3-(glycylamino)pyrrolidine, (R)-1-(2,4-dimethylbenzyl)-3-(glycylamino)pyrrolidine and (R)-1-(3,5-dimethylisoxazol-4-ylmethyl)-3-(glycylamino)pyrrolidine were synthesized by using the respective corresponding starting materials and reactants according to the methods of Reference Examples 1, 2 and 3.

(R)-3-(glycylamino)-1-(4-methylbenzyl)pyrrolidine: 4.65 g, yield 62% (yield from 3-[(tert-butoxycarbonyl)amino]pyrrolidine).

(R)-1-(4-bromobenzyl)-3-(glycylamino)pyrrolidine: 2.55 g, yield 68% (yield from (R)-3-amino-1-(4-bromobenzyl) pyrrolidine); $^1$H NMR ($CDCl_3$ 270 MHz) δ 1.37-1.78 (m, 3H), 2.23-2.39 (m, 2H), 2.50-2.67 (m, 2H), 2.80-2.89 (m, 1H), 3.32 (s, 2H), 3.58 (s, 2H), 4.39-4.55 (m, 1H), 7.21 (d, J=6.5 Hz, 2H), 7.45 (d, J=6.5 Hz, 2H).

(R)-1-(2,4-dimethylbenzyl)-3-(glycylamino)pyrrolidine: 1.56 g, yield 58% (yield from 3-[(tert-butroxycarbonyl) amino]pyrrolidine); $^1$H NMR ($CDCl_3$, 270 MHz) δ 1.55-1.78 (m, 3H), 2.30 (s, 3H), 2.23-2.31 (m, 2H), 2.33 (s, 3H), 2.51-2.63 (m, 2H), 2.78-2.87 (m, 1H), 3.30 (s, 2H), 3.55 (s, 2H), 4.38-4.60 (m, 1H), 6.95 (d, J=7.6 Hz, 1H), 6.97 (s, 1H), 7.13 (d, J=7.6 Hz, 1H), 7.43 (br-s, 1H).

(R)-1-(3,5-dimethylisoxazol-4-ylmethyl)-3-(glycylamino)pyrrolidine: 3.14 g, yield 45% (yield from 3-[(tert-butoxycarbonyl)amino]pyrrolidine).

Example 33

Synthesis of (S)-3-[N-[3,5-bis(trifluoromethyl)benzoyl]glycyl]amino-1-(4-chlorobenzyl)pyrrolidine (Compd. No. 5).

A chloroform solution (0.4 mL) of 3,5-bis(trifluoromethyl) benzoyl chloride (0.060 mmol) was added to a chloroform (1.0 mL) solution of (S)-1-(4-3-chlorobenzyl)-3-(glycylamino)pyrrolidine (0.050 mmol) and triethylamine (0.070 mmol). The resulting reaction mixture was stirred at room temperature for 2.5 hours, and an (aminomethyl)polystyrene resin (1.04 mmol/g, 50 mg, 50 mmol) was then added. The prepared mixture was stirred at room temperature for 12 hours. The reaction mixture was filtered, and the resin was washed with dichloromethane (0.5 mL). The filtrate and the washing were combined, and dichloromethane (4 mL) was added. The resulting solution was washed with a 2 M aqueous solution (0.5 mL) of NaOH and concentrated to thereby provide (S)-3-[N-[3,5-bis(trifluoromethyl)benzoyl]glycyl] amino-1-(4-chlorobenzyl)pyrrolidine (Compd. No. 5) (14.4 mg, 57%). The purity was determined by RPLC/MS (97%). ESI/MS m/e 508.0 ($M^+$+H, $C_{22}H_{20}ClF_6N_3O_2$).

Examples 34 to 239

The compounds used in the present invention were synthesized by using the respective corresponding starting materials and reactants according to the method of Example 33. Data of ESI/MS, yields (mg) and yields (%) are collectively shown on Table 3.

TABLE 3

| Example | Compd. No. | Molecular Formula | ESI/MS m/e | Yield (mg) | Yield (%) |
|---|---|---|---|---|---|
| 34 | 5 | $C_{22}H_{20}ClF_6N_3O_2$ | 508.0 | 14.4 | 57 |
| 35 | 6 | $C_{21}H_{21}ClF_3N_3O_2$ | 440.0 | 17.0 | 77 |
| 36 | 7 | $C_{20}H_{21}BrClN_3O_2$ | 450.0 | 17.7 | 79 |
| 37 | 8 | $C_{20}H_{21}ClFN_3O_2$ | 390.0 | 12.7 | 65 |
| 38 | 9 | $C_{20}H_{20}Cl_3N_3O_2$ | 440.0 | 39.0 | Q |
| 39 | 10 | $C_{21}H_{24}ClN_3O_3$ | 402.5 | 23.5 | Q |
| 40 | 11 | $C_{22}H_{26}ClN_3O_4$ | 432.5 | 22.4 | Q |
| 41 | 12 | $C_{22}H_{26}ClN_3O_4$ | 432.5 | 15.9 | 74 |
| 42 | 13 | $C_{21}H_{21}ClF_3N_3O_2$ | 440.0 | 13.1 | 60 |
| 43 | 14 | $C_{21}H_{24}ClN_3O_2$ | 386.0 | 16.4 | 85 |
| 44 | 15 | $C_{20}H_{21}Cl_2N_3O_2$ | 406.0 | 15.7 | 77 |
| 45 | 16 | $C_{21}H_{24}ClN_3O_2$ | 402.0 | 28.2 | Q |
| 46 | 17 | $C_{20}H_{20}Cl_3N_3O_2$ | 442.0 | 35.6 | Q |
| 47 | 18 | $C_{21}H_{21}ClN_4O_2$ | 397.5 | 22.8 | Q |
| 48 | 19 | $C_{21}H_{22}ClN_3O_4$ | 416.0 | 16.3 | 78 |
| 49 | 20 | $C_{21}H_{20}ClF_4N_3O_2$ | 458.0 | 24.9 | Q |
| 50 | 21 | $C_{21}H_{20}ClF_4N_3O_2$ | 458.0 | 17.9 | 78 |
| 51 | 22 | $C_{21}H_{20}ClF_4N_3O_2$ | 458.0 | 9.4 | 41 |
| 52 | 23 | $C_{21}H_{20}ClF_4N_3O_2$ | 458.0 | 15.4 | 67 |
| 53 | 24 | $C_{21}H_{21}ClF_3N_3O_3$ | 456.0 | 20.7 | 91 |
| 54 | 25 | $C_{21}H_{20}ClF_4N_3O_2$ | 458.0 | 18.5 | 81 |

TABLE 3-continued

| Example | Compd. No. | Molecular Formula | ESI/MS m/e | Yield (mg) | Yield (%) |
|---|---|---|---|---|---|
| 55 | 26 | $C_{20}H_{21}ClN_4O_4$ | 417.0 | 21.9 | Q |
| 56 | 27 | $C_{20}H_{21}ClN_4O_4$ | 417.0 | 16.8 | 81 |
| 57 | 28 | $C_{20}H_{21}ClN_4O_4$ | 417.0 | 6.8 | 33 |
| 58 | 29 | $C_{22}H_{20}ClF_6N_3O_2$ | 508.0 | 20.8 | 82 |
| 59 | 30 | $C_{21}H_{21}ClF_3N_3O_2$ | 440.0 | 15.2 | 69 |
| 60 | 31 | $C_{20}H_{21}BrClN_3O_2$ | 450.0 | 15.6 | 69 |
| 61 | 32 | $C_{20}H_{21}ClFN_3O_2$ | 390.0 | 11.8 | 61 |
| 62 | 33 | $C_{20}H_{20}Cl_3N_3O_2$ | 440.0 | 15.8 | 72 |
| 63 | 34 | $C_{21}H_{24}ClN_3O_3$ | 402.5 | 33.8 | Q |
| 64 | 35 | $C_{22}H_{26}ClN_3O_4$ | 432.5 | 56.1 | Q |
| 65 | 36 | $C_{22}H_{26}ClN_3O_4$ | 432.5 | 37.6 | Q |
| 66 | 37 | $C_{21}H_{21}ClF_3N_3O_2$ | 440.0 | 12.6 | 57 |
| 67 | 38 | $C_{21}H_{24}ClN_3O_2$ | 386.0 | 12.3 | 64 |
| 68 | 39 | $C_{20}H_{21}Cl_2N_3O_2$ | 406.0 | 15.9 | 78 |
| 69 | 40 | $C_{21}H_{24}ClN_3O_2$ | 402.0 | 11.6 | 58 |
| 70 | 41 | $C_{20}H_{20}Cl_3N_3O_2$ | 442.0 | 17.8 | 81 |
| 71 | 42 | $C_{21}H_{21}ClN_4O_2$ | 397.5 | 22.4 | Q |
| 72 | 43 | $C_{21}H_{22}ClN_3O_4$ | 416.0 | 30.1 | Q |
| 73 | 44 | $C_{21}H_{20}ClF_4N_3O_2$ | 458.0 | 13.4 | 59 |
| 74 | 45 | $C_{21}H_{20}ClF_4N_3O_2$ | 458.0 | 13.2 | 58 |
| 75 | 46 | $C_{21}H_{20}ClF_4N_3O_2$ | 458.0 | 14.4 | 63 |
| 76 | 47 | $C_{21}H_{21}ClF_3N_3O_3$ | 456.0 | 16.4 | 72 |
| 77 | 48 | $C_{21}H_{20}ClF_4N_3O_2$ | 458 | 16.5 | 72 |
| 78 | 49 | $C_{20}H_{21}ClN_4O_4$ | 417.0 | 12.5 | 60 |
| 79 | 50 | $C_{21}H_{20}ClF_4N_3O_2$ | 458.0 | 26.3 | Q |
| 80 | 51 | $C_{20}H_{21}BrClN_3O_2$ | 450.0 | 8.6 | 38 |
| 81 | 52 | $C_{20}H_{21}ClFN_3O_2$ | 390.5 | 4.1 | 21 |
| 82 | 53 | $C_{20}H_{21}Cl_2N_3O_2$ | 406.0 | 5.4 | 27 |
| 83 | 54 | $C_{20}H_{20}Cl_3N_3O_2$ | 440.0 | 8.8 | 40 |
| 84 | 55 | $C_{20}H_{20}BrCl_4N_3O_2$ | 440.0 | 7.7 | 35 |
| 85 | 56 | $C_{21}H_{24}ClN_3O_2$ | 386.0 | 4.8 | 25 |
| 86 | 57 | $C_{22}H_{26}ClN_3O_4$ | 429.5 | 4.9 | 23 |
| 87 | 58 | $C_{20}H_{21}Cl_2N_3O_2$ | 406.0 | 4.1 | 20 |
| 88 | 59 | $C_{20}H_{21}BrClN_3O_2$ | 452.0 | 3.5 | 16 |
| 89 | 60 | $C_{26}H_{26}ClN_3O_2$ | 448.5 | 7.3 | 33 |
| 90 | 61 | $C_{21}H_{21}ClF_3N_3O_2$ | 440.0 | 7.1 | 32 |
| 91 | 62 | $C_{21}H_{24}ClN_3O_2$ | 386.0 | 10.4 | 54 |
| 92 | 63 | $C_{22}H_{26}ClN_3O_2$ | 400.5 | 6.0 | 30 |
| 93 | 64 | $C_{21}H_{21}ClN_4O_2$ | 397.0 | 7.0 | 35 |
| 94 | 65 | $C_{24}H_{24}ClN_3O_2$ | 422.0 | 7.7 | 36 |
| 95 | 66 | $C_{24}H_{24}ClN_3O_2$ | 422.0 | 6.3 | 30 |
| 96 | 67 | $C_{20}H_{20}ClF_2N_3O_2$ | 408.0 | 4.7 | 23 |
| 97 | 68 | $C_{20}H_{20}ClF_2N_3O_2$ | 408.0 | 7.8 | 38 |
| 98 | 69 | $C_{20}H_{20}ClF_2N_3O_2$ | 408.0 | 7.3 | 36 |
| 99 | 70 | $C_{20}H_{20}ClF_2N_3O_2$ | 408.0 | 9.1 | 45 |
| 100 | 71 | $C_{22}H_{26}ClN_3O_4$ | 429.0 | 5.6 | 26 |
| 101 | 72 | $C_{21}H_{21}ClF_3N_3O_2$ | 456.0 | 6.2 | 27 |
| 102 | 73 | $C_{21}H_{21}ClF_3N_3O_2$ | 456.5 | 16.8 | 74 |
| 103 | 74 | $C_{22}H_{24}ClN_3O_4$ | 430.0 | 16.4 | 76 |
| 104 | 75 | $C_{21}H_{20}ClF_4N_3O_2$ | 458.0 | 16.1 | 70 |
| 105 | 76 | $C_{21}H_{20}ClF_4N_3O_2$ | 458.0 | 17.0 | 74 |
| 106 | 77 | $C_{20}H_{19}ClF_3N_3O_2$ | 426.0 | 16.2 | 76 |
| 107 | 78 | $C_{20}H_{19}ClF_3N_3O_2$ | 426.0 | 18.0 | 85 |
| 108 | 79 | $C_{22}H_{20}ClF_6N_3O_2$ | 508.0 | 18.8 | 74 |
| 109 | 80 | $C_{22}H_{20}ClF_6N_3O_2$ | 508.0 | 16.4 | 65 |
| 110 | 81 | $C_{22}H_{26}ClN_3O_2$ | 400.0 | 13.9 | 70 |
| 111 | 83 | $C_{20}H_{21}ClN_4O_4$ | 417.0 | 16.0 | 77 |
| 112 | 84 | $C_{20}H_{21}ClN_4O_4$ | 417.0 | 21.6 | Q |
| 113 | 87 | $C_{23}H_{22}ClF_6N_3O_2$ | 522.0 | 17.5 | 67 |
| 114 | 88 | $C_{22}H_{23}ClF_3N_3O_2$ | 454.0 | 13.9 | 61 |
| 115 | 89 | $C_{21}H_{23}BrClN_3O_2$ | 466.0 | 15.4 | 66 |
| 116 | 90 | $C_{21}H_{23}ClFN_3O_2$ | 404.0 | 10.7 | 53 |
| 117 | 91 | $C_{21}H_{22}Cl_3N_3O_2$ | 456.0 | 13.7 | 60 |
| 118 | 92 | $C_{22}H_{26}ClN_3O_3$ | 416.0 | 38.4 | Q |
| 119 | 93 | $C_{23}H_{28}ClN_3O_4$ | 446.0 | 25.2 | Q |
| 120 | 94 | $C_{23}H_{28}ClN_3O_4$ | 446.0 | 16.5 | 74 |
| 121 | 95 | $C_{22}H_{23}ClF_3N_3O_2$ | 454.0 | 16.3 | 72 |
| 122 | 96 | $C_{22}H_{26}ClN_3O_2$ | 400.5 | 16.7 | 84 |
| 123 | 97 | $C_{21}H_{23}Cl_2N_3O_2$ | 420.0 | 11.2 | 53 |
| 124 | 98 | $C_{22}H_{26}ClN_3O_2$ | 416.5 | 11.8 | 57 |
| 125 | 99 | $C_{21}H_{22}Cl_3N_3O_2$ | 454.0 | 14.8 | 65 |
| 126 | 100 | $C_{22}H_{23}ClN_4O_2$ | 411.0 | 9.5 | 46 |
| 127 | 101 | $C_{22}H_{24}ClN_3O_4$ | 430.5 | 13.2 | 61 |
| 128 | 102 | $C_{22}H_{22}ClF_4N_3O_2$ | 472.0 | 13.1 | 56 |
| 129 | 103 | $C_{22}H_{22}ClF_4N_3O_2$ | 472.0 | 36.5 | Q |
| 130 | 104 | $C_{22}H_{22}ClF_4N_3O_2$ | 472.0 | 22.8 | 97 |

TABLE 3-continued

| Example | Compd. No. | Molecular Formula | ESI/MS m/e | Yield (mg) | Yield (%) |
|---|---|---|---|---|---|
| 131 | 105 | $C_{22}H_{22}ClF_4N_3O_2$ | 472.0 | 20.1 | 85 |
| 132 | 106 | $C_{22}H_{23}ClF_3N_3O_3$ | 470.0 | 27.4 | Q |
| 133 | 107 | $C_{22}H_{22}ClF_4N_3O_2$ | 472.0 | 18.5 | 78 |
| 134 | 108 | $C_{21}H_{23}ClN_4O_4$ | 431.0 | 11.9 | 55 |
| 135 | 109 | $C_{21}H_{23}ClN_4O_4$ | 431.0 | 23.9 | Q |
| 136 | 110 | $C_{21}H_{23}ClN_4O_4$ | 431.0 | 24.4 | Q |
| 137 | 111 | $C_{23}H_{22}ClF_6N_3O_2$ | 522.0 | 9.5 | 36 |
| 138 | 112 | $C_{22}H_{23}ClF_3N_3O_2$ | 454.0 | 3.9 | 17 |
| 139 | 113 | $C_{21}H_{23}BrClN_3O_2$ | 466.0 | 7.5 | 32 |
| 140 | 114 | $C_{21}H_{23}ClFN_3O_2$ | 404.0 | 6.1 | 30 |
| 141 | 115 | $C_{21}H_{22}Cl_3N_3O_2$ | 456.0 | 6.6 | 29 |
| 142 | 116 | $C_{22}H_{26}ClN_3O_3$ | 416.0 | 4.8 | 23 |
| 143 | 117 | $C_{23}H_{28}ClN_3O_4$ | 446.0 | 6.4 | 29 |
| 144 | 118 | $C_{23}H_{28}ClN_3O_4$ | 446.0 | 24.6 | Q |
| 145 | 119 | $C_{22}H_{23}ClF_3N_3O_2$ | 454.0 | 5.2 | 23 |
| 146 | 120 | $C_{22}H_{26}ClN_3O_2$ | 400.5 | 4.4 | 22 |
| 147 | 121 | $C_{21}H_{23}Cl_2N_3O_2$ | 420.0 | 7.8 | 37 |
| 148 | 122 | $C_{22}H_{26}ClN_3O_2$ | 416.5 | 14.1 | 68 |
| 149 | 123 | $C_{21}H_{22}Cl_3N_3O_2$ | 454.0 | 5.4 | 24 |
| 150 | 124 | $C_{22}H_{23}ClN_4O_2$ | 411.0 | 34.0 | Q |
| 151 | 125 | $C_{22}H_{24}ClN_3O_4$ | 430.5 | 32.0 | Q |
| 152 | 126 | $C_{22}H_{22}ClF_4N_3O_2$ | 472.0 | 4.6 | 19 |
| 153 | 127 | $C_{22}H_{22}ClF_4N_3O_2$ | 472.0 | 10.4 | 44 |
| 154 | 128 | $C_{22}H_{22}ClF_4N_3O_2$ | 472.0 | 7.3 | 31 |
| 155 | 129 | $C_{22}H_{22}ClF_4N_3O_2$ | 472.0 | 13.5 | 57 |
| 156 | 130 | $C_{22}H_{23}ClF_3N_3O_3$ | 470.0 | 15.1 | 64 |
| 157 | 131 | $C_{22}H_{22}ClF_4N_3O_2$ | 472.0 | 8.6 | 36 |
| 158 | 132 | $C_{21}H_{23}ClN_4O_4$ | 431.0 | 4.4 | 20 |
| 159 | 133 | $C_{21}H_{23}ClN_4O_4$ | 431.0 | 32.0 | Q |
| 160 | 134 | $C_{21}H_{23}ClN_4O_4$ | 431.0 | 6.9 | 32 |
| 161 | 135 | $C_{21}H_{23}BrClN_3O_2$ | 466.0 | 7.8 | 34 |
| 162 | 136 | $C_{21}H_{23}ClFN_3O_2$ | 404.0 | 13.7 | 68 |
| 163 | 137 | $C_{21}H_{23}Cl_2N_3O_2$ | 420.5 | 14.6 | 69 |
| 164 | 138 | $C_{21}H_{22}Cl_3N_3O_2$ | 454.0 | 17.7 | 78 |
| 165 | 139 | $C_{21}H_{22}BrCl_4N_3O_2$ | 454.0 | 17.2 | 76 |
| 166 | 140 | $C_{22}H_{26}ClN_3O_2$ | 400.0 | 15.0 | 75 |
| 167 | 141 | $C_{23}H_{28}ClN_3O_4$ | 443.5 | 13.9 | 62 |
| 168 | 142 | $C_{21}H_{23}Cl_2N_3O_2$ | 420.0 | 13.7 | 65 |
| 169 | 143 | $C_{21}H_{23}BrClN_3O_2$ | 464.0 | 16.1 | 69 |
| 170 | 144 | $C_{27}H_{28}ClN_3O_2$ | 462.0 | 17.6 | 76 |
| 171 | 145 | $C_{22}H_{23}ClF_3N_3O_2$ | 454.0 | 16.0 | 71 |
| 172 | 146 | $C_{22}H_{26}ClN_3O_2$ | 400.0 | 14.9 | 75 |
| 173 | 147 | $C_{23}H_{28}ClN_3O_2$ | 414.0 | 16.2 | 78 |
| 174 | 148 | $C_{22}H_{23}ClN_4O_2$ | 411.0 | 14.9 | 73 |
| 175 | 149 | $C_{25}H_{26}ClN_3O_2$ | 436.0 | 17.1 | 78 |
| 176 | 150 | $C_{25}H_{26}ClN_3O_2$ | 436.0 | 13.1 | 60 |
| 177 | 151 | $C_{21}H_{22}ClF_2N_3O_2$ | 422.0 | 14.8 | 70 |
| 178 | 152 | $C_{21}H_{22}ClF_2N_3O_2$ | 422.0 | 15.3 | 73 |
| 179 | 153 | $C_{21}H_{22}ClF_2N_3O_2$ | 422.0 | 15.3 | 73 |
| 180 | 154 | $C_{21}H_{22}ClF_2N_3O_2$ | 422.0 | 16.4 | 78 |
| 181 | 155 | $C_{23}H_{28}ClN_3O_4$ | 443.0 | 16.9 | 76 |
| 182 | 156 | $C_{22}H_{23}ClF_3N_3O_2$ | 470.5 | 12.6 | 54 |
| 183 | 157 | $C_{22}H_{23}ClF_3N_3O_2$ | 470.0 | 20.0 | 85 |
| 184 | 158 | $C_{23}H_{26}ClN_3O_4$ | 444.0 | 17.4 | 78 |
| 185 | 159 | $C_{22}H_{22}ClF_4N_3O_2$ | 472.0 | 18.4 | 78 |
| 186 | 160 | $C_{22}H_{22}ClF_4N_3O_2$ | 472.0 | 19.6 | 83 |
| 187 | 161 | $C_{21}H_{21}ClF_3N_3O_2$ | 440.0 | 17.0 | 77 |
| 188 | 162 | $C_{21}H_{21}ClF_3N_3O_2$ | 440.0 | 17.1 | 78 |
| 189 | 163 | $C_{23}H_{22}ClF_6N_3O_2$ | 522.0 | 20.8 | 80 |
| 190 | 164 | $C_{23}H_{22}ClF_6N_3O_2$ | 522.0 | 2.7 | 10 |
| 191 | 165 | $C_{23}H_{28}ClN_3O_2$ | 414.0 | 16.4 | 79 |
| 192 | 166 | $C_{22}H_{23}ClF_3N_3O_2$ | 454.0 | 8.6 | 38 |
| 193 | 167 | $C_{21}H_{23}BrClN_3O_2$ | 464.0 | 11.6 | 50 |
| 194 | 168 | $C_{21}H_{23}Cl_2N_3O_2$ | 420.0 | 11.5 | 55 |
| 195 | 169 | $C_{21}H_{22}Cl_3N_3O_2$ | 454.0 | 10.0 | 44 |
| 196 | 170 | $C_{22}H_{22}ClF_4N_3O_2$ | 472.0 | 10.4 | 44 |
| 197 | 171 | $C_{21}H_{23}Cl_2N_3O_2$ | 420.0 | 8.9 | 42 |
| 198 | 172 | $C_{21}H_{24}ClN_3O_2$ | 386.0 | 10.3 | 53 |
| 199 | 173 | $C_{21}H_{23}ClN_4O_4$ | 431.0 | 14.6 | 68 |
| 200 | 174 | $C_{22}H_{23}ClF_3N_3O_2$ | 454.0 | 10.4 | 46 |
| 201 | 175 | $C_{21}H_{23}BrClN_3O_2$ | 464.0 | 13.4 | 58 |
| 202 | 176 | $C_{21}H_{23}Cl_2N_3O_2$ | 420.0 | 12.7 | 60 |
| 203 | 177 | $C_{21}H_{22}Cl_3N_3O_2$ | 454.0 | 13.2 | 58 |
| 204 | 178 | $C_{22}H_{22}ClF_4N_3O_2$ | 472.0 | 12.9 | 55 |
| 205 | 179 | $C_{21}H_{23}Cl_2N_3O_2$ | 420.0 | 13.3 | 63 |
| 206 | 180 | $C_{21}H_{24}ClN_3O_2$ | 386.0 | 24.2 | Q |

TABLE 3-continued

| Example | Compd. No. | Molecular Formula | ESI/MS m/e | Yield (mg) | Yield (%) |
|---|---|---|---|---|---|
| 207 | 181 | $C_{21}H_{23}ClN_4O_4$ | 431.0 | 1.0 | 1 |
| 208 | 182 | $C_{23}H_{25}ClF_3N_3O_2$ | 468.0 | 15.1 | 65 |
| 209 | 183 | $C_{22}H_{25}BrClN_3O_2$ | 478.0 | 18.0 | 75 |
| 210 | 184 | $C_{22}H_{25}Cl_2N_3O_2$ | 434.0 | 16.3 | 75 |
| 211 | 185 | $C_{22}H_{24}Cl_3N_3O_2$ | 468.0 | 18.6 | 79 |
| 212 | 186 | $C_{23}H_{24}ClF_4N_3O_2$ | 486.0 | 16.5 | 68 |
| 213 | 187 | $C_{22}H_{25}Cl_2N_3O_2$ | 434.0 | 14.4 | 66 |
| 214 | 188 | $C_{22}H_{26}ClN_3O_2$ | 400.0 | 14.0 | 70 |
| 215 | 189 | $C_{22}H_{25}ClN_4O_4$ | 445.0 | 16.8 | 76 |
| 216 | 190 | $C_{26}H_{25}ClF_3N_3O_2S$ | 536.0 | 17.7 | 66 |
| 217 | 191 | $C_{26}H_{25}BrClN_3O_2S$ | 546.0 | 20.4 | 75 |
| 218 | 192 | $C_{25}H_{25}Cl_2N_3O_2S$ | 502.0 | 16.9 | 67 |
| 219 | 193 | $C_{25}H_{24}Cl_3N_3O_2S$ | 536.0 | 18.3 | 68 |
| 220 | 194 | $C_{26}H_{24}ClF_4N_3O_2S$ | 554.0 | 19.4 | 70 |
| 221 | 195 | $C_{25}H_{25}Cl_2N_3O_2S$ | 502.0 | 19.1 | 76 |
| 222 | 196 | $C_{25}H_{26}ClN_3O_2S$ | 468.0 | 16.0 | 68 |
| 223 | 197 | $C_{25}H_{25}ClN_4O_4S$ | 513.0 | 18.4 | 72 |
| 224 | 198 | $C_{26}H_{25}ClF_3N_3O_2S$ | 536.0 | 13.9 | 52 |
| 225 | 199 | $C_{25}H_{25}BrClN_3O_2S$ | 546.0 | 12.9 | 47 |
| 226 | 200 | $C_{25}H_{25}Cl_2N_3O_2S$ | 502.0 | 15.6 | 62 |
| 227 | 201 | $C_{25}H_{24}Cl_3N_3O_2S$ | 536.0 | 17.3 | 64 |
| 228 | 202 | $C_{26}H_{24}ClF_4N_3O_2S$ | 554.0 | 15.4 | 56 |
| 229 | 203 | $C_{25}H_{25}Cl_2N_3O_2S$ | 502.0 | 13.5 | 54 |
| 230 | 204 | $C_{25}H_{26}ClN_3O_2S$ | 468.0 | 13.7 | 59 |
| 231 | 205 | $C_{25}H_{25}ClN_4O_4S$ | 513.0 | 13.9 | 54 |
| 232 | 206 | $C_{24}H_{27}ClF_3N_3O_4S$ | 546.0 | 10.0 | 37 |
| 233 | 207 | $C_{23}H_{27}BrClN_3O_4S$ | 558.0 | 17.1 | 61 |
| 234 | 208 | $C_{23}H_{27}Cl_2N_3O_4S$ | 512.0 | 17.0 | 66 |
| 235 | 209 | $C_{23}H_{26}Cl_3N_3O_4S$ | 546.0 | 7.3 | 27 |
| 236 | 210 | $C_{24}H_{26}ClF_4N_3O_4S$ | 564.0 | 19.2 | 68 |
| 237 | 211 | $C_{23}H_{27}Cl_2N_3O_4S$ | 512.0 | 7.9 | 31 |
| 238 | 212 | $C_{23}H_{28}ClN_3O_4S$ | 478.0 | 13.7 | 57 |
| 239 | 213 | $C_{23}H_{27}ClN_4O_4S$ | 523.0 | 5.5 | 21 |

Note:
Q means "Quantitative".

Example 240

Synthesis of (R)-3-[N-[3-fluoro-5-(trifluoromethyl)benzoyl]glycyl]amino-1-(3,5-dimethylisoxazol-4-ylmethyl)-pyrrolidine (Compd. No. 1191)

A dichloromethane solution (1 mL) of 3-fluoro-5-(trifluoromethyl)benzoyl chloride (0.058 mmol) was added to a solution of (R)-1-(3,5-dimethylisoxazol-4-ylmethyl)-3-(glycylamino)pyrrolidine (0.050 mmol) and a piperidinomethylpolystyrene (58 mg) in chloroform (0.2 mL) and dichloromethane (0.75 ml). The reaction mixture was stirred at room temperature for 2 hours, and methanol (1.0 mL) was then added. The resulting mixture was stirred at room temperature for 10 hours. The reaction mixture was loaded onto a Varian™ SCX column and washed with methanol (16 mL). The obtained crude product was eluted with a solution of 2 M $NH_3$ in methanol (6 mL) and concentrated to provide (R)-3-[N-[3-fluoro-5-(trifluoromethyl)benzoyl]glycyl]amino-1-(3,5-dimethylisoxazol-4-ylmethyl)pyrrolidine (Compd. No. 1191) (19.5 mg, 88%). The purity was determined by RPLC/MS (100%). ESI/MS m/e 443.2 ($M^+$+H, $C_{20}H_{22}F_4N_4O_3$).

Examples 241 to 265

The compounds used in the present invention were synthesized by using the respective corresponding starting materials and reactants according to the method of Example 240. Data of ESI/MS, yields (mg) and yields (%) are collectively shown in Table 4.

TABLE 4

| Example | Compd. No. | Molecular Formula | ESI/MS m/e | Yield (mg) | Yield (%) |
|---|---|---|---|---|---|
| 241 | 1192 | $C_{20}H_{22}F_4N_4O_3$ | 443.2 | 19.2 | 87 |
| 242 | 1193 | $C_{20}H_{23}F_3N_4O_4$ | 441.0 | 17.5 | 79 |
| 243 | 1194 | $C_{21}H_{22}F_6N_4O_3$ | 493.0 | 20.4 | 83 |
| 244 | 1195 | $C_{19}H_{23}BrN_4O_3$ | 435.1 | 16.8 | 77 |
| 245 | 1196 | $C_{19}H_{23}N_5O_5$ | 402.2 | 16.2 | 81 |
| 246 | 1197 | $C_{20}H_{22}F_4N_4O_3$ | 443.2 | 17.6 | 80 |
| 247 | 1198 | $C_{19}H_{23}ClN_4O_3$ | 391.0 | 16.5 | 84 |
| 248 | 1199 | $C_{20}H_{26}N_4O_3$ | 371.0 | 16.1 | 87 |
| 249 | 1200 | $C_{19}H_{22}Cl_2N_4O_3$ | 425.0 | 18.0 | 85 |
| 250 | 1201 | $C_{19}H_{22}F_2N_4O_3$ | 393.0 | 16.6 | 85 |
| 251 | 1202 | $C_{20}H_{22}F_4N_4O_3$ | 443.2 | 16.8 | 76 |
| 252 | 1203 | $C_{22}H_{24}F_3N_3O_3$ | 436.2 | 17.1 | 79 |
| 253 | 1204 | $C_{23}H_{23}F_6N_3O_2$ | 488.2 | 18.1 | 74 |
| 254 | 1205 | $C_{21}H_{24}BrN_3O_2$ | 430.0 | 17.5 | 81 |
| 255 | 1206 | $C_{21}H_{24}N_4O_4$ | 397.0 | 16.2 | 82 |
| 256 | 1207 | $C_{22}H_{23}F_4N_3O_2$ | 438.2 | 17.5 | 80 |
| 257 | 1208 | $C_{21}H_{24}ClN_3O_2$ | 386.0 | 15.8 | 82 |
| 258 | 1209 | $C_{22}H_{27}N_3O_2$ | 366.0 | 15.7 | 86 |
| 259 | 1210 | $C_{21}H_{23}Cl_2N_3O_2$ | 420.0 | 17.8 | 85 |
| 260 | 1211 | $C_{21}H_{23}F_2N_3O_2$ | 388.0 | 16.3 | 84 |
| 261 | 1212 | $C_{22}H_{23}F_4N_3O_2$ | 438.2 | 17.4 | 80 |
| 262 | 1213 | $C_{24}H_{24}ClF_6N_3O_2$ | 536.2 | 24.0 | 90 |
| 263 | 1214 | $C_{23}H_{24}ClF_4N_3O_3$ | 486.2 | 22.2 | 91 |
| 264 | 1215 | $C_{22}H_{24}Cl_3N_3O_2$ | 467.9 | 20.9 | 89 |
| 265 | 1216 | $C_{22}H_{24}ClF_2N_3O_2$ | 436.0 | 19.3 | 89 |

Example 266

Synthesis of (R)-1-(4-chlorobenzyl)-3-[[N-(4-dimethylaminobenzoyl)glycyl]amino]pyrrolidine (Compd. No. 952)

Triethylamine (0.021 mL, 0.15 mmol), 4-(dimethylamino) benzoic acid (10 mg, 0.061 mmol), EDCI (10.2 mg, 0.053 mmol) and HOBt (7.5 mg, 0.055 mmol) were added to a chloroform (2 mL) solution of (R)-1-(4-chlorobenzyl)-3-(glycylamino)pyrrolidine (13.8 mg, 0.052 mmol). The resulting reaction mixture was stirred at room temperature for 15 hours. The solution was washed with a 2 M aqueous solution of NaOH (2 mL×2) and brine (2 mL), filtered through a PTFE membrane by using dichloromethane (3 mL), dried and concentrated to thereby afford (R)-1-(4-chlorobenzyl)-3-[[N-(4-dimethylaminobenzoyl)glycyl]amino]pyrrolidine (Compd. No. 952) (24.9 mg). The purity was determined by RPLC/MS (91%). ESI/MS m/e 415.0 ($M^+$+H, $C_{22}H_{27}ClN_4O_2$).

Examples 267 to 347

The compounds used in the present invention were synthesized by using the respective corresponding starting materials and reactants according to the method of Example 266. The obtained products, if necessary, were purified by solid-phase extraction (Varian™ SCX column) or chromatography (HPLC-$C_{18}$) to provide the objective compounds. Data of ESI/MS, yields (mg) and yields (%) are collectively shown in Table 5.

TABLE 5

| Example | Compd. No. | Molecular Formula | ESI/MS m/e | Yield (mg) | Yield (%) |
|---|---|---|---|---|---|
| 267 | 951 | $C_{22}H_{24}ClN_3O_4$ | 430.0 | 26.3 | Q |
| 268 | 953 | $C_{23}H_{29}ClN_4O_2$ | 429.0 | 28.8 | Q |
| 269 | 954 | $C_{21}H_{25}ClN_4O_2$ | 401.0 | 27.9 | Q |
| 270 | 955 | $C_{22}H_{27}ClN_4O_2$ | 415.0 | 26.8 | Q |
| 271 | 956 | $C_{21}H_{24}ClN_3O_3$ | 402.0 | 10.3 | 51 |
| 272 | 957 | $C_{20}H_{22}ClN_3O_3$ | 388.0 | 1.4 | 7 |
| 273 | 958 | $C_{21}H_{24}ClN_3O_3$ | 402.5 | 1.2 | 6 |
| 274 | 959 | $C_{22}H_{25}ClN_4O_3$ | 429.5 | 4.7 | 22 |
| 275 | 960 | $C_{23}H_{27}ClN_4O_3$ | 443.0 | 10.9 | 49 |
| 276 | 961 | $C_{21}H_{25}ClN_4O_2$ | 401.0 | 28.4 | Q |
| 277 | 962 | $C_{22}H_{27}ClN_4O_2$ | 415.0 | 24.9 | Q |
| 278 | 963 | $C_{21}H_{24}ClN_3O_3$ | 402.0 | 4.4 | 22 |
| 279 | 964 | $C_{22}H_{24}ClN_3O_4$ | 430.0 | 29.5 | Q |
| 280 | 965 | $C_{23}H_{26}ClN_3O_4$ | 444.0 | 27.2 | Q |
| 281 | 966 | $C_{22}H_{24}ClN_3O_3$ | 414.0 | 27.0 | Q |
| 282 | 967 | $C_{23}H_{26}ClN_3O_3$ | 428.0 | 27.0 | Q |
| 283 | 968 | $C_{22}H_{23}ClN_4O_2$ | 411.0 | 21.4 | Q |
| 284 | 969 | $C_{23}H_{25}ClN_4O_2$ | 425.0 | 27.6 | Q |
| 285 | 970 | $C_{22}H_{27}ClN_4O_2$ | 415.0 | 28.6 | Q |
| 286 | 971 | $C_{23}H_{29}ClN_4O_2$ | 429.0 | 27.9 | Q |
| 287 | 972 | $C_{20}H_{23}ClN_4O_2$ | 387.0 | 26.2 | Q |
| 288 | 973 | $C_{21}H_{25}ClN_4O_2$ | 401.0 | 26.8 | Q |
| 289 | 974 | $C_{20}H_{23}ClN_4O_2$ | 387.0 | 26.6 | Q |
| 290 | 975 | $C_{21}H_{25}ClN_4O_2$ | 401.0 | 28.2 | Q |
| 291 | 976 | $C_{22}H_{23}ClN_4O_2$ | 411.0 | 29.2 | Q |
| 292 | 977 | $C_{23}H_{25}ClN_4O_2$ | 425.0 | 29.5 | Q |
| 293 | 978 | $C_{20}H_{21}ClN_6O_2$ | 413.0 | 2.2 | 11 |
| 294 | 979 | $C_{21}H_{23}ClN_6O_2$ | 427.0 | 10.2 | 48 |
| 295 | 980 | $C_{22}H_{25}ClN_4O_3$ | 429.0 | 28.8 | Q |
| 296 | 981 | $C_{23}H_{27}ClN_4O_3$ | 443.0 | 11.9 | 54 |
| 297 | 982 | $C_{22}H_{27}ClN_4O_2$ | 415.0 | 27.4 | Q |
| 298 | 983 | $C_{23}H_{29}ClN_4O_2$ | 429.5 | 28.1 | Q |
| 299 | 984 | $C_{21}H_{24}ClN_3O_3$ | 402.0 | 27.7 | Q |
| 300 | 985 | $C_{22}H_{26}ClN_3O_3$ | 416.0 | 28.6 | Q |
| 301 | 1149 | $C_{21}H_{28}N_4O_4$ | 401 | 15.5* | 38 |
| 302 | 1150 | $C_{21}H_{28}N_4O_3$ | 385 | 10.9* | 28 |
| 303 | 1151 | $C_{21}H_{25}F_3N_4O_3$ | 439 | 17.3* | 39 |
| 304 | 1152 | $C_{21}H_{24}FN_5O_3$ | 415 | 12.7* | 30 |
| 305 | 1153 | $C_{21}H_{24}ClN_5O_3$ | 430 | 17.5* | 41 |
| 306 | 1154 | $C_{22}H_{27}N_5O_3$ | 410 | 20.6* | 50 |
| 307 | 1155 | $C_{19}H_{23}F_3N_4O_4$ | 429 | 13.8* | 32 |
| 308 | 1156 | $C_{21}H_{30}N_4O_4$ | 403 | 17.7* | 43 |
| 309 | 1157 | $C_{18}H_{24}N_4O_3S_2$ | 409 | 12.6* | 30 |
| 310 | 1158 | $C_{19}H_{23}Cl_2N_5O_3$ | 440 | 16.9* | 38 |
| 311 | 1159 | $C_{22}H_{31}N_5O_6$ | 462 | 38.6* | 85 |
| 312 | 1160 | $C_{20}H_{26}BrN_5O_3$ | 464 | 20.4 | 45 |
| 313 | 1289 | $C_{20}H_{27}N_5O_4$ | 403 | 5.8* | 14 |
| 314 | 1290 | $C_{21}H_{29}N_5O_3$ | 400 | 6.9* | 17 |
| 315 | 1291 | $C_{24}H_{28}N_4O_2$ | 405 | 22.4 | 68 |
| 316 | 1292 | $C_{22}H_{27}BrN_4O_2$ | 461 | 23.8 | 15 |
| 317 | 1293 | $C_{22}H_{23}F_4N_3O_2$ | 438 | 20.9 | 59 |
| 318 | 1294 | $C_{22}H_{23}F_4N_3O_2$ | 438 | 20.8 | 59 |
| 319 | 1295 | $C_{23}H_{31}N_3O_3$ | 398 | 17.5 | 54 |
| 320 | 1296 | $C_{20}H_{25}N_3O_2S_2$ | 404 | 18.8 | 58 |
| 321 | 1297 | $C_{21}H_{24}F_3N_3O_3$ | 424 | 18.1 | 53 |
| 322 | 1388 | $C_{21}H_{32}N_6O_3$ | 417 | 7.4* | 24 |
| 323 | 1389 | $C_{19}H_{22}N_6O_4$ | 399 | 15.2 | 48 |
| 324 | 1401 | $C_{23}H_{25}ClN_4O_2$ | 425 | 8.3* | 16 |
| 325 | 1402 | $C_{24}H_{32}N_4O_5$ | 457 | 8.3* | 15 |
| 326 | 1403 | $C_{20}H_{24}N_4O_2$ | 353 | 14.8 | 52 |
| 327 | 1404 | $C_{20}H_{24}N_4O_2$ | 353 | 17.0 | 60 |
| 328 | 1405 | $C_{21}H_{26}N_4O_2S$ | 399 | 17.3 | 54 |
| 329 | 1407 | $C_{22}H_{28}N_4O_2S$ | 413 | 19.1 | 57 |
| 330 | 1410 | $C_{19}H_{24}N_4O_3$ | 357 | 9.7* | 59 |
| 331 | 1769 | $C_{22}H_{26}ClF_3N_4O_5$ | 519 | 11.6* | 20 |
| 332 | 1770 | $C_{26}H_{28}Cl_2N_6O_4$ | 559 | 13.1* | 21 |
| 333 | 1771 | $C_{26}H_{37}N_5O_4$ | 484 | 12.7* | 23 |
| 334 | 1772 | $C_{28}H_{39}N_5O_4$ | 510 | 5.5* | 9 |
| 335 | 1773 | $C_{28}H_{37}N_5O_4$ | 509 | 6.2* | 11 |
| 336 | 1774 | $C_{28}H_{34}N_6O_6$ | 551 | 13.6* | 22 |
| 337 | 2039 | $C_{19}H_{24}N_4O_2$ | 341 | 5.2* | 14 |
| 338 | 2040 | $C_{22}H_{27}N_3O_4$ | 398 | 2.0* | 5 |
| 339 | 2041 | $C_{23}H_{29}N_3O_3$ | 396 | 6.2* | 15 |
| 340 | 2042 | $C_{25}H_{37}N_3O_2$ | 413 | 2.6* | 6 |
| 341 | 2043 | $C_{24}H_{31}N_3O_2$ | 394 | 6.8* | 17 |
| 342 | 2044 | $C_{25}H_{28}N_4O_4$ | 449 | 8.7* | 16 |
| 343 | 2045 | $C_{26}H_{29}ClN_6O_4$ | 525 | 11.4* | 19 |
| 344 | 2046 | $C_{27}H_{32}N_6O_4$ | 505 | 7.7* | 13 |
| 345 | 2047 | $C_{28}H_{32}N_4O_4$ | 489 | 10.0* | 18 |

TABLE 5-continued

| Example | Compd. No. | Molecular Formula | ESI/MS m/e | Yield (mg) | Yield (%) |
|---|---|---|---|---|---|
| 346 | 2048 | $C_{28}H_{37}N_5O_5$ | 524 | 3.7* | 6 |
| 347 | 2049 | $C_{28}H_{37}N_5O_4$ | 509 | 5.3* | 9 |

Note:
*indicated "yield (mg) of trifluoroacetate".
Q means "Quantitative".

Example 348

Synthesis of (R)-1-(4-chlorobenzyl)-3-[[N-(2-amino-5-chlorobenzoyl)glycyl]amino]pyrrolidine (Compd. No. 1084)

2-Amino-5-chlorobenzoic acid (0.060 mL) and diisopropylcarbodiimide (0.060 mol) were added to a chloroform (2 mL) solution of (R)-1-(4-chlorobenzyl)-3-(glycylamino)pyrrolidine (0.050 mmol). The resulting reaction solution was stirred at room temperature for 15 hours. The mixture solution was loaded onto a Varian™ SCX column and washed with methanol (15 mL). The obtained crude product was eluted with a solution of 2 M $NH_3$ in methanol (5 mL) and concentrated to thereby afford (R)-1-(4-chlorobenzyl)-3-[N-[2-amino-5-chlorobenzoyl]glycyl]amino]pyrrolidine (Compd. No. 1084) (12.7 mg, 60%). The purity was determined by RPLC/MS (87%). ESI/MS m/e 421.0 ($M^+$+H, $C_{20}H_{22}Cl_2N_4O_2$).

Examples 349 to 361

The compounds used in the present invention were synthesized by using the respective corresponding starting materials and reactants according to the method of Example 348. When the starting amine remained, a chloroform (1 mL) solution of an isocyanatomethylated polystyrene (50 mg) was added and reacted at room temperature. The resulting reaction mixtures were filtered and concentrated to thereby afford the objective compounds. Data of ESI/MS, yields (mg) and yields (%) are collectively shown in Table 6.

TABLE 6

| Example | Compd. No. | Molecular Formula | ESI/MS m/e | Yield (mg) | Yield (%) |
|---|---|---|---|---|---|
| 349 | 1085 | $C_{20}H_{22}ClN_8O_4$ | 432.0 | 4.1 | 19 |
| 350 | 1086 | $C_{20}H_{23}ClN_4O_2$ | 387.0 | 7.9 | 41 |
| 351 | 1087 | $C_{22}H_{23}ClN_4O_2$ | 411.0 | 15.0 | 73 |
| 352 | 1088 | $C_{18}H_{20}ClN_3O_3$ | 362.0 | 12.9 | 71 |
| 353 | 1089 | $C_{22}H_{22}ClFN_4O_2$ | 429.0 | 16.0 | 75 |
| 354 | 1090 | $C_{22}H_{26}ClN_3O_3$ | 416.0 | 15.8 | 76 |
| 355 | 1091 | $C_{21}H_{24}Cl_2N_4O_2$ | 435.0 | 10.9 | 50 |
| 356 | 1092 | $C_{21}H_{24}ClN_5O_4$ | 446.0 | 7.9 | 35 |
| 357 | 1093 | $C_{21}H_{25}ClN_4O_2$ | 401.0 | 9.5 | 47 |
| 358 | 1094 | $C_{23}H_{25}ClN_4O_2$ | 425.0 | 15.8 | 74 |
| 359 | 1095 | $C_{19}H_{22}ClN_3O_3$ | 376.0 | 13.5 | 72 |
| 360 | 1096 | $C_{23}H_{24}ClFN_4O_2$ | 443.0 | 11.8 | 53 |
| 361 | 1097 | $C_{23}H_{28}ClN_3O_3$ | 430.0 | 15.1 | 70 |

Example 362

Synthesis of (R)-1-(4-chlorobenzyl-3-[[N-(3-bromo-4-methylbenzoyl)glycyl]amino]pyrrolidine (Compd. No. 1098)

3-Brmo-4-methylbenzoic acid (0.060 mL), diisopropylcarbodiimide (0.060 mmol) and HOBt (0.060 mmol) were added to a solution of (R)-1-(4-chlorobenzyl)-3-(glycylamino)pyrrolidine (0.050 mmol) in chloroform (1.35 mL) and tert-butanol (0.15 mL). The resulting reaction mixture was stirred at room temperature for 15 hours. The mixture solution was loaded onto a Varian™ SCX column and washed with methanol/chloroform=1:1 (12 mL) and methanol (12 mL). The crude product was eluted with a solution of 2 M $NH_3$ in methanol (5 mL) and concentrated to thereby provide (R)-1-(4-chlorobenzyl)-3-[[N-(3-bromo-4-methylbenzoyl) glycyl]amino]pyrrolidine (Compd. No. 1098) (11.6 mg, 50%). The purity was determined by RPLC/MS (94%). ESI/MS m/e 466.0 ($M^+$+H, $C_{21}H_{23}BrClN_3O_2$).

Examples 363 to 572

The compounds used in the present invention were synthesized by using the respective corresponding starting materials and reactants according to the method of Example 362. The obtained products, if necessary, were purified by preparative TLC to afford the objective compounds. Data of ESI/MS, yields (mg) and yields (%) are collectively shown in Table 7.

The following three compounds were obtained as by-products of the Compd. Nos. 1415, 1416 and 1417.

Compd. No. 1419: 7.9 mg, yield 38%, ESI/MS m/e 419.0 ($C_{20}H_{23}ClN_4O_2S$).

Compd. No. 1420: 7.1 mg, yield 36%, ESI/MS m/e 399.2 ($C_{23}H_{26}N_4O_2S$).

Compd. No. 1421: 7.4 mg, yield 37%, ESI/MS m/e 404.2 ($C_{19}H_{25}N_5O_3S$).

TABLE 7

| Example | Compd. No. | Molecular Formula | ESI/MS m/e | Yield (mg) | Yield (%) |
|---|---|---|---|---|---|
| 363 | 1099 | $C_{20}H_{20}BrClFN_3O_2$ | 470.0 | 3.1 | 13 |
| 364 | 1100 | $C_{20}H_{20}Cl_2FN_3O_2$ | 424.0 | 3.1 | 15 |
| 365 | 1101 | $C_{21}H_{23}ClIN_3O_2$ | 512.0 | 12.5 | 49 |
| 366 | 1102 | $C_{21}H_{23}ClN_4O_4$ | 431.2 | 7.7 | 36 |
| 367 | 1103 | $C_{22}H_{26}BrN_3O_2$ | 446.0 | 13.8 | 62 |
| 368 | 1104 | $C_{21}H_{23}BrFN_3O_2$ | 450.0 | 16.5 | 74 |
| 369 | 1105 | $C_{21}H_{23}ClFN_3O_2$ | 404.2 | 14.7 | 73 |
| 370 | 1106 | $C_{22}H_{26}IN_3O_2$ | 492.0 | 18.5 | 75 |
| 371 | 1107 | $C_{22}H_{26}N_4O4$ | 411.2 | 15.2 | 74 |
| 372 | 1108 | $C_{20}H_{25}BrN_4O_3$ | 449.0 | 12.8 | 57 |
| 373 | 1109 | $C_{19}H_{22}BrFN_4O_3$ | 455.0 | 16.2 | 71 |
| 374 | 1110 | $C_{19}H_{22}ClFN_4O_3$ | 409.2 | 14.4 | 70 |
| 375 | 1111 | $C_{20}H_{25}IN_4O_3$ | 497.0 | 17.9 | 72 |
| 376 | 1112 | $C_{20}H_{25}N_5O_5$ | 416.2 | 14.9 | 72 |
| 377 | 1113 | $C_{23}H_{27}BrClN_3O_2$ | 494.0 | 16.1 | 65 |
| 378 | 1114 | $C_{22}H_{24}BrClFN_3O_2$ | 498.0 | 20.2 | 81 |
| 379 | 1115 | $C_{22}H_{24}Cl_2FN_3O_2$ | 452.2 | 18.6 | 82 |
| 380 | 1116 | $C_{23}H_{27}ClIN_3O_2$ | 539.1 | 21.9 | 81 |
| 381 | 1117 | $C_{23}H_{27}ClN_4O_4$ | 459.2 | 18.7 | 81 |
| 382 | 1171 | $C_{21}H_{23}BrClN_3O_2$ | 466.0 | 4.9 | 21 |
| 383 | 1172 | $C_{22}H_{23}ClN_4O_3$ | 427.2 | 16.1 | 75 |
| 384 | 1173 | $C_{23}H_{25}ClN_4O_3$ | 441.2 | 22.8 | Q |
| 385 | 1174 | $C_{2O}H_{22}ClFN_4O_2$ | 405.2 | 21.4 | Q |
| 386 | 1175 | $C_{22}H_{26}BrN_3O_2$ | 446.0 | 15.8 | 71 |
| 387 | 1176 | $C_{23}H_{26}N_4O_3$ | 407.2 | 17.6 | 87 |
| 388 | 1177 | $C_{24}H_{28}N_4O_3$ | 421.2 | 20.2 | 96 |
| 389 | 1178 | $C_{21}H_{25}FN_4O_2$ | 385.0 | 16.2 | 84 |
| 390 | 1179 | $C_{21}H_{25}N_5O_4$ | 412.2 | 2.3 | 11 |
| 391 | 1180 | $C_{23}H_{26}N_4O_2$ | 391.0 | 21.6 | Q |

TABLE 7-continued

| Example | Compd. No. | Molecular Formula | ESI/MS m/e | Yield (mg) | Yield (%) |
|---|---|---|---|---|---|
| 392 | 1181 | $C_{20}H_{25}BrN_4O_3$ | 451.0 | 20.1 | 89 |
| 393 | 1182 | $C_{21}H_{25}N_5O_4$ | 412.2 | 13.3 | 65 |
| 394 | 1183 | $C_{22}H_{27}N_5O_4$ | 426.2 | 20.9 | 98 |
| 395 | 1184 | $C_{19}H_{24}FN_5O_3$ | 390.0 | 20.0 | Q |
| 396 | 1185 | $C_{19}H_{24}N_6O_5$ | 417.2 | 18.2 | 87 |
| 397 | 1186 | $C_{21}H_{25}N_5O_3$ | 396.2 | 17.6 | 89 |
| 398 | 1187 | $C_{23}H_{27}BrClN_3O_2$ | 494.0 | 22.1 | 90 |
| 399 | 1188 | $C_{24}H_{27}ClN_4O_3$ | 455.2 | 17.2 | 76 |
| 400 | 1189 | $C_{25}H_{29}ClN_4O_3$ | 469.2 | 21.1 | 90 |
| 401 | 1190 | $C_{22}H_{26}ClFN_4O_2$ | 433.2 | 20.4 | 94 |
| 402 | 1217 | $C_{21}H_{20}Cl_2F_3N_3O_2$ | 474.0 | 38.5 | 81 |
| 403 | 1218 | $C_{21}H_{23}ClFN_3O_2$ | 404.2 | 35.6 | 88 |
| 404 | 1219 | $C_{21}H_{23}Cl_2N_3O_2$ | 420.0 | 3.7 | 9 |
| 405 | 1220 | $C_{20}H_{22}ClIN_4O_2$ | 513.0 | 53.0 | Q |
| 406 | 1221 | $C_{20}H_{21}ClF_2N_4O_2$ | 423.0 | 38.7 | 92 |
| 407 | 1222 | $C_{19}H_{23}ClN_4O_2$ | 375.2 | 33.6 | 90 |
| 408 | 1223 | $C_{26}H_{26}ClN_3O_2S$ | 496.0 | 43.7 | 88 |
| 409 | 1224 | $C_{20}H_{21}ClN_4O_5$ | 433.0 | 40.6 | 94 |
| 410 | 1225 | $C_{22}H_{23}ClF_3N_3O_2$ | 454.2 | 18.4 | 41 |
| 411 | 1226 | $C_{22}H_{26}FN_3O_2$ | 384.0 | 17.1 | 45 |
| 412 | 1227 | $C_{22}H_{26}ClN_3O_2$ | 400.2 | 17.5 | 44 |
| 413 | 1228 | $C_{21}H_{25}IN_4O_2$ | 493.0 | 23.3 | 47 |
| 414 | 1229 | $C_{21}H_{24}F_2N_4O_2$ | 403.2 | 18.4 | 46 |
| 415 | 1230 | $C_{20}H_{26}N_4O_2$ | 355.2 | 15.7 | 44 |
| 416 | 1231 | $C_{27}H_{29}N_3O_2S$ | 476.0 | 20.9 | 88 |
| 417 | 1232 | $C_{21}H_{24}N_4O_5$ | 413.0 | 19.9 | 96 |
| 418 | 1233 | $C_{20}H_{22}ClF_3N_4O_3$ | 459.0 | 19.4 | 85 |
| 419 | 1234 | $C_{20}H_{25}FN_4O_3$ | 389.0 | 17.8 | 92 |
| 420 | 1235 | $C_{20}H_{25}ClN_4O_3$ | 405.2 | 18.7 | 92 |
| 421 | 1236 | $C_{19}H_{24}IN_5O_3$ | 498.0 | 23.9 | 96 |
| 422 | 1237 | $C_{19}H_{23}F_2N_5O_3$ | 408.2 | 19.0 | 93 |
| 423 | 1238 | $C_{18}H_{25}N_5O_3$ | 360.0 | 16.3 | 91 |
| 424 | 1239 | $C_{25}H_{28}N_4O_3S$ | 481.2 | 21.4 | 89 |
| 425 | 1240 | $C_{19}H_{23}N_5O_6$ | 418.0 | 19.9 | 95 |
| 426 | 1241 | $C_{23}H_{24}Cl_2F_3N_3O_2$ | 502.0 | 22.5 | 90 |
| 427 | 1242 | $C_{23}H_{27}ClFN_3O_2$ | 432.2 | 21.2 | 98 |
| 428 | 1243 | $C_{23}H_{27}Cl_2N_3O_2$ | 448.0 | 21.6 | 96 |
| 429 | 1244 | $C_{22}H_{26}ClIN_4O_2$ | 541.0 | 26.4 | 98 |
| 430 | 1245 | $C_{22}H_{25}ClF_2N_4O_2$ | 451.0 | 21.3 | 94 |
| 431 | 1246 | $C_{21}H_{27}ClN_4O_2$ | 403.2 | 19.4 | 96 |
| 432 | 1247 | $C_{28}H_{30}ClN_3O_2S$ | 524.0 | 24.7 | 94 |
| 433 | 1248 | $C_{22}H_{25}ClN_4O_5$ | 461.0 | 20.7 | 90 |
| 434 | 1249 | $C_{20}H_{20}Cl_2N_4O_4$ | 451.0 | 7.4 | 33 |
| 435 | 1250 | $C_{21}H_{23}ClN_4O_4$ | 431.2 | 15.5 | 72 |
| 436 | 1251 | $C_{19}H_{22}ClN_5O_5$ | 436.0 | 22.9 | Q |
| 437 | 1252 | $C_{23}H_{28}ClN_3O_2$ | 414.2 | 17.9 | 86 |
| 438 | 1253 | $C_{24}H_{31}N_3O_2$ | 394.2 | 15.8 | 80 |
| 439 | 1254 | $C_{22}H_{30}N_4O_3$ | 399.2 | 17.3 | 87 |
| 440 | 1255 | $C_{20}H_{22}BrClN_4O_2$ | 467.0 | 21.3 | 91 |
| 441 | 1256 | $C_{21}H_{25}BrN_4O_2$ | 445.0 | 20.7 | 93 |
| 442 | 1257 | $C_{19}H_{24}BrN_5O_3$ | 450.0 | 21.8 | 97 |
| 443 | 1258 | $C_{21}H_{25}ClN_4O_2$ | 401.2 | 18.1 | 90 |
| 444 | 1259 | $C_{19}H_{24}ClN_5O_3$ | 406.0 | 20.1 | 99 |
| 445 | 1260 | $C_{23}H_{29}N_3O_3$ | 396.2 | 16.8 | 85 |
| 446 | 1261 | $C_{23}H_{30}ClN_3O_3$ | 432.2 | 19.8 | 92 |
| 447 | 1262 | $C_{24}H_{33}N_3O_3$ | 412.2 | 17.4 | 85 |
| 448 | 1263 | $C_{22}H_{32}N_4O_4$ | 417.2 | 18.7 | 90 |
| 449 | 1264 | $C_{25}H_{26}ClN_3O_3$ | 452.2 | 29.1 | Q |
| 450 | 1265 | $C_{26}H_{29}N_3O_3$ | 432.2 | 18.1 | 84 |
| 451 | 1266 | $C_{24}H_{28}N_4O_4$ | 437.2 | 19.3 | 88 |
| 452 | 1267 | $C_{23}H_{22}ClF_3N_4O_3$ | 495.2 | 20.6 | 83 |
| 453 | 1268 | $C_{21}H_{23}Cl_2N_3O_3$ | 436.0 | 17.5 | 80 |
| 454 | 1269 | $C_{20}H_{21}BrClN_3O_3$ | 468.0 | 19.2 | 82 |
| 455 | 1270 | $C_{20}H_{21}Cl_2N_3O_3$ | 422.2 | 17.3 | 82 |
| 456 | 1271 | $C_{20}H_{20}ClFN_4O_4$ | 435.0 | 17.1 | 79 |
| 457 | 1272 | $C_{24}H_{25}F_3N_4O_3$ | 475.2 | 21.7 | 91 |
| 458 | 1273 | $C_{22}H_{26}ClN_3O_3$ | 416.2 | 17.8 | 86 |
| 459 | 1274 | $C_{21}H_{24}BrN_3O_3$ | 448.0 | 19.5 | 87 |
| 460 | 1275 | $C_{21}H_{24}ClN_3O_3$ | 402.2 | 16.7 | 83 |
| 461 | 1276 | $C_{21}H_{23}FN_4O_4$ | 415.2 | 18.1 | 87 |
| 462 | 1277 | $C_{22}H_{24}F_3N_5O_4$ | 480.2 | 20.3 | 85 |
| 463 | 1278 | $C_{20}H_{25}ClN_4O_4$ | 421.2 | 18.6 | 88 |
| 464 | 1279 | $C_{19}H_{23}BrN_4O_4$ | 451.0 | 21.3 | 94 |
| 465 | 1280 | $C_{19}H_{23}ClN_4O_4$ | 407.2 | 19.1 | 94 |
| 466 | 1281 | $C_{19}H_{22}FN_5O_5$ | 420.2 | 19.1 | 91 |
| 467 | 1282 | $C_{25}H_{26}ClF_3N_4O_3$ | 523.2 | 25.0 | 96 |

TABLE 7-continued

| Example | Compd. No. | Molecular Formula | ESI/MS m/e | Yield (mg) | Yield (%) |
|---|---|---|---|---|---|
| 468 | 1283 | $C_{23}H_{27}Cl_2N_3O_3$ | 464.2 | 12.2 | 53 |
| 469 | 1284 | $C_{22}H_{28}BrClN_3O_3$ | 496.0 | 24.1 | 97 |
| 470 | 1285 | $C_{22}H_{25}Cl_2N_3O_3$ | 450.2 | 21.8 | 97 |
| 471 | 1321 | $C_{20}H_{20}BrCl_2N_3O_2$ | 486.0 | 5.1 | 21 |
| 472 | 1322 | $C_{21}H_{23}Cl_2N_3O_2$ | 420.0 | 10.5 | 50 |
| 473 | 1323 | $C_{20}H_{20}Cl_2IN_3O_2$ | 532.0 | 7.1 | 27 |
| 474 | 1324 | $C_{21}H_{24}ClN_3O_3$ | 402.2 | 22.2 | Q |
| 475 | 1325 | $C_{27}H_{26}ClN_3O_3$ | 476.0 | 22.2 | 93 |
| 476 | 1326 | $C_{20}H_{21}ClIN_3O_3$ | 514.0 | 26.9 | Q |
| 477 | 1327 | $C_{21}H_{25}ClN_4O_2$ | 401.2 | 24.2 | Q |
| 478 | 1328 | $C_{21}H_{23}BrClN_3O_2$ | 466.0 | 23.1 | 99 |
| 479 | 1329 | $C_{22}H_{26}ClN_3O_2$ | 400.2 | 16.4 | 82 |
| 480 | 1330 | $C_{21}H_{23}ClIN_3O_2$ | 512.2 | 20.8 | 81 |
| 481 | 1331 | $C_{21}H_{24}N_3O_3$ | 382.2 | 19.6 | Q |
| 482 | 1332 | $C_{28}H_{29}N_3O_3$ | 456.2 | 21.1 | 93 |
| 483 | 1333 | $C_{21}H_{24}IN_3O_3$ | 494.0 | 25.3 | Q |
| 484 | 1334 | $C_{22}H_{28}N_4O_2$ | 381.2 | 19.0 | Q |
| 485 | 1335 | $C_{19}H_{22}BrClN_4O_3$ | 471.0 | 25.8 | Q |
| 486 | 1336 | $C_{20}H_{25}ClN_4O_3$ | 405.2 | 18.5 | 91 |
| 487 | 1337 | $C_{19}H_{22}ClIN_4O_3$ | 517.0 | 23.1 | 89 |
| 488 | 1338 | $C_{20}H_{26}N_4O_4$ | 387.2 | 20.6 | Q |
| 489 | 1339 | $C_{26}H_{28}N_4O_4$ | 461.2 | 23.7 | Q |
| 490 | 1340 | $C_{19}H_{23}IN_4O_4$ | 499.0 | 28.2 | Q |
| 491 | 1341 | $C_{20}H_{26}N_4O_4$ | 386.0 | 20.5 | Q |
| 492 | 1342 | $C_{22}H_{24}BrCl_2N_3O_2$ | 514.0 | 27.2 | Q |
| 493 | 1343 | $C_{23}H_{27}Cl_2N_3O_2$ | 448.0 | 21.4 | 95 |
| 494 | 1344 | $C_{22}H_{24}Cl_2IN_3O_2$ | 560.0 | 27.0 | 96 |
| 495 | 1345 | $C_{23}H_{28}ClN_3O_3$ | 430.2 | 23.8 | Q |
| 496 | 1346 | $C_{22}H_{25}ClIN_3O_3$ | 542.0 | 29.4 | Q |
| 497 | 1347 | $C_{19}H_{22}ClN_3O_2S$ | 392.0 | 16.9 | 43 |
| 498 | 1348 | $C_{20}H_{25}N_3O_2S$ | 372.2 | 6.9 | 19 |
| 499 | 1349 | $C_{18}H_{24}N_4O_3S$ | 377.2 | 8.1 | 43 |
| 500 | 1350 | $C_{21}H_{26}ClN_3O_2S$ | 420.0 | 13.0 | 62 |
| 501 | 1351 | $C_{22}H_{24}BrClN_4O_3$ | 509.2 | 5.0 | 10 |
| 502 | 1352 | $C_{23}H_{27}BrN_4O_3$ | 489.2 | 3.6 | 15 |
| 503 | 1353 | $C_{21}H_{26}BrN_5O_4$ | 494.0 | 2.8 | 11 |
| 504 | 1354 | $C_{24}H_{28}BrClN_4O_3$ | 537.2 | 5.2 | 19 |
| 505 | 1355 | $C_{21}H_{22}ClN_5O_2$ | 412.0 | 25.5 | Q |
| 506 | 1356 | $C_{22}H_{25}N_5O_2$ | 392.0 | 16.5 | 84 |
| 507 | 1357 | $C_{20}H_{24}N_6O_3$ | 397.2 | 19.9 | Q |
| 508 | 1358 | $C_{23}H_{26}ClN_5O_2$ | 440.2 | 21.8 | 99 |
| 509 | 1368 | $C_{21}H_{20}Cl_2F_3N_3O_2$ | 474.0 | 18.4 | 78 |
| 510 | 1369 | $C_{24}H_{24}ClF_6IN_3O_4$ | 568.0 | 24.1 | 85 |
| 511 | 1370 | $C_{18}H_{19}BrClN_3O_2S$ | 458.0 | 19.4 | 85 |
| 512 | 1371 | $C_{26}H_{26}ClN_3O_4S$ | 512.2 | 22.1 | 86 |
| 513 | 1372 | $C_{26}H_{26}ClN_3O_2$ | 448.0 | 19.1 | 85 |
| 514 | 1373 | $C_{22}H_{23}ClF_3N_3O_2$ | 454.2 | 16.2 | 71 |
| 515 | 1374 | $C_{25}H_{27}F_6IN_3O_4$ | 548.2 | 22.1 | 81 |
| 516 | 1375 | $C_{19}H_{22}BrN_3O_2S$ | 436.0 | 17.1 | 78 |
| 517 | 1376 | $C_{27}H_{29}N_3O_4S$ | 492.0 | 19.4 | 79 |
| 518 | 1377 | $C_{27}H_{29}N_3O_2$ | 428.2 | 18.1 | 85 |
| 519 | 1378 | $C_{20}H_{22}ClF_3N_4O_3$ | 459.0 | 17.3 | 75 |
| 520 | 1379 | $C_{23}H_{26}F_6IN_4O_5$ | 553.2 | 21.0 | 76 |
| 521 | 1380 | $C_{17}H_{21}BrN_4O_3S$ | 443.0 | 16.4 | 74 |
| 522 | 1381 | $C_{25}H_{28}N_4O_5S$ | 497.0 | 18.4 | 74 |
| 523 | 1382 | $C_{25}H_{28}N_4O_3$ | 433.2 | 17.3 | 80 |
| 524 | 1383 | $C_{23}H_{24}Cl_2F_3N_3O_2$ | 502.0 | 20.0 | 80 |
| 525 | 1384 | $C_{20}H_{23}BrClN_3O_2S$ | 486.0 | 21.0 | 87 |
| 526 | 1385 | $C_{28}H_{30}ClN_3O_4S$ | 540.2 | 23.8 | 88 |
| 527 | 1386 | $C_{28}H_{30}ClN_3O_2$ | 476.0 | 20.0 | 84 |
| 528 | 1411 | $C_{22}H_{24}Cl_2N_4O_3$ | 463.0 | 0.4 | 2 |
| 529 | 1412 | $C_{23}H_{27}ClN_4O_2$ | 443.0 | 1.3 | 6 |
| 530 | 1413 | $C_{21}H_{26}ClN_5O_4$ | 448.0 | 1.1 | 5 |
| 531 | 1414 | $C_{24}H_{28}Cl_2N_4O_3$ | 491.0 | 0.8 | 3 |
| 532 | 1415 | $C_{21}H_{22}ClN_5O_2S$ | 444.0 | 6.8 | 31 |
| 533 | 1416 | $C_{22}H_{25}N_5O_2S$ | 424.0 | 4.8 | 23 |
| 534 | 1417 | $C_{20}H_{24}N_6O_3S$ | 429.2 | 4.5 | 21 |
| 535 | 1418 | $C_{23}H_{26}ClN_6O_2S$ | 472.0 | 10.4 | 44 |
| 536 | 1423 | $C_{27}H_{26}ClN_3O_3$ | 476.0 | 23.9 | Q |
| 537 | 1424 | $C_{27}H_{29}N_3O_4S$ | 456.2 | 28.0 | Q |
| 538 | 1425 | $C_{26}H_{28}N_4O_4$ | 461.2 | 22.3 | 97 |
| 539 | 1426 | $C_{29}H_{30}ClN_3O_3$ | 504.2 | 26.8 | Q |
| 540 | 1583 | $C_{21}H_{22}ClF_3N_4O_2$ | 455.0 | 14.6 | 64 |
| 541 | 1584 | $C_{21}H_{22}ClF_3N_4O_3$ | 471.0 | 17.4 | 74 |
| 542 | 1585 | $C_{19}H_{20}BrClN_4O_2$ | 453.0 | 15.6 | 69 |
| 543 | 1586 | $C_{19}H_{20}Cl_2N_4O_2$ | 407.2 | 2.3 | 11 |

TABLE 7-continued

| Example | Compd. No. | Molecular Formula | ESI/MS m/e | Yield (mg) | Yield (%) |
|---|---|---|---|---|---|
| 544 | 1587 | $C_{26}H_{26}ClN_3O_3$ | 464.0 | 15.4 | 66 |
| 545 | 1588 | $C_{20}H_{23}ClN_4O_2$ | 387.0 | 14.8 | 77 |
| 546 | 1589 | $C_{22}H_{25}F_3N_4O_2$ | 435.2 | 11.1 | 51 |
| 547 | 1590 | $C_{20}H_{25}F_3N_4O_3$ | 451.2 | 16.3 | 72 |
| 548 | 1591 | $C_{20}H_{23}BrN_4O_2$ | 433.0 | 15.4 | 71 |
| 549 | 1592 | $C_{20}H_{23}ClN_4O_2$ | 387.0 | 15.6 | 81 |
| 550 | 1593 | $C_{27}H_{29}N_3O_3$ | 444.2 | 14.8 | 67 |
| 551 | 1594 | $C_{20}H_{24}F_3N_5O_3$ | 440.2 | 16.2 | 74 |
| 552 | 1595 | $C_{20}H_{24}F_3N_5O_4$ | 456.2 | 15.4 | 68 |
| 553 | 1596 | $C_{18}H_{22}BrN_5O_3$ | 436.0 | 15.6 | 72 |
| 554 | 1597 | $C_{18}H_{22}ClN_5O_3$ | 391.8 | 14.4 | 73 |
| 555 | 1598 | $C_{25}H_{28}N_4O_4$ | 449.2 | 15.9 | 71 |
| 556 | 1599 | $C_{19}H_{25}N_5O_3$ | 372.2 | 15.8 | 85 |
| 557 | 1606 | $C_{21}H_{21}ClF_3N_3O_2S$ | 472.0 | 17.0 | 72 |
| 558 | 1607 | $C_{21}H_{21}ClF_3N_3O_2S$ | 452.2 | 15.3 | 68 |
| 559 | 1608 | $C_{20}H_{23}F_3N_4O_3S$ | 457.2 | 15.9 | 70 |
| 560 | 1660 | $C_{21}H_{22}BrF_3N_4O_2$ | 501.0 | 19.0 | 76 |
| 561 | 1661 | $C_{21}H_{22}BrF_3N_4O_3$ | 517.0 | 16.2 | 63 |
| 562 | 1662 | $C_{20}H_{21}BrF_2N_4O_2$ | 469.0 | 15.1 | 65 |
| 563 | 1663 | $C_{20}H_{22}BrClN_4O_2$ | 467.0 | 14.5 | 62 |
| 564 | 1692 | $C_{20}H_{23}Br_2N_3O_2$ | 514 | 7.3 | 28 |
| 565 | 1693 | $C_{22}H_{26}F_2N_4O_2$ | 417 | 16.2 | 78 |
| 566 | 1694 | $C_{22}H_{27}FN_4O_2$ | 399 | 21.8 | Q |
| 567 | 1695 | $C_{22}H_{27}BrN_4O_2$ | 459 | 24.5 | Q |
| 568 | 1696 | $C_{22}H_{27}IN_4O_2$ | 507 | 27.4 | Q |
| 569 | 1697 | $C_{22}H_{27}ClN_4O_2$ | 415 | 22.1 | Q |
| 570 | 1698 | $C_{23}H_{27}F_3N_4O_3$ | 465 | 24.3 | Q |
| 571 | 1699 | $C_{23}H_{27}F_3N_4O_2$ | 449 | 25.3 | Q |
| 572 | 1700 | $C_{22}H_{25}BrClN_3O_2$ | 480 | 17.8 | 74 |

Note: Q means "Quantitative".

For example, Compd. No. 1583 exhibited the following NMR: $^1$H NMR (400 MHz, $CD_{30}D$) δ 1.64-1.72 (m, 1H), 2.20-2.30 (m, 1H), 2.41-2.51 (m, 2H), 52.71-2.78 (m, 2H), 3.59 (dd, J=15.4, 12.9 Hz, 2H), 3.94 (s, 2H), 4.35-4.41 (m, 1H), 6.82 (d, J=8.6 Hz, 1H), 7.29 (s, 4H), 7.40 (dd, J=8.6, 1.7 Hz, 1H), 7.85 (d, J=0.96 Hz, 1H).

Reference Example 4

Synthesis of (S)-3-[N-[3-(trifluoromethyl)benzoyl]glycyl]aminopyrrolidine

A suspension of (S)-1-(4-chlorobenzyl)-3-[N-[3-(trifluoromethyl)benzoyl]glycyl]aminopyrrolidine (2.93 g. 6.66 mmol) and $Pd(OH)_2$ in a 5% formic acid/methanol (70 mL) was stirred at 60° C., for 3 hours. The palladium catalyst was removed by filtration through Celite to concentrate the filtrate. A 2 M solution of NaOH (100 mL) was added to the resulting residue, and the resulting mixture was extracted with ethyl acetate (100 mL×3). The extracts were combined, washed with brine, dried over anhydrous sodium sulfate, filtered, concentrated and purified by column chromatography [$SiO_2$, ethyl acetate/methanol/triethylamine=(85:10:5) to (60:30:5)] to thereby provide (S)-3-[N-3-(trifluoromethyl)benzoyl]glycyl]aminopyrrolidine (1.70 g, 81%) as an oil. $^1$H NMR ($CDCl_3$, 270 MHz) δ 1.76 (d, J=7.3 Hz, 1H), 2.07-2.25 (m, 1H), 2.81-2.98 (m, 2H), 3.02-3.11 (m, 2H), 4.12 (s, 2H), 4.41 (br, 1H), 6.90 (br, 1H), 7.45 (br, 1H), 7.58 (dd, J=7.3 and 7.3 Hz, 1H), 7.77 (d, J=7.3 Hz, 1H), 8.02 (d, J=7.3 Hz, 1H), 8.11 (s, 1H); ESI/MS m/e 316.0 ($M^+$+H, $C_{14}H_{16}F_3N_3O_2$).

Further, (R)-3-[N-[3-(trifluoromethyl)benzoyl]glycyl]aminopyrrolidine was synthesized by using the corresponding starting material and reactants according to the above method. 1.49 g, 68%. The product exhibited the same $^1$H NMR and ESI/MS as those of the (S)-isomer.

In addition, (R)-3-[N-[2-amino-5-(trifluoromethyl)benzoyl]glycyl]aminopyrrolidine was synthesized by using the corresponding starting material and reactants according to the above method. 316 mg, 93%; ESI/MS m/e 331.2 ($M^+$+H, $C_{14}H_{17}F_3N_4O_2$).

Moreover, (R)-3-[N-[2-(tert-butoxycarbonylamino)-5-(trifluoromethoxyl)benzoyl]glycyl]aminopyrrolidine was synthesized by using the corresponding starting material and reactants according to the above method. Quantitative yield; $^1$H NMR ($CDCl_3$, 400 MHz) δ 1.51 (s, 9H), 1.60-1.70 (m, 2H), 2.10-2.25 (m, 1H), 2.80-2.88 (m, 1H), 2.89-2.98 (m, 1H), 3.04-3.18 (m, 2H), 4.05 (d, J=4.9 Hz, 2H), 4.43 (br, 1H), 6.15 (br, 1H), 7.03 (br, 1H), 7.32 (d, J=9.3 Hz, 1H), 7.38 (s, 1H), 8.42 (d, J=9.3 Hz, 1H).

Example 573

Synthesis of (R)-3-[[N-[2-(tert-butoxycarbonylamino)-5-trifluoromethylbenzoyl]glycyl]amino]-1-(4-chlorobenzyl)pyrrolidine Triethylamine (2.9 mL, 20.5 mmol), 2-(tert-butoxycarbonylamino)-5-(trifluoromethyl)benzoic acid (6.27 g, 20.5 mmol), EDCI (3.9 g, 20.5 mmol) and HOBt (2.8 g, 20.5 mmol) were added to a dichloromethane (100 mL) solution of (R)-1-(4-chlorobenzyl)-3-(glycylamino)pyrrolidine (5.0 g, 18.7 mmol). The resulting reaction mixture was stirred at room temperature overnight. A 2 M aqueous solution (80 mL) of NaOH was added to the reaction mixture, and the resulting mixture was extracted with dichloromethane. The obtained extract was dried over anhydrous $Na_2SO_4$, filtered, concentrated and purified by column chromatography [$SiO_2$, hexane/ethyl acetate=(1:1) to (1:4)] to thereby afford (R)-3-[[N-(2-(tert-butoxycarbonylamino)-5-trifluoromethylbenzoyl)glycyl]amino]-1-(4-chlorobenzyl)pyrrolidine (9.41 g, 91%) as a white amorphous solid. ESI/MS m/e 555.2 ($M^+$+H, $C_{26}H_{30}ClF_3N_4O_4$).

Reference Example 5

Synthesis of (R)-3-[[N-(2-(tert-butoxycarbonylamino)-5-trifluoromethylbenzoyl)glycyl]amino]pyrrolidine A mixture of (R)-3-[[N-(2-(tert-butoxycarbonylamino)-5-trifluoromethylbenzoyl)glycyl]amino]-1-(4-chlorobenzyl)pyrrolidine (6.3 g, 11.4 mmol) with $Pd(OH)_2$ (1.68 g), formic acid (3.7 mL) and methanol (80 mL) was stirred at 50° C. overnight. The mixture was cooled to room temperature, and the palladium catalyst was then removed by filtration through Celite. The resulting filtrate was concentrated and purified by column chromatography [$SiO_2$, ethyl acetate/methanol=(5:1) to (4:1)] to thereby provide (R)-3-[[N-(2-(tert-butoxycarbonylamino)-5-trifluoromethylbenzoyl)glycyl]amino]pyrrolidine (4.42 g, 90%) as a white solid. $^1$H NMR ($CDCl_3$, 400 MHz) δ 1.48 (s, 9H), 2.0-2.4 (m, 2H), 3.42-3.71 (m, 5H), 4.00-4.22 (m, 2H), 4.56 (br, 1H), 7.48 (d, J=9.0 Hz, 1H), 7.93 (s, 1H), 8.17 (br, 1H), 8.33 (d, J=9.0 Hz, 1H), 8.45 (br, 1H).

Example 574

Synthesis of (S)-1-benzyl-3-[N-[3-(trifluoromethyl)benzoyl]glycyl]aminopyrrolidine (Compd. No. 239)

An acetonitrile (1.1 mL) solution of (S)-3-[N-[3-(trifluoromethyl)benzoyl]glycyl]aminopyrrolidine (0.06 mmol) and a (piperidinomethyl)polystyrene (2.6 to 2.8 mmol/g, 30 mg)

were added to an acetonitrile (0.4 mL) solution of benzyl bromide (0.050 mmol). The resulting reaction mixture was stirred at 45° C. for 5 hours. The mixture solution was cooled to room temperature, and the resin was then removed by filtration to concentrate the filtrate. The resulting residue was dissolved in acetonitrile (1.0 mL), and phenyl isocyanate (0.008 mL, 0.05 mmol) was then added to the obtained solution. The mixture solution was stirred at room temperature for 1 hour, loaded onto a Varian™ SCX column and washed with methanol (15 mL). The obtained crude product was eluted with a solution of 2 M $NH_3$ in methanol (6 mL) and concentrated to thereby provide (S)-1-benzyl-3-[N-[3-(trifluoromethyl)benzoyl]glycyl]aminopyrrolidine (Compd. No. 239) (9.0 mg, 44%). The purity was determined by RPLC/MS (99%). ESI/MS m/e 406.0 ($M^+$+H, $C_{21}H_{22}F_3N_3O_2$).

Example 575

Synthesis of (R)-1-(4-butylbenzyl)-3-[[N-(3-trifluoromethylbenzoyl)glycyl]amino]pyrrolidine (Compd. No. 1648)

Acetic acid (0.060 mL) was added to a mixture of (R)-3-[N-[3-(trifluoromethyl)benzoyl]glycyl]aminopyrrolidine (0.050 mL) with 4-butylbenzaldehyde (0.18 mmol), $NaBH_3CN$ (0.23 mmol) and methanol (1.85 mL). The resulting reaction mixture was stirred at 60° C. for 12 hours, cooled to room temperature, loaded onto a Varian™ SCX column and washed with methanol (15 mL). The obtained crude product was eluted with a solution of 2 M $NH_3$ in methanol (5 mL) and concentrated to thereby afford (R)-1-(4-butylbenzyl)-3-[[N-(3-trifluoromethylbenzoyl)glycyl]amino]pyrrolidine (Compd. No. 1648) (20.6 mg, 89%). The purity was determined by RPLC/MS (91%). ESI/MS m/e 462.2 ($M^+$+H, $C_{25}H_{30}F_3N_3O_2$).

Examples 576 to 738

The compounds used in the present invention were synthesized by using the respective corresponding starting materials and reactants according to the method of Example 574 or 575. The obtained crude products, if necessary, were purified by preparative TLC or chromatography (HPLC-$C_{18}$) to provide the objective compounds. Data of ESI/MS, yields (mg) and yields (%) are collectively shown in Table 8.

TABLE 8

| Example | Compd. No. | Molecular Formula | ESI/MS m/e | Yield (mg) | Yield (%) |
|---|---|---|---|---|---|
| 576 | 240 | $C_{21}H_{21}F_4N_3O_2$ | 424.0 | 10.2 | 48 |
| 577 | 241 | $C_{21}H_{21}ClF_3N_3O_2$ | 440.0 | 12.1 | 55 |
| 578 | 242 | $C_{21}H_{20}Cl_2F_3N_3O_2$ | 474.0 | 13.9 | 59 |
| 579 | 243 | $C_{21}H_{20}Cl_2F_3N_3O_2$ | 474.0 | 13.8 | 58 |
| 580 | 244 | $C_{22}H_{24}F_3N_3O_2$ | 420.0 | 13.1 | 62 |
| 581 | 245 | $C_{21}H_{21}F_4N_3O_2$ | 424.0 | 11.9 | 56 |
| 582 | 246 | $C_{21}H_{21}ClF_3N_3O_2$ | 440.0 | 8.5 | 39 |
| 583 | 247 | $C_{21}H_{20}Cl_2F_3N_3O_2$ | 474.0 | 10.5 | 44 |
| 584 | 248 | $C_{22}H_{24}CF_3N_3O_3$ | 436.0 | 11.0 | 51 |
| 585 | 249 | $C_{22}H_{21}ClF_6N_3O_2$ | 474.0 | 12.8 | 54 |
| 586 | 250 | $C_{22}H_{24}F_3N_3O_2$ | 420.0 | 11.0 | 52 |
| 587 | 251 | $C_{21}H_{21}F_4N_3O_2$ | 424.0 | 13.5 | 64 |
| 588 | 252 | $C_{22}H_{24}F_3N_3O_3$ | 436.0 | 11.8 | 54 |
| 589 | 253 | $C_{22}H_{24}F_3N_3O_2$ | 420.0 | 11.1 | 53 |
| 590 | 254 | $C_{21}H_{20}ClF_3N_4O_4$ | 485.0 | 2.4 | 10 |
| 591 | 255 | $C_{21}H_{21}F_3N_4O_4$ | 451.0 | 12.2 | 54 |
| 592 | 256 | $C_{21}H_{21}F_3N_4O_4$ | 451.0 | 11.4 | 51 |
| 593 | 257 | $C_{22}H_{21}F_6N_3O_2$ | 474.0 | 11.1 | 47 |
| 594 | 258 | $C_{24}H_{26}F_3N_3O_4$ | 478.0 | 15.3 | 64 |
| 595 | 259 | $C_{22}H_{23}ClF_3N_3O_2$ | 420.0 | 6.4 | 31 |

TABLE 8-continued

| Example | Compd. No. | Molecular Formula | ESI/MS m/e | Yield (mg) | Yield (%) |
|---|---|---|---|---|---|
| 596 | 260 | $C_{21}H_{20}Cl_2F_3N_3O_2$ | 474.0 | 12.1 | 51 |
| 597 | 261 | $C_{22}H_{21}ClF_6N_3O_2$ | 474.0 | 13.6 | 57 |
| 598 | 262 | $C_{21}H_{21}BrF_3N_3O_2$ | 484.0 | 15.2 | 63 |
| 599 | 263 | $C_{21}H_{21}BrF_3N_3O_2$ | 484.0 | 14.5 | 60 |
| 600 | 264 | $C_{27}H_{26}F_3N_3O_3$ | 498.0 | 9.3 | 37 |
| 601 | 265 | $C_{21}H_{21}BrF_3N_3O_2$ | 484.0 | 11.6 | 48 |
| 602 | 266 | $C_{22}H_{22}F_3N_3O_4$ | 450.0 | 8.9 | 40 |
| 603 | 267 | $C_{22}H_{24}F_3N_3O_3$ | 436.0 | 10.3 | 47 |
| 604 | 268 | $C_{23}H_{25}F_3N_4O_3$ | 463.0 | 6.3 | 27 |
| 605 | 269 | $C_{22}H_{24}F_3N_3O_4S$ | 484.0 | 8.0 | 33 |
| 606 | 270 | $C_{23}H_{24}F_3N_3O_4$ | 464.0 | 8.9 | 38 |
| 607 | 271 | $C_{21}H_{20}F_6N_3O_2$ | 442.0 | 6.1 | 28 |
| 608 | 272 | $C_{21}H_{22}F_3N_3O_3$ | 422.0 | 13.6 | 59 |
| 609 | 273 | $C_{22}H_{21}F_3N_4O_2$ | 431.0 | 12.6 | 59 |
| 610 | 274 | $C_{22}H_{21}F_3N_4O_2$ | 431.0 | 7.7 | 36 |
| 611 | 275 | $C_{22}H_{21}F_3N_4O_2$ | 431.0 | 12.7 | 59 |
| 612 | 276 | $C_{21}H_{20}F_5N_3O_2$ | 442.0 | 11.7 | 53 |
| 613 | 277 | $C_{27}H_{26}F_3N_3O_2$ | 482.0 | 9.5 | 39 |
| 614 | 278 | $C_{23}H_{24}F_3N_3O_4$ | 464.0 | 13.0 | 56 |
| 615 | 279 | $C_{22}H_{21}F_6N_3O_3$ | 490.0 | 10.4 | 42 |
| 616 | 280 | $C_{22}H_{21}F_6N_3O_3$ | 490.0 | 12.0 | 49 |
| 617 | 281 | $C_{22}H_{22}F_3N_3O_4$ | 450.0 | 4.9 | 22 |
| 618 | 282 | $C_{25}H_{30}F_3N_3O_2$ | 462.0 | 12.0 | 52 |
| 619 | 283 | $C_{20}H_{23}F_3N_4O_3$ | 425.0 | 8.1 | 38 |
| 620 | 284 | $C_{27}H_{25}ClF_3N_3O_2$ | 516.0 | 4.8 | 19 |
| 621 | 285 | $C_{21}H_{22}F_3N_3O_2$ | 406.0 | 4.8 | 24 |
| 622 | 286 | $C_{21}H_{21}F_4N_3O_2$ | 424.0 | 4.5 | 21 |
| 623 | 287 | $C_{21}H_{21}ClF_3N_3O_2$ | 440.0 | 5.8 | 26 |
| 624 | 288 | $C_{21}H_{20}Cl_2F_3N_3O_2$ | 474.0 | 8.1 | 34 |
| 625 | 289 | $C_{21}H_{20}Cl_2F_3N_3O_2$ | 474.0 | 8.0 | 34 |
| 626 | 290 | $C_{22}H_{24}F_3N_3O_2$ | 420.0 | 6.0 | 29 |
| 627 | 291 | $C_{21}H_{21}F_4N_3O_2$ | 424.0 | 6.2 | 29 |
| 628 | 292 | $C_{21}H_{21}ClF_3N_3O_2$ | 440.0 | 4.5 | 20 |
| 629 | 293 | $C_{21}H_{20}Cl_2F_3N_3O_2$ | 474.0 | 5.1 | 22 |
| 630 | 294 | $C_{22}H_{24}CF_3N_3O_3$ | 436.0 | 4.2 | 19 |
| 631 | 295 | $C_{22}H_{21}ClF_6N_3O_2$ | 474.0 | 6.0 | 25 |
| 632 | 296 | $C_{22}H_{24}F_3N_3O_2$ | 420.0 | 4.3 | 21 |
| 633 | 297 | $C_{21}H_{21}F_4N_3O_2$ | 424.0 | 8.2 | 39 |
| 634 | 298 | $C_{22}H_{24}F_3N_3O_3$ | 436.0 | 12.2 | 56 |
| 635 | 299 | $C_{22}H_{24}F_3N_3O_2$ | 420.0 | 8.1 | 39 |
| 636 | 300 | $C_{21}H_{20}ClF_3N_4O_4$ | 485.0 | 13.7 | 57 |
| 637 | 301 | $C_{21}H_{21}F_3N_4O_4$ | 451.0 | 15.1 | 67 |
| 638 | 302 | $C_{21}H_{21}F_3N_4O_4$ | 451.0 | 16.6 | 74 |
| 639 | 303 | $C_{22}H_{21}F_6N_3O_2$ | 474.0 | 12.6 | 53 |
| 640 | 304 | $C_{24}H_{26}F_3N_3O_4$ | 478.0 | 14.5 | 61 |
| 641 | 305 | $C_{22}H_{23}ClF_3N_3O_2$ | 420.0 | 8.4 | 37 |
| 642 | 306 | $C_{21}H_{20}Cl_2F_3N_3O_2$ | 474.0 | 13.5 | 57 |
| 643 | 307 | $C_{22}H_{21}ClF_6N_3O_2$ | 474.0 | 3.7 | 16 |
| 644 | 308 | $C_{21}H_{21}BrF_3N_3O_2$ | 484.0 | 7.2 | 30 |
| 645 | 309 | $C_{21}H_{21}BrF_3N_3O_2$ | 484.0 | 6.7 | 28 |
| 646 | 310 | $C_{27}H_{26}F_3N_3O_3$ | 498.0 | 4.2 | 17 |
| 647 | 311 | $C_{21}H_{21}BrF_3N_3O_2$ | 484.0 | 6.3 | 26 |
| 648 | 312 | $C_{22}H_{22}F_3N_3O_4$ | 450.0 | 2.4 | 11 |
| 649 | 313 | $C_{22}H_{24}F_3N_3O_3$ | 436.0 | 1.9 | 9 |
| 650 | 314 | $C_{23}H_{25}F_3N_4O_3$ | 463.0 | 5.0 | 22 |
| 651 | 315 | $C_{22}H_{24}F_3N_3O_4S$ | 484.0 | 2.5 | 10 |
| 652 | 316 | $C_{23}H_{24}F_3N_3O_4$ | 464.0 | 3.3 | 14 |
| 653 | 317 | $C_{21}H_{20}F_5N_3O_2$ | 442.0 | 4.5 | 20 |
| 654 | 318 | $C_{21}H_{22}F_3N_3O_3$ | 422.0 | 7.9 | 34 |
| 655 | 319 | $C_{22}H_{21}F_3N_4O_2$ | 431.0 | 6.5 | 30 |
| 656 | 320 | $C_{22}H_{21}F_3N_4O_2$ | 431.0 | 14.2 | 66 |
| 657 | 321 | $C_{22}H_{21}F_3N_4O_2$ | 431.0 | 14.9 | 69 |
| 658 | 322 | $C_{21}H_{20}F_5N_3O_2$ | 442.0 | 13.6 | 62 |
| 659 | 323 | $C_{27}H_{26}F_3N_3O_2$ | 482.0 | 3.9 | 16 |
| 660 | 324 | $C_{23}H_{24}F_3N_3O_4$ | 464.0 | 15.2 | 66 |
| 661 | 325 | $C_{22}H_{21}F_6N_3O_3$ | 490.0 | 16.1 | 66 |
| 662 | 326 | $C_{22}H_{21}F_6N_3O_3$ | 490.0 | 13.6 | 56 |
| 663 | 327 | $C_{22}H_{22}F_3N_3O_4$ | 450.0 | 5.4 | 24 |
| 664 | 328 | $C_{26}H_{30}F_3N_3O_2$ | 462.0 | 10.9 | 47 |
| 665 | 329 | $C_{20}H_{23}F_3N_4O_3$ | 425.0 | 12.0 | 57 |
| 666 | 986 | $C_{27}H_{25}ClF_3N_3O_2$ | 516.0 | 1.5 | 6 |
| 667 | 1118 | $C_{28}H_{27}F_3N_4O_3$ | 525 | 21.5 | 62 |
| 668 | 1119 | $C_{22}H_{24}F_3N_3O_2S$ | 452 | 16.9 | 57 |
| 669 | 1120 | $C_{23}H_{26}F_3N_3O_4$ | 466 | 20.5 | 67 |
| 670 | 1121 | $C_{22}H_{23}F_3N_4O_4$ | 465 | 16.8 | 55 |
| 671 | 1122 | $C_{28}H_{36}F_3N_3O_2$ | 504 | 21.0 | 63 |

TABLE 8-continued

| Example | Compd. No. | Molecular Formula | ESI/MS m/e | Yield (mg) | Yield (%) |
|---|---|---|---|---|---|
| 672 | 1123 | $C_{25}H_{23}BrF_3N_3O_2$ | 534 | 26.6 | 75 |
| 673 | 1124 | $C_{19}H_{19}F_3N_4O_5$ | 441 | 21.3 | 73 |
| 674 | 1133 | $C_{23}H_{26}F_3N_3O_4$ | 467 | 33.6 | 84 |
| 675 | 1134 | $C_{24}H_{28}F_3N_3O_5$ | 496 | 34.8 | 82 |
| 676 | 1135 | $C_{22}H_{21}F_3N_4O_6$ | 495 | 32.6 | 77 |
| 677 | 1136 | $C_{23}H_{24}F_3N_3O_5$ | 480 | 36.6 | 89 |
| 678 | 1137 | $C_{22}H_{21}BrF_3N_3O_4$ | 529 | 30.8 | 69 |
| 679 | 1138 | $C_{24}H_{26}F_3N_3O_2$ | 446 | 32.7 | 86 |
| 680 | 1139 | $C_{22}H_{24}F_3N_3O_2$ | 420 | 18.6 | 51 |
| 681 | 1140 | $C_{21}H_{20}F_3N_5O_6$ | 496 | 20.5 | 49 |
| 682 | 1141 | $C_{25}H_{24}F_3N_3O_2$ | 456 | 22.5 | 58 |
| 683 | 1142 | $C_{25}H_{24}F_3N_3O_2$ | 456 | 21.6 | 55 |
| 684 | 1143 | $C_{35}H_{34}F_3N_3O_4$ | 618 | 27.3 | 53 |
| 685 | 1144 | $C_{23}H_{26}F_3N_3O_4$ | 466 | 25.5 | 64 |
| 686 | 1145 | $C_{23}H_{25}F_3N_4O_6$ | 511 | 38.0 | 88 |
| 687 | 1146 | $C_{28}H_{28}F_3N_3O_3$ | 512 | 38.3 | 89 |
| 688 | 1147 | $C_{23}H_{25}F_3N_4O_3$ | 463 | 27.1 | 62 |
| 689 | 1148 | $C_{27}H_{26}F_3N_3O_2$ | 482 | 22.4 | 57 |
| 690 | 1161 | $C_{22}H_{24}F_3N_3O_4$ | 452 | 13.5 | 58 |
| 691 | 1162 | $C_{24}H_{28}F_3N_3O_3$ | 464 | 16.7 | 70 |
| 692 | 1163 | $C_{22}H_{23}F_4N_3O_3$ | 454 | 15.8 | 68 |
| 693 | 1164 | $C_{23}H_{26}F_3N_3O_3$ | 450 | 15.7 | 68 |
| 694 | 1165 | $C_{23}H_{24}F_3N_3O_4$ | 464 | 16.3 | 68 |
| 695 | 1166 | $C_{22}H_{23}BrF_3N_3O_3$ | 513 | 15.0 | 57 |
| 696 | 1168 | $C_{17}H_{17}ClF_3N_5O_2S$ | 448 | 6.9* | 23 |
| 697 | 1169 | $C_{20}H_{22}F_3N_5O_3S$ | 470 | 1.7* | 6 |
| 698 | 1170 | $C_{22}H_{22}F_3N_5O_2$ | 446 | 2.3* | 8 |
| 699 | 1286 | $C_{26}H_{33}F_3N_4O_3$ | 507 | 25.3* | 51 |
| 700 | 1287 | $C_{21}H_{20}F_3N_5O_6$ | 496 | 4.0* | 8 |
| 701 | 1288 | $C_{22}H_{24}F_3N_3O_4$ | 452 | 3.6* | 13 |
| 702 | 1298 | $C_{23}H_{25}BrF_3N_3O_4$ | 544 | 28.4 | Q |
| 703 | 1299 | $C_{24}H_{28}F_3N_3O_5$ | 496 | 1.4 | 6 |
| 704 | 1300 | $C_{23}H_{26}F_3N_3O_4$ | 466 | 7.3 | 33 |
| 705 | 1301 | $C_{24}H_{28}F_3N_3O_5$ | 496 | 12.6 | 53 |
| 706 | 1302 | $C_{24}H_{28}F_3N_3O_3$ | 464 | 24.5 | Q |
| 707 | 1303 | $C_{23}H_{25}BrF_3N_3O_4$ | 544 | 22.2 | Q |
| 708 | 1304 | $C_{29}H_{30}F_3N_3O_4$ | 542 | 28.6 | Q |
| 709 | 1305 | $C_{26}H_{26}F_3N_3O_3$ | 486 | 35.4 | Q |
| 710 | 1306 | $C_{24}H_{28}F_3N_3O_4$ | 480 | 8.1 | 35 |
| 711 | 1307 | $C_{23}H_{26}F_3N_3O_5$ | 482 | 27.9 | Q |
| 712 | 1308 | $C_{23}H_{24}F_3N_3O_3$ | 448 | 5.9 | 28 |
| 713 | 1309 | $C_{23}H_{25}F_3IN_3O_4$ | 592 | 24.0 | 85 |
| 714 | 1310 | $C_{22}H_{24}F_3N_3O_4$ | 452 | 3.4 | 16 |
| 715 | 1311 | $C_{22}H_{22}F_3N_3O_4$ | 450 | 3.4 | 16 |
| 716 | 1312 | $C_{21}H_{21}F_3IN_3O_2$ | 532 | 18.1 | 72 |
| 717 | 1313 | $C_{21}H_{21}BrF_3N_3O_2$ | 484 | 17.4 | 76 |
| 718 | 1314 | $C_{19}H_{19}F_3N_4O_4S$ | 457 | 16.8 | 77 |
| 719 | 1315 | $C_{20}H_{22}F_3N_3O_3$ | 410 | 13.6 | 70 |
| 720 | 1316 | $C_{22}H_{20}ClF_6N_3O_2$ | 508 | 18.6 | 77 |
| 721 | 1317 | $C_{21}H_{20}ClF_3N_4O_4$ | 485 | 17.0 | 74 |
| 722 | 1318 | $C_{21}H_{20}ClF_4N_3O_2$ | 458 | 17.0 | 78 |
| 723 | 1319 | $C_{21}H_{20}ClF_4N_3O_2$ | 458 | 17.6 | 81 |
| 724 | 1320 | $C_{21}H_{20}BrF_4N_3O_2$ | 502 | 18.5 | 77 |
| 725 | 1390 | $C_{26}H_{32}F_3N_3O_2$ | 476 | 16.1 | 51 |
| 726 | 1391 | $C_{23}H_{26}F_3N_3O_2$ | 434 | 20.0 | 76 |
| 727 | 1392 | $C_{22}H_{23}ClF_3N_3O_2$ | 454 | 20.0 | 67 |
| 728 | 1393 | $C_{23}H_{26}F_3N_3O_2$ | 434 | 20.1 | 70 |
| 729 | 1394 | $C_{22}H_{23}F_3N_4O_4$ | 465 | 18.4 | 60 |
| 730 | 1395 | $C_{23}H_{24}F_3N_3O_2$ | 432 | 21.4 | 75 |
| 731 | 1396 | $C_{26}H_{26}F_3N_3O_2$ | 470 | 20.4 | 66 |
| 732 | 1397 | $C_{21}H_{20}Br_2F_3N_3O_2$ | 562 | 14.5 | 54 |
| 733 | 1398 | $C_{22}H_{22}Cl_2F_3N_3O_2$ | 488 | 10.8 | 47 |
| 734 | 1399 | $C_{22}H_{22}Cl_2F_3N_3O_2$ | 488 | 9.4 | 40 |
| 735 | 1400 | $C_{22}H_{23}ClF_3N_3O_2$ | 454 | 19.1 | 88 |
| 736 | 1614 | $C_{22}H_{21}F_6N_3S$ | 506.0 | 24.2 | 96 |
| 737 | 2050 | $C_{20}H_{22}F_3N_3O_2S$ | 426 | 6.0 | 30 |
| 738 | 2051 | $C_{21}H_{23}F_3N_4O_2$ | 421 | 6.5 | 32 |

Notes:
*indicates "yield (mg) of trifluoroacetate".
Q means "Quantitative".

Examples 739 to 748

The compounds used in the present invention were synthesized by using the respective corresponding starting materials and reactants according to the method of Example 575. The obtained products, if necessary, were purified with preparative TLC to afford the objective compounds. Data of ESI/MS, yields (mg) and yields (%) are collectively shown in Table 9.

TABLE 9

| Example | Compd. No. | Molecular Formula | ESI/MS m/e | Yield (mg) | Yield (%) |
|---|---|---|---|---|---|
| 739 | 1650 | $C_{24}H_{28}F_3N_3O_2$ | 448.0 | 20.4 | 91 |
| 740 | 1706 | $C_{23}H_{25}F_3N_4O_3$ | 463.2 | 3.7 | 11 |
| 741 | 1707 | $C_{22}H_{25}F_3N_4O_2S$ | 467.0 | 10.3 | 29 |
| 742 | 1708 | $C_{23}H_{27}F_3N_4O_2$ | 449.2 | 11.4 | 34 |
| 743 | 1709 | $C_{24}H_{29}F_3N_4O_2$ | 463.2 | 15.2 | 44 |
| 744 | 1775 | $C_{22}H_{25}F_3N_4O_4$ | 467.2 | 9.2 | 26.3 |
| 745 | 1776 | $C_{22}H_{25}F_3N_4O_4$ | 467.2 | 8.9 | 25.4 |
| 746 | 1787 | $C_{24}H_{29}F_3N_4O_2$ | 463.2 | 5.6 | 16.1 |
| 747 | 1802 | $C_{23}H_{27}F_3N_4O_4$ | 481.2 | 11.7 | 32.5 |
| 748 | 1803 | $C_{22}H_{25}F_3N_4O_3$ | 451.2 | 9.6 | 28.4 |

Example 749

Synthesis of (R)-3-[[N-2-amino-5-trifluoromethoxybenzoyl)glycyl]amino]-1-(3-hydroxy-4-methoxybenzyl)pyrrolidine (Compd. No. 1896)

Acetic acid (0.050 mL) was added to a mixture of (R)-3-[N-[2-(tert-butoxycarbonylamino)-5-(trifluoromethoxybenzoyl)glycyl]amino]pyrrolidine (0.050 mmol) with 3-hydroxy-4-methoxybenzaldehyde (0.060 mmol), $NaBH_3CN$ (0.15 mmol) and methanol (1.3 mL). The resulting reaction mixture was stirred at 60° C. for 8 hours, cooled to room temperature, then loaded onto a Varian™ SCX column and washed with methanol (10 mL). The obtained crude product was eluted with a solution of 2 M $NH_3$ in methanol (5 mL) and concentrated. A 1,4-dioxane solution of 4 M HCl was added to the prepared residue, and the solution was stirred at room temperature overnight, concentrated and then purified by preparative TLC to thereby provide (R)-3-[[N-(2-amino-5-trifluoromethoxybenzoyl)glycyl]amino]-1-(3-hydroxy-4-methoxybenzyl)pyrrolidine (Compd. No. 1896) (9.1 mg, 38%). The purity was determined by RPLC/MS (93%). ESI/MS m/e 483 ($M^+$+H, $C_{22}H_{25}F_3N_4O_5$).

Examples 750 to 757

The compounds used in the present invention were synthesized by using the respective corresponding starting materials and reactants according to the method of Example 749. Data of ESI/MS, yields (mg) and yields (%) are collectively shown in Table 10.

TABLE 10

| Example | Compd. No. | Molecular Formula | ESI/MS m/e | Yield (mg) | Yield (%) |
|---|---|---|---|---|---|
| 750 | 1897 | $C_{22}H_{25}F_3N_4O_3S$ | 483 | 22.7 | 94.1 |
| 751 | 1898 | $C_{23}H_{27}F_3N_4O_3$ | 465 | 12.2 | 52.5 |
| 752 | 1899 | $C_{24}H_{29}F_3N_4O_3$ | 479 | 14.4 | 60.2 |
| 753 | 1900 | $C_{22}H_{25}F_3N_4O_5$ | 483 | 2.6 | 10.8 |
| 754 | 1901 | $C_{24}H_{29}F_3N_4O_3$ | 479 | 14.5 | 60.6 |
| 755 | 1902 | $C_{23}H_{25}F_3N_4O_4$ | 479 | 12.0 | 50.2 |
| 756 | 1915 | $C_{23}H_{27}F_3N_4O_5$ | 467.2 | 2.5 | 6.7 |
| 757 | 1916 | $C_{22}H_{25}F_3N_4O_4$ | 467.2 | 3.1 | 8.9 |

Example 758

Synthesis of (R)-3-[[N-(2-amino-5-trifluoromethyl) benzoyl)glycyl]amino]-1-(4-vinylbenzyl)pyrrolidine (Compd. No. 1701)

A mixture of (R)-3.-[[N-(2-amino-5-(trifluoromethyl)benzoyl)glycyl]amino]pyrrolidine (0.050 mmol) with 4-vinylbenzyl chloride (9.9 mg, 0.065 mL), a piperidinopolystyrene (60 mg), acetonitrile (1.0 mL) and chloroform (0.30 mL) was stirred at 50° C. for 12 hours. The resulting reaction mixture was cooled to room temperature, loaded onto a Varian™ SCX column and washed with methanol (15 mL). The obtained crude product was eluted with solution of 2 M $NH_3$ in a methanol (5 mL) and concentrated to thereby afford (R)-3-[[N-(2-amino-5-(trifluoromethyl)benzoyl)glycyl]amino]-1-(4-vinylbenzyl)pyrrolidine (Compd. No. 1701) (19.6 mg, 88%). The purity was determined by RPLC/MS (92%). ESI/MS m/e 547.2 ($M^+$+H, $C_{23}H_{25}ClF_3N_4O_2$).

Examples 759 to 762

The compounds used in the present invention were synthesized by using the respective corresponding starting materials and reactants according to the method of Example 758. The obtained products, if necessary, were purified with preparative TLC to provide the objective substances. Data of ESI/MS, yields (mg) and yields (%) are collectively shown in Table 11.

TABLE 11

| Example | Compd. No. | Molecular Formula | ESI/MS m/e | Yield (mg) | Yield (%) |
|---|---|---|---|---|---|
| 759 | 1702 | $C_{22}H_{25}F_3N_4O_3$ | 451.2 | 5.3 | 24 |
| 760 | 1703 | $C_{22}H_{23}F_3N_4O_4$ | 465.2 | 5.0 | 22 |
| 761 | 1704 | $C_{21}H_{23}F_3N_4O_3$ | 437.2 | 20.9 | 96 |
| 762 | 1705 | $C_{21}H_{21}Cl_2F_3N_4O_2$ | 489.2 | 9.3 | 38 |

Example 763

Synthesis of (R)-3-[[N-(2-amino-5-(trifluoromethoxy)benzoyl)glycyl]amino]-1-(2,4-dichlorobenzyl)pyrrolidine (Compd. No. 1905)

A mixture of (R)-3-[[N-(2-amino-5-(trifluoromethoxyl) benzoyl)glycyl]amino]pyrrolidine (0.050 mmol) with 2,4-dichlorobenzyl chloride (0.066 mL), a piperidinomethylpolystyrene (60 mg), acetonitrile (0.8 mL) and chloroform (0.5 mL) was stirred at 60° C. for 12 hours. The resulting reaction mixture was cooled to room temperature, loaded onto a Varian™ SCX column and washed with a 50% chloroform/methanol (10 mL) and methanol (10 mL). The obtained crude product was eluted with a solution of 2 M $NH_3$ in methanol (5 mL) and concentrated. A 1,4-dioxane (2 mL) solution of 4 M HCl was added to the resulting residue, and the obtained mixture was stirred at room temperature overnight, concentrated and then purified by preparative TLC to afford (R)-3-[[N-(2-amino-5-(trifluoromethoxy)benzoyl] glycyl]amino]-1-(2,4-dichlorobenzyl)pyrrolidine (Compd. No. 1905) (17.6 mg, 70%). The purity was determined by RPLC/MS (93%). ESI/MS m/e 505 ($M^+$+H, $C_{21}H_{21}Cl_2F_3N_4O_3$).

Examples 764 to 770

The compounds used in the present invention were synthesized by using the respective corresponding starting materials and reactants according to the method of Example 763. Data of ESI/MS, yields (mg) and yields (%) are collectively shown in Table 12.

TABLE 12

| Example | Compd. No. | Molecular Formula | ESI/MS m/e | Yield (mg) | Yield (%) |
|---|---|---|---|---|---|
| 764 | 1906 | $C_{22}H_{23}F_3N_4O_5$ | 481 | 9.4 | 39.1 |
| 765 | 1907 | $C_{21}H_{23}F_3N_4O_4$ | 453 | 7.5 | 33.2 |
| 766 | 1908 | $C_{22}H_{25}F_3N_4O_4$ | 467 | 7.7 | 33.0 |
| 767 | 2180 | $C_{22}H_{24}ClF_3N_4O_2$ | 469 | 1.3 | 26 |
| 768 | 2181 | $C_{23}H_{25}F_3N_6O_3$ | 491 | 4.3 | 52 |
| 769 | 2182 | $C_{19}H_{22}F_3N_5O_2S$ | 442 | 7.0 | 51 |
| 770 | 1909 | $C_{23}H_{25}F_3N_4O_3$ | 463 | 8.7 | 37.6 |

Example 771

Synthesis of (R)-3-[[N-(2-amino-5-trifluoromethoxybenzoyl)glycyl]amino]-1-(2-amino-4-chlorobenzyl)pyrrolidine (Compd. No. 1921)

A mixture of (R)-3-[[N-(2-amino-5-trifluoromethoxybenzoyl)glycyl]amino]pyrrolidine (0.050 mmol) with 4-chloro-2-nitrobenzyl chloride (0.050 mmol), a piperidinomethylpolystyrene (60 mg), acetonitrile (1.0 mL) and chloroform (0.7 mL) was stirred at 50® C. overnight. The resulting reaction mixture was cooled, loaded onto a Varian™ SCX column and washed with 50% chloroform/methanol (10 mL) and methanol (10 mL). The obtained crude product was eluted with a solution of 2 M $NH_3$ in methanol (5 mL) and concentrated. Ethanol (3 mL) and 10% palladium carbon were added to the resulting residue, and the solution was stirred at room temperature under a hydrogen atmosphere for 1.5 hours. The obtained solution was filtered, concentrated and then purified by preparative TLC to thereby provide (R)-3-[[N-(2-amino-5-trifluoromethoxybenzoyl)glycyl]amino]-1-(2-amino-4-chlorobenzyl)pyrrolidine (Compd. No. 1921) (2.2 mg, 6%). The purity was determined by RPLC/MS (81%). ESI/MS m/e 486.2 ($M^+$+H, $C_{21}H_{23}ClF_3N_5O_3$).

Example 772

Synthesis of (R)-3-[[N-(2-amino-5-trifluoromethylbenzoyl)glycyl]amino]-1-(4-bromo-2-fluorobenzyl) pyrrolidine (Compd. No. 2120)

A methanol (0.50 mL) solution of $NaBH_3CN$ (0.25 mmol) was added to a mixture of (R)-3-[[N-(2-tert-butoxycarbonylamino)-5-trifluoromethylbenzoyl)glycyl]amino]pyrrolidine (0.050 mmol) with 4-bromo-2-fluorobenzaldehyde (0.015 mmol), methanol (1.5 mL) and acetic acid (0.016 mL). The resulting reaction mixture was stirred at 50° C. overnight, cooled to room temperature, then loaded onto a Varian™ SCX column and washed with methanol (5 mL×2). The obtained product was eluted with a solution of 2 M $NH_3$ in methanol (5 mL) and concentrated. The resulting residue was dissolved in methanol (0.25 mL), and a dioxane solution of 4 M HCl was added to the obtained solution. The resulting solution was stirred at room temperature for 5 hours and concentrated. The obtained residue was dissolved in methanol, loaded onto a Varian™ SCX column and washed with methanol (5 mL×2). The resulting crude product was eluted with a solution of 2 M $NH_3$ in methanol (5 mL) and concentrated. The obtained residue was dissolved in ethyl acetate (0.5 mL), loaded onto a Varian™ SCX column, eluted with ethyl acetate/methanol=5:1 (6 mL) and concentrated to thereby afford (R)-3-[[N-(2-amino-5-trifluoromethylbenzoyl)glycyl]amino]-1-(4-bromo-2-fluorobenzyl)pyrrolidine (Compd. No. 2120) (16.0 mg, 31%). The purity was determined by RPLC/MS (99%). ESI/MS m/e 517.0 ($M^+$+H, $C_{21}H_{21}BrF_4N_4O_2$).

Examples 773 to 793

The compounds used in the present invention were synthesized by using the respective starting materials and reactants according to the method of Example 772. Data of ESI/MS, yields (mg) and yields (%) are collectively shown in Table 13.

TABLE 13

| Example | Compd. No. | Molecular Formula | ESI/MS m/e | Yield (mg) | Yield (%) |
|---|---|---|---|---|---|
| 773 | 2083 | $C_{22}H_{24}BrF_3N4O4$ | 545.2 | 2.9 | 11 |
| 774 | 2084 | $C_{23}H_{27}F_3N_4O_5$ | 497.2 | 5.1 | 21 |
| 775 | 2085 | $C_{22}H_{25}F_3N_4O_4$ | 467.2 | 3.1 | 13 |
| 776 | 2086 | $C_{21}H_{22}ClF_3N_4O_3$ | 471.0 | 4.6 | 20 |
| 777 | 2087 | $C_{23}H_{28}F_3N_5O_2$ | 464.2 | 5.6 | 24 |
| 778 | 2088 | $C_{25}H_{32}F_3N_5O_2$ | 492.2 | 5.9 | 24 |
| 779 | 2089 | $C_{21}H_{21}F_5N_4O_2$ | 457.2 | 4.5 | 20 |
| 780 | 2090 | $C_{27}H_{27}F_3N_4O_3$ | 513.2 | 8.0 | 31 |
| 781 | 2118 | $C_{21}H_{23}F_3N_4O_4$ | 453.1 | 2.7 | 12 |
| 782 | 2119 | $C_{21}H_{23}F_3N_4O_4$ | 453.1 | 4.3 | 19 |
| 783 | 2121 | $C_{22}H_{25}F_3N_4O_4$ | 467.0 | 1.2 | 2 |
| 784 | 2122 | $C_{21}H_{21}ClF_4N_4O_2$ | 472.9 | 13.1 | 28 |
| 785 | 2123 | $C_{22}H_{22}F_3N_5O_6$ | 510.1 | 13.1 | 51 |
| 786 | 2124 | $C_{21}H_{21}ClF_3N_5O_4$ | 500.1 | 15.6 | 62 |
| 787 | 2125 | $C_{22}H_{24}F_3N_5O_5$ | 496.0 | 16.0 | 65 |
| 788 | 2126 | $C_{22}H_{24}F_3N_5O_4$ | 480.1 | 15.6 | 65 |
| 789 | 2137 | $C_{22}H_{24}ClF_3N_4O_2$ | 469.2 | 2.6 | 11 |
| 790 | 2138 | $C_{26}H_{29}F_3N_6O_2$ | 515.3 | 25.1 | 98 |
| 791 | 2139 | $C_{20}H_{24}ClF_3N_6O_2$ | 473.2 | 25.0 | 98 |
| 792 | 2149 | $C_{21}H_{22}F_3N_5O_5$ | 482.3 | 4.9 | 34 |
| 793 | 2157 | $C_{22}H_{25}F_3N_4O_3$ | 451.2 | 15.5 | 70 |

Example 794

Synthesis of (R)-3-[[N-(2-amino-5-trifluoromethylbenzoyl)glycyl]amino]-1-(2,4-dimethoxypyrimidin-5-ylmethyl)pyrrolidine (Compd. No. 2175)

(R)-3-[[N-(2-Amino-5-trifluoromethylbenzoyl)glycyl]amino]pyrrolidine (17.2 mg, 0.04 mmol) was dissolved in THF (1 mL), and 2,4-dimethoxy-5-pyrimidinecarboxaldehyde (6.7 mg, 0.04 mmol) was added to the resulting solution. Sodium triacetoxyborohydride (12.7 mg, 0.06 mmol) and glacial acetic acid (2.4 mg, 0.04 mmol) were subsequently added to the mixture. The resulting mixture was stirred at 50° C. for 24 hours and then concentrated. The residue was dissolved in dichloromethane (1 mL) and washed with a 1 M aqueous solution (1 mL) of NaOH. The organic layer was collected and concentrated, and a dichloromethane solution of 25% trifluoroacetic acid (1 mL) was added. The resulting mixture was stirred at room temperature for 1 hour and then concentrated. The obtained residue was purified by HPLC to thereby provide (R)-3-[[N-(2-amino-5-trifluoromethylbenzoyl)glycyl]amino]-1-(2,4-dimethoxypyrimidin-5-ylmethyl)pyrrolidine (Compd. No. 2175) (18.6 mg, 78%). The purity was determined by RPLC/MS (98%). ESI/MS m/e 483 ($M^+$+H, $C_{21}H_{25}F_3N_6O_4$).

Examples 795 to 803

The compounds used in the present invention were synthesized by using the respective corresponding starting materials and reactants according the method of Example 794. Data of ESI/MS, yields (mg) and yields (%) are collectively shown in Table 14.

TABLE 14

| Example | Compd. No. | Molecular Formula | ESI/MS m/e | Yield (mg) | Yield (%) |
|---|---|---|---|---|---|
| 795 | 2165 | $C_{18}H_{21}F_3N_6O_2$ | 411 | 2.0 | 27 |
| 796 | 2166 | $C_{18}H_{20}F_3N_5O_2S$ | 428 | 9.9 | 66 |
| 797 | 2167 | $C_{24}H_{25}F_3N_6O_2$ | 487 | 15.1 | 73 |
| 798 | 2169 | $C_{24}H_{29}F_3N_4O_2$ | 463 | 1.2 | 24 |
| 799 | 2170 | $C_{26}H_{25}ClF_3N_5O_2$ | 520 | 6.0 | 40 |
| 800 | 2171 | $C_{19}H_{23}F_3N_6O_2$ | 425 | 16.8 | 88 |
| 801 | 2174 | $C_{23}H_{24}BrF_3N_4O_2S_2$ | 591 | 5.3 | 53 |
| 802 | 2178 | $C_{25}H_{28}F_3N_5O_4$ | 518 | 5.4 | 62 |
| 803 | 2179 | $C_{25}H_{28}F_3N_5O_3$ | 502 | 6.3 | 60 |

Example 804

Synthesis of (R)-1-(2-amino-4,5-methylenedioxybenzyl)-3-[[N-(2-amino-5-trifluoromethylbenzoyl)glycyl]amino]pyrrolidine (Compd. No. 2127)

A mixture of (R)-3-[[N-(2-amino-5-trifluoromethylbenzoyl)glycyl]amino]-1-(4,5-methylenedioxy-2-nitrobenzyl)pyrrolidine (30.5 mg) with 10% Pd carbon (6 mg) and methanol (3 mL) was stirred at room temperature under a hydrogen atmosphere for 10 hours. The palladium catalyst was filtered through Celite, and the filtrate was concentrated and purified by solid-phase extraction (Bond Elut™ SI, 20% methanol/ethyl acetate) to thereby afford (R)-1-(2-amino-4,5-methylenedioxybenzyl)-3-[[$N^2$-amino-5-trifluoromethylbenzoyl]glycyl]amino]pyrrolidine (Compd. No. 2127) (21.9 mg, 76%). The purity was determined by RPLC/MS (95%). ESI/MS m/e 480.1 ($M^+$+H, $C_{22}H_{24}F_3N_5O_4$).

Examples 805 to 806

The compounds used in the present invention were synthesized by using the respective corresponding starting materials and reactants according to the method of Example 804. Data of ESI/MS, yields (mg) and yields (%) are collectively shown in Table 15.

TABLE 15

| Example | Compd. No. | Molecular Formula | ESI/MS m/e | Yield (mg) | Yield (%) |
|---|---|---|---|---|---|
| 805 | 2128 | $C_{22}H_{26}F_3N_5O_3$ | 466.0 | 8.6 | 30 |
| 806 | 2129 | $C_{22}H_{26}F_3N_5O_2$ | 450.1 | 13.1 | 37 |

Example 807

Synthesis of (R)-1-(3-amino-4-chlorobenzyl)-3-[[N-(2-amino-5-trifluoromethylbenzoyl)glycyl]amino]pyrrolidine (Compd. No. 2132)

A mixture of (R)-3-[[N-(2-amino-5-trifluoromethylbenzoyl)glycyl]amino]-1-(4-chloro-3-nitrobenzyl)pyrrolidine (32.6 mg) with 10% palladium carbon (8 mg), ethyl acetate (2.7 mL) and methanol (0.3 mL) was stirred at room temperature under a hydrogen atmosphere for 15 hours. The palladium carbon was removed by filtration, and the filtrate was concentrated and purified by solid-phase extraction (Bond Elut™ SI, 20% methanol/ethyl acetate) to thereby provide (R)-1-(3-amino-4-chlorobenzyl)-3-[[N-(2-amino-5-trifluoromethylbenzoyl)glycyl]amino]pyrrolidine (Comp d. No. 2132) (10.5 mg, 34%). The purity was determined by RPLC/MS (84%). ESI/MS m/e 470.2 ($M^{+}$+H, $C_{21}H_{23}F_3N_5O_2$).

Example 808

Synthesis of (R)-1-(2-amino-4,5-methylenedioxybenzyl)-3-[[N-(2-(tert-butoxycarbonylamino)-5-trifluoromethylbenzoyl)glycyl]amino]pyrrolidine A methanol (1.50 mL) solution of $NaBH_3CN$ (0.75 mmol) was added to a mixture of (R)-3-[[N-(2-(tert-butoxycarbonylamino)-5-trifluoromethylbenzoyl)glycyl]amino]pyrrolidine (0.150 mmol) with 4,5-methylenedioxy-2-nitrobenzaldehyde (0.45 mmol), methanol (4.5 mL) and acetic acid (0.048 mL). The resulting reaction mixture was stirred at 50° C. overnight, cooled to room temperature, loaded onto a Varian™ SCX column and washed with methanol. The obtained crude product was eluted with a 2 M methanol solution of $NH_3$ and concentrated to thereby afford (R)-3-[[N-(2-(tert-butoxycarbonylamino)-5-trifluoromethylbenzoyl)glycyl]amino]-1-(4,5-methylenedioxy-2-nitrobenzyl) pyrrolidine.

A mixture of the resulting (R)-3-[[N-(2-(tert-butoxycarbonylamino)-5-trifluoromethylbenzoyl) glycyl]amino]-1-(4,5-methylenedioxy-2-nitrobenzyl)pyrrolidine (0.150 mmol) with 10% Pd carbon (22 mg) and methanol (4.5 mL) was stirred at room temperature under a hydrogen atmosphere overnight. The palladium catalyst was removed by filtration, and the filtrate was concentrated to thereby afford (R)-1-(2-amino-4,5-methylenedioxybenzyl)-3-[[N-(2-(tert-butoxycarbonylamino)-5-trifluoromethylbenzoyl)glycyl]amino] pyrrolidine (87.1 mg, quantitative). Any noticeable by-product was not detected in TLC.

Further, (R)-1-(3-amino-4-methoxybenzyl)-3-[[N-(2-(tert-butoxycarbonylamino)-5-trifluoromethylbenzoyl)glycyl]amino]pyrrolidine and (R)-1-(3-amino-4-methylbenzyl)-3-[[N-(2-(tert-butoxycarbonylamino)-5-trifluoromethylbenzoyl)glycyl]amino] pyrrolidine were synthesized by using the respective corresponding starting materials and reactants according to the method of Example 808.

(R)-1-(3-amino-4-methoxybenzyl)-3-[[N-(2-(tert-butoxycarbonylamino)-5-trifluoromethylbenzoyl)glycyl]amino] pyrrolidine: 101 mg, quantitative. Any noticeable by-product was not detected in TLC.

(R)-1-(3-amino-4-methylbenzyl)-3-[[N-(2-(tert-butoxycarbonylamino)-5-trifluoromethylbenzoyl)glycyl]amino] pyrrolidine: 97.2 mg, quantitative. Any noticeable by-product was not detected in TLC.

Example 809

Synthesis of (R)-1-(3-amino-4-chlorobenzyl)-3-[[N-(2-(tert-butoxycarbonylamino)-5-trifluoromethylbenzoyl)glycyl]amino]pyrrolidine A methanol (1.50 mL) solution of $NaBH_3CN$ (0.75 mmol) was added to a mixture of (R)-3-[[N-(2-(tert-butoxycarbonylamino)-5-trifluoromethylbenzoyl)glycyl]amino]pyrrolidine (0.150 mmol) with 4-chloro-3-nitrobenzaldehyde (0.45 mmol), methanol (4.5 mL) and acetic acid (0.048 mL). The resulting reaction mixture was then stirred at 50° C. overnight, cooled to room temperature, loaded onto a Varian™ SCX column and washed with methanol. The obtained product was eluted with a 2 M methanol solution of $NH_3$ and concentrated to thereby provide (R)-3-[[N-(2-(tert-butoxycarbonylamino)-5-trifluoromethylbenzoyl)glycyl]amino]-1-(4-chloro-3-nitrobenzyl)pyrrolidine.

A mixture of the resulting (R)-3-[[N-(2-tert-butoxycarbonylamino)-5-trifluoromethylbenzoyl)glycyl]amino]-1-(4-chloro-3-nitrobenzyl)pyrrolidine with 10% Pd carbon (22 mg), ethyl acetate (2.7 mL) and methanol (0.3 mL) was stirred at room temperature under a hydrogen atmosphere for 15 hours. The palladium catalyst was removed by filtration, and the filtrate was concentrated to afford (R)-1-(3-amino-4-chlorobenzyl)-3-[[N-(2-tert-butoxycarbonylamino)-5-trifluoromethylbenzoyl)glycyl]amino]pyrrolidine (89.7 mg, quantitative). Any noticeable by-product was not detected in TLC.

Example 810

Synthesis of (R)-1-(3-amino-4-hydroxybenzyl)-3-[[N-(2-amino-5-trifluoromethylbenzoyl)glycyl] amino]pyrrolidine (Compd. No. 2187)

A 4 M HCl dioxane (2.0 mL) solution of (R)-1-(3-amino-4-hydroxybenzyl)-3-[[N-(2-(tert-butoxycarbonylamino)-5-trifluoromethylbenzoyl)glycyl]amino]pyrrolidine (20 mg) synthesized according to the method of Example 808 was stirred at room temperature overnight. The solution was concentrated, and the residue was then dissolved in methanol, loaded onto a VarianM SCX column, washed with methanol, subsequently eluted with a 2 M methanol solution of $NH_3$, concentrated and then purified by preparative TLC ($SiO_2$, ethyl acetate/methanol=4:1) to thereby provide (R)-1-(3-amino-4-hydroxybenzyl)-3-[[N-(2-amino-5-trifluoromethylbenzoyl)glycyl]amino]pyrrolidine (Compd. No. 2187) (9.6 mg, 59%). The purity was determined by RPLC/MS (86%). ESI/MS m/e 452.3 ($M^{+}$+H, $C_{21}H_{24}F_3N_5O_3$).

Example 811

Synthesis of (R)-3-[[N-(2-amino-5-trifluoromethylbenzoyl)glycyl]amino]-1-[4-chloro-3-(dimethylamino)benzyl]pyrrolidine (Compd. No. 2133)

$NaBH_3CN$ (38 mg) was added to a mixture of (R)-1-(3-amino-4-chlorobenzyl)-3-[[N-(2-tert-butoxycarbonylamino)-5-trifluoromethylbenzoyl]glycyl]amino]pyrrolidine (44.9 mg) with methanol (0.95 mL), acetic acid (0.05 mL) and a 37% aqueous solution of HCHO (0.15 mL). The resulting reaction mixture was stirred at 50° C. overnight, cooled to room temperature and concentrated. A 2 M aqueous solution of NaOH and ethyl acetate were then added to the residue to separate the organic layer. The aqueous layer was extracted with ethyl acetate. The organic layers were combined, dried and concentrated. The residue was loaded onto a Varian™ SCX column and washed with methanol. The resulting product was' eluted with a 2 M methanol solution of $NH_3$ and concentrated. The residue was dissolved in a 50% concentrated hydrochloric acid/dioxane and stirred at room temperature for 1 hour. The reaction solution was adjusted to pH 10 with a 5 M aqueous solution of NaOH and extracted with ethyl acetate (twice). The extracts were combined, dried over $Na_2SO_4$, filtered, concentrated and purified by preparative TLC ($SiO_2$, 20% methanol/ethyl acetate) to thereby afford (R)-3-[[$N^2$-amino-5-trifluoromethylbenzoyl)glycyl]amino]-

1-[4-chloro-3-(dimethylamino)benzyl]pyrrolidine (Compd. No. 2133) (10.9 mg, 28%). The purity was determined by RPLC/MS (95%). ESI/MS m/e 498.3 ($M^+$+H, $C_{23}H_{27}ClF_3N_5O_2$).

Examples 812 to 814

The compounds used in the present invention were synthesized by using the respective starting materials and reactants according to the method of Example 811. Data of ESI/MS, yields (mg) and yields (%) are collectively shown in Table 16.

TABLE 16

| Example | Compd. No. | Molecular Formula | ESI/MS m/e | Yield (mg) | Yield (%) |
|---|---|---|---|---|---|
| 812 | 2134 | $C_{24}H_{28}F_3N_5O_4$ | 508.4 | 19.0 | 50 |
| 813 | 2135 | $C_{24}H_{30}F_3N_5O_3$ | 494.4 | 21.8 | 50 |
| 814 | 2136 | $C_{24}H_{30}F_3N_5O_2$ | 478.4 | 29.2 | 69 |

Example 815

Synthesis of (R)-3-[[N-(2-amino-5-trifluoromethylbenzoyl)glycyl]amino]-1-(3-methylamino-4-hydroxybenzyl)pyrrolidine (Compd. No. 2158)

$NaBH_3CN$ (9.2 mg) was added to a mixture of (R)-1-(3-amino-4-hydroxybenzyl)-3-[[N-(2-(tert-butoxycarbonylamino)-5-trifluoromethylbenzoyl)glycyl]amino]pyrrolidine (27.3 mg, 0.049 mmol) with a 37% HCHO solution (4.0 mg, 0.049 mmol), acetic acid (0.10 mL) and methanol (1.3 mL). The resulting reaction mixture was stirred at 60° C. overnight, cooled to room temperature, loaded onto a Varian™ SCX column and washed with methanol (5 mL×2). The obtained crude product was eluted with a 2 M methanol solution of $NH_3$ (8 mL) and concentrated.

The resulting residue was dissolved in methanol (1 mL), and a 4 M dioxane solution of HCl (1.0 mL) was added to the solution. The resulting mixture was stirred at room temperature for 3 hours and concentrated. The residue was dissolved in methanol (1 mL), loaded onto a Varian™ column, washed with methanol (5 mL×2), eluted with a 2 M methanol solution of $NH_3$ (8 mL), concentrated and then purified by preparative TLC ($SiO_2$) to thereby provide (R)-3-[[N-(2-amino-5-trifluoromethylbenzoyl)glycyl]amino]-1-(3-methylamino-4-hydroxybenzyl)pyrrolidine (Compd. No. 2158) (4.3 mg, 19%). The purity was determined by RPLC/MS (71%). ESI/MS m/e 480.3 ($M^+$+H, $C_{22}H_{26}F_3N_5O_3$).

Example 816

Synthesis of (R)-1-(3-acetylamino-4-methoxybenzyl)-3-[[N-(2-amino-5-trifluoromethylbenzoyl)glycyl]amino]pyrrolidine (Compd. No. 2152)

Acetic anhydride (1 mL) was added to a pyridine (1 mL) solution of (R)-1-(3-amino-4-hydroxybenzyl)-3-[[N-(2-(tert butoxycarbonylamino)-5-trifluoromethylbenzoyl)glycyl] amino]pyrrolidine (50.5 mg). The resulting reaction mixture was stirred at room temperature overnight, and methanol was added to the mixture. The obtained mixture was concentrated, and a 1 M NaOH solution was then added to the concentrate. The resulting mixture was extracted with ethyl acetate, and the organic layer was concentrated and purified by preparative TLC ($SiO_2$) to thereby afford (R)-1-(3-acetylamino-4-methoxybenzyl)-3-[[N-(2-(tert-butoxycarbonylamino)-5-trifluoromethylbenzoyl)glycyl]amino]pyrrolidine.

The resulting (R)-1-(3-acetylamino-4-methoxybenzyl)-3-[[N-(2-(tert-butoxycarbonylamino)-5-trifluoromethylbenzoyl)glycyl]amino]pyrrolidine was dissolved in a 50% dioxane solution of 6 M hydrochloric acid, and the obtained solution was stirred at room temperature for 2 hours, adjusted to pH 10 with a 5 M NaOH solution and extracted with ethyl acetate. The organic layer was concentrated and purified by preparative TLC ($SiO_2$) to thereby provide (R)-1-(3-acetylamino-4-methoxybenzyl)-3-[[N-(2-amino-5-trifluoromethylbenzoyl)glycyl]amino]pyrrolidine (Compd. No. 2152) (3.7 mg, 8%). The purity was determined by RPLC/MS (100%). ESI/MS m/e 508.3 ($M^+$+H, $C_{24}H_{28}F_3N_5O_4$).

Examples 817 to 819

The compounds used in the present invention were synthesized by using the respective corresponding starting materials and reactants according to the method of Example 816. Data of ESI/MS, yields.(mg) and yields (%) are collectively shown in Table 17.

TABLE 17

| Example | Compd. No. | Molecular Formula | ESI/MS m/e | Yield (mg) | Yield (%) |
|---|---|---|---|---|---|
| 817 | 2150 | $C_{23}H_{25}ClF_3N_5O_3$ | 512.3 | 3.8 | 9 |
| 818 | 2151 | $C_{24}H_{26}F_3N_5O_5$ | 522.2 | 3.1 | 8 |
| 819 | 2153 | $C_{24}H_{28}F_3N_5O_3$ | 492.3 | 4.3 | 10 |

Example 820

Synthesis of (R)-3-[[N(2-amino-5-trifluoromethylbenzoyl)glycyl]amino]-1-(benz[d]oxazol-5-yl)pyrrolidine (Compd. No. 2189)

Triethyl orthoformate (0.20 mL, 3.3 equivalents) and pyridinium p-toluenesulfonate (1.2 mg, 0.4 equivalent) were added to a THF (2 mL) solution of (R)-1-(3-amino-4-hydroxybenzyl)-3-[[N-(2-(tert-butoxycarbonylamino)-5-trifluoromethylbenzoyl)glycyl]amino]pyrrolidine (20 mg) synthesized according to the method of Example 808. The resulting reaction mixture was stirred at room temperature overnight under reflux. The reaction mixture was cooled to room temperature and then concentrated. The obtained residue was dissolved in ethyl acetate, loaded onto a Bond Elut™ Si column, eluted with ethyl acetate/methanol=4:1 and concentrated.

The resulting residue was dissolved in ethyl acetate (1.5 mL), and a 4 M dioxane solution of HCl was added to the obtained solution. The resulting solution was stirred overnight, adjusted to pH 10 with a 5 M aqueous solution of NaOH and extracted with ethyl acetate. The obtained extract was concentrated and purified by preparative TLC ($SiO_2$, ethyl acetate/methanol=4:1) to thereby provide (R)-3-[[N-(2-amino-5-trifluoromethylbenzoyl)glycyl]amino]-1-(benz[d]oxazol-5-yl)pyrrolidine (Comp d. No. 2189) (0.5 mg, 3%). The purity was determined by RPLC/MS (97%). ESI/MS m/e 462.3 ($M^+$+H, $C_{22}H_{22}F_3N_5O_3$).

Example 821

Synthesis of (R)-3-[[N-(2-amino-5-trifluoromethyl-benzoyl)glycyl]amino]-1-[benzo[c]thiadiazol-5-yl] pyrrolidine (Compd. No. 2183)

Methanesulfonyl chloride (0.0042 mL) was added to a mixture of 5-(hydroxymethyl)benzo[c]thiadiazole (8.3 mg, 0.050 mmol) with a (piperidinomethyl)polystyrene (86 mg) and chloroform (1 mL). The resulting mixture was stirred at room temperature for 1.5 hours. Acetonitrile (1 ml) and (R)-3-[[N-(2-(tert-butoxycarbonylamino)-5-trifluoromethylbenzyl)glycyl]amino]pyrrolidine (0.060 mmol) were added to the mixture. The resulting mixture was stirred at 50° C. for 3 hours. After cooling to room temperature, phenyl isocyanate (30 mg) was added, and the obtained mixture was stirred at room temperature for 1 hour, loaded onto a Varian™ SCX column and washed with methanol (5 mL) and chloroform (5 mL). The resulting crude product was eluted with a 2 M methanol solution of $NH_3$ (3 mL) and concentrated.

The obtained substance was dissolved in dichloromethane (1 mL), and a dichloromethane solution (1 mL) of 1 M chlorotrimethylsilane (1 M) and phenol (1 M) was added to the solution. The resulting solution was stirred at room temperature for 5 hours, loaded onto a Varian™ SCX column and washed with methanol and dichloromethane. The obtained product was eluted with a 2 M methanol solution of $NH_3$ and concentrated.

The resulting crude product was purified by preparative TLC ($SiO_2$, ethyl acetate/methanol=3:1) to thereby afford (R)-3-[[N-(2-amino-5-trifluoromethylbenzoyl)glycyl] amino]-1-[benzo[c]thiadiazol-5-yl]pyrrolidine (Compd. No. 2183) (11.5 mg, 58%). The purity was determined by RPLC/MS (86%). ESI/MS m/e 479.2 ($M^{+}$+H, $C_{21}H_{21}F_3N_6O_2S$).

Reference Example 6

Synthesis of 4-[[N-(1-(9-fluorenylmethoxycarbonyl) pyrrolidin-3-yl)carbamoylmethyl]aminomethyl]3-methoxyphenyloxymethyl-polystyrene Acetic acid (0.3 mL), sodium triacetoxyborohydride (1.92 g) and a 4-formyl-3-(methoxyphenyloxymethyl)-polystyrene (1 mmol/g, 200 g) were added to a DMF (65 mL) solution of (R)-1-(9-fluorenylmethoxycarbonyl)-3-glycylaminopyrrolidine hydrochloride (4.38 g, 10 mmol). The resulting mixture was shaken for 2 hours and then filtered. The resin was washed with methanol, DMF, dichloromethane and methanol and dried to thereby provide the objective substance (2.73 g).

Examples 822 to 912

Solid-phase synthesis of 3-aminopyrrolidines

Disopropylethylamine (3.6 mL) was added to a mixture of the corresponding carboxylic acid (1.6 mmol) with HBTU (1.6 mmol) and DMF (6 mL), and the resulting mixture was shaken for 2 minutes. A 4-[[N-(1-(9-fluorenylmethoxycarbonyl)pyrrolidin-3-yl)carbamoylmethyl]aminomethyl]-3-methoxyphenyloxymethyl-polystyrene (400 mg, 0.4 mmol) was added, and the obtained mixture was shaken for 1 hour and then filtered. The resin was washed with DMF and dichloromethane and dried.

A mixture of the resulting resin with piperidine (3.2 mL) and DMF (12.8 mL) was shaken for 10 minutes and then filtered. The resin was washed with DMF and dichloromethane and dried.

A mixture of $NaBH(OAc)_3$ (0.25 mmol) with acetic acid (0.025 mL) and DMF (1 mL) was added to the dried resin (0.05 mL). The corresponding aldehyde (2.5 mmol) was added, and the mixture was shaken for 2 hours, then filtered and washed with methanol, a 10% solution of diisopropylethylamine in DMF, DMF, dichloromethane and methanol. A mixture of the resin with water (0.050 mL) and trifluoroacetic acid (0.95 mL) was shaken for 1 hour and then filtered. The resin was washed with dichloromethane and methanol. The filtrate and washings were combined and concentrated. The resulting crude product was loaded onto a Varian™ SCX column and washed with methanol (15 mL). The product was eluted with a 2 M methanol solution of $NH_3$ (5 mL) and concentrated.

The obtained products, if necessary, were purified with preparative TLC or HPLC to thereby afford the objective compounds. Data of ESI/MS, yields (mg) and yields (%) are collectively shown in Table 18.

TABLE 18

| Example | Compd. No. | Molecular Formula | ESI/MS m/e | Yield (mg) | Yield (%) |
|---|---|---|---|---|---|
| 822 | 1805 | $C_{21}H_{21}BrF_3N_3O_2S$ | 516 | 13.3 | 76 |
| 823 | 1806 | $C_{22}H_{24}F_3N_3O_3S$ | 468 | 12.8 | 81 |
| 824 | 1807 | $C_{22}H_{24}F_3N_3O_4S$ | 484 | 13.7 | 83 |
| 825 | 1808 | $C_{22}H_{24}F_3N_3O_4S$ | 484 | 14.9 | 91 |
| 826 | 1809 | $C_{21}H_{22}F_3N_3O_3S$ | 454 | 12.9 | 84 |
| 827 | 1810 | $C_{22}H_{22}F_3N_3O_4S$ | 482 | 12.9 | 79 |
| 828 | 1811 | $C_{24}H_{26}F_3N_3O_2S$ | 478 | 12.9 | 79 |
| 829 | 1812 | $C_{22}H_{24}F_3N_3O_2S_2$ | 484 | 5.3 | 32 |
| 830 | 1813 | $C_{23}H_{26}F_3N_3O_2S$ | 466 | 12.8 | 81 |
| 831 | 1814 | $C_{23}H_{24}F_3N_3O_3S$ | 480 | 9.7 | 59 |
| 832 | 1815 | $C_{23}H_{26}F_3N_3O_2S$ | 466 | 12.7 | 80 |
| 833 | 1816 | $C_{24}H_{28}F_3N_3O_2S$ | 480 | 14.4 | 88 |
| 834 | 1817 | $C_{25}H_{30}F_3N_3O_2S$ | 494 | 14.1 | 84 |
| 835 | 1818 | $C_{21}H_{22}BrF_2N_3O_3$ | 482 | 13.4 | 82 |
| 836 | 1819 | $C_{22}H_{25}F_2N_3O_4$ | 434 | 11.7 | 79 |
| 837 | 1820 | $C_{22}H_{25}F_2N_3O_5$ | 450 | 11.8 | 77 |
| 838 | 1821 | $C_{22}H_{25}F_2N_3O_5$ | 450 | 13.3 | 87 |
| 839 | 1822 | $C_{21}H_{23}F_2N_3O_4$ | 420 | 11.9 | 83 |
| 840 | 1823 | $C_{22}H_{23}F_2N_3O_5$ | 448 | 11.9 | 78 |
| 841 | 1824 | $C_{24}H_{27}F_2N_3O_3$ | 444 | 9.1 | 60 |
| 842 | 1825 | $C_{22}H_{25}F_2N_3O_3S$ | 450 | 11.3 | 74 |
| 843 | 1826 | $C_{23}H_{27}F_2N_3O_3$ | 432 | 10.8 | 74 |
| 844 | 1827 | $C_{23}H_{25}F_2N_3O_4$ | 446 | 12.7 | 84 |
| 845 | 1828 | $C_{23}H_{27}F_2N_3O_3$ | 432 | 11.7 | 80 |
| 846 | 1829 | $C_{24}H_{29}F_2N_3O_3$ | 446 | 14.3 | 94 |
| 847 | 1830 | $C_{24}H_{29}F_2N_3O_3$ | 446 | 10.0 | 66 |
| 848 | 1831 | $C_{22}H_{28}BrN_3O_3$ | 462 | 4.8 | 31 |
| 849 | 1832 | $C_{23}H_{31}N_3O_4$ | 414 | 10.4 | 74 |
| 850 | 1833 | $C_{23}H_{31}N_3O_5$ | 430 | 12.1 | 83 |
| 851 | 1834 | $C_{23}H_{31}N_3O_5$ | 430 | 12.0 | 82 |
| 852 | 1835 | $C_{22}H_{29}N_3O_4$ | 400 | 7.9 | 58 |
| 853 | 1836 | $C_{23}H_{29}N_3O_5$ | 428 | 11.1 | 76 |
| 854 | 1837 | $C_{25}H_{33}N_3O_3$ | 424 | 13.3 | 92 |
| 855 | 1838 | $C_{23}H_{31}N_3O_3S$ | 430 | 8.7 | 60 |
| 856 | 1839 | $C_{24}H_{33}N_3O_3$ | 412 | 11.3 | 81 |
| 857 | 1840 | $C_{24}H_{31}N_3O_4$ | 426 | 12.9 | 89 |
| 858 | 1841 | $C_{24}H_{33}N_3O_3$ | 413 | 12.8 | 91 |
| 859 | 1842 | $C_{25}H_{35}N_3O_3$ | 426 | 8.7 | 60 |
| 860 | 1843 | $C_{25}H_{35}N_3O_3$ | 426 | 12.2 | 84 |
| 861 | 1844 | $C_{26}H_{37}N_3O_3$ | 440 | 11.3 | 76 |
| 862 | 1845 | $C_{31}H_{37}BrN_4O_2$ | 577 | 6.4 | 30 |
| 863 | 1846 | $C_{23}H_{28}F_3N_3O_2S$ | 480 | 12.8 | 81 |
| 864 | 1847 | $C_{25}H_{31}F_2N_3O_3$ | 460 | 12.2 | 78 |
| 865 | 1848 | $C_{27}H_{29}N_3O_4$ | 460 | 6.1 | 39 |
| 866 | 1849 | $C_{29}H_{31}N_3O_2$ | 454 | 15.1 | 98 |
| 867 | 1850 | $C_{28}H_{31}N_3O_2$ | 442 | 12.7 | 85 |
| 868 | 1851 | $C_{28}H_{31}N_3O_2$ | 442 | 14.3 | 95 |
| 869 | 1852 | $C_{28}H_{29}N_3O_3$ | 456 | 3.4 | 22 |
| 870 | 1853 | $C_{27}H_{29}N_3O_6S$ | 524 | 15.4 | 87 |
| 871 | 1854 | $C_{29}H_{31}N_3O_4S$ | 518 | 15.8 | 90 |
| 872 | 1855 | $C_{28}H_{31}N_3O_4S$ | 506 | 17.0 | 99 |
| 873 | 1856 | $C_{28}H_{31}N_3O_4S$ | 506 | 3.0 | 17 |
| 874 | 1857 | $C_{28}H_{29}N_3O_5S$ | 520 | 10.0 | 57 |

TABLE 18-continued

| Example | Compd. No. | Molecular Formula | ESI/MS m/e | Yield (mg) | Yield (%) |
|---|---|---|---|---|---|
| 875 | 1858 | $C_{20}H_{22}Br_2N_4O_2$ | 511 | 9.3* | 37 |
| 876 | 1859 | $C_{21}H_{25}BrN_4O_3$ | 461 | 6.7* | 29 |
| 877 | 1860 | $C_{21}H_{25}BrN_4O_4$ | 477 | 9.5* | 40 |
| 878 | 1861 | $C_{21}H_{25}BrN_4O_4$ | 477 | 10.0* | 42 |
| 879 | 1862 | $C_{20}H_{23}BrN_4O_3$ | 447 | 7.8* | 34 |
| 880 | 1863 | $C_{21}H_{23}BrN_4O_4$ | 475 | 3.4* | 14 |
| 881 | 1864 | $C_{21}H_{25}BrN_4O_2S$ | 477 | 3.9* | 16 |
| 882 | 1865 | $C_{22}H_{25}BrN_4O_3$ | 473 | 6.4* | 27 |
| 883 | 1866 | $C_{23}H_{29}BrN_4O_2$ | 472 | 7.0* | 29 |
| 884 | 1867 | $C_{23}H_{29}BrN_4O_2$ | 473 | 7.6* | 32 |
| 885 | 1868 | $C_{24}H_{31}BrN_4O_2$ | 487 | 9.1* | 37 |
| 886 | 1869 | $C_{20}H_{22}BrIN_4O_2$ | 557 | 8.9* | 33 |
| 887 | 1870 | $C_{21}H_{25}IN_4O_3$ | 509 | 9.2* | 37 |
| 888 | 1871 | $C_{21}H_{25}IN_4O_4$ | 525 | 6.3* | 25 |
| 889 | 1872 | $C_{21}H_{25}IN_4O_4$ | 525 | 5.9* | 23 |
| 890 | 1873 | $C_{20}H_{23}IN_4O_3$ | 495 | 7.7* | 31 |
| 891 | 1874 | $C_{21}H_{23}IN_4O_4$ | 523 | 8.2* | 32 |
| 892 | 1875 | $C_{23}H_{27}IN_4O_2$ | 519 | 6.7* | 26 |
| 893 | 1876 | $C_{21}H_{25}IN_4O_2$ | 525 | 4.3* | 17 |
| 894 | 1877 | $C_{22}H_{27}IN_4O_2$ | 507 | 7.9* | 32 |
| 895 | 1878 | $C_{22}H_{25}IN_4O_3$ | 521 | 8.4* | 33 |
| 896 | 1879 | $C_{23}H_{29}IN_4O_2$ | 521 | 8.2* | 32 |
| 897 | 1880 | $C_{23}H_{29}IN_4O_2$ | 521 | 8.1* | 32 |
| 898 | 1881 | $C_{24}H_{31}IN_4O_2$ | 535 | 8.6* | 33 |
| 899 | 1882 | $C_{20}H_{22}BrN_5O_4$ | 476 | 5.3* | 22 |
| 900 | 1883 | $C_{21}H_{25}N_5O_5$ | 428 | 5.7* | 26 |
| 901 | 1884 | $C_{21}H_{28}N_5O_6$ | 444 | 8.2* | 36 |
| 902 | 1885 | $C_{21}H_{25}N_5O_6$ | 444 | 5.0* | 22 |
| 903 | 1886 | $C_{20}H_{23}N_5O_5$ | 414 | 8.7* | 40 |
| 904 | 1887 | $C_{21}H_{23}N_5O_6$ | 442 | 7.8* | 34 |
| 905 | 1888 | $C_{23}H_{27}N_5O_4$ | 438 | 5.6* | 25 |
| 906 | 1889 | $C_{21}H_{25}N_5O_4S$ | 444 | 13.2* | 58 |
| 907 | 1890 | $C_{22}H_{27}N_5O_4$ | 426 | 11.3* | 51 |
| 908 | 1891 | $C_{22}H_{25}N_5O_5$ | 440 | 7.4* | 33 |
| 909 | 1892 | $C_{22}H_{27}N_5O_4$ | 426 | 5.5* | 25 |
| 910 | 1893 | $C_{23}H_{29}N_5O_4$ | 440 | 5.7* | 25 |
| 911 | 1894 | $C_{23}H_{29}N_5O_4$ | 440 | 9.4* | 41 |
| 912 | 1895 | $C_{24}H_{31}N_5O_4$ | 455 | 8.5* | 37 |

Note: *indicates "yield (mg) of trifluoroacetate".

Reference Example 7

Synthesis of 2-carbamoyl-1-(4-chlorobenzyl)pyrrolidine

Triethylamine (7.45 mL) and 4-chlorobenzyl chloride (3.88 g, 24.1 mmol) were added to an acetonitrile (35 mL) solution of dl-prolinamide hydrochloride (2.5 g, 21.8 mmol). The resulting reaction mixture was stirred at 70° C. for 4 hours and subsequently stirred at 25° C. for 16 hours. The resulting mixture was diluted with dichloromethane (20 mL) and washed with water (30 mL×3). The organic layer was dried (over $MgSO_4$) and concentrated. The obtained crude product was purified by chromatography ($SiO_2$, methanol-dichloromethane) to thereby provide 2-carbamoyl-1-(4-chlorobenzyl)pyrrolidine (5.21 g, 81%).

Reference Example 8

Synthesis of 2-(aminomethyl)-1-(4-chlorobenzyl)pyrrolidine

2-Carbamoyl-1-(4-chlorobenzyl)pyrrolidine was dissolved in 1 M $BH_3$-THF (9.4 mL), and the resulting solution was heated at 70° C. A 1 M $BH_3$-THF (0.5 equivalent) was further added twice after 16 hours and 25 hours. After 40 hours, a 1 M hydrochloric acid was added, and the resulting mixture was refluxed for 3 hours. A 3 M hydrochloric acid (6 mL) was added, and the reaction product was stirred for another 3 hours with heating, then cooled to 25° C., alkalinized with a 6 M aqueous solution of NaOH and extracted with dichloromethane (4×15 mL). The obtained crude product was purified by chromatography ($SiO_2$, PrOH/$H_2O$/$NH_4OH$=8:1:1) to thereby afford 2-(aminomethyl)-1-(4-chlorobenzyl)pyrrolidine (1.21 g, 86%).

Furthermore, optically active (S)-2-(aminomethyl)-1-(4-chlorobenzyl)pyrrolidine and (R)-2-(aminomethyl)-1-(4-chlorobenzyl)pyrrolidine were synthesized by using the respective corresponding starting materials and reactants according to the above method.

(S)-2-(aminomethyl)-1-(4-chlorobenzyl)pyrrolidine: $^1H$ NMR ($CDCl_3$, 400 MHz) δ 1.40-1.80 (m, 5H), 1.80-1.95 (m, 1H), 2.12-2.21 (m, 1H), 2.48-2.65 (m, 1H), 2.66-2.78 (m, 2H), 2.85-2.95 (m, 1H), 3.26 (d, J=13.2 Hz, 1H), 3.93 (d, J=13.2, 1H), 7.20-7.40 (m, 4H).

(R)-2-(Aminomethyl)-1-(4-chlorobenzyl)pyrrolidine exhibited the same $^1H$ NMR as that of the (S)-isomer.

Example 913

Synthesis of 2-[[N(benzoylleucyl)aminomethyl]-1-(4-chlorobenzyl)pyrrolidine (Compd. No. 344)

EDCI (23 mg), HOBt (16.2 mg) and triethylamine (15.2 μL) were added to a chloroform (1 mL) solution of 2-(aminomethyl)-1-(4-chlorobenzyl)pyrrolidine (22.5 mg, 0.10 mmol) and dl-benzoylleucine (0.12 mL), and the resulting mixture was stirred at 25° C. for 16 hours. The reaction mixture was diluted with dichloromethane (0.5 mL), washed with a 2 M aqueous solution of NaOH (0.75 mL×2), filtered through a PTFE membrane, thereby dried and concentrated to provide 2-[(N-benzoylleucyl)aminomethyl]-1-(4-chlorobenzyl)pyrrolidine (Compd. No. 344) (74 mg, quantitative). The purity was determined by RPLC/MS (85%). ESI/MS m/e 442 ($M^+$+H, $C_{23}H_{32}ClN_3O_2$).

Examples 914 to 933

The compounds used in the present invention were synthesized by using the respective corresponding starting materials and reactants according to the method of Example 913. The obtained products, if necessary, were purified by chromatography (HPLC-$C_{18}$, acetonitrile/$H_2O$/TFA), and the objective compounds were obtained as TFA salts. Data of ESI/MS, yields (mg) and yields (%) are collectively shown in Table 19. Compd. Nos. 339 and 340 exhibited the following $^1H$ NMR, respectively.

TABLE 19

| Example | Compd. No. | Molecular Formula | ESI/MS m/e | Yield (mg) | Yield (%) |
|---|---|---|---|---|---|
| 914 | 330 | $C_{21}H_{24}ClN_3O_2$ | 386 | 75* | Q |
| 915 | 331 | $C_{22}H_{26}Cl_3O_2$ | 400 | 44* | 70 |
| 916 | 332 | $C_{24}H_{30}ClN_3O_5$ | 476 | 57 | Q |
| 917 | 333 | $C_{20}H_{23}ClN_4O_2$ | 387 | 40 | Q |
| 918 | 334 | $C_{22}H_{26}ClN_3O_2$ | 400 | 68 | Q |
| 919 | 335 | $C_{21}H_{23}ClN_4O_4$ | 431 | 73 | Q |
| 920 | 336 | $C_{22}H_{23}ClF_3N_3O_2$ | 454 | 75 | Q |
| 921 | 337 | $C_{22}H_{26}ClN_3O_2$ | 400 | 68 | Q |
| 922 | 338 | $C_{22}H_{26}ClN_3O_2$ | 400 | 70 | Q |
| 923 | 341 | $C_{22}H_{26}ClN_3O_2$ | 400 | 80* | Q |
| 924 | 342 | $C_{22}H_{26}ClN_3O_2$ | 400 | 68 | Q |
| 925 | 343 | $C_{24}H_{30}ClN_3O_2$ | 428 | 63 | Q |
| 926 | 345 | $C_{23}H_{27}ClN_2O_2$ | 399 | 68* | Q |
| 927 | 346 | $C_{23}H_{26}ClFN_2O_3$ | 433 | 51 | Q |
| 928 | 347 | $C_{24}H_{29}ClN_2O_2$ | 413 | 47 | Q |

TABLE 19-continued

| Example | Compd. No. | Molecular Formula | ESI/MS m/e | Yield (mg) | Yield (%) |
|---|---|---|---|---|---|
| 929 | 348 | $C_{23}H_{27}ClN_2O_2$ | 399 | 26 | Q |
| 930 | 349 | $C_{21}H_{25}ClN_2O_3S$ | 421 | 42 | Q |
| 931 | 350 | $C_{26}H_{33}ClN_2O_3$ | 457 | 12.4 | 54 |
| 932 | 351 | $C_{22}H_{26}ClN_3O_3$ | 416 | 34 | 81 |
| 933 | 352 | $C_{22}H_{25}Cl_2N_3O_3$ | 450 | 51 | Q |

Notes
*indicates "yield (mg) of trifluoroacetate".
Q means "Quantitative".

Example 934

Compd. No. 339: 82%; $^1$H NMR ($CDCl_3$) δ 1.52-1.75 (m, 4 H), 1.84-1.95 (m, 1H), 2.10-2.20 (m, 1H), 2.67-2.78 (m, 1H), 2.80-2.90 (m, 1H), 3.10-3.20 (m, 1H), 3.25 (d, J=13.1 Hz, 1H), 3.50-3.60 (m, 1H), 3.89 (d, J=13.1 Hz, 1H), 4.28-4.20 (m, 2H), 7.00-7.05 (m, 1H), 7.12-7.29 (m, 4H), 7.51 (t, J=7.8 Hz, 1H), 7.74 (d, J=7.8 Hz, 1H), 7.99 (d, J=7.8 Hz, 1H), 8.10-8.27 (m, 2H).

Example 935

Compd. No. 340: 68%; $^1$H NMR ($CDCl_3$) δ 1.55-1.73 (m, 4H), 1.86-1.97 (m, 1H), 2.12-2.21 (m, 1H), 2.67-2.76 (m, 1H), 2.86-2.93 (m, 1H), 3.14-3.21 (m, 1H), 3.27 (d, J=13.1 Hz, 1H), 3.52-3.59 (m, 1H), 3.89 (d, J=13.1 Hz, 1H), 4.09-4.21 (m, 2H), 7.00-7.07 (m, 1H), 7.12-7.30 (m, 4H), 7.50 (t, J=7.8 Hz, 1H), 7.73 (d, J=7.8 Hz, 1H), 8.01 (d, J=7.8 Hz, 1H), 8.10-8.25 (m, 2H).

Reference Example 9

Synthesis of 3-(aminomethyl)-1-(4-chlorobenzyl)pyrrolidine

A 0.5 M dioxane solution of ammonia (60 mL, 30 mmol) was added to a mixture of 4-carboxy-1-(4-chlorobenzyl)pyrrolidin-2-one (5.05 g, 20 mmol) with EDCI (2.85 g, 22 mmol), HOBt (2.97 g, 22 mmol) and dichloromethane (100 mL). The resulting reaction mixture was stirred at room temperature for 15 hours and washed with 2 M HCl (three times) and a 2 M aqueous solution of NaOH (100 mL×4). The organic layer was dried over anhydrous magnesium sulfate, filtered and concentrated to thereby provide 4-carbamoyl-(4-chlorobenzyl)pyrrolidin-2-one (1.49 g) as a colorless solid.

A 1.0 M THF solution of $BH_3$ (25 mL) was added to a THF (15 mL) solution of 4-carbamoyl-1-(4-chlorobenzyl)pyrrolidin-2-one (1.49 g). The resulting reaction mixture was stirred for 15 hours and cooled to room temperature. The solvent was then removed under reduced pressure. Water (30 mL) and concentrated hydrochloric acid (10 mL) were added, and the mixture was stirred at 100° C. for 2 hours and at room temperature for 1 hour. A 2 M aqueous solution of NaOH (100 mL) was added, and the obtained mixture was extracted with ethyl acetate (50 mL×3). The organic layers were combined, dried over $K_2CO_3$, filtered, concentrated and purified by column chromatography ($SiO_2$, 15% methanol-5% triethylamine/dichloromethane) to thereby afford 3-(aminomethyl)-1-(4-chlorobenzyl)pyrrolidine (860 mg, 19%) as a colorless oil.

Reference Example 10

Synthesis of 1-(4-chlorobenzyl)-3-[(glycylamino) methyl]pyrrolidine

A mixture of 3-(aminomethyl)-1-(4-chlorobenzyl)pyrrolidine (860 mg, 3.8 mmol) with triethylamine (5.7 mmol), N-tert-butoxycarbonylglycine (704 mg), EDCI (594 mg), HOBt (673 mg) and dichloromethane (20 mL) was stirred at room temperature for 15 hours, and dichloromethane (50 mL) was added to the mixture. The resulting solution was washed with a 2 M aqueous solution of NaOH (50 mL×2), dried over anhydrous sodium sulfate, filtered and concentrated to thereby provide 3-[[N-(tert-butoxycarbonyl)glycl]aminomethyl]-1,1-(4-chlorobenzyl)pyrrolidine (1.31 g, 90%).

A 4 M dioxane solution of HCl (5 mL) was added to a methanol (10 mL) solution of 3-[[N-tert-butoxycarbonyl)glycyl]aminomethyl]-1-(4-chlorobenzyl)pyrrolidine (804 mg, 2.11 mmol). The resulting solution was stirred at room temperature for 3.5 hours and then concentrated, and a 1 M aqueous solution of NaOH (20 mL) was added. The resulting mixture was extracted with dichloromethane (20 mL×3), and the extracts were combined, dried over sodium sulfate and concentrated to thereby afford 1-(4-chlorobenzyl)-3-[(glycylamino)methyl]pyrrolidione (599 mg, 100%). The purity was determined by RPLC/MS (100%). ESI/MS m/e 282.2 ($M^+$+H, $C_{14}H_{20}ClN_3O$).

Example 936

Synthesis of 3-[[N-[3-trifluoromethylbenzoyl]glycyl] aminomethyl]-1-(4-chlorobenzyl)pyrrolidine (Compd. No. 1463)

A dichloromethane (0.2 mL) solution of 3-(trifluoromethyl)benzoyl chloride (0.058 mmol) was added to a mixture of a chloroform (0.2 m-L) solution of 1-(4-chlorobenzyl)-3-[(glycylamino)methyl]pyrrolidine (0.050 mmol) with a dichloromethane (1 mL) solution of a piperidinomethylpolystyrene (60 mg). The resulting reaction mixture was stirred at room temperature for 2.5 hours, and methanol (0.30 mL) was then added. The reaction mixture was loaded onto a Varian™ SCX column and washed with methanol (15 mL). The obtained crude product was eluted with a methanol (5 mL) solution of 2 M $NH_3$ and concentrated to thereby provide 3-[[N-[3-trifluoromethylbenzoyl]glycyl]aminomethyl]-1-(4-chlorobenzyl)pyrrolidine (Compd. No. 1463) (22.4 mg, 99%). The purity was determined by RPLC/MS (97%). ESI/MS m/e 454.2 ($M^+$+H, $C_{22}H_{23}ClF_3N_3O_2$).

Examples 937 to 944

The compounds used in the present invention were synthesized by using the respective corresponding starting materials and reactants according to the method of Example 936. Data of ESI/MS, yields (mg) and yields (%) are collectively shown in Table 20.

TABLE 20

| Example | Compd. No. | Molecular Formula | ESI/MS m/e | Yield (mg) | Yield (%) |
|---|---|---|---|---|---|
| 937 | 1464 | $C_{22}H_{23}ClF_3N_3O_3$ | 470.0 | 21.0 | 89 |
| 938 | 1465 | $C_{23}H_{22}ClF_6N_3O_2$ | 522.0 | 24.5 | 94 |
| 939 | 1466 | $C_{21}H_{23}BrClN_3O_2$ | 466.0 | 20.8 | 90 |
| 940 | 1467 | $C_{21}H_{23}Cl_2N_3O_2$ | 420.0 | 19.6 | 93 |
| 941 | 1468 | $C_{21}H_{23}ClN_4O_4$ | 431.2 | 19.5 | 91 |

TABLE 20-continued

| Example | Compd. No. | Molecular Formula | ESI/MS m/e | Yield (mg) | Yield (%) |
|---|---|---|---|---|---|
| 942 | 1469 | $C_{22}H_{22}ClF_4N_3O_2$ | 472.0 | 21.8 | 92 |
| 943 | 1470 | $C_{21}H_{22}Cl_3N_3O_2$ | 456.0 | 22.1 | 97 |
| 944 | 1471 | $C_{21}H_{22}ClF_2N_3O_2$ | 422.0 | 20.9 | 99 |

Example 945

Synthesis of 3-[[N-(2-amino-4,5-difluorobenzoyl) glycyl]aminomethyl]-1-(4-chlorobenzyl)pyrrolidine (Compd. No. 1506)

2-Amino-4,5-difluorobenzoic acid (0.060 mmol), diisopropylcarbodiimide (0.060 mmol) and HOBt (0.060 mmol) were added to a solution of 1-(4-chlorobenzyl)-3-[(glycylamino)methyl]pyrrolidine (0.050 mmol) in chloro form (1.35 mL) and tert-butanol (0.05 mL). The resulting reaction Mixture was stirred at room temperature for 19 hours, then loaded onto a Varian™ SCX column and washed with methanol/chloroform=1:1 (10 mL) and methanol (10 mL). The obtained crude product was eluted with a 2 M methanol solution of $NH_3$ (5 mL) and concentrated to thereby afford 3-[[N-(2-amino-4,5-difluorobenzoyl)glycyl]aminomethyl]-1-(4-chlorobenzyl)pyrrolidine (Compd. No. 1506) (22.0 mg, quantitative). The purity was determined by RPLC/MS (92%). ESI/MS m/e 437 ($M^+$+H, $C_{21}H_{23}ClF_2N_4O_2$).

Examples 946 to 952

The compounds used in the present invention were synthesized by using the respective corresponding starting materials and reactants according to the method of Example 945. Data of ESI/MS, yields (mg) and yields (%) are collectively shown in Table 21.

TABLE 21

| Example | Compd. No. | Molecular Formula | ESI/MS m/e | Yield (mg) | Yield (%) |
|---|---|---|---|---|---|
| 946 | 1506 | $C_{21\,24}BrClN_4O_2$ | 481 | 20.6 | 86 |
| 947 | 1507 | $C_{21}H_{24}FClN_4O_2$ | 419 | 21.7 | Q |
| 948 | 1509 | $C_{27}H_{28}ClN_3O_2$ | 462 | 26.5 | Q |
| 949 | 1510 | $C_{21}H_{24}ClIN_4O_2$ | 527 | 22.0 | 84 |
| 950 | 1511 | $C_{19}H_{21}BrClN_3O_2S$ | 472 | 23.7 | Q |
| 951 | 1512 | $C_{21}H_{24}Cl_2N_4O_2$ | 435 | 22.3 | Q |
| 952 | 1513 | $C_{27}H_{28}ClN_3O_4S$ | 526 | 24.6 | 94 |

Note:
Q means "Quantitative".

Reference Example 11

Synthesis of 1-(4-chlorobenzyl)nipecotic acid

4-Chlorobenzyl chloride (6.42 g, 39.9 mmol) and $^i Pr_2NEt$ (7.74 g, 40.0 mmol) were added to an acetonitrile (15 mL) solution of ethyl nipecotate (6.29 g, 40.0 mmol). The resulting reaction mixture was stirred at 70° C. for 1.5 hours, and the solvent was removed under reduced pressure. A saturated aqueous solution of $NaHCO_3$ (50 mL) was added to the residue, and the resulting mixture was extracted with ethyl acetate (100 mL). The organic layer was washed with a saturated aqueous solution of $NaHCO_3$ and dried over $Na_2SO_4$. The solvent was removed under reduced pressure to thereby provide ethyl 1-(4-chlorobenzyl)nipecotate as a reddish yellow oil. (11.0 g, 97.8%). The resulting oil was used without purification. The purity was determined by RPLC/MS (97%). ESI/MS m/e 382.2 ($M^+$+H, $C_{15}H_{21}ClNO_2$).

An $H_2O$ (25 mL) solution of LiOH (1.66 g) was added to a THF (60 mL) solution of ethyl 1-(4-chlorobenzyl)nipecotate. The resulting reaction mixture was stirred at room temperature for 1.5 hours. The solvent was removed under reduced pressure to provide an amorphous solid. The obtained crude product was purified by column chromatography ($SiO_2$, 50% methanol-dichloromethane) to afford 1-(4-chlorobenzyl) nipecotic acid (9.75 g, 98.2%) as an off-while amorphous solid. The purity was determined by RPLC/MS (>95%). ESI/MS m/e 254.0 ($M^+$+H, $C_{13}H_{17}ClNO_2$).

Reference Example 12

Synthesis of 1-(4-chlorobenzyl-3-[(tert-butoxcyarbonyl)amino]piperidine

Triethylamine (3.38 g) and activated 3 Å molecular sieve (30 g) were added to a $^t$BuOH (500 mL) solution of 1-(4-chlorobenzyl)nipecotic acid (7.06 g, 27.8 mmol). Diphenylphosphoryl azide (8.58 g) was added, and the resulting reaction mixture was stirred under reflux for 18 hour and cooled. The solvent was removed under reduced pressure. The obtained residue was then dissolved in ethyl acetate (500 mL), and the organic layer was washed with a saturated aqueous solution of $NaHCO_3$ (100 mL×2) and brine (50 mL), then dried (over $Na_2SO_4$) and concentrated under reduced pressure. The obtained crude product was purified by chromatography ($SiO_2$, 25% ethyl acetate-hexane) to provide 1-(4-chlorobenzyl-3-[(tert-butoxycarbonyl)amino]piperidine (2.95 g, 32.6%) as a white crystalline solid. $^1H$ NMR ($CDCl_3$, 300 MHz) δ 1.4-1.75 (br, 4H), 2.2-2.7 (br, 4H), 3.5 (br, 2H), 3.8 (br, 4H), 7.3 (br, 4H). The purity was determined by RPLC/MS (>99%). ESI/MS m/e 269.2 ($M^+$+H-56, $C_{17}H_{26}ClN_2O_2$).

Reference Example 13

Synthesis of 3-amino-1-(4-chlorobenzyl)piperidine

To a methanol (25 mL) solution of 1-(4-chlorobenzyl)-3-[(tert-butoxycarbonyl)amino]piperidine (2.55 g, 7.85 mmol), was added 1M HCl-$Et_2O$ (50 mL). The resulting reaction mixture was stirred at 25° C. for 15 hours, and the solvent was removed under reduced pressure to afford 3-amino 1-(4-chlorobenzyl)piperidine dihydrochloride as an amorphous solid (2.49 g, quantitative). The purity was determined by RPLC/MS (>95%). ESI/MS m/e 225.2 ($M^+$+H, $C_{12}H_{18}ClN_2$).

Example 953

Synthesis of 1-(4-chlorobenzyl)-3-[[N-(3-methylbenzoyl)glycyl]amino]piperidine (Compd. No. 355)

N-(3-Methylbenzoyl)glycine (10.6 mg, 0.055 mmol), EDCI (10.5 mg) and 1-hydroxybenzotriazole hydrate (7.4 g) were added to a chloroform (2.5 mL) solution of 1-(4-chlorobenzyl)-3-aminopiperidine dihydrochloride (1.49 mg, 0.050 mmol) and triethylamine (15.2 mg). The resulting reaction mixture was stirred at 25° C. for 16 hours and washed with a 2 N aqueous solution of NaOH (2 mL×2) and brine (1 mL). After filtration through a PTFE membrane, the solvent was removed under reduced pressure to provide 1-(4-chlorobenzyl)-3-[[N-(3-methylbenzoyl)glycyl]amino]piperidine (Compd. No. 355) (17.4 mg, 87%). The purity was determined by RPLC/MS (97%). ESI/MS m/e 400.0 ($M^+$+H, $C_{22}H_{26}ClN_3O_2$).

Examples 954 to 982

The compounds used in the present invention were synthesized by using the respective corresponding starting materials and reactants according to the method of Example 953. Data of ESI/MS, yields (mg) and yields (%) are collectively shown in Table 22. The Compd. No. 358 exhibited the following $^1$H NMR.

TABLE 22

| Example | Compd. No. | Molecular Formula | ESI/MS m/e | Yield (mg) | Yield (%) |
|---|---|---|---|---|---|
| 954 | 354 | $C_{21}H_{24}ClN_3O_2$ | 386 | 16.1 | 83 |
| 955 | 356 | $C_{20}H_{23}ClN_4O_2$ | 387 | 19.4 | 100 |
| 956 | 357 | $C_{22}H_{26}ClN_3O_2$ | 400 | 16.8 | 84 |
| 957 | 359 | $C_{22}H_{26}ClN_3O_2$ | 400 | 8.9 | 17 |
| 958 | 360 | $C_{22}H_{25}ClN_4O_4$ | 445 | 25.6 | Q |
| 959 | 361 | $C_{23}H_{27}ClN_2O_2$ | 399 | 15.5 | 29 |
| 960 | 362 | $C_{24}H_{29}ClN_2O_3$ | 429 | 12.4 | 58 |
| 961 | 363 | $C_{21}H_{25}ClN_2O_2S$ | 405 | 22.2 | Q |
| 962 | 364 | $C_{24}H_{29}ClN_2O_4$ | 445 | 20.7 | 93 |
| 963 | 365 | $C_{24}H_{29}ClN_2O_2$ | 413 | 15.6 | 75 |
| 964 | 366 | $C_{23}H_{26}ClFN_2O_3$ | 433 | 21.6 | 100 |
| 965 | 367 | $C_{23}H_{27}ClN_2O_2$ | 399 | 11.9 | 60 |
| 966 | 368 | $C_{22}H_{25}ClN_2O_2$ | 385 | 16.0 | 83 |
| 967 | 369 | $C_{22}H_{24}Cl_2N_2O_2$ | 419 | 13.9 | 60 |
| 968 | 370 | $C_{26}H_{33}ClN_2O_3$ | 457 | 15.9 | 54 |
| 969 | 371 | $C_{25}H_{31}ClN_2O_3$ | 443 | 19.6 | 84 |
| 970 | 372 | $C_{21}H_{25}ClN_2O_3S$ | 421 | 23.0 | Q |
| 971 | 373 | $C_{23}H_{28}ClN_3O_2$ | 414 | 19.1 | 92 |
| 972 | 374 | $C_{24}H_{30}ClN_3O_3$ | 444 | 18.6 | 84 |
| 973 | 375 | $C_{23}H_{27}Cl_2N_3O_2$ | 448 | 18.0 | 80 |
| 974 | 376 | $C_{24}H_{30}ClN_3O_3$ | 444 | 19.6 | 88 |
| 975 | 377 | $C_{25}H_{31}Cl_2N_3O_2$ | 476 | 20.7 | 87 |
| 976 | 378 | $C_{27}H_{33}ClFN_3O_2$ | 486 | 23.9 | 98 |
| 977 | 379 | $C_{25}H_{30}ClN_3O_3$ | 456 | 33.3 | Q |
| 978 | 380 | $C_{24}H_{30}ClN_3O_2$ | 428 | 9.8 | 46 |
| 979 | 381 | $C_{21}H_{26}ClN_3O_3S$ | 436 | 10.3 | 47 |
| 980 | 382 | $C_{22}H_{26}ClN_3O_3$ | 416 | 24.4 | Q |
| 981 | 383 | $C_{22}H_{25}Cl_2N_3O_3$ | 450 | 27.5 | Q |

Note:
Q means "Quantitative".

Example 982

Compd. No. 358: 88%; $^1$H NMR ($CDCl_3$) δ 1.53-1.75 (m, 4 H), 2.12-2.20 (m, 1H), 2.37-2.50 (m, 2H), 2.53-2.61 (m, 1H), 3.38-3.50 (m, 2H), 2.53-2.61 (m, 1H), 3.38-3.50 (m, 2H), 4.06-4.20 (m, 3H), 7.10-7.13 (m, 1H), 7.18-7.30 (m, 4H), 7.59 (t, J=7.8 Hz, 1H), 7.79 (d, J=7.8 Hz, 1H), 8.01 (d, J=7.8 Hz, 1H), 8.11 (s, 1H).

Reference Example 14

Synthesis of 1-benzyl-4-[[N-(tert-butoxycarbonyl) glycyl]amino]piperidine

N-(tert-Butoxycarbonyl)glycine (3.48 g, 20 mmol), EDCI (4.02 g, 21 mmol) and HOBt (2.83 g, 21 mmol) were added to a dichloromethane (40 mL) solution of 4- amino-1-benzylpiperidine (3.80 g, 20 mmol). The resulting reaction mixture was stirred at room temperature for 12 hours, and a 2 M solution of NaOH was then added. The organic layer was separated, and the aqueous layer was extracted with dichloromethane (20 mL×2). The organic layers were combined, washed with water (20 mL) and brine (20 mL), dried over anhydrous sodium sulfate, filtered and concentrated. The obtained crude product was purified by column chromatography ($SiO_2$, ethyl acetate/methanol/triethylamine=85:12:3) to afford 1-benzyl-4-[[N-(tert-butoxycarbonyl)glycyl] amino]piperidine (6.59 g, 95%).

Reference Example 15

Synthesis of 1-benzyl-4-(glycylamino)piperidine

A 4 M dioxane solution of HCl was added to a methanol (80 mL) solution of 1-benzyl-4-[N-(tert-butoxycarbonyl)glycyl]aminopiperidine (6.59 g). The resulting solution was stirred at room temperature for 2 hours and concentrated. A 2 M aqueous solution of NaOH (20 mL) was then added to the solution. The resulting mixture was extracted with dichloromethane (40 mL). The extracts were combined, dried over anhydrous sodium sulfate and concentrated. The obtained crude product was purified by column chromatography ($SiO_2$, ethyl acetate/methanol/triethylamine=85:12:3) to thereby provide 1-benzyl-4-(glycylamino)piperidine (3.91 g, 83%). $^1$H NMR ($CDCl_3$, 400 MHz) δ 1.47-1.59 (m, 2H), 1.59 (br, 2H), 1.76-1.96 (m, 2H), 2.10-2.19 (m, 2H), 2.75-2.87 (m, 2H), 3.29 (s, 2H), 3.50 (s, 2H), 3.65-3.89 (m, 1H), 7.15-7.23 (m, 1H), 7.23-7.33 (m, 5H).

Other 4-acylamino-1-benzylpiperidines were synthesized by using the respective corresponding starting materials and reactants according to the methods of Reference Examples 14 and 15.

4-(β-alanylamino)-1-benzylpiperidine: 2.46 g, 51% (two steps)

1-benzyl-4-((S)-leucylamino)piperidine: 1.78 g, 74% (two steps) and 1-benzy-4-((R)-leucylamine)piperidine: 1.48 g, 61% (two steps).

Example 983

Synthesis of 4-(N-benzoylglycyl)amino-1-benzylpiperidine (Compd. No. 386)

A chloroform (0.4 mL) solution of benzoyl chloride (0.060 mmol) was added to a chloroform (1.0 mL) solution of 1-benzyl-4-(glycylamino)piperidine (0.050 mmol) and triethylamine (0.070 mmol). The resulting reaction mixture was shaken at room temperature for 12 hours, and an (aminomethyl)polystyrene resin (1.04 mmol/g, 50 mg, 50 mmol) was added to the mixture. The obtained mixture was shaken at room temperature for 12 hours. The resulting reaction mixture was filtered, and the resin was washed with dichloromethane (0.5 mL). The filtrate and washings were combined, and dichloromethane (4 mL) was added. The solution was washed with a 2 M aqueous solution of NaOH (0.5 mL) to provide 4-(N-benzoylglycyl)amino-1-benzylpiperidine (Compd. No. 386) (11.3 mg, 64%). The purity was determined by RPLC/MS (94%). ESI/MS m/e 352.0 ($M^+$+H, $C_{21}H_{25}N_3O_2$).

Examples 984 to 1034

The compounds used in the present invention were synthesized by using the respective corresponding starting materials and reactants according to the method of Example 983. Data of ESI/MS, yields (mg) and yields (%) are collectively shown in Table 23.

TABLE 23

| Example | Compd. No. | Molecular Formula | ESI/MS m/e | Yield (mg) | Yield (%) |
|---|---|---|---|---|---|
| 984 | 384 | $C_{22}H_{26}ClN_3O_2$ | 400 | 60.0 | Q |
| 985 | 385 | $C_{21}H_{23}ClN_4O_4$ | 431 | 58.7 | 91 |
| 986 | 387 | $C_{25}H_{27}N_3O_2$ | 402.5 | 15.5 | 77 |
| 987 | 388 | $C_{21}H_{24}N_4O_4$ | 397.0 | 16.2 | 82 |
| 988 | 389 | $C_{23}H_{27}N_3O_4$ | 410.0 | 16.2 | 79 |
| 989 | 390 | $C_{22}H_{24}F_3N_3O_2$ | 420.0 | 17.4 | 83 |
| 990 | 391 | $C_{22}H_{23}F_4N_3O_2$ | 438.0 | 18.4 | 84 |
| 991 | 392 | $C_{22}H_{24}F_3N_3O_3$ | 436.0 | 17.1 | 79 |
| 992 | 393 | $C_{21}H_{24}BrN_3O_2$ | 430.0 | 18.0 | 84 |
| 993 | 394 | $C_{21}H_{24}ClN_3O_2$ | 386.0 | 16.4 | 85 |
| 994 | 395 | $C_{21}H_{24}BrN_3O_2$ | 430.0 | 17.2 | 80 |
| 995 | 396 | $C_{21}H_{23}F_2N_3O_2$ | 388.0 | 15.1 | 78 |
| 996 | 397 | $C_{21}H_{23}Cl_2N_3O_2$ | 420.0 | 11.7 | 56 |
| 997 | 398 | $C_{22}H_{27}N_3O_2$ | 366.0 | 13.1 | 72 |
| 998 | 399 | $C_{26}H_{29}N_3O_2$ | 416.0 | 15.8 | 76 |
| 999 | 400 | $C_{22}H_{26}N_4O_4$ | 411.0 | 17.4 | 85 |
| 1000 | 401 | $C_{24}H_{29}N_3O_4$ | 424.0 | 16.9 | 80 |
| 1001 | 402 | $C_{23}H_{26}F_3N_3O_2$ | 434.0 | 17.7 | 82 |
| 1002 | 403 | $C_{23}H_{25}F_4N_3O_2$ | 452.0 | 18.6 | 82 |
| 1003 | 404 | $C_{23}H_{26}F_3N_3O_3$ | 450.0 | 17.8 | 79 |
| 1004 | 405 | $C_{22}H_{26}BrN_3O_2$ | 444.0 | 17.9 | 81 |
| 1005 | 406 | $C_{22}H_{26}ClN_3O_2$ | 400.0 | 15.5 | 78 |
| 1006 | 407 | $C_{22}H_{26}BrN_3O_2$ | 444.0 | 17.8 | 80 |
| 1007 | 408 | $C_{22}H_{25}F_2N_3O_2$ | 402.0 | 15.6 | 78 |
| 1008 | 409 | $C_{22}H_{25}Cl_2N_3O_2$ | 434.0 | 17.6 | 81 |
| 1009 | 410 | $C_{25}H_{33}N_3O_2$ | 408.0 | 16.2 | 79 |
| 1010 | 411 | $C_{29}H_{35}N_3O_2$ | 458.5 | 18.8 | 82 |
| 1011 | 412 | $C_{25}H_{32}N_4O_4$ | 453.0 | 19.4 | 86 |
| 1012 | 413 | $C_{27}H_{35}N_3O_4$ | 466.0 | 19.8 | 85 |
| 1013 | 414 | $C_{26}H_{32}F_3N_3O_2$ | 476.0 | 20.2 | 85 |
| 1014 | 415 | $C_{26}H_{31}F_4N_3O_2$ | 494.0 | 20.5 | 83 |
| 1015 | 416 | $C_{26}H_{32}F_3N_3O_3$ | 492.0 | 19.5 | 79 |
| 1016 | 417 | $C_{25}H_{32}BrN_3O_2$ | 486.0 | 19.1 | 79 |
| 1017 | 418 | $C_{25}H_{32}ClN_3O_2$ | 442.0 | 17.7 | 80 |
| 1018 | 419 | $C_{25}H_{32}BrN_3O_2$ | 486.0 | 20.3 | 83 |
| 1019 | 420 | $C_{25}H_{31}F_2N_3O_2$ | 444.0 | 18.6 | 84 |
| 1020 | 421 | $C_{25}H_{31}Cl_2N_3O_2$ | 476.0 | 19.4 | 81 |
| 1021 | 422 | $C_{25}H_{33}N_3O_2$ | 408.0 | 14.4 | 71 |
| 1022 | 423 | $C_{29}H_{35}N_3O_2$ | 458.0 | 16.4 | 72 |
| 1023 | 424 | $C_{25}H_{32}N_4O_4$ | 453.0 | 18.1 | 80 |
| 1024 | 425 | $C_{27}H_{35}N_3O_4$ | 466.0 | 16.4 | 70 |
| 1025 | 426 | $C_{26}H_{32}F_3N_3O_2$ | 476.0 | 17.3 | 73 |
| 1026 | 427 | $C_{26}H_{31}F_4N_3O_2$ | 494.0 | 18.8 | 76 |
| 1027 | 428 | $C_{26}H_{32}F_3N_3O_3$ | 492.0 | 18.4 | 75 |
| 1028 | 429 | $C_{25}H_{32}BrN_3O_2$ | 486.0 | 17.9 | 74 |
| 1029 | 430 | $C_{25}H_{32}ClN_3O_2$ | 442.0 | 15.7 | 71 |
| 1030 | 431 | $C_{25}H_{32}BrN_3O_2$ | 486.0 | 17.7 | 73 |
| 1031 | 432 | $C_{25}H_{31}F_2N_3O_2$ | 444.0 | 16.6 | 75 |
| 1032 | 433 | $C_{25}H_{31}Cl_2N_3O_2$ | 476.0 | 18.7 | 78 |
| 1033 | 1016 | $C_{22}H_{23}ClF_3N_3O_2$ | 454 | 32.5* | 53 |
| 1034 | 1017 | $C_{21}H_{24}ClN_3O_2$ | 386 | 55.2* | Q |

Notes: *indicates "yield (mg) of trifluoroacetate".
Q means "Quantitative".

Reference Example 16

Synthesis of 3-carbamoyl-1-(4-chlorobenzyl)piperidine

Triethylamine (7.0 mL, 50 mmol) and 4-chlorobenzyl chloride (8.05 g, 50 mmol) were added to a solution of nipecotamide (6.40 g, 50 mmol) in acetonitrile (150 mL) and ethanol (20 mL). The resulting reaction mixture was stirred at 50° C. for 16 hours and cooled to room temperature. A saturated aqueous solution of $NaHCO_3$ (50 mL) and water (150 mL) were then added, and the resulting mixture was extracted with ethyl acetate (150 mL×3). The extracts were washed with brine, dried over $Na_2SO_4$ and concentrated to afford a light-red solid. The obtained crude solid was washed with ether (100 mL) to provide 3-carbamoyl-1-(4-chlorobenzyl) piperidine (6.98 g, 54%).

Reference Example 17

Synthesis of 3-(aminomethyl)-1-(4-chlorobenzyl)piperidine

3-Carbamoyl-1-(4-chlorobenzyl)piperidine (3.80 g, 15 mmol) was dissolved in THF (30 mL), and 1 M $BH_3$-THF (9.4 mL) was added to the obtained solution. The resulting mixture was stirred at 70° C. for 15 hours. After cooling to 0° C., a 2 M hydrochloric acid (50 mL) was added, and the mixture was stirred at room temperature for another 3 hours, basicified with an 4 M aqueous solution of NaOH and extracted with ethyl acetate (100 mL×3). The extracts were combined, washed with brine, dried over anhydrous $Na_2SO_4$, filtered and concentrated. The obtained crude product was purified by column chromatography ($SiO_2$, ethyl acetate/ethanol/triethylamine=80:15:5) to thereby provide 3-(aminomethyl)-1-(4-chlorobenzyl)piperidine (2.05 g, 55%). $^1H$ NMR ($CDCl_3$, 400 MHz) δ 1.00-1.09 (m, 1H), 1.50-1.87 (m, 7H), 1.97-2.06 (m, 1H), 2.65-2.77 (m, 2H), 3.16-3.26 (m, 2H), 3.32 (s, 2H), 3.40 (d, J=13.3 Hz, 1H), 3.49 (d, J=13.3 Hz, 1H), 7.22-7.33 (m, 5H).

Example 1035

Synthesis of 3-[(N-benzoylglycyl)amino]methyl-1-(4-chlorobenzyl)piperidine (Compd. No. 434)

A chloroform (0.4 mL) solution of benzoyl chloride (0.060 mmol) was added to a chloroform (1.0 mL) solution of 3-[(glycylamino)methyl]-1-(4-chlorobenzyl)piperidine (0.050 mmol) and triethylamine (0.070 mmol). The resulting reaction mixture was shaken at room temperature for 2.5 hours, and an (aminomethyl)polystyrene resin (1.04 mmol/g, 50 mg, 50 mmol) was then added to the obtained mixture. The resulting mixture was shaken at room temperature for 12 hours and filtered, and the resin was washed with dichloromethane (0.5 mL). The filtrate and washings were combined, and dichloromethane (4 mL) was added. The obtained mixture was washed with an 2 M aqueous solution of NaOH (0.5 mL) and concentrated to thereby afford 3-[(N-benzoylglycyl)amino]methyl-1-(4-chlorobenzyl)piperidine (Compd. No. 434) -(14.7 mg, 74%). The purity was determined by RPLC/MS (91%). ESI/MS m/e 400 ($M^+$+H, $C_{22}H_{26}ClN_3O_2$).

Examples 1036 to 1058

The compounds used in the present invention were synthesized by using the respective corresponding starting materials and reactants according to the method of Example 1035. Data of ESI/MS, yields (mg) and yields (%) are collectively shown in Table 24.

TABLE 24

| Example | Compd. No. | Molecular Formula | ESI/MS m/e | Yield (mg) | Yield (%) |
|---|---|---|---|---|---|
| 1036 | 435 | $C_{26}H_{28}ClN_3O_2$ | 450 | 16.0 | 71 |
| 1037 | 436 | $C_{22}H_{25}ClN_4O_4$ | 445 | 18.9 | 85 |
| 1038 | 437 | $C_{24}H_{28}ClN_3O_4$ | 458 | 18.2 | 79 |
| 1039 | 438 | $C_{23}H_{25}ClF_3N_3O_2$ | 468 | 19.0 | 81 |
| 1040 | 439 | $C_{23}H_{24}ClF_4N_3O_2$ | 486 | 20.2 | 83 |
| 1041 | 440 | $C_{23}H_{25}ClF_3N_3O_3$ | 484 | 18.9 | 78 |
| 1042 | 441 | $C_{22}H_{25}BrClN_3O_2$ | 478 | 19.2 | 80 |
| 1043 | 442 | $C_{22}H_{25}Cl_2N_3O_2$ | 434 | 17.3 | 80 |
| 1044 | 443 | $C_{22}H_{25}BrClN_3O_2$ | 478 | 18.8 | 79 |
| 1045 | 444 | $C_{22}H_{24}ClF_2N_3O_2$ | 436 | 16.7 | 77 |
| 1046 | 445 | $C_{22}H_{24}Cl_3N_3O_2$ | 468 | 17.9 | 76 |

TABLE 24-continued

| Example | Compd. No. | Molecular Formula | ESI/MS m/e | Yield (mg) | Yield (%) |
|---|---|---|---|---|---|
| 1047 | 446 | $C_{23}H_{28}ClN_3O_2$ | 414 | 14.6 | 71 |
| 1048 | 447 | $C_{27}H_{30}ClN_3O_2$ | 464 | 17.0 | 73 |
| 1049 | 448 | $C_{23}H_{27}ClN_4O_4$ | 459 | 19.5 | 85 |
| 1050 | 449 | $C_{25}H_{30}ClN_3O_4$ | 472 | 17.1 | 72 |
| 1051 | 450 | $C_{24}H_{27}ClF_3N_3O_2$ | 482 | 19.4 | 81 |
| 1052 | 451 | $C_{24}H_{26}ClF_4N_3O_2$ | 500 | 18.2 | 73 |
| 1053 | 452 | $C_{24}H_{27}ClF_3N_3O_3$ | 498 | 18.8 | 76 |
| 1054 | 453 | $C_{23}H_{27}BrClN_3O_2$ | 492 | 19.4 | 79 |
| 1055 | 454 | $C_{23}H_{27}Cl_2N_3O_2$ | 448 | 16.5 | 74 |
| 1056 | 455 | $C_{23}H_{27}BrClN_3O_2$ | 492 | 19.3 | 78 |
| 1057 | 456 | $C_{23}H_{26}ClF_2N_3O_2$ | 450 | 17.1 | 76 |
| 1058 | 457 | $C_{23}H_{26}Cl_3N_3O_2$ | 482 | 16.9 | 70 |

Reference Example 18

Synthesis of 4-(aminomethyl)-1-(4-chlorobenzyl)piperidine $K_2CO_3$ (3.02 g) and 4-chlorobenzyl chloride (3.52 g, 21.8 mmol) were successively added to an acetonitrile (100 mL) solution of 4-(aminomethyl)piperidine (7.00 g, 61.3 mmol). The resulting reaction mixture was stirred at 60° C. for 16 hours, cooled to 25° C. and concentrated. The obtained residue was fractionated between dichloromethane (75 mL) and water (50 mL) and then washed with water (50 mL×2) and brine (50 mL×1). The organic layer was dried (over $MgSO_4$), concentrated and then purified by chromatography ($SiO_2$, 4% $H_2O$-$^i$PrOH) to provide 4-(aminomethyl)-1-(4-chlorobenzyl) piperidine (3.58 g, 69%).

Example 1059

Synthesis of 4-[(N-benzoylglycyl)amino]methyl-1-(4-chlorobenzyl)piperidine (Compd. No. 458)

Hippuric acid (38 mg, 0.21 mmol), EDCI (48 mg, 0.24 mmol), HOBt (31 mg, 0.23 mmol) and triethylamine (38 μL, 0.27 mmol) were added to a dichloromethane (1 mL) solution of 4-(aminomethyl)-1-(4-chlorobenzyl)piperidine (50 mg, 0.21 mmol). The resulting reaction mixture was shaken at 25° C. for 16 hours, then diluted with 1 mL of dichloromethane, washed with a 2 M aqueous solution of NaOH (0.75 mL×2), dried (over $MgSO_4$), concentrated and purified by chromatography ($SiO_2$, 6-8% methanol/dichloromethane) to thereby afford 4-[(N-benzoylglycyl)amino]methyl-1-(4-chlorobenzyl)piperidine (Compd. No. 458). The resulting compound was treated with TFA to provide a TFA salt (105 mg, 97%). The purity was determined by RPLC/MS (85%). ESI/MS m/e 400 ($M^+$+H, $C_{22}H_{26}ClN_3O_2$).

Examples 1060 to 1086

The compounds used in the present invention were synthesized by using the respective corresponding starting materials and reactants according to the method of Example 1059. Data of ESI/MS, yields (mg) and yields (%) are collectively shown in Table 25.

TABLE 25

| Example | Compd. No. | Molecular Formula | ESI/MS m/e | Yield (mg) | Yield (%) |
|---|---|---|---|---|---|
| 1060 | 459 | $C_{23}H_{28}ClN_3O_2$ | 414 | 86* | 78 |
| 1061 | 460 | $C_{23}H_{28}ClN_3O_2$ | 414 | 55 | Q |
| 1062 | 461 | $C_{23}H_{25}ClF_3N_3O_2$ | 468 | 65 | Q |
| 1063 | 462 | $C_{23}H_{28}ClN_3O_2$ | 414 | 61 | Q |
| 1064 | 463 | $C_{23}H_{28}ClN_3O_2$ | 414 | 54 | Q |
| 1065 | 464 | $C_{25}H_{32}ClN_3O_5$ | 490 | 56 | Q |
| 1066 | 465 | $C_{21}H_{25}ClN_4O_2$ | 401 | 38 | 96 |
| 1067 | 466 | $C_{22}H_{25}ClN_4O_4$ | 445 | 15 | 34 |
| 1068 | 557 | $C_{23}H_{28}ClN_3O_2$ | 414 | 58* | 66 |
| 1069 | 558 | $C_{23}H_{28}ClN_3O_2$ | 414 | 55 | Q |
| 1070 | 618 | $C_{25}H_{32}ClN_3O_2$ | 442 | 58 | Q |
| 1071 | 686 | $C_{26}H_{34}ClN_3O_2$ | 456 | 62 | Q |
| 1072 | 749 | $C_{34}H_{37}ClN_4O_2$ | 569 | 7.2* | 18 |
| 1073 | 750 | $C_{24}H_{30}ClN_3O_3$ | 444 | 4.7* | 14 |
| 1074 | 840 | $C_{24}H_{29}ClN_2O_2$ | 413 | 52* | 58 |
| 1075 | 841 | $C_{23}H_{27}ClN_2O_2$ | 399 | 52 | Q |
| 1076 | 842 | $C_{23}H_{26}Cl_2N_2O_2$ | 433 | 55 | Q |
| 1077 | 843 | $C_{25}H_{31}ClN_2O_2$ | 427 | 58 | Q |
| 1078 | 844 | $C_{24}H_{29}ClN_2O_2$ | 413 | 56 | Q |
| 1079 | 845 | $C_{24}H_{29}ClN_2O_4S$ | 477 | 62 | Q |
| 1080 | 846 | $C_{29}H_{31}ClN_2O_3$ | 491 | 43 | 88 |
| 1081 | 847 | $C_{24}H_{28}ClFN_2O_3$ | 447 | 54 | Q |
| 1082 | 848 | $C_{25}H_{31}ClN_2O_2$ | 427 | 47 | Q |
| 1083 | 849 | $C_{25}H_{31}ClN_2O_4$ | 459 | 55 | Q |
| 1084 | 850 | $C_{22}H_{27}ClN_2O_3S$ | 435 | 46 | Q |
| 1085 | 873 | $C_{20}H_{28}ClN_3O_2$ | 378 | 44.8 | Q |
| 1086 | 874 | $C_{23}H_{27}Cl_2N_3O_3$ | 464 | 51 | Q |

Notes:
*indicates "yield (mg) of trifluoroacetate".
Q means "Quantitative".

Reference Example 19

Synthesis of 1-(4-chlorobenzyl)-4-[N-(3,3-diphenylpropyl)aminomethyl]piperidine 4-(Aminomethyl)-1-(4-chlorobenzyl)piperidine (120 mg) was reacted with 3,3-diphenylpropyl methanesulfonate (1.0 equivalent) in the presence of NaI (2.6 equivalents) in acetonitrile at 70° C. for 16 hours. After treatment by a conventional method, the obtained crude product was purified by column chromatography ($SiO_2$) to afford 1-(4-chlorobenzyl)-4-[N-(3,3-diphenylpropyl)aminomethyl]piperidine (118 mg, 54%). The purity was determined by RPLC/MS (98%).

Reference Example 20

Synthesis of 1-(4-chlorobenzyl)-4-[N-(2,2-diphenylethyl)aminomethyl]piperidine 4-(Aminomethyl)-1-(4-chlorobenzyl)piperidine (120 mg) was subjected to reducing amination in methanol by using 2,2-diphenylacetaldehyde (0.66 equivalent) and a polymer-supported boron hydride at 25° C. for 16 hours and then subjected to treatment according to a conventional method and column chromatography ($SiO_2$) to thereby provide 1-(4-chlorobenzyl)-4-[N-(2,2-diphenylethyl)aminomethyl]piperidine (70 mg, 49%). The purity was determined by RPLC/MS (98%).

Example 1087

Synthesis of 4-[N-(N-benzoylglycyl)-N-(2,2-diphenylethyl)aminomethyl]-1-(4-chlorobenzyl)piperidine (Compd. No. 524)

Hippuric acid (1.1 equivalents), HBTU (1.1 equivalents) and HOBt (1.1 equivalents) were added to a dichloromethane solution of 1-(4-chlorobenzyl)-4-[N-(2,2-diphenylethyl) aminomethyl]piperidine (0.084 mmol). The resulting reaction mixture was stirred at 40° C. for 24 hours. The obtained crude product was subjected to treatment according to a conventional method and preparative TLC ($SiO_2$) to thereby provide 4-[N-(N-benzoylglycyl)-N-(2,2-diphenylethyl)aminomethyl]-1-(4-chlorobenzyl)piperidine (Compd. No. 524) (8.5 mg, 17%). The purity was determined by RPLC/MS (98%). ESI/MS m/e 580 ($M^+$+H, $C_{36}H_{38}ClN_3O_2$).

Examples 1088 to 1090

The compounds used in the present invention were synthesized by using the respective corresponding starting materials and reactants according to the method of Example 1087. Data of ESI/MS, yields (mg) and yields (%) are collectively shown in Table 26.

TABLE 26

| Example | Compd. No. | Molecular Formula | ESI/MS m/e | Yield (mg) | Yield (%) |
|---|---|---|---|---|---|
| 1088 | 521 | $C_{38}H_{39}ClF_3N_3O_2$ | 662 | 5.5 | 10 |
| 1089 | 522 | $C_{37}H_{37}ClF_3N_3O_2$ | 648 | 8.6 | 16 |
| 1090 | 523 | $C_{37}H_{40}ClN_3O_2$ | 594 | 4.8 | 10 |

Reference Example 21

Synthesis of 1-(4-chlorobenzyl)-4-[(valylamino) methyl]piperidine

Triethylamine (0.76 mL, 5.44 mmol), dl-N-(tert-butoxycarbonyl)valine (1.09 g, 5.03 mmol), EDCI (883 mg, 4.61 mmol) and HOBt (623 mg, 4.61 mmol) were added to a dichloromethane (21 mL) solution of 4-(aminomethyl)-1-(4-chlorobenzyl)piperidine (1.0 g, 4.2 mmol). The resulting reaction mixture was stirred at 25° C. for 16 hours, then diluted with dichloromethane (20 mL), washed with a 2 M aqueous solution of NaOH (20 mL×2) and brine (20 mL×1), dried (over $MgSO_4$) and concentrated. The obtained crude product was purified by chromatography ($SiO_2$, 3% methanol/dichloromethane) to thereby afford 1-(4-chlorobenzyl)-4-[[(N-Boc-valyl)amino]methyl]piperidine (1.1 g, 60%) as a light amber oil. ESI/MS m/e 438 ($M^+$+H).

1-(4-Chlorobenzyl)-4-[[(N-Boc-valyl)amino]methyl]piperidine (1.1 g, 2.51 mmol) was dissolved in a 3 M HCl-methanol solution (25 mL) and stirred at 25° C. for 1 hour. The resulting reaction mixture was concentrated, and the obtained salt was dissolved in $^t$BuOH/$H_2O$=3:1 (25 mL). An anion ($OH^-$) exchange resin was added until the solution became slightly basic. The obtained mixture was filtered and concentrated to provide 1-(4-chlorobenzyl)-4-[(valylamino) methyl]piperidine (819 mg, 97%). Further purification was not required for the resulting compound. ESI/MS m/e 338.1 ($M^+$+H, $C_{18}H_{28}ClN_3O$).

Other 4-[(acylamino)methyl]-1-(4-chlorobenzyl)piperidines were synthesized by using the respective corresponding starting materials and reactants according to the method of Reference Example 21.

1-(4-chlorobenzyl)-4-[(glycylamino)methyl]piperidine: 0.830 g, 67% (two steps), ESI/MS 269 ($M^+$+H).

1-(4-chlorobenzyl)-4-[(serylamino)methyl]piperidine: 0.286 g, 20% (two steps), ESI/MS 326 ($M^+$+H).

4-[(alanylamino)methyl]-1-(4-chlorobenzyl)piperidine: 1.20 g, 65% (two steps), ESI/MS 310 ($M^+$+H).

1-(4-chlorobenzyl)-4-[(prolylamino)methyl]piperidine: 1.48 g, 86% (two steps), ESI/MS 336 ($M^+$+H).

1-(4-chlorobenzyl)-4-[(glutaminylamino)methyl]piperidine: 0.830 g, 27% (two steps), ESI/MS 367 ($M^+$+H).

1-(4-chlorobenzyl)-4-[((2-methylalanyl)amino)methyl] piperidine: 2.24 g, 62% (two steps), ESI/MS 324 ($M^+$+H).

1-(4-chlorobenzyl)-4-[((O-methylseryl)amino)methyl]piperidine: 0.686 g, 38% (two steps), ESI/MS 340 ($M^+$+H).

1-4-chlorobenzyl)-4-[((1-aminocyclopropylcarbonyl) amino)methyl]piperidine: 2.03 g, 82% (two steps), ESI/MS 322 ($M^+$+H).

1-(4-chlorobenzyl)-4-[(leucylamino)methyl]piperidine: 1.30 g, 58% (two steps), ESI/MS 352 ($M^+$+H).

1-(4-chlorobenzyl)-4: [((O-benzylseryl)amino)methyl]piperidine: 1.34 g, 56% (two steps), ESI/MS 416 ($M^+$+H).

Reference Example 22

Synthesis of 1-(tert-butoxycarbonyl)-4-[[N-(9-fluorenylmethyloxycarbonyl)glycyl]aminomethyl]piperidine Triethylamine (3.51 g), N-(9-fluorenylmethyloxycarbonyl)glycine (7.93 g, 26.7 mmol), EDCI (3.80 g) and HOBt (4.33 g) were added to a dichloromethane (150 mL) solution of 4-(aminomethyl)-1-(tert-butoxycarbonyl)piperidine (5.72 g). The resulting reaction mixture was stirred at room temperature for 18 hours, then washed with water (100 mL×3) and brine (100 mL×2), dried over anhydrous sodium sulfate, concentrated and recrystallized from acetonitrile/methanol (150 mL/1 mL) at 0° C. to provide 1-(tert-butoxycarbonyl)-4-[[N-(9-fluorenylmethyloxycarbonyl)glycyl]aminomethyl] piperidine (5.75 g, 44%) as an off-white crystal.

Reference Example 23

Synthesis of 4-[[N-(9-fluorenylmethyloxycarbonyl) glycyl]aminomethyl]piperidine 1-(tert-Butoxycarbonyl)-4-[[N-(9-fluorenylmethyloxycarbonyl)glycyl]aminomethyl]piperidine (3.17 g, 6.42 mmol) was added to a 4 M dioxane solution of HCl. The resulting solution was stirred at room temperature for 5 hours and concentrated to afford 4-[[N-(9-fluorenylmethyloxycarbonyl)glycyl]aminomethyl]piperidine (3.85 g) as an off-white solid. The obtained product was used without further purification.

Reference Example 24

Synthesis of 4-[[N-(9-fluorenylmethyloxycarbonyl) glycyl]aminomethyl]-1-(4-methylthiobenzyl)piperidine 4-Methylthiobenzaldehyde (1.24 g) and $NaBH(OAc)_3$ (2.56 g) were added to a 1% acetic acid/DMF (15 mL) solution of 4-[[N-(9-fluorenylmethyloxycarbony)glycyl]aminomethyl]piperidine (1.00 g, 2.33 mmol). The resulting reaction mixture was stirred at 60° C. for 1 hour, cooled to room temperature and concentrated. A saturated aqueous solution (50 mL) of $NaHCO_3$ was added to the resultant residue, and the obtained mixture was extracted with ethyl acetate (50 mL×2). The extracts were combined, dried over anhydrous sodium sulfate, filtered and concentrated. The resulting crude product was purified by column chromatography ($SiO_2$, 50%-10% methanol-dichloromethane) to thereby afford 4-[[N-(9-fluorenylmethyloxycarbonyl)glycyl]aminomethyl]-1-(4-methylthiobenzyl)piperidine (602 mg) as a colorless oil.

Reference Example 25

Synthesis of 1-(4-ethylbenzyl)-4-[[N-(9-fluorenylmethyloxycarbonyl)glycyl]aminomethyl]piperidine 4-Ethylbenzaldehyde (1.09 g, 8.16 mmol) and $NaBH_3CN$ (6.59 g, 10.5 mmol) were added to a 2.5% acetic acid/methanol (80 mL) solution of 4-[[N-(9-fluorenylmethyloxycarbonyl)glycyl]aminomethyl]piperidine (1.00 g, 2.33 mmol). The resulting reaction mixture was stirred at 60° C. for 13 hours and cooled to room temperature. A 1 M aqueous solution of NaOH (50 mL) and dichloromethane (50 mL) were then added, and the organic layer was separated. The aqueous layer was extracted with dichloromethane (50 mL×3). The organic layers were combined, washed with brine, dried over anhydrous sodium sulfate, filtered and concentrated. The obtained crude product was purified by column chromatography ($SiO_2$, methanol/ethyl acetate=2:8) to thereby provide 1-(4-ethylbenzyl)-4-[[N-(9-fluorenylmethyloxycarbonyl)glycyl]aminomethyl]piperidine (740 mg, 62%).

Reference Example 26

Synthesis of 4-[(glycylamino)methyl]-1-(4-methylthiobenzyl)piperidine

A DMF (4 mL) solution of 4-[[N-(9-fluorenylmethyloxycarbonyl)glycyl]aminomethyl]-1-(4-methylthiobenzyl)piperidine (590 mg) and piperidine (1 mL) was stirred at 60° C. for 2 hours. After concentrating, the obtained crude product was purified by column chromatography ($SiO_2$,triethylamine/methanol/dichloromethane=1:1:9) to thereby afford 4-[(glycylamino)methyl]-1-(4-methylthiobenzyl)piperidine (365 mg) as a white solid. $^1H$ NMR ($CDCl_3$, 270 MHz) δ 1.25 (dd, J=12 Hz, 4.1 Hz, 2H), 1.34 (dd, J=12 Hz, 4.1 Hz, 2H), 1.51 (br-s, 2H), 1.66 (d, J=12 Hz, 2H), 1.77 (d, J=7.3 Hz, 1H), 1.94 (t, J=9.5 Hz, 2H), 2.48 (s, 3H), 2.80 (d, J=12 Hz, 2H), 3.18 (t, J=6.2 Hz, 2H), 3.35 (s, 2H), 3.45 (s, 2H), 7.18-7.29 (m, 4H), 7.35 (br-s, 1H).

Further, 1-(4-ethylbenzyl)-4-[(glycylamino)methyl]piperidine was synthesized by using the corresponding starting material and reactants according to the method of Reference Example 26: 333 mg, 79%.

Reference Example 27

Synthesis of 4-[(glycylamino)methyl]-1-(4-fluorobenzyl)piperidine

An acetonitrile (200 mL) solution of 4-[[N-(9-fluorenylmethyloxycarbonyl)glycyl]aminomethyl]piperidine (1.50 g, 3.49 mmol), 4-fluorobenzyl bromide (0.478 mL, 3.84 mmol) and triethylamine (1.47 mL, 10.5 mmol) was stirred at room temperature for 13 hours. The obtained product was purified by column chromatography ($SiO_2$, 10% methanol/dichloromethane) to thereby provide 4-[[N-(9-fluorenylmethyloxycarbonyl)glycyl]aminomethyl]piperidine.

A DMF (5 mL) solution of the 4-[[N-(9-fluorenylmethyloxycarbonyl)glycyl]aminomethyl]piperidine and piperidine (5 mL) was further stirred at room temperature for 17 hours. After concentrating, the obtained crude product was purified by column chromatography ($SiO_2$, triethylamine/methanol/dichloromethane=0.5:2:8) to afford 4-[(glycylamino)methyl]-1-(4-fluorobenzyl)piperidine (453 mg, 46%).

Reference Example 28

Synthesis of 4-[(glycylamino)methyl]-1-[4-(N-phenylcarbamoyl)benzyl]piperidine

An acetonitrile (100 mL) solution of 4-(N-phenylcarbamoyl)benzyl chloride (800 mg, 3.26 mmol) was dropped into a mixture of 4-[[N-(9-fluorenylmethyloxycarbonyl)glycyl]aminomethyl]piperidine (1.27 g, 2.96 mmol) with triethylamine (1.25 mL, 8.88 mmol), KI (50 mg, 0.30 mmol) and acetonitrile (200 mL). The resulting mixture was stirred at room temperature for 19 hours and stirred at 60° C. for another 5 hours. After concentrating, the obtained crude product was purified by column chromatography ($SiO_2$, 5% methanol/dichloromethane-triethylamine/methanol/dichloromethane=2:2:96) to provide 4-[(glycylamino)methyl]-1-[4-(N-phenylcarbamoyl)benzyl]piperidine (340 mg, 30%).

Example 1091

Synthesis of 1-(4-chlorobenzyl)-4-[[N-(3-cyanobenzoyl)valyl]aminomethyl]piperidine (Compd. No. 619)

Triethylamine (0.011 mL, 0.077 mmol), m-cyanobenzoic acid (28 mg, 0.071 mmol), EDCI (13 mg, 0.065 mmol) and HOBt (9 mg, 0.065 mmol) were added to a dichloromethane (0.60 mL) solution of 1-(4-chlorobenzyl)-4-[(valylamino)methyl]piperidine (20 mg, 0.059 mmol). The resulting reaction mixture was stirred at 25° C. for 16 hours, and the obtained solution was diluted with dichloromethane (0.75 mL), washed with a 2 M aqueous solution of NaOH (0.75 mL×2) and dried by filtration through a PTFE membrane. The dried solution was concentrated to thereby afford 1-(4-chlorobenzyl)-4-[[N-(3-cyanobenzoyl)valyl]aminomethyl]piperidine (Compd. No. 619) (24.2 mg, 88%). Further purification was not required for the resulting compound. The purity was determined by RPLC/MS (85%). ESI/MS m/e 467 ($M^+$+H, $C_{26}H_{31}ClN_4O_2$).

Examples 1092 to 1543

The compounds used in the present invention were synthesized by using the respective corresponding starting materials and reactants according to the method of Example 1091. Data of ESI/MS, yields (mg) and yields (%) are collectively shown in Table 27.

TABLE 27

| Example | Compd. No. | Molecular Formula | ESI/MS m/e | Yield (mg) | Yield (%) |
|---|---|---|---|---|---|
| 1092 | 467 | $C_{22}H_{25}BrClN_3O_2$ | 478 | 11 | 46 |
| 1093 | 468 | $C_{24}H_{31}ClN_4O_2$ | 443 | 9 | 41 |
| 1094 | 469 | $C_{23}H_{28}ClN_3O_3$ | 430 | 7* | 27 |
| 1095 | 470 | $C_{23}H_{25}ClN_4O_2$ | 425 | 21 | Q |
| 1096 | 471 | $C_{24}H_{28}ClN_3O_4$ | 458 | 7 | 29 |
| 1097 | 472 | $C_{29}H_{31}N_3O_3$ | 504 | 5* | 21 |
| 1098 | 473 | $C_{24}H_{28}ClN_3O_3$ | 442 | 16 | 71 |
| 1099 | 474 | $C_{23}H_{25}ClF_3N_3O_2$ | 468 | 14 | 60 |
| 1100 | 475 | $C_{25}H_{32}ClN_3O_2$ | 442 | 5 | 22 |
| 1101 | 476 | $C_{22}H_{25}ClN_4O_4$ | 445 | 4 | 17 |

TABLE 27-continued

| Example | Compd. No. | Molecular Formula | ESI/MS m/e | Yield (mg) | Yield (%) |
|---|---|---|---|---|---|
| 1102 | 477 | $C_{25}H_{32}ClN_3O_3$ | 458 | 10* | 36 |
| 1103 | 478 | $C_{21}H_{27}ClN_4O_2$ | 403 | 9 | 47 |
| 1104 | 479 | $C_{20}H_{24}ClN_3O_3$ | 390 | 17 | 87 |
| 1105 | 480 | $C_{20}H_{23}BrClN_3O_3$ | 470 | 23 | Q |
| 1106 | 481 | $C_{20}H_{24}ClN_3O_2S$ | 406 | 7 | 33 |
| 1107 | 482 | $C_{21}H_{26}ClN_3O_2S$ | 420 | 9 | 45 |
| 1108 | 483 | $C_{21}H_{26}ClN_3O_2S$ | 420 | 8 | 40 |
| 1109 | 484 | $C_{24}H_{27}ClN_4O_2$ | 439 | 9* | 34 |
| 1110 | 485 | $C_{24}H_{24}ClF_6N_3O_2$ | 536 | 13 | 49 |
| 1111 | 486 | $C_{23}H_{25}ClN_4O_2$ | 425 | 16 | 74 |
| 1112 | 487 | $C_{22}H_{25}Cl_2N_3O_2$ | 434 | 5 | 24 |
| 1113 | 488 | $C_{22}H_{27}ClN_4O_2$ | 415 | 7 | 32 |
| 1114 | 489 | $C_{24}H_{24}ClF_6N_3O_2$ | 536 | 21 | 78 |
| 1115 | 490 | $C_{24}H_{30}ClN_3O_3$ | 444 | 8 | 35 |
| 1116 | 491 | $C_{23}H_{24}ClF_4N_3O_2$ | 486 | 19 | 79 |
| 1117 | 492 | $C_{23}H_{25}ClF_3N_3O_3$ | 484 | 18 | 76 |
| 1118 | 493 | $C_{23}H_{24}Cl_2F_3N_3O_2$ | 502 | 23 | 92 |
| 1119 | 494 | $C_{23}H_{24}ClF_4N_3O_2$ | 486 | 19 | 79 |
| 1120 | 495 | $C_{23}H_{24}ClF_4N_3O_2$ | 486 | 20 | 83 |
| 1121 | 496 | $C_{23}H_{24}ClF_4N_3O_2$ | 486 | 12 | 48 |
| 1122 | 497 | $C_{25}H_{32}ClN_3O_3$ | 458 | 4 | 16 |
| 1123 | 498 | $C_{23}H_{26}ClF_3N_4O_2$ | 483 | 13 | 52 |
| 1124 | 499 | $C_{24}H_{31}ClN_4O_2$ | 443 | 8 | 36 |
| 1125 | 500 | $C_{23}H_{28}ClN_3O_3$ | 430 | 10 | 48 |
| 1126 | 501 | $C_{22}H_{24}BrClN_4O_4$ | 523 | 10 | 39 |
| 1127 | 502 | $C_{22}H_{24}ClFN_4O_4$ | 463 | 4 | 17 |
| 1128 | 503 | $C_{22}H_{24}Cl_2N_4O_4$ | 479 | 12 | 52 |
| 1129 | 504 | $C_{24}H_{30}ClN_3O_4$ | 460 | 11 | 43 |
| 1130 | 505 | $C_{22}H_{24}BrClN_4O_4$ | 523 | 2 | 8 |
| 1131 | 506 | $C_{20}H_{23}ClN_4O_5$ | 435 | 2 | 10 |
| 1132 | 507 | $C_{21}H_{26}ClN_3O_3$ | 404 | 9 | 44 |
| 1133 | 508 | $C_{24}H_{26}ClN_3O_2S$ | 456 | 1 | 5 |
| 1134 | 509 | $C_{20}H_{23}BrClN_3O_2S$ | 484 | 12 | 48 |
| 1135 | 510 | $C_{22}H_{28}ClN_3O_3$ | 418 | 9 | 44 |
| 1136 | 511 | $C_{24}H_{32}ClN_3O_3$ | 446 | 9 | 40 |
| 1137 | 512 | $C_{25}H_{29}ClN_4O_2$ | 453 | 10 | 45 |
| 1138 | 513 | $C_{24}H_{28}ClN_3O_3$ | 442 | 9 | 41 |
| 1139 | 514 | $C_{26}H_{34}ClN_3O_2$ | 456 | 11 | 49 |
| 1140 | 515 | $C_{23}H_{28}ClN_3O_3$ | 430 | 5 | 24 |
| 1141 | 525 | $C_{23}H_{28}ClN_3O_4S$ | 478 | 20 | 85 |
| 1142 | 526 | $C_{20}H_{24}ClN_3O_3$ | 390 | 6 | 31 |
| 1143 | 527 | $C_{20}H_{24}ClN_3O_2S$ | 406 | 8 | 39 |
| 1144 | 528 | $C_{25}H_{30}ClF_3N_4O_4$ | 543 | 28.2 | 95 |
| 1145 | 529 | $C_{20}H_{23}ClN_4O_4S$ | 451 | 9 | 39 |
| 1146 | 530 | $C_{31}H_{33}ClN_4O_2$ | 529 | 5 | 17 |
| 1147 | 531 | $C_{21}H_{26}ClN_3O_3S$ | 436 | 8 | 37 |
| 1148 | 532 | $C_{22}H_{28}ClN_3O_3$ | 418 | 8 | 40 |
| 1149 | 533 | $C_{21}H_{26}ClN_3O_3$ | 404 | 6 | 32 |
| 1150 | 534 | $C_{21}H_{25}ClN_4O_5$ | 449 | 5 | 20 |
| 1151 | 535 | $C_{22}H_{26}ClN_3O_3S$ | 448 | 8 | 37 |
| 1152 | 536 | $C_{23}H_{31}ClN_4O_2$ | 431 | 6 | 28 |
| 1153 | 537 | $C_{25}H_{34}ClN_3O_3$ | 460 | 8 | 34 |
| 1154 | 538 | $C_{27}H_{30}ClN_3O_3$ | 480 | 9 | 36 |
| 1155 | 539 | $C_{22}H_{25}ClF_3N_3O_3$ | 472 | 18 | 75 |
| 1156 | 540 | $C_{25}H_{29}ClN_4O_2$ | 453 | 8 | 36 |
| 1157 | 541 | $C_{22}H_{26}ClN_5O_4$ | 460 | 2.4 | 10 |
| 1158 | 542 | $C_{24}H_{30}ClN_3O_2$ | 428 | 4.6* | 51 |
| 1159 | 543 | $C_{24}H_{30}ClN_3O_2$ | 428 | 20.6* | 71 |
| 1160 | 544 | $C_{22}H_{25}ClFN_3O_2$ | 418 | 15.8* | 56 |
| 1161 | 545 | $C_{22}H_{24}Cl_3N_3O_2$ | 468 | 7.3* | 23 |
| 1162 | 546 | $C_{22}H_{24}Cl_3N_3O_2$ | 468 | 17.4* | 55 |
| 1163 | 547 | $C_{22}H_{24}Cl_3N_3O_2$ | 468 | 14.1* | 44 |
| 1164 | 548 | $C_{22}H_{24}Cl_3N_3O_2$ | 468 | 6.8* | 22 |
| 1165 | 549 | $C_{22}H_{24}Cl_2N_4O_4$ | 479 | 5.7* | 18 |
| 1166 | 550 | $C_{22}H_{24}Cl_2N_4O_4$ | 479 | 18.9* | 58 |
| 1167 | 551 | $C_{24}H_{30}ClN_3O_2$ | 428 | 14.2* | 49 |
| 1168 | 552 | $C_{24}H_{27}ClF_3N_3O_2$ | 482 | 30.6* | 94 |
| 1169 | 553 | $C_{25}H_{26}ClF_6N_3O_2$ | 550 | 38.0* | Q |
| 1170 | 554 | $C_{24}H_{26}ClFN_4O_2$ | 457 | 0.9* | 3 |
| 1171 | 555 | $C_{24}H_{26}Cl_2N_4O_2$ | 473 | 11.1* | 35 |
| 1172 | 556 | $C_{25}H_{29}ClN_4O_2$ | 453 | 12.5* | 41 |
| 1173 | 559 | $C_{25}H_{26}ClF_6N_3O_2$ | 550 | 15 | 72 |
| 1174 | 560 | $C_{24}H_{27}ClN_4O_2$ | 439 | 12 | 68 |
| 1175 | 561 | $C_{23}H_{27}BrClN_3O_2$ | 494 | 14 | 73 |
| 1176 | 562 | $C_{23}H_{27}Cl_2N_3O_2$ | 448 | 13 | 75 |
| 1177 | 563 | $C_{25}H_{26}ClF_6N_3O_2$ | 550 | 14 | 66 |

TABLE 27-continued

| Example | Compd. No. | Molecular Formula | ESI/MS m/e | Yield (mg) | Yield (%) |
|---|---|---|---|---|---|
| 1178 | 564 | $C_{25}H_{32}ClN_3O_3$ | 458 | 5 | 28 |
| 1179 | 565 | $C_{24}H_{26}ClF_4N_3O_2$ | 500 | 12 | 61 |
| 1180 | 566 | $C_{24}H_{27}ClF_3N_3O_3$ | 498 | 12 | 62 |
| 1181 | 567 | $C_{24}H_{26}Cl_2F_3N_3O_2$ | 516 | 12 | 61 |
| 1182 | 568 | $C_{24}H_{26}ClF_4N_3O_2$ | 500 | 15 | 77 |
| 1183 | 569 | $C_{24}H_{26}ClF_4N_3O_2$ | 500 | 11 | 59 |
| 1184 | 570 | $C_{24}H_{26}ClF_4N_3O_2$ | 500 | 16 | 84 |
| 1185 | 571 | $C_{26}H_{34}ClN_3O_3$ | 472 | 14 | 77 |
| 1186 | 572 | $C_{24}H_{28}ClF_3N_4O_2$ | 497 | 11 | 55 |
| 1187 | 573 | $C_{21}H_{25}BrClN_3O_2S$ | 500 | 12 | 64 |
| 1188 | 574 | $C_{21}H_{25}BrClN_3O_2S$ | 500 | 15 | 75 |
| 1189 | 575 | $C_{25}H_{34}ClN_3O_3$ | 460 | 16 | 87 |
| 1190 | 576 | $C_{22}H_{28}ClN_3O_2S_2$ | 466 | 13 | 71 |
| 1191 | 577 | $C_{22}H_{28}ClN_3O_3$ | 418 | 12 | 72 |
| 1192 | 578 | $C_{25}H_{28}ClN_3O_2S$ | 470 | 15 | 81 |
| 1193 | 579 | $C_{25}H_{29}ClN_4O_2$ | 453 | 17 | 94 |
| 1194 | 580 | $C_{22}H_{28}ClN_3O_2S$ | 434 | 15 | 91 |
| 1195 | 581 | $C_{21}H_{26}ClN_3O_2S$ | 420 | 13 | 80 |
| 1196 | 582 | $C_{22}H_{28}ClN_3O_2S$ | 434 | 10 | 59 |
| 1197 | 583 | $C_{26}H_{31}ClN_4O_2$ | 467 | 6 | 31 |
| 1198 | 584 | $C_{30}H_{32}ClN_3O_3$ | 518 | 18 | 92 |
| 1199 | 585 | $C_{24}H_{27}ClN_4O_2$ | 439 | 14 | 85 |
| 1200 | 586 | $C_{23}H_{27}Cl_2N_3O_2$ | 448 | 17 | 97 |
| 1201 | 587 | $C_{24}H_{27}ClF_3N_3O_2$ | 482 | 17 | 91 |
| 1202 | 588 | $C_{23}H_{29}ClN_4O_2$ | 429 | 5 | 29 |
| 1203 | 589 | $C_{27}H_{36}ClN_3O_2$ | 470 | 4 | 24 |
| 1204 | 590 | $C_{26}H_{34}ClN_3O_2$ | 456 | 6 | 36 |
| 1205 | 591 | $C_{25}H_{33}ClN_4O_2$ | 457 | 7 | 38 |
| 1206 | 592 | $C_{24}H_{30}ClN_3O_3$ | 444 | 4 | 20 |
| 1207 | 593 | $C_{24}H_{30}ClN_3O_3$ | 444 | 2 | 14 |
| 1208 | 594 | $C_{23}H_{28}ClN_3O_3$ | 430 | 4 | 25 |
| 1209 | 595 | $C_{25}H_{30}ClN_3O_4$ | 472 | 7 | 38 |
| 1210 | 596 | $C_{25}H_{30}ClN_3O_3$ | 456 | 7 | 40 |
| 1211 | 597 | $C_{25}H_{30}ClN_3O_3$ | 456 | 15 | 85 |
| 1212 | 598 | $C_{21}H_{26}ClN_3O_3$ | 404 | 15 | 94 |
| 1213 | 599 | $C_{22}H_{29}ClN_4O_2$ | 417 | 5 | 30 |
| 1214 | 600 | $C_{21}H_{25}BrClN_3O_3$ | 484 | 6 | 34 |
| 1215 | 601 | $C_{24}H_{30}ClN_3O_3$ | 444 | 5 | 28 |
| 1216 | 602 | $C_{25}H_{33}ClN_4O_2$ | 457 | 5 | 28 |
| 1217 | 603 | $C_{23}H_{29}ClN_4O_2$ | 429 | 4 | 22 |
| 1218 | 604 | $C_{21}H_{27}ClN_4O_2$ | 403 | 9 | 58 |
| 1219 | 605 | $C_{21}H_{26}ClN_3O_3$ | 404 | 17 | 87 |
| 1220 | 606 | $C_{21}H_{26}ClN_3O_2S$ | 420 | 15 | 74 |
| 1221 | 607 | $C_{22}H_{28}ClN_3O_3S$ | 450 | 31 | Q |
| 1222 | 608 | $C_{23}H_{30}ClN_3O_3$ | 432 | 17 | 80 |
| 1223 | 609 | $C_{22}H_{28}ClN_3O_3$ | 418 | 18 | 89 |
| 1224 | 610 | $C_{23}H_{28}ClN_3O_3S$ | 462 | 20 | 86 |
| 1225 | 611 | $C_{26}H_{36}ClN_3O_3$ | 474 | 21 | 90 |
| 1226 | 612 | $C_{28}H_{32}ClN_3O_3$ | 494 | 20 | 84 |
| 1227 | 613 | $C_{23}H_{27}ClF_3N_3O_3$ | 486 | 19 | 81 |
| 1228 | 614 | $C_{24}H_{33}ClN_4O_2$ | 445 | 23 | Q |
| 1229 | 615 | $C_{25}H_{29}ClN_4O_2$ | 453 | 4 | 20 |
| 1230 | 616 | $C_{32}H_{35}ClN_4O_2$ | 543 | 11 | 40 |
| 1231 | 617 | $C_{25}H_{27}ClF_3N_3O_2$ | 482 | 6.7 | 37 |
| 1232 | 620 | $C_{25}H_{31}BrClN_3O_2$ | 520 | 15 | 49 |
| 1233 | 621 | $C_{25}H_{31}Cl_2N_3O_2$ | 476 | 18 | 64 |
| 1234 | 622 | $C_{27}H_{37}ClN_4O_2$ | 485 | 14 | 50 |
| 1235 | 623 | $C_{26}H_{34}ClN_3O_3$ | 472 | 19 | 69 |
| 1236 | 624 | $C_{25}H_{31}ClN_4O_4$ | 487 | 21 | 73 |
| 1237 | 625 | $C_{25}H_{33}ClN_4O_2$ | 457 | 19 | 69 |
| 1238 | 626 | $C_{27}H_{30}ClF_6N_3O_2$ | 578 | 8 | 25 |
| 1239 | 627 | $C_{27}H_{36}ClN_3O_3$ | 486 | 16 | 55 |
| 1240 | 628 | $C_{27}H_{34}ClN_3O_4$ | 500 | 24 | 80 |
| 1241 | 629 | $C_{26}H_{30}ClF_4N_3O_2$ | 528 | 18 | 56 |
| 1242 | 630 | $C_{26}H_{31}ClF_3N_3O_3$ | 526 | 21 | 68 |
| 1243 | 631 | $C_{26}H_{30}Cl_2F_3N_3O_2$ | 544 | 15 | 48 |
| 1244 | 632 | $C_{26}H_{30}ClF_4N_3O_2$ | 528 | 13 | 41 |
| 1245 | 633 | $C_{26}H_{30}ClF_4N_3O_2$ | 528 | 20 | 63 |
| 1246 | 634 | $C_{26}H_{30}ClF_4N_3O_2$ | 528 | 19 | 62 |
| 1247 | 635 | $C_{28}H_{38}ClN_3O_3$ | 500 | 11 | 36 |
| 1248 | 636 | $C_{26}H_{34}ClN_3O_2$ | 456 | 21 | 89 |
| 1249 | 637 | $C_{26}H_{31}ClF_3N_3O_2$ | 510 | 20 | 95 |
| 1250 | 638 | $C_{26}H_{31}ClN_4O_2$ | 467 | 15 | 54 |
| 1251 | 639 | $C_{27}H_{37}ClN_4O_2$ | 485 | 19 | 66 |
| 1252 | 640 | $C_{26}H_{34}ClN_3O_3$ | 472 | 16 | 56 |
| 1253 | 641 | $C_{27}H_{34}ClN_3O_4$ | 500 | 18 | 59 |

TABLE 27-continued

| Example | Compd. No. | Molecular Formula | ESI/MS m/e | Yield (mg) | Yield (%) |
|---|---|---|---|---|---|
| 1254 | 642 | $C_{32}H_{36}ClN_3O_3$ | 546 | 24 | 73 |
| 1255 | 643 | $C_{26}H_{31}ClF_3N_3O_2$ | 510 | 16 | 54 |
| 1256 | 644 | $C_{29}H_{40}ClN_3O_2$ | 498 | 18 | 61 |
| 1257 | 645 | $C_{25}H_{33}ClN_4O_2$ | 457 | 22 | 78 |
| 1258 | 646 | $C_{26}H_{34}ClN_3O_3$ | 472 | 13 | 47 |
| 1259 | 647 | $C_{27}H_{34}ClN_3O_3$ | 500 | 13 | 46 |
| 1260 | 648 | $C_{28}H_{38}ClN_3O_2$ | 484 | 17 | 60 |
| 1261 | 649 | $C_{28}H_{38}ClN_3O_3$ | 500 | 12.5 | 42 |
| 1262 | 650 | $C_{32}H_{36}ClN_3O_3$ | 546 | 1* | 2 |
| 1263 | 651 | $C_{28}H_{35}ClN_4O_2$ | 495 | 4* | 12 |
| 1264 | 652 | $C_{25}H_{31}ClN_4O_4$ | 487 | 5* | 14 |
| 1265 | 653 | $C_{30}H_{42}ClN_3O_3$ | 528 | 1* | 3 |
| 1266 | 654 | $C_{27}H_{34}ClN_3O_3$ | 484 | 7* | 21 |
| 1267 | 655 | $C_{26}H_{32}ClF_3N_4O_2$ | 525 | 6* | 16 |
| 1268 | 656 | $C_{23}H_{30}ClN_3O_3$ | 432 | 6* | 18 |
| 1269 | 657 | $C_{23}H_{30}ClN_3O_2S$ | 448 | 4* | 13 |
| 1270 | 658 | $C_{27}H_{33}ClN_4O_2$ | 48 | 1* | 4 |
| 1271 | 659 | $C_{23}H_{29}ClN_4O_4S$ | 493 | 4* | 10 |
| 1272 | 660 | $C_{34}H_{39}ClN_4O_2$ | 571 | 3* | 7 |
| 1273 | 661 | $C_{24}H_{32}ClN_3O_3S$ | 478 | 3* | 7 |
| 1274 | 662 | $C_{25}H_{34}ClN_3O_3$ | 460 | 2* | 6 |
| 1275 | 663 | $C_{24}H_{32}ClN_3O_3$ | 446 | 2* | 5 |
| 1276 | 664 | $C_{24}H_{31}ClN_4O_5$ | 491 | 2* | 5 |
| 1277 | 665 | $C_{25}H_{32}ClN_3O_3S$ | 490 | 1* | 3 |
| 1278 | 666 | $C_{26}H_{37}ClN_4O_2$ | 473 | 3* | 7 |
| 1279 | 667 | $C_{30}H_{36}ClN_3O_3$ | 522 | 3* | 7 |
| 1280 | 668 | $C_{25}H_{31}ClF_3N_3O_3$ | 514 | 2* | 6 |
| 1281 | 669 | $C_{24}H_{33}ClN_4O_2$ | 445 | 15* | 45 |
| 1282 | 670 | $C_{23}H_{29}BrClN_3O_3$ | 510 | 3* | 7 |
| 1283 | 671 | $C_{23}H_{29}ClN_4O_5$ | 477 | 2* | 5 |
| 1284 | 672 | $C_{23}H_{31}ClN_4O_2$ | 431 | 2* | 7 |
| 1285 | 673 | $C_{23}H_{30}ClN_3O_2S$ | 448 | 2* | 6 |
| 1286 | 674 | $C_{24}H_{32}ClN_3O_2S$ | 462 | 3* | 9 |
| 1287 | 675 | $C_{24}H_{32}ClN_3O_2S$ | 462 | 1* | 4 |
| 1288 | 676 | $C_{27}H_{33}ClN_4O_2$ | 482 | 2* | 6 |
| 1289 | 677 | $C_{28}H_{35}ClN_4O_2$ | 495 | 2* | 6 |
| 1290 | 678 | $C_{24}H_{32}ClN_3O_3$ | 446 | 3* | 9 |
| 1291 | 679 | $C_{27}H_{32}ClN_3O_2S$ | 498 | 1* | 3 |
| 1292 | 680 | $C_{23}H_{29}BrClN_3O_2S$ | 526 | 2* | 6 |
| 1293 | 681 | $C_{25}H_{34}ClN_3O_3$ | 460 | 2* | 5 |
| 1294 | 682 | $C_{27}H_{38}ClN_3O_3$ | 488 | 2* | 4 |
| 1295 | 683 | $C_{24}H_{32}ClN_3O_2S_2$ | 494 | 1* | 4 |
| 1296 | 684 | $C_{26}H_{36}ClN_3O_4S_2$ | 554 | 2* | 5 |
| 1297 | 685 | $C_{24}H_{32}ClN_3O_4S_2$ | 526 | 3* | 7 |
| 1298 | 687 | $C_{25}H_{30}ClN_3O_2$ | 440 | 24 | Q |
| 1299 | 688 | $C_{27}H_{28}ClF_6N_3O_2$ | 576 | 28 | 98 |
| 1300 | 689 | $C_{26}H_{29}ClN_4O_2$ | 465 | 23 | 99 |
| 1301 | 690 | $C_{25}H_{29}BrClN_3O_2$ | 518 | 26 | 99 |
| 1302 | 691 | $C_{27}H_{35}ClN_4O_2$ | 483 | 24 | 97 |
| 1303 | 692 | $C_{26}H_{32}ClN_3O_3$ | 470 | 24 | Q |
| 1304 | 693 | $C_{27}H_{28}ClF_6N_3O_2$ | 576 | 16 | 55 |
| 1305 | 694 | $C_{27}H_{34}ClN_3O_3$ | 484 | 25 | Q |
| 1306 | 695 | $C_{27}H_{32}ClN_3O_4$ | 498 | 12 | 47 |
| 1307 | 696 | $C_{26}H_{29}ClF_3N_3O_3$ | 524 | 25 | 95 |
| 1308 | 697 | $C_{26}H_{29}ClN_4O_2$ | 465 | 15 | 64 |
| 1309 | 698 | $C_{27}H_{35}ClN_4O_2$ | 483 | 24 | Q |
| 1310 | 699 | $C_{26}H_{32}ClN_3O_3$ | 470 | 26 | Q |
| 1311 | 700 | $C_{27}H_{32}ClN_3O_4$ | 498 | 15 | 62 |
| 1312 | 701 | $C_{27}H_{32}ClN_3O_3$ | 482 | 11 | 44 |
| 1313 | 702 | $C_{26}H_{29}ClF_3N_3O_2$ | 508 | 23 | 94 |
| 1314 | 703 | $C_{28}H_{36}ClN_3O_2$ | 482 | 26 | Q |
| 1315 | 704 | $C_{25}H_{29}ClN_4O_4$ | 485 | 11 | 43 |
| 1316 | 705 | $C_{24}H_{30}ClN_3O_2S$ | 460 | 25 | Q |
| 1317 | 706 | $C_{24}H_{30}ClN_3O_2S$ | 460 | 25 | Q |
| 1318 | 707 | $C_{26}H_{29}ClF_3N_3O_2$ | 508 | 15 | 55 |
| 1319 | 708 | $C_{23}H_{27}BrClN_3O_2S$ | 526 | 25 | 92 |
| 1320 | 709 | $C_{24}H_{30}ClN_3O_2S_2$ | 492 | 26 | Q |
| 1321 | 710 | $C_{23}H_{27}BrClN_3O_2S$ | 526 | 25 | 94 |
| 1322 | 711 | $C_{25}H_{32}ClN_3O_3$ | 458 | 26 | Q |
| 1323 | 712 | $C_{27}H_{30}ClN_3O_2S$ | 496 | 26 | Q |
| 1324 | 713 | $C_{24}H_{30}ClN_3O_3$ | 444 | 26 | Q |
| 1325 | 714 | $C_{28}H_{33}ClN_4O_2$ | 493 | 12 | 50 |
| 1326 | 715 | $C_{23}H_{28}ClN_3O_2S$ | 446 | 24 | Q |
| 1327 | 716 | $C_{27}H_{31}ClN_4O_2$ | 479 | 32 | Q |
| 1328 | 717 | $C_{23}H_{21}ClN_4O_5$ | 475 | 23 | 95 |
| 1329 | 718 | $C_{23}H_{29}ClN_4O_2$ | 429 | 24 | Q |

TABLE 27-continued

| Example | Compd. No. | Molecular Formula | ESI/MS m/e | Yield (mg) | Yield (%) |
|---|---|---|---|---|---|
| 1330 | 719 | $C_{23}H_{28}ClN_3O_3$ | 430 | 24 | Q |
| 1331 | 720 | $C_{23}H_{27}BrClN_3O_3$ | 510 | 24 | 95 |
| 1332 | 721 | $C_{24}H_{31}ClN_4O_2$ | 443 | 22 | 98 |
| 1333 | 722 | $C_{26}H_{32}ClN_3O_3$ | 470 | 9 | 37 |
| 1334 | 723 | $C_{25}H_{31}ClN_4O_2$ | 455 | 10 | 44 |
| 1335 | 724 | $C_{29}H_{38}ClN_3O_2$ | 496 | 28 | Q |
| 1336 | 725 | $C_{32}H_{34}ClN_3O_3$ | 544 | 26 | 95 |
| 1337 | 726 | $C_{27}H_{33}ClN_4O_3$ | 497 | 3 | 11 |
| 1338 | 727 | $C_{25}H_{29}Cl_2N_3O_2$ | 474 | 25 | Q |
| 1339 | 728 | $C_{25}H_{31}ClN_4O_2$ | 455 | 21 | 92 |
| 1340 | 729 | $C_{25}H_{29}ClN_4O_4$ | 485 | 26 | Q |
| 1341 | 730 | $C_{25}H_{29}Cl_2N_3O_2$ | 474 | 21 | 90 |
| 1342 | 731 | $C_{27}H_{32}ClN_3O_3$ | 482 | 10 | 41 |
| 1343 | 732 | $C_{26}H_{28}ClF_4N_3O_2$ | 526 | 27 | Q |
| 1344 | 733 | $C_{28}H_{36}ClN_3O_3$ | 498 | 22 | 89 |
| 1345 | 734 | $C_{26}H_{28}ClF_4N_3O_2$ | 526 | 25 | 94 |
| 1346 | 735 | $C_{26}H_{28}ClF_4N_3O_2$ | 526 | 23 | 87 |
| 1347 | 736 | $C_{26}H_{30}ClF_3N_4O_2$ | 523 | 24 | 78 |
| 1348 | 737 | $C_{26}H_{28}ClF_4N_3O_2$ | 526 | 21 | 66 |
| 1349 | 738 | $C_{25}H_{32}ClN_3O_3$ | 458 | 23 | 84 |
| 1350 | 739 | $C_{27}H_{31}ClN_4O_2$ | 479 | 19 | 66 |
| 1351 | 740 | $C_{24}H_{31}ClN_4O_5$ | 489 | 23 | 77 |
| 1352 | 741 | $C_{23}H_{27}ClN_4O_4S$ | 491 | 26 | 88 |
| 1353 | 742 | $C_{24}H_{30}ClN_3O_3S$ | 476 | 23 | 82 |
| 1354 | 743 | $C_{23}H_{28}ClN_3O_3$ | 430 | 21 | 81 |
| 1355 | 744 | $C_{26}H_{32}ClN_3O_2$ | 454 | 25 | 91 |
| 1356 | 745 | $C_{27}H_{36}ClN_3O_3$ | 486 | 23 | 80 |
| 1357 | 746 | $C_{26}H_{35}ClN_4O_2$ | 471 | 27 | 96 |
| 1358 | 747 | $C_{25}H_{29}ClF_3N_3O_3$ | 512 | 23 | 74 |
| 1359 | 748 | $C_{23}H_{28}ClN_3O_2S$ | 446 | 22 | 82 |
| 1360 | 751 | $C_{24}H_{30}ClN_3O_3$ | 444 | 3 | 11 |
| 1361 | 752 | $C_{25}H_{26}ClF_6N_3O_3$ | 566 | 7 | 20 |
| 1362 | 753 | $C_{24}H_{27}ClN_4O_3$ | 455 | 6 | 22 |
| 1363 | 754 | $C_{23}H_{27}Cl_2N_3O_3$ | 464 | 8 | 29 |
| 1364 | 755 | $C_{24}H_{30}ClN_3O_4$ | 460 | 6 | 22 |
| 1365 | 756 | $C_{23}H_{27}ClN_4O_5$ | 475 | 5 | 18 |
| 1366 | 757 | $C_{25}H_{32}ClN_3O_4$ | 474 | 5 | 18 |
| 1367 | 758 | $C_{25}H_{30}ClN_3O_5$ | 488 | 5 | 18 |
| 1368 | 759 | $C_{24}H_{27}ClF_3N_3O_4$ | 514 | 6 | 20 |
| 1369 | 760 | $C_{24}H_{26}ClF_4N_3O_3$ | 516 | 6 | 18 |
| 1370 | 761 | $C_{24}H_{26}ClF_4N_3O_3$ | 516 | 3 | 10 |
| 1371 | 762 | $C_{24}H_{27}ClF_3N_3O_3$ | 498 | 2 | 95 |
| 1372 | 763 | $C_{23}H_{28}ClN_3O_3$ | 430 | 4 | 95 |
| 1373 | 764 | $C_{24}H_{30}ClN_3O_2$ | 428 | 9 | 42 |
| 1374 | 765 | $C_{25}H_{32}ClN_3O_2$ | 442 | 10 | 47 |
| 1375 | 766 | $C_{25}H_{29}ClF_3N_3O_2$ | 496 | 10 | 42 |
| 1376 | 767 | $C_{25}H_{32}ClN_3O_4S$ | 506 | 8 | 32 |
| 1377 | 768 | $C_{24}H_{29}BrClN_3O_2$ | 506 | 9 | 35 |
| 1378 | 769 | $C_{25}H_{29}ClF_3N_3O_3$ | 512 | 6 | 22 |
| 1379 | 770 | $C_{25}H_{28}ClF_4N_3O_2$ | 514 | 3 | 10 |
| 1380 | 771 | $C_{25}H_{28}ClF_4N_3O_2$ | 514 | 10 | 37 |
| 1381 | 772 | $C_{25}H_{29}ClF_3N_3O_2$ | 496 | 8 | 33 |
| 1382 | 773 | $C_{26}H_{36}ClN_3O_3$ | 474 | 10 | 41 |
| 1383 | 774 | $C_{23}H_{30}ClN_3O_2S_2$ | 480 | 12 | 50 |
| 1384 | 775 | $C_{27}H_{38}ClN_3O_3$ | 488 | 14 | 57 |
| 1385 | 776 | $C_{29}H_{34}ClN_3O_3$ | 508 | 12 | 49 |
| 1386 | 777 | $C_{24}H_{29}ClF_3N_3O_3$ | 500 | 22 | 87 |
| 1387 | 778 | $C_{24}H_{28}Cl_2N_4O_4$ | 507 | 6 | 22 |
| 1388 | 779 | $C_{24}H_{29}Cl_2N_3O_2$ | 462 | 10 | 46 |
| 1389 | 780 | $C_{24}H_{29}ClN_4O_4$ | 473 | 15 | 65 |
| 1390 | 781 | $C_{26}H_{31}ClN_4O_2$ | 467 | 7* | 20 |
| 1391 | 782 | $C_{25}H_{32}ClN_3O_3$ | 458 | 8* | 23 |
| 1392 | 783 | $C_{26}H_{34}ClN_3O_3$ | 472 | 7* | 19 |
| 1393 | 784 | $C_{26}H_{31}ClF_3N_3O_2$ | 510 | 7* | 17 |
| 1394 | 785 | $C_{26}H_{34}ClN_3O_4$ | 488 | 6* | 17 |
| 1395 | 786 | $C_{24}H_{28}ClN_3O_2$ | 426 | 22 | 9 |
| 1396 | 787 | $C_{25}H_{30}ClN_3O_2$ | 440 | 21 | 94 |
| 1397 | 788 | $C_{25}H_{27}ClF_3N_3O_2$ | 494 | 4* | 14 |
| 1398 | 789 | $C_{25}H_{30}ClN_3O_4S$ | 504 | 9 | 35 |
| 1399 | 790 | $C_{24}H_{27}Cl_2N_3O_2$ | 460 | 5* | 16 |
| 1400 | 791 | $C_{24}H_{27}ClN_4O_4$ | 471 | 3* | 10 |
| 1401 | 792 | $C_{25}H_{27}ClF_3N_3O_3$ | 510 | 5* | 16 |
| 1402 | 793 | $C_{25}H_{26}ClF_4N_3O_2$ | 511 | 5* | 16 |
| 1403 | 794 | $C_{25}H_{26}ClF_4N_3O_2$ | 512 | 5* | 16 |
| 1404 | 795 | $C_{25}H_{27}ClF_3N_3O_2$ | 494 | 6* | 21 |
| 1405 | 796 | $C_{23}H_{28}ClN_3O_2S_2$ | 478 | 4* | 14 |

TABLE 27-continued

| Example | Compd. No. | Molecular Formula | ESI/MS m/e | Yield (mg) | Yield (%) |
|---|---|---|---|---|---|
| 1406 | 797 | $C_{27}H_{36}ClN_3O_3$ | 486 | 7* | 29 |
| 1407 | 798 | $C_{29}H_{32}ClN_3O_3$ | 506 | 3 | 13 |
| 1408 | 799 | $C_{24}H_{27}ClF_3N_3O_3$ | 498 | 3* | 11 |
| 1409 | 800 | $C_{24}H_{26}Cl_2N_4O_4$ | 505 | 5* | 15 |
| 1410 | 801 | $C_{26}H_{29}ClN_4O_2$ | 465 | 12 | 41 |
| 1411 | 802 | $C_{25}H_{30}ClN_3O_3$ | 456 | 5* | 15 |
| 1412 | 803 | $C_{26}H_{32}ClN_3O_3$ | 470 | 6* | 16 |
| 1413 | 804 | $C_{26}H_{29}ClF_3N_3O_2$ | 508 | 8* | 20 |
| 1414 | 805 | $C_{26}H_{32}ClN_3O_4$ | 486 | 6* | 15 |
| 1415 | 806 | $C_{24}H_{27}BrClN_3O_2$ | 506 | 5* | 14 |
| 1416 | 807 | $C_{27}H_{32}ClN_5O_3$ | 510 | 29.7 | Q |
| 1417 | 808 | $C_{26}H_{33}ClN_4O_3$ | 485 | 29.9 | Q |
| 1418 | 809 | $C_{25}H_{30}Cl_2N_4O_3$ | 505 | 30.2 | Q |
| 1419 | 810 | $C_{30}H_{35}ClN_4O_4$ | 551 | 31.0 | Q |
| 1420 | 811 | $C_{25}H_{29}Cl_2N_5O_5$ | 550 | 30.4 | Q |
| 1421 | 812 | $C_{24}H_{31}ClN_4O_3S_2$ | 523 | 25.0 | 88 |
| 1422 | 813 | $C_{26}H_{30}ClF_3N_4O_3$ | 539 | 20.5 | 70 |
| 1423 | 814 | $C_{26}H_{30}ClF_3N_4O_4$ | 555 | 22.7 | 75 |
| 1424 | 815 | $C_{26}H_{29}ClF_4N_4O_3$ | 557 | 25.8 | 85 |
| 1425 | 816 | $C_{26}H_{30}ClF_3N_4O_3$ | 539 | 25.3 | 86 |
| 1426 | 817 | $C_{26}H_{29}ClF_4N_4O_3$ | 557 | 26.8 | 88 |
| 1427 | 818 | $C_{25}H_{30}BrClN_4O_3$ | 551 | 27.1 | 90 |
| 1428 | 819 | $C_{27}H_{29}ClF_6N_4O_3$ | 607 | 13.9 | 42 |
| 1429 | 820 | $C_{25}H_{30}ClN_5O_5$ | 516 | 14.1 | 51 |
| 1430 | 821 | $C_{24}H_{28}Cl_2N_4O_5$ | 523 | 40 | 86 |
| 1431 | 822 | $C_{23}H_{30}ClN_3O_3S_2$ | 496 | 41 | 93 |
| 1432 | 823 | $C_{26}H_{31}ClN_4O_3$ | 483 | 43 | Q |
| 1433 | 824 | $C_{27}H_{38}ClN_3O_4$ | 503 | 37 | 83 |
| 1434 | 825 | $C_{29}H_{34}ClN_3O_4$ | 524 | 28 | 61 |
| 1435 | 826 | $C_{24}H_{29}ClF_3N_3O_4$ | 516 | 40 | 87 |
| 1436 | 827 | $C_{26}H_{31}ClN_4O_3$ | 483 | 31 | 72 |
| 1437 | 828 | $C_{25}H_{29}ClF_3N_3O_4$ | 528 | 40 | 86 |
| 1438 | 829 | $C_{25}H_{28}ClF_4N_3O_3$ | 530 | 45 | 97 |
| 1439 | 830 | $C_{25}H_{28}ClF_4N_3O_3$ | 530 | 35 | 74 |
| 1440 | 831 | $C_{24}H_{29}BrClN_3O_3$ | 523 | 45 | 98 |
| 1441 | 832 | $C_{24}H_{29}Cl_2N_3O_3$ | 478 | 38 | 91 |
| 1442 | 833 | $C_{24}H_{29}ClN_4O_5$ | 488 | 38 | 87 |
| 1443 | 834 | $C_{25}H_{29}ClF_3N_3O_3$ | 512 | 42 | 93 |
| 1444 | 835 | $C_{24}H_{30}ClN_3O_3$ | 444 | 43 | Q |
| 1445 | 836 | $C_{25}H_{32}ClN_3O_3$ | 458 | 37 | 91 |
| 1446 | 837 | $C_{25}H_{29}ClF_3N_3O_3$ | 512 | 41 | 91 |
| 1447 | 838 | $C_{26}H_{34}ClN_3O_4$ | 488 | 34 | 78 |
| 1448 | 839 | $C_{27}H_{36}ClN_3O_6$ | 534 | 37 | 71 |
| 1449 | 942 | $C_{27}H_{30}ClF_6N_3O_2$ | 578 | 17 | 48 |
| 1450 | 997 | $C_{26}H_{34}ClN_3O_2$ | 456 | 7.6* | 23 |
| 1451 | 998 | $C_{27}H_{33}ClF_3N_3O_2$ | 524 | 6 | 15 |
| 1452 | 999 | $C_{27}H_{36}ClN_3O_2$ | 470 | 8 | 24 |
| 1453 | 1000 | $C_{27}H_{36}ClN_3O_3$ | 486 | 9 | 24 |
| 1454 | 1001 | $C_{28}H_{38}ClN_3O_3$ | 500 | 4 | 10 |
| 1455 | 1002 | $C_{27}H_{33}ClF_3N_3O_3$ | 540 | 9 | 23 |
| 1456 | 1003 | $C_{28}H_{38}ClN_3O_2$ | 484 | 7 | 21 |
| 1457 | 1004 | $C_{28}H_{38}ClN_3O_4$ | 516 | 11 | 30 |
| 1458 | 1005 | $C_{29}H_{40}ClN_3O_5$ | 547 | 9 | 23 |
| 1459 | 1006 | $C_{30}H_{42}ClN_3O_4$ | 544 | 8 | 21 |
| 1460 | 1007 | $C_{32}H_{46}ClN_3O_5$ | 589 | 7 | 17 |
| 1461 | 1008 | $C_{25}H_{31}ClN_4O_3$ | 471 | 25 | 79 |
| 1462 | 1009 | $C_{26}H_{33}ClN_4O_4$ | 501 | 35 | 97 |
| 1463 | 1010 | $C_{27}H_{35}ClN_4O_4$ | 515 | 35 | 9 |
| 1464 | 1011 | $C_{27}H_{35}ClN_4O_3$ | 499 | 32 | 54 |
| 1465 | 1012 | $C_{27}H_{35}ClN_4O_5$ | 531 | 27 | 77 |
| 1466 | 1013 | $C_{28}H_{37}ClN_4O_6$ | 561 | 14 | 37 |
| 1467 | 1014 | $C_{29}H_{39}ClN_4O_5$ | 559 | 24 | 66 |
| 1468 | 1015 | $C_{31}H_{43}ClN_4O_6$ | 603 | 25 | 65 |
| 1469 | 1018 | $C_{26}H_{34}ClN_3O_4$ | 488 | 13.0* | 39 |
| 1470 | 1019 | $C_{28}H_{38}ClN_3O_5$ | 532 | 13.4* | 37 |
| 1471 | 1020 | $C_{25}H_{32}ClN_3O_4$ | 474 | 12.7* | 40 |
| 1472 | 1021 | $C_{26}H_{28}ClF_6N_3O_4$ | 596 | 13.8* | 34 |
| 1473 | 1022 | $C_{25}H_{32}ClN_3O_4$ | 474 | 14.2* | 37 |
| 1474 | 1023 | $C_{25}H_{32}ClN_3O_2$ | 442 | 11.5* | 32 |
| 1475 | 1024 | $C_{26}H_{34}ClN_3O_5$ | 504 | 12.0* | 30 |
| 1476 | 1025 | $C_{27}H_{36}ClN_3O_4$ | 502 | 14.7* | 37 |
| 1477 | 1026 | $C_{29}H_{40}ClN_3O_5$ | 546 | 13.5* | 32 |
| 1478 | 1027 | $C_{26}H_{34}ClN_3O_4$ | 488 | 11.9* | 31 |
| 1479 | 1028 | $C_{27}H_{30}ClF_6N_3O_4$ | 610 | 14.6* | 31 |
| 1480 | 1029 | $C_{25}H_{32}ClN_3O_3$ | 458 | 14.0* | 38 |
| 1481 | 1030 | $C_{24}H_{27}ClF_3N_3O_3$ | 498 | 14.0* | 35 |

TABLE 27-continued

| Example | Compd. No. | Molecular Formula | ESI/MS m/e | Yield (mg) | Yield (%) |
|---|---|---|---|---|---|
| 1482 | 1031 | $C_{24}H_{30}ClN_3O_3$ | 444 | 10.4* | 29 |
| 1483 | 1032 | $C_{25}H_{32}ClN_3O_4$ | 474 | 14.9* | 39 |
| 1484 | 1033 | $C_{25}H_{32}ClN_3O_2$ | 442 | 13.3* | 37 |
| 1485 | 1034 | $C_{26}H_{34}ClN_3O_5$ | 504 | 13.7* | 34 |
| 1486 | 1035 | $C_{27}H_{36}ClN_3O_4$ | 502 | 16.7* | 42 |
| 1487 | 1036 | $C_{29}H_{40}ClN_3O_5$ | 547 | 15.5* | 36 |
| 1488 | 1037 | $C_{26}H_{34}ClN_3O_4$ | 488 | 14.1* | 36 |
| 1489 | 1038 | $C_{27}H_{30}ClF_6N_3O_4$ | 610 | 17.5* | 37 |
| 1490 | 1039 | $C_{25}H_{32}ClN_3O_3$ | 458 | 15.1* | 41 |
| 1491 | 1040 | $C_{24}H_{27}ClF_3N_3O_3$ | 498 | 15.4* | 39 |
| 1492 | 1041 | $C_{24}H_{30}ClN_3O_3$ | 444 | 12.7* | 35 |
| 1493 | 1042 | $C_{22}H_{26}BrClN_4O_2$ | 495 | 10.4* | 25 |
| 1494 | 1043 | $C_{22}H_{26}Cl_2N_4O_2$ | 449 | 11.1* | 29 |
| 1495 | 1044 | $C_{23}H_{29}ClN_4O_2$ | 429 | 5.2* | 14 |
| 1496 | 1045 | $C_{23}H_{29}ClN_4O_3$ | 445 | 12.4* | 33 |
| 1497 | 1046 | $C_{22}H_{25}Cl_3N_4O_2$ | 483 | 10.0* | 25 |
| 1498 | 1047 | $C_{24}H_{31}ClN_4O_2$ | 443 | 12.1* | 32 |
| 1499 | 1048 | $C_{25}H_{33}ClN_4O_5$ | 505 | 16.1* | 39 |
| 1500 | 1049 | $C_{23}H_{28}BrClN_4O_2$ | 507 | 12.0* | 29 |
| 1501 | 1050 | $C_{28}H_{38}ClN_3O_4$ | 516 | 39.2* | Q |
| 1502 | 1051 | $C_{28}H_{38}ClN_3O_2$ | 484 | 34.0* | Q |
| 1503 | 1052 | $C_{29}H_{40}ClN_3O_5$ | 546 | 14.5* | 39 |
| 1504 | 1053 | $C_{30}H_{42}ClN_3O_4$ | 544 | 11.8* | 32 |
| 1505 | 1054 | $C_{32}H_{46}ClN_3O_5$ | 588 | 12.2* | 31 |
| 1506 | 1055 | $C_{29}H_{40}ClN_3O_4$ | 530 | 44.5* | Q |
| 1507 | 1056 | $C_{30}H_{36}ClF_6N_3O_4$ | 652 | 46.0* | Q |
| 1508 | 1057 | $C_{28}H_{38}ClN_3O_3$ | 500 | 11.2* | Q |
| 1509 | 1058 | $C_{27}H_{36}ClN_3O_3$ | 486 | 35.5* | Q |
| 1510 | 1059 | $C_{27}H_{33}ClF_3N_3O_3$ | 540 | 41.4* | Q |
| 1511 | 1060 | $C_{29}H_{40}ClN_3O_4$ | 530 | 13.6* | 37 |
| 1512 | 1061 | $C_{30}H_{36}ClF_6N_3O_4$ | 652 | 44.2* | Q |
| 1513 | 1062 | $C_{28}H_{38}ClN_3O_3$ | 500 | 39.9* | Q |
| 1514 | 1063 | $C_{27}H_{36}ClN_3O_3$ | 486 | 12.0* | 35 |
| 1515 | 1064 | $C_{27}H_{33}ClF_3N_3O_3$ | 540 | 37.8* | Q |
| 1516 | 1065 | $C_{28}H_{38}ClN_3O_4$ | 516 | 12.3* | 34 |
| 1517 | 1066 | $C_{28}H_{38}ClN_3O_2$ | 484 | 30.7* | 90 |
| 1518 | 1067 | $C_{29}H_{40}ClN_3O_5$ | 546 | 13.8* | 37 |
| 1519 | 1068 | $C_{30}H_{42}ClN_3O_4$ | 544 | 13.1* | 35 |
| 1520 | 1069 | $C_{32}H_{46}ClN_3O_5$ | 589 | 14.1* | 35 |
| 1521 | 1070 | $C_{29}H_{34}ClN_3O_3S_2$ | 572 | 38.3 | 93 |
| 1522 | 1071 | $C_{32}H_{35}ClN_4O_3$ | 559 | 39.6 | 98 |
| 1523 | 1072 | $C_{33}H_{42}ClN_3O_4$ | 580 | 40.9 | 98 |
| 1524 | 1073 | $C_{35}H_{38}ClN_3O_4$ | 600 | 40.5 | 94 |
| 1525 | 1074 | $C_{30}H_{33}ClF_3N_3O_4$ | 592 | 38.7 | 91 |
| 1526 | 1075 | $C_{31}H_{33}ClF_3N_3O_4$ | 604 | 38 | 87 |
| 1527 | 1076 | $C_{30}H_{33}ClN_4O_5$ | 565 | 38.5 | 94 |
| 1528 | 1077 | $C_{31}H_{33}ClF_3N_3O_3$ | 588 | 35.8 | 84 |
| 1529 | 1078 | $C_{30}H_{34}ClN_3O_3$ | 520 | 34.7 | 93 |
| 1530 | 1079 | $C_{31}H_{36}ClN_3O_3$ | 534 | 38.4 | Q |
| 1531 | 1080 | $C_{32}H_{38}ClN_3O_4$ | 564 | 39.3 | 97 |
| 1532 | 1081 | $C_{33}H_{40}ClN_3O_6$ | 610 | 45.5 | Q |
| 1533 | 1082 | $C_{28}H_{36}ClN_3O_3$ | 498 | 4.1* | 10 |
| 1534 | 1083 | $C_{28}H_{36}ClN_3O_3$ | 498 | 6.4* | 16 |
| 1535 | 1125 | $C_{30}H_{32}Cl_2N_4O_5$ | 599 | 3.4* | 8 |
| 1536 | 1126 | $C_{30}H_{32}BrClN_4O_5$ | 644 | 3.4* | 7 |
| 1537 | 1127 | $C_{32}H_{35}ClN_4O_3$ | 559 | 1.6* | 4 |
| 1538 | 1128 | $C_{31}H_{32}ClF_4N_3O_3$ | 606 | 4.3* | 10 |
| 1539 | 1129 | $C_{31}H_{32}ClF_4N_3O_3$ | 606 | 5.9* | 14 |
| 1540 | 1130 | $C_{30}H_{33}BrClN_3O_3$ | 599 | 5.7* | 13 |
| 1541 | 1131 | $C_{30}H_{33}Cl_2N_3O_3$ | 554 | 6.4* | 16 |
| 1542 | 1132 | $C_{31}H_{33}ClF_3N_3O_3$ | 588 | 6.3* | 15 |
| 1543 | 1167 | $C_{27}H_{34}ClN_3O_3$ | 484 | 1.8* | 4 |

Notes:
*indicates "yield (mg) of trifluoroacetate".
Q means "Quantitative".

Example 1544

Synthesis of 1-(4-chlorobenzyl)-4-[[N-(3,5-bis(trifluoromethyl)benzoyl)glycyl]aminomethyl]piperidine (Compd. No. 1213)

A dichloromethane (1 mL) solution of 3,5-bis(trifluoromethyl)benzoyl chloride (0.058 mmol) was added to a mixture of 1-(4-chlorobenzyl)-4-[(glycylamino)methyl]piperidine (0.050 mmol) with chloroform (0.2 mL), a piperidinomethylpolystyrene (58 mg) and dichloromethane (0.75 mL). The resulting reaction mixture was stirred at room temperature for 2 hours, and methanol (1.0 mL) was then added to the obtained mixture. The resulting mixture was stirred at room temperature for 30 minutes. The reaction mixture was loaded onto a Varian™ SCX column and washed with methanol (16 mL). The obtained crude product was eluted with a 2 M methanol solution of $NH_3$ (6 mL) and concentrated to thereby provide 1-(4-chlorobenzyl)-4-[[N-(3,5-bis(trifluoromethyl)benzoyl)glycyl]aminomethyl]piperidine (Compd. No. 1213) (24.0 mg, 90%). The purity was determined by RPLC/MS (100%). ESI/MS m/e 536.2 ($M^+$+H, $C_{24}H_{24}ClF_6N_3O_2$).

Examples 1545 to 1547

The compounds used in the present invention were synthesized by using the respective corresponding starting materials and reactants according to the method of Example 1544. Data of ESI/MS, yields (mg) and yields (%) are collectively shown in Table 28.

TABLE 28

| Example | Compd. No. | Molecular Formula | ESI/MS m/e | Yield (mg) | Yield (%) |
|---|---|---|---|---|---|
| 1545 | 1214 | $C_{23}H_{24}ClF_4N_3O_3$ | 486.2 | 22.2 | 91 |
| 1546 | 1215 | $C_{22}H_{24}Cl_3N_3O_2$ | 467.9 | 20.9 | 89 |
| 1547 | 1216 | $C_{22}H_{24}ClF_2N_3O_2$ | 436.0 | 19.3 | 89 |

Example 1548

Synthesis of 4-[[N-(3-bromo-4-methylbenzoyl)glycyl]aminomethyl]-1-(4-chlorobenzyl)piperidine (Compd. No. 1113)

3-Bromo-4-methylbenzoic acid (0.060 mmol), diisopropylcarbodiimide (0.060 mmol) and HOBt (0.060 mmol) were added to a solution of 1-(4-chlorobenzyl)-4-[(glycylamino)methyl]piperidine (0.050 mmol) in chloroform (1.35 mL) and tert-butanol (0.15 mL). The resulting reaction mixture was stirred at room temperature for 15 hours. The mixture was then loaded onto a Varian™ SCX column and washed with methanol/chloroform=1:1 (12 mL) and methanol (12 mL). The obtained crude product was eluted with a 2 M methanol solution of $NH_3$ (5 mL) and concentrated to thereby afford 4-[[N-(3-bromo-4-methylbenzoyl)glycyl]aminomethyl]-1-(4-chlorobenzyl)piperidine (Compd. No. 1113) (16.1 mg, 65%). The purity was determined by RPLC/MS (95%). ESI/MS m/e 494.0 ($C_{23}H_{27}BrClN_3O_2$).

Examples 1549 to 1619

The compounds used in the present invention were synthesized by using the respective corresponding starting materials and reactants according to the method of 1548. The obtained products, if necessary, were purified by preparative TLC to provide the objective compounds. Data of ESI/MS, yields (mg) and yields (%) are collectively shown in Table 29.

Compd. No. 1422 was obtained as a by-product of Compd. No. 1418: 5.6 mg, yield: 25%; ESI/MS m/e 447.2 ($C_{22}H_{27}ClN_4O_2S$).

TABLE 29

| Example | Compd. No. | Molecular Formula | ESI/MS m/e | Yield (mg) | Yield (%) |
|---|---|---|---|---|---|
| 1549 | 1114 | $C_{22}H_{24}BrClFN_3O_2$ | 498.0 | 20.2 | 81 |
| 1550 | 1115 | $C_{22}H_{24}Cl_2FN_3O_2$ | 452.2 | 18.6 | 82 |
| 1551 | 1116 | $C_{23}H_{27}ClIN_3O_2$ | 539.1 | 21.9 | 81 |
| 1552 | 1117 | $C_{23}H_{27}ClN_4O_4$ | 459.2 | 18.7 | 81 |
| 1553 | 1187 | $C_{23}H_{27}BrClN_3O_2$ | 494.0 | 22.1 | 90 |
| 1554 | 1188 | $C_{24}H_{27}ClN_4O_3$ | 455.2 | 17.2 | 76 |
| 1555 | 1189 | $C_{25}H_{29}ClN_4O_3$ | 469.2 | 21.1 | 90 |
| 1556 | 1190 | $C_{22}H_{26}ClFN_4O_2$ | 433.2 | 20.4 | 94 |
| 1557 | 1241 | $C_{23}H_{24}Cl_2F_3N_3O_2$ | 502.0 | 22.5 | 90 |
| 1558 | 1242 | $C_{23}H_{27}ClFN_3O_2$ | 432.2 | 21.2 | 98 |
| 1559 | 1243 | $C_{23}H_{27}Cl_2N_3O_2$ | 448.0 | 21.6 | 96 |
| 1560 | 1244 | $C_{22}H_{26}ClIN_4O_2$ | 541.0 | 26.4 | 98 |
| 1561 | 1245 | $C_{22}H_{25}ClF_2N_4O_2$ | 451.0 | 21.3 | 94 |
| 1562 | 1246 | $C_{21}H_{27}ClN_4O_2$ | 403.2 | 19.4 | 96 |
| 1563 | 1247 | $C_{28}H_{30}ClN_3O_2S$ | 524.0 | 24.7 | 94 |
| 1564 | 1248 | $C_{22}H_{25}ClN_4O_5$ | 461.0 | 20.7 | 90 |
| 1565 | 1282 | $C_{25}H_{26}ClF_3N_4O_3$ | 523.2 | 25.0 | 96 |
| 1566 | 1283 | $C_{23}H_{27}Cl_2N_3O_3$ | 464.2 | 12.2 | 53 |
| 1567 | 1284 | $C_{22}H_{25}BrClN_3O_3$ | 496.0 | 24.1 | 97 |
| 1568 | 1285 | $C_{22}H_{25}Cl_2N_3O_3$ | 450.2 | 21.8 | 97 |
| 1569 | 1342 | $C_{22}H_{24}BrCl_2N_3O_2$ | 514.0 | 27.2 | Q |
| 1570 | 1343 | $C_{23}H_{27}Cl_2N_3O_2$ | 448.0 | 21.4 | 95 |
| 1571 | 1344 | $C_{22}H_{24}Cl_2IN_3O_2$ | 560.0 | 27.0 | 96 |
| 1572 | 1345 | $C_{23}H_{28}ClN_3O_2$ | 430.2 | 23.8 | Q |
| 1573 | 1346 | $C_{22}H_{25}ClIN_3O_3$ | 542.0 | 29.4 | Q |
| 1574 | 1350 | $C_{21}H_{26}ClN_3O_2S$ | 420.0 | 13.0 | 62 |
| 1575 | 1354 | $C_{24}H_{28}BrClN_4O_3$ | 537.2 | 5.2 | 19 |
| 1576 | 1358 | $C_{23}H_{26}ClN_5O_2$ | 440.2 | 21.8 | 99 |
| 1577 | 1383 | $C_{23}H_{24}Cl_2F_3N_3O_2$ | 502.0 | 20.0 | 80 |
| 1578 | 1384 | $C_{20}H_{23}BrClN_3O_2S$ | 486.0 | 21.0 | 87 |
| 1579 | 1385 | $C_{28}H_{30}ClN_3O_4S$ | 540.2 | 23.8 | 88 |
| 1580 | 1386 | $C_{28}H_{30}ClN_3O_2$ | 476.0 | 20.0 | 84 |
| 1581 | 1414 | $C_{24}H_{28}Cl_2N_4O_3$ | 491.0 | 0.8 | 3 |
| 1582 | 1418 | $C_{23}H_{26}ClN_5O_2S$ | 472.0 | 10.4 | 44 |
| 1583 | 1436 | $C_{29}H_{30}ClN_3O_3$ | 504.2 | 26.8 | Q |
| 1584 | 1600 | $C_{23}H_{26}ClF_3N_4O_2$ | 483.2 | 16.5 | 68 |
| 1585 | 1601 | $C_{23}H_{26}ClF_3N_4O_3$ | 499.0 | 20.0 | 80 |
| 1586 | 1602 | $C_{21}H_{24}BrClN_4O_2$ | 481.0 | 18.1 | 75 |
| 1587 | 1603 | $C_{21}H_{24}Cl_2N_4O_2$ | 435.0 | 5.5 | 25 |
| 1588 | 1604 | $C_{27}H_{30}ClN_3O_3$ | 492.0 | 18.6 | 76 |
| 1589 | 1605 | $C_{21}H_{27}ClN_4O_2$ | 415.2 | 18.1 | 87 |
| 1590 | 1609 | $C_{23}H_{25}N_3O_2S$ | 500.0 | 18.3 | 73 |
| 1591 | 1659 | $C_{22}H_{26}Cl_2N_4O_2$ | 449.0 | 366.0 | 83 |
| 1592 | 1664 | $C_{24}H_{29}F_3N_4O_2S$ | 495.2 | 13.7 | 55 |
| 1593 | 1665 | $C_{24}H_{29}F_3N_4O_3S$ | 511.2 | 14.9 | 58 |
| 1594 | 1666 | $C_{23}H_{28}F_2N_4O_2S$ | 463.2 | 12.9 | 56 |
| 1595 | 1667 | $C_{22}H_{27}Br_2N_3O_3$ | 542 | 26.1 | 96 |
| 1596 | 1668 | $C_{24}H_{30}F_2N_4O_2$ | 445 | 22.9 | Q |
| 1597 | 1669 | $C_{24}H_{31}FN_4O_2$ | 427 | 24.0 | Q |
| 1598 | 1670 | $C_{24}H_{31}IN_4O_2$ | 535 | 28.1 | Q |
| 1599 | 1671 | $C_{25}H_{31}F_3N_4O_3$ | 493 | 26.8 | Q |
| 1600 | 1672 | $C_{25}H_{31}F_3N_4O_2$ | 478 | 24.7 | Q |
| 1601 | 1673 | $C_{24}H_{29}BrClN_3O_2$ | 508 | 24.9 | 98 |
| 1602 | 1674 | $C_{20}H_{22}Br_2FN_3O_3$ | 532 | 25.6 | 96 |
| 1603 | 1675 | $C_{22}H_{25}F_3N_4O_2$ | 435 | 21.5 | 99 |
| 1604 | 1676 | $C_{22}H_{26}F_2N_4O_2$ | 417 | 21.4 | Q |
| 1605 | 1677 | $C_{22}H_{26}BrFN_4O_2$ | 479 | 23.4 | 98 |
| 1606 | 1678 | $C_{22}H_{26}FIN_4O_2$ | 525 | 27.4 | Q |
| 1607 | 1679 | $C_{22}H_{26}ClFN_4O_2$ | 433 | 22.4 | Q |
| 1608 | 1680 | $C_{23}H_{26}F_4N_4O_3$ | 483 | 25.5 | Q |
| 1609 | 1681 | $C_{23}H_{26}F_4N_4O_2$ | 467 | 23.2 | 99 |
| 1610 | 1682 | $C_{23}H_{26}BrClFN_3O$ | 498 | 24.2 | 98 |
| 1611 | 1683 | $C_{27}H_{28}Br_2N_4O_4$ | 633 | 31.8 | Q |
| 1612 | 1684 | $C_{29}H_{31}F_2N_5O_3$ | 536 | 28.3 | Q |
| 1613 | 1685 | $C_{29}H_{32}FN_5O_3$ | 518 | 31.1 | Q |
| 1614 | 1686 | $C_{29}H_{32}BrN_5O_3$ | 578 | 29.6 | Q |
| 1615 | 1687 | $C_{29}H_{32}IN_5O_3$ | 626 | 32.4 | Q |
| 1616 | 1688 | $C_{29}H_{32}ClN_5O_3$ | 534 | 28.2 | Q |
| 1617 | 1689 | $C_{30}H_{32}F_3N_5O_4$ | 584 | 31.7 | Q |

TABLE 29-continued

| Example | Compd. No. | Molecular Formula | ESI/MS m/e | Yield (mg) | Yield (%) |
|---|---|---|---|---|---|
| 1618 | 1690 | $C_{30}H_{32}F_3N_5O_3$ | 568 | 30.6 | Q |
| 1619 | 1691 | $C_{29}H_{30}BrClN_4O_3$ | 599 | 31.4 | Q |

Note:
Q means "Quantitative".

For example Compd. Nos. 1245 and 1600 exhibited the following NMR spectra.

Comps. No. 1245: $^1$H NMR (270 MHz, $CDCl_3$) δ 1.20-1.97 (m, 7H), 2.80-2.86 (m, 2H), 3.19 (t, J=6.5 Hz, 2H), 3.43 (s, 2H), 4.02 (d, J=5.3 Hz, 2H), 5.52 (br s, 2H), 6.44 (d, J=11.9, 6.6 Hz, 1H), 7.02 (br s, 1H), 7.21-7.32 (m, 5H).

Compd. No. 1600: $^1$H NMR (270 MHz, $CDCl_3$) δ 1.25-1.97 (m, 9H), 2.82-2.87 (m, 2H), 3.21 (t, J=6.5 Hz, 2H), 3.44 (s, 2H), 4.06 (d, J=5.1 Hz, 2H), 5.98 (br s, 1H), 6.71 (d, J=8.3 Hz, 1H), 6.87 (br s, 1H), 7.26 (s, 4H), 7.43 (dd, J=5.9 Hz, 1H), 7.64 (s, 1H).

Example 1620

Synthesis of 1-(4-chorobenzyl)-4-[[N-(4-isopropylphenylsulfonyl)glycyl]aminomethyl]piperidine (Compd. No. 869)

A (piperidinomethyl)polystyrene resin (28 mg, 2.8 mmol/g) and 4-isopropylbenzenesulfonyl chloride (1.5 equivalents) were added to a chloroform (2 mL) solution of 1-(4-chlorobenzyl)-4-[(glycylamino)methyl]piperidine (14.8 mg, 0.05 mmol). The resulting mixture was stirred at 25° C. for 16 hours, then filtered and concentrated to thereby afford 1-(4-chlorobenzyl)-4-[[N-(4-isopropylphenylsulfonyl)glycyl] aminomethyl]piperidine (Compd. No. 869) (22.1 mg, 92%). The purity was determined by RPLC/MS (86%). ESI/MS m/e 478 ($M^+$+H, $C_{24}H_{32}N_3O_3S$).

Examples 1621 to 1627

The compounds used in the present invention were synthesized by using the respective corresponding starting materials and reactants according to the method of Example 1620. Data of ESI/MS, yields (mg) and yields (%) are collectively shown in Table 30.

TABLE 30

| Example | Compd. No. | Molecular Formula | ESI/MS m/e | Yield (mg) | Yield (%) |
|---|---|---|---|---|---|
| 1621 | 865 | $C_{22}H_{28}ClN_3O_3S$ | 450 | 16.2 | 72 |
| 1622 | 866 | $C_{22}H_{25}ClF_3N_3O_3S$ | 504 | 8.8 | 35 |
| 1623 | 867 | $C_{23}H_{24}ClF_6N_3O_3S$ | 572 | 8.0 | 28 |
| 1624 | 868 | $C_{23}H_{30}ClN_3O_3S$ | 464 | 9.6 | 41 |
| 1625 | 870 | $C_{22}H_{28}ClN_3O_3S$ | 450 | 8.8 | 39 |
| 1626 | 871 | $C_{25}H_{34}ClN_3O_3S$ | 492 | 11.1 | 45 |
| 1627 | 872 | $C_{21}H_{26}ClN_3O_3S$ | 436 | 9.6 | 44 |

Example 1628

Synthesis of 1-(4-chlorobenzyl-4-[[2-(3-(4-trifluoromethylphenyl)ureido)acetylamino]methyl]piperidine (Compd. No. 852)

A (piperidinomethyl)polystyrene resin (28 mg, 2.8 mmol/g) and 3-(trifluoromethyl)phenyl isocyanate (1.3 equivalents) were added to a chloroform (2 mL) solution of 1-(4-chlorobenzyl)-4-[(glycylamino)methyl]piperidine (14.8 mg, 0.05 mmol). The resulting mixture was stirred at 25° C. for 16 hours, and an (aminomethyl)polystyrene resin was added to the obtained mixture. The resulting mixture was stirred at 25° C. for 16 hours to trap the remaining isocyanate. The obtained mixture was filtered and concentrated to thereby provide 1-(4-chlorobenzyl)-4-[[2-(3-(4-trifluoromethylphenyl)ureido) acetylamino]methyl]piperidine (Comp d. No. 852) (19 mg, 78%). The purity was determined by RPLC/MS (92%). ESI/MS m/e 483 ($M^+$+H, $C_{23}H_{26}ClF_3N_4O_2$).

Examples 1629 to 1641

The compounds used in the present invention were synthesized by using the respective corresponding starting materials and reactants according to the method of Example 1628. Data of ESI/MS, yields (mg) and yields (%) are collectively shown in Table 31.

TABLE 31

| Example | Compd. No. | Molecular Formula | ESI/MS m/e | Yield (mg) | Yield (%) |
|---|---|---|---|---|---|
| 1629 | 851 | $C_{23}H_{26}ClF_3N_4O_2$ | 483 | 13.2 | 55 |
| 1630 | 853 | $C_{22}H_{27}ClN_4O_2$ | 416 | 8.5* | 32 |
| 1631 | 854 | $C_{23}H_{29}ClN_4O_2$ | 429 | 11.4* | 42 |
| 1632 | 855 | $C_{23}H_{29}ClN_4O_2$ | 429 | 10.1* | 37 |
| 1633 | 856 | $C_{24}H_{29}ClN_4O_3$ | 457 | 10.3* | 36 |
| 1634 | 857 | $C_{23}H_{29}ClN_4O_3$ | 445 | 10.9* | 39 |
| 1635 | 858 | $C_{23}H_{29}ClN_4O_3$ | 445 | 8.6* | 31 |
| 1636 | 859 | $C_{22}H_{26}Cl_2N_4O_2$ | 449 | 11.0* | 39 |
| 1637 | 860 | $C_{23}H_{26}ClN_5O_2$ | 440 | 9.2* | 33 |
| 1638 | 861 | $C_{22}H_{27}ClN_4OS$ | 431 | 13.3 | 62 |
| 1639 | 862 | $C_{23}H_{29}ClN_4OS$ | 445 | 15.3 | 69 |
| 1640 | 863 | $C_{23}H_{29}ClN_4O_2S$ | 461 | 14.7 | 64 |
| 1641 | 864 | $C_{23}H_{29}ClN_4O_2S$ | 461 | 13.1 | 57 |

Note:
*indicates "yield (mg) of trifluoroacetate".

Example 1642

Synthesis of 1-(4-chlorobenzyl)-4-[[N-(3-ethoxybenzoyl)-D-phenylalanyl]aminomethyl]piperidine (Compd. No. 2091)

Triethylamine (0.090 mL), N-(tert-butoxycarbonyl)-D-(phenylalanine) (122 mg), EDCI (89 mg) and HOBt (62 mg) were added to a chloroform (3 mL) solution of 1-(4-chlorobenzyl)-4-(aminomethyl)piperidine (100 mg). The resulting mixture was stirred at room temperature for 17 hours, and the reaction mixture was washed with a 1 M aqueous solution of NaOH (2 mL×2) and brine (2 mL). The organic layer was dried and concentrated to thereby afford 1-(4-chlorobenzyl)-4-[[N-(tert-butoxycarbonyl)-D-phenylalanyl]aminomethyl] piperidine.

The resulting 1-(4-chlorobenzyl)-4-[[N-(tert-butoxycarbonyl)-D-phenylalanyl]aminomethyl]piperidine was dissolved in methanol (5 mL), and a 4 M dioxane solution of HCl was then added to the solution. The obtained solution was stirred at room temperature for 19 hours and concentrated.

Triethylamine (0.090 mL), EDCI (90 mg) and HOBt (68 mg) were added to a chloroform solution (1 mL) of the obtained residue and 3-ethoxybenzoic acid (80 mg, 0.48 mmol). The resulting mixture was stirred at room temperature for 17 hours. The resulting reaction mixture was washed with a 1 M aqueous solution of NaOH (1.5 mLX 2) and brine (1.5 mL). The organic layer was dried, concentrated and purified by column chromatography ($SiO_2$, dichloromethane/methanol=95:5) to provide 1-(4-chlorobenzyl)-4-[[N-(3-ethoxybenzoyl)-D-phenylalanyl]aminomethyl]piperidine (Compd. No. 2091) (183.5 mg, 82%). The purity was determined by RPLC/MS (99%). ESI/MS m/e 534.0 ($M^+$+H, $C_{31}H_{36}ClN_3O_3$).

Examples 1643 to 1657

The compounds used in the present invention were synthesized by using the respective corresponding starting materials and reactants according to the method of 1642. Data of ESI/MS, yields (mg) and yields (%) are collectively shown in Table 32.

TABLE 32

| Example | Compd. No. | Molecular Formula | ESI/MS m/e | Yield (mg) | Yield (%) |
|---|---|---|---|---|---|
| 1643 | 2092 | $C_{33}H_{37}ClN_4O_3$ | 572.8 | 152.9 | 64 |
| 1644 | 2093 | $C_{27}H_{36}ClN_3O_3S$ | 518.0 | 177.4 | 82 |
| 1645 | 2094 | $C_{29}H_{34}ClN_3O_3S$ | 539.9 | 164.4 | 73 |
| 1646 | 2095 | $C_{28}H_{38}ClN_3O_3$ | 500.0 | 139.1 | 66 |
| 1647 | 2096 | $C_{31}H_{42}ClN_3O_3$ | 540.0 | 161.7 | 71 |
| 1648 | 2097 | $C_{27}H_{36}ClN_3O_3$ | 485.8 | 157.8 | 78 |
| 1649 | 2098 | $C_{31}H_{35}Cl_2N_3O_3$ | 567.9 | 172.2 | 72 |
| 1650 | 2099 | $C_{30}H_{34}ClN_3O_3$ | 519.8 | 144.7 | 66 |
| 1651 | 2100 | $C_{32}H_{38}ClN_3O_4$ | 564.0 | 181.5 | 77 |
| 1652 | 2101 | $C_{38}H_{42}ClN_3O_4$ | 639.9 | 192.3 | 72 |
| 1653 | 2103 | $C_{33}H_{40}ClN_3O_4$ | 577.8 | 159.9 | 66 |
| 1654 | 2104 | $C_{28}H_{36}ClN_3O_5$ | 530.1 | 99.7 | 45 |
| 1655 | 2115 | $C_{27}H_{36}ClN_3O_3$ | 486.2 | 122.9 | 60 |
| 1656 | 2116 | $C_{28}H_{38}ClN_3O_3$ | 500.1 | 118.3 | 57 |
| 1657 | 2117 | $C_{28}H_{34}ClN_5O_3$ | 524.1 | 98.3 | 45 |

Reference Example 29

Synthesis of 1-(tert-butoxycarbonyl)-4-[[N-(3-(trifluoromethyl)benzoyl)glycyl]aminomethyl]piperidine N-[3-(Trifluoromethyl)benzoyl]glycine (4.22 g, 17.0 mmol), EDCI (4.25 g, 22.1 mmol), 1-hydroxybenzotriazole hydrate (2.99 g, 22.1 mmol) and triethylamine (1.72 g) were added to an anhydrous dichloromethane (200 mL) solution of 1-(tert-butoxycarbonyl)-4-(aminomethyl)piperidine (4.03 g). The resulting reaction mixture was stirred at 25° C. for 20 hours, and $H_2O$ (100 mL) was then added to the mixture. The obtained mixture was extracted with dichloromethane (50 mLX 2). The extracts were combined, washed with $H_2O$ (50 mL×2) and brine (50 mL), dried (over $MgSO_4$) and concentrated to thereby afford a yellow oil. The obtained crude product was purified by column chromatography ($SiO_2$,70% ethyl acetate-hexane) to provide 1-(tert-butoxycarbonyl)-4-[[N-(3-(trifluoromethyl)benzoyl)glycyl]aminomethyl]piperidine as a white solid (6.39 g, 85%). $^1H$ NMR ($CDCl_3$, 300 MHz) δ 1.4 (s, 9H), 1.0-1.8 (m, 5H), 2.6-2.8 (m, 2H), 3.15-3.3 (m, 2H), 4.0-4.3 (m, 4H), 6.6-6.7 (m, 1H), 7.64 (s, 1H), 7.60 (dd, 1H, J=7.2, 7.2 Hz), 7.79 (d, 1H, J=7.2 Hz), 8.0 (d, 1H, J=7.2 Hz), 8.11 (s, 1H). The purity was determined by RPLC/MS (97%). ESI/MS m/e 444.3 ($M^+$+H, $C_{21}H_{28}N_3O_4$).

Reference Example 30

Synthesis of 4-[[N-(3-(trifluoromethyl)benzoyl)glycyl]aminomethyl]piperidine

A 1 M HCl-$Et_2O$ (55 mL) was added to a methanol (40 mL) solution of 1-(tert- butoxycarbonyl)-4-[[N-(3-trifluoromethyl)benzoyl)glycyl]aminomethyl]piperidine (2.29 g, 5.16 mmol). The obtained mixture was stirred at 25 t for 15 hours, and the solvent was removed under reduced pressure. A 2 M aqueous solution of NaOH (100 mL) was added to the mixture, and the resulting mixture was extracted with ethyl acetate (100 mL×3). The extracts were combined, washed with brine (50 mL), dried (over $K_2CO_3$) and concentrated to thereby afford a white solid. The obtained crude solid was purified by column chromatography ($SiO_2$, methanol/dichloromethane/triethylamine=7:6:1) to provide 4-[[N-(3-(trifluoromethyl)benzoyl)glycyl]aminomethyl]piperidine as a white solid (1.27 g, 72%). The purity was determined by RPLC/MS (98%). ESI/MS m/e 344.1 ($M^+$+H, $C_{16}H_{20}N_3O_2$).

Example 1658

Synthesis of 1-[3-(trifluoromethoxy)benzyl]-4-[(N-(3-(trifluoromethyl)benzoyl)glycyl)aminomethyl]piperidine (Compd. No. 927)

An acetonitrile (1.0 mL) solution of 4-[[N-(3-trifluoromethyl)benzoyl]glycyl]aminomethyl]piperidine (19.9 mg, 0.058 mmol) and a (piperidinomethyl)polystyrene (55 mg, 2.7 mmol base/g resin) were added to an acetonitrile (1.0 mL) solution of 3-(trifluoromethoxy)benzyl bromide (12.3 mg, 0.048 mmol). The obtained mixture was stirred at 60° C. for 2.5 hours. Phenyl isocyanate (6.9 mg, 0.048 mmol) was added to the cooled reaction mixture, and the resulting mixture was stirred at 25° C. for 1 hour. The reaction mixture was loaded onto a Varian™ SCX column and washed with methanol (20 mL). The product was eluted with a 2 M methanol solution of $NH_3$ and concentrated to provide 1-[3-(trifluoromethoxy)benzyl]-4-[(N-(3-(trifluoromethyl)benzoyl)glycyl)aminomethyl]piperidine (Compd. No. 927) as an off-white oil (22.8 mg, 91%). The purity was determined by RPLC/MS (99%). ESI/MS m/e 518.1 ($M^+$+H, $C_{24}H_{25}F_6N_3O_3$).

Examples 1659 to 1710

The compounds used in the present invention were synthesized by using the respective corresponding starting materials and reactants according to the method of Example 1658. Data of ESI/MS, yields (mg) and yields (%) are collectively shown in Table 33.

TABLE 33

| Example | Compd. No. | Molecular Formula | ESI/MS m/e | Yield (mg) | Yield (%) |
|---|---|---|---|---|---|
| 1659 | 875 | $C_{23}H_{26}F_3N_3O_2$ | 434 | 6.3 | 40 |
| 1660 | 876 | $C_{23}H_{25}BrF_3N_3O_2$ | 512 | 4.3 | 23 |
| 1661 | 877 | $C_{24}H_{25}F_3N_4O_2$ | 459 | 11.3 | 68 |
| 1662 | 878 | $C_{23}H_{25}F_3N_4O_4$ | 479 | 8.3 | 48 |
| 1663 | 884 | $C_{25}H_{29}F_3N_4O_3$ | 491 | 10.8 | 61 |
| 1664 | 885 | $C_{24}H_{28}F_3N_3O_4S$ | 512 | 9.0 | 49 |
| 1665 | 886 | $C_{23}H_{25}F_4N_3O_2$ | 452 | 12.7 | 78 |
| 1666 | 887 | $C_{24}H_{25}F_6N_3O_2$ | 502 | 13.9 | 77 |
| 1667 | 888 | $C_{23}H_{26}F_3N_3O_3$ | 450 | 11.5 | 71 |
| 1668 | 889 | $C_{29}H_{30}F_3N_3O_2$ | 510 | 12.4 | 68 |
| 1669 | 890 | $C_{27}H_{28}F_3N_3O_2$ | 484 | 12.0 | 69 |
| 1670 | 891 | $C_{23}H_{24}Cl_2F_3N_3O_2$ | 502 | 11.4 | 63 |
| 1671 | 892 | $C_{24}H_{28}F_3N_3O_3$ | 464 | 11.7 | 70 |
| 1672 | 893 | $C_{24}H_{26}F_3N_5O_5$ | 522 | 13.9 | 74 |
| 1673 | 894 | $C_{26}H_{32}F_3N_3O_3$ | 492 | 11.3 | 64 |
| 1674 | 895 | $C_{24}H_{28}F_3N_3O_2$ | 448 | 4.8 | 30 |
| 1675 | 896 | $C_{24}H_{25}F_3N_4O_2$ | 459 | 17.5 | Q |
| 1676 | 897 | $C_{24}H_{26}F_3N_3O_4$ | 478 | 9.2 | 57 |
| 1677 | 898 | $C_{24}H_{26}F_3N_3O_4$ | 478 | 8.9 | 55 |
| 1678 | 899 | $C_{24}H_{28}F_3N_3O_3$ | 464 | 13.7 | 82 |
| 1679 | 900 | $C_{25}H_{28}F_3N_3O_4$ | 492 | 18.6 | Q |

TABLE 33-continued

| Example | Compd. No. | Molecular Formula | ESI/MS m/e | Yield (mg) | Yield (%) |
|---|---|---|---|---|---|
| 1680 | 901 | $C_{29}H_{30}F_3N_3O_2$ | 510 | 13.7 | 75 |
| 1681 | 902 | $C_{23}H_{24}F_3N_5O_6$ | 524 | 12.6 | 67 |
| 1682 | 903 | $C_{25}H_{30}F_3N_3O_4$ | 494 | 14.0 | 79 |
| 1683 | 906 | $C_{25}H_{30}F_3N_3O_2$ | 462 | 11.2 | 67 |
| 1684 | 907 | $C_{31}H_{34}F_3N_3O_2$ | 538 | 19.6 | 75 |
| 1685 | 908 | $C_{30}H_{31}F_3N_4O_3$ | 553 | 30.4 | 76 |
| 1686 | 909 | $C_{30}H_{31}F_3N_4O_3$ | 553 | 12.6 | 63 |
| 1687 | 910 | $C_{23}H_{24}Cl_2F_3N_3O_2$ | 502 | 11.0 | 61 |
| 1688 | 911 | $C_{23}H_{25}ClF_3N_3O_2$ | 468 | 20.2 | 89 |
| 1689 | 912 | $C_{23}H_{24}Br_2F_3N_3O_2$ | 590 | 20.2 | 95 |
| 1690 | 913 | $C_{24}H_{28}F_3N_3O_3$ | 464 | 12.6 | 76 |
| 1691 | 914 | $C_{30}H_{32}F_3N_3O_3$ | 540 | 13.9 | 72 |
| 1692 | 915 | $C_{24}H_{28}F_3N_3O_3$ | 464 | 8.3 | 25 |
| 1693 | 916 | $C_{22}H_{25}F_3N_4O_2$ | 435 | 2.5 | 8 |
| 1694 | 917 | $C_{22}H_{25}F_3N_4O_2$ | 435 | 2.7 | 9 |
| 1695 | 918 | $C_{26}H_{30}F_3N_3O_4$ | 506 | 3.9 | 22 |
| 1696 | 919 | $C_{24}H_{28}F_3N_3O_2$ | 448 | 15.9 | 99 |
| 1697 | 920 | $C_{24}H_{25}F_6N_3O_3$ | 518 | 20.3 | 81 |
| 1698 | 921 | $C_{27}H_{28}F_3N_3O_2$ | 484 | 15.5 | 89 |
| 1699 | 922 | $C_{20}H_{26}F_3N_3O_2$ | 398 | 7.3 | 51 |
| 1700 | 923 | $C_{29}H_{29}ClF_3N_3O_2$ | 544 | 12.5 | 48 |
| 1701 | 928 | $C_{24}H_{25}F_6N_3O_3$ | 518 | 21.4 | 86 |
| 1702 | 929 | $C_{24}H_{28}F_3N_3O_2S$ | 480 | 23.7 | Q |
| 1703 | 930 | $C_{24}H_{28}F_3N_3O_2$ | 448 | 21.3 | 99 |
| 1704 | 931 | $C_{24}H_{25}F_3N_4O_2$ | 459 | 21.4 | 97 |
| 1705 | 932 | $C_{23}H_{24}ClF_3N_4O_4$ | 513 | 15.6 | 63 |
| 1706 | 933 | $C_{24}H_{28}F_3N_3O_2$ | 448 | 16.6 | 77 |
| 1707 | 934 | $C_{22}H_{25}F_3N_4O_2$ | 435 | 18.0 | 43 |
| 1708 | 935 | $C_{23}H_{25}F_3N_4O_4$ | 479 | 15.1 | 65 |
| 1709 | 936 | $C_{23}H_{25}F_3N_4O_4$ | 479 | 15.4 | 67 |
| 1710 | 1615 | $C_{24}H_{25}F_6N_3O_2S$ | 534.2 | 26.3 | 99 |

Note:
Q means "Quantitative".

Example 1711

Synthesis of 1-[4-(dimethylamino)benzyl]-4-[[N-(3-(trifluoromethyl)benzoyl)glycyl]aminomethyl]piperidine (Compd. No. 937)

A methanol (1.0 mL) solution of 4-[[N-(3-(trifluoromethyl)benzoyl)glycyl]aminomethyl]piperidine (20.0 mg, 0.058 mmol) and $NaBH_3CN$ (16.5 mg) were added to a 5% acetic acid solution (1.0 mL) of 4-(dimethylamino)benzaldehyde (30.4 mg, 0.204 mmol), and the resulting mixture was stirred at 60° C. for 19 hours. The solvent was evaporated to provide a solid. Acetonitrile (2.0 mL) and phenyl isocyanate (6.9 mg, 0.048 mmol) were added to the solid, and resulting mixture was stirred at 25° C. for 1 hour. The reaction mixture was loaded onto a Varian™ SCX column and washed with methanol (20 mL). The obtained crude product was eluted with a 2 M $NH_3$-methanol (6 mL), and the eluate was concentrated to thereby afford 1-[4-(dimethylamino)benzyl]-4-[[N-(3-(trifluoromethyl)benzoyl)glycyl]aminomethyl]piperidine (Compd. No. 937) as an off-white oil (13.5 mg, 49%). The purity was determined by RPLC/MS (87%). ESI/MS m/e 477.3 ($M^+$+H, $C_{25}H_{31}F_3N_4O_2$).

Examples 1712 to 1729

The compounds used in the present invention were synthesized by using the respective corresponding starting materials and reactants according to Example 1711. The obtained products, if necessary, were purified by preparative TLC ($SiO_2$) to provide the objective compounds. Data of ESI/MS, yields (mg) and yields (%) are collectively shown in Table 34.

TABLE 34

| Example | Compd. No. | Molecular Formula | ESI/MS m/e | Yield (mg) | Yield (%) |
|---|---|---|---|---|---|
| 1712 | 879 | $C_{24}H_{26}F_3N_3O_4$ | 478 | 13.0 | 62 |
| 1713 | 880 | $C_{24}H_{26}F_3N_3O_4$ | 478 | 16.3 | 78 |
| 1714 | 881 | $C_{23}H_{25}BrF_3N_3O_2$ | 512 | 11.4 | 51 |
| 1715 | 882 | $C_{29}H_{30}F_3N_3O_3$ | 526 | 13.4 | 58 |
| 1716 | 883 | $C_{23}H_{25}ClF_3N_3O_2$ | 468 | 7.9 | 39 |
| 1717 | 904 | $C_{23}H_{26}F_3N_3O_3$ | 450 | 3.3 | 17 |
| 1718 | 905 | $C_{21}H_{23}F_3N_4O_4S$ | 485 | 27.7 | 98 |
| 1719 | 938 | $C_{23}H_{24}ClF_4N_3O_2$ | 486 | 8.6 | 30 |
| 1720 | 939 | $C_{23}H_{24}ClF_3N_4O_4$ | 513 | 11.0 | 37 |
| 1721 | 940 | $C_{23}H_{26}F_3N_3O_3$ | 450 | 5.5 | 21 |
| 1722 | 941 | $C_{24}H_{24}ClF_6N_3O_2$ | 536 | 11.2 | 36 |
| 1723 | 987 | $C_{30}H_{32}F_3N_3O_2$ | 524 | 17.5 | 76 |
| 1724 | 1449 | $C_{25}H_{30}F_3N_3O_2$ | 462 | 21.6 | 80 |
| 1725 | 1450 | $C_{26}H_{32}F_3N_3O_2$ | 476 | 23.5 | 85 |
| 1726 | 1452 | $C_{27}H_{35}F_3N_4O_2$ | 505 | 5.1 | 17 |
| 1727 | 1453 | $C_{26}H_{32}F_3N_3O_3$ | 492 | 22.0 | 77 |
| 1728 | 1454 | $C_{25}H_{30}F_3N_3O_3$ | 478 | 21.4 | 77 |
| 1729 | 1456 | $C_{25}H_{28}F_3N_3O_4$ | 492 | 23.8 | 83 |

Example 1730

Synthesis of 1-[3-hydroxy-4-methoxybenzyl]-4-[[N-(3-(trifluoromethyl)benzoyl)glycyl]aminomethyl]piperidine (Compd. No. 1452)

A 5% acetic acid/methanol (1.0 mL) solution of 4-[[N-(3-(trifluoromethyl)benzoyl)glycyl]aminomethyl]piperidine (20.0 mg, 0.058 mm ol) and 3-hydroxy-4-methoxybenzaldehyde (33 mg) was added to a 5% acetic acid/methanol (1.0 mL) solution of $NaBH_3CN$ (16.5 mg), and the mixture was stirred at 60° C. for 15 hours. The resulting reaction mixture wa's then loaded onto a Varian™ SCX column and washed with methanol (15 mL). The obtained crude product was eluted with a 2 M $NH_3$-methanol (5 mL) and concentrated to thereby afford 1-[3-hydroxy-4-methoxybenzyl]4-[[N-(3-(trifluoromethyl)benzoyl)glycyl]aminomethyl]piperidine (Comp d. No. 1452) (25.8 mg, 92%). The purity was determined by RPLC/MS (91%). ESI/MS m/e 480 ($M^+$+H, $C_{24}H_{28}F_3N_3O_4$).

Examples 1731 to 1733

The compounds used in the present invention were synthesized by using the respective corresponding starting materials and reactants according to the method of Example 1730. The obtained products, if necessary, were purified by preparative TLC to provide the objective compounds. Data of ESI/MS, yields (mg) and yields (%) are collectively shown in Table 35.

TABLE 35

| Example | Compd. No. | Molecular Formula | ESI/MS m/e | Yield (mg) | Yield (%) |
|---|---|---|---|---|---|
| 1731 | 1455 | $C_{24}H_{28}F_3N_3O_4$ | 480 | 24.0 | 86 |
| 1732 | 1647 | $C_{27}H_{34}F_3N_3O_2$ | 490.2 | 23.6 | 96 |
| 1733 | 1649 | $C_{26}H_{32}F_3N_3O_2$ | 476.2 | 23.1 | 97 |

Example 1734

Synthesis of 1-(4-benzylbenzyl)-4-[[N-(3-(trifluoromethyl)benzoyl)glycyl]aminomethyl]piperidine (Compd. No. 926)

A chloroform (1.0 mL) solution of methanesulfonyl chloride (4.2 mg, 0.037 mmol) and a (piperidinomethyl)polystyrene (54 mg, 2.7 mmol base/g resin) were added to a chloroform (1.0 mL) solution of 4-(benzyl)benzyl alcohol (8.7 mg, 0.044 mmol), and the resulting mixture was stirred at 25° C. for 15 hours. 4-[[N-(3-(Trifluoromethyl)benzoyl)glycyl]aminomethyl]piperidine (15.1 mg, 0.044 mmol) and KI (2 mg) were then added to the reaction mixture, and the resulting mixture solution was further stirred at 65° C. for 5 hours. Phenyl isocyanate (5.2 mg) was added to the cooled reaction mixture, and the obtained mixture was stirred at 25° C. for 1 hour. The resulting reaction mixture was loaded onto a Varian™ SCX column and washed with methanol (20 mL). The obtained crude product was eluted with a 2 M methanol solution of $NH_3$ (5 mL) and concentrated to thereby afford 1-(4-benzylbenzyl)-4-[[N-(3-(trifluoromethyl)benzoyl)glycyl]aminomethyl]piperidine (Compd. No. 926) as an off-white oil (5.6 mg, 29%). The purity was determined by RPLC/MS (94%). ESI/MS m/e 524.1 ($M^+$+H, $C_{30}H_{32}F_3N_3O_2$).

Reference Example 31

Synthesis of 4-[[(N-(benzyloxycarbonyl)glycyl) amino]methyl]-1-(tert-butoxycarbonyl)piperidine Triethylamine (2.8 mL, 20 mmol), N-(benzyloxycarbonyl) glycine (3.77 g, 18 mmol), EDCI (3.45 g, 18 mmol) and HOBt (2.43 g, 18 mmol) were added to a chloroform (80 mL) solution of 4-(aminomethyl)-1-(tert-butoxycarbonyl)piperidine (3.54 g, 16.5 mmol). The resulting mixture was stirred at room temperature for 15 hours, and a 2 M aqueous solution of NaOH (100 mL) was then added to the mixture. The organic layer was separated, and the aqueous layer was extracted with dichloromethane (100 mLX 3). The organic layers were combined, dried over anhydrous sodium sulfate, filtered and concentrated. The obtained crude product was purified by column chromatography ($SiO_2$, ethyl acetate) to provide 4-[[N-(benzyloxycarbonyl) glycyl)amino]methyl]-1-(tert-butoxycarbonyl)piperidine as an amorphous solid (6.27 g, 94%).

Reference Example 32

Synthesis of 4-[(glycylamino)methyl]-1-(tert-butoxycarbonyl)piperidine

A methanol (100 mL) solution of 4-[[(N-(benzyloxycarbonyl)glycyl)amino]methyl]-1-(tert-butoxycarbonyl)piperidine (6.26 g, 15.4 mmol) was hydrogenated in the presence of a 5% palladium carbon (620 mg) at room temperature for 7 hours. The catalyst was removed by filtration through Celite, and the filtrate was then concentrated to thereby afford 4-[(glycylamino)methyl]-1-(tert- butoxycarbonyl)piperidine as a solid (3.84 g, 92%).

Reference Example 33

Synthesis of 4-[[(N-(2-amino-5-chlorobenzoyl)glycyl)amino]methyl]-1-(tert-butoxycarbonyl)piperidine Triethylamine (0.75 mL, 5.4 mmol), 2-amino-5-chlorobenzoic acid (840 mg, 4.9 mmol), EDCI (940 mg, 4.9 mmol) and HOBt (660 mg, 4.9 mmol) were added to a chloroform (25 mL) solution of 4-[(glycylamino)methyl]-1-(tert-butoxycarbonyl)piperidine (1.33 g, 4.90 mmol). The resulting mixture was stirred at room temperature for 3 hours, and a 2 M aqueous solution of NaOH (20 mL) was then added to the mixture. The organic layer was separated, and the aqueous layer was extracted with dichloromethane (20 mL×3). The organic layers were combined, dried over anhydrous sodium sulfate, filtered and concentrated. The obtained crude product was purified by column chromatography ($SiO_2$, ethyl acetate) to thereby provide 4-[[(N-(2-amino-5-chlorobenzoyl) glycyl) amino]methyl]-1-(tert-butoxycarbonyl)piperidine as a solid (1.63 g, 78%).

Reference Example 34

Synthesis of 4-[[(N-(2-amino-5-chlorobenzoyl)glycyl)amino]methyl]piperidine

A 4 M dioxane solution of HCl (9.5 mL) was added to a methanol (20 mL) solution of 4-[[(N-(2-amino-5-chlorobenzoyl)glycyl)amino]methyl]-1-(tert-butoxycarbonyl)piperidine (1.63 g, 3.84 mmol), and the resulting mixture was stirred at room temperature for 6 hours. The reaction mixture was concentrated, and a 2 M aqueous solution of NaOH (20 mL) was added to the resulting residue. The obtained mixture was extracted with dichloromethane (20 mLX 3). The organic layers were combined, dried over anhydrous sodium sulfate, filtered and concentrated to thereby afford 4-[[(N-(2-amino-5-chlorobenzoyl)glycyl)amino]methyl]piperidine (1.19 g, 95%). $^1H$ NMR ($CDCl_3$, 270 MHz) δ 1.10-1.76 (m, 4H), 2.55 (td, J=2.4 and 12.2 Hz, 2H), 3.00-3.10 (m, 2H), 3.17 (t, J=6.2 Hz, 2H), 3.48 (s, 2H), 4.03 (d, J=4.9 Hz, 2H), 5.50 (br. s, 2H), 6.11-6.23 (m, 1H), 6.60 (d. J=8.8 Hz, 1H), 6.85-7.02 (m, 1H), 7.15 (dd, J=2.7 and 8.8 Hz, 1H), 7.38 (d, J=2.4 Hz, 1H). ESI/MS m/e 325.2 ($M^+$+H, $C_{15}H_{23}ClN_4O_2$).

Further, 4-[[(N-(2-amino-5-bromobenzoyl)glycyl)amino] methyl]piperidine was synthesized by using the corresponding starting material and reactants according to Reference Examples 33 and 34.951 mg, 64% (two steps); ESI/MS m/e 369.2 ($M^+$+H, $C_{15}H_{21}BrN_4O_2$).

Example 1735

Synthesis of 4-[[(N-(2-(tert-butoxycarbonylamino)-4,5-difluorobenzoyl)glycyl)amino]methyl]-1-(4-chlorobenzyl)piperidine Triethylamine (1.1 mL, 8 mmol), 2-(tert-butoxycarbonylamino)-4,5-difluorobenzoic acid (607 mg, 2.2 mmol), EDCI (422 mg, 2.2 mmol) and HOBt (337 mg, 2.2 mmol) were added to a dichloromethane (20 mL) solution of 1-(4-chlorobenzyl)-4-[(glycylamino)methyl]piperidine dihydrochloride (738 mg, 2 mmol), and the resulting mixture was stirred at room temperature for 14 hours. A 0.6 M aqueous solution of NaOH (50 mL) was then added to the mixture, and the obtained mixture was extracted with dichloromethane (3 times). The organic layers were combined, dried over anhydrous sodium sulfate, filtered and concentrated to thereby provide 4-[[(N-(2-(tert-butoxycarbonylamino)-4,5-difluorobenzoyl) glycyl)amino]methyl]-1-(4-chlorobenzyl)piperidine (1.01 g, 92%). ESI/MS m/e 551.3 ($M^+$+H, $C_{27}H_{33}ClF_2N_4O_4$).

Moreover, 4-[[(N-(2-(tert-butoxycarbonylamino)-5-trifluoromethylbenzoyl)glycyl)amino]methyl]-1-(4 chlorobenzyl)piperidine was synthesized by using the corresponding starting material and reactants according to the above method. 3.03 g, 82%; ESI/MS m/e 583.2 ($M^+$+H, $C_{28}H_{34}ClF_3N_4O_4$).

Reference Example 35

Synthesis of 4-[[(N-(2-amino-5-trifluoromethylbenzoyl) glycyl)amino]methyl]piperidine A 5% formic acid/methanol solution (10 mL) of 1-(4-chlorobenzyl)-4-[[(N-(2-amino-5-trifluoromethylbenzoyl) glycyl)amino]methyl]piperidine (447 mg, 0.93 mmol) and Pd(OH) 2 (60 mg, 0.23 mmol) was stirred at 50° C. for 14 hours. The palladium catalyst was removed by filtration through Celite, and the filtrate was concentrated. A 1 M aqueous solution of NaOH (15 mL) was added to the resulting residue, and the obtained mixture was extracted with ethyl acetate (30 mL×3). The organic layers were combined, dried over anhydrous sodium sulfate, filtered and concentrated. The obtained crude product was purified by column chromatography ($SiO_2$ ethyl acetate/methanol/triethylamine=70:25:5) to thereby afford 4-[[(N-(2-amino-5-trifluoromethylbenzoyl) glycyl)amino]methyl]piperidine (284 mg, 86%). ESI/MS m/e 359.0 ($M^+$+H, $C_{16}H_{21}F_3N_4O_2$). Furthermore, 4-[[(N-(2-amino-4,5-difluorobenzoyl)glycyl)amino]methyl]piperidine, 4-[[N-(2-(tert-butoxycarbonylamino)-5-trifluoromethoxybenzoyl)glycyl]aminomethyl]piperidine and 4-[[(N-(2-(tert-butoxycarbonylamino)-5-trifluoromethoxybenzoyl)glycyl)amino]methyl]piperidine were synthesized by using the respective corresponding starting materials and reactants according to the above method. 4-[[(N-(2-amino-4,5-difluorobenzoyl)glycyl)amino]methyl]piperidine: 564 mg, 89%; ESI/MS m/e 327.2 ($M^+$+H, $C_{15}H_{20}F_2N_4O_2$).

4-[[(N-(2-(tert-butoxycarbonylamino)-5-trifluoromethoxybenzoyl) glycyl)amino]methyl]piperidine: quantitative; $^1$H NMR ($CDCl_3$, 400 MHz) δ 1.10-1.25 (m, 2H), 1.45-1.73 (m, 3H), 1.51 (s, 9H), 2.53-2.64 (m, 2H), 3.04-3.13 (m, 2H), 3.22 (t, J=6.3 Hz, 2H), 4.09 (d, J=4.6 Hz, 2H), 5.91 (br. s, 1H), 7.08 (br, s., 1H), 7.32 (d. J=9.0 Hz, 1H), 7.38 (s, 1H), 8.43 (d, J=9.0 Hz, 1H).

4-[[(N-(2-(tert-butoxycarbonylamino)-4,5-difluorobenzoyl)glycyl)amino]methyl]piperidine: 310 mg, 40%; ESI/MS m/e 427.3 ($M^+$+H, $C_{20}H_{28}F_2N_4O_4$).

4-[[(N-(2-(tert-butoxycarbonylamino)-5-trifluoromethylbenzoyl)glycyl)amino]methyl]piperidine: 1.35 g, 57%; ESI/MS m/e 459.3 ($M^+$+H, $C_{21}H_{29}F_3N_4O_4$).

Example 1736

Synthesis of 4-[[N-(2-amino-5-chlorobenzoyl)glycyl]aminomethyl]-1-(4-ethoxybenzyl)piperidine (Compd. No. 1429) and 1-(4-ethoxybenzyl)-4-[[N-(2-(4-ethoxybenzyl)amino-5-chlorobenzoyl)glycyl]aminomethyl]piperidine (Compd. No. 1433)

A methanol (0.4 mL) solution of sodium cyanoborohydride (140 mmol) was added to a mixture of 4-[[N-(2-amino-5-chlorobenzoyl)glycyl]aminomethyl]piperidine (0.10 mmol) with 4-ethoxybenzaldehyde (0.10 mmol), acetic acid (0.050 mL) and methanol (1.6 mL), and the resulting mixture was stirred at 60° C. for 14 hours. The obtained reaction mixture was loaded onto a Varian™ SCX column and washed with methanol (20 mL). The resulting products were eluted with a 2 M methanol solution of $NH_3$, concentrated and purified by preparative TLC ($SiO_2$, ethyl acetate/methanol) to thereby provide 4-[[N-(2-amino-5-chlorobenzoyl)glycyl] aminomethyl]-1-(4-ethoxybenzyl)piperidine (Compd. No. 1429) and 1-(4-ethoxybenzyl)-4-[[N-(2-(4-ethoxybenzyl) amino-5-chlorobenzoyl)glycyl]aminomethyl]piperidine (Compd. No. 1433).

Compd. No. 1429: 4.5 mg, 20%. The purity was determined by RPLC/MS (95%). ESI/MS m/e 459.2 ($M^+$+H, $C_{24}H_{31}ClN_4O_3$).

Compd. No. 1433: 8.4 mg, 28%. The purity was determined by RPLC/MS (98%). ESI/MS m/e 593.2 ($M^+$+H, $C_{33}H_{41}ClN_4O_4$).

Examples 1737 to 1779

The compounds used in the present invention were synthesized by using respective starting materials and reactants according to the method of Example 1736. Data of ESI/MS, yields (mg) and yields (%) are collectively shown in Table 36.

TABLE 36

| Example | Compd. No. | Molecular Formula | ESI/MS m/e | Yield (mg) | Yield (%) |
|---|---|---|---|---|---|
| 1737 | 1430 | $C_{24}H_{29}ClN_4O_4$ | 473.0 | 3.1 | 13 |
| 1738 | 1431 | $C_{24}H_{31}BrN_4O_3$ | 505.2 | 5.8 | 23 |
| 1739 | 1432 | $C_{24}H_{29}BrN_4O_4$ | 517.0 | 4.1 | 16 |
| 1740 | 1434 | $C_{33}H_{41}BrN_4O_6$ | 637.2 | 9.7 | 30 |
| 1741 | 1435 | $C_{24}H_{31}ClN_4O_2$ | 443.2 | 9.7 | 44 |
| 1742 | 1436 | $C_{25}H_{33}ClN_4O_2$ | 457.2 | 12.5 | 55 |
| 1743 | 1437 | $C_{25}H_{33}ClN_4O_3$ | 473.2 | 9.4 | 40 |
| 1744 | 1438 | $C_{24}H_{31}BrN_4O_2$ | 489.2 | 5.9 | 24 |
| 1745 | 1439 | $C_{25}H_{33}BrN_4O_2$ | 503.2 | 15.2 | 61 |
| 1746 | 1440 | $C_{25}H_{33}BrN_4O_3$ | 519.2 | 11.0 | 43 |
| 1747 | 1441 | $C_{23}H_{29}BrN_4O_2S$ | 507.2 | 9.3 | 37 |
| 1748 | 1442 | $C_{33}H_{41}ClN_4O_2$ | 561.4 | 6.8 | 24 |
| 1749 | 1443 | $C_{35}H_{45}ClN_4O_2$ | 589.4 | 9.8 | 33 |
| 1750 | 1444 | $C_{35}H_{45}ClN_4O_4$ | 621.4 | 9.4 | 30 |
| 1751 | 1445 | $C_{33}H_{41}BrN_4O_2$ | 605.2 | 6.5 | 21 |
| 1752 | 1446 | $C_{35}H_{45}BrN_4O_2$ | 635.2 | 10.7 | 34 |
| 1753 | 1447 | $C_{35}H_{45}BrN_4O_4$ | 665.4 | 12.4 | 37 |
| 1754 | 1448 | $C_{31}H_{37}BrN_4O_2S_2$ | 643.2 | 7.6 | 24 |
| 1755 | 1457 | $C_{24}H_{32}ClN_5O_2$ | 458.2 | 4.5 | 20 |
| 1756 | 1458 | $C_{23}H_{29}ClN_4O_4$ | 461.2 | 6.0 | 26 |
| 1757 | 1459 | $C_{24}H_{32}BrN_5O_2$ | 504.0 | 6.8 | 27 |
| 1758 | 1460 | $C_{23}H_{29}BrN_4O_4$ | 505.0 | 8.0 | 32 |
| 1759 | 1461 | $C_{31}H_{37}ClN_4O_6$ | 597.2 | 5.9 | 20 |
| 1760 | 1462 | $C_{31}H_{37}BrN_4O_6$ | 643.2 | 6.0 | 19 |
| 1761 | 1514 | $C_{26}H_{36}ClN_5O_2$ | 486.2 | 5.5 | 23 |
| 1762 | 1515 | $C_{23}H_{29}ClN_4O_4$ | 463.0 | 5.8 | 25 |
| 1763 | 1516 | $C_{26}H_{36}BrN_5O_2$ | 530.2 | 4.2 | 16 |
| 1764 | 1517 | $C_{23}H_{29}BrN_4O_4$ | 505.0 | 6.5 | 26 |
| 1765 | 1518 | $C_{31}H_{37}ClN_4O_6$ | 597.2 | 4.3 | 14 |
| 1766 | 1519 | $C_{31}H_{37}BrN_4O_6$ | 641.2 | 5.3 | 17 |
| 1767 | 1570 | $C_{23}H_{29}ClN_4O_2S$ | 461.0 | 2.7 | 12 |
| 1768 | 1571 | $C_{31}H_{37}ClN_4O_2S_2$ | 597.2 | 4.9 | 16 |
| 1769 | 1651 | $C_{37}H_{49}BrN_4O_2$ | 663.2 | 5.5 | 17 |
| 1770 | 1652 | $C_{26}H_{35}BrN_4O_2$ | 515.2 | 6.0 | 23 |
| 1771 | 1653 | $C_{36}H_{45}BrN_4O_2$ | 633.2 | 5.0 | 16 |
| 1772 | 1654 | $C_{25}H_{33}BrN_4O_2$ | 501.0 | 6.2 | 25 |
| 1773 | 1655 | $C_{37}H_{49}ClN_4O_2$ | 617.4 | 5.6 | 18 |
| 1774 | 1656 | $C_{26}H_{35}ClN_4O_2$ | 471.2 | 5.9 | 25 |
| 1775 | 1657 | $C_{35}H_{45}ClN_4O_2$ | 589.2 | 4.6 | 16 |
| 1776 | 1658 | $C_{25}H_{33}ClN_4O_2$ | 457.2 | 5.3 | 23 |
| 1777 | 1785 | $C_{26}H_{33}F_3N_4O_2$ | 491.2 | 4.7 | 12.8 |
| 1778 | 1786 | $C_{25}H_{29}F_3N_4O_3$ | 491.2 | 3.7 | 10.1 |
| 1779 | 1804 | $C_{25}H_{32}F_2N_4O_2$ | 459.2 | 3.3 | 9.6 |

Example 1780

Synthesis of 4-[[N-(2-amino-5-trifluoromethoxybenzoyl)glycyl]aminomethyl]-1-(4-isopropylbenzyl) piperidine (Compd. No. 1903)

Acetic acid (10 mL) was added to a mixture of 4-[[N-(2-(tert-butoxycarbonylamino)-5-(trifluoromethoxy)benzoyl) glycyl]aminomethyl]piperidine (0.050 mmol) with 4-isopropylbenzaldehyde (0.060 mmol), $NaH_3CN$ (0.15 mmol) and methanol (1.3 mL), and the resulting mixture was stirred at 60° C. for 8 hours, cooled to room temperature, then loaded onto a Varian™ SCX column and washed with methanol (10 mL). The obtained crude product was eluted with a 2 M methanol solution of $NH_3$ (5 mL) and concentrated. A 4 M dioxane solution of HCl (2 mL) was then added to the resulting residue, and the obtained solution was stirred at room temperature overnight, concentrated and then purified by preparative TLC to provide 4-[[N-(2-amino-5-trifluoromethoxybenzoyl)glycyl]aminomethyl]-1-(4-isopropylbenzyl)piperidine (Compd. No. 1903) (6.6 mg, 26%). The purity was determined by RPLC/MS (93%). ESI/MS m/e 507 ($M^+$+H, $C_{26}H_{33}F_3N_4O_3$).

Examples 1781 to 1783

The compounds used in the present invention were synthesized by using the respective corresponding starting materials and reactants according to the method of Example 1780. Data of ESI/MS, yields (mg) and yields (%) are collectively shown in Table 37.

TABLE 37

| Example | Compd. No. | Molecular Formula | ESI/MS m/e | Yield (mg) | Yield (%) |
|---|---|---|---|---|---|
| 1781 | 1904 | $C_{26}H_{33}F_3N_4O_3$ | 507 | 9.6 | 37.9 |
| 1782 | 1917 | $C_{25}H_{31}F_3N_4O_5$ | 525.2 | 1.2 | 3.1 |
| 1783 | 1918 | $C_{24}H_{29}F_3N_4O_4$ | 495.2 | 2.8 | 7.5 |

Example 1784

Synthesis of 4-[[N-(2-amino-4,5-difluorobenzoyl) glycyl]aminomethyl]-1-(5-bromo-2-ethoxybenzyl) piperidine (Compd. No. 2052)

$NaBH_3CN$ (0.25 mmol) was added to a mixture of 4-[[N-(2-(tert-butoxycarbonylamino)-4,5-difluorobenzoyl)glycyl)]aminomethyl]piperidine (0.050 mmol) with 5-bromo-2-ethoxybenzaldehyde (0.15 mmol), methanol (1.2 mL) and acetic acid (0.030 mL). The resulting mixture was stirred at 50° for 13 hours, cooled to room temperature, loaded onto a Varian™ SCX column and washed with methanol (5 mL×3). The obtained crude product was eluted with a 2 M methanol solution of $NH_3$ (5 mL) and concentrated. Dichloromethane (1 mL) and trifluoroacetic acid (0.50 mL) were added to the resulting residue, and the mixture was stirred at room temperature for 10 minutes. The reaction mixture was concentrated, and the residue was dissolved in methanol. The resulting solution was loaded onto a Varian™ SCX column and washed with methanol (5 mL). The obtained crude product was eluted with a 2 M methanol solution of $NH_3$ (5 mL), concentrated and purified by preparative TLC ($SiO_2$, ethyl acetate/methanol=10:1) to provide 4-[[N-(2-amino-4,5-difluorobenzoyl)glycyl]aminomethyl]-1-(5-bromo-2-ethoxybenzyl)piperidine (Compd. No. 2052) (10.2 mg, 38%). The purity was determined by RPLC/MS (96%). ESI/MS m/e 539.2 ($M^+$+H, $C_{24}H_{29}BrF_2N_4O_3$).

Examples 1785 to 1792

The compounds used in the present invention were synthesized by using the respective corresponding starting materials and reactants according to the method of Example 1784. Data of ESI/MS, yields (mg) and yields (%) are collectively shown in Table 38.

TABLE 38

| Example | Compd. No. | Molecular Formula | ESI/MS m/e | Yield (mg) | Yield (%) |
|---|---|---|---|---|---|
| 1785 | 2053 | $C_{30}H_{34}F_2N_4O_4$ | 553.4 | 12.7 | 46 |
| 1786 | 2054 | $C_{27}H_{30}F_2N_4O_3$ | 497.2 | 13.7 | 55 |
| 1787 | 2055 | $C_{23}H_{28}F_2N_4O_4$ | 463.2 | 10.1 | 44 |
| 1788 | 2056 | $C_{22}H_{24}BrF_3N_4O_2$ | 515.2 | 7.7 | 30 |
| 1789 | 2057 | $C_{23}H_{27}BrF_2N_4O_3$ | 527.0 | 8.6 | 33 |
| 1790 | 2058 | $C_{24}H_{30}F_2N_4O_4$ | 477.2 | 6.4 | 27 |
| 1791 | 2059 | $C_{28}H_{30}F_2N_4O_3$ | 509.4 | 6.7 | 26 |
| 1792 | 2060 | $C_{25}H_{32}F_2N_4O_5$ | 507.2 | 7.2 | 28 |

Example 1793

Synthesis of 4-[[N-(2-amino-4,5-difluorobenzoyl) glycyl]aminomethyl]-1-(3,4-diethoxybenzyl)-piperidine (Compd. No. 2065)

$NaBH_3CN$ (0.25 mmol) was added to a mixture of 4-[[N-(2-(tert-butoxycarbonylamino)-4,5-difluorobenzoyl)glycyl] aminomethyl]piperidine (0.050 mmol) with 3,4-diethoxybenzaldehyde (0.15 mol), methanol (1.2 mL) and acetic acid (0.050 mL), and the obtained mixture was stirred at 50° C. overnight, cooled to room temperature, loaded onto a Varian™ SCX column and washed with methanol (5 mL×2). The obtained product was eluted with a 2 M methanol solution of $NH_3$ (5 mL) and concentrated. Dichloromethane (2 mL) and phenyl isocyanate (0.10 mL) were added to the obtained residue, and the resulting mixture was stirred at room temperature for 1 hour, loaded onto a Varian™ SCX column and washed with methanol (5 mL). The obtained product was eluted with a 2 M methanol solution of $NH_3$ (5 mL) and concentrated. The residue was dissolved in methanol (0.25 mL); and a 4 M dioxane solution of HCl (0.125 mL) was added to the resulting solution. The obtained mixture was stirred at room temperature overnight and concentrated. The resulting residue was dissolved in methanol, loaded onto a Varian™ SCX column and washed with methanol (5 mL×2). The obtained crude product was eluted with a 2 M methanol solution of $NH_3$ (5 mL) and concentrated to thereby afford 4-[[N-(2-amino-4,5-difluorobenzoyl)glycyl]aminomethyl]-1-(3,4-diethoxybenzyl)piperidine (Compd. No. 2065) (21.2 mg, 84%). The purity was determined by RPLC/MS (97%). ESI/MS m/e 505.2 ($M^+$+H, $C_{26}H_{34}F_2N_4O_4$).

Examples 1794 to 1808

The compounds used in the present invention were synthesized by using the respective corresponding raw materials and reactants according to the method of Example 1793. Data of ESI/MS, yields (mg) and yields (%) are collectively shown in Table 39.

TABLE 39

| Example | Compd. No. | Molecular Formula | ESI/MS m/e | Yield (mg) | Yield (%) |
|---|---|---|---|---|---|
| 1794 | 2061 | $C_{23}H_{27}F_3N_4O_2$ | 449.2 | 12.6 | 56 |
| 1795 | 2062 | $C_{23}H_{27}F_3N_4O_3$ | 465.2 | 19.7 | 85 |
| 1796 | 2063 | $C_{25}H_{32}F_2N_4O_4$ | 491.2 | 19.8 | 81 |
| 1797 | 2064 | $C_{22}H_{24}BrF_3N_4O_2$ | 515.2 | 17.5 | 68 |
| 1798 | 2066 | $C_{29}H_{32}F_2N_4O_3$ | 523.2 | 18.0 | 69 |
| 1799 | 2067 | $C_{26}H_{34}F_2N_4O_2$ | 473.2 | 21.9 | 93 |
| 1800 | 2068 | $C_{22}H_{24}ClF_3N_4O_2$ | 469.2 | 11.2 | 48 |
| 1801 | 2069 | $C_{24}H_{30}F_2N_4O_3$ | 461.4 | 20.2 | 88 |
| 1802 | 2070 | $C_{23}H_{27}BrF_2N_4O_3$ | 527.2 | 17.7 | 67 |
| 1803 | 2071 | $C_{24}H_{30}F_2N_4O_4$ | 477.2 | 10.9 | 46 |
| 1804 | 2072 | $C_{25}H_{32}F_2N_4O_3$ | 475.2 | 19.3 | 81 |
| 1805 | 2073 | $C_{29}H_{32}F_2N_4O_3$ | 523.2 | 22.8 | 87 |
| 1806 | 2074 | $C_{29}H_{32}F_2N_4O_4$ | 539.2 | 22.5 | 84 |
| 1807 | 2075 | $C_{23}H_{27}F_3N_4O_3$ | 465.2 | 14.9 | 64 |
| 1808 | 2076 | $C_{22}H_{24}F_4N_4O_2$ | 453.2 | 21.9 | 97 |

Example 1809

Synthesis of 4-[[N-(2-amino-4,5-difluorobenzoyl) glycyl]aminomethyl]-1-(2-hydroxy-3-methylbenzyl) piperidine (Compd. No. 2106)

$NaBH_3CN$ (0.40 mmol) was added to a mixture of 4-[[N-(2-(tert-butoxycarbonylamino)-4,5-difluorobenzoyl)glycyl] aminomethyl]piperidine (0.050 mmol) with 2-hydroxy-3-methylbenzaldehyde (0.25 mmol), methanol (1.0 mL) and acetic acid (0.040 mL). The resulting mixture was stirred at 50 overnight, cooled to room temperature, loaded onto a Varian™ SCX column and washed with methanol (5 mL×2). The obtained crude product was eluted with a 2 M methanol solution of $NH_3$ (5 mL) and concentrated. The residue was dissolved in ethyl acetate/methanol=5:1 (1 mL), loaded onto a Varian™ SCX column, eluted with ethyl acetate/methanol=5:1 (5 mL) and concentrated. The residue was dissolved in methanol (2 mL), and a 4 M dioxane solution of HCl (0.50 mL) was added to the resulting solution. The obtained mixture was stirred at room temperature overnight and concentrated. The residue was dissolved in methanol, loaded onto a Varian™ SCX column and washed with methanol (5 mL×2). The obtained crude product was eluted with a 2 M methanol solution of $NH_3$ (5 mL), concentrated and purified by preparative TLC to thereby provide 4-[[N-(2-amino-4,5-difluorobenzoyl) glycyl]aminomethyl]-1-(2-hydroxy-3-methylbenzyl)piperidine (Compd. No. 2106). The purity was determined by RPLC/MS (97%). ESI/MS m/e 447.0 ($M^+$+H, $C_{23}H_{28}F_2N_4O_3$).

Examples 1810 to 1823

The compounds used in the present invention were synthesized by using the respective corresponding starting materials and reactants according to the method of Example 1809. Data of ESI/MS, yields (mg) and yields (%) are collectively shown in Table 40.

TABLE 40

| Example | Compd. No. | Molecular Formula | ESI/MS m/e | Yield (mg) | Yield (%) |
|---|---|---|---|---|---|
| 1810 | 2077 | $C_{22}H_{25}ClF_2N_4O_3$ | 467.2 | 3.7 | 16 |
| 1811 | 2078 | $C_{24}H_{30}F_2N_4O_4$ | 477.2 | 1.9 | 8 |
| 1812 | 2079 | $C_{30}H_{34}F_2N_4O_4$ | 553.4 | 4.8 | 17 |
| 1813 | 2080 | $C_{22}H_{25}ClF_2N_4O_3$ | 467.2 | 13.5 | 58 |
| 1814 | 2081 | $C_{22}H_{25}ClF_2N_4O_3$ | 467.2 | 13.8 | 59 |
| 1815 | 2082 | $C_{23}H_{28}F_2N_4O_4$ | 463.2 | 9.6 | 42 |
| 1816 | 2105 | $C_{23}H_{28}F_2N_4O_4$ | 463.2 | ND | ND |
| 1817 | 2106 | $C_{23}H_{28}F_2N_4O_3$ | 447.0 | ND | ND |
| 1818 | 2107 | $C_{20}H_{23}BrF_2N_4O_2S$ | 503.1 | ND | ND |
| 1819 | 2108 | $C_{25}H_{28}F_2N_4O_2S$ | 487.2 | ND | ND |
| 1820 | 2109 | $C_{20}H_{23}BrF_2N_4O_3$ | 487.0 | ND | ND |
| 1821 | 2110 | $C_{22}H_{28}F_2N_4O_3$ | 435.1 | ND | ND |
| 1822 | 2111 | $C_{22}H_{24}ClF_3N_4O_2$ | 469.0 | ND | ND |
| 1823 | 2112 | $C_{24}H_{29}BrF_2N_4O_4$ | 557.0 | ND | ND |

Note:
ND means "Not Determined".

Example 1824

Synthesis of 4-[[N-(2-amino-4,5-difluorobenzoyl) glycyl]aminomethyl]-1-(3-amino-4-methylbenzyl) piperidine (Compd. No. 2114)

$NaBH_3CN$ (0.50 mmol) was added to a mixture of 4-[[N-(2-(tert-butoxycarbonylamino)-4,5-difluorobenzoyl)glycyl] aminomethyl]piperidine (0.050 mmol) with 4-methyl-3-nitrobenzaldehyde (0.25 mmol), methanol (1.2 mL) and acetic acid (0.050 mL). The resulting mixture was stirred at 50° C. overnight, cooled to room temperature, loaded onto a Varian™ SCX column and washed with methanol (5 mL×2). The obtained product was eluted with a 2 M methanol solution of $NH_3$ (5 mL) and concentrated. The residue was dissolved in ethyl acetate/methanol=2:1 (2 mL), loaded onto a Varian™ Si column, eluted with ethyl acetate/methanol=2:1 (6 mL) and concentrated. The obtained residue was dissolved in methanol (1 mL), and a 4 M dioxane solution of HCl (0.50 mL) was added to the resulting solution. The obtained mixture was stirred at room temperature overnight and concentrated. The resulting residue was dissolved in methanol, loaded onto a Varian™ SCX column, washed with methanol (5 mL×2), then eluted with a 2 M methanol solution of $NH_3$ (5 mL) and concentrated to thereby afford 4-[[N-(2-amino-4,5-difluorobenzoyl)glycyl]aminomethyl]-1-(4-methyl-3-nitrobenzyl)piperidine.

A mixture of the resulting 4-[[N-(2-amino-4,5-difluorobenzoyl)glycyl]aminomethyl]-1-(4-methyl-3-nitrobenzyl) piperidine with a 5% palladium carbon (15 mg) and methanol (2 mL) was stirred at room temperature under a hydrogen atmosphere for 4 hours. The palladium catalyst was removed by filtration through Celite, and the filtrate was concentrated and purified by preparative TLC ($SiO_2$, ethyl acetate/methanol=3:1) to thereby provide 4-[[N-(2-amino-4,5-difluorobenzoyl)glycyl]aminomethyl]-1-(3-amino-4-methylbenzyl)piperidine (Compd. No. 2114) (2.9 mg, 13%). The purity was determined by RPLC/MS (100%). ESI/MS m/e 446.1 ($M^+$+H, $C_{23}H_{29}F_2N_5O_2$).

Example 1825

Synthesis of 4-[[N-(2-amino-4,5-difluorobenzoyl) glycyl]aminomethyl]-1-(3-amino-4-methoxybenzyl) piperidine (Compd. No. 2113)

The title compound 4-[[N-(2-amino-4,5-difluorobenzoyl) glycyl]aminomethyl]-1-(3-amino-4-methoxybenzyl)piperidine (Compd. No. 2113) was synthesized by using the corresponding starting material and reactants according to the method of Example 1824. 4.6 mg, 20% yield; ESI/MS m/e 462.2 ($M^+$+H, $C_{23}H_{29}F_2N_5O_3$).

Example 1826

Synthesis of 1-(3-amino-4-hydroxybenzyl)-4-[[N-(2-(tert-butoxycarbonylamino)-4,5-difluorobenzoyl)glycyl]aminomethyl]piperidine A methanol (3.2 mL) solution of $NaBH_3CN$ (1.58 mmol) was added to a mixture of 4-[[N-(2-(tert-butoxycarbonylamino)-4,5-difluorobenzoyl)glycyl]aminomethyl]piperidine (0.35 mmol) with 4-hydroxy-3-nitrobenzaldehyde-(1.22 mmol), methanol (3.8 mL) and acetic acid (0.175 mL), and the resulting mixture was stirred at 50° C. overnight, cooled to room temperature, loaded onto a Varian™ SCX column and washed with methanol (5 mL×2). The obtained crude product was eluted with a 2 M methanol solution of $NH_3$ (5 mL) and concentrated. The residue was dissolved in ethyl acetate/methanol=5:1, loaded onto a Varian™ Si column, eluted with ethyl acetate/methanol=5:1 (10 mL) and concentrated to thereby afford 4-[[N-(2-(tert-butoxycarbonylamino)-4,5-difluorobenzoyl)glycyl]aminomethyl]-1-(4-hydroxy-3-nitrobenzyl)piperidine (175 mg, 87%).

A mixture of the resulting 4-[[N-(2-(tert-butoxycarbonylamino)-4,5-difluorobenzoyl)glycyl]aminomethyl]-1-(4-hydroxy-3-nitrobenzyl)piperidine with a 10% palladium carbon (45 mg) and methanol (5 mL) was stirred at room temperature under a hydrogen atmosphere for 4 hours. The palladium catalyst was removed by filtration, and the filtrate was concentrated to provide 1-(3-amino-4-hydroxybenzyl)-4-[[N-(2-(tert-butoxycarbonylamino)-4,5-difluorobenzoyl)glycyl]aminomethyl]piperidine (100 mg, 60%).

Example 1827

Synthesis of 4-[[N-(2-amino-4,5-difluorobenzoyl)glycyl]aminomethyl]-1-(3-amino-4-hydroxybenzyl)piperidine (Compd. No. 2141)

A 4 M dioxane solution of HCl (0.50 mL) was added to a methanol (1 mL) solution of 1-(3-amino-4-hydroxybenzyl)-4-[[N-(2-(tert-butoxycarbonylamino)-4,5-difluorobenzoyl)glycyl]aminomethyl]piperidine (20.0 mg, 0.035 mmol), and the resulting mixture was stirred at room temperature overnight and concentrated. The obtained residue was then dissolved in methanol, loaded onto a Varian™ SCX column, washed with methanol (5 mL×2), eluted with a 2 M methanol solution of $NH_3$ (5 mL) and concentrated to thereby afford 4-[[N-(2-amino-4,5-difluorobenzoyl)glycyl]aminomethyl]-1-(3-amino-4-hydroxybenzyl)piperidine (Compd. No. 2141) (17.6 mg, quantitative). The purity was determined by RPLC/MS (85%). ESI/MS m/e 448.3 ($M^+$+H, $C_{22}H_{27}F_2N_5O_3$).

Examples 1828 to 1831

The compounds used in the present invention were synthesized by using the respective corresponding starting materials and reactants according to the methods of Examples 1826 and 1827. The obtained products, if necessary, were purified by preparative TLC to provide the objective compounds. Data of ESI/MS and yields (mg) and yields (%) in the final steps are collectively shown in Table 41.

TABLE 41

| Example | Compd. No. | Molecular Formula | ESI/MS m/e | Yield (mg) | Yield (%) |
|---|---|---|---|---|---|
| 1828 | 2140 | $C_{23}H_{27}F_2N_5O_4$ | 476.3 | 6.7 | 28.4 |
| 1829 | 2144 | $C_{24}H_{30}F_3N_5O_3$ | 494.2 | 18.7 | 82.0 |
| 1830 | 2145 | $C_{23}H_{28}F_3N_5O_3$ | 480.3 | 19.8 | 63.7 |
| 1831 | 2146 | $C_{24}H_{28}F_3N_5O_4$ | 508.3 | 13.5 | 81.7 |

Example 1832

Synthesis of 1-(3-amino-4-chlorobenzyl)-4-[[N-(2-(tert-butoxycarbonylamino)-4,5-difluorobenzoyl)glycyl]aminomethyl]piperidine A methanol (1.3 mL) solution of $NaBH_3CN$ (0.63 mmol) was added to a mixture of 4-[[N-(2-(tert-butoxycarbonylamino)-4,5-difluorobenzoyl)glycyl]aminomethyl]piperidine (0.14 mmol) with 4-dichloro-3-nitrobenzaldehyde (0.50 mmol), methanol (1.5 mL) and acetic acid (0.070 mL). The resulting mixture was stirred at 50° C. overnight, cooled to room temperature, loaded onto a Varian™ SCX column and washed with methanol. The obtained product was eluted with a 2 M methanol solution of $NH_3$ and concentrated. The residue was dissolved in ethyl acetate/methanol=5:1, loaded onto a Varian™ Si column, eluted with ethyl acetate/methanol=5:1 (6 mL) and concentrated to there by provide 4-[[N-(2-(tert-butoxycarbonylamino)-4,5-difluorobenzoyl)glycyl]aminomethyl]-1-(4-chloro-3-nitrobenzyl)piperidine (44 mg, 53%). ESI/MS m/e 596.3 ($M^+$+H).

A mixture of 4-[[N-(2-(tert-butoxycarbonylamino)-4,5-difluorobenzoyl)glycyl]aminomethyl]-1-(4-chloro-3-nitrobenzyl)piperidine (121 mg, 0.20 mmol) with a 10% palladium carbon (85 mg), ethyl acetate (10 mL) and methanol (1 mL) was stirred at room temperature under a hydrogen atmosphere for 19 hours. The palladium catalyst was removed by filtration, and the filtrate was concentrated to thereby afford 1-(3-amino-4-chlorobenzyl)-4-[[N-(2-(tert-butoxycarbonylamino)-4,5-difluorobenzoyl)glycyl]aminomethyl]piperidine (78 mg, 68%).

Example 1833

Synthesis of 1-(3-amino-4-chlorobenzyl)-4-[[N-(2-amino-4,5-difluorobenzoyl)glycyl]aminomethyl]piperidine (Compd. No. 2142)

The title compound 1-(3-amino-4-chlorobenzyl)-4-[[N-(2-amino-4,5-difluorobenzoyl)glycyl]aminomethyl]piperidine (Compd. No. 2142) was synthesized by using the corresponding starting material and reactants according to the method of Example 1827. 13.7 mg, 98%. The purity was determined by RPLC/MS (83%). ESI/MS m/e 466.2 ($M^+$+H, $C_{22}H_{26}ClF_2N_5O_2$).

Example 1834

Synthesis of 1-(3-acetylamino-4-hydroxybenzyl)-4-[[N-(2-amino-4,5-difluorobenzoyl)glycyl]aminomethyl]piperidine (Compd. No. 2148).

A dichloromethane (0.12 mL) solution of acetic anhydride (0.12 mmol) was added to a mixture of 1-(3-amino-4-hydroxybenzyl)-4-[[N-(2-(tert-butoxycarbonylamino)-4,5-difluorobenzoyl)glycyl]aminomethyl]piperidine (27 mg, 0.049 mmol) with a (piperidinomethyl)polystyrene (2.7 mmol/g, 60 mg, 0.15 mmol) and dichloromethane (2 mL), and the resulting mixture was stirred at room temperature for 3 hours. The mixture was loaded onto a Varian™ SCX column and washed with methanol. The obtained crude product was eluted with a 2 M methanol solution of $NH_3$ and concentrated. The residue was dissolved in ethyl acetate/methanol=5:1, loaded onto a Varian™ Si column, eluted with ethyl acetate/methanol=5:1 (6 mL) and concentrated to thereby provide 1-(3-acetylamino-4-hydroxybenzyl)-4-[[N-(2-(tert-butoxycarbonylamino)-4,5-difluorobenzoyl)glycyl]aminomethyl]piperidine (30 mg, quantitative). ESI/MS m/e 590.4 ($M^++H$, $C_{29}H_{37}N_5O_6$).

A 4 M dioxane solution of HCl (0.50 mL) was added to a methanol (1 mL) solution of the 1-(3-acetylamino-4-hydroxybenzyl)-4-[[N-(2-(tert-butoxycarbonylamino)-4,5-difluorobenzoyl)glycyl]aminomethyl]piperidine obtained above, and the resulting solution was stirred at room temperature overnight and concentrated. The resulting residue was then dissolved in methanol, loaded onto a Varian™ SCX column, washed with methanol (5 mL×2), eluted with a 2 M methanol solution of $NH_3$ (5 mL), concentrated and then purified by preparative TLC ($SiO_2$, ethyl acetate/methanol=3:2) to thereby afford 1-(3-acetylamino-4-hydroxybenzyl)-4-[[N-(2-amino-4,5-difluorobenzoyl)glycyl]aminomethyl]piperidine (Compd. No. 2148) (2.3 mg, 9.2%). The purity was determined by RPLC/MS (98%). ESI/MS m/e 490.3 ($M^++H$, $C_{24}H_{29}F_2N_5O_4$).

Examples 1835 to 1839

The compounds used in the present invention were synthesized by using the respective corresponding starting materials and reactants according to the methods of Examples 1826 and 1834. Data of ESI/MS and yields (mg) and yields (%) in the final steps are collectively shown in Table 42.

TABLE 42

| Example | Compd. No. | Molecular Formula | ESI/MS m/e | Yield (mg) | Yield (%) |
|---|---|---|---|---|---|
| 1835 | 2143 | $C_{25}H_{29}F_2N_5O_5$ | 518.3 | 4.8 | 45 |
| 1836 | 2147 | $C_{25}H_{31}F_2N_5O_4$ | 504.3 | 3.0 | 23 |
| 1837 | 2154 | $C_{26}H_{32}F_3N_5O_4$ | 536.4 | 4.1 | 66 |
| 1838 | 2155 | $C_{25}H_{30}F_3N_5O_4$ | 522.3 | 5.5 | 71 |
| 1839 | 2156 | $C_{26}H_{30}F_3N_5O_6$ | 550.3 | 7.0 | 78 |

Example 1840

Synthesis of 4-[[N-(2-amino-4,5-difluorobenzoyl)glycyl]aminomethyl]-1-(3-methylamino-4-hydroxybenzyl)piperidine (Compd. No. 2160)

A methanol (0.2 mL) solution of $NaBH_3CN$ (7.0 mg) was added to a mixture of 4-[[N-(2-(tert-butoxycarbonylamino)-4,5-difluorobenzoyl)glycyl]aminomethyl]-1-(3-amino-4-hydroxy)piperidine (20.4 mg, 0.037 mmol) with a 37% HCHO solution (3.0 mg, 0.037 mmol), acetic acid (0.1 mL) and methanol (1.3 mL), and the resulting mixture was stirred at 60° C. overnight, cooled to room temperature, loaded onto a Varian™ SCX column and washed with methanol (5 mLX 2). The obtained crude product was eluted with a 2 M methanol solution of $NH_3$ (8 mL) and concentrated to thereby provide 4-[[N-(2-tert-butoxycarbonylamino)-4,5- difluorobenzoyl]glycyl]aminomethyl]-1-(3-methylamino-4-hydroxybenzyl)piperidine.

A 4 M dioxane solution of HCl (1.0 mL) was added to a methanol (1.0 mL) solution of the 4-[[N-(2-tert-butoxycarbonylamino)-4,5-difluorobenzoyl]glycyl]aminomethyl]-1-(3-methylamino-4-hydroxybenzyl)piperidine obtained above, and the resulting mixture was stirred at room temperature for 3 hours and concentrated. The obtained residue was then dissolved in methanol (1 mL), loaded onto a Varian™ SCX column, washed with methanol (5 mL×2), eluted with a 2 M methanol solution of $NH_3$ (8 mL), concentrated and then purified by preparative TLC ($SiO_2$) to thereby afford 4-[[N-(2-amino-4,5-difluorobenzoyl)glycyl]aminomethyl]-1-(3-methylamino-4-hydroxybenzyl)piperidine (Compd. No. 2160) (3.4 g, 20%). The purity was determined by RPLC/MS (96%). ESI/MS m/e 462.4 ($M^++H$, $C_{23}H_{29}F_2N_5O_3$).

Examples 1841 to 1844

The compounds used in the present invention were synthesized by using the respective corresponding starting materials and reactants according to the methods of Examples 1826 and 1840. Data of ESI/MS and yields (mg) and yields (%) in the final steps are collectively shown in Table 43.

TABLE 43

| Example | Compd. No. | Molecular Formula | ESI/MS m/e | Yield (mg) | Yield (%) |
|---|---|---|---|---|---|
| 1841 | 2159 | $C_{24}H_{31}F_2N_5O_3$ | 476.3 | 7.6 | 48 |
| 1842 | 2161 | $C_{23}H_{28}ClF_2N_5O_2$ | 480.3 | 7.3 | 45 |
| 1843 | 2162 | $C_{25}H_{32}F_3N_5O_3$ | 508.4 | 6.0 | 24 |
| 1844 | 2163 | $C_{24}H_{30}F_3N_5O_3$ | 494.3 | 4.3 | 15 |

Example 1845

Synthesis of 4-[[N-(2-amino-4,5-difluorobenzoyl)glycyl]aminomethyl]-1-(benzo[c]furazan-5-yl)piperidine (Compd. No. 2130)

A mixture of 4-[[N-(2-(tert-butoxycarbonylamino)-4,5-difluorobenzoyl)glycyl]aminomethyl]piperidine (0.050 mmol) with 5-(bromomethyl)benzo[c]furazan (0.75 mL), a (piperidinomethyl)polystyrene (2.6-2.8 mmol/g, 60 mg, 0.15 mmol), methanol (0.2 mL), acetonitrile (1.0 mL) and chloroform (0.50 mL) was stirred at 50° C. overnight, cooled to room temperature, loaded onto a Varian™ SCX column and washed with methanol (5 mL×2). The obtained crude product was eluted with a 2 M methanol solution of $NH_3$ (5 mL) and concentrated. Chloroform (1.5 mL) and phenyl isocyanate (0.075 mL) were added to the residue, and the resulting mixture was stirred at room temperature for 1 hour, loaded onto a Varian™ SCX column and washed with methanol (5 mLX 2). The obtained crude product was eluted with a 2 M methanol solution of $NH_3$ (5 mL) and concentrated. The resulting residue was dissolved in methanol (1 mL), and a 4 M dioxane solution of HCl (0.50 ml) was added to the obtained solution. The resulting mixture was stirred at room temperature overnight and concentrated. The residue was then dissolved in methanol, loaded onto a Varian™ SCX column, washed with methanol (5 mL×2), eluted with a 2 M methanol solution of $NH_3$ (5 mL), concentrated and then purified by preparative TLC ($SiO_2$, ethyl acetate/methanol=5:1) to provide 4-[[N-(2-amino-4,5-difluorobenzoyl)glycyl]aminomethyl]-1-(benzo[c]furazan-5-yl)piperidine (Compd. No. 2130) (3.6 mg, 16%). The purity was determined by RPLC/MS (87%). ESI/MS m/e 459.3 ($M^++H$, $C_{22}H_{24}F_2N_6O_3$).

Example 1846

Synthesis of 4-[[N-(2-amino-4,5-difluorobenzoyl) glycyl]aminomethyl]-1-(3,5-dimethylisoxazol-4-yl) piperidine (Compd. No. 2131)

The title compound 4-[[N-(2-amino-4,5-difluorobenzoyl) glycyl]aminomethyl]-1-(3,5-dimethylisoxazol-4-yl)piperidine (Compd. No. 2131) was synthesized by using the corresponding starting material and reactants according to the method of Example 1845. 3.8 mg, 18% yield; ESI/MS m/e 436.2 ($M^++H$, $C_{21}H_{27}F_2N_5O_3$).

Example 1847

Synthesis of 4-[[N-(2-amino-5-chlorobenzoyl) glycyl]aminomethyl]-1-[4-(trifluoromethylthio)benzyl] piperidine (Compd. No. 1616)

A mixture of 4-[[N-(2-amino-5-chlorobenzoyl)glycyl] aminomethyl]piperidine (16.2 mg, 0.050 mmol) with 4-(trifluoromethylthio)benzyl chloride (20.3 mg, 0.075 mmol), acetonitrile (1.0 mL) and chloroform (0.56 mL) was stirred at 60° C. for 15 hours, cooled, then loaded onto a VarianM SCX column and washed with methanol (15 mL). The obtained crude product was eluted with a 2 M methanol solution of $NH_3$ (5 mL) and concentrated to thereby afford 4-[[N-(2-amino-5-chlorobenzoyl) glycyl]aminomethyl]-1-[4-(trifluoromethylthio)benzyl]piperidine (Compd. No. 1616) (21.9 mg, 85%). The purity was determined by RPLC/MS (96%). ESI/MS m/e 545.2 ($M^++H$, $C_{23}H_{26}ClF_3N_4O_2S$).

Examples 1848 to 1868

The compounds used in the present invention were synthesized by using the respective corresponding starting materials and reactants according to the method of Example 1847. The obtained products, if necessary, were purified by preparative TLC to provide the objective compounds. Data of ESI/MS and yields (mg) and yields (%) in the final steps are collectively shown in Table 44.

TABLE 44

| Example | Compd. No. | Molecular Formula | ESI/MS m/e | Yield (mg) | Yield (%) |
|---|---|---|---|---|---|
| 1848 | 1617 | $C_{23}H_{26}BrF_3N_4O_2S$ | 559.0 | 21.0 | 75 |
| 1849 | 1777 | $C_{23}H_{25}Cl_2F_3N_4O_2$ | 517.0 | 16.3 | 63.0 |
| 1850 | 1778 | $C_{24}H_{29}F_3N_4O_2$ | 463.2 | 9.5 | 41.1 |
| 1851 | 1779 | $C_{24}H_{27}F_3N_4O_4$ | 493.2 | 12.7 | 51.6 |
| 1852 | 1780 | $C_{23}H_{26}BrF_3N_4O_2$ | 527.0 | 16.4 | 62.2 |
| 1853 | 1781 | $C_{23}H_{27}F_3N_4O_3$ | 465.2 | 10.0 | 28.7 |
| 1854 | 1782 | $C_{25}H_{29}F_3N_4O_2$ | 475.2 | 12.2 | 34.3 |
| 1855 | 1783 | $C_{24}H_{26}F_3N_5O_2$ | 474.2 | 17.2 | 48.4 |
| 1856 | 1784 | $C_{23}H_{27}F_3N_4O_2$ | 449.2 | 11.3 | 33.6 |
| 1857 | 1788 | $C_{25}H_{31}F_3N_4O_2$ | 477.2 | 10.0 | 42.0 |
| 1858 | 1789 | $C_{24}H_{29}F_3N_4O_3$ | 479.2 | 10.0 | 27.9 |
| 1859 | 1792 | $C_{24}H_{30}F_2N_4O_2$ | 445.2 | 5.9 | 26.5 |
| 1860 | 1793 | $C_{22}H_{24}Cl_2F_2N_4O_2$ | 485.2 | 9.2 | 37.9 |
| 1861 | 1794 | $C_{23}H_{28}F_2N_4O_2$ | 431.2 | 5.7 | 26.5 |
| 1862 | 1795 | $C_{23}H_{26}F_2N_4O_4$ | 461.2 | 6.0 | 26.1 |
| 1863 | 1796 | $C_{22}H_{25}BrF_2N_4O_2$ | 497.0 | 10.5 | 42.4 |
| 1864 | 1797 | $C_{22}H_{26}F_2N_4O_3$ | 433.2 | 3.5 | 16.2 |
| 1865 | 1798 | $C_{23}H_{28}F_2N_4O_3$ | 447.2 | 5.6 | 25.1 |
| 1866 | 1799 | $C_{24}H_{28}F_2N_4O_2$ | 443.2 | 5.5 | 24.9 |
| 1867 | 1800 | $C_{23}H_{25}F_2N_5O_2$ | 442.2 | 9.4 | 42.6 |
| 1868 | 1801 | $C_{22}H_{26}F_2N_4O_2$ | 417.2 | 6.5 | 31.2 |

Example 1869

Synthesis of 4-[[N-(2-amino-5-trifluoromethylbenzoyl)glycyl]aminomethyl]-1-(4-bromobenzyl)piperidine (Compd. No. 1910)

A mixture of 4-[[N-(2-tert-butoxycarbonylamino)-5-trifluoromethoxybenzoyl]glycyl]aminomethyl]piperidine (0.050 mmol) with 4-bromobenzyl bromide (0.060 mmol), a piperidinomethylpolystyrene (60 mg), acetonitrile (0.8 mL) and chloroform (0.5 mL) was stirred at 60° C. for 12 hours, cooled, then loaded onto a Varian™ SCX column and washed with a 50% chloroform/methanol (10 mL) and methanol (10 mL). The obtained product was eluted with a 2 M methanol solution of $NH_3$ (5 mL) and concentrated. A 4 M 1, 4-dioxane solution of HCl (2 mL) was added to the resulting residue, and the obtained mixture was stirred at room temperature overnight, concentrated and then purified by preparative TLC to thereby provide 4-[[N-(2-amino-5-trifluoromethoxybenzoyl)glycyl]aminomethyl]-1-(4-bromobenzyl)piperidine (Compd. No. 1910) (6.5 mg, 24%). The purity was determined by RPLC/MS (96%). ESI/MS m/e 545 ($M^++H$, $C_{23}H_{26}BrF_3N_4O_3$).

Examples 1870 to 1873

The compounds used in the present invention were synthesized by using the respective corresponding starting materials and reactants according to the method of Example 1869. Data of ESI/MS and yields (mg) and yields (%) in the final steps are collectively shown in Table 45.

TABLE 45

| Example | Compd. No. | Molecular Formula | ESI/MS m/e | Yield (mg) | Yield (%) |
|---|---|---|---|---|---|
| 1870 | 1911 | $C_{23}H_{25}Cl_2F_3N_4O_3$ | 533 | 10.6 | 39.7 |
| 1871 | 1912 | $C_{23}H_{27}F_3N_4O_4$ | 481 | 12.5 | 52.0 |
| 1872 | 1913 | $C_{25}H_{31}F_3N_4O_3$ | 493 | 7.5 | 30.5 |
| 1873 | 1914 | $C_{24}H_{29}F_3N_4O_3$ | 479 | 11.0 | 46.0 |

Example 1874

Synthesis of 4-[[N-(2-amino-5-trifluoromethylbenzoyl) glycyl]aminomethyl]-1-(benz[d]imidazol-5-yl) piperidine (Compd. No. 2186)

A mixture of 4-[[N-(2-(tert-butoxycarbonylamino)-5-trifluoromethylbenzoyl)glycyl]aminomethyl]piperidine (0.060 mmol) with 1-(tert-butoxycarbonyl)-6-(bromomethyl)benz[d]imidazole (15.6 mg, 0.050 mmol), a (piperidinomethyl) polystyrene (86 mg, 0.15 mmol) and acetonitrile (2 mL) was stirred at 50° C. for 3 hours and cooled to room temperature. Phenyl isocyanate (30 mg) was then added to the cooled mixture, and the resulting mixture was stirred at room temperature for 1 hour, loaded onto a Varian™ SCX column and washed with methanol (5 mL) and chloroform (5 mL). The obtained product was eluted with a 2 M methanol solution of $NH_3$ (5 mL) and concentrated.

The resulting substance was dissolved in methanol (1 mL), and a 4 M dioxane solution of HCl (1 mL) was added to the obtained solution. The resulting mixture was stirred at room temperature overnight, loaded onto a Varian™ SCX column, washed with methanol (5 mL) and dichloromethane. The resulting product was eluted with a 2 M methanol solution of $NH_3$ and concentrated. The obtained crude product was purified by preparative TLC ($SiO_2$, ethyl acetate/methanol=3:1) to thereby afford 4-[[N-(2-amino-5-trifluoromethylbenzoyl) glycyl]aminomethyl]-1-(benz[d]imidazol-5-yl)piperidine (Compd. No. 2186) (1.9 mg, 7.8%). The purity was determined by RPLC/MS (100%). ESI/Ms m/e 489.4 ($M^{+}$+H, $C_{24}H_{27}F_3N_6O_2$).

Example 1875

Synthesis of 4-[[N-(2-amino-4,5-difluorobenzoyl) glycyl]aminomethyl]-1-(benzo[c]thiadiazol-5-yl) piperidine (Compd. No. 2184)

Methanesulfonyl chloride (0.0042 mL) was added to a mixture of 5-(hydroxymethyl)benzo[c]thiadiazole (8.3 mg, 0.050 mmol) with a (piperidinomethyl)polystyrene (86 mg) and chloroform (1 mL), and the resulting mixture was stirred at room temperature for 1.5 hours. Acetonitrile (1 mL) and 4-[[(N-(2-(tert-butoxycarbonylamino)-4,5-difluorobenzoyl) glycyl]aminomethyl]piperidine were added to the mixture, and the resulting reaction mixture was stirred at 50° C. for 3 hours and cooled to room temperature. Phenyl isocyanate (30 mg) was then added to the cooled mixture, and the resulting mixture was stirred at room temperature for 1 hour, loaded onto a Varian™ SCX column and washed with methanol (5 mL) and chloroform (5 mL). The product was eluted with a 2 M methanol solution of $NH_3$ (3 mL) and concentrated. The resulting residue was dissolved in dichloromethane (1 mL), and a dichloromethane (1 mL) solution of chlorotrimethylsilane (1 M) and phenol (1 M) was added to the obtained solution. The resulting mixture was stirred at room temperature for 5 hours, then loaded onto a Varian™ SCX column and washed with methanol and dichloromethane. The obtained crude product was eluted with a 2 M methanol solution of $NH_3$ and purified by preparative TLC ($SiO_2$, ethyl acetate/methanol=3:1) to thereby provide 4-[[N-(2-amino-4,5-difluorobenzoyl)glycyl]aminomethyl]-1-(benzo[c]thiadiazol-5-yl)piperidine (Compd. No. 2184) (1.3 mg, 5.5%). The purity was determined by RPLC/MS (100%). ESI/MS m/e 475.2 ($M^{+}$+H, $C_{22}H_{24}F_2N_6O_2S$).

Example 1876

Synthesis of 4-[[N-(2-amino-5-trifluoromethylbenzoyl)glycyl]aminomethyl]-1-(benzo[c]thiadiazol-5-yl)piperidine (Compd. No. 2185)

4-[[N-(2-Amino-5-trifluoromethylbenzoyl)glycyl]aminomethyl]-1-(benzo[c]thiadiazol-5-yl)piperidine (Compd. No. 2185) was synthesized by using the corresponding starting material and reactants according to the method of Example 1875. 7.2 mg, 28% yield; ESI/MS m/e 507.4 ($M^{+}$+H, $C_{23}H_{25}F_3N_6O_2S$).

Example 1877

Synthesis of 4-[[N-(2-amino-5-trifluoromethylbenzoyl)glycyl]aminomethyl]-1-(2-amino-4-chlorobenzyl)piperidine (Compd. No. 1919)

A mixture of 4-[[N-(2-amino-5-trifluoromethylbenzoyl) glycyl]aminomethyl]piperidine (0.050 mmol) with 4-chloro-2-nitrobenzyl chloride (0.050 mmol), a piperidinomethylpolystyrene (60 mg), acetonitrile (1.0 mL) and chloroform (0.7 mL) was stirred at 50° C. overnight, cooled, then loaded onto a Varian™ SCX column and washed with chloroform/methanol (10 mL) and methanol (10 mL). The obtained product was eluted with a 2 M methanol solution of $NH_3$ (5 mL) and concentrated. Ethanol (3 mL) and a 10% palladium carbon (15 mg) were added to the resulting residue, and the obtained mixture was stirred at room temperature under a hydrogen atmosphere for 1.5 hours and filtered. The filtrate was concentrated and then purified by preparative TLC to thereby afford 4-[[N-(2-amino-5-trifluoromethylbenzoyl) glycyl]aminomethyl]-1-(2-amino-4-chlorobenzyl)piperidine (Compd. No. 1919) (5.1 mg, 14%). The purity was determined by RPLC/MS (90%). $^{1}$H NMR (400 MHz, $CDCl_3$) δ 1.09-1.32 (m, 4H), 1.41-1.59 (m, 1H), 1.66 (d, J=12.5 Hz, 2H), 1.88 (t, J=11.5 Hz, 2H), 2.82 (d, J=11.5 Hz, H), 3.17 (t. J=6.5 Hz, 2H), 3.42 (s, 2H), 4.05 (d, J=3.5 Hz, 2H), 4.85 (br s, 1H), 5.92 (br s, 2H), 6.25-6.36 (m, 1H), 6.55-6.66 (m, 1H), 6.70 (d, J=8.5 Hz, 1H), 6.85 (d, J=8.5 Hz, 1H), 7.26 (s, 1H), 7.42 (d, J=8.5 Hz, 1H), 7.68 (s, 1H); ESI/MS m/e 498.2 ($M^{+}$+H, $C_{23}H_{27}ClF_3N_5O_2$).

Examples 1878 to 1879

The compounds used in the present invention were synthesized by using the respective corresponding starting materials and reactants according to the method of Example 1877. Data of ESI/MS and yields (mg) and yields (%) in the final steps are collectively shown in Table 46.

TABLE 46

| Example | Compd. No. | Molecular Formula | ESI/MS m/e | Yield (mg) | Yield (%) |
|---|---|---|---|---|---|
| 1878 | 1920 | $C_{22}H_{26}ClF_2N_5O_2$ | 466.2 | 3.5 | 10.0 |
| 1879 | 1922 | $C_{23}H_{27}ClF_3N_5O_3$ | 514.2 | 1.2 | 3.1 |

Example 1880

Synthesis of 4-[[N-(2-amino-5-trifluoromethylbenzoyl)glycyl]aminomethyl]-1-(benz[d]oxazol-5-yl) piperidine (Compd. No. 2188)

Triethyl orthoformate (0.033 mL, 3.3 equivalents) and pyridinium p-toluenesulfonate (2 mg, 0.4 equivalent) were added to a THF (2 mL) solution of 1-(3-amino-4-hydroxybenzyl)-4-[[N-(2-(tert-butoxycarbonylamino)-5-trifluoromethylbenzoyl)glycyl]aminomethyl]piperidine (34.8 mg, 0.060 mL) synthesized according to the method of Example 1826. The resulting mixture was stirred under reflux overnight and cooled to room temperature. The obtained mixture was then concentrated, and the resulting residue was dissolved in ethyl acetate, loaded onto a Bond ElUt™ Si column, eluted with ethyl acetate/methanol=4:1 and concentrated.

The obtained residue was dissolved in ethyl acetate (1.5 mL), and a 4 M dioxane solution of HCl (0.5 mL) was added to the obtained solution. The resulting mixture was stirred at room temperature overnight, then adjusted to pH10 with a 5 M aqueous solution of NaOH and extracted with ethyl acetate. The extracts was concentrated and purified by preparative TLC ($SiO_2$, ethyl acetate/methanol=4:1) to thereby provide 4-[[N-(2-amino-5-trifluoromethylbenzoyl) glycyl] aminomethyl]-1-(benz[d]oxazol-5-yl)piperidine (Compd. No. 2188) (1.6 mg, 5%). The purity was determined by RPLC/MS (94%). ESI/MS m/e 490.3 ($M^{+}$+H, $C_{24}H_{26}F_3N_5O_3$).

Example 1881

Synthesis of 4-[[N-(2-amino-4,5-difluorobenzoyl) glycyl]aminomethyl]-1-(2-oxo-2,3-dihydro-1,3-benzoxazol-5-yl)piperidine (Compd. No. 2190)

Phenyl chloroformate (0.040 mL) was added to a mixture of 1-(3-amino-4-hydroxy)-4-[[N-(2-(tert-butoxycarbonylamino)-4,5-difluorobenzoyl)glycyl]aminomethyl]piperidine (22 mg, 0.040 mmol) with $NaHCO_3$ (0.040 mmol), water (0.7 mL) and methanol (1.5 mL), and the resulting mixture was stirred at room temperature for 3 hours. A 1 M aqueous solution of NaOH (0.040 mL) was added, and the obtained mixture was further stirred for 1.5 hours. The mixture was then extracted with ethyl acetate, and the extracts was concentrated. The resulting residue was dissolved in methanol, loaded onto a Varian™ SCX column and washed with methanol (5 mL×2). The obtained product was eluted with a 2 M methanol solution of $NH_3$ (5 mL) and concentrated. A dichloromethane (2 mL) solution of chlorotrimethylsilane (1 M) and phenol (1 M) was added to the obtained residue. The mixture was stirred at room temperature for 2 hours and concentrated. The resulting residue was dissolved in methanol, loaded onto a Varian™ SCX column and washed with methanol (5 mL×2). The obtained crude product was eluted with a 2 M methanol solution of $NH_3$ (5 mL), concentrated and purified by preparative TLC ($SiO_2$, ethyl acetate/methanol=5:2) to thereby afford 4-[[N-(2-amino-4,5-difluorobenzoyl)glycyl]aminomethyl]-1-(2-oxo-2,3-dihydro-1,3-benzoxazol-5-yl)piperidine (Compd. No. 2190) (4.1 mg, 22%). The purity was determined by RPLC/MS (100%). ESI/MS m/e 474.2 ($M^+$+H, $C_{23}H_{25}F_2N_5O_4$).

Examples 1882 to 1884

The compounds used in the present invention were synthesized by using the respective corresponding starting materials and reactants according to the method of Example 1881 (phenyl chlorothioformate was used in place of the phenyl chloroformate for synthesizing Compd. Nos. 2192 and 2193). Data of ESI/MS and yields (mg) and yields (%) in the final steps are collectively shown in Table 47.

TABLE 47

| Example | Compd. No. | Chemical Formula | ESI/MS m/e | Yield (mg) | Yield (%) |
|---|---|---|---|---|---|
| 1882 | 2191 | $C_{24}H_{26}F_3N_5O_4$ | 506.3 | 3.1 | 10 |
| 1883 | 2192 | $C_{23}H_{25}F_2N_5O_3S$ | 490.2 | 6.9 | 35 |
| 1884 | 2193 | $C_{24}H_{26}F_3N_5O_3S$ | 522.2 | 3.6 | 11 |

Reference Example 36

4-[[N-(1-(9- fluorenylmethoxycarbonyl)piperidin-4-ylmethyl)carbamoylmethyl]aminomethyl]-3-methoxyphenyloxymethyl-polystyrene Acetic acid (0.3 mL), sodium triacetoxyborohydride (1.92 g) and 4-formyl-3-(methoxyphenyloxymethyl)-polystyrene (1 mmol/g, 200 g) were added to a DMF (65 mL) solution of 1-(9-fluorenylmethoxycarbonyl)-4-(glycylaminomethyl)piperidine hydrochloride (10 mmol), and the resulting mixture was shaken for 2 hours and then filtered. The resin was washed with methanol, DMF, dichloromethane and methanol and dried to provide the objective substance.

Examples 1885 to 2000

Solid-phase synthesis of 4-aminomethylpiperidines

Diisopropylethylamine (3.6 mmol) was added to a mixture of the corresponding carboxylic acid (1.6 mmol) with HBTU (1.6 mmol) and DMF (6 mL), and the resulting mixture was shaken for 2 minutes. 4-[[N-(1-(9-Fluorenylmethoxycarbonyl)piperidin-4-ylmethyl)carbamoylmethyl]aminomethyl]-3-methoxyphenyloxymethyl-polystyrene (0.4 mmol) was added to the resulting mixture, and the obtained mixture was shaken for 1 hour and filtered. The resin was washed with dichloromethane and dried.

A mixture of $NaBH(OAc)_3$ (0.25 mmol) with acetic acid (0.025 mmol) and DMF was added to the obtained resin (0.05 mmol), and the corresponding aldehyde (2.5 mmol) was further added. The resulting mixture was shaken for 2 hours, then filtered and washed with methanol, a 10% DMF solution of diisopropylethylamine, DMF, dichloromethane and methanol. A mixture of the resin with water (0.050 mL) and trifluoroacetic acid (0.95 mL) was shaken for 1 hour and filtered. The resin was washed with dichloromethane and methanol. The filtrate and washings were combined and concentrated. The resulting residue was loaded onto a Varian™ SCX column and washed with methanol (15 mL). The obtained crude product was eluted with a 2 M methanol solution of $NH_3$ (5 mL) and concentrated. The obtained product, if necessary, was purified by preparative TLC or HPLC to provide the objective compounds. Data of ESI/MS, yields (mg) and yields (%) are collectively shown in Table 48.

TABLE 48

| Example | Compd. No. | Molecular Formula | ESI/MS m/e | Yield (mg) | Yield (%) |
|---|---|---|---|---|---|
| 1885 | 1923 | $C_{23}H_{25}BrF_3N_3O_2S$ | 544 | 15.7 | 87 |
| 1886 | 1924 | $C_{24}H_{28}F_3N_3O_3S$ | 496 | 14.6 | 89 |
| 1887 | 1925 | $C_{23}H_{25}F_4N_3O_2S$ | 484 | 11.7 | 73 |
| 1888 | 1926 | $C_{23}H_{24}F_5N_3O_2S$ | 502 | 13.9 | 84 |
| 1889 | 1927 | $C_{23}H_{26}F_3N_3O_3S$ | 482 | 10.7 | 67 |
| 1890 | 1928 | $C_{24}H_{26}F_3N_3O_4S$ | 510 | 14.3 | 85 |
| 1891 | 1929 | $C_{26}H_{30}F_3N_3O_2S$ | 506 | 14.7 | 88 |
| 1892 | 1930 | $C_{24}H_{28}F_3N_3O_2S_2$ | 512 | 14.4 | 85 |
| 1893 | 1931 | $C_{25}H_{30}F_3N_3O_2S$ | 494 | 14.3 | 88 |
| 1894 | 1932 | $C_{25}H_{28}F_3N_3O_3S$ | 509 | 7.1* | 35 |
| 1895 | 1933 | $C_{25}H_{30}F_3N_3O_2S$ | 494 | 14.3 | 88 |
| 1896 | 1934 | $C_{26}H_{32}F_3N_3O_2S$ | 509 | 14.4 | 86 |
| 1897 | 1935 | $C_{23}H_{25}F_3N_4O_4S$ | 511 | 14.9 | 88 |
| 1898 | 1936 | $C_{24}H_{28}F_3N_3O_2S$ | 480 | 13.3 | 84 |
| 1899 | 1937 | $C_{26}H_{32}F_3N_3O_2S$ | 509 | 11.1 | 66 |
| 1900 | 1938 | $C_{23}H_{27}Br_2N_3O_2$ | 538 | 5.3* | 25 |
| 1901 | 1939 | $C_{24}H_{30}BrN_3O_3$ | 488 | 5.0* | 25 |
| 1902 | 1940 | $C_{23}H_{27}BrFN_3O_2$ | 476 | 4.9* | 25 |
| 1903 | 1941 | $C_{23}H_{26}BrF_2N_3O_2$ | 494 | 6.1* | 30 |
| 1904 | 1942 | $C_{23}H_{28}BrN_3O_3$ | 474 | 1.7* | 9 |
| 1905 | 1943 | $C_{24}H_{28}BrN_3O_4$ | 502 | 6.6* | 32 |
| 1906 | 1944 | $C_{26}H_{32}BrN_3O_2$ | 498 | 7.0* | 35 |
| 1907 | 1945 | $C_{24}H_{30}BrN_3O_2S$ | 504 | 11.1 | 67 |
| 1908 | 1946 | $C_{28}H_{32}BrN_3O_2$ | 488 | 3.2* | 16 |
| 1909 | 1947 | $C_{25}H_{30}BrN_3O_3$ | 500 | 5.7 | 35 |
| 1910 | 1948 | $C_{25}H_{32}BrN_3O_2$ | 486 | 4.9* | 25 |
| 1911 | 1949 | $C_{26}H_{34}BrN_3O_2$ | 500 | 6.7* | 33 |
| 1912 | 1950 | $C_{23}H_{27}BrN_4O_4$ | 503 | 5.0* | 25 |
| 1913 | 1951 | $C_{24}H_{30}BrN_3O_2$ | 472 | 5.1* | 26 |
| 1914 | 1952 | $C_{22}H_{24}Br_2FN_3O_2$ | 542 | 14.9 | 83 |
| 1915 | 1953 | $C_{23}H_{27}BrFN_3O_3$ | 492 | 13.9 | 86 |
| 1916 | 1954 | $C_{22}H_{24}BrF_2N_3O_2$ | 480 | 12.5 | 79 |
| 1917 | 1955 | $C_{22}H_{23}BrF_3N_3O_2$ | 498 | 13.2 | 80 |
| 1918 | 1956 | $C_{22}H_{25}BrFN_3O_3$ | 478 | 7.0 | 44 |
| 1919 | 1957 | $C_{23}H_{25}BrFN_3O_4$ | 506 | 4.0* | 20 |
| 1920 | 1958 | $C_{25}H_{29}BrFN_3O_2$ | 502 | 14.6 | 88 |
| 1921 | 1959 | $C_{23}H_{27}BrFN_3O_2S$ | 508 | 13.1 | 78 |
| 1922 | 1960 | $C_{24}H_{29}BrFN_3O_2$ | 490 | 13.8 | 85 |

TABLE 48-continued

| Example | Compd. No. | Molecular Formula | ESI/MS m/e | Yield (mg) | Yield (%) |
|---|---|---|---|---|---|
| 1923 | 1961 | $C_{24}H_{27}BrFN_3O_3$ | 504 | 2.7* | 13 |
| 1924 | 1962 | $C_{24}H_{29}BrFN_3O_2$ | 490 | 12.7 | 78 |
| 1925 | 1963 | $C_{25}H_{31}BrFN_3O_2$ | 504 | 13.5 | 81 |
| 1926 | 1964 | $C_{22}H_{24}BrFN_4O_4$ | 507 | 14.8 | 88 |
| 1927 | 1965 | $C_{23}H_{27}BrFN_3O_2$ | 476 | 12.1 | 77 |
| 1928 | 1966 | $C_{25}H_{31}BrFN_3O_2$ | 504 | 13.4 | 80 |
| 1929 | 1967 | $C_{22}H_{26}BrFN_4O_2$ | 477 | 4.7* | 20 |
| 1930 | 1968 | $C_{23}H_{29}FN_4O_3$ | 429 | 6.9* | 32 |
| 1931 | 1969 | $C_{22}H_{27}FN_4O_3$ | 415 | 3.7* | 17 |
| 1932 | 1970 | $C_{23}H_{27}FN_4O_4$ | 443 | 5.4* | 24 |
| 1933 | 1971 | $C_{25}H_{31}FN_4O_2$ | 439 | 4.3* | 20 |
| 1934 | 1972 | $C_{23}H_{29}FN_4O_2S$ | 445 | 6.2* | 28 |
| 1935 | 1973 | $C_{24}H_{31}FN_4O_2$ | 427 | 6.3* | 29 |
| 1936 | 1974 | $C_{24}H_{31}FN_4O_2$ | 427 | 4.9* | 23 |
| 1937 | 1975 | $C_{22}H_{26}FN_5O_4$ | 444 | 5.9* | 27 |
| 1938 | 1976 | $C_{23}H_{29}FN_4O_2$ | 413 | 6.7* | 32 |
| 1939 | 1977 | $C_{23}H_{26}FN_5O_2$ | 424 | 5.1* | 24 |
| 1940 | 1978 | $C_{25}H_{33}FN_4O_2$ | 441 | 6.3* | 29 |
| 1941 | 1979 | $C_{25}H_{30}F_2N_4O_2$ | 457 | 8.0* | 35 |
| 1942 | 1980 | $C_{24}H_{28}F_2N_4O_3$ | 459 | 6.0* | 26 |
| 1943 | 1981 | $C_{22}H_{25}F_2N_5O_4$ | 462 | 9.3* | 41 |
| 1944 | 1982 | $C_{23}H_{25}F_2N_5O_2$ | 442 | 6.0* | 27 |
| 1945 | 1983 | $C_{25}H_{32}F_2N_4O_2$ | 459 | 8.3* | 37 |
| 1946 | 1984 | $C_{22}H_{26}BrIN_4O_2$ | 585 | 9.7* | 36 |
| 1947 | 1985 | $C_{23}H_{29}IN_4O_3$ | 537 | 9.2* | 36 |
| 1948 | 1986 | $C_{22}H_{27}IN_4O_3$ | 523 | 5.8* | 23 |
| 1949 | 1987 | $C_{23}H_{27}IN_4O_4$ | 551 | 8.2* | 32 |
| 1950 | 1988 | $C_{25}H_{31}IN_4O_2$ | 547 | 6.7* | 26 |
| 1951 | 1989 | $C_{23}H_{29}IN_4O_2S$ | 553 | 6.4* | 25 |
| 1952 | 1990 | $C_{24}H_{31}IN_4O_2$ | 535 | 7.2* | 29 |
| 1953 | 1991 | $C_{24}H_{29}IN_4O_3$ | 549 | 5.6* | 22 |
| 1954 | 1992 | $C_{24}H_{31}IN_4O_2$ | 535 | 6.2* | 25 |
| 1955 | 1993 | $C_{22}H_{26}IN_5O_4$ | 552 | 10.2* | 40 |
| 1956 | 1994 | $C_{23}H_{29}IN_4O_2$ | 521 | 7.5* | 30 |
| 1957 | 1995 | $C_{23}H_{26}IN_5O_2$ | 532 | 6.8* | 27 |
| 1958 | 1996 | $C_{25}H_{33}IN_4O_2$ | 549 | 7.1* | 28 |
| 1959 | 1997 | $C_{25}H_{33}IN_4O_2$ | 549 | 3.0* | 12 |
| 1960 | 1998 | $C_{22}H_{25}BrClN_3O_2$ | 478 | 7.6* | 39 |
| 1961 | 1999 | $C_{23}H_{28}ClN_3O_3$ | 430 | 7.0* | 39 |
| 1962 | 2000 | $C_{22}H_{25}ClFN_3O_2$ | 418 | 14.1 | 102 |
| 1963 | 2001 | $C_{22}H_{26}ClN_3O_3$ | 416 | 6.3* | 36 |
| 1964 | 2002 | $C_{23}H_{26}ClN_3O_4$ | 444 | 7.1* | 39 |
| 1965 | 2003 | $C_{25}H_{30}ClN_3O_2$ | 440 | 15.3 | 105 |
| 1966 | 2004 | $C_{23}H_{28}ClN_3O_2S$ | 446 | 8.4* | 45 |
| 1967 | 2005 | $C_{24}H_{30}ClN_3O_2$ | 428 | 7.4* | 41 |
| 1968 | 2006 | $C_{24}H_{30}ClN_3O_2$ | 428 | 13.8 | 98 |
| 1969 | 2007 | $C_{22}H_{25}ClN_4O_4$ | 445 | 16.0 | 109 |
| 1970 | 2008 | $C_{23}H_{28}ClN_3O_2$ | 414 | 14.1 | 103 |
| 1971 | 2009 | $C_{23}H_{25}ClN_4O_2$ | 425 | 14.8 | 106 |
| 1972 | 2010 | $C_{25}H_{32}ClN_3O_2$ | 442 | 14.5 | 99 |
| 1973 | 2011 | $C_{25}H_{32}ClN_3O_2$ | 442 | 14.5 | 99 |
| 1974 | 2012 | $C_{22}H_{24}Br_2ClN_3O_2$ | 558 | 12.8* | 58 |
| 1975 | 2013 | $C_{23}H_{27}BrClN_3O_3$ | 508 | 8.6* | 42 |
| 1976 | 2014 | $C_{22}H_{25}BrClN_3O_3$ | 494 | 6.0* | 30 |
| 1977 | 2015 | $C_{23}H_{25}BrClN_3O_4$ | 522 | 8.4* | 40 |
| 1978 | 2016 | $C_{25}H_{29}BrClN_3O_2$ | 518 | 17.6 | 103 |
| 1979 | 2017 | $C_{23}H_{27}BrClN_3O_2S$ | 524 | 17.1 | 99 |
| 1980 | 2018 | $C_{24}H_{29}BrClN_3O_2$ | 506 | 14.7 | 88 |
| 1981 | 2019 | $C_{24}H_{27}BrClN_3O_3$ | 520 | 8.0* | 38 |
| 1982 | 2020 | $C_{24}H_{29}BrClN_3O_2$ | 506 | 14.7 | 88 |
| 1983 | 2021 | $C_{22}H_{24}BrClN_4O_4$ | 523 | 12.0* | 57 |
| 1984 | 2022 | $C_{23}H_{27}BrClN_3O_2$ | 492 | 8.5* | 42 |
| 1985 | 2023 | $C_{23}H_{24}BrClN_4O_2$ | 503 | 6.3* | 31 |
| 1986 | 2024 | $C_{25}H_{31}BrClN_3O_2$ | 520 | 9.6* | 46 |
| 1987 | 2025 | $C_{25}H_{31}BrClN_3O_2$ | 520 | 15.0 | 87 |
| 1988 | 2026 | $C_{22}H_{23}BrClF_2N_3O_2$ | 514 | 15.8 | 93 |
| 1989 | 2027 | $C_{22}H_{26}Br_2N_4O_2$ | 537 | 10.7* | 42 |
| 1990 | 2028 | $C_{23}H_{29}BrN_4O_3$ | 489 | 8.5* | 36 |
| 1991 | 2029 | $C_{22}H_{27}BrN_4O_3$ | 475 | 7.5* | 32 |
| 1992 | 2030 | $C_{23}H_{27}BrN_4O_4$ | 503 | 6.8* | 28 |
| 1993 | 2031 | $C_{25}H_{31}BrN_4O_2$ | 499 | 6.2* | 26 |
| 1994 | 2032 | $C_{24}H_{29}BrN_4O_3$ | 501 | 8.9* | 37 |
| 1995 | 2033 | $C_{24}H_{31}BrN_4O_2$ | 487 | 9.1* | 39 |
| 1996 | 2034 | $C_{22}H_{26}BrN_5O_4$ | 504 | 6.4* | 26 |
| 1997 | 2035 | $C_{23}H_{29}BrN_4O_2$ | 473 | 6.5* | 28 |
| 1998 | 2036 | $C_{23}H_{26}BrN_5O_2$ | 484 | 6.3* | 27 |
| 1999 | 2037 | $C_{25}H_{33}BrN_4O_2$ | 501 | 5.4* | 22 |
| 2000 | 2038 | $C_{22}H_{25}BrF_2N_4O_2$ | 495 | 5.4* | 23 |

Note:
*indicates "yield (mg) of trifluoroacetate".

Example 2001

Synthesis of 1-(3-carbamoylbenzyl)-4-[[N-(3-trifluoromethyl)benzoyl]alycyl]aminomethyl]piperidine (Compd. No. 924)

EDCI (10.7 mg), 1-hydroxybenzotriazole hydrate (7.5 mg), triethylamine (15.4 mg), a 0.5 M dioxane solution of $NH_3$ (0.1 mL, 0.05 mmol) and DMF (0.5 mL) were added to a chloroform (2.5 mL) solution of 1-(3-carboxybenzoyl)-4-[[N-(3-trifluoromethyl)benzoyl]glycyl]aminomethyl]piperidine (19.4 mg, 0.041 mmol), and the resulting mixture was shaken at 25° C. for 20 hours and then washed with a 2 M aqueous solution of NaOH (2 X(2 mL) and brine (1 mL). The organic layer was filtered through a PTFE membrane filter, and the solvent was then removed under reduced pressure to provide 1-(3-carbamoylbenzyl)-4-[[N-(3-trifluoromethyl)benzoyl]glycyl]aminomethyl]piperidine (Compd. No. 924) as an off-white solid (17.9 mg, 92%). The purity was determined by RPLC/MS (89%). ESI/MS m/e 447.3 ($M^++H$, $C_{24}H_{27}F_3N_4O_3$).

Example 2002

Synthesis of 1-(4-carbamoylbenzyl)-4-[[N-(3-trifluoromethyl)benzoyl]glycyl]aminomethyl]piperidine (Compd. No. 925)

The Compd. No. 925 was synthesized by using the corresponding starting material and reactants according to the method of Example 2001. 14.2 mg, 72%. The purity was determined by RPLC/MS (86%). ESI/MS m/e 447 ($M^++H$, $C_{24}H_{27}F_3N_4O_3$).

Example 2003

Synthesis of 1-(4-aminobenzyl)-4-[[N-(3-trifluoromethyl)benzoyl]glycyl]aminomethyl]piperidine (Compd. No. 516)

An ethanol (3 mL) solution of 1-(4-nitrobenzyl)-4-[[N-(3-trifluoromethyl)benzoyl]glycyl]aminomethyl]piperidine (22.4 mg, 0.047 mmol) was hydrogenated in the presence of a 5% palladium carbon (10 mg) at 25° C. in a hydrogen atmosphere under 1 atm for 1 hour. The catalyst was removed by filtration, and washed with ethanol (5 mL). The filtrates were collected and concentrated to thereby afford 1-(4-aminobenzyl)-4-[[N-(3-trifluoromethyl)benzoyl]glycyl]aminomethyl]piperidine (Compd. No. 516) as an off-white solid (20.1 mg, 96%). The purity was determined by RPLC/MS (99%). ESI/MS m/e 449.1 ($M^++H$, $C_{23}H_{27}F_3N_4O_2$).

Examples 2004 to 2005

Compd. Nos. 517 and 518 were synthesized by using the respective corresponding starting materials and reactants according to the method of Example 2003. Data of ESI/MS and yields (mg) and yields (%) in the final steps are collectively shown in Table 49.

TABLE 49

| Example | Compd. No. | Molecular Formula | ESI/MS m/e | Yield (mg) | Yield (%) |
|---|---|---|---|---|---|
| 2004 | 517 | $C_{23}H_{27}F_3N_4O_2$ | 449 | 26.5 | 78 |
| 2005 | 518 | $C_{23}H_{27}F_3N_4O_2$ | 449 | 25.3 | 71 |

Example 2006

Synthesis of 1-[4-(benzoylamino)benzyl]-4-[[N-(3-(trifluoromethyl)benzoyl)glycyl]aminomethyl]piperidine (Compd. No. 519)

EDCI (4.7 mg), 1-hydroxybenzotriazole hydrate (3.3 mg), triethylamine (2.5 mg) and benzoic acid (3.0 mg) were added to a dichloromethane (2.5 mL) solution of 1-(4-aminobenzyl)-4-[[N-(3-(trifluoromethyl)benzoyl)glycyl]aminomethyl]piperidine (10.1 mg, 0.023 mmol), and the resulting mixture was shaken at 25° C. for 16 hours. The reaction mixture was washed with a 2 M aqueous solution of NaOH (2 mL×2) and brine (1 mL) and then filtered through a PTFE membrane filter. The solvent was evaporated under reduced pressure to thereby provide yellow oil. The obtained yellow oil was purified by preparative TLC ($SiO_2$, 10% methanol/dichloromethane) to afford 1-[4-(benzoylamino)benzyl]-4-[[N-(3-(trifluoromethyl)benzoyl)glycyl]aminomethyl]piperidine (Compd. No. 519) as a colorless oil (4.6 mg, 36%). The purity was determined by RPLC/MS (99%). ESI/MS m/e 553.2 ($M^+$+H, $C_{30}H_{31}F_3N_4O_3$).

Example 2007

Synthesis of 1-[4-(piperidinocarbonyl)benzyl]-4-[[N-(3-(trifluoromethyl)benzoyl)glycyl]aminomethyl]piperidine (Compd. No. 1572)

Piperidine (0.048 mg), and a DMF (0.15 mL) solution of diisopropylcarbodiimide (0.45 mmol) and 1-hydroxybenzotriazole hydrate (0.45 mmol) were added to a DMF (1.0 mL) solution of 1-(4-carboxybenzyl)-4-[[N-(3-(trifluoromethyl)benzoyl)glycyl]aminomethyl]piperidine (0.040 mmol), and the resulting mixture was shaken at room temperature for 17 hours, then loaded onto a Varian™ SCX column and washed with chloroform/methanol=1:1 (5 mL) and methanol (5 mL). The obtained crude product was eluted with a 2 M methanol solution of $NH_3$ (5 mL) and concentrated to thereby provide 1-[4-(piperidinocarbonyl)benzyl]-4-[[N-(3-(trifluoromethyl)benzoyl)glycyl]aminomethyl]piperidine (Compd. No. 0.1572) (14.3 mg, 66%). The purity was determined by RPLC/MS (99%). ESI/MS m/e 545 ($M^+$+H, $C_{29}H_{35}F_3N_4O_3$).

Examples 2008 to 2015

The compounds used in the present invention were synthesized by using the respective corresponding starting materials and reactants according to the method of Example 2007. Data of ESI/MS and yields (mg) and yields (%) in the final steps are collectively shown in Table 50.

TABLE 50

| Example | Compd. No. | Molecular Formula | ESI/MS m/e | Yield (mg) | Yield (%) |
|---|---|---|---|---|---|
| 2008 | 1573 | $C_{31}H_{33}F_3N_4O_4$ | 583 | 17.6 | 76 |
| 2009 | 1574 | $C_{31}H_{33}F_3N_4O_3$ | 567 | 18.8 | 83 |
| 2010 | 1575 | $C_{30}H_{30}ClF_3N_4O_3$ | 587 | 3.2 | 14 |
| 2011 | 1576 | $C_{28}H_{33}F_3N_4O_4$ | 547 | 21.1 | 97 |
| 2012 | 1577 | $C_{26}H_{31}F_3N_4O_4$ | 521 | 5.1 | 24 |
| 2013 | 1578 | $C_{31}H_{33}F_3N_4O_3$ | 567 | 16.9 | 75 |
| 2014 | 1579 | $C_{31}H_{33}F_3N_4O_3$ | 567 | 6.0 | 26 |
| 2015 | 1580 | $C_{29}H_{35}F_3N_4O_3$ | 545 | 15.1 | 69 |

Example 2016

Synthesis of 1-[4-(chloroformyl)benzyl]-4-[[N-(3-(trifluoromethyl)benzoyl)glycyl]aminomethyl]piperidine A mixture of 1-(4-carboxybenzyl)-4-[[N-(3-(trifluoromethyl)benzoyl)glycyl]aminomethyl]piperidine (240 mg) with thionyl chloride (1 mL) was stirred at room temperature for 12 hours, and the excess thionyl chloride was removed under reduced pressure to thereby afford 1-[4-(chloroformyl)benzyl]-4-[[N-(3-(trifluoromethyl)benzoyl)glycyl]aminomethyl]piperidine. The resulting acid chloride was used without being further purified.

Example 2017

Synthesis of 1-[4-[N-(2-methoxyethyl)carbamoyl]benzyl]-4-[[N-(3-(trifluoromethyl)benzoyl)glycyl]aminomethyl]piperidine (Compd. No. 1612)

A mixture of 1-[4-(chloroformyl)benzyl]-4-[[N-(3-(trifluoromethyl)benzoyl)glycyl]aminomethyl]piperidine (0.042 mmol) with 2-methoxyethylamine (3.8 mg, 0.050 mmol), a piperidinomethylpolystyrene (46 mg) and dichloromethane (1.5 mL) was stirred at room temperature for 17 hours. Water (0.020 mL) was then added to the mixture, and the resulting mixture was stirred for 30 minutes. Methanol (1 mL) was then added to the obtained mixture, and the resulting mixture was loaded onto a Varian™ SCX column and washed with methanol (10 mL). The obtained crude product was eluted with a 2 M methanol solution of $NH_3$ and concentrated to thereby provide 1-[4-[N-(2-methoxyethyl)carbamoyl]benzyl]-4-[[N-(3-(trifluoromethyl)benzoyl)glycyl]aminomethyl]piperidine (Compd. No. 1612) (26.7 mg, 100%). The purity was determined by RPLC/MS (92%). ESI/MS m/e 535.2 ($M^+$+H, $C_{27}H_{33}F_3N_4O_4$).

Examples 2018 to 2020

The compounds used in the present invention were synthesized by using the respective corresponding starting materials and reactants according to Example 2017. The obtained products, if necessary, were purified by preparative TLC to afford the objective compounds. Data of ESI/MS and yields (mg) and yields (%) are collectively shown in Table 51.

TABLE 51

| Example | Compd. No. | Molecular Formula | ESI/MS m/e | Yield (mg) | Yield (%) |
|---|---|---|---|---|---|
| 2018 | 1610 | $C_{31}H_{30}F_6N_4O_3$ | 621.2 | 4.4 | 14 |
| 2019 | 1611 | $C_{30}H_{29}Cl_2F_3N_4O_3$ | 621.2 | 35.7 | Q |
| 2020 | 1613 | $C_{32}H_{35}F_3N_4O_3$ | 581.2 | 29.9 | Q |

Note:
Q means "Quantitative".

Example 2021

Synthesis of 4-[N-[5-bromo-2-(methylamino)benzoyl]glycyl]aminomethyl-1-(4-chlorobenzyl)piperidine (Compd. No. 1427)

A triethyl orthoformate (6.5 mL) solution of 4-[N-(2-amino-5-bromobenzoyl)glycyl]aminomethyl-1-(4-chlorobenzyl)piperidine (Compd. No. 1042) (50 mg, 0.10 mmol) was stirred at 150° C. for 17 hours and concentrated to thereby provide a yellow solid. Sodium borohydride (7.6 mg, 0.2 mmol) was added to an ethanol (3 mL) solution of the yellow solid, and the mixture was stirred at room temperature for 14 hours. The resulting white precipitate was dissolved in dichloromethane, and the obtained solution was washed with a 1 M aqueous solution of NaOH (2 mL). The organic layer was separated, dried over $K_2CO_3$, filtered and concentrated, and the obtained crude product was purified by column chromatography ($SiO_2$, 20% methanol/chloroform) to provide 4-[N-[5-bromo-2-(methylamino)benzoyl]glycyl]aminomethyl-1-(4-chlorobenzyl)piperidine (Compd. No. 1427) (40 mg, 80%). The purity was determined by RPLC/MS (100%). ESI/MS m/e 505 ($M^+$+H, $C_{23}H_{28}BrClF_6N_4O_2$).

Example 2022

Synthesis of 4-[N-[5-bromo-2-(dimethylamino)benzoyl]glycyl]aminomethyl-1-(4-chlorobenzyl)piperidine (Compd. No. 1428)

Sodium cyanoborohydride (26 mg, 0.42 mmol) and acetic acid (14 mL) were added to a mixture of 4-[N-(2-amino-5-bromobenzoyl)glycyl]aminomethyl-1-(4-chlorobenzyl)piperidine (Compd. No. 1042) (67 mg, 0.14 mmol) with a 37% aqueous solution of formaldehyde (0.112 mL, 1.4 mmol), acetonitrile (2 mL) and methanol (1.5 mL), and the resulting mixture was stirred at 50° C. for 30 hours. A 1 M aqueous solution of NaOH and dichloromethane were added to the mixture. The aqueous layer was separated, and the organic layer was dried over $K_2CO_3$, filtered, concentrated and purified by column chromatography ($SiO_2$, 20% methanol/ethyl acetate) to afford 4-[N-[5-bromo-2-(dimethylamino)benzoyl]glycyl]aminomethyl-1-(4-chlorobenzyl)piperidine (Compd. No. 1428) (60 mg, 82%). The purity was determined by RPLC/MS (100%). ESI/MS m/e 523 ($M^+$+H, $C_{24}H_{30}BrClF_6N_4O_2$).

Example 2023

Synthesis of 4-[[N-[5-bromo-2-(methylsulfonylamino)benzoyl]glycyl]aminomethyl]-1-(4-chlorobenzyl)piperidine (Compd. No. 1581)

A mixture of 4-[[N-[2-amino-5-bromobenzoyl]glycyl]aminomethyl]-1-(4-chlorobenzyl)piperidine (25 mg, 0.05 mmol) with methanesulfonyl chloride (0.0045 mL), triethylamine (0.026 mL) and dichloromethane (2 mL) was stirred at room temperature for 17 hours. The resulting reaction mixture was purified by column chromatography ($SiO_2$), loaded onto a Varian™ SAX column and washed with methanol (5 mL). The obtained crude product was eluted with a 0.1 M methanol solution of HCl (5 mL) and concentrated to thereby provide 4-[[N-[5-bromo-2-(methylsulfonylamino)benzoyl]glycyl]aminomethyl]-1-(4-chlorobenzyl)piperidine (Compd. No. 1581) (5.4 mg, 19%). ESI/MS m/e 573.0 ($M^+$+H, $C_{23}H_{28}BrClN_4O_4S$).

Example 2024

Synthesis of 4-[[N-[5-bromo-2-(bis(methylsulfonyl)amino)benzoyl]glycyl]aminomethyl]-1-(4-chlorobenzyl)piperidine (Compd. No. 1582)

A mixture of 1-(4-chlorobenzyl)-4-[[N-[2-amino-5-bromobenzoyl]glycyl]aminomethyl]piperidine (57 mg, 0.10 mmol) with methanesulfonyl chloride (0.018 mL, 0.024 mmol), triethylamine (0.068 mL) and dichloromethane (2 mL) was stirred at room temperature for 8 hours. A 1 M aqueous solution of NaOH (1 mL) was added to the mixture, and the resulting mixture was extracted with dichloromethane (2 mL×3). The extracts were combined, dried over $K_2CO_3$, filtered, concentrated and purified by column chromatography ($SiO_2$) to afford 4-[[N-[5-bromo-2-(bis(methylsulfonyl)amino)benzoyl]glycyl]aminomethyl]-1-(4-chlorobenzyl)piperidine (Compd. No. 1582) (40 mg, 62%). ESI/MS m/e 651 ($M^+$+H, $C_{24}H_{30}BrClN_4O_6S_2$).

Example 2025

Synthesis of 1-(4-chlorobenzyl)-1-methyl-4-[[N-[3-(trifluoromethyl)benzoyl]glycyl]aminomethyl]piperidinium iodide (methylammonium iodide of Compd. No. 461)

An acetonitrile (1.0 mL) solution of 4-[[N-[3-(trifluoromethyl)benzoyl]glycyl]aminomethyl]piperidine (30 mg, 0.087 mmol) and a (piperidinomethyl)polystyrene (80 mg, 2.7 mmol base/g resin) were added to a chloroform (1.0 mL) solution of 4-chlorobenzyl chloride (11.7 mg, 0.073 mmol), and the resulting mixture was stirred at 60° C. for 2 hours. Phenyl isocyanate (10.4 mg, 0.087 mmol) was then added to the reaction mixture cooled to room temperature, and the obtained mixture was stirred at 25° C. for 1 hour, then loaded onto a Varian™ SCX column and washed with methanol (20 mL). The obtained crude product was eluted with a 2 M methanol solution of $NH_3$ (6 mL) and concentrated to thereby provide 1-(4-chlorobenzyl)-4-[[N-[3-(trifluoromethyl)benzoyl]glycyl]aminomethyl]piperidine as a colorless oil.

Methyl iodide (28 mg, 0.20 mmol) was added to an acetonitrile (2.0 mL) solution of 1-(4-chlorobenzyl)-4-[[N-[3-(trifluoromethyl)benzoyl]glycyl]aminomethyl]piperidine. The resulting reaction mixture was stirred at 70° C. for 4 hours. The solvent was removed under reduced pressure to provide 1-(4-chlorobenzyl)-1-methyl-4-[[N-[3-(trifluoromethyl)benzoyl]glycyl]aminomethyl]piperidinium iodide as yellow oil. (31.7 mg, 71%). The purity was determined by RPLC/MS (99%). ESI/MS m/e 482.1 ($M^+$+H, $C_{24}H_{28}ClF_3N_3O_2$).

Example 2026

Synthesis of 1-(4-chlorobenzyl)-4-[N-methyl-N—[N-(3-(trifluoromethyl)benzoyl) lycyl]aminomethyl] piperidine (Compd. No. 520)

An aqueous solution of formaldehyde (108 mg, 1.33 mmol, 37 wt. %) was added to a 10% acetic acid/methanol (3 mL) solution of 1-(4-chlorobenzyl)-4-(aminomethyl)piperidine (318 mg, 1.33 mmol) and $NaBH_3CN$ (668 mg), and the resulting mixture was stirred at 25° C. for 1 hour. The reaction mixture was loaded onto a Dowex™ 50W×2 column (10 mL) and washed with methanol (20 mL). The obtained crude product was eluted with a 2 M methanol solution of $NH_3$ (6 mL) and concentrated to thereby afford 1-(4-chlorobenzyl)-

4-[(methylamino)methyl]piperidine as a colorless oil. The resulting oil was used without being purified.

EDCI (85 mg) and 1-hydroxybenzotriazole hydrate (60 mg) were added to a dichloromethane (4 mL) solution of 1-(4-chlorobenzyl)-4-[(methylamino)methyl]piperidine (111 mg, 0.44 mmol), and the resulting mixture was stirred at 25° C. for 1 hour, then washed with a 2 M aqueous solution of NaOH (2 mL×2) and filtered through a PTFE membrane filter. The solvent was subsequently removed under reduced pressure to provide a yellow oil, which was then purified by preparative TLC to afford 1-(4-chlorobenzyl)-4-[N-methyl-N—[N-(3-(trifluoromethyl)benzoyl) glycyl]aminomethyl] piperidine (Compd. No. 520) as an off-white oil (14.0 mg, 3.4%). The purity was determined by RPLC/MS (99%). ESI/MS m/e 482.1 ($M^+$+H, $C_{24}H_{27}ClF_3N_3O_2$).

Reference Example 37

Synthesis of 3-aminohomopiperidine

A 1 M $BH_3$-THF solution (80 mL) was added to a THF (70 mL) solution of DL-α-amino-ε-caprolactam (2 g, 16 mmol), and the resulting mixture was refluxed for 3 hours. A 2 M hydrochloric acid (50 mL) was added, and the reaction mixture was further heated and refluxed for 1 hour and then cooled to 25° C. A 4 M NaOH solution was added to basicify the reaction mixture (pH10), and the resulting mixture was extracted with ethyl acetate (200 mL×3). The organic layers were combined, washed with a saturated aqueous $NaHCO_3$, dried (over $MgSO_4$) and concentrated to thereby provide the objective compound (990 mg, 54%). The obtained compounds was used without being purified.

Reference Example 38

Synthesis of 3-amino-1-(4-chlorobenzyl)homopiperidine p-Chlorobenzyl chloride (463 mg, 2.9 mmol) and $K_2CO_3$ (828 g, 6 mmol) were added to an acetonitrile (45 mL) solution of 3-aminohomopiperidine (1.71 g, 15 mmol), and the resulting mixture was stirred at 70° C. with heating for 9 hours, cooled to 25° C. and concentrated to afford a yellow solid. The resulting residue was partitioned between $H_2O$ (5 mL) and ethyl acetate (50 mL) and the aqueous layer was extracted with ethyl acetate (50 mL×2). The organic layers were combined, washed with brine (20 mL), dried (over $MgSO_4$) and concentrated. The obtained yellow oil was purified by column chromatography ($SiO_2$, 5-20% methanol/dichloromethane gradient elution) to afford the objective compounds as yellow oil (639 mg, 93%).

Example 2027

Synthesis of 1-(4-chlorobenzyl)-3-[(4-benzoylbutyryl)amino]homopiperidine (Comp d. No. 994)

EDCI (23 mg), HOBt (16.2 mg) and triethylamine (15.2 μL) were added to a chloroform (1 mL) solution of 3-amino-1-(4-chlorobenzyl)homopiperidine (24 mg, 0.10 mmol) and 4-benzoylbutyric acid (1.2 equivalents), and the resulting mixture was stirred at 25° C. for 16 hours. The reaction mixture was diluted with dichloromethane (0.5 mL), filtered through a PTFE membrane and concentrated to provide 1-(4-chlorobenzyl)-3-[(4-benzoylbutyryl)amino]homopiperidine (Compd. No. 994) (43 mg, 99%). The purity was determined by RPLC/MS (98%). ESI/MS m/e 413 ($M^+$+H, $C_{24}H_{29}ClN_2O_2$).

Examples 2028 to 2042

The compounds used in the present invention were synthesized by using the respective corresponding starting materials and reactants according to the method of Example 2027. The obtained products, if necessary, were purified by chromatography (HPLC-$Cl_8$) to afford the objective compounds as TFA salts. Data of ESI/MS, yields (mg) and yields (%) are collectively shown in Table 52.

TABLE 52

| Example | Compd. No. | Molecular Formula | ESI/MS m/e | Yield (mg) | Yield (%) |
|---|---|---|---|---|---|
| 2028 | 943 | $C_{23}H_{25}ClF_3N_3O_2$ | 468 | 6 | 28 |
| 2029 | 944 | $C_{23}H_{28}ClN_3O_2$ | 414 | 5 | 29 |
| 2030 | 945 | $C_{22}H_{25}ClN_4O_4$ | 445 | 6 | 30 |
| 2031 | 946 | $C_{23}H_{27}ClN_4O_4$ | 459 | 5 | 24 |
| 2032 | 947 | $C_{25}H_{31}ClN_2O_4$ | 459 | 4 | 20 |
| 2033 | 948 | $C_{24}H_{29}Cl_2N_3O_2$ | 462 | 6 | 32 |
| 2034 | 949 | $C_{25}H_{32}ClN_3O_2$ | 442 | 6 | 31 |
| 2035 | 988 | $C_{23}H_{25}ClF_3N_3O_2$ | 468 | 45 | 92 |
| 2036 | 989 | $C_{23}H_{28}ClN_3O_3$ | 430 | 44 | 97 |
| 2037 | 990 | $C_{22}H_{26}ClN_3O_2$ | 400 | 41 | 99 |
| 2038 | 991 | $C_{23}H_{27}ClN_2O_2$ | 399 | 41 | 97 |
| 2039 | 992 | $C_{25}H_{31}ClN_2O_4$ | 459 | 47 | 98 |
| 2040 | 993 | $C_{25}H_{31}ClN_2O_2$ | 427 | 44 | 98 |
| 2041 | 995 | $C_{25}H_{31}ClN_2O_3$ | 443 | 44 | 95 |
| 2042 | 996 | $C_{24}H_{31}ClN_4O_2$ | 443 | 5* | 11 |

Note
*indicates "yield (mg) of trifluoroacetate".

Example 2043

Measurement of Inhibitory Activity of Test Compounds Against Binding of MIP-1 α to THP-1 Cells THP-1 cells which are human monocytic leukemia cell line were suspended in an assay buffer [prepared by adding 0.1% of BSA and 25 mM of HEPES to RPMI-1640 (Gibco-BRL Co.) and adjusting the pH to 7.4] so as to provide $1\times10^7$ cells/mL to thereby afford a cell suspension. A solution obtained by diluting the test compound with the assay buffer was used as a test compound solution. A solution prepared by diluting an iodine-labeled human MIP-1 α (DuPont NEN Co.) with the assay buffer so as to provided 250 nCi/mL was used as a labeled ligand solution. In a 96-well filter plate (Millipore Co.), were aliquoted 25 μL of the test compound solution, 25 μL of the labeled ligand solution and 50 μL of the cell suspension in the order mentioned for each well. The solutions were stirred (100 μL of the reaction solution) and then incubated at 18° C. for 1 hour.

After completing the reaction, the reaction solution was filtered through a filter, and the filter was washed with 200 μL of cold PBS twice (the reaction solution was filtered after adding 200 μL of the cold PBS). The filter was air-dried, and 25 μL of liquid scintillator was then added into each well to count the radioactivity retained by the cells on the filter using TopCount (Packard Instrument Co.).

The count when 100 ng of an unlabeled human MIP-1 α (Peprotech Co.) instead of the test compound was added was subtracted as nonspecific adsorption, and the count when the test compound was not added was taken as 100%. Thereby, the inhibitory activity of the test compound against binding of the human MIP-1 α to THP-1 cells was calculated.

$$\text{Inhibition ratio (\%)}=[1-(A-B)/(C-B)]\times100$$

(wherein A is the count when the test compound is added; B is the count when 100 ng of the unlabeled human MIP-1 α is added; C is the count when only the [$^{125}$I]-labeled human MIP-1 α is added).

When the inhibitory activity of the cyclic amine derivatives which are active ingredients of the present invention was measured, for example, the following compounds respectively manifested an inhibitory activity of 20% to 50%, 50% to 80% and >80% at a concentration of 2 μM or 10 μM.

Compounds which manifested an inhibitory activity of 20% to 50% at a concentration of 10 μM:

Compd. Nos. 29, 37, 41, 45, 46, 47, 50, 82, 85, 107, 120, 134, 214, 217, 218, 220, 222, 225, 226, 227, 228, 229, 230, 231, 233, 234, 236, 237, 238, 333, 334, 335, 336, 338, 340, 342, 347, 348, 349, 350, 352, 357, 359, 361, 366, 372, 374, 375, 376, 380, 382, 383, 385, 470, 471, 472, 4731, 474, 483, 484, 488, 489, 491, 497, 499, 500, 502, 506, 508, 510, 514, 515, 518, 524, 543, 553, 554, 555, 556, 563, 571, 575, 576, 578, 579, 580, 583, 586, 587, 588, 590, 591, 592, 595, 596, 598, 603, 610, 611, 612, 614, 624, 625, 626, 629, 635, 638, 639, 640, 641, 642, 643, 644, 646, 647, 648, 649, 652, 653, 658, 659, 660, 665, 666, 669, 671, 675, 677, 679, 681, 682, 684, 691, 695, 696, 700, 702, 704, 706, 711, 712, 714, 717, 721, 723, 724, 726, 727, 728, 729, 731, 737, 739, 740, 741, 742, 744, 746, 765, 767, 772, 773, 774, 775, 776, 780, 781, 785, 786, 787, 788, 790, 791, 792, 793, 795, 796, 797, 798, 805, 806, 807, 810, 813, 820, 821, 822, 824, 825, 827, 829, 830, 833, 834, 837, 838, 844, 853, 855, 873, 877, 878, 880, 882, 887, 888, 891, 894, 901, 903, 904, 905, 911, 929, 932, 933, 935, 938, 940, 948, 993, 996, 1006, 1018, 1026, 1028, 1035, 1048, 1053, 1054, 1055, 1056, 1068, 1070, 1071, 1072, 1073, 1075, 1076, 1081, 1763 and 1764 Compounds which manifested an inhibitory activity of 50% to 80% at a concentration of 10 μM:

Compd. Nos. 1, 2, 3, 4, 7, 13, 22, 23, 24, 25, 27, 31, 32, 38, 48, 83, 119, 121, 123, 131, 215, 216, 221, 235, 337, 351, 354, 358, 362, 363, 365, 367, 368, 369, 373, 378, 381, 384, 458, 459, 463, 465, 466, 467, 468, 478, 479, 480, 482, 485, 486, 487, 492, 493, 494, 495, 496, 498, 501, 503, 504, 507, 511, 512, 513, 520, 523, 527, 529, 530, 531, 532, 533, 534, 535, 536, 537, 538, 539, 540, 541, 542, 545, 546, 547, 548, 549, 550, 551, 552, 558, 559, 560, 561, 562, 565, 567, 568, 569, 570, 572, 573, 574, 577, 581, 582, 594, 597, 599, 600, 602, 604, 606, 607, 608, 609, 613, 615, 616, 618, 619, 620, 621, 628, 630, 631, 632, 633, 634, 636, 637, 645, 651, 654, 655, 657, 661, 662, 664, 673, 674, 676, 678, 680, 683, 685, 687, 688, 689, 693, 703, 705, 707, 708, 709, 710, 713, 716, 718, 719, 720, 725, 730, 732, 733, 734, 735, 736, 749, 750, 751, 752, 753, 754, 756, 758, 760, 762, 763, 764, 766, 768, 769, 770, 771, 777, 778, 779, 784, 794, 799, 800, 802, 804, 808, 809, 811, 812, 815, 816, 819, 828, 831, 832, 835, 836, 839, 840, 845, 846, 847, 848, 850, 851, 854, 857, 858, 859, 860, 861, 862, 863, 865, 866, 867, 868, 872, 874, 876, 886, 899, 910, 942, 998, 1004, 1005, 1007, 1013, 1015, 1016, 1017, 1019, 1020, 1021, 1022, 1024, 1030, 1037, 1042, 1043, 1044, 1045, 1046, 1047, 1049, 1050, 1052, 1059, 1060, 1061, 1067, 1069, 1074, 1078, 1079, 1080 and 1766

Compounds which manifested an inhibitory activity of >80% at a concentration of 10 μM:

Compd. Nos. 461, 464, 469, 481, 490, 505, 509, 521, 526, 528, 544, 564, 566, 601, 605, 617, 622, 623, 627, 650, 656, 663, 668, 672, 686, 690, 692, 694, 715, 743, 747, 748, 755, 757, 759, 761, 782, 783, 803, 814, 817, 818, 826, 849, 856, 864, 869, 870, 871, 999, 1000, 1001, 1002, 1003, 1008, 1009, 1010, 1011, 1012, 1023, 1029, 1031, 1032, 1033, 1034, 1036, 1038, 1039, 1040, 1041, 1051, 1057, 1058, 1062, 1063; 1064, 1065, 1066, 1082 and 1083 Compounds which manifested an inhibitory activity of 20% to 50% at a concentration of 2 μM:

Compd. Nos. 1042, 1043, 1244, 1245, 1416, 1435, 1436, 1438, 1441, 1480, 1570, 1583, 1584, 1589, 1590, 1594, 1595, 1601, 1660, 1672, 1687, 1724, 1779, 1780, 1787, 1795, 1796, 1798, 1799, 1802, 1893, 1894, 1898, 1900, 1915, 1919, 1920, 2092, 2096, 2098 and 2100

Compounds which manifested an inhibitory activity of 50% to 80% at a concentration of 2 μM:

Compd. Nos. 1190, 1414, 1600, 2091, 2094 and 2095 Compounds which manifested an inhibitory activity of >80% at a concentration of 2 M:

Compd. Nos. 2093, 2097, 2099, 2103 and 2104.

Example 2044

Measurement of Inhibitory Activity Against Binding of MCP-1 to THP-1 Cells

1. Preparation of Human MCP-1 Gene-Carrying Recombinant Baculovirus

Two kinds of DNA synthetic primers (5'-CACTCTAGACTCCAGCATGA-3' (SEQ ID NO:1) and 5'-TAGCTGCAGATTCTTGGGTTG-3') (SEQ ID NO:2) having restriction enzyme recognition sites applied on the basis of the known human MCP-1 gene sequence (see, for example, Yoshimura, T. et al. FEBS Letters 1989, 244, 487-493) were used to amplify a cDNA derived from human vascular endothelial cells (purchased from Kurabow) according to a PCR method. The amplified fragment was cleaved with restriction enzymes (PstI and XbaI) and then ligated into a transfer vector pVL1393 (Invitrogen Co.). The resulting vector was co-transfected with an infectious baculovirus into Sf-9 insect cells. Human MCP-1 gene recombinant baculoviruses were isolated from the obtained supernatant by a plaque assay method.

2. Synthesis of [$^{125}$I]-Labeled Human MCP-1 Expressed with Baculovirus

According to the method of Ishii, K. et al. (see Biochemical and Biophysical Research Communications, 1995, 206, 955-961), $5\times10^6$ cells of Sf-9 insect cells were infected with $5\times10^7$ PFU (plaque-forming units) of the above human MCP-1 gene recombinant baculoviruses and cultured in EX-CELL 401 medium for 7 days. The resulting culture supernatant was affinity purified by a heparin-Sepharose column (Pharmacia Co.) and then subjected to reverse phase HPLC (Vydac C18 column) to afford a purified human MCP-1. The protein labeling of the resulting purified human MCP-1 was requested for Amersham Co. to obtain a [$^{125}$I]-labeled human MCP-1 expressed with baculovirus (specific activity: 2000 Ci/mmol) prepared by the Bolten Hunter method. The resulting [$^{125}$I]-labeled human MCP-1 was used for the following tests.

3-1. Measurement of Inhibitory Activity Against Binding of [$^{125}$I]-Labeled Human MCP-1 Expressed with Baculovirus to THP-1 Cells (Method 1)

THP-1 cells which are human monocytic leukemia cell line were suspended in an assay buffer [prepared by adding 0.1% of BSA and 25 mM of HEPES to RPMI-1640 (Gibco-BRL Co.) and adjusting the pH to 7.4] so as to provide $1\times10^7$ cells/mL to thereby afford a cell suspension. A solution obtained by diluting the test compound with the assay buffer was used as a test compound solution. A solution prepared by diluting the above [$^{125}$I]-labeled human MCP-1 expressed with baculovirus with the assay buffer so as to provide 1 μCi/mL was used as a lebeled ligand solution. In a 96-well filter plate (Millipore Co.), were aliquoted 25 μL of the test compound solution, 25 μL of the labeled ligand solution and 50 μL of the cell suspension in the order mentioned for each well. The solutions were stirred (100 μL of the reaction solution) and then incubated at 18° C. for 1 hour.

After completing the reaction, the reaction solution was filtered through a filter, and the filter was washed with 200 μL of cold PBS twice (the reaction solution was filtered after adding 200 μL of the cold PBS). The filter was air-dried and 25% L of liquid scintillator was then added into each well to count the radioactivity retained by the cells on the filter using TopCount (Packard Instrument Co.).

The count when 100 ng of the above human MCP-1 expressed with baculovirus (unlabeled) instead of the test compound was added was subtracted as nonspecific adsorption, and the count when the test compound was not added was taken as 100%. Thereby, the inhibitory activity of the test compound against binding of the human MCP-1 to THP-1 cells was calculated.

$$\text{Inhibition ratio } (\%)=\{1-(A-B)/(C-B)\}\times 100$$

(wherein A is the count when the test compound is added; B is the count when 100 ng of the unlabeled human MCP-1 is added; C is the count when only the [$^{125}$I]-labeled human MCP-1 is added).

When the inhibitory activity of the cyclic amine derivatives which are active ingredients of the present invention was measured, for example, the following compounds respectively manifested an inhibitory activity of 20 to 50%, 50% to 80% and >80% at a concentration of 1 μM, 10 μM or 100 μM.

Compounds which manifested an inhibitory activity of 20% to 50% at a concentration of 100 μM:

Compd. Nos. 3, 6, 11, 15, 16, 19, 28, 44, 88, 92, 94, 104, 111, 112, 124, 125, 133, 219, 220, 224, 228, 236, 338, 343, 346, 347, 348, 349, 362, 363, 367, 368, 371, 373, 381, 618, 847, 849, 850, 866, 867, 869, 870, 871, 872 and 873 Compounds which manifested an inhibitory activity of 50% to 80% at a concentration of 100 μM:

Compd. Nos. 1, 8, 10, 12, 18, 21, 26, 30, 33, 35, 39, 84, 89, 90, 91, 96, 97, 98, 99, 100, 101, 103, 106, 108, 109, 110, 116, 122, 126, 216, 218, 221, 225, 226, 231, 330, 332, 333, 334, 337, 341, 342, 350, 352, 354, 356, 359, 360, 361, 364, 366, 374, 375, 379, 382, 462, 463, 464, 557, 686, 840, 841, 842, 843, 844, 845, 846, 848, 862, 863, 864, 865, 868

Compounds which manifested an inhibitory activity of >80% at a concentration of 100 μM:

Compd. Nos. 2, 4, 5, 7, 13, 14, 17, 20, 22, 23, 24, 25, 27, 29, 31, 32, 34, 36, 38, 40, 41, 42, 43, 45, 46, 47, 48, 49, 50, 83, 85, 86, 95, 102, 105, 107, 113, 114, 115, 119, 120, 121, 123, 127, 128, 129, 130, 131, 132, 134, 214, 215, 217, 227, 237, 238, 331, 335, 336, 339, 340, 345, 351, 355, 357, 358, 383, 458, 459, 460, 466, 558, 851, 852, 861 and 874

Compounds which manifested an inhibitory activity of 20% to 50% at a concentration of 10 t M:

Compd. Nos. 12, 18, 30, 34, 40, 42, 43, 51, 52, 53, 54, 55, 56, 57, 59, 60, 64, 66, 75, 76, 77, 78, 79, 82, 89, 90, 97, 98, 102, 103, 116, 127, 128, 129, 130, 132, 135, 136, 140, 141, 144, 156, 157, 159, 160, 161, 162, 163, 166, 167, 168, 169, 170, 171, 172, 173, 174, 175, 176, 178, 179, 190, 191, 192, 195, 197, 200, 202, 203, 204, 205, 208, 233, 234, 235, 239, 240, 241, 242, 243, 245, 247, 249, 250, 255, 263, 264, 269, 274, 278, 279, 282, 306, 316, 317, 323, 324, 380, 404, 409, 433, 446, 448, 449, 451, 470, 471, 473, 476, 479, 486, 488, 489, 497, 498, 499, 501, 504, 507, 508, 509, 510, 512, 514, 516, 519, 527, 530, 532, 542, 545, 560, 563, 564, 565, 566, 568, 569, 572, 573, 574, 575, 578, 583, 584, 586, 587, 589, 590, 599, 600, 601, 603, 606, 612, 613, 620, 621, 622, 624, 625, 627, 629, 630, 632, 634, 636, 637, 640, 641, 642, 643, 644, 645, 646, 647, 648, 649, 658, 678, 682, 687, 692, 694, 764, 775, 856, 857, 860, 881, 882, 883, 884, 890, 892, 899, 900, 903, 905, 907, 908, 911, 912, 916, 917, 921, 922, 923, 925, 927, 931, 932, 935, 939, 940, 968, 986, 1039, 1041, 1045, 1047, 1062, 1063 and 1083

Compounds which manifested an inhibitory activity of 50% to 80% at a concentration of 10 μM:

Compd. Nos. 7, 32, 36, 61, 62, 63, 65, 67, 69, 70, 71, 72, 73, 74, 81, 91, 105, 114, 121, 123, 134, 137, 138, 139, 146, 147, 148, 149, 151, 154, 165, 177, 232, 244, 248, 251, 252, 253, 256, 259, 261, 266, 267, 276, 286, 292, 293, 295, 301, 305, 307, 310, 314, 315, 320, 322, 328, 434, 435, 436, 437, 439, 440, 443, 447, 450, 452, 453, 454, 455, 456, 468, 469, 472, 474, 475, 477, 478, 480, 481, 482, 483, 485, 490, 493, 494, 500, 505, 511, 517, 520, 529, 534, 540, 543, 544, 548, 555, 556, 561, 562, 570, 576, 579, 611, 617, 853, 854, 855, 858, 859, 875, 877, 879, 880, 885, 886, 887, 888, 891, 894, 895, 904, 906, 909, 910, 913, 914, 918, 928, 930, 933, 937, 938, 945, 970, 1040, 1044 and 1046 Compounds which manifested an inhibitory activity of >80% at a concentration of 10 μM:

Compd. Nos. 31, 45, 46, 48, 58, 68, 80, 83, 113, 115, 142, 143, 145, 150, 152, 265, 268, 272, 275, 283, 285, 287, 288, 290, 291, 294, 296, 297, 302, 308, 309, 313, 321, 325, 326, 358, 438, 441, 442, 444, 445, 457, 466, 467, 484, 487, 491, 492, 495, 496, 503, 518, 537, 538, 547, 554, 876, 878, 919, 929 and 943 Compounds which manifested an inhibitory activity of 20% to 50% at a concentration of 1 μM:

Compd. Nos. 1118, 1121, 1136, 1143, 1146, 1158, 1159, 1167, 1170, 1359, 1361, 1362 and 1363

Compounds which manifested an inhibitory activity of 50% to 80% at a concentration of 1 μM:

Compd. Nos. 1133, 1134, 1137, 1141, 1156, 1161, 1162, 1163, 1164 and 1166

Compounds which manifested an inhibitory activity of >80% at a concentration of 1 μM:

Compd. No. 1147.

3-2. Measurement of Inhibitory Activity Against Binding of [$^{125}$I]-Labeled Human MCP-1 expressed with baculovirus to THP-1 cells (method 2)

THP-1 cells which are human monocytic leukemia cell line were suspended in an assay buffer (containing 50 mM of HEPES, 11.0 mM of $CaCl_2$, 5.0 mM of $MgCl_2$ and 0.5% of BSA at pH 7.4) so as to provide $1\times10^7$ cells/mL to thereby obtain a cell suspension. A solution obtained by diluting the test compound with the assay buffer was used as a test compound solution. A solution prepared by diluting the above [$^{125}$I]-labeled human MCP-1 expressed with baculovirus with the assay buffer so as to provide 1 μCi/mL was used as a labeled ligand solution. In a 96-well filter plate (Millipore Co.), were aliquoted 25 μL of the test compound solution, 25 μL of the labeled ligand solution and 50 μL of the cell suspension in the order mentioned for each well. The solutions were stirred (100 μL of the reaction solution) and then incubated at 18° C. for 1 hour.

After completing the reaction, the reaction solution was filtered through a filter, and the filter was washed with 200 μL of cold PBS twice (the reaction solution was filtered after adding 200 μL of the cold PBS). The filter was air-dried, and 25% L of liquid scintillator was then added by into each well to count the radioactivity retained by the cells on the filter using TopCount (Packard Instrument Co.). The count when 100 ng of the above human MCP-1 expressed with baculovirus(unlabeled) instead of the test compound was added was subtracted as nonspecific adsorption, and the count when the test compound was not added was 100%. Thereby, the inhibitory activity of the test compound against binding of the human MCP-1 to THP-1 cells was calculated.

$$\text{Inhibition ratio (\%)}=\{1-(A-B)/(C-B)\}\times 100$$

(wherein A is the count when the test compound is added; B is the count when 100 ng of the unlabeled human MCP-1 is added; C is the count when only the [$^{125}$I]-labeled human MCP-1 is added).

When the inhibitory activity of the cyclic amine derivatives which are the active ingredients of the present invention was measured, for example, the following compounds respectively manifested an inhibitory activity of 20% to 50%, 50% to 80% and >80% at a concentration of 0.2 μM, 1 μM or 10 μM.

Compounds which manifested an inhibitory activity of 20% to 50% at a concentration of 10 μM:

Compd. No. 1560

Compounds which manifested an inhibitory activity of 50% to 80% at a concentration of 10 μM:

Compd. No. 1550

Compounds which manifested an inhibitory activity of >80% at a concentration of 10 μM:

Compd. Nos. 541, 1042, 1043 and 1559

Compounds which Manifested an Inhibitory Activity of 20% to 50% at a Concentration of 1 μM:

Compd. Nos. 1098, 1100, 1101, 1104, 1105, 1109, 1110, 1116, 1174, 1175, 1176, 11178, 1187, 1188, 1189, 1197, 1198, 1199, 1200, 1201, 1202, 1209, 1210, 1211, 1212, 1222, 1225, 1229, 1230, 1237, 1238, 1243, 1250, 1259, 1261, 1265, 1266, 1272, 1277, 1282, 1294, 1299, 1302, 1307, 1315, 1318, 1319, 1320, 1329, 1330, 1335, 1336, 1337, 1343, 1344, 1353, 1355, 1356, 1357, 1358, 1368, 1372, 1385, 1386, 1392, 1400, 1413, 1422, 1423, 1425, 1426, 1429, 1430, 1432, 1437, 1440, 1445, 1446, 1447, 1448, 1450, 1452, 1453, 1455, 1458, 1459, 1461, 1463, 1464, 1466, 1468, 1469, 1470, 1471, 1474, 1479, 1482, 1485, 1507, 1508, 1510, 1511, 1512, 1513, 1514, 1515, 1516, 1518, 1519, 1521, 1522, 1524, 1535, 1538, 1540, 1542, 1544, 1571, 1573, 1574, 1575, 1576, 1577, 1578, 1579, 1580, 1581, 1582, 1585, 1587, 1598, 1602, 1603, 1604, 1609, 1611, 1612, 1613, 1614, 1615, 1616, 1617, 1618, 1622, 1627, 1630, 1643, 1646, 1662, 1669, 1716, 1717, 1723, 1728, 1731, 1733, 1736, 1739, 1740, 1747, 1750, 1755, 1757, 1758, 1759, 1760, 1761, 1762, 1769, 1770, 1771, 1772, 1773, 1774, 1777, 1783, 1784, 1785, 1791, 1793, 1904, 1911, 1917, 2057, 2061, 2063, 2064, 2065, 2066, 2067, 2068, 2069, 2071, 2072, 2073, 2074, 2075, 2076, 2080, 2081, 2082, 2110, 2112, 2123, 2130, 2131, 2139, 2170, 2180, 2181, 2182, 2212, 2216, 2217, 2219, 2220, 2222, 2224, 2225, 2228, 2247, 2253, 2254, 2255, 2256 and 2257

Compounds which manifested an inhibitory activity of 50% to 80% at a concentration of 1 μM:

Compd. Nos. 37, 298, 318, 1084, 1091, 1103, 1106, 1108, 1111, 1113, 1114, 1115, 1138, 1142, 1165, 1179, 1190, 1192, 1193, 1195, 1196, 1204, 1205, 1206, 1207, 1208, 1245, 1246, 1255, 1257, 1258, 1262, 1263, 1293, 1300, 1342, 1351, 1352, 1354, 1370, 1371, 1373, 1375, 1377, 1378, 1380, 1381, 1383, 1384, 1391, 1411, 1412, 1414, 1417, 1418, 1419, 1421, 1424, 1431, 1436, 1439, 1449, 1454, 1456, 1457, 1460, 1462, 1472, 1473, 1487, 1502, 1504, 1506, 1517, 1525, 1526, 1527, 1529, 1530, 1531, 1532, 1533, 1534, 1536, 1537, 1539, 1541, 1545, 1593, 1600, 1601, 1606, 1608, 1619, 1620, 1621, 1623, 1624, 1625, 1626, 1628, 1629, 1645, 1650, 1654, 1658, 1663, 1664, 1665, 1670, 1671, 1672, 1673, 1675, 1678, 1679, 1681, 1684, 1687, 1688, 1689, 1690, 1711, 1712, 1714, 1718, 1722, 1725, 1726, 1727, 1729, 1730, 1732, 1734, 1735, 1737, 1741, 1742, 1743, 1744, 1745, 1746, 1748, 1751, 1753, 1754, 1756, 1779, 1781, 1782, 1786, 1788, 1789, 1790, 1792, 1795, 1797, 1798, 1800, 1801, 1804, 1848, 1862, 1883, 1885, 1886, 1887, 1889, 1893, 1894, 1903, 1905, 1910, 1912, 1913, 1914, 1918, 1922, 1976, 1985, 2027, 2035, 2062, 2083, 2084, 2088, 2089, 2090, 2111, 2124, 2125, 2126, 2135, 2167, 2171, 2175, 2211, 2221, 2226, 2231 and 2240 Compounds which manifested an inhibitory activity of >80% at a concentration of 1 μM:

Compd. Nos. 299, 311, 312, 329, 1042, 1043, 1085, 1119, 1191, 1203, 1220, 1228, 1236, 1244, 1256, 1288, 1295, 1308, 1310, 1376, 1382, 1393, 1395, 1415, 1416, 1420, 1435, 1438, 1441, 1480, 1481, 1570, 1583, 1584, 1589, 1590, 1594, 1595, 1607, 1634, 1660, 1661, 1666, 1668, 1695, 1696, 1697, 1698, 1699, 1701, 1702, 1703, 1704, 1705, 1706, 1707, 1708, 1709, 1713, 1724, 1749, 1752, 1775, 1776, 1778, 1780, 1787, 1794, 1796, 1799, 1802, 1803, 1841, 1869, 1870, 1871, 1872, 1876, 1877, 1892, 1896, 1897, 1898, 1899, 1900, 1901, 1902,1906, 1907, 1908, 1909, 1915, 1916, 1919, 1920, 1921, 2085, 2086, 2087, 2113, 2114, 2118, 2119, 2120, 2121, 2122, 2127, 2128, 2129, 2132, 2133, 2136, 2137, 2138, 2159, 2161, 2162, 2169, 2172, 2178, 2179, 2187, 2189, 2193, 2210, 2213, 2214, 2215, 2218, 2227, 2229, 2230, 2232, 2233, 2235, 2236, 2237, 2238, 2241, 2242, 2243, 2244, 2245, 2246, 2248, 2249, 2250, 2251 and 2252

Compounds which manifested an inhibitory activity of 20% to 50% at a concentration of 2 μM:

Compd. Nos. 1680, 1682, 1686, 1691, 1694, 1700, 1805, 1810, 1811, 1812, 1813, 1815, 1816, 1817, 1818, 1819, 1820, 1824, 1825, 1826, 1827, 1828, 1832, 1833, 1834, 1835, 1836, 839, 1840, 1842, 1843, 1851, 1852, 1853, 1854, 1855, 1856, 1858, 1859, 1860, 1863, 1864, 1865, 1866, 1868, 1874, 1878, 1879, 1880, 1888, 1890, 1891, 1895, 1926, 1927, 1928, 1929, 1930, 1934, 1935, 1937, 1945, 1946, 1951, 1952, 1953, 1954, 1959, 1960, 1961, 1962, 1966, 1969, 1970, 1971, 1972, 1973, 1977, 1978, 1979, 1980, 1981, 1985, 2014, 2027, 2028, 2033, 2035, 2039, 2040, 2041, 2042, 2044, 2045 and 2046

Compounds which manifested an inhibitory activity of 50% to 80% at a concentration of 0.2 g M:

Compd. Nos. 1677, 1678, 1679, 1681, 1687, 1688, 1689, 1690, 1695, 1697, 1808, 1809, 1841, 1848, 1861, 1862, 1869, 1870, 1871, 1872, 1873, 1876, 1877, 1883, 1884, 1885, 1886, 1887, 1889, 1893, 1894 and 1976 Compounds which manifested an inhibitory activity of >80% at a concentration of 0.2 M:

Compd. Nos. 1696 and 1892.

Example 2045

Measurement of Inhibitory Activity Against Binding of MCP-1 to Cells Expressing the MCP-1 Receptor (Evaluation using [$^{125}$I]-Labeled Human MCP-1)

1. Obtaining of Cells Expressing the MCP-1 Receptor

An MCP-1 receptor cDNA fragment obtained by Yamagami, S. et al. (see Biochemical and Biophysical Research Communications, 1994, 202, 1156-1162) was cloned into an NotI site of an expression plasmid pCEP-4 (Invitrogen Co.), and the resulting plasmid was transfected into human kidney epithelial cell line 293-EBNA with a Lipofectamine reagent (Gibco-BRL Co.) and the cells were cultured in the presence of a selective agent (Hygromycin) to provide a stably expressing transfactant line. The expression of the receptor was confirmed by binding properties of the [$^{125}$I]-labeled human MCP-1.

2. Measurement of Inhibitory Activity Against Binding of [$^{125}$I]-Labeled Human MCP-1 Expressed with Baculovirus to MCP-1 Receptor-Expressing Cells The MCP-1 receptor-expressing cells on a tissue culture dish were scraped using a cell scraper and suspended in the assay buffer [prepared by adding 0.1% of BSA and 25 mM of HEPES to D-MEM (Gibco-BRL Co.) and adjusting the pH to 7.4] to thereby provide a cell suspension of a concentration $6\times10^6$ cells/ml. The same subsequent procedures were performed as described in Example 2044.

When the inhibitory activity of the cyclic amine derivatives, which were the active ingredients of the present invention, was measured, the inhibitory activity of the representative compounds in the Example was approximately the same as that described in Example 2044.

Example 2046

Measurement of Inhibitory Activity Against Cell Chemotaxis

In order to determine the inhibitory activity of the compounds according to the present invention against the cell chemotaxis, human monocytic leukemia cell line THP-1 was used as chemotactic cells according to the method of Fall et al. (J. Immunol. Methods, 1980, 33, 239-247) to determine the cell chemotaxis caused by monocyte chemotactic factor MCP-1 as follows: Namely, $2\times10^6$ cells/mL of the THP-1 cells [suspended in RPMI-1640 (Flow Laboratories Co.) 10% FCS] were placed in the upper chamber (200 μL) of a 96-well microchemotaxis chamber (Neuroprobe®), and human recombinant MCP-1 (Peprotech Co.) diluted with the same solution so as to provide the final concentration of 20 ng/mL was placed in the lower chamber (35 μL). A polycarbonate filter (PVP-free, Neuroprobe®) was placed between the two chambers. These were incubated in the presence of 5% of $CO_2$ at 37° C. for 2 hours.

The filter was removed, and the cells which had migrated to the undersurface of the filter were immobilized, stained using Diff Quick (Kokusai Shiyaku Co.) and then measured at a measuring wavelength of 550 nm using a plate reader (Molecular Device Co.) to determine the means of 3 wells. Thereby, the indication of the number of cells migrated was obtained. The test compound together with the THP-1 cells was added to the upper chamber at various concentrations to determine the inhibitory activity against cell chemotaxis [degree of inhibition: $IC_{50}$ (μM)]. The degree of inhibition was defined as {(number of cells migrated with MCP-1 when no test compound was added to the upper chamber)−(number of cells migrated when no MCP-1 was added to the lower chamber)=100%}, and the concentration of the compound manifested 50% of the inhibition was designated as $IC_{50}$.

When the inhibitory activity of the cyclic amine derivatives which are the active ingredients of the present invention was determined, for example, the $IC_{50}$ value of the following compounds was 0.1 μM or below.

Examples of compounds which manifested an $IC_{50}$ value of 0.1 μM or below:

Compd. Nos. 4, 37, 298, 299, 311, 312, 318, 329, 461, 886, 909, 1042, 1043, 1085, 1119, 1138, 1142, 1165, 1179, 1191, 1203, 1205, 1220, 1228, 1236, 1244, 1245, 1256, 1288, 1293, 1295, 1308, 1310, 1352, 1376, 1382, 1393, 1395, 1416, 1420, 1435, 1436, 1438, 1441, 1480, 1531, 1532, 1570, 1583, 1584, 1589, 1590, 1594, 1595, 1600, 1601, 1607, 1660, 1661, 1664, 1666, 1668, 1698, 1699, 1701, 1702, 1703, 1704, 1706, 1707, 1708, 1709, 1713, 1775, 1776, 1778, 1779, 1787, 1794, 1796, 1799, 1802, 1803, 1896, 1898, 1899, 1900, 1901, 1902, 1906, 1907, 1908, 1909, 1915, 1916, 1919, 1920, 1921, 2087, 2114, 2128, 2129, 2132, 2137, 2141, 2144, 2157, 2158, 2189, 2213, 2214, 2235, 2236, 2241, 2242, 2244, 2249, 2250 and 2251.

The results in Examples 2043, 2044. 2045 and 2046 definitely show that the compounds of the present invention as a receptor antagonist of chemokines such as MIP-1 α and/or MCP-1 have the inhibitory activity against actions of the chemokines on target cells.

Example 2047

Studies on Inhibitors Effects on Collagen-Induced Arthritis in Mice

Collagen-induced arthritis in mice was induced according to the method of Kato et al. (Arthritis in mice induced by a single immunization with collagen, Ann. Rheum. Dis., 55, 535-539, 1996).

1. Method

Type II collagen derived from a bovine joint (Collagen Gijutsu-kenshukai) was emulsified with an volume of a Freund's complete adjuvant (ICN Immunobiologicals) to prepare a homogeneous emulsion. An ultrasonic homogenizer (Taitec) was used to prepare the emulsion. The emulsion (in a dose of 0.15 mg/0.1 mL/body) was intracutaniously injected into the base of the tail of DBA/1 mice (Charles River, Japan Inc.) by using a glass syringe for tuberculin and a 27G injection needle.

The test compound was suspended in a 0.5% aqueous solution of sodium carboxymethyl cellulose (CMC, Wako Pure Chemical Industries, Ltd.) with a mortar to prepare a prescribed administration suspension, which was orally administered from the date after the administration of the emulsion.

The experimental groups are three of a group administered with 0.5% of CMC (hereinafter referred to as the control group) and groups administered with 30 mg/kg or 100 mg/kg of the test compound. The solution or the test compound was administered once a day, and the number of animals in each group was 16.

2. Evaluation of Arthritis

The degree of joint swelling was scored for each digital joint of four limbs after the passage of 12 weeks from the administration of the emulsion according to the method of Abe (immunotherapy in arthritis model, Japanese Journal of Inflammations 12, 417-422, 1992). Each limb was scored in four grades of scores 0 to 3, and the maximum was score 12.

3. Actions on Synovial Hyperlasia, Chondrolysis of Articular Cartilages and Osteolysis of Subchondral Bone After observing the arthritis scores, the right hindlimbs were removed. After embedding in paraffin, thin slice of knee joint were prepared and subjected to hematoxylin-eosin staining to evaluate actions on synovial hyperplasia, chondrolysis, destruction of articular cartilages and osteolysis of subchondral bone according to a conventional method. The rating was carried out in five grades of scores 0 to 4 for each measurement item.

4. Results of evaluation

The category type Dunnett's tests compared with the control group were carried out, and a p value of 0.05 or below was taken as significantly different.

The following graphs are expressed as mean ±standard deviation (SD). FIG. 1 illustrates the results of arthritis when Compd. No. 1583 was orally administered for 12 weeks. The group administered with Compd. No. 1583 significantly inhibited arthritis scores as compared with the control group.

Figure 2:
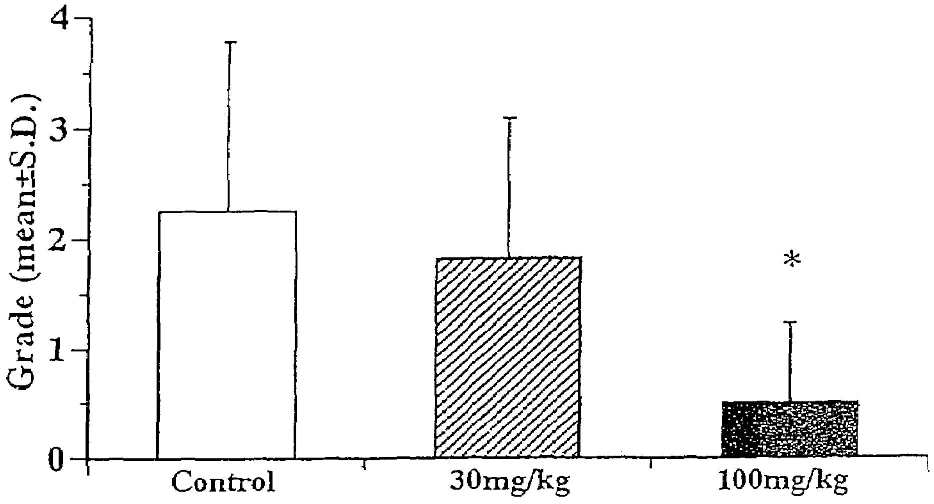
FIG. 2 is a drawing illustrating effects of the Compd. No. 1,583 on synovial hyperplasia.
Figure 3:
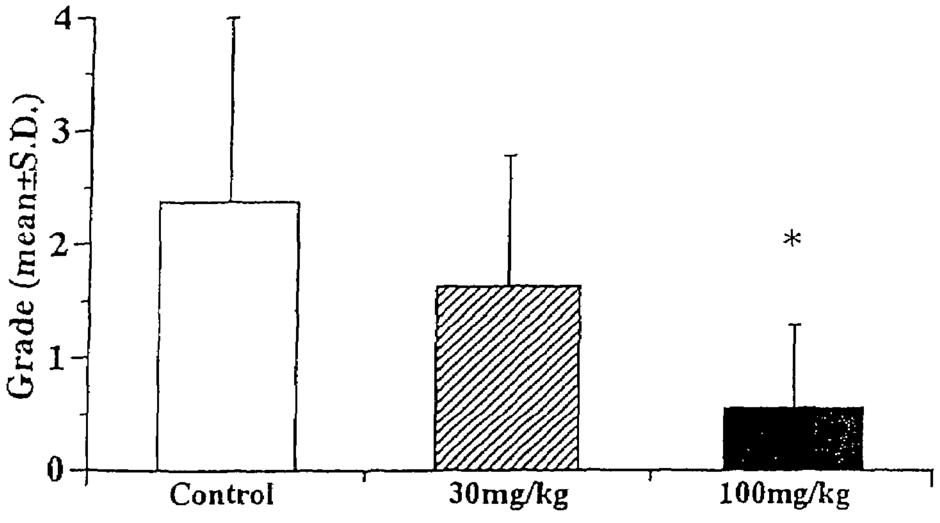
FIG. 3 is a drawing illustrating effects of the Compd. No. 1583 on the chondrolysis of articular cartilages.
Figure 4:
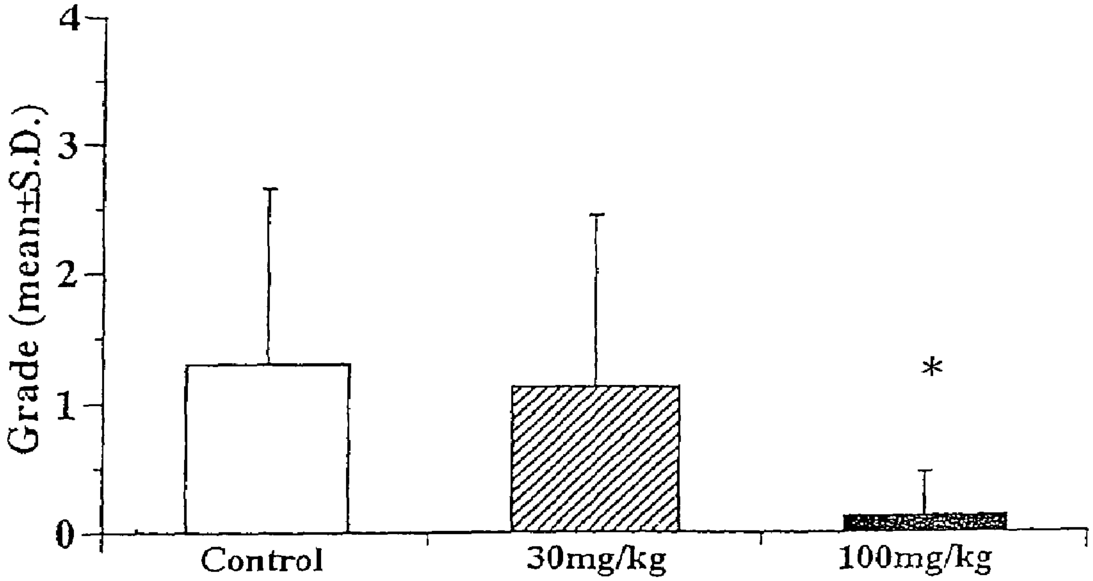
FIG. 4 is a drawing illustrating effects of the Compd. No. 1583 on the osteolysis of subchondral bone.

FIGS. 2 to 4 respectively illustrates results of Compd. No. 1583 on synovial hyperplasia, chondrolysis of articular cartilages and osteolysis of subchondral bone. Compd. No. 1583 significantly inhibited for all the evaluation items.

Example 2048

Studies on Inhibitory Effects on Collagen-Induced Arthritis in Rats

Collagen-induced arthritis in rats was induced by modifying the method of Trentham et al. (Autoimmunity to type II collagen: an experimental model of arthritis. J. Exp. Med., 146, 857-68 (1977) as follows:

1. Method

Type II collagen derived from a bovine joint (Collagen Gijutsu-kenshukai) and muramyl dipeptide (CHEMICON International) were mixed with an Freund's incomplete adjuvant so as to provide each final concentration of 0.08% and 0.02% to thereby prepare a homogenous emulsion. The resulting emulsion was prepared by vigorous stirring at 4° C. in two glass syringes connected with a connector. One mL of the emulsion was injected intradermally in 10 sites on the back of Lewis female rats (Charles River Japan, Inc., 6-weeks-old) by using a glass syringe for tuberculin and a 26G injection needle. After one week, the base of the tail was additionally immunized (boosted) intradermally with 0.1 mL of the emulsion prepared by the same method as described above.

The test compound was suspended in a 0.5% aqueous solution of sodium carboxymethylcellulose (CMC, Wako Pure Chemical Industries, Ltd.) with a mortar to prepare a prescribed administration suspension, which was orally administered every day for 3 weeks after the date of the initial administration of the emulsion.

The experimental groups were a group of no treatment (intact group), a group administered with 0.5% of the CMC (hereinafter referred to as the control group) and a group administered with 300 mg/kg of Compd. No. 1245. The solution or the test compound was administered once a day. The number of animals in each group was 8.

2. Evaluation of Arthritis

The limb joint swelling of hindlimbs was evaluated by determining a change in the volume of the limb joints. The footpad volumes of the right and left hindlimbs of rats were measured total 7 times of the date of boosting, 2, 5, 7, 9, 12 and 14 days after the date of boosting by using a rat hindlimb footpad volume meter (TK-105, UNICON). The obtained results were expressed as an increasing rate after the date of boosting by taking the footpad volume on the date of boosting as 100%. The mean of the group was obtained as the mean of all the left and right hindlimb volumes in each group.

3. Results of evaluation

Figure 5:
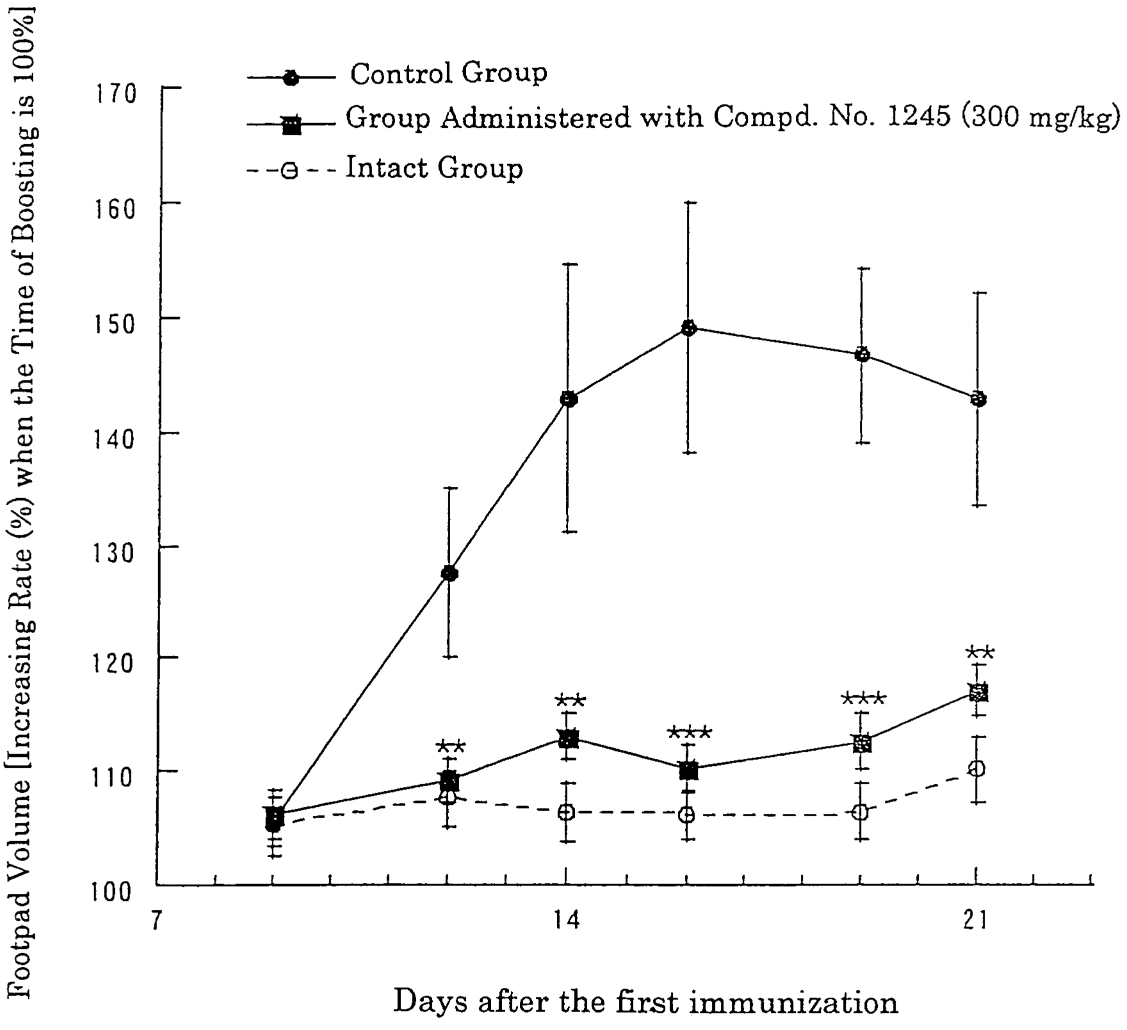
FIG. 5 is a drawing illustrating effects of Compd. No. 1245 on hindlimb footpads swelling when the compound is orally administered for 3 weeks.

FIG. 5 illustrates results of arthritis when Compd. No. 1245 was orally administered every day for 3 weeks. Values in the figure are expressed as mean ±S.E. Student's t-tests or Wilcoxon tests were carried out comparing with the control group, and a P value of 0.05 or below was taken as significantly different. The group administered with Compd. No. 1245 significantly inhibited joint swelling (after 5, 7 and 14 days: $P<0.01$ and after 9 and 12 days: $P<0.001$) as compared with the control group at each time point of 5, 7, 9, 12 and 14 days after the boosting.

The results of Examples 2047 and 2048 show that the compounds of the present invention have effective remedial or prophylactic effects on diseases in association with chondrolysis of cartilage or osteolysis such as arthritis, rheumatoid arthritis, osteoarthritis, traumatic articular destruction, osteoporosis or tumor.

Example 2049

Studies on Inhibitors Actions in Masugi's Nephritis Model in WKY-Rats

1. Method (Common to Experiments 1 and 2)

Rabbits were immunized with a trypsin fraction of rat kidney cortex to provide an anti-glomerular basement membrane serum which was intravenously injected to 4-weeks-old female WKY rats (Charles River) in a dose of 2.5 mL/kg body weight to induce glomerulonephritis.

After injection of the antiserum, urine of each animal was collected for 24 hours with metabolic cages for rats (Clea Japan, Inc.) on the 1st, 4th, 7th, 10th and 14th days after the injection. The amount of the urine was measured by urine weight and the protein content in the urine was measured by using a kit for assaying proteins in urine and cerebrospinal fluid (Tonein TP-II, Otsuka Pharmaceutical Co., Ltd.) to determine the amount of proteins excreted in urine per day.

Serum of the animals subjected to the experiments was collected on the 15th day after injecting the antiserum, and creatinine concentration in blood was measured with a creatinine assay kit (Autosera®), Daiichi Pure Chemicals Co., Ltd.) using a Hitach±7070 model autoanalyzer.

The test compound was daily orally administered in a dose of 100 mg/kg body weight twice a day from the date of injecting the anti-glomerular basement membrane serum (about 10:00 a.m. and about 6:00 p.m. in Experiment 1 and about 10:00 a.m. and about 5:00 p.m. in Experiment 2). In the control group, only the solution (a 0.5% aqueous solution of sodium carboxymethylcellulose) was orally administered. The administration volume was 10 mL/kg body weight, and the number of animals (N) was 10.

2. Results and Discussion

Figure 6:
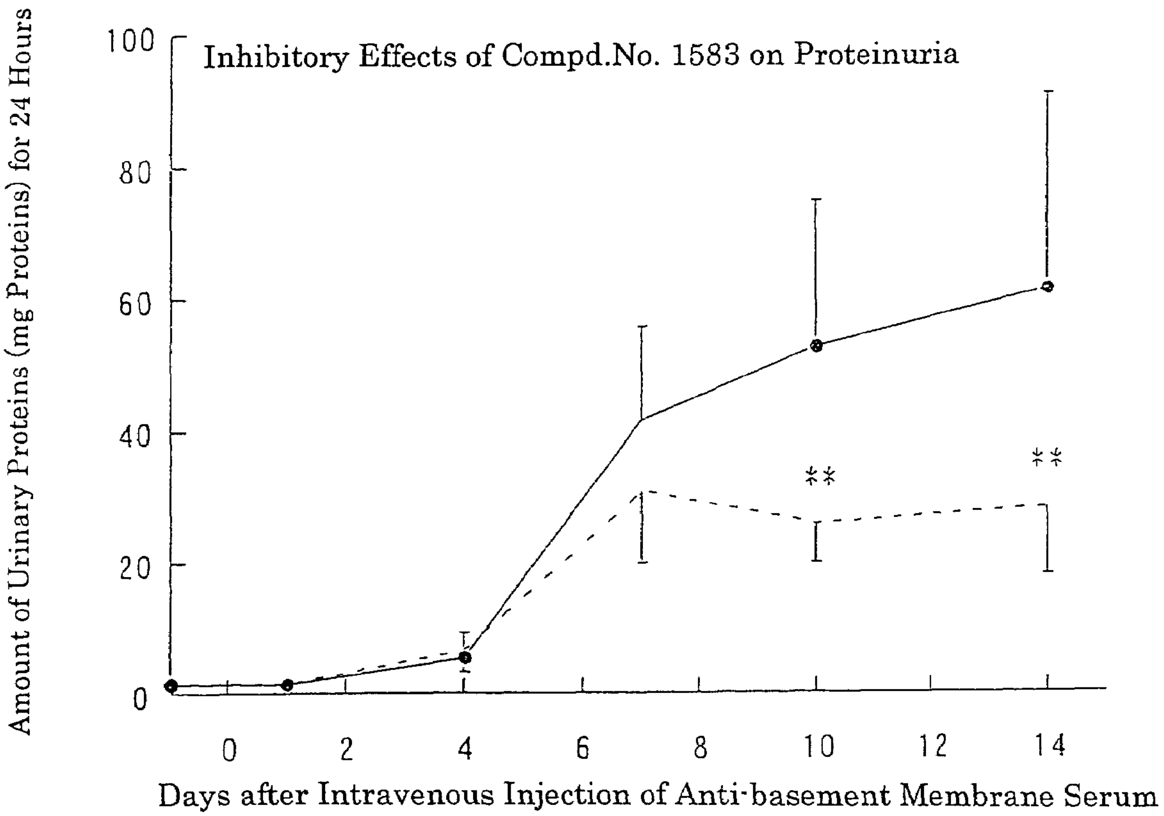
FIG. 6 is a drawing illustrating suppressive effects of the Compd. No. 1583 on proteinuria.

The detection of proteinuria began in each experimental group on the 4th day after injecting the anti-glomerular basement membrane serum, and the concentration of the urinary proteins was subsequently increased to the 14th day with time to induce nephritis. In the group administered with Compd. No. 1583, a tendency to inhibit the concentration of urinary proteins by 26% was found as compared with the control group on the 7th day after injecting the antiserum. A significant inhibition of the concentration of urinary proteins was found by 51 and 54% on the 10th and 14th days ($p<0.01$, Mann-Whitney U test). (FIG. 6). When the creatinine concentration in blood was measured on the 15th day after injecting the anti-glomerular basement membrane serum, a significant decrease of 20% ($p<0.01$, Mann-Whitney U test) was found in the group administered with Compd. No. 1583 as compared with the control group (Table 53).

Therefore, it is found that the glomerular injury and renal function exacerbation of rats were alleviated with Compd. No. 1583 to inhibit nephritis.

TABLE 53

| Inhibitory Effects on Serum Creatinine Serum Creatinine Concentration (mg/dl) on the 15th Day of Administering Compound | |
|---|---|
| Placebo | Compd. No. 1583 |
| 0.49 ± 0.06 | 0.39 ± 0.03** |

2-2. Experiment 2

Figure 7:
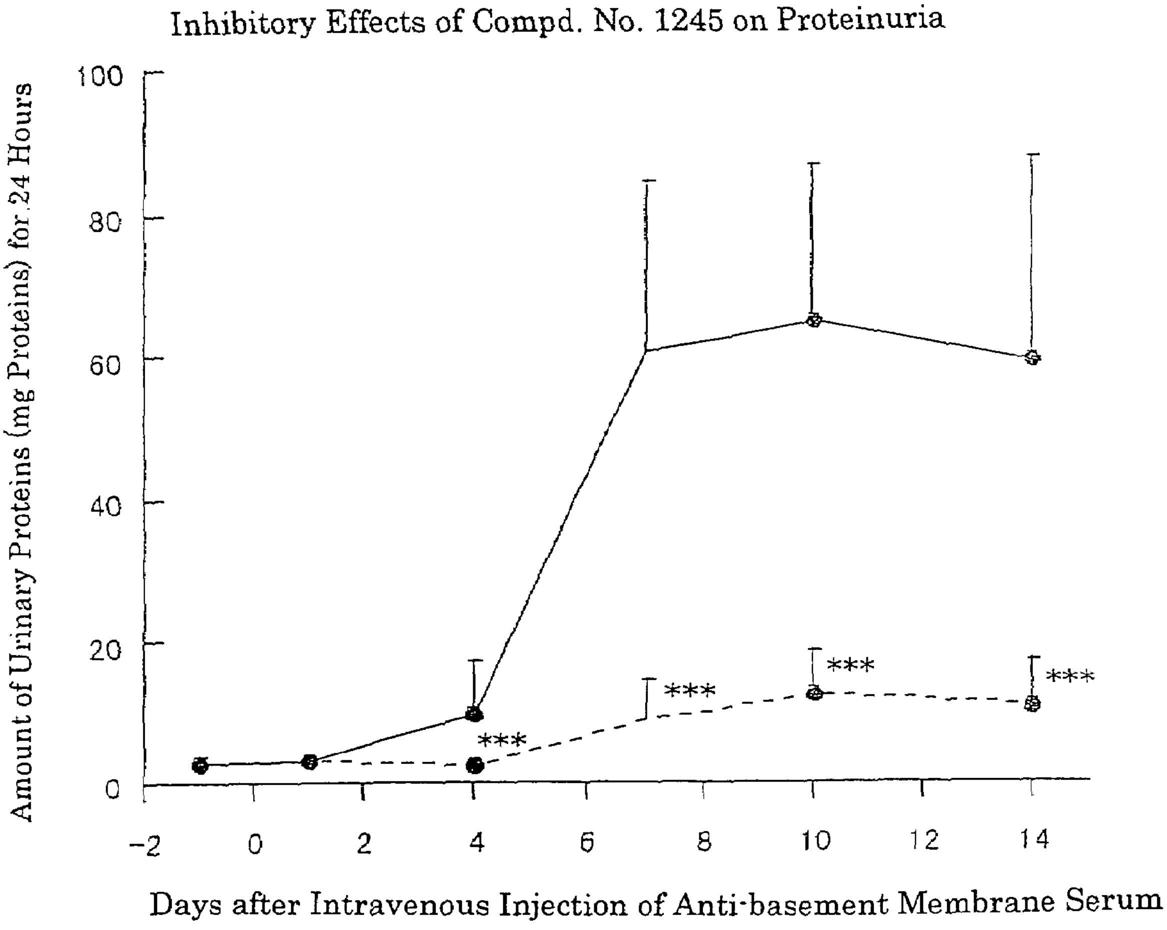
FIG. 7 is a drawing illustrating suppressive effects of the Compd. No. 1245 on proteinuria.

The detection of proteinuria began in each experimental group on about the 4th day after injecting the anti-glomerular basement membrane serum, and the concentration of the urinary proteins was subsequently increased to the 14th day with time to confirm the induction of nephritis. In the group administered with Compd. No. 1245, a significant ($p<0.001$, Mann-Whitney U test) inhibition of the concentration of urinary proteins was respectively found by 74, 85, 81 and 82% on the 4th, 7th, 10th and 14th days after injecting the antiserum as compared with the control group (FIG. 7). When the creatinine concentration in blood was measured on the 15th day after injecting the anti-glomerular basement membrane serum, a significant decrease of 10% ($p<0.05$, Student's t-test) was found in the group administered with compound 1245 as compared with the control group (Table 54).

Therefore, it is found that the glomular injury and renal function exacerbation of rats were alleviated with Compd. No. 1245 to inhibit nephritis.

TABLE 54

| Inhibitory Effects on Serum Creatinine Serum Creatinine Concentration (mg/dl) on the 15th Day of Administering Compd. No. 1245 | |
|---|---|
| Control | Compd. No. 1245 |
| 0.53 ± 0.05 | 0.48 ± 0.04‡ |

The above results show that the compound of the present invention has effective remedial or prophylactic effects on nephritis or nephropathy such as glomerulonephritis, interstitial nephritis or nephrotic syndrome.

Example 2050

Studies on Inhibitory Effects in Chronic Relapsing Experimental Allergic Encephalomyelitis in Mice 1. Method Animal models of chronic recurrent experimental allergic encephalomyelitis were prepared according to the method described in the report by Okuda et al. [Okuda Y., et al. J. Neuroimmunol. 81, 201-210 (1998)]. Into the abdomen of 8-weeks-old female SJL/J×PL/J F1 mice (Jackson Lab.), were subcutaneously injected 100 μL of an emulsion of an Freund's incomplete adjuvant (Diffco) containing 500 μg of rabbit myelin basic protein (Sigma) and 500 μg of *Mycobacterium tuberculosis* H37Ra (Difco)/isotonic sodium chloride solution=1:1 (volume ratio). After 24 hours, 100 μL of isotonic sodium chloride solution containing 400 ng of *Bordetella pertussis* toxin (Sigma) was intraperitoneally injected to induce the chronic relapsing experimental allergic encephalomyelitis. The number of animals in each group was 10.

The test compound was suspended in a 0.5% (weight/volume) aqueous solution of sodium carboxymethylcellulose (Wako Pure Chemical Industries, Ltd.) with a mortar to prepare a prescribed suspension, which was orally administered from the date of injection of the emulsion.

Clinical symptoms of the chronic relapsing experimental allergic encephalomyelitis were evaluated by observation on animal individuals once a day by using the method described by Tahira et al. ["Methods of Immunological Experimental Procedures" p. 1178-1181, Nankodo (1995)]. Namely, score 0=normal; score 1=limp tail; score 2=slight walking abnormality; sore 3=apparent hindlimb paresis; score 4=complete hindlimb paralysis and score 5=moribund or death.

2. Results and Discussion 2-1. Experiment 1: Effects of Compd. No. 1583

Figure 8:
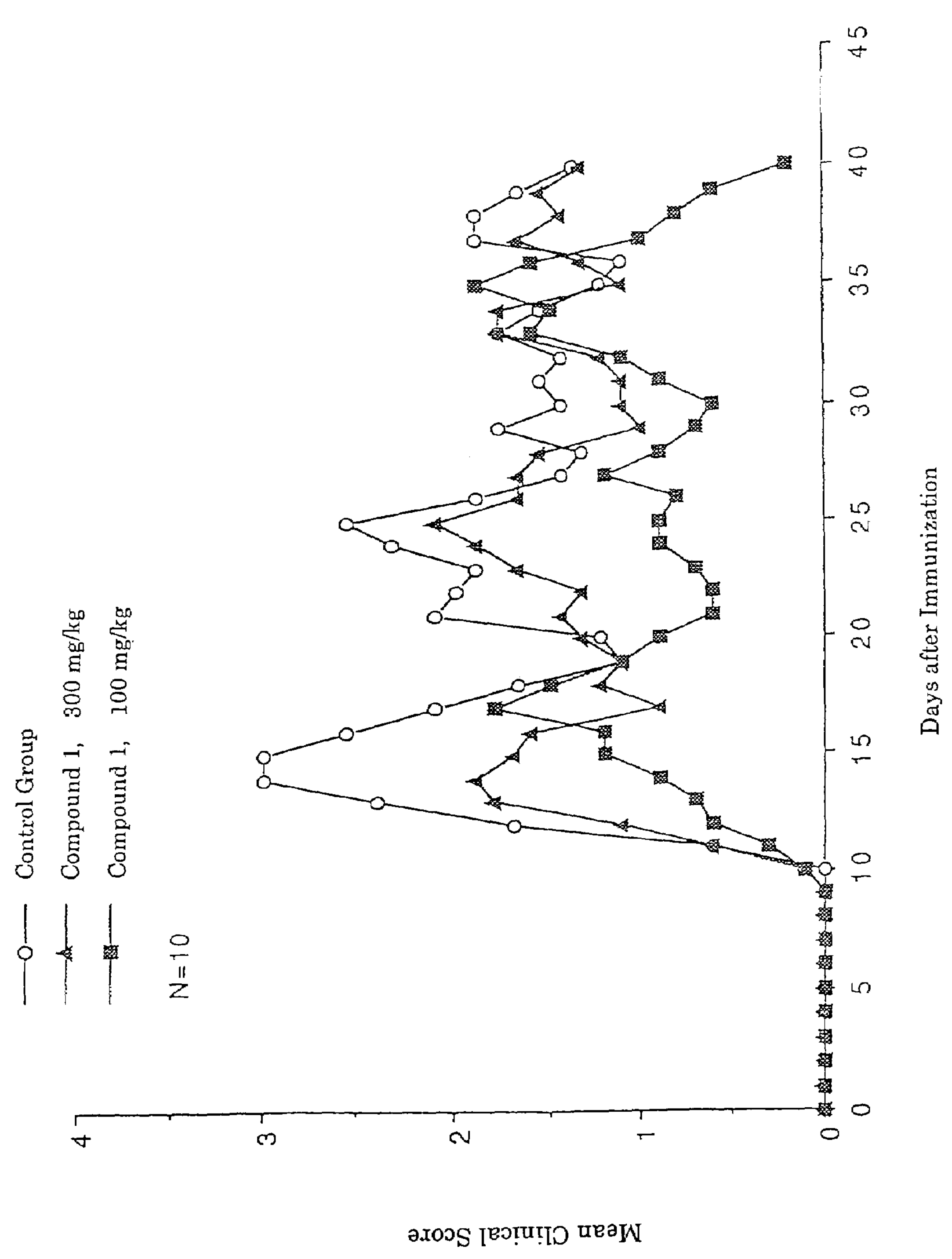
FIG. 8 is a drawing illustrating effects of the Compd. No. 1583 in animal models of chronic relapsing experimental allergic encephalomyelitis.

Table 55 and FIG. 8 show the results to 41 days after injection of the emulsion.

The change in symptoms was expressed by means of the respective experimental groups on each observation day. In the maximal clinical scores in Table 55, the maximal value of the clinical scores shown in the observation period by the respective animals were adopted as the representative scores of the example. As to statistical analytical methods, nonparametric tests among some groups without comparison with to the control group were used for clinical scores and multiple comparisons with the control group (Dunnett's multiple comparison) were used for other evaluation items.

A tendency to delay the onset date (no significant difference), symptom inhibition ($p<0.05$) and shortening of onset period ($p<0.05$) were found at the first attack in the group administered with 100 mg/kg body weight of Compd. No. 1583 as compared with the control group. In the group administered with 30 mg/kg body weight of Compd. No. 1583, distinct effects on the items were not found; however, the tendency of dose-dependent effects was found. In FIG. 8, "compound 1" is not Compd. No. 1 in the present invention, but means the compound of Compd. No. 1583.

TABLE 55

| Experimental Group | Control Group | Compd. No. 1583 30 mg/kg body weight | Compd. No. 1583 100 mg/kg body weight |
|---|---|---|---|
| First Attack | | | |
| Onset Date | 12.6 ± 1.9 | 12.3 ± 1.9 | 13.6 ± 2.0 |
| Maximal Clinical Score | 3.9 ± 0.6 | 3.5 ± 0.9 | 2.4 ± 1.3* |
| Duration of Clinical Sign | 8.8 ± 2.5 | 9.8 ± 3.3 | 5.7 ± 3.8* |
| Second Attack (Relapse) | | | |
| Onset Date | 26.8 ± 7.5 | 26.3 ± 3.4 | 28.5 ± 4.7* |
| Maximal Clinical Score | 3.8 ± 0.8 | 3.7 ± 0.6 | 3.0 ± 0.9* |
| Duration of Clinical Sign | Not calculated | Not calculated | Not calculated |

Note:
*$p < 0.05$ 2-2. Experiment 2: Effects of Compd. No. 1245

Figure 9:
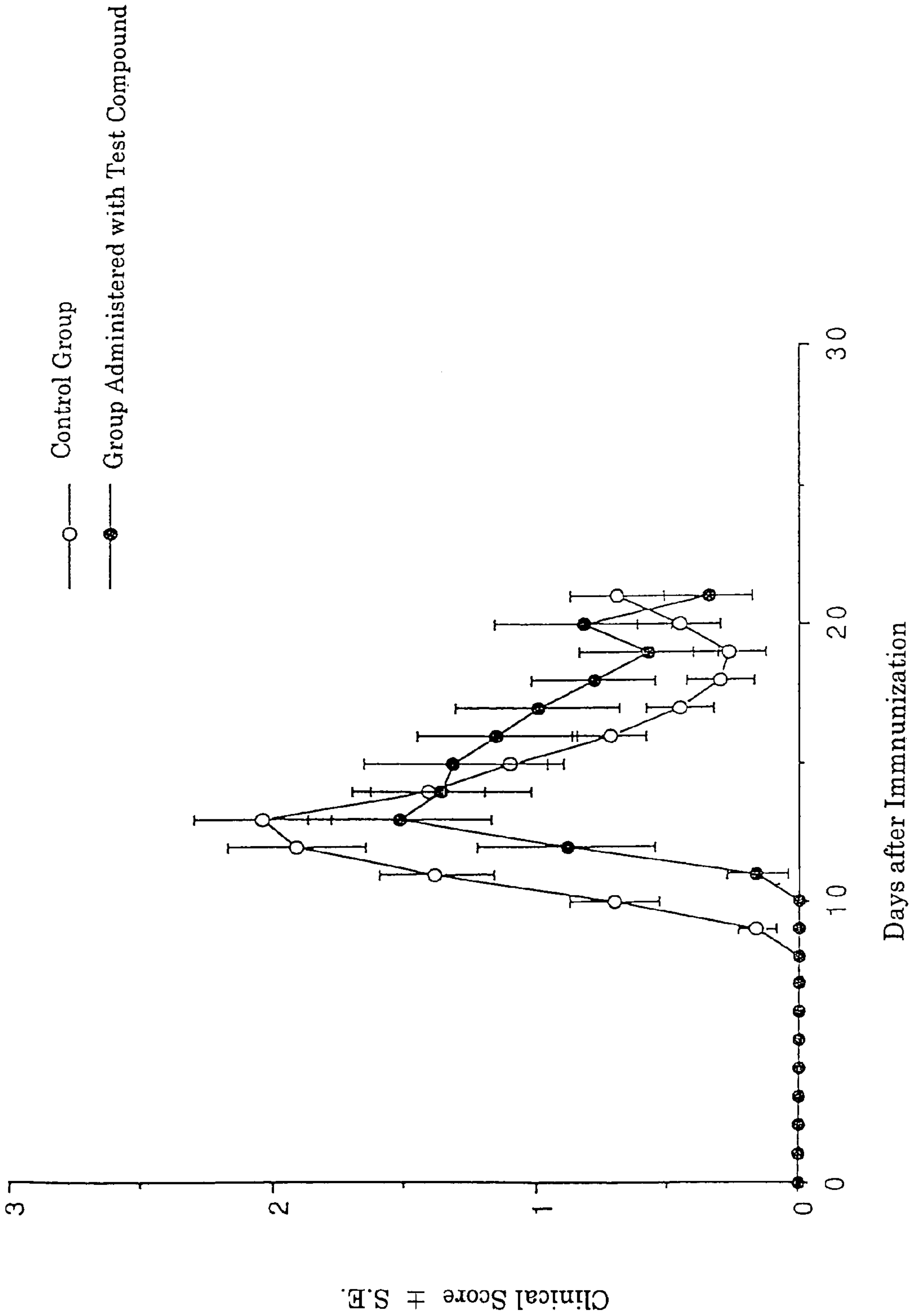
FIG. 9 is a drawing illustrating effects of the Compd. No. 1245 in animal models of chronic relapsing experimental allergic encephalomyelitis.

Table 56 and FIG. 9 illustrate the results to 21 days after injection of the emulsion.

The change in symptoms was expressed as means of the respective experimental groups on each observation day. As to the maximal clinical scores in Table 56, the maximal values of clinical scores manifested by the respective animals during the observation period were adopted as representative scores of the example. As to statistical analytical methods, nonparametric tests between two groups without comparison with to the control group were used for clinical scores and two group comparison with the control group (Student's t-tests) was used for the other evaluation items.

The delay in onset date ($p<0.05$) and a tendency to inhibit symptoms (no significant difference) were found in the group administered with 300 mg/kg body weight of Compd. No. 1245 as compared with the control group.

TABLE 56

| Experimental Group | Control Group | Compd. No. 1245 300 mg/kg body weight |
|---|---|---|
| Incidence (Number of Onset Animals/Number of Immunized Animals) | 34/39 | 17/19 |
| Onset Date | 11.2 ± 2.0 | 13.2 ± 2.4* |
| Maximal Clinical Score | 3.0 ± 0.9 | 2.5 ± 1.5 |
| Duration of Clinical Sign | 5.5 ± 1.7 | 5.4 ± 2.4 |

*p < 0.05

The above results show that the compound of the present invention has effective remedial or prophylactic effects on demyelinating diseases such as multiple sclerosis.

The results shown in Examples 2043 to 2050 reveal that the compound of the present invention as a chemokine receptor antagonist can be useful as remedies or prophylactics for various diseases considered to be associated with chemokines such as MIP-1 α and/or MCP-1 such as atherosclerosis, rheumatoid arthritis, psoriasis, asthma, ulcerative colitis, nephritis (nephropathy), multiple sclerosis, pulmonary fibrosis, cardiomyopathy, hepatitis, pancreatitis, sarcoidosis, Crohn's disease, endometriosis, congestive heart failure, viral meningitis, cerebral infarction, neuropathy, Kawasaki disease, sepsis, allergic rhinitis and allergic dermatitis.

Example 2051

Production of Tablets

A tablet containing 30 mg of Compd. No. 1583 was prepared according to the following prescription:

| | |
|---|---|
| Compd. No. 1583 | 30 mg |
| Lactose | 87 mg |
| Starch | 30 mg |
| Magnesium stearate | 3 mg |

Example 2052

Production of Parenteral Injection

Solutions for injection containing 0.3 mg of hydrochloride of Compd. No. 1583 in 1 mL were prepared according to the following prescription:

| | |
|---|---|
| Compd. No. 1583 (hydrochloride) | 30 mg |
| Sodium chloride | 900 mg |
| Distilled water for injection | 100 mL |

INDUSTRIAL APPLICABILITY

Cyclic amine compounds used in the present invention, pharmaceutically acceptable acid addition salts thereof or pharmaceutically acceptable $C_1$-$C_6$ alkyl addition salts thereof as a chemokine receptor antagonist have inhibitory activities on actions of chemokines such as MIP-1 α and/or MCP-1 on target cells. Therefore, the cyclic amine compounds, pharmaceutically acceptable acid addition salts thereof or pharmaceutically acceptable $C_1$-$C_6$ alkyl addition salts thereof are useful as remedies and/or prophylactics for diseases such as atherosclerosis, rheumatoid arthritis, psoriasis, asthma, ulcerative colitis, nephritis (nephropathy), multiple sclerosis, pulmonary fibrosis, cardiomyopathy, hepatitis, pancreatitis, sarcoidosis, Crohn's disease, endometriosis, congestive heart failure, viral meningitis, cerebral infarction, neuropathy, Kawasaki disease, sepsis, allergic rhinitis and allergic dermatitis wherein infiltration of leukocytes such as monocytes or lymphocytes into tissues plays a principal role in progression and maintenance of diseases.

The invention claimed is:

1. A method for treatment of (nephropathy) or multiple sclerosis comprising administering to a subject an effective amount of at least one compound represented by the following formula (I), pharmaceutically acceptable acid addition salts thereof or pharmaceutically acceptable $C_1$-$C_6$ alkyl addition salts thereof as an active ingredient, (I)

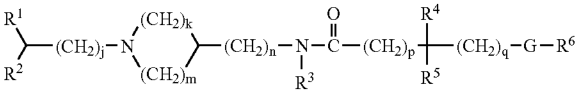

wherein $R^1$ is a phenyl group, or an indolyl group; the phenyl group or the indolyl group in the above $R^1$ is optionally substituted with an optional number of halogen atoms or $C_1$-$C_6$ alkyl groups;

$R^2$ is a hydrogen atom; j is 0; k is 1 or 2;

m is 2;

n is 0 or 1;

$R^3$ is a hydrogen atom;

$R^4$ is a hydrogen atom;

$R^5$ is a hydrogen atom;

p is 0;

q is 0;

G is a group represented by —NH—CO—;

$R^6$ is a phenyl group; the phenyl group, in the above $R^6$ is optionally substituted with an optional number of halogen atoms, $C_1$-$C_6$ alkyl groups, $C_1$-$C_6$ alkoxyl groups, or amino groups; wherein the $C_1$-$C_6$ alkyl groups or the $C_1$-$C_6$ alkoxyl groups may further be substituted with 1 to 3 halogen atoms.

2. The method according to claim 1, wherein the method is for treatment of nephropathy.

3. The method according to claim 1, wherein the method is for treatment of multiple sclerosis.

4. The method according to claim 1, wherein the nephropathy is nephritis.

* * * * *